(12) United States Patent
Serrano-Wu et al.

(10) Patent No.: US 11,603,523 B2
(45) Date of Patent: *Mar. 14, 2023

(54) PCSK9 INHIBITORS AND METHODS OF USE THEREOF

(71) Applicant: ASTRAZENECA AB, Sodertalje (SE)

(72) Inventors: Michael H. Serrano-Wu, Belmont, MA (US); Brian K. Hubbard, Boxford, MA (US); Virendar Kaushik, Bedford, MA (US); Doug Daniels, Oakwood, OH (US)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/744,932

(22) Filed: Jan. 16, 2020

(65) Prior Publication Data

US 2020/0231584 A1    Jul. 23, 2020

Related U.S. Application Data

(60) Provisional application No. 62/794,239, filed on Jan. 18, 2019.

(51) Int. Cl.
| C12N 9/64 | (2006.01) |
| C07D 413/12 | (2006.01) |
| C12N 9/06 | (2006.01) |
| A61P 3/06 | (2006.01) |
| C07D 417/12 | (2006.01) |
| C07D 403/12 | (2006.01) |
| C07D 417/14 | (2006.01) |

(52) U.S. Cl.
CPC .............. *C12N 9/6424* (2013.01); *A61P 3/06* (2018.01); *C07D 413/12* (2013.01); *C12N 9/0012* (2013.01); *C07D 403/12* (2013.01); *C07D 417/12* (2013.01); *C07D 417/14* (2013.01)

(58) Field of Classification Search
CPC ................................ C12N 9/6424; A61P 3/06
See application file for complete search history.

(56) References Cited

U.S. PATENT DOCUMENTS

| 5,874,438 A | 2/1999 | Schohe-Loop et al. |
| 11,248,001 B2 * | 2/2022 | Serrano-Wu ....... C07D 491/107 |
| 2004/0138284 A1 | 7/2004 | Wiesner et al. |
| 2007/0203236 A1 | 8/2007 | Smith et al. |
| 2019/0374526 A1 | 12/2019 | Fischer et al. |

FOREIGN PATENT DOCUMENTS

| AR | 92240 A1 | 4/2015 |
| CN | 104558685 A | 4/2015 |
| CN | 109384712 A | 2/2019 |
| EP | 2578574 A1 | 4/2013 |
| JP | 2007291087 A | 11/2007 |
| JP | 2013061465 A | 4/2013 |
| WO | 199535287 A1 | 12/1995 |
| WO | 199618616 A1 | 6/1996 |
| WO | 199811103 A1 | 3/1998 |
| WO | 2001/093682 A1 | 12/2001 |
| WO | 2002020500 A2 | 3/2002 |
| WO | 2002051831 A1 | 7/2002 |
| WO | 2003026652 A1 | 4/2003 |
| WO | 2003059891 A1 | 7/2003 |
| WO | 2003099276 A1 | 12/2003 |
| WO | 2004017920 A2 | 3/2004 |
| WO | 2004087669 A1 | 10/2004 |
| WO | 2004/094471 A2 | 11/2004 |
| WO | WO-2005/123686 A1 | 12/2005 |
| WO | 2006034341 A2 | 3/2006 |
| WO | 2006035967 A1 | 4/2006 |
| WO | 2006047528 A2 | 5/2006 |
| WO | 2006051311 A1 | 5/2006 |
| WO | 2006067466 A2 | 6/2006 |
| WO | 2006126081 A2 | 11/2006 |
| WO | 2006138304 A2 | 12/2006 |
| WO | 2008013838 A2 | 1/2008 |
| WO | 2008046216 A1 | 4/2008 |
| WO | 2008061796 A2 | 5/2008 |
| WO | 2008072963 A1 | 6/2008 |
| WO | WO-2009/055783 A2 | 4/2009 |
| WO | 2009149188 A1 | 12/2009 |
| WO | 2010048149 A2 | 4/2010 |
| WO | 2011015037 A1 | 2/2011 |
| WO | 2011147199 A1 | 12/2011 |
| WO | 2012009649 A1 | 1/2012 |
| WO | 2012016133 A2 | 2/2012 |
| WO | 2012088438 A1 | 6/2012 |
| WO | 2012101062 A1 | 8/2012 |
| WO | 2012142498 A2 | 10/2012 |
| WO | 2012162635 A1 | 11/2012 |
| WO | 2013137371 A1 | 9/2013 |
| WO | 2013177536 A2 | 11/2013 |
| WO | 2014012360 A1 | 1/2014 |
| WO | 2014/121040 A1 | 8/2014 |

(Continued)

OTHER PUBLICATIONS

International Search Report and Written Opinion for International Application No. PCT/US2020/013882 dated Mar. 23, 2020.
Lo Surdo et al., "Mechanistic implications for LDL receptor degradation from PCSK9/LDLR structure at neutral pH," EMBO Reports, 12(12):1300-1305 (2011).
Seidah et al., "PCK9: a key modulator of cardiovascular health," Circulation Research 114(6):1022-1036 (2014).
International Search Report and Written Opinion for PCT/US2020/013881, dated Dec. 30, 2020.
CAS Registry No. 2217215-43-3; STN Entry Date Apr. 22, 2018; rel-(1R,2S,3R,5R)-5-(3-Fluorophenoxy)-2-[(2-hydroxyethyl)methylamino]-3-(2-pyrimidinylamino)cyclopentanol.
CAS Registry No. 2061864-46-6; STN Entry Date Jan. 30, 2017; rel-(1R,2S,3R,5R)-5-Phenoxy-3-(2-pyrimidinylamino)-2-(1-pyrrolidinyl)cyclopentanol.

(Continued)

*Primary Examiner* — Kevin E Weddington

(57) ABSTRACT

The invention relates to a novel inhibitor pharmacophore of PCSK9 and heteroaryl compounds that bind the PCSK9 protein.

28 Claims, 9 Drawing Sheets

Specification includes a Sequence Listing.

(56) References Cited

FOREIGN PATENT DOCUMENTS

| WO | 2014117919 | A1 | 8/2014 |
| WO | 2014/159690 | A1 | 10/2014 |
| WO | 2014201206 | A1 | 12/2014 |
| WO | 2015181387 | A1 | 12/2015 |
| WO | 2015195656 | A2 | 12/2015 |
| WO | 2016049524 | A1 | 3/2016 |
| WO | 2016054388 | A1 | 4/2016 |
| WO | 2016118638 | A1 | 7/2016 |
| WO | 2017125506 | A1 | 7/2017 |
| WO | 2017161028 | A1 | 9/2017 |
| WO | 2017193063 | A1 | 11/2017 |
| WO | 2018106818 | A1 | 6/2018 |
| WO | 2018106820 | A1 | 6/2018 |
| WO | 2018175746 | A1 | 9/2018 |
| WO | 2018231745 | A1 | 12/2018 |
| WO | 2019079701 | A1 | 4/2019 |
| WO | 2019090076 | A1 | 5/2019 |
| WO | 2019111225 | A1 | 6/2019 |
| WO | 2019143675 | A1 | 7/2019 |
| WO | 2019209757 | A1 | 10/2019 |
| WO | 2020150473 | A2 | 7/2020 |

OTHER PUBLICATIONS

CAS Registry No. 2060972-19-0; STN Entry Date Jan. 29, 2017; rel-1-[(1R,2S,3S,5S)-2-Hydroxy-3-phenoxy-5-(2-pyrimidinylamino)cyclopentyl]-4-piperidinol.

CAS Registry No. 2060972-14-5; STN Entry Date Jan. 29, 2017; rel-(1R,2S,3R,5R)-5-(3-Fluorophenoxy)-2-(4-morpholinyl)-3-(2-pyrimidinylamino)cyclopentanol.

CAS Registry No. 2058649-45-7; STN Entry Date Jan. 25, 2017; rel-(1R,2S,3R,5R)-2-(4-Morpholinyl)-5-phenoxy-3-(2-pyrimidinylamino)cyclopentanol.

CAS Registry No. 2058649-39-9; STN Entry Date Jan. 25, 2017; rel-(1R,2S,3R,5R)-2-KDimethylamino)-5-phenoxy-3-(2-pyrimidinylamino)cyclopentanol.

Anonymous, "4 Compounds in Registry Without References".

McDermott et al., "Design and evaluation of novel gluataminase inhibitors", Bioorganic & Medicinal Chemistry (2016), pp. 1819-1839, vol. 24(8).

Extended European Search Report for European Patent Application No. 20740953.3 dated Sep. 27, 2022.

Extended European Search Report for European Patent Application No. 20741354.3 dated Sep. 23, 2022.

Daluge et al, "Synthesis of Carbocyclic Aminonuceleosides", Journal of Organic Chemistry (1978), pp. 2311-2320, vol. 43(12).

Gong et al., "Duplex Molecular Strands Based on the 3,6-Diaminopyridazine Hydrogen Bonding Motif: Amplifying Small-Molecule Self-Assembly Preferences through Preorganization and Iterative Arrangement of Binding Residues", Journal of the American Chemistry Society (2005), pp. 1719-1725, vol. 127(6).

Ghate et al., "Distributed Succinic Acids and Their Derivatives", Journal of the University of Bombay, Science: Physical Sciences, Mathematics and Biological Sciences and Medicine (1957) 25A(Pt. 5), 17-24 Coden: Jubas; ISSNN 0368-4644.

Xu et al., "Small molecules as inhibitors of PCSK9: Current status and future challenges", European Journal of Medicinal Chemistry (2018), pp. 212-233.

\* cited by examiner

− − − Disordered segments in PCKS9

PCSK9 INHIBITORS AND METHODS OF USE THEREOF

RELATED APPLICATIONS

This application claims the benefit of priority to U.S. Provisional Patent Application No. 62/794,239, filed on Jan. 18, 2019, which is hereby incorporated by reference in its entirety.

SEQUENCE LISTING

The instant application contains a Sequence Listing which has been filed electronically in ASCII format and is hereby incorporated by reference in its entirety. Said ASCII copy, created on Mar. 10, 2020, is named DGH-00201 SL.txt and is 42,026 bytes in size.

BACKGROUND

PCSK9, also referred to as "proprotein convertase subtilisin/kexin 9", is a member of the secretory proprotein convertase family and plays an important role in cholesterol metabolism. PCSK9 increases the levels of circulating LDL cholesterol via the enhanced degradation of the LDL receptors independently of its catalytic activity. Secreted PCSK9 binds to the Epidermal Growth Factor domain A (EGFA) of the LDL receptor (LDLR) at the cell surface and the PCSK9/LDL receptor complex is internalized into endosomal/lysosomal compartments. The enhanced binding affinity of PCSK9 to the LDL receptor at the acidic pH of late endosomes/lysosomes reduces LDL receptor recycling and instead targets LDL receptors for lysosomal degradation. Genetic association studies have demonstrated that loss-of-function mutations in PCSK9 are associated with low plasma LDL-C levels and a reduction in the incidence of adverse cardiovascular events.

Another biological pathway involving the effect of PCSK9 on LDL receptors is the onset of septic shock. Septic shock is an often fatal complication of a severe microbial infection (sepsis) that triggers an uncontrolled systemic inflammatory response and subsequent organ failure. Sepsis originates with the microbial cell walls that contain pathogenic lipid moieties such as lipopolysaccharide (LPS; Gram-negative bacteria). LPS are potent ligands for mammalian innate immune receptors [Toll-like receptors (TLRs)] and thus figure prominently in the septic inflammatory response (septic shock, or sepsis).

PCSK9 reduces LPS uptake by the liver's LDL receptors, such that free LPS overstimulates the body's immune response to the pathogen leading to sepsis. Thus, inhibiting PCSK9 is beneficial in retaining liver LDL receptors to effect systemic pathogen clearance and detoxification in response to sepsis. However, beyond antibiotic therapy, there are currently no effective treatments for sepsis or septic shock.

For cardiovascular disease, few options exist for inhibiting PCSK9. Statins actually upregulate PCSK9 in HepG2 cells and in human primary hepatocytes through the increased expression of SREBP-2, a transcription factor that upregulates both the LDLR and PCSK9 genes. Since an elevated level of PCSK9 decreases the abundance of LDL receptor on the cell surface, increasing doses of statins have failed to achieve proportional LDL-cholesterol lowering effects.

Two monoclonal antibodies (mAbs) that bind selectively to extracellular PCSK9 and prevent its interaction with the LDL receptor, alirocumab and evolocumab, have recently received FDA approval for lowering LDL-C levels. In clinical trials, alirocumab showed an about 50% decrease in LDL levels compared to placebo. Elbitar et al., *Expert Opin Therapeutic Patents* 2016 26:1377-1392. Patients taking evolocumab showed an about 60-75% decrease in LDL levels. The potency of these drugs demonstrates the potential for inhibitors of PCSK9 to be effective treatments for those with hypercholesterolemia and other cardiovascular diseases. However, both antibody drugs require intravenous administration and can cause allergic reactions or other deleterious immune responses in the body.

Designing and developing efficacious drugs is often aided by information about how a compound interacts with its biological target, such as PCSK9. Cunningham et al. have described the three-dimensional crystal structure of PCSK9 and identified different regions, such as the C-terminal domain which is more flexible than other sections of the protein. (Cunningham et al. *Nature Struct. Bio.* 2007 14:413-419). Thus, interest in inhibitors of PCSK9 has been focused on how various small molecules can interact with the surface or pockets in PCSK9.

Cardiovascular diseases often require management over a person's lifetime, unlike an infection that could be episodic. Thus, ease of dosing and administration become key factors to patient compliance with maintenance drug treatments. There is a need for PCSK9 inhibitors with increased efficacy and greater ease of administration, which can be achieved with small molecule PCSK9 inhibitors.

SUMMARY

Disclosed herein are compounds of Formula (I):

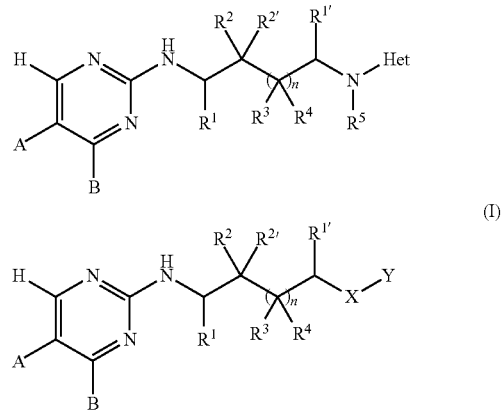

wherein:
A is selected from H, halo, hydroxy, alkyl, thioalkyl, alkenyl, alkoxy, acyloxy, cyano, cycloalkyl, —C(O)OR$^6$, and —C(O)NR$^6$R$^7$;
B is selected from H, alkyl, and halo, or
A and B are taken together with the carbon atoms to which they are attached to form a 5- or 6-membered heteroaryl;
X is NR$^5$ or O;
R$^1$ and R$^{1'}$ are each independently selected from H and alkyl; or
  if n is 0, R$^1$ and R$^{1'}$, together with the atoms to which they are attached, form a 4-8 membered cycloalkyl or cycloalkenyl ring;
R$^2$ is selected from H, halo, alkyl, alkoxy, amidoalkyl, aminoalkyl, hydroxyalkyl, alkylamino, cyano, and hydroxy; or R¹ and R², together with the atoms to which they are attached, form a 3-8 membered cycloalkyl or heterocyclyl ring; or R¹' and R², together with the atoms to which they are attached, form a 3-8 membered cycloalkyl or heterocyclyl ring;

R²' is selected from H, halo, alkyl, alkoxy, amidoalkyl, aminoalkyl, and cyano, or R² and R²', taken together with the carbon atom to which they are attached, form a 3- to 8-membered cycloalkyl or heterocyclyl ring;

each R³ and R⁴ is independently H or alkyl; or

R² and R³, together with the atoms to which they are attached, form a 3-8 membered cycloalkyl or heterocyclyl ring; and R⁵ is H or alkyl; or R¹ and R⁵, together with the atoms to which they are attached, form a 6-8 membered cycloalkyl or heterocyclyl ring; or R² and R⁵, together with the atoms to which they are attached, form a 5-8 membered cycloalkyl or heterocyclyl ring;

each R⁶ and R⁷ is independently H or alkyl;

Y is selected from aryl, heteroaryl and heterocyclyl; and n is 0 or 1 In certain embodiments, the present invention provides a pharmaceutical composition suitable for use in a subject in the treatment or prevention of cardiovascular diseases comprising an effective amount of any of the compounds described herein (e.g., a compound of the invention, such as a compound of formula (I)), and one or more pharmaceutically acceptable excipients. In certain embodiments, the pharmaceutical preparations may be for use in treating or preventing a condition or disease as described herein.

Disclosed herein are methods of treating diseases and conditions that benefit from the inhibition of PCSK9. These diseases include, but are not limited to cardiovascular diseases, such as hypercholesterolemia, hyperlipidemia, hyperlipoproteinemia, hypertriglyceridemia, dyslipidemia, dyslipoproteinemia, atherosclerosis, hepatic steatosis, metabolic syndrome and coronary artery disease.

Other diseases and conditions that can be treated using the methods described herein include, but are not limited to, sepsis and septic shock.

Provided herein are combination therapies of compounds of formula (I) with monoclonal antibodies, statins and other cardiovascular agents that can enhance the cardiovascular therapeutic benefit beyond the ability of the adjuvant therapy alone. Also provided herein are combination therapies of compounds of formula (I) with antibiotic agents that can reduce the occurrence and severity of sepsis and septic shock beyond the ability of the adjuvant therapy alone.

Also disclosed herein is a new binding site on PCSK9, that compounds of Formula I interact with. Certain features common to these compounds, such as a triad of H-bonds between the compounds disclosed herein and certain residues in the C-terminal domain of PCSK9, contribute to the selectivity and affinity of the compounds for PCSK9. This C-terminal binding site is distinct from the PCSK9 catalytic domain, which is understood to be the target of many previously identified inhibitors.

DETAILED DESCRIPTION

Compounds

Figure 1:
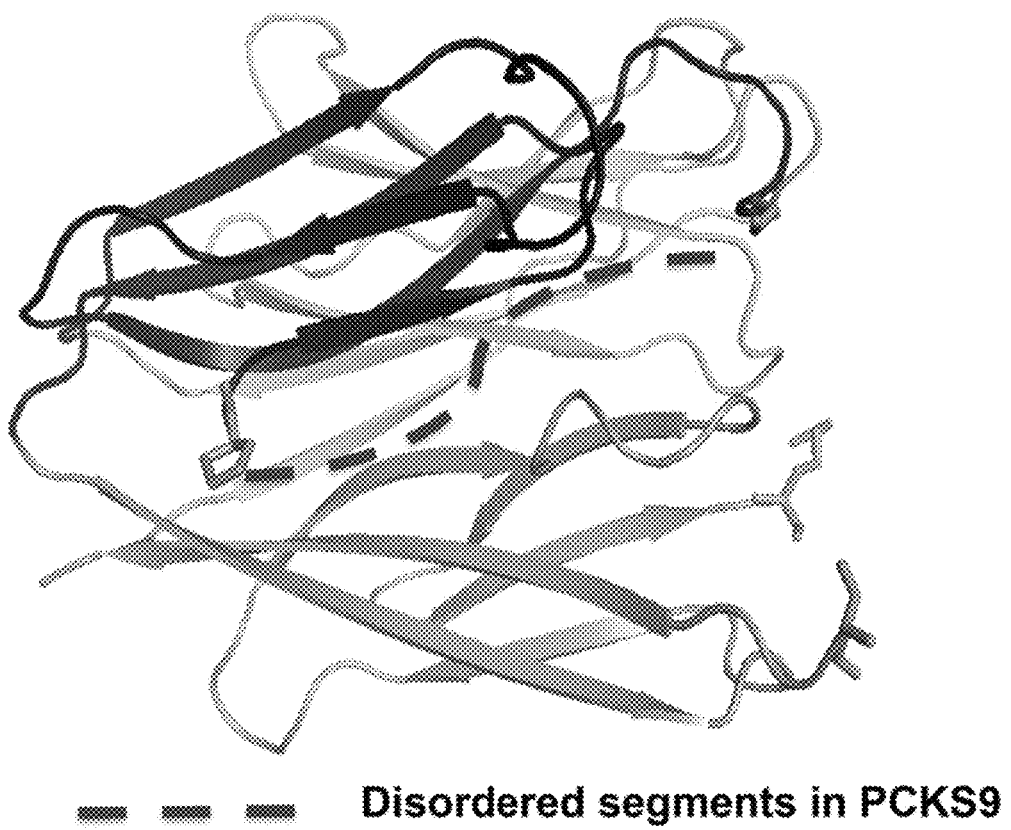
FIG. 1 depicts a crystal structure of PCSK9 showing the disordered segments in a dashed line.

Disclosed herein are compounds of Formula (I):

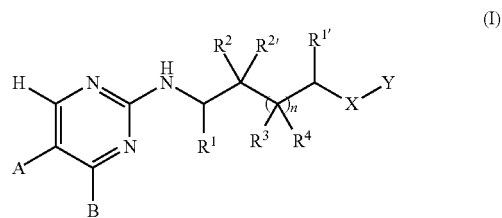

wherein:
A is selected from H, halo, hydroxy, alkyl, thioalkyl, alkenyl, alkoxy, acyloxy, cyano, cycloalkyl, —C(O)OR⁶, and —C(O)NR⁶R⁷;
B is selected from H, alkyl, and halo, or
A and B are taken together with the carbon atoms to which they are attached to form a 5- or 6-membered heteroaryl;
X is NR⁵ or O;
R¹ and R¹' are each independently selected from H and alkyl; or
  if n is 0, R¹ and R¹', together with the atoms to which they are attached, form a 4-8 membered cycloalkyl or cycloalkenyl ring;
R² is selected from H, halo, alkyl, alkoxy, amidoalkyl, aminoalkyl, hydroxyalkyl, alkylamino, cyano, and hydroxy; or
  R¹ and R², together with the atoms to which they are attached, form a 3-8 membered cycloalkyl or heterocyclyl ring; or
  R¹' and R², together with the atoms to which they are attached, form a 3-8 membered cycloalkyl or heterocyclyl ring;

R$^{2'}$ is selected from H, halo, alkyl, alkoxy, amidoalkyl, aminoalkyl, and cyano, or
  R$^2$ and R$^{2'}$, taken together with the carbon atom to which they are attached, form a 3- to 8-membered cycloalkyl or heterocyclyl ring;
each R$^3$ and R$^4$ is independently H or alkyl; or
  R$^2$ and R$^3$, together with the atoms to which they are attached, form a 3-8 membered cycloalkyl or heterocyclyl ring; and
R$^5$ is H or alkyl; or
  R$^1$ and R$^5$, together with the atoms to which they are attached, form a 6-8 membered cycloalkyl or heterocyclyl ring; or
  R$^2$ and R$^5$, together with the atoms to which they are attached, form a 5-8 membered cycloalkyl or heterocyclyl ring;
each R$^6$ and R$^7$ is independently H or alkyl;
Y is selected from aryl, heteroaryl and heterocyclyl; and
n is 0 or 1.

Disclosed herein are compounds of Formula (I')

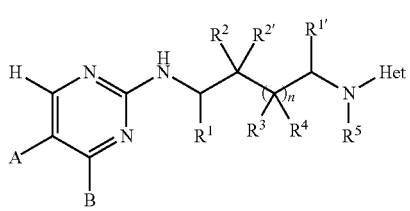

wherein:
A is selected from H, halo, alkyl, thioalkyl, alkenyl, alkoxy, acyloxy, cyano, cycloalkyl, —C(O)OR$^6$, and —C(O)NR$^6$R$^7$;
B is selected from H, alkyl, and halo;
R$^1$ and R$^{1'}$ are each independently selected from H and alkyl; or
  if n is 0, R$^1$ and R$^{1'}$, together with the atoms to which they are attached, form a 4-8 membered cycloalkyl ring;
R$^2$ is selected from H, halo, alkyl, alkoxy, amidoalkyl, aminoalkyl, hydroxyalkyl, alkylamino, cyano, and hydroxy; or
  R$^1$ and R$^2$, together with the atoms to which they are attached, form a 3-8 membered cycloalkyl or heterocyclyl ring; or
  R$^{1'}$ and R$^2$, together with the atoms to which they are attached, form a 3-8 membered cycloalkyl or heterocyclyl ring;
R$^{2'}$ is selected from H, halo, alkyl, alkoxy, amidoalkyl, aminoalkyl, and cyano; or
  R$^2$ and R$^{2'}$, taken together with the carbon atom to which they are attached, form a 3- to 8-membered cycloalkyl or heterocyclyl ring;
each R$^3$ and R$^4$ is independently H or alkyl; or
  R$^2$ and R$^3$, together with the atoms to which they are attached, form a 3-8 membered cycloalkyl or heterocyclyl ring; and
R$^5$ is H or alkyl; or
  R$^1$ and R$^5$, together with the atoms to which they are attached, form a 6-8 membered cycloalkyl or heterocyclyl ring; or
  R$^2$ and R$^5$, together with the atoms to which they are attached, form a 5-8 membered cycloalkyl or heterocyclyl ring;
each R$^6$ and R$^7$ is independently H or alkyl;
Het is heteroaryl or heterocyclyl; and
n is 0 or 1.

All of the embodiments below and herein are understood to be embodiments of both Formula (I) and Formula (I').

In certain embodiments, The compound of claim 1, wherein A is selected from H, hydroxy, thioalkyl, alkyl, alkoxy, acyloxy, cyano, cycloalkyl, —C(O)OR$^6$, and —C(O)NR$^6$R$^7$.

In certain embodiments, A is H, while in other embodiments, A is alkyl, such as thioalkyl. In certain embodiments, A is selected from —SCH$_3$, —SCHF$_2$, and —OCHF$_2$. In some embodiments, A is alkoxy. In other embodiments, A is cycloalkyl. In certain embodiments, B is H.

In certain embodiments, A and B are taken together with the carbon atoms to which they are attached to form a pyrrolyl or thienyl ring, which is unsubstituted or substituted with one or more alkyl.

In certain embodiments, X is preferably NR5. In other embodiments, Y is preferably heteroaryl or heterocyclyl.

In certain embodiments, R$^1$ and R$^{1'}$ are each H. However, when n is 0, le and R$^{1'}$, together with the atoms to which they are attached, can form a 4- to 8-membered cycloalkyl ring. In some embodiments, the cycloalkyl is monocyclic or bicyclic. In other embodiments, R$^1$ and R$^{1'}$, together with the atoms to which they are attached, can form a 4- to 8-membered cycloalkenyl ring. In some embodiments, the cycloalkyl ring is a cyclopentyl ring, such as S,S-cyclopentyl. In some embodiments, the cycloalkyl ring is substituted with hydroxyl or hydroxyalkyl.

In certain embodiments, R$^2$ is selected from H, halo, alkyl, alkoxy, amidoalkyl, aminoalkyl, alkylamino, cyano, and hydroxyl. In certain embodiments, R$^2$ is C$_{1-3}$alkyl. R$^2$ can be substituted with one or more substituents selected from amino, amido, cyano, hydroxy, and heterocyclyl. In some embodiments, R$^{2'}$ is C$_{1-3}$alkyl, while in other embodiments, R$^{2'}$ is H.

In certain embodiments, R$^1$ and R$^2$, together with the atoms to which they are attached, form a 3-8 membered cycloalkyl or heterocyclyl ring. In other embodiments, R$^{1'}$ and R$^2$, together with the atoms to which they are attached, form a 3-8 membered cycloalkyl or heterocyclyl ring. In certain embodiments, R$^2$ and R$^{2'}$, taken together with the carbon atom to which they are attached, form a 3- to 8-membered cycloalkyl or heterocyclyl ring.

In certain embodiments, R$^3$ is C$_{1-3}$alkyl, while in other embodiments, R$^3$ is H. In certain embodiments, R$^4$ is H.

In certain embodiments, R$^2$ and R$^3$, together with the atoms to which they are attached, form a 3-8 membered cycloalkyl or heterocylcyl ring. In other embodiments, le and R$^5$, together with the atoms to which they are attached, form a 6-8 membered cycloalkyl or heterocyclyl ring. In other embodiments, R$^2$ and R$^5$, together with the atoms to which they are attached, form a 5-8 membered cycloalkyl or heterocyclyl ring.

In certain embodiments, Y is monocyclic heteroaryl, such as, but not limited to, pyridinyl, pyrazinyl, pyrimidinyl, and thiazolyl. In other embodiments, Y is monocyclic heteroaryl, such as, but not limited to, pyridinyl, pyrazinyl, and pyrimidinyl. In some embodiments, Y is selected from triazenyl, oxazolyl, isoxazolyl, imidazolyl, pyrazolyl and triazolyl. The monocyclic heteroaryl can be unsubstituted, or substituted with one or more substituents selected from alkyl, thioalkyl alkoxy, alkoxycarbonyl, amido, carboxy, cyano, halo, heteroaryl, nitro, sulfonamido, and thioalkyl. In another embodiment, Y is a monocyclic heteroaryl can be unsubstituted, or substituted with one or more substituents selected from alkyl, thioalkyl, alkoxy, alkoxycarbonyl, amido, carboxy, cyano, halo, aryl, heteroaryl, heterocyclyl, nitro, sulfonamido, and thioalkyl.

In certain embodiments, the monocyclic heteroaryl is substituted with an aryl, heteroaryl or heterocyclyl selected from phenyl, pyridinyl, 2-hydroxypyridinyl, piperidinonyl, 2-hydroxy-1-methylpyridinyl, triazolyl, imidazolidinonyl, pyrimidonyl, 2-hydroxyisoquinolinyl, 3-hydroxypyridazinyl, pyrrolidinonyl, pyrazolyl, and morpholinonyl. In certain preferred embodiments, Y is a 6-membered monocyclic heteroaryl. In some embodiments, the monocyclic heteroaryl is substituted with an heteroaryl or heterocyclyl that is substituted with one or more substituents selected from halo, CN, alkyl, alkoxy, hydroxy, carboxy, —$CO_2$alkyl, and tetrazolyl. In certain preferred embodiments, the monocyclic heteroaryl is disposed on the para position of A relative to X.

In other embodiments, Y is bicyclic heteroaryl, such as, but not limited to, benzothiazolyl, benzimidazolyl, benzoxazolyl, triazolopyridinyl, thiazolopyrindinyl, quinolinyl, and quinoxalinyl. The bicyclic heteroaryl can be unsubstituted, or substituted with one or more substituents selected from alkyl, haloalkyl, hydroxyalkyl, thioalkyl, alkoxy, alkoxycarbonyl, amido, carboxy, cyano, halo, heteroaryl, nitro, and sulfonamido. In certain embodiments, the bicyclic heteroaryl is unsubstituted, or substituted with one or more substituents selected from thioalkyl, alkoxycarbonyl, amido, carboxy, halo, and heteroaryl.

In certain embodiments, Y is substituted with an amido substituent of the formula —C(O)NR$^8$R$^9$ or —NR$^9$C(O)R$^{10}$, wherein R$^8$ and R$^9$ are each independently selected from H, alkyl, heterocyclyl and heteroaryl; or R$^8$ and R$^9$, taken together with the nitrogen atom to which they are attached, form a 4-, 5-, 6-, or 7-membered heterocyclic or heteroaryl ring; and R$^{10}$ is alkyl.

In certain embodiments, Y is substituted with a sulfonamido substituent of the formula —S(O)$_2$NR$^8$R$^9$ or —NR$^9$S(O)$_2$R$^{10}$; wherein R$^8$ and R$^9$ are each independently selected from H, alkyl, and heteroaryl; or R$^8$ and R$^9$, taken together with the nitrogen atom to which they are attached, form a 4-, 5-, 6-, or 7-membered heterocyclic ring; and R$^{10}$ is alkyl.

All the foregoing embodiments of variable Y in Formula (I) are understood to also be embodiments of variable Het in Formula (I').

In certain embodiments, R$^8$ and R$^9$ are each independently selected from H, methyl, ethyl, triazolyl, and pyrazolyl. In embodiments where one or both of R$^8$ and R$^9$ are alkyl, each alkyl is independently unsubstituted, or substituted with one or more substituents selected from methyl, methoxy, carboxy, cyano, hydroxy, dimethylamino, ethoxycarbonyl, phenyl, methoxyphenyl, oxadiazolyl, tetrazolyl, 2-methyl-tetrazolyl, triazolyl, 1-methyltriazolyl, 4-methyltriazolyl, and 2,4-dihydro-3H-1,2,4-triazol-3-onyl. In certain embodiments, R$^8$ and R$^9$, taken together with the nitrogen atom to which they are attached, form a heterocyclic ring selected from aziradine, isothiazolidine-1,1-dioxide, azetidine, thiazol-4(5Hn)-one, morpholine, piperidine, piperazine, pyrrolidine, thiomorpholine-1,1-dioxide, 2-oxa-6-azaspiro[3.3]heptane. In some embodiments, R$^8$ and R$^9$, taken together with the nitrogen atom to which they are attached, form a heterocyclic ring selected from 2,8-diazaspiro[5,5]undecene, tetrahydroimidazo[1,2-a]pyrazine, octahydropyrazino[2,1-c][1,4]oxazine, tetrahydropyrido[3,4-d]pyrimidine, 2-oxa-8-azaspiro[4.5]decane, tetrahydropyrrolo[3,4-c]pyrazole, thiomorpholine, 2-oxa-7-azaspiro[3.5]nonane, 2,8-diazaspiro[4.5]decan-3-one, tetrahydro-1,7-naphthyridine, 1-oxa-4,9-diazaspiro[5.5]undecan-3-one, tetrahydropyrrolo[3,4-d]imidazole, pyrimidine, 8-oxa-2-azaspiro[4.5]decane, hexahydro-3H-oxazolo[3,4-a]pyrazin-3-one, 1-oxa-7-azaspiro[3.5]nonane, octahydrocyclopenta[c]pyrrole, tetrahydro-[1,2,4]triazolo[4,3-a]pyrazine, 2,7-diazaspiro[4.4]nonane, 2,6-diazaspiro[3.4]octane, 7-oxa-2-azaspiro[3.5]nonane, 1-oxa-8$\lambda^2$-azaspiro[4.5]decane, 2-oxa-6-azaspiro[3.3]heptane, tetrahydrofuran, oxadiazole, triazole, pyridinone, tetrahydro-[1,2,4]triazolo[4,3-a]pyrazin-3(2H)-one, piperidinone, 3,6-diazabicyclo[3.1.1]heptane, 5-oxa-2,7-diazaspiro[3.5]nonane, pyrazole, and pyridazin-3(2H)-one.

In some embodiments, the heterocyclic ring is unsubstituted, or substituted with one or more substituents selected from alkyl, alkoxycarbonyl, halo, hydroxy, cyano, carboxy, and heterocyclyl. In certain embodiments, the heterocyclic ring is unsubstituted, or substituted with one or more substituents selected from methyl, ethoxycarbonyl, halo, hydroxy, cyano, carboxy, and oxetanyl.

In certain embodiments, the present invention provides a pharmaceutical preparation suitable for use in a human patient, comprising any of the compounds shown above (e.g., a compound of the invention, such as a compound of formula (I), and one or more pharmaceutically acceptable excipients. In certain embodiments, the pharmaceutical preparations may be for use in treating or preventing a condition or disease as described herein.

Any of the disclosed compounds may be used in the manufacture of medicaments for the treatment of any diseases or conditions disclosed herein.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

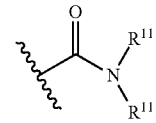

wherein each $R^{11}$ independently represents a hydrogen or hydrocarbyl group, or two $R^{11}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

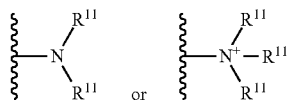

wherein each $R^{11}$ independently represents a hydrogen or a hydrocarbyl group, or two $R^{11}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

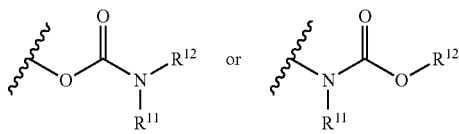

wherein $R^{11}$ and $R^{12}$ independently represent hydrogen or a hydrocarbyl group, such as an alkyl group, or $R^{11}$ and $R^{12}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2$-$R^{10}$, wherein $R^{10}$ represents a hydrocarbyl group.

The term "carboxy", as used herein, refers to a group represented by the formula $—CO_2H$.

The term "ester", as used herein, refers to a group $—C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a $=O$ or $=S$ substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a $=O$ substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

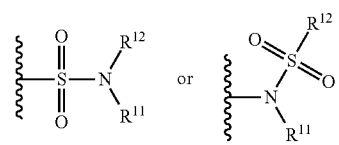

wherein R$^{11}$ and R$^{12}$ independently represents hydrogen or hydrocarbyl, such as alkyl, or R$^{11}$ and R$^{12}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

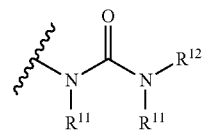

wherein R$^{11}$ and R$^{12}$ independently represent hydrogen or a hydrocarbyl, such as alkyl, or either occurrence of taken together with R'$^2$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The present invention includes all pharmaceutically acceptable isotopically-labelled compounds as described herein wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds as disclosed herein, for example, those incorporating a radioactive isotope, are useful in drug and/or substrate tissue distribution studies. The radioactive isotopes tritium, i.e. $^3$H, and carbon-14, i.e. $^{14}$C, are useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, a N, can be useful in Positron Emission Tomography (PET) studies for examining substrate receptor occupancy.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

Allosteric Inhibitors of PCSK9

Applicants have identified and characterized a previously uncharacterized site of PCSK9, to which the compounds disclosed herein bind. As a result, Applicants have identified a set of chemical features, or a pharmacophore, that characterizes compounds that can interact with this site and inhibit the activity of PCSK9.

The concept of a 'pharmacophore' is not recent. It was first introduced by Paul Ehrlich in 1909 as "a molecular framework that carries (pharos) the essential features responsible for a drug's (pharmacon's) biological activity". Ehrlich, *Uber den jetzigen stand derchemotherapie. Chem. Ber.* 42:17. This definition was further updated in 1977 by Peter Gund to "a set of structural features in a molecule that is recognized at a receptor site and is responsible for that molecule's biological activity" Gund, *Three dimensional pharmacophoric pattern searching. Prog. Mol. Subcell. Biol.* 5:117-143. More recently, the official IUPAC recommendation from 1997 has summarized the concept as follows: "A pharmacophore is the ensemble of steric and electronic features that is necessary to ensure the optimal supramolecular interactions with a specific biological target and to trigger (or block) its biological response" Wermuth, C.-G. et al. 1998 *Glossary of terms used in medicinal chemistry (IUPAC Recommendations* 1998). *Pure Appl. Chem.* 70:1129-1143. Thus, a pharmacophore does not represent a unique molecule or a specific association of functional groups, but an understanding that accounts for the common molecular interaction capacities of a group of compounds towards their target structure. The pharmacophore can be considered as the largest common denominator shared by a set of active molecules. Pharmacophores are normally defined by pharmacophoric descriptors which include H-bonding, hydrophobic and electrostatic interaction sites, defined by atoms, ring centers and virtual points.

Using the structure-activity relationships described below and herein, Applicants have identified a pharmacophore that binds PCSK9 and inhibits its activity. PCSK9 has three known domains: the prodomain, the catalytic domain, and the C-terminal domain. *Cunningham* at p. 414. In the active site of PCSK9, a serine protease catalytic triad of Ser386, His226 and Asp186 has been identified that interacts with LDLR and facilitates its internalization within the cell and eventual degradation. Studies of lack-of-function mutants have shown that the C-terminal domain is also necessary for degradation activity, but not may not bind LDLR. The binding site identified herein is located in the C-terminal domain. Without wishing to be bound by any theory, the disclosed inhibitors can act allosterically to modify the PCSK9 C-terminal domain conformation and function elsewhere, rather than binding directly at the catalytic domain site of the enzyme.

The C-terminal domain of PCSK9 has three modules, denoted M1, M2, and M3. The boundaries of the modules have been described as including slightly different ranges of amino acid residues as research into PCSK9 has developed. The differences in the ranges serve mainly as location descriptors and do not connote any specific activity of one or more specific residues. In some embodiments, the M1 domain ranges from residues 457-527, the M2 domain ranges from residues 534-601, and the M3 domain ranges from residues 608-679. In other embodiments, the M1 domain ranges from residues 447-530, the M2 domain ranges from residues 531-604, and the M3 domain ranges from residues 608-683.

FIG. 1 provides a crystal structure of the C-terminal domain. Halgren et al., *J. Chem. Inf. Model.* 2009 49:377-389. In the crystal structure, the C-terminal domain had several disordered segments and a greater level of flexibility. *Cunningham* at p. 416. Experimental results in the art suggest that the C-terminal domain is involved in the secretion of PCSK9, which is needed for its activity in LDLR degradation. *Cunningham* at p. 417. The C-terminal domain also plays a role in targeting the PCSK9-LDLR complex to the endosomes/lysosome organelles inside cells for degradation. Saavedra et al. *J. Biol. Chem.* 2012 287: 43492-43501. Mutant studies where the M2 domain of PCSK9 was removed resulted in loss of the enzyme's extracellular activity, but not its intracellular activity. *Saavedra* at p. 43500. Thus, the presently described binding site located in the C-terminal domain could influence PCSK9 activity in any of a number of known or undetermined pathways.

Figure 2:
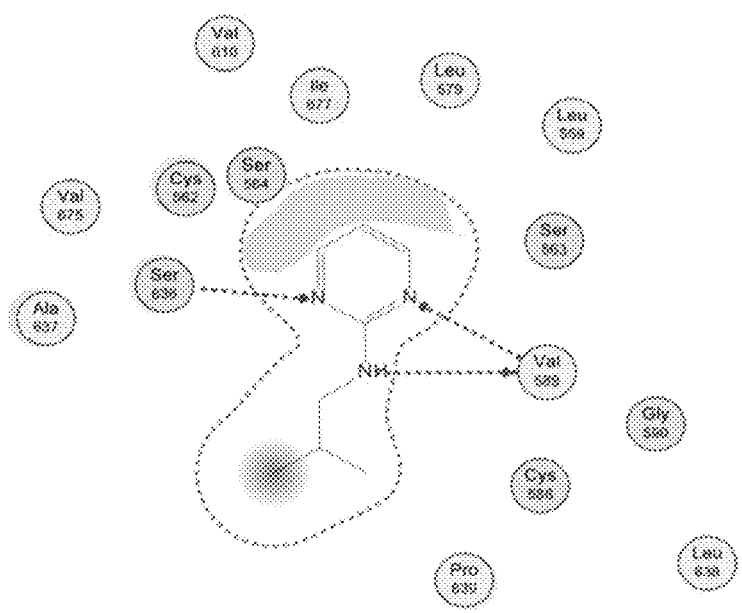
FIG. 2 is a schematic of a crystal structure of PCSK9 bound to compound 152 showing H-bond donor and acceptors with dashed arrows. The pharmacophore spans the M2 and M3 domains.

Key features of the binding site include a triad of hydrogen-bonded atom pairs that span the M2 and M3 domains as shown in FIG. 2. Based on crystal structures of PCSK9 bound to disclosed compounds, compounds of Formula I interact with the binding site as follows:

| H-Bonding Type | PCSK9 Residue | 2-aminopyrimidine atom |
|---|---|---|
| Acceptor A | Val 589 | Acceptor is one pyrimidine N |
| Donor B | Val 589 | Donor is 2-NH group |
| Acceptor C | Ser 636 | Acceptor is the other pyrimidine N |

The numbers of these residue positions are relative to the most common isoform of PCSK9. An isoform is a peptide or protein that has differences in its amino acid sequence, but is translated from the same gene. However, due to inclusion and deletion of some residues during transcription and translation, the numbering of amino acids described herein may shift in a different isoform. Isoforms may also occur due to natural variations in genetic sequence. The present disclosure includes all isoforms of PCSK9 and their corresponding residue positions in isoforms or other mutant sequences. In some embodiments, isoforms of PCSK9 can have about 90%, about 91%, about 92%, about 93%, about 94%, about 95%, about 96%, about 97%, about 98%, about 99%, about 99.2%, about 99.4%, about 99.6%, about 98.8%, or about 99.9% sequence homology with human PCSK9 having the sequence given in the Biological Assays section below. Isoform sequences (SEQ ID Nos 1-6) are given after the Biological Assays section.

Figure 3:
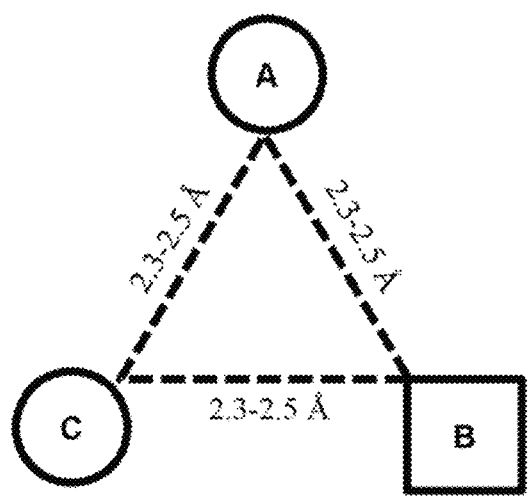
FIG. 3 is a schematic of the pharmacophore H-bond triad, showing the distances between the Val589 acceptor (A), the Val589 donor (B), and the Ser636 acceptor (C).

Because the disclosed compounds acts as both an H-bond acceptor A at a pyrimidinyl nitrogen and a donor B at the 2-NH— of its 2-amino pyrimidinyl group with Val589, a bonding triad in the binding site is formed out of two PCSK9 residues. The other pyrimidinyl nitrogen binds as an H-bond acceptor C to Ser636. The bond distance between each triad atom of the pharmacophore as disclosed herein is about 2.3 Å to about 2.5 Å as shown in FIG. 3. For example, acceptor A is 2.3-2.4 Å from donor B and 2.3-2.5 Å from acceptor C. Donor B is 2.3-2.5 Å from acceptor C.

As shown below, the three nitrogen atoms of the 2-aminopyrimidinyl core of the disclosed compounds interact with the triad. Analogs lacking one of these bonding features do not exhibit detectable binding to human PCSK9.

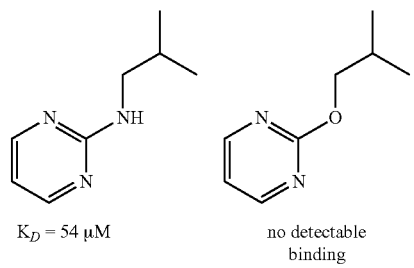

$K_D = 54$ μM                no detectable binding

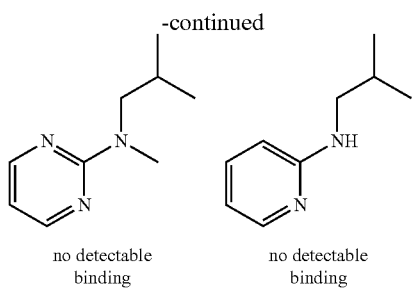

no detectable binding    no detectable binding

Figure 4:
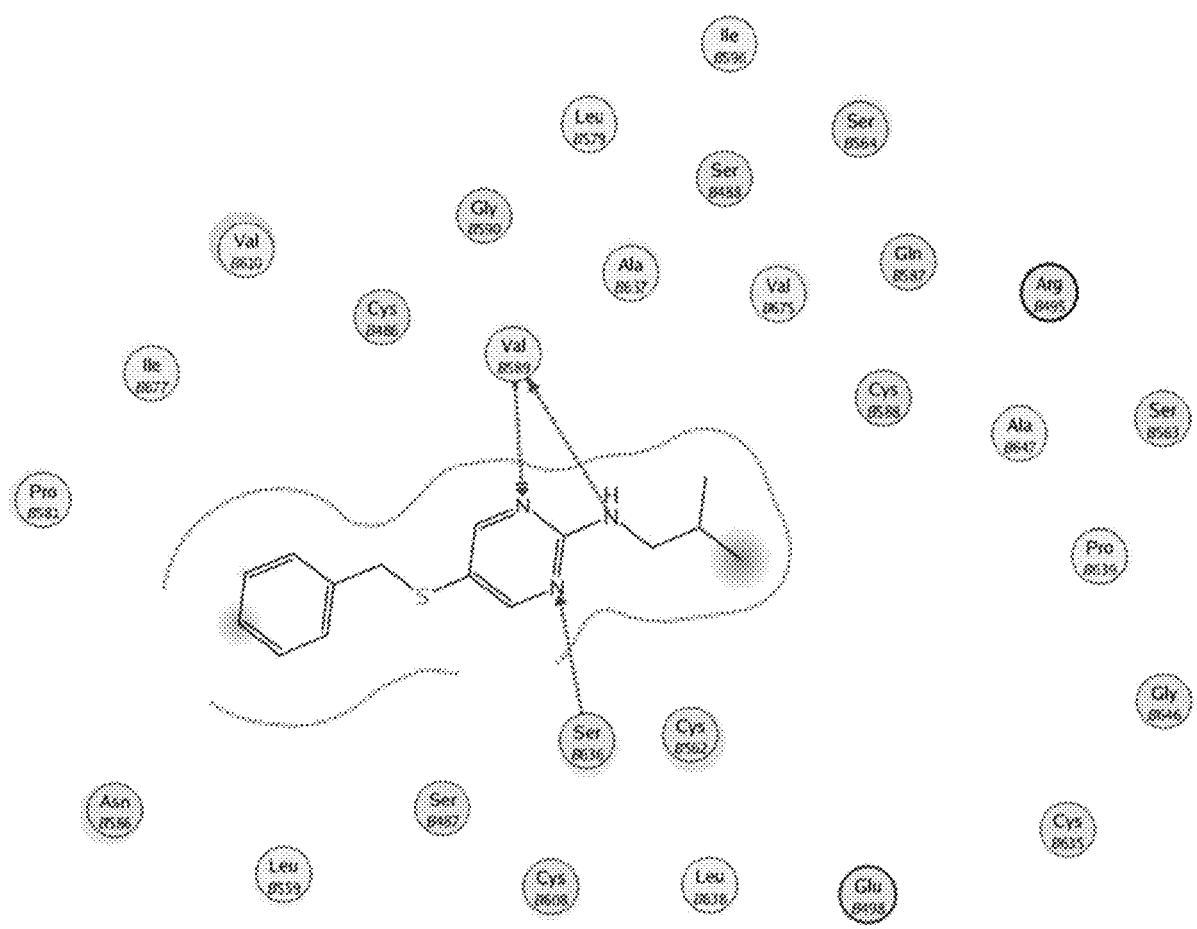
FIG. 4 is a schematic of a crystal structure of PCSK9 bound to compound 162 showing H-bond donor and acceptors with dashed arrows.

As shown in FIG. 4, this H-bond triad is evident in fully elaborated compounds of the invention, such as compound 162.

Disclosed herein are methods of inhibiting PCSK9, comprising contacting PCSK9 with an inhibitor of PCSK9 that binds to a binding pocket defined by amino acid residues Val589 and Ser636 of human PCSK9. In some embodiments, the inhibitor is of PCSK9 is an allosteric inhibitor. In some embodiments, the method comprises contacting the surface of a cell that secretes PCSK9 with an inhibitor of PCSK9 that binds to a binding pocket defined by amino acid residues Val589 and Ser636 of human PCSK9. In certain embodiments, the method comprises binding PCSK9 that is intracellular with an inhibitor of PCSK9 that binds to a binding pocket defined by amino acid residues Val589 and Ser636 of human PCSK9. In some embodiments, the method comprises contacting a cell that expresses PCSK9 with an inhibitor of PCSK9 that binds to a binding pocket defined by amino acid residues Val589 and Ser636 of human PCSK9. In other embodiments, the method comprises binding PCSK9 that is in plasma, with an inhibitor of PCSK9 that binds to a binding pocket defined by amino acid residues Val589 and Ser636 of human PCSK9.

In some embodiments, the inhibitor comprises an H-bond acceptor/donor group having two H-bond acceptor moieties and one H-bond donor moiety disposed to donate an H-bond to and accept an H-bond from the backbone amide functionality of residue Val589, and accept an H-bond from the hydroxymethyl sidechain of Ser636 of human PCSK9.

In certain embodiments, the inhibitor comprises an H-bond acceptor/donor group having two H-bond donor moieties and one H-bond acceptor moiety disposed to donate an H-bond to and accept an H-bond from the backbone amide functionality of residue Val589, and donate an H-bond to the hydroxymethyl sidechain of Ser636 of human PCSK9.

In certain embodiments, the inhibitor further comprises one or more of:
 a) an H-bond acceptor moiety disposed to bind with amino acid residues Ser642, His643 or Val 644,
 b) an H-bond donor moiety disposed to bind with amino acid residue Ala637 or Thr641, and
 c) a cation-pi stacking interaction moiety disposed to bind with amino acid residue Arg495 or His591,
wherein the H-bond acceptor/donor group is bound to amino acid residues Val589 and Ser636 of human PCSK9. In certain embodiments, the inhibitor further comprises an H-bond acceptor moiety disposed to bind with amino acid residue Glu612. The binding may be a direct H-bond or indirect H-bond (e.g., where water-mediated H-bonding occurs).

Figure 5:
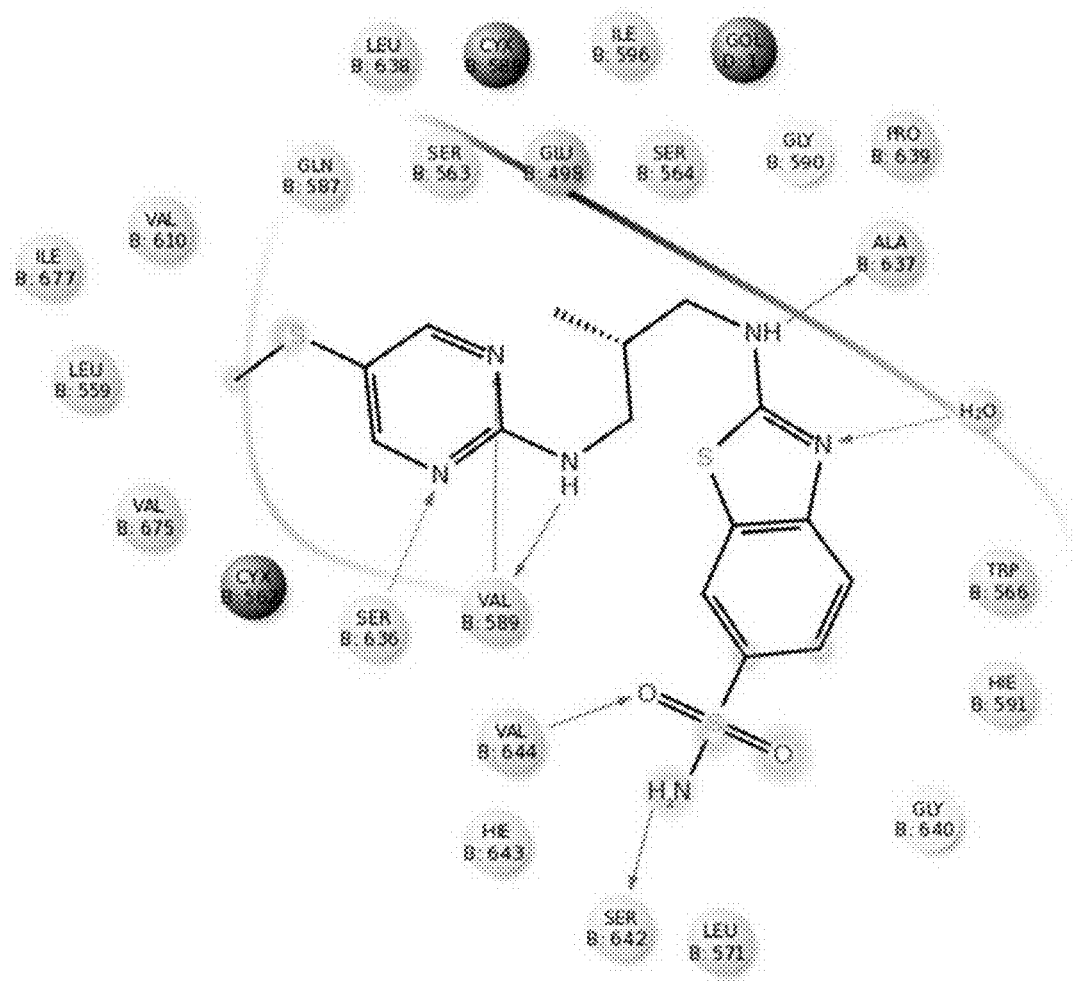
FIG. 5 is a schematic of a crystal structure of PCSK9 bound to compound 43, showing H-bond donor and acceptors with dashed arrows.

While the triad H-bonding is common to the inhibitory compounds disclosed herein, some compounds have additional H-bonds to other residues in the pharmacophore. For example, as shown in FIG. 5, compound 43 forms the common 2-aminopyrimidine H-bond triad with the pharmacophore and the 2-aminobenzothiazole forms an H-bond with Ala637 and a molecule of water. Additional H-binding occurs with the sulfonamido substituent on the benzothiazole ring. Residue Val644 is an H-bond donor and Ser642 is a H-bond acceptor.

Figure 6:
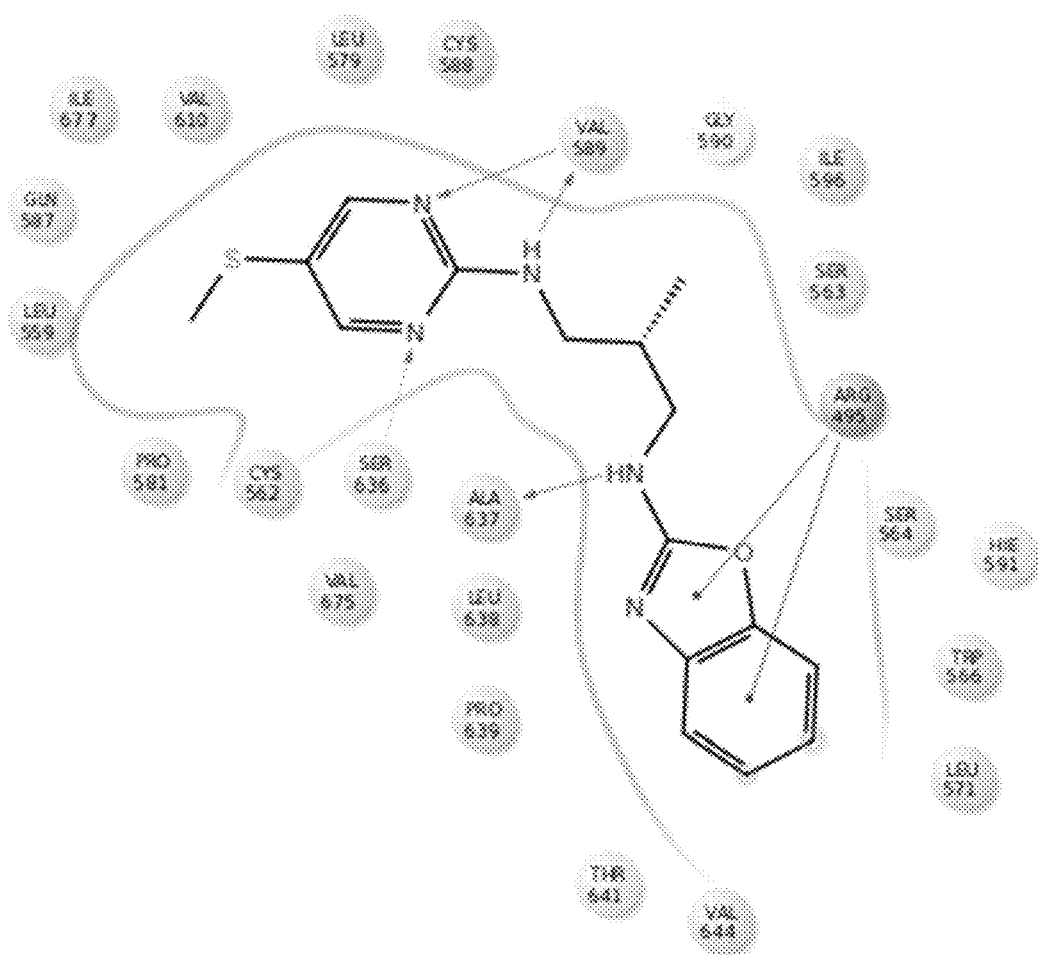
FIG. 6 is a schematic of a crystal structure of PCSK9 bound to compound 60, showing H-bond donor and acceptors with dashed arrows and cation-pi bonding with pin dots.
Figure 7:
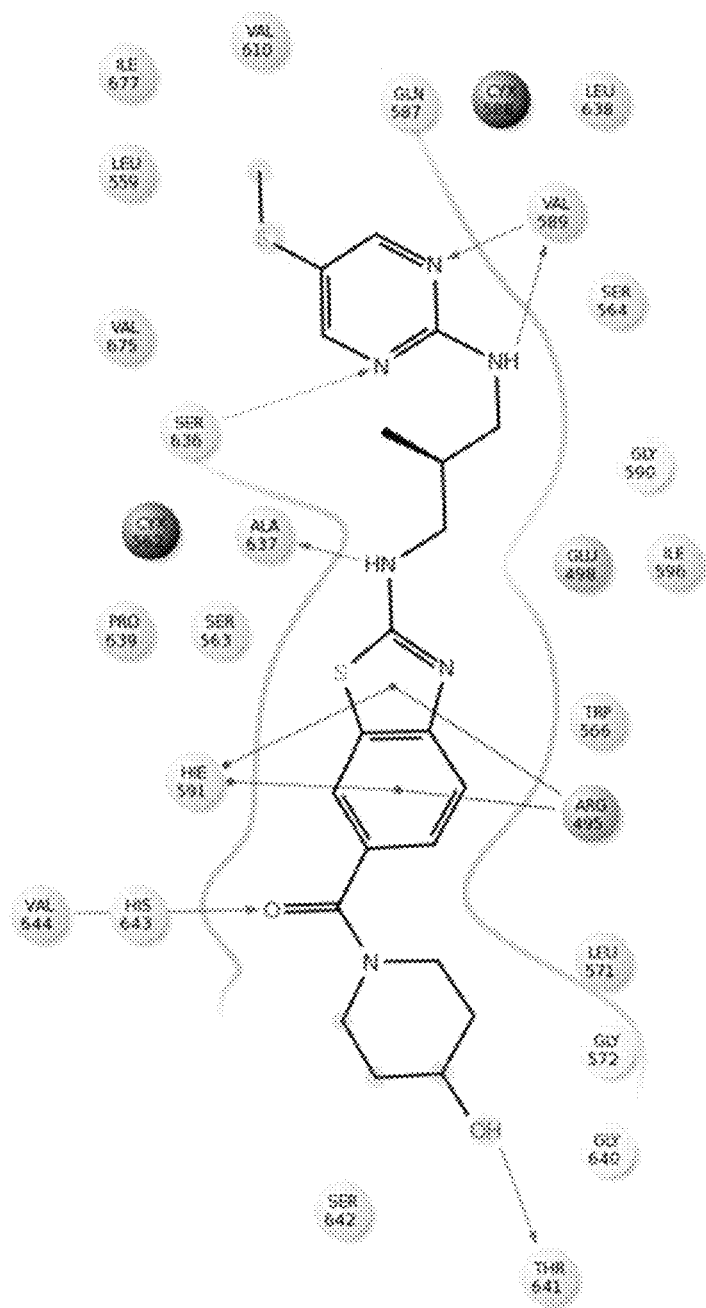
FIG. 7 is a schematic of a crystal structure of PCSK9 bound to compound 5, showing H-bond donor and acceptors with dashed arrows and cation-pi bonding with pin dots.

The crystal structure of compound 60 bound to the pharmacophore, shown in FIG. 6, illustrates that, in addition to the H-bond triad, cation-pi stacking interactions occur between Arg495 in the M1 domain and the benzoxazole ring. These cation-pi stacking interactions can also occur with His591 (shown as HIE591) in the M2 domain as shown in compound 5 bound to the binding site in FIG. 7. Compound 5 has additional H-bonds between His643 and the carbonyl oxygen and between Thr641 and the hydroxyl group hydrogen.

Figure 8:
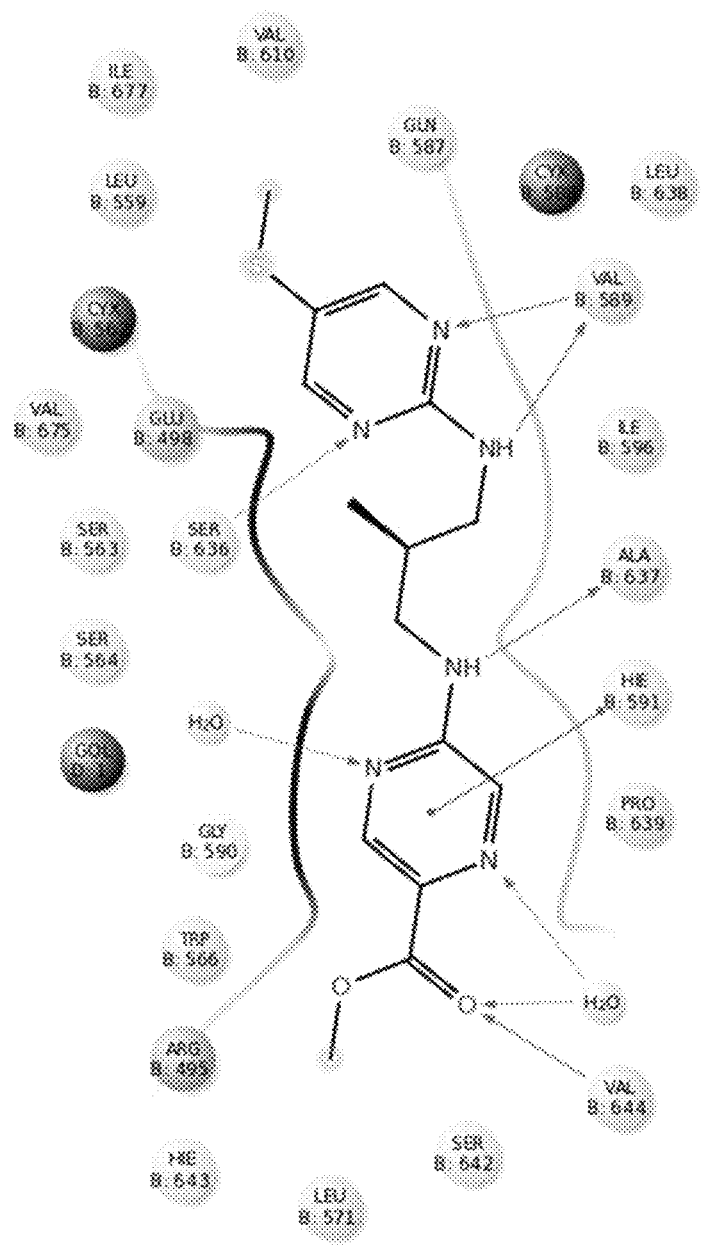
FIG. 8 is a schematic of a crystal structure of PCSK9 bound to compound 133, showing H-bond donor and acceptors with dashed arrows and cation-pi bonding with pin dots.
Figure 9:
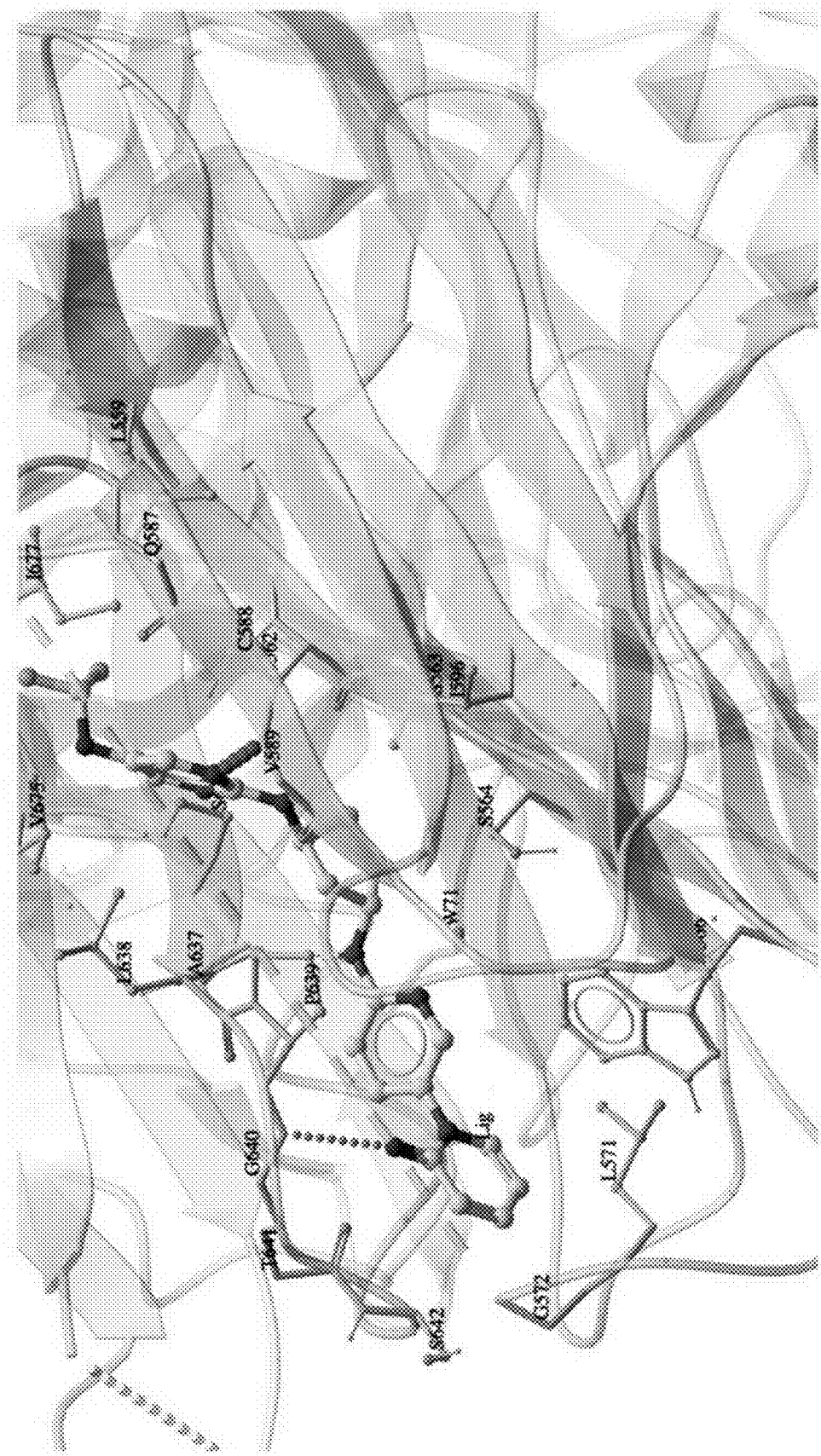
FIG. 9 is a schematic of a crystal structure of PCSK9 bound to compound 458B, showing the interaction with the N—H of glycine 640.

The binding site's versatility to bind compounds of varying structure is further illustrated by compound 133. As shown in FIG. 8, compound 133 has two 2-aminopyrimidinyl functional groups that interact with the binding site. The pyrimidinyl ring with its thiomethyl substituent binds to the common H-bond triad formed from Ser 636 and Val 589. The pyrimidyl ring substituted with a methyl ester forms five additional H-bonds with Ala637, Val644, and two molecules of water. A cation-pi stacking interaction occurs between His591 (shown as HIE591) and the pyrimidine ring. In addition, FIG. 9 illustrates the interaction of compound 458B with the N—H of glycine 640.

Substitution around the 2-aminopyrmidinyl core can be selected to engage a combination of these affinity features to foster increased H-bonding or cation-pi stacking, thereby increasing a compound's affinity for the binding site, thereby increasing its inhibitory effect. The binding site engages residues from all three subdomains of the C-terminal domain. The flexibility of the pharmacophore that engages this binding site provides numerous opportunities to design compounds, such as compounds having the core 2-aminopyrimidyl group or a bioisosteric equivalent, with structures that hydrogen-bond to the triad (e.g., with two donor and one acceptor H-bonds) and engage one or more of the other affinity elements (e.g., the cation-pi stacking interaction and the additional H-bond sites).

As used herein, the term "interacts" in the context of an inhibitor in relation to one or more residues of PCSK9 refers to direct or indirect associations of the inhibitor with either the backbone of the enzyme or the side chain of any given residue. For example, interactions include covalent bonds, hydrogen bonds, hydrophobic attractions, cation-pi interactions, anion-pi interactions and others well known in the art.

The amino acids binding to the pharmacophore of the inhibitors, the triad formed between Val589 and Se 636, can also be further interacting with amino acid residue(s) in the M1, M2, and M3 domains. In certain embodiments, the inhibitor interacts with at least one residue in the M2 C-terminal domain and at least one residue in the M3 C-terminal domain. In some embodiments, the inhibitor further interacts with at least one residue in the M1 C-terminal domain. In certain embodiments, the inhibitor interacts with at least one residue in the M1 C-terminal domain and at least one residue in the M3 C-terminal domain. In other embodiments, the inhibitor interacts with at least one residue in the M1 C-terminal domain and at least one residue in the M2 C-terminal domain. In certain embodiments, the inhibitor interacts with PCSK9 between amino acid residues 558-590 in the M2 C-terminal domain and amino acids residues 631-650 in the M3 C-terminal domain.

In certain embodiments, the inhibitor interacts with at least one residue in beta strand 3 and beta strand 5 of the M2 C-terminal domain and beta strand 3 and beta strand 4 of the M3 C-terminal domain. In certain embodiments, the inhibitor interacts with PCSK9 created between amino acid residues 558-566 in beta strand 3 of the M2 C-terminal domain and amino acids residues 587-590 in beta strand 5 of the M2 C-terminal domain. In other embodiments, the inhibitor interacts with a pocket in PCSK9 created between amino acid residues 631-637 in beta strand 3 of the M3 C-terminal domain and amino acids residues 644-650 in beta strand 4 of the M3 C-terminal domain.

Structural evaluation of the PCSK9 binding site can be performed using a number of techniques well known to the skilled artisan. For instance, FIGS. 4-8 illustrate 3-D renderings of PCSK9-compound interactions as determined from X-ray crystal structures. Details on the preparation and analysis of the crystal structures are given in the examples below. Analysis of the X-ray data provides a 3D rendering of the compound bound to PCSK9 where atom orientation and distances can indicate the type of bonds present, such as covalent, H-bond, pi-stacking, and others.

Other methods include 3D computer modeling techniques that render a computer generated image of a compound interacting with a substrate. As with crystal structure data, computer modeling programs can present 3D information as a shell of the surface or in ball/stick format showing atoms in 3D array. In a non-limiting example, it is well within the skill in the art to use a computer model of a presently disclosed compound bound to PCSK9 to identify how and where the compound interacts with PCSK9.

Methods of Use

The PCSK9 gene was identified using genetic mapping techniques on DNA from subjects with autosomal dominant hypercholesterolemia (Abifadel, et al. *Nat. Genet.* 2003 34:154-6). The encoded protein is a serine protease that is mostly expressed in the liver, gut, kidney, and nervous system. While not wishing to be bound by any particular theory, studies on mutations in the gene indicated that its putative role was in reducing LDL receptors at the cell surface independently of its catalytic activity. (Abifadel, et al. *Expert Opin. Ther. Pat.* 2010 20:1547-71). Binding of PCSK9 to the receptors results in their lysosomal degradation. This enhanced degradation results in increases in the amount of circulating low-density lipoprotein LDL (LDL-c). PCSK9 is upregulated by statins, SREBP-1a and SREBP-2, LXR agonist, and insulin, but downregulated by dietary cholesterol, glucagon, ethinylestradiol, chenodeoxycholic acid and the bile acid-activated farnesoid X receptor (FXR) (Maxwell, et al. *J. Lipid Res.* 2003 44:2109-19; Persson et al. *Endocrinology* 2009 150:1140-6; Langhi et al. *FEBS Lett.* 2008 582:949-55). Since an elevated level of PCSK9 decreases the abundance of LDL receptor on the cell surface, increasing doses of statins fail to achieve proportional LDL-cholesterol lowering results. Thus, disclosed herein are methods for treating a wide range of cardiovascular diseases and conditions that benefit from inhibiting PCSK9 thereby lowering LDL-c.

In certain embodiments, the disclosed methods of inhibiting PCSK9 occurs in a subject in need thereof, thereby treating a disease or disorder mediated by PCSK9. Also, disclosed herein are methods of treating or preventing a disease or a disorder mediated by PCSK9 comprising administering a compound of Formula (I) or a pharmaceutically acceptable salt thereof. In certain embodiments, disclosed herein are methods of treating a disease or disorder mediated by PCSK9 comprising administering a compound of Formula (I) or a pharmaceutically acceptable salt thereof. In certain embodiments, disclosed herein are methods of preventing a disease or a disorder mediated by PCSK9 comprising administering a compound of Formula I or a pharmaceutically acceptable salt thereof. The prevention of cardiovascular events through the inhibition of PCSK9 has been described, e.g., in Robinson et al., *Artherosclerosis* 2015 243:593-597.

Exemplary cardiovascular diseases and conditions include, but are not limited to, dyslipidemia, hypercholesterolemia, hypertriglyceridemia, hyperlipidemia, hypoalphalipoproteinemia, metabolic syndrome, diabetic complications, atherosclerosis, stroke, vascular dimensia, chronic kidney disease, coronary heart disease, coronary artery disease, retinopathy, inflammation, thrombosis, peripheral vascular disease or congestive heart failure.

In certain embodiments, exemplary cardiovascular diseases and conditions include, but are not limited to, hypercholesterolemia, hyperlipidemia, hyperlipoproteinemia, hypertriglyceridemia, dyslipidemia, dyslipoproteinemia, atherosclerosis, hepatic steatosis, metabolic syndrome and coronary artery disease. In certain embodiments, the disease is hypercholesterolemia, such as familial hypercholesterolemia or autosomal dominant hypercholesterolemia. In certain embodiments, the disease is hyperlipidemia. In certain embodiments, the disease is coronary artery disease.

In certain embodiments, the disclosed methods of treatment can decrease high levels of circulating serum cholesterol, such as LDL-cholesterol and VLDL-cholesterol. In addition, the disclosed methods are useful for decreasing circulating serum triglycerides, circulating serum lipoprotein A, circulating serum LDL and atherogenic lipoproteins. In certain embodiments, the diseases or conditions treated with the disclosed compounds and compositions include atherosclerosis and atherosclerotic plaque formation. Subjects having a gain-of-function mutation in the PCSK9 gene also benefit with treatment with the disclosed compounds and compositions counteracting the mutation through their inhibition of PCSK9.

Inhibition of PCSK9 has also shown therapeutic benefit in treating sepsis in a subject. Septic shock is an often fatal complication of a severe microbial infection (sepsis) that triggers an uncontrolled systemic inflammatory response and subsequent organ failure. Sepsis originates with the microbial cell walls that contain pathogenic lipid moieties such as lipopolysaccharide (LPS; Gram-negative bacteria). LPS are potent ligands for mammalian innate immune receptors [Toll-like receptors (TLRs)] and thus figure prominently in the septic inflammatory response (septic shock or sepsis). PCSK9 reduces LPS uptake by the liver's LDL receptors, such that free LPS overstimulates the body's immune response to the pathogen leading to sepsis. Inhibiting PCSK9 is beneficial in retaining liver LDL receptors to effect systemic pathogen clearance and detoxification in response to sepsis (See, e.g., Walley et al *Sci. Translat. Med.* 2014 6:1-10).

Disclosed herein are methods of treating sepsis or septic shock comprising administering a compound of Formula (I) or a pharmaceutically acceptable salt thereof. In certain embodiments, the disclosed methods of treatment are useful for increasing LPS uptake. Certain embodiments provide a method of decreasing the inflammatory response induced by sepsis or septic shock.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

Examples of compounds of Formula (I), or pharmaceutically acceptable salts thereof, having useful biological activity are listed in Tables 1-10. $^1$H NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift. Chemical shift are reported as δ values in ppm relative to trimethylsilane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

A. Analytical Methods

Method 1 (Acid FA)

UPLC Setup

Solvents:—A Water (High purity via PureLab Option unit) with 0.1% formic acid B Acetonitrile (Far UV grade) with 0.1% (V/V) formic acid Column:—Acquity UPLC HSS C18 1.8 um 100×2.1 mm. (Plus guard cartridge)

Flow Rate:—0.5 mL/min

Gradient:

| Time (min) | % A | % B |
|---|---|---|
| 0.00 | 95 | 5 |
| 1.2 | 95 | 5 |
| 3.5 | 0 | 100 |
| 4.9 | 0 | 100 |
| 5 | 95 | 5 |
| 6 | 95 | 5 |

Injections 0.5-2 uL
UV detection via Waters DAD

| Start Range (nm) | 210 | End Range (nm) | 400 | Resolution (nm) | 1.2 |
|---|---|---|---|---|---|

MS detection: Waters SQD2, single quadrapole UPLC-MS

Scan range for MS Data (m/z)

Start (m/z) 100

End (m/z) 700 or 1500 when required

With +ve/−ye switching

Ionisation is ESI.

ESI voltages and temperatures are:

| Source 150 C. | 3.5 KV capillary | 25 V cone |
|---|---|---|

Method 2 (Basic FA)

UPLC Setup

Solvents:—Acetonitrile (Far UV grade)

Water (High purity via PureLab Option unit) with 10 mM ammonium bicarbonate (ammonium hydrogen carbonate)

Column:—Acquity UPLC BEH Shield RP18 1.7 um 100×2.1 mm. (Plus guard cartridge)

Flow Rate:—0.5 mL/min

Gradient:—A: Water/Basic B: MeCN/Basic

| Time | A % | B % |
|---|---|---|
| 0.00 | 95 | 5 |
| 1.20 | 95 | 5 |
| 3.5 | 0 | 100 |
| 4.90 | 0 | 100 |
| 5.00 | 95 | 5 |
| 6.00 | 95 | 5 |

Typical Injections 0.5-2 uL (concentration ~0.2-1 mg/mL).
UV detection via Waters DAD Start Range (nm) 210 End Range (nm) 400 Resolution (nm) 1.2

Other wavelength traces are extracted from the DAD data.
MS detection: Waters SQD2, single quadrapole UPLC-MS
Flow splitter gives approximately 300 ul/min to mass spec
Scan range for MS Data (m/z)
Start (m/z) 100
End (m/z) 700 or 1500 when required
With +ve/−ve switching
Preparative reverse-phase HPLC conditions
Preparative HPLC Waters Micromass ZQ/Sample manager 2767
Photodiode array detector 2996;
Column: XTerra Prep MS C18 Column (5 μm, 19×150 mm, Waters)
Flow rate: 20 mL/min with MS detection
UV wavelength: 254 nm.
Mobile phase: Solvent A (water:MeCN:HCO2H 95:5:0.05); Solvent B (water:MeCN:HCO2H 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Flash chromatography is carried out using an Isolera MPLC system (manufactured by Biotage) using pre-packed silica gel or reverse-phase cartridges (supplied by Biotage or Interchim).

B. Chemical Syntheses

The general procedures used in the methods to prepare the compounds of the present invention are described below:

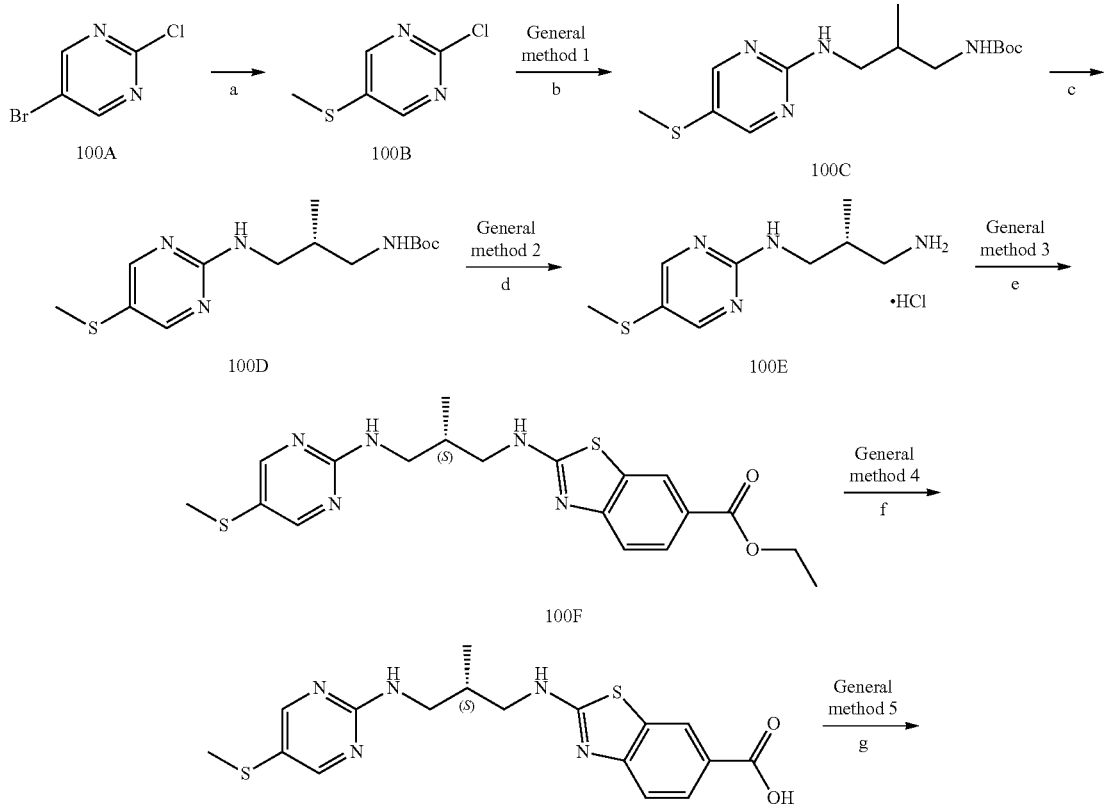

-continued

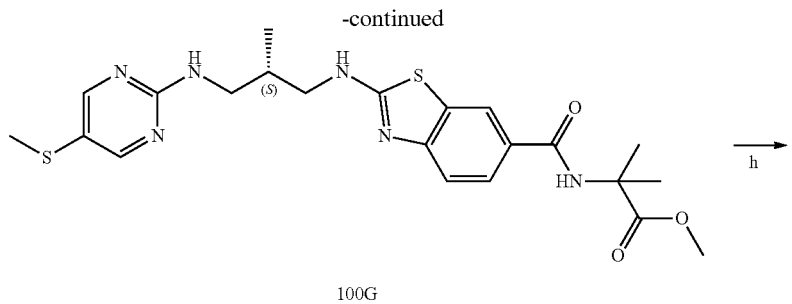

100G

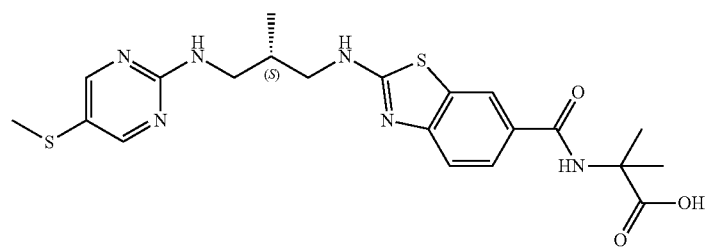

2 a) nBuLi, MeSSMe, THF; b) NH₂CH₂CHCH₃CH₂NHBoc, Cs₂CO₃, DMF; c) SFC chiral resolution; d) 4M HCl in 1,4-dioxane; e) ethyl-2-chlorobenzo[d]thiazole-6-carboxylate, Et₃N, DMF; f) LiOH, EtOH, THF; g) Amine, HATU, Et₃N, DMF; h) LiOH, EtOH, THF 2-Chloro-5-(methylthio)pyrimidine (100B)

Dimethyl disulphide (13.96 mL, 155.4 mmol, 1.0 eq) was added under nitrogen to a −75° C. cooled solution of 5-bromo-2-chloropyrimidine (100A) (30 g, 155.4 mmol, 1.0 eq) in anhydrous tetrahydrofuran (700 mL). To this mixture was added a solution of n-butyl lithium (2.5 M, 68.4 mL, 170.9 mmol, 1.0 eq) dropwise over 1.5 h, with the internal temperature maintained at −70° C. to −75° C. throughout the addition. After complete addition, the mixture was stirred at −75° C. for 4.5 h and was then quenched by the slow addition of a saturated solution of ammonium chloride (100 mL). The cooling bath was removed and the reaction was allowed to warm to room temperature under nitrogen over 18 h. The reaction mixture was diluted with ethyl acetate (500 mL), washed with water (50 mL) and then saturated brine (50 mL). The organic phase was dried over anhydrous magnesium sulfate, filtered and then concentrated under reduced pressure. The crude pale yellow oil obtained was purified by flash chromatography (eluting isohexane to ethyl acetate, 0-50%) to give the desired product 2-chloro-5-(methylthio)pyrimidine as a waxy pale yellow solid (100B).

Yield: 7.39 g (29%). $^1$H NMR (CDCl₃) δ 8.48 (2H, s), 2.54 (3H, s); MS (ESI+) m/z 161 (M+H)$^+$.

General Method 1 tert-Butyl (2-methyl-3-((5-(methylthio)pyrimidin-2-yl)amino)propyl)carbamate (100C)

tert-Butyl(3-amino-2-methylpropyl)carbamate (4.79 g, 25.52 mmol, 1.05 eq) was added to a stirred suspension of 2-chloro-5-(methylthio)pyrimidine (100B) (3.89 g, 24.31 mmol, 1.0 eq) and cesium carbonate (11.85 g, 36.46 mmol, 1.4 eq) in anhydrous dimethylformamide (50 mL). The mixture was stirred at room temperature for 18 h and then concentrated under reduced pressure to −20 mL. The liquor was diluted with ethyl acetate (100 mL), washed with water (75 mL) and brine (50 mL) and then dried over magnesium sulfate. The solvents were removed under vacuum to afford a crude residue that was purified by flash chromatography (eluting isohexane to ethyl acetate, 0-50%) to give the desired product tert-butyl (2-methyl-3-((5-(methylthio)pyrimidin-2-yl)amino)propyl) carbamate (100C) as a pale yellow oil.

Yield: 6.59 g (86%). MS (ESI+) m/z 313 (M+H)$^+$.

tert-Butyl (S)-(2-methyl-3((5-(methylthio)pyrimidin-2-yl)amino)propyl) carbamate (100D)

Racemic tert-butyl (2-methyl-3-((5-(methylthio)pyrimidin-2-yl)amino)propyl)carbamate (100C) (5 g) was purified by chiral SFC using the following conditions: YMC amylose-C 30/70 MeOH/CO$_2$, 100 mL/min, 120 bar, 40° C., GLS 40 psi, System 3900 psi, drop 140 bar, Stacker, DAD 245 nm.

First-eluting isomer, 1.3 minutes. tert-Butyl (R)-(2-methyl-3-((5-(methylthio)pyrimidin-2-yl)amino)propyl)carbamate Yield: 2.05 g. $^1$H NMR (400 MHz, CDCl$_3$) δ 8.34 (s, 2H), 5.79 (dd, J=6.7, 6.7 Hz, 1H), 5.18 (dd, J=5.8, 5.8 Hz, 1H), 3.50-3.39 (m, 1H), 3.33-3.14 (m, 2H), 3.04-2.94 (m, 1H), 2.36 (s, 3H), 1.94-1.85 (m, 1H), 1.45 (s, 9H), 0.95 (d, J=6.9 Hz, 3H). MS (ESI+) m/z 313 (M+H)$^+$.

Second-eluting isomer, 1.7 minutes. tert-Butyl (S)-(2-methyl-3-((5-(methylthio)pyrimidin-2-yl)amino)propyl)carbamate (100D)

Yield: 2.48 g. $^1$HNMR (400 MHz, CDCl$_3$) δ 8.34 (s, 2H), 5.77-5.69 (m, 1H), 5.15 (dd, J=6.5, 6.5 Hz, 1H), 3.50-3.40 (m, 1H), 3.33-3.16 (m, 2H), 3.03-2.94 (m, 1H), 2.36 (s, 3H), 1.95-1.85 (m, 1H), 1.47 (s, 9H), 0.95 (d, J=6.9 Hz, 3H); MS (ESI+) m/z 313 (M+H)$^+$.

General Method 2

(R)-2-Methyl-N$^1$-(5-(methylthio)pyrimidin-2-yl) propane-1,3-diamine hydrochloride (100E)

A solution of hydrogen chloride (15 mL, 4M in 1,4-dioxane) was added to tert-butyl (S)-(2-ethyl-3-((5-(methylthio)pyrimidin-2-yl)amino)propyl)carbamate (100D) (600 mg, 2.48 mmol) and the mixture was stirred at room temperature for 1 hour. The solvents were removed under vacuum to afford the desired product (R)-2-methyl-N$^1$-(5-(methylthio)pyrimidin-2-yl)propane-1,3-diamine hydrochloride (100E) as a pale yellow semi-solid.

Yield: 548 mg (100%) HCl salt. $^1$H NMR (400 MHz, DMSO) δ 8.39 (s, 2H), 8.00-7.96 (m, 3H), 7.72-7.72 (m, 1H), 3.32-3.18 (m, 2H), 2.88-2.80 (m, 1H), 2.66-2.55 (m, 1H), 2.38 (s, 3H), 2.13-2.00 (m, 1H), 0.96 (d, J=6.8 Hz, 3H); MS (ESI+) m/z 213 (M+H)$^+$.

General Method 3

Ethyl (S)-2-((2-methyl-3-((5-(methylthio)pyrimidin-2-yl)amino)propyl)amino) benzo[d]thiazole-6-carboxylate (100F)

Ethyl-2-chlorobenzothiazole-6-carboxylate (600 mg, 2.48 mmol, 1.0 eq was added to a stirred solution of (R)-2-methyl-N$^1$-(5-(methylthio)pyrimidin-2-yl)propane-1,3-diamine hydrochloride (100E) (548 mg, 2.48 mmol, 1.0 eq) and triethylamine (1.73 mL, 12.44 mmol, 5.0 eq) in anhydrous dimethylformamide (20 mL) under nitrogen. The mixture was stirred at room temperature for 48 h and then concentrated under vacuum to ~5 mL. Water (25 mL) was added and the mixture was extracted with ethyl acetate (3×50 mL). The combined organic phases were washed with water (20 mL) and brine (25 mL) then dried over magnesium sulfate. The solvents were removed under vacuum to give a crude yellow oil which was purified by flash chromatography (eluting isohexane to ethyl acetate, 0-100%) to give the desired ethyl (S)-2-((2-methyl-3-((5-(methylthio)pyrimidin-2-yl)amino)propyl)amino)benzo[d]thiazole-6-carboxylate (100F) as an off white solid.

Yield: 647 mg (62%). $^1$H NMR (400 MHz, CDCl$_3$) δ 8.37 (s, 2H), 8.27 (d, J=1.5 Hz, 1H), 7.99 (dd, J=1.8, 8.5 Hz, 1H), 7.51 (d, J=8.4 Hz, 1H), 7.02-6.98 (m, 1H), 5.83 (dd, J=6.7, 6.7 Hz, 1H), 4.38 (q, J=7.2 Hz, 2H), 3.67-3.47 (m, 2H), 3.42-3.24 (m, 2H), 2.37 (s, 3H), 2.20-2.11 (m, 1H), 1.40 (dd, J=7.2, 7.2 Hz, 3H), 1.07 (d, J=7.0 Hz, 3H); MS (ESI+) m/z 418 (M+H)$^+$.

General Method 4

(S)-2-((2-Methyl-3-((5-(methylthio)pyrimidin-2-yl) amino)propyl)amino)benzo[d]thiazole-6-carboxylic acid (Example 1)

Lithium hydroxide monohydrate (318 mg, 7.75 mmol, 5.0 eq) was added to a stirred solution of ethyl (S)-2-((2-methyl-3-((5-(methylthio)pyrimidin-2-yl)amino)propyl)amino) benzo[d]thiazole-6-carboxylate (100F) (647 mg, 1.55 mmol, 1.0 eq) in ethanol (7 mL) and water (5 mL). The mixture was stirred at ambient temperature for 18 h and then concentrated under reduced pressure. Water (5 mL) was added to the residue and this mixture was acidified to pH ~3 with a solution of aqueous hydrochloric acid (2M). A precipitate that formed was collected by filtration, washed with water and then dried under high vacuum to give the desired product (S)-2-((2-methyl-3-((5-(methylthio)pyrimidin-2-yl) amino)propyl) amino)benzo[d]thiazole-6-carboxylic acid (Example 1) as a pale yellow solid.

General Method 5

Methyl (S)-2-methyl-2-(2-((2-methyl-3-((5-(methylthio)pyrimidin-2-yl)amino)propyl) amino)benzo[d] thiazole-6-carboxamido)propanoate (100G)

1-[Bis(dimethylamino)methylene]-1H-1,2,3-triazolo[4,5-b]pyridinium 3-oxide hexafluorophosphate (HATU, 146 mg, 0.385 mmol, 1.5 eq) was added to a solution of (S)-2-((2-methyl-3-((5-(methylthio)pyrimidin-2-yl)amino)propyl) amino)benzo[d]thiazole-6-carboxylic acid (1) (100 mg, 0.257 mmol, 1.0 eq), triethylamine (0.36 mL, 2.57 mmol, 10.0 eq) and methyl-2-amino-2-methylpropanoate hydrochloride (196 mg, 1.28 mmol, 4.9 eq) in dimethylformamide (5 mL) and the reaction mixture was stirred at room temperature for 18 h. The solvents were removed under reduced pressure and the crude residue obtained was purified by flash chromatography (eluting isohexane to ethyl acetate, 0-75%) to give the desired methyl (S)-2-methyl-2-(2-((2-methyl-3-((5-(methylthio)pyrimidin-2-yl)amino)propyl) amino)benzo [d]thiazole-6-carboxamido) propanoate (G) as an off-white solid.

Yield: 120 mg (95%). $^1$H NMR (400 MHz, MeOD) δ 8.34 (s, 2H), 8.10 (d, J=1.8 Hz, 1H), 7.77 (dd, J=1.9, 8.5 Hz, 1H), 7.47 (d, J=8.5 Hz, 1H), 3.74 (s, 3H), 3.45 (dd, 22.4 Hz, 4H), 2.34 (s, 3H), 2.29-2.16 (m, 1H), 1.59 (s, 6H), 1.08 (d, J=6.9 Hz, 3H) NH exchangeable protons not observed; MS (ESI+) m/z 489 (M+H)$^+$.

(S)-2-Methyl-2-(2-((2-methyl-3-((5-(methylthio) pyrimidin-2-yl)amino)propyl) amino)benzo[d]thiazole-6-carboxamido)propanoic acid (Example 2)
Method Analogous to General Method 4

Lithium hydroxide mono-hydrate (50 mg, 1.22 mmol, 5.0 eq) was added to a stirred solution of methyl (S)-2-methyl-2-(2-((2-methyl-3-((5-(methylthio)pyrimidin-2-yl)amino) propyl)amino)benzo[d]thiazole-6-carboxamido) propanoate (100G) (120 mg, 0.245 mmol, 1.0 eq) in ethanol (5 mL) and water (5 mL) and the mixture was stirred at room tempera ture for 1 hour. The solvents were removed under vacuum and the residue was diluted with water (3 mL) and acidified to pH ~3 with aqueous solution of hydrochloride acid (2M). A precipitate that formed was collected by filtration, washed with water and then dried under high vacuum to give the title compound as an off-white solid.

Using the above procedures, the following examples were synthesized:

TABLE 1

| Structure | Ex. # | 1H NMR | LC-MS (M + H)+ |
|---|---|---|---|
| 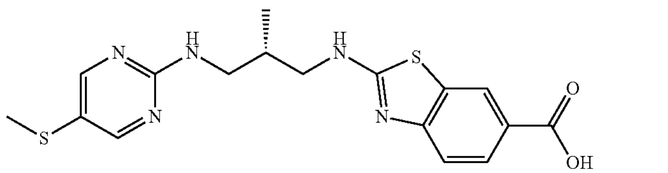 [SMILES: CSc1cnc(NC[C@H](C)CNc2nc3ccc(C(=O)O)cc3s2)nc1] | 1 | $^1$H NMR (400 MHz, DMSO) δ 8.43 (dd, J = 4.8, 4.8 Hz, 1H), 8.33 (s, 2H), 8.26 (d, J = 1.8 Hz, 1H), 7.81 (dd, J = 1.8, 8.5 Hz, 1H), 7.53 (dd, J = 5.6, 5.6 Hz, 1H), 7.38 (d, J = 8.4 Hz, 1H), 3.35-3.23 (m, 4H), 2.34 (s, 3H), 2.17-2.07 (m, 1H), 0.96 (d, J = 6.7 Hz, 3H). | 390 |
| 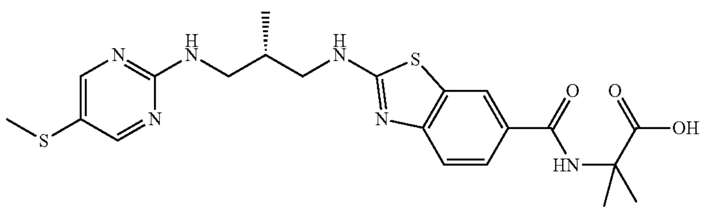 [SMILES: CSc1cnc(NC[C@H](C)CNc2nc3ccc(C(=O)NC(C)(C)C(=O)O)cc3s2)nc1] | 2 | $^1$H NMR (400 MHz, CDCl$_3$) δ 8.34 (s, 2H), 8.00 (d, J = 1.1 Hz, 1H), 7.72 (d, J = 8.3 Hz, 1H), 7.32 (d, J = 8.5 Hz, 1H), 7.20-7.20 (m, 1H), 3.54-3.48 (m, 1H), 3.43-3.27 (m, 3H), 2.36 (s, 3H), 2.19-2.13 (m, 1H), 1.74 (d, J = 3.2 Hz, 6H), 1.03 (d, J = 6.9 Hz, 3H) NH protons not observed. | 475 |
| 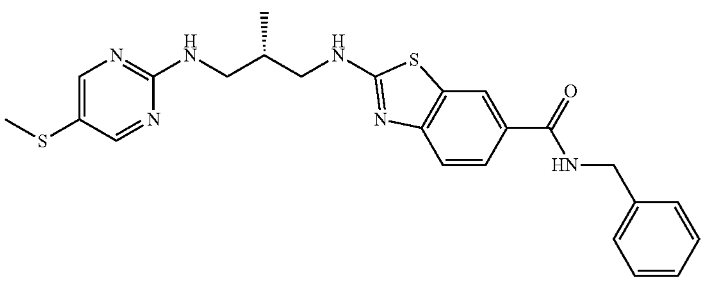 [SMILES: CSc1cnc(NC[C@H](C)CNc2nc3ccc(C(=O)NCc4ccccc4)cc3s2)nc1] | 3 | $^1$H NMR (400 MHz, DMSO) δ 8.90 (dd, J = 6.0, 6.0 Hz, 1H), 8.34 (s, 2H), 8.30 (dd, J = 5.5, 5.5 Hz. 1H), 8.21 (d, J = 1.6 Hz, 1H), 7.79 (dd, J = 1.8, 8.4 Hz, 1H), 7.52 (dd, J = 5.8, 5.8 Hz, 1H), 7.38 (d, 7 = 8.4 Hz, 1H), 7.33 (d, J = 4.4 Hz, 4H), 7.27-7.22 (m, 1H), 4.48 (d, J = 6.0 Hz, 2H), 3.48-3.41 (m, 1H), 3.31-3.23 (m, 3H), 2.34 (s, 3H), 2.17-2.00 (m, 1H), 0.96 (d, J = 6.8 Hz, 3H). | 479 |
| 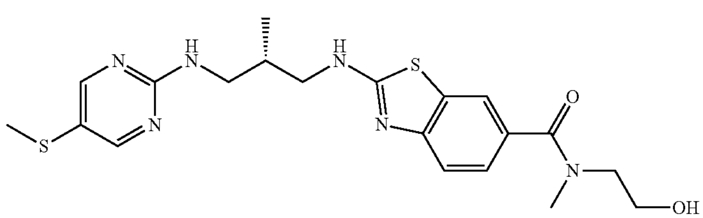 [SMILES: CSc1cnc(NC[C@H](C)CNc2nc3ccc(C(=O)N(C)CCO)cc3s2)nc1] | 4 | $^1$H NMR (400 MHz, CDCl$_3$) δ 8.38 (s, 2H), 7.73 (d, J = 1.3Hz, 1H), 7.51 (d, J = 8.3 Hz, 1H), 7.39 (dd, J = 1.5, 8.3 Hz, 1H), 6.77 (s, 1H), 5.77-5.74 (m, 1H), 3.89-3.85 (m, 2H), 3.71 (s, 2H), 3.63-3.47 (m, 2H), 3.42-3.25 (m, 2H), 3.12 (s, 3H), 2.37 (s, 3H), 2.20-2.10 (m, 1H), 1.06 (d, J = 6.8 Hz, 3H) NH protons not observed. | 447 |
| 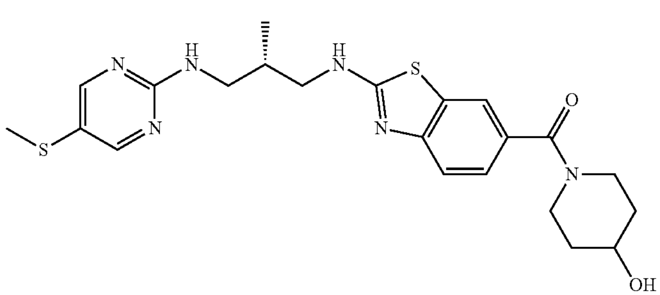 [SMILES: CSc1cnc(NC[C@H](C)CNc2nc3ccc(C(=O)N4CCC(O)CC4)cc3s2)nc1] | 5 | $^1$H NMR (400 MHz, CDCl$_3$) δ 8.38 (s, 2H), 7.67 (d, J = 1.5 Hz, 1H), 7.51 (d, J = 8.1 Hz, 1H), 7.32 (dd, J = 1.8, 8.1 Hz, 1H), 6.67-6.64 (m, 1H), 5.70 (dd, J = 6.8, 6.8 Hz, 1H), 4.02-3.95 (m, 2H), 3.63-3.49 (m, 2H), 3.42-3.29 (m, 4H), 2.37 (s. 3H), 2.20-2.09 (m, 1H), 1.95-1.88 (m, 2H). 1.06 (d, J = 6.8 Hz, 3H) NH protons not observed. | 473 |

TABLE 1-continued

| Structure | Ex. # | 1H NMR | LC-MS (M + H)+ |
|---|---|---|---|
| 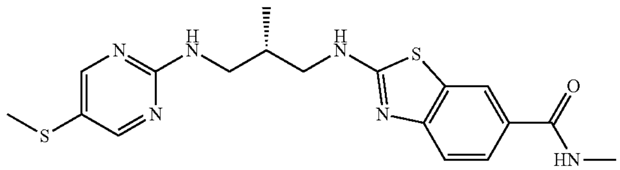 | 6 | ¹H NMR (400 MHz DMSO) δ 8.38 (s, 2H), 8.36-8.30 (m, 2H), 8.18 (d, J = 1.8 Hz, 1H), 7.76 (dd, J = 1.9, 8.5 Hz, 1H), 7.56 (dd, J = 6.1, 6.1 Hz, 1H), 7.40 (d, J = 8.6 Hz, 1H), 3.52-3.44 (m, 1H), 3.34-3.27 (m, 3H), 2.83 (d, J = 4.5 Hz, 3H), 2.39 (s, 3H), 2.22-2.10 (m, 1H), 1.00 (d, J = 6.8 Hz, 3H). | 403 |
| 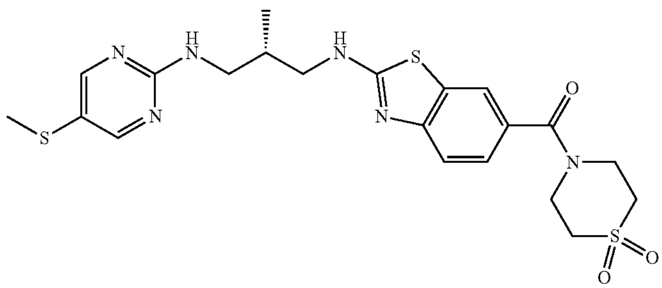 [SMILES: CSc1cnc(NC[C@H](C)CNc2nc3ccc(C(=O)N4CCS(=O)(=O)CC4)cc3s2)nc1] | 7 | ¹H NMR (400 MHz. DMSO) δ 8.34 (s, 2H), 8.26 (dd, J = 5.6, 5.6 Hz, 1H), 7.85 (s, 1H), 7.51 (dd, J = 5.8, 5.8 Hz, 1H), 7.37 (s, 2H), 3.94-3.83 (m, 4H), 3.48-3.40 (m, 1H), 3.31-3.24 (m, 8H), 2.34 (s, 3H), 2.14-1.99 (m, 1H), 0.96 (d, J = 6.8 Hz, 3H). | 507 |
| 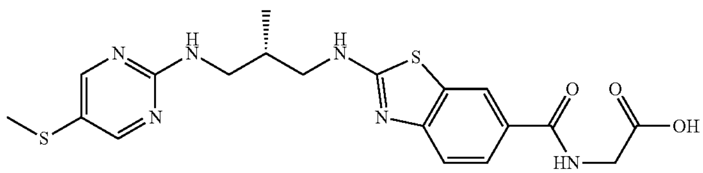 [SMILES: CSc1cnc(NC[C@H](C)CNc2nc3ccc(C(=O)NCC(=O)O)cc3s2)nc1] | 8 | ¹H NMR (400 MHz, DMSO) δ 8.34 (s, 2H), 8.31 (d, J = 5.6 Hz, 2H), 8.17 (d, J = 1.8 Hz, 1H), 7.73 (dd, J = 1.8, 8.4 Hz, 1H), 7.52 (dd, J = 5.9, 5.9 Hz, 1H), 7.37 (d, J = 8.4 Hz, 1H), 3.76 (d, J = 5.1 Hz, 2H), 3.49-3.40 (m, 1H), 3.33-3.22 (m, 3H), 2.34 (s, 3H), 2.17-2.07 (m, 1H), 0.96 (d, J = 6.8 Hz, 3H). | 447 |
| 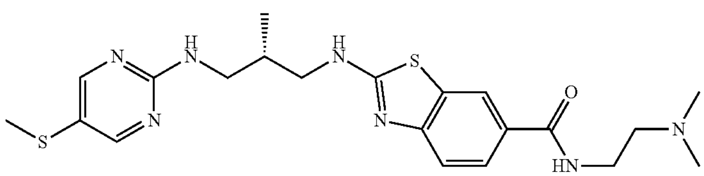 | 9 | ¹H NMR (400 MHz, CDCl₃) δ 8.33 (s, 2H), 8.02 (s, 1H), 7.72 (dd, J = 1.4, 8.5 Hz, 1H), 7.55 (s, 1H), 7.45 (d, J = 8.3 Hz, 1H), 6.20-6.18 (m, 1H), 3.73-3.38 (m, 3H), 3.49 (dd, J = 4.2, 13.8 Hz, 1H), 3.40-3.20 (m, 2H), 3.01-2.91 (m, 2H), 2.59 (s, 6H), 2.36 (s, 4H), 2.20-2.13 (m, 1H), 1.07 (d, J = 6.8 Hz, 3H). | 460 |
| 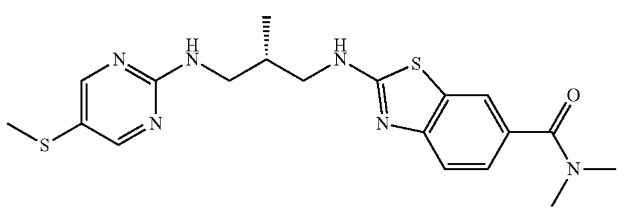 | 10 | ¹H NMR (400 MHz, CDCl₃) δ 8.38 (s, 2H), 7.69 (d, J = 1.5 Hz, 1H), 7.51 (d, J = 8.3 Hz, 1H), 7.36 (dd, J = 1.8, 8.3 Hz, 1H), 6.75-6.74 (m, 1H), 5.70 (dd, J = 6.4, 6.4 Hz, 1H), 3.63-3.47 (m, 2H), 3.42-3.25 (m, 2H), 3.08 (s, 6H), 2.37 (s, 3H), 2.20-2.10 (m, 1H), 1.06 (d, J = 6.9 Hz, 3H). | 417 |
| 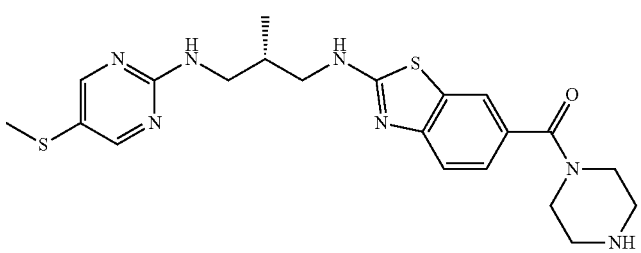 [SMILES: CSc1cnc(NC[C@H](C)CNc2nc3ccc(C(=O)N4CCNCC4)cc3s2)nc1] | 11 | ¹H NMR (400 MHz, CDCl₃) δ 8.37 (s, 2H), 8.32 (s, 1H), 7.68 (s, 1H), 7.50 (d, J = 8.3 Hz, 1H), 7.35-7.30 (m, 1H), 5.90 (dd, J = 5.8, 5.8 Hz, 1H), 3.76 (s, 4H), 3.62-3.53 (m, 1H), 3.48 (dd, J = 4.8, 13.8 Hz, 1H), 3.43-3.35 (m, 1H), 3.29 (dd, J = 7.5, 13.7 Hz, 1H), 3.05-2.98 (m, 4H), 2.62 (s, 1H), 2.37 (s, 3H), 2.19-2.12 (m, 1H), 1.07 (d, J = 6.9 Hz, | 458 |

TABLE 1-continued

| Structure | Ex. # | 1H NMR | LC-MS (M + H)+ |
|---|---|---|---|
| | | 3H). | |
| 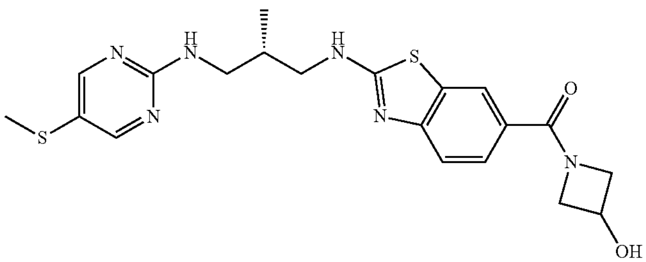 [SMILES: CSc1cnc(NC[C@H](C)CNc2nc3ccc(C(=O)N4CC(O)C4)cc3s2)nc1] | 12 | ¹H NMR (400 MHz, CDCl₃) δ 8.36 (s, 2H), 7.90 (s, 1H), 7.52-7.44 (m, 2H), 7.00 (s, 1H), 5.90 (s, 1H), 4.75-4.68 (m, 1H), 4.51 (dd, J = 8.0, 8.0 Hz, 2H), 4.15-4.15 (m, 2H), 3.65-3.57 (m, 1H), 3.55-3.48 (m, 1H), 3.41-3.33 (m, 1H), 3.30-3.24 (m, 1H), 2.61 (s, 1H), 2.37 (s, 3H), 2.20-2.12 (m, 1H), 1.07 (d, J = 6.9 Hz, 3H). | 455 |
| 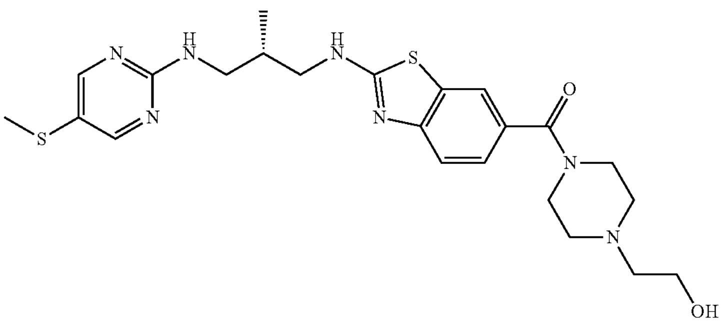 [SMILES: CSc1cnc(NC[C@H](C)CNc2nc3ccc(C(=O)N4CCN(CCO)CC4)cc3s2)nc1] | 13 | ¹H NMR (400 MHz, DMSO) δ 8.33 (s, 2H), 8.22 (dd, J = 5.4, 5.4 Hz, 1H), 8.15 (s, 1H), 7.74 (d, J = 1.5 Hz, 1H), 7.51 (dd, J = 5.8, 5.8 Hz, 1H), 7.36 (d, J = 8.3 Hz, 1H), 7.25 (dd, J = 1.8, 8.3 Hz, 1H), 4.49 (s, 1H), 3.52 (dd, J = 6.0, 6.0 Hz, 5H), 3.47-3.40 (m, 2H), 3.29-3.19 (m, 4H), 2.48 (d, J = 7.5 Hz, 4H), 2.34 (s, 3H), 2.14-2.08 (m, 1H), 0.96 (d, J = 6.8 Hz, 3H). | 502 |
| 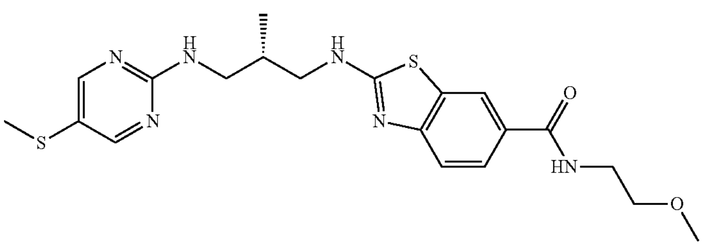 | 14 | ¹H NMR (400 MHz, CDCl₃) δ 8.38 (s, 2H), 8.09 (d, J = 1.5 Hz, 1H), 7.66 (dd, J = 1.9, 8.5 Hz, 1H), 7.52 (d, J = 8.3 Hz, 1H), 6.80 (s, 1H), 6.50 (dd, J = 52, 5.2 Hz, 1H), 5.69 (dd, J = 6.7, 6.7 Hz, 1H), 3.69-3.55 (m, 5H), 3.40 (s, 6H), 2.37 (s, 3H), 2.20-2.10 (m, 1H), 1.07 (d, J = 6.8 Hz, 3H). | 447 |
| 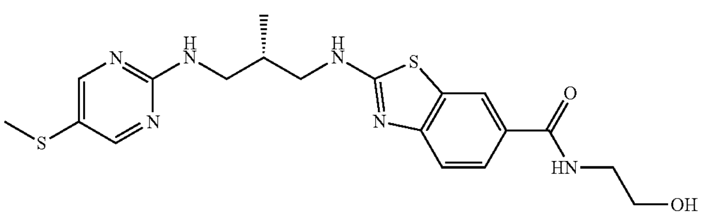 [SMILES: CSc1cnc(NC[C@H](C)CNc2nc3ccc(C(=O)NCCO)cc3s2)nc1] | 15 | ¹H NMR (400 MHz, DMSO) δ 8.34 (s, 2H), 8.29 (dd, J = 5.4, 5.4 Hz, 2H), 8.17 (d, J = 1.8 Hz, 1H), 7.74 (dd, J = 1.8, 8.5 Hz, 1H), 7.52 (dd, J = 6.0, 6.0 Hz, 1H), 7.36 (d, J = 8.4 Hz, 1H), 4.71 (dd, J = 5.4, 5.4 Hz, 1H), 3.55-3.41 (m, 3H), 3.31-3.23 (m, 5H), 2.34 (s, 3H), 2.17-2.06 (m, 1H), 0.96 (d, J = 6.8 Hz, 3H). | 433 |
| 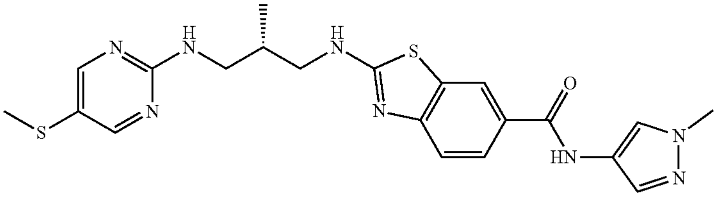 | 16 | ¹H NMR (400 MHz, CDCl₃) δ 8.35 (s, 2H), 8.09 (s, 1H), 8.06 (s, 1H), 7.90-7.90 (m, 1H), 7.72 (dd, J = 1.9, 8.4 Hz, 1H), 7.52 (d, J = 9.0 Hz, 2H), 7.14 (s, 1H), 5.99 (s, 1H), 3.91 (s, 3H), 3.62 (ddd, J = 4.4, 6.9, 14.3 Hz, 1H), 3.51 (d, J = 13.4 Hz, 1H), 3.41-3.33 (m, 1H), 3.29-3.22 (m, 1H), 2.37 (s, 3H), 2.21-2.13 (m, 1H), 1.08 (d, J = 6.9 Hz, 3H). | 469 |

TABLE 1-continued

| Structure | Ex. # | 1H NMR | LC-MS (M + H)+ |
|---|---|---|---|
| 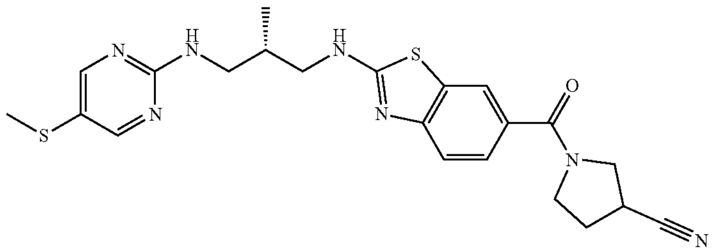 [SMILES: CSc1cnc(NC[C@H](C)CNc2nc3ccc(C(=O)N4CCC(C#N)C4)cc3s2)nc1] | 17 | ¹H NMR (400 MHz, CDCl₃) δ 8.38 (s, 2H), 7.80 (s, 1H), 7.52 (d, J = 8.3 Hz, 1H), 7.46 (d, J = 7.9 Hz, 1H), 6.79-6.78 (m, 1H), 5.67 (dd, J = 6.5, 6.5 Hz, 1H), 3.95-3.81 (m, 3H), 3.73 (s, 1H), 3.64-3.56 (m, 1H), 3.55-3.48 (m, 1H), 3.42-3.34 (m, 1H), 3.32-3.25 (m, 1H), 3.19 (s, 1H), 2.37 (s, 3H), 2.30 (d, J = 6.0 Hz, 2H), 2.20-2.10 (m, 1H), 1.07 (d, J = 6.9 Hz, 3H). | 468 |
| 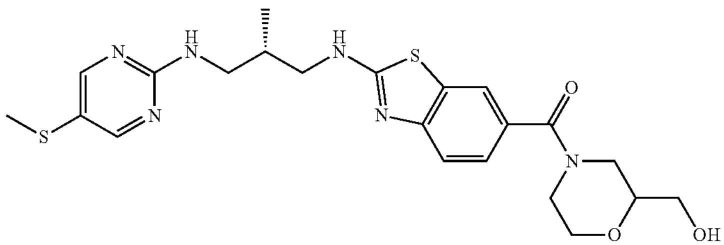 [SMILES: CSc1cnc(NC[C@H](C)CNc2nc3ccc(C(=O)N4CCOC(CO)C4)cc3s2)nc1] | 18 | ¹H NMR (400 MHz, CDCl₃) δ 8.38 (s, 2H), 7.69 (d, J = 1.5 Hz, 1H), 7.52 (d, J = 8.3 Hz, 1H), 7.33 (dd, J = 1.6, 8.3 Hz, 1H), 6.77 (s, 1H), 5.69 (dd, J = 6.5, 6.5 Hz, 1H), 3.96 (d, J = 9.9 Hz, 1H), 3.67 (d, J = 13.4 Hz, 1H), 3.64-3.55 (m, 5H), 3.51 (dd, J = 4.5, 13.7 Hz, 1H), 3.42-3.34 (m, 1H), 3.29 (dd, J = 7.5, 14.2 Hz, 1H), 3.18 (s, 1H), 3.03 (s, 1H), 2.37 (s, 3H), 2.20-2.10 (m, 1H), 1.07 (d, J = 6.9 Hz, 3H). | 489 |
| 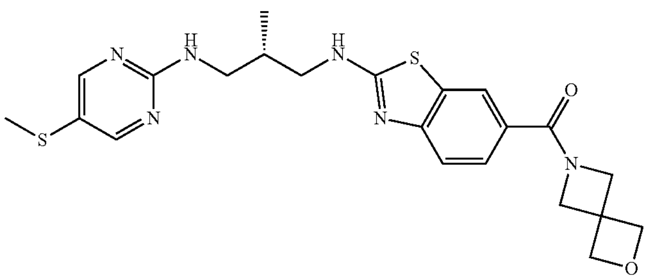 [SMILES: CSc1cnc(NC[C@H](C)CNc2nc3ccc(C(=O)N4CC5(COC5)C4)cc3s2)nc1] | 19 | ¹H NMR (400 MHz, CDCl₃) δ 8.37 (s, 2H), 7.92 (d, J = 1.1 Hz, 1H), 7.52-7.50 (m, 2H), 6.87-6.87 (m, 1H), 5.73 (dd, J = 6.1, 6.1 Hz, 1H), 4.82 (s, 4H), 4.43-4.43 (m, 4H), 3.64-3.48 (m, 2H), 3.42-3.26 (m, 2H), 2.37 (s, 3H), 2.20-2.10 (m, 1H), 1.07 (d, J = 6.9 Hz, 3H). | 471 |
| 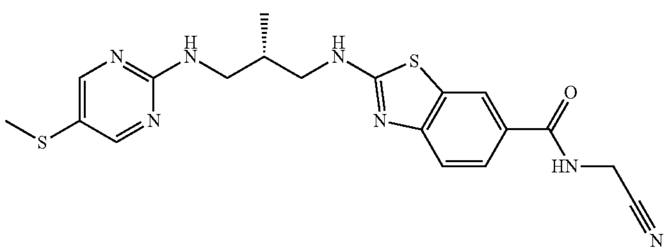 [SMILES: CSc1cnc(NC[C@H](C)CNc2nc3ccc(C(=O)NCC#N)cc3s2)nc1] | 20 | ¹H NMR (400 MHz, CDCl₃) δ 8.35 (s, 2H), 8.03 (s, 1H), 7.64 (dd, J = 1.9, 8.4 Hz, 1H), 7.49 (d, J = 8.4 Hz, 1H), 6.53-6.53 (m, 1H), 6.01-5.99 (m, 1H), 4.41 (d, J = 5.8 Hz, 2H), 3.62 (ddd, J = 4.3, 6.7, 14.3 Hz, 1H), 3.51 (dd, J = 4.3, 13.8 Hz, 1H), 3.41-3.22 (m, 2H), 2.37 (s, 3H), 2.20-2.13 (m, 1H), 1.08 (d, J = 6.9 Hz, 3H) NH protons not observed. | 428 |
| 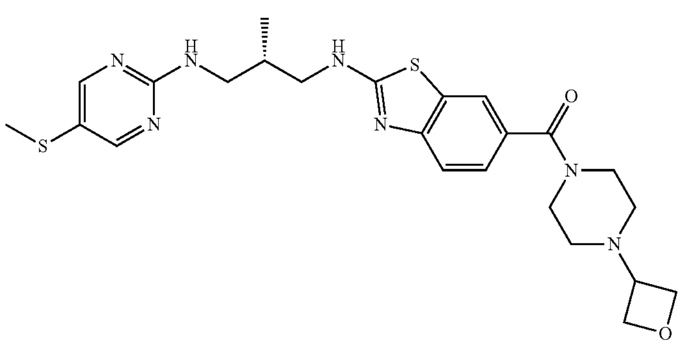 [SMILES: CSc1cnc(NC[C@H](C)CNc2nc3ccc(C(=O)N4CCN(C5COC5)CC4)cc3s2)nc1] | 21 | ¹H NMR (400 MHz. CDCl₃) δ 8.38 (s, 2H), 7.68 (d, J = 1.6 Hz, 1H), 7.51 (d, J = 8.3 Hz, 1H), 7.33 (dd, J = 1.6, 8.3 Hz, 1H), 6.87-6.86 (m, 1H), 5.77 (dd, J = 6.2, 6.2 Hz, 1H), 4.70-4.60 (m, 4H), 3.70 (s, 3H), 3.63-3.47 (m, 3H), 3.42-3.25 (m, 2H), 2.37 (s, 6H), 2.20-2.12 (m, 2H), 1.06 (d, J = 6.9 Hz, 3H) NH protons not observed. ¹H NMR (400 MHz, DMSO) δ 8.33 (s, 2H), 8.23 (dd, J = 5.5, 5.5 Hz, 1H), 7.75 (s, 1H), 7.51 (dd, J = 5.9, 5.9 Hz, 1H), 7.36 (d, J = 8.2 Hz, 1H), 7.27-7.23 (m, 1H), 4.58-4.51 (m, 2H), 4.45 (dd, J = 5.7, 5.7 Hz, 2H), 3.53-3.53 (m, 4H), 3.47-3.39 (m, 2H), 3.29-3.22 (m, 3H), 2.34 (s, | 514 |

TABLE 1-continued

| Structure | Ex. # | 1H NMR | LC-MS (M + H)+ |
|---|---|---|---|
| | | 3H), 2.29 (s, 4H), 2.17-2.06 (m, 1H), 0.95 (d, J = 6.7 Hz, 3H). NH protons not observed | |
| 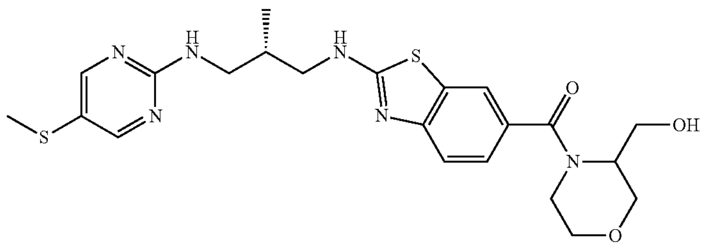 [SMILES: CSc1cnc(NC[C@H](C)CNc2nc3ccc(C(=O)N4CCOCC4CO)cc3s2)nc1] | 22 | ¹H NMR (400 MHz, DMSO) δ 8.34 (s, 2H), 8.22 (dd, J = 5.5, 5.5 Hz, 1H), 7.76 (d, J = 1.5 Hz, 1H), 7.52 (dd, J = 5.9, 5.9 Hz, 1H), 7.36 (d, J = 8.2 Hz, 1H), 7.29 (dd, J = 1.6, 8.3 Hz, 1H), 4.90-4.90 (m, 1H), 3.79-3.79 (m, 3H), 3.65 (s, 1H), 3.59-3.40 (m, 4H), 3.31-3.20 (m, 4H), 2.34 (s, 3H), 2.17-2.05 (m, 1H), 0.95 (d, J = 6.7 Hz, 3H) NH protons not observed. | 489 |
| 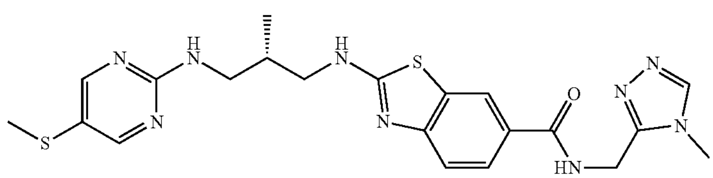 | 23 | ¹H NMR (400 MHz, CDCl₃) δ 8.35 (s, 2H), 8.10 (s, 1H), 8.05 (s, 1H), 7.72 (dd, J = 1.9, 8.5 Hz, 1H), 7.49-7.45 (m, 2H), 7.18-7.17 (m, 1H), 6.04 (d, J = 4.9 Hz, 1H), 4.83 (d, J = 5.5 Hz, 2H), 3.80 (s, 3H), 3.64-3.48 (m, 2H), 3.41-3.26 (m, 2H), 2.36 (s, 3H), 2.21-2.13 (m, 1H), 1.06 (d, J = 6.9 Hz, 3H). | 484 |
| 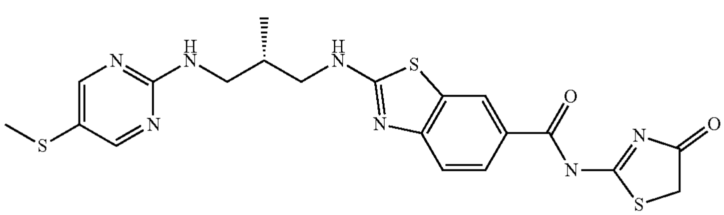 [SMILES: CSc1cnc(NC[C@H](C)CNc2nc3ccc(C(=O)NC4=NC(=O)CS4)cc3s2)nc1] | 24 | ¹H NMR (400 MHz, DMSO) δ 12.42-12.42 (m, 1H), 8.48 (s, 1H), 8.41 (d, J = 1.6 Hz, 1H), 8.33 (s, 2H), 8.03 (dd, J = 1.6, 8.5 Hz, 1H), 7.51 (dd, J = 5.9, 5.9 Hz, 1H), 7.41 (d, J = 8.4 Hz, 1H), 3.95 (s, 2H), 3.49-3.38 (m, 2H), 3.29-3.20 (m, 2H), 2.34 (s, 3H), 2.17-2.08 (m, 1H), 0.96 (d, J = 6.8 Hz, 3H). | 488 |
| 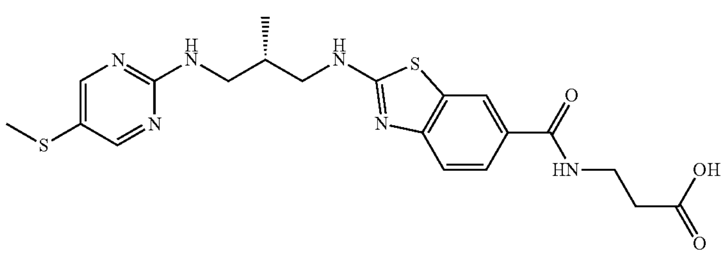 [SMILES: CSc1cnc(NC[C@H](C)CNc2nc3ccc(C(=O)NCCC(=O)O)cc3s2)nc1] | 25 | ¹H NMR (400 MHz, DMSO) δ 12.21 (s, 1H), 8.39 (dd, J = 5.5, 5.5 Hz, 1H), 8.34 (s, 3H), 8.15 (d, J = 1.6 Hz, 1H), 7.72 (dd, J = 1.8, 8.5 Hz, 1H), 7.52 (dd, J = 5.3, 5.3 Hz, 1H), 7.36 (d, J = 8.4 Hz, 1H), 3.48-3.43 (m, 4H), 3.33-3.23 (m, 4H), 2.34 (s, 3H), 2.17-2.06 (m, 1H), 0.96 (d, J = 6.8 Hz, 3H). | 461 |
| 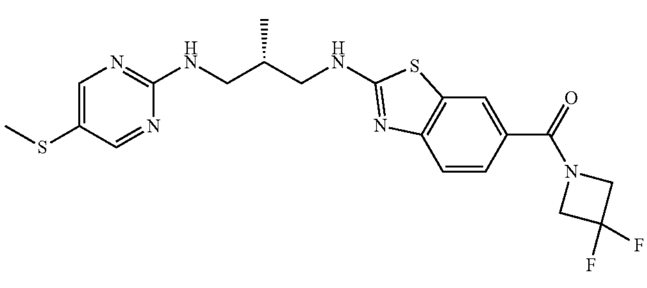 [SMILES: CSc1cnc(NC[C@H](C)CNc2nc3ccc(C(=O)N4CC(F)(F)C4)cc3s2)nc1] | 26 | ¹H NMR (400 MHz, CDCl₃) δ 8.39 (s, 2H), 7.95 (s, 1H), 7.52 (s, 2H), 6.93-6.93 (m, 1H), 5.65 (dd, J = 6.6, 6.6 Hz, 1H), 4.56 (dd, J = 12.0, 12.0 Hz, 4H), 3.60 (ddd, J = 4.5, 7.2, 14.4 Hz, 1H), 3.51 (s, 1H), 3.42-3.26 (m, 2H), 2.38 (s, 3H), 2.20-2.11 (m, 1H), 1.07 (d, J = 6.9 Hz, 3H). | 465 |

TABLE 1-continued

| Structure | Ex. # | 1H NMR | LC-MS (M + H)+ |
|---|---|---|---|
| 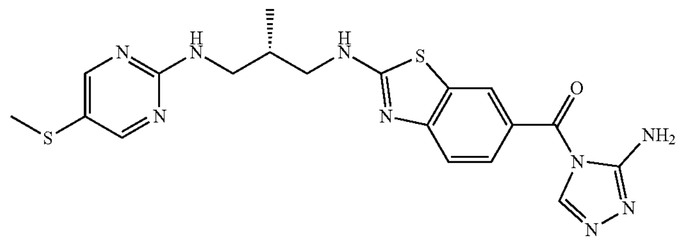 [SMILES: CSc1cnc(NC[C@H](C)CNc2nc3ccc(C(=O)n4cnnc4N)cc3s2)nc1] | 27 | ¹H NMR (400 MHz, DMSO) δ 8.55-8.52 (m, 2H), 8.34 (s, 2H), 8.05 (dd, J = 1.8, 8.6 Hz, 1H), 7.65 (s, 3H), 7.51 (dd, J = 5.8, 5.8 Hz, 1H), 7.43 (d, J = 8.5 Hz, 1H), 3.52-3.44 (m, 1H), 3.30-3.20 (m, 3H), 2.34 (s, 3H), 2.16-2.08 (m, 1H), 0.97 (d, J = 6.8 Hz, 3H). | 456 |
| 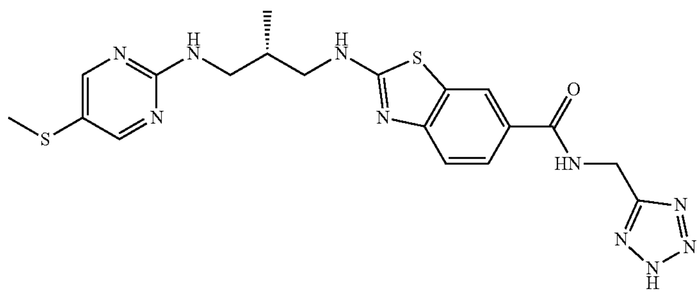 [SMILES: CSc1cnc(NC[C@H](C)CNc2nc3ccc(C(=O)NCc4nn[nH]n4)cc3s2)nc1] | 28 | ¹H NMR (400 MHz, DMSO) δ 9.13 (dd. J = 5.3, 5.3 Hz, 1H), 8.57-8.57 (m, 1H), 8.34 (s, 2H), 8.24 (s, 1H), 7.83-7.79 (m, 1H), 7.57-7.57 (m, 1H), 7.42 (d, J = 8.4 Hz, 1H), 4.76 (d, J = 5.6 Hz, 2H), 3.50-3.43 (m, 1H), 3.35-3.23 (m, 3H), 2.34 (s, 3H), 2.17-2.08 (m, 1H), 0.97 (d, J = 6.8 Hz, 3H) NH protons not observed. | 471 |
| 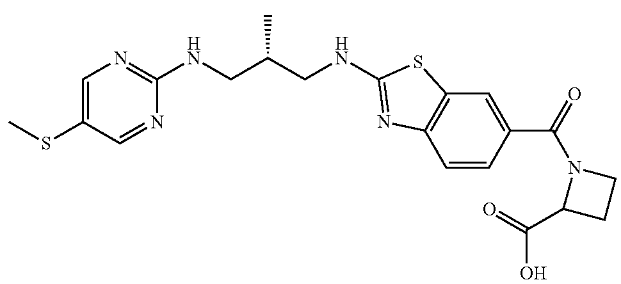 [SMILES: CSc1cnc(NC[C@H](C)CNc2nc3ccc(C(=O)N4CCC4C(=O)O)cc3s2)nc1] | 29 | ¹H NMR (400 MHz, DMSO) δ 8.29 (s, 2H), 8.03 (s, 1H), 7.93 (d, J =1.5 Hz, 1H), 7.49 (dd, J = 1.8, 8.4 Hz, 1H), 7.33 (d, J = 8.4 Hz, 1H), 7.12 (dd, J = 5.8, 5.8 Hz, 1H), 4.82 (dd, J = 5.3, 9.4 Hz. 1H), 4.33-4.25 (M, 1H), 4.14-4.07 (m, 1H), 3.47-3.23 (m, 4H), 2.66-2.55 (m, 1H), 2.33 (s, 3H), 2.21-2.08 (m, 2H), 0.97 (d, J = 6.8 Hz, 3H) NH protons not observed, VT @ 85° C. | 473 |
| 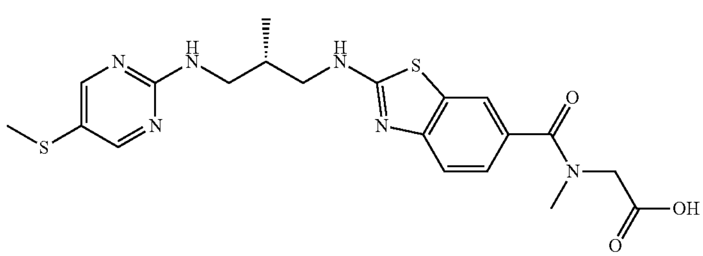 [SMILES: CSc1cnc(NC[C@H](C)CNc2nc3ccc(C(=O)N(C)CC(=O)O)cc3s2)nc1] | 30 | ¹H NMR (400 MHz, DMSO) δ 8.32 (s, 2H), 7.85 (s, 1H), 7.71 (d, J = 1.4 Hz, 1H), 7.37 (d, J = 8.3 Hz, 1H), 7.29 (dd, J = 1.6, 8.2 Hz, 1H), 7.02 (s, 1H), 3.97 (s, 2H), 3.50-3.30 (m, 4H), 3.01 (s, 3H), 2.36 (s, 3H), 2.22-2.13 (m, 1H), 1.01 (d, J = 6.8 Hz, 3H) NH protons not observed, VT @ 125°C. | 461 |
| 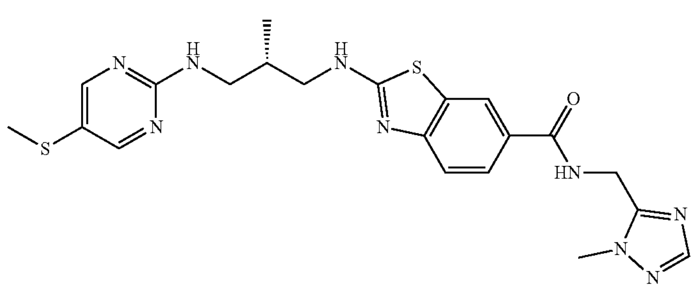 [SMILES: CSc1cnc(NC[C@H](C)CNc2nc3ccc(C(=O)NCc4ncnn4C)cc3s2)nc1] | 31 | ¹H NMR (400 MHz, DMSO) δ 9.03 (dd, J = 5.6, 5.6 Hz, 1H), 8.38 (s, 3H), 8.24 (d, J = 1.8 Hz, 1H), 7.88 (s, 1H), 7.81 (dd, J = 1.9, 8.5 Hz, 1H), 7.57 (dd, J = 5.9, 5.9 Hz, 1H), 7.41 (d, J = 8.3 Hz, 1H), 4.64 (d, J = 5.6 Hz, 2H), 3.94 (s, 3H), 3.53-3.44 (m, 1H), 3.35-3.27 (m, 3H), 2.38 (s, 3H), 2.21-2.10 (m, 1H), 1.00 (d, J = 6.8 Hz, 3H). | 484 |

TABLE 1-continued

| Structure | Ex. # | 1H NMR | LC-MS (M + H)+ |
|---|---|---|---|
| 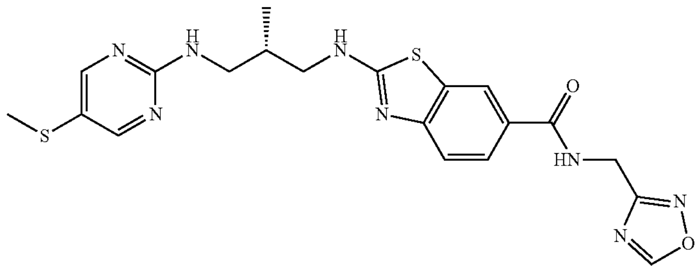 [SMILES: CSc1cnc(NC[C@H](C)CNc2nc3ccc(C(=O)NCc4ncon4)cc3s2)nc1] | 32 | ¹H NMR (400 MHz, DMSO) δ 9.60 (1H, s), 9.09 (1H, dd, J = 5.7, 5.7 Hz), 8.38 (3H, s), 8.24 (1H, d, J = 1.8 Hz), 7.81 (1H, dd, J = 1.8, 8.3 Hz), 7.58 (1H, dd, J = 5.9, 5.9 Hz), 7.43 (1 H, d, J = 8.3 Hz), 4.67 (2H, d, J = 5.8 Hz), 3.54-3.45 (2H, m), 3.36-3.27 (2H, m), 2.38 (3H, s), 2.21-2.10 (1H, m), 1.01 (3H, d, J = 6.8 Hz). | 471 |
| 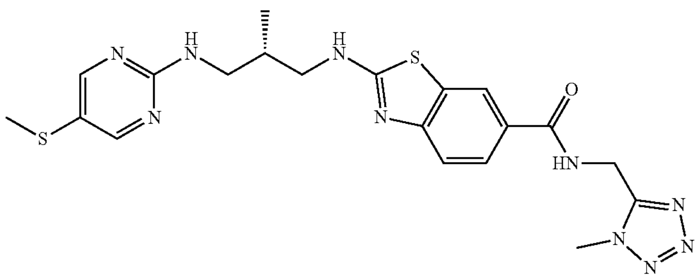 [SMILES: CSc1cnc(NC[C@H](C)CNc2nc3ccc(C(=O)NCc4nnnn4C)cc3s2)nc1] | 33 | ¹H NMR (400 MHz, DMSO) δ 9.16 (dd, J = 5.6, 5.6 Hz, 1H), 8.41 (d, J = 5.6 Hz, 1H), 8.38 (s, 2H), 8.23 (d, J = 1.8 Hz, 1H), 7.80 (dd, J = 1.8, 8.6 Hz, 1H), 7.57 (dd, J = 5.9, 5.9 Hz, 1H), 7.42 (d, J = 8.6 Hz, 1H), 4.80 (d, J = 5.6 Hz, 2H), 4.15 (s, 3H), 3.53-3.45 (m, 1H), 3.36-3.27 (m, 3H), 2.38 (s, 3H), 2.21-2.10 (m, 1H), 1.00 (d, J = 6.6 Hz, 3H). | 485 |
| 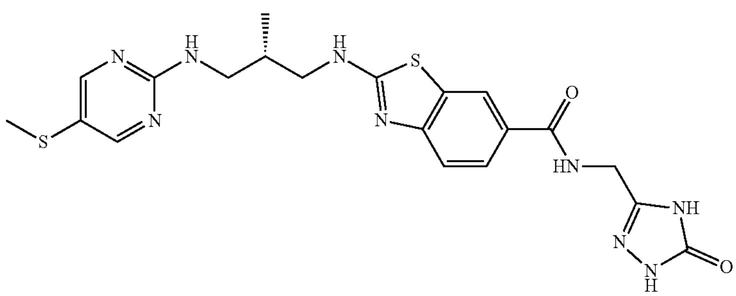 [SMILES: CSc1cnc(NC[C@H](C)CNc2nc3ccc(C(=O)NCc4n[nH]c(=O)[nH]4)cc3s2)nc1] | 34 | ¹H NMR (400 MHz, DMSO) δ 11.30 (2H, s), 8.80 (1H, dd, J = 5.3, 5.3 Hz), 8.38 (3H, s), 8.24 (1H, d, J = 1.5 Hz), 7.81 (1H, dd, J = 1.6, 8.5 Hz), 7.58 (1H, dd, J = 5.9, 5.9 Hz), 7.42 (1H, d, J = 8.3 Hz), 4.30 (2H, d, J = 5.3 Hz), 3.53-3.45 (1H, m), 3.35-3.27 (3H, m), 2.39 (3H,s), 2.21-2.11 (1H, m), 1.00 (3H, d, J = 6.6 Hz). | 486 |
| 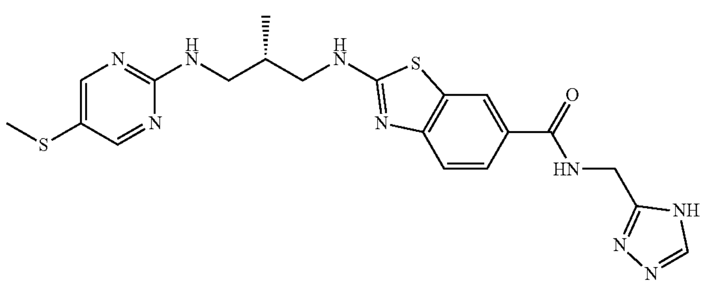 [SMILES: CSc1cnc(NC[C@H](C)CNc2nc3ccc(C(=O)NCc4nnc[nH]4)cc3s2)nc1] | 35 | ¹H NMR (400 MHz, DMSO) δ 8.94 (s, 1H), 8.38 (s, 2H), 8.36 (d, J = 5.6 Hz, 1H), 8.25 (d, J = 1.5 Hz, 1H), 7.83 (dd, J = 1.8, 8.3 Hz, 1H), 7.58 (dd, J = 5.9, 5.9 Hz, 1H), 7.42 (d, J = 8.3 Hz, 1H), 4.59 (d, J = 4.8 Hz, 2H), 3.53-3.45 (m, 1H), 3.36-3.27 (m, 3H), 2.39 (s, 3H). 2.21-2.11 (m, 1H), 1.00 (d, J = 6.8 Hz, 3H) NH protons not observed. | 470 |
| 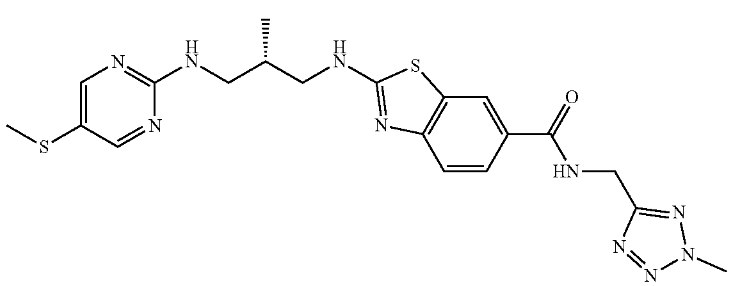 | 36 | ¹H NMR (400 MHz, DMSO) δ 9.09 (dd, J = 5.8, 5.8 Hz, 1H), 8.18 (s, 3H), 8.23 (d, J = 1.5 Hz, 1H), 7.81 (dd, J = 1.8, 8.6 Hz, 1H), 7.58 (dd, J = 5.9, 5.9 Hz, 1H), 7.42 (d, J = 8.3 Hz, 1H), 4.74 (d, J = 5.6 Hz, 2H), 4.38 (s, 3H), 3.53-3.45 (m, 1H), 3.36-3.27 (m, 3H), 2.39 (s, 3H), 2.21-2.11 (m, 1H), 1.00 (d, J = 6.8 Hz, 3H). | 485 |

TABLE 1-continued

| Structure | Ex. # | 1H NMR | LC-MS (M + H)+ |
|---|---|---|---|
| 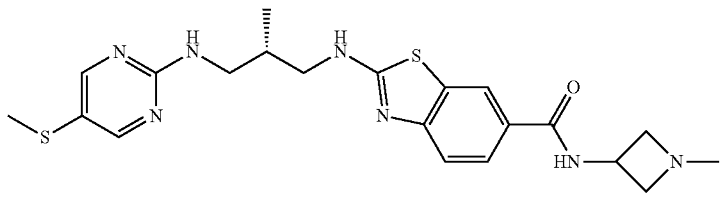 | 37 | ¹H NMR (400 MHz, CDCl₃) δ 8.37 (s, 2H), 8.14 (d, J = 1.6 Hz, 1H), 7.93-7.93 (m, 1H), 7.79 (dd, J = 1.7, 8.5 Hz, 1H), 7.52 (d, J = 8.4 Hz, 1H), 6.92 (s, 1H), 5.82-5.81 (m, 1H), 4.94-4.87 (m, 1H), 3.88-3.82 (m, 2H), 3.61 (ddd, J = 4.5, 7.0, 14.4 Hz, 2H), 3.53-3.50 (m, 1H), 3.41-3.24 (m, 3H), 2.56 (s, 3H), 2.37 (s, 3H), 2.20-2.11 (m, 1H), 1.07 (d, J = 6.9 Hz, 3H). | 458 |
| 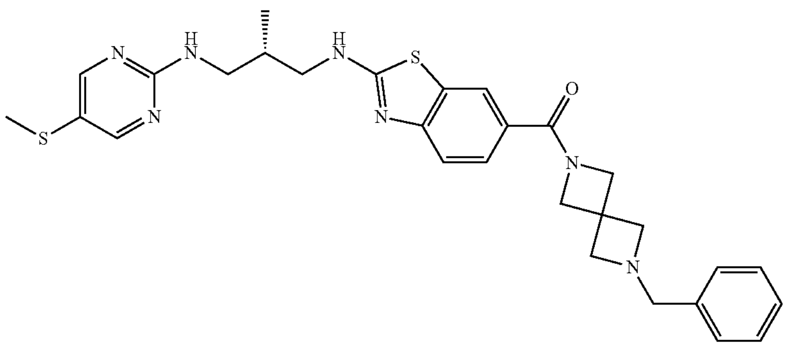 [SMILES: CSc1cnc(NC[C@H](C)CNc2nc3ccc(C(=O)N4CC5(CN(Cc6ccccc6)C5)C4)cc3s2)nc1] | 38 | ¹H NMR (400 MHz, DMSO) δ 8.41 (s, 2H), 8.38 (d, J = 5.5 Hz, 1H), 8.40-8.37 (m, 1H), 8.04 (d, J = 1.6 Hz, 1H), 7.61-7.54 (m, 2H), 7.49 (d, J = 6.9 Hz, 5H), 7.43 (d, J = 8.3 Hz, 2H), 4.57-4.57 (m, 2H), 4.26-4.25 (m, 3H), 3.55-3.45 (m, 2H), 3.33 (dd, J = 6.8, 13.3 Hz, 3H), 2.42 (s, 3H), 2.24-2.16 (m, 1H), 1.03 (d, J = 6.7 Hz, 3H). | 560 |
| 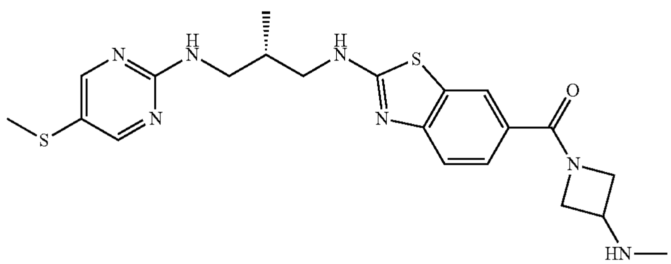 | 39 | ¹H NMR (400 MHz, CDCl₃) δ 8.38 (2H, s), 7.94 (1H, d, J = 1.4 Hz), 7.56-7.53 (1H, m), 7.50 (1H, d, J = 8.3 Hz), 6.76 (1H, s), 5.68 (1H, dd, J = 6.6, 6.6 Hz), 4.42 (2H, s), 4.04-3.92 (2H, m), 3.68-3.49 (3H, m), 3.42-3.26 (2H, m), 2.40 (6H, d, J = 18.1 Hz), 2.25-2.11 (1H, m), 1.06 (3H, d, J = 6.9 Hz); One NH proton not observed | 458 |
| 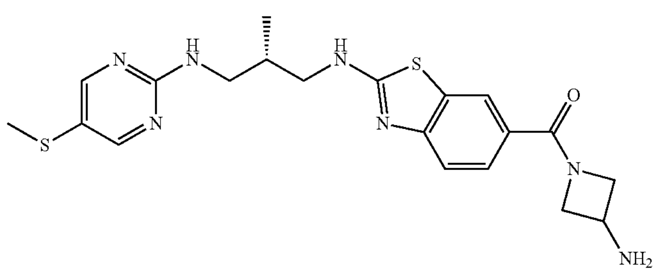 [SMILES: CSc1cnc(NC[C@H](C)CNc2nc3ccc(C(=O)N4CC(N)C4)cc3s2)nc1] | 40 | ¹H NMR (400 MHz, DMSO) δ 8.33 (2H, s), 8.30 (1H, dd, J = 5.6, 5.6 Hz), 7.96 (1H, d, J = 1.6 Hz), 7.54-7.47 (2H, m), 7.34 (1H, d, J = 8.3 Hz), 4.45 (1H, s), 4.17 (1H, s), 3.92 (1H, s), 3.76-3.69 (2H, m), 3.47-3.40 (2H, m), 3.29-3.23 (3H, m), 2.34 (3H, s), 2.17-2.06 (1H, m), 0.96 (3H, d, J = 6.8 Hz); One NH proton not observed | 444 |
| 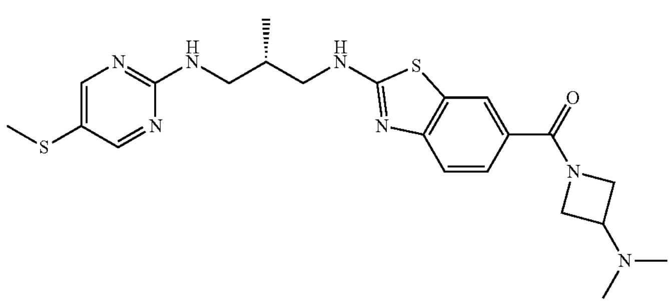 | 41 | ¹H NMR (400 MHz, MeOD) δ 8.33 (2H, s), 7.97 (1H, d, J = 1.6 Hz), 7.60 (1H, dd, J = 1.8, 8.4 Hz), 7.48 (1H, d, J = 8.5 Hz), 4.59-4.10 (4H, m), 3.52-3.40 (6H, m), 2.45 (6H, s), 2.34 (3H, s), 2.24-2.16 (1H, m), 1.08 (3H, d, J = 6.8 Hz); One NH proton not observed | 472 |

TABLE 1-continued

| Structure | Ex. # | 1H NMR | LC-MS (M + H)+ |
|---|---|---|---|
| 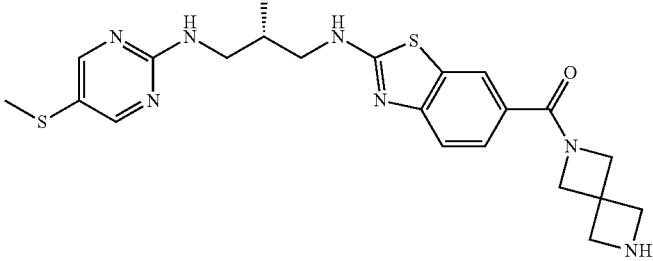 | 42 | ¹H NMR (400 MHz, DMSO) δ 8.49-8.47 (m, 3H), 8.34 (s, 1H), 7.98 (d, J = 1.6 Hz, 1H), 7.54 (s, 1H), 7.49 (dd, J = 1.8, 8.4 Hz, 1H), 7.37 (d, J = 8.4 Hz, 1H), 4.52-4.52 (m, 2H), 4.21 (s, 2H), 4.14-4.06 (m, 4H), 3.97 (s, 1H), 3.33-3.26 (m, 3H), 2.34 (s, 3H), 2.09 (s, 1H), 0.96 (d, J = 6.8 Hz, 3H). Formate salt. One NH not observed. | 470 |
| 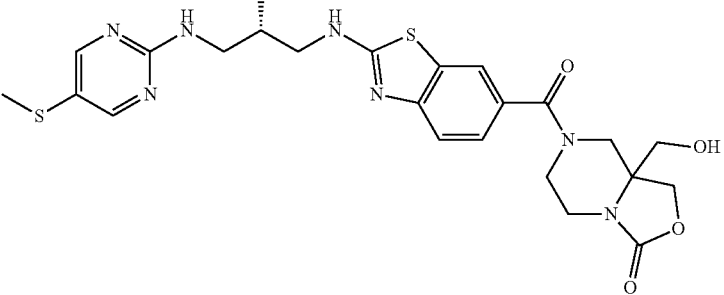 | 43 | ¹H NMR (400 MHz, CDCl₃) δ 8.38 (s, 2H), 7.75 (s, 1H), 7.54 (d, J = 8.3 Hz, 1H), 7.39 (dd, J = 1.6, 8.3 Hz, 1H), 6.89-6.89 (m, 1H), 5.69-5.66 (m, 1H), 4.80 (s, 1H), 4.43 (d, J = 9.2 Hz, 1H), 4.10-4.08 (m, 2H), 3.80-3.49 (m, 6H), 3.43-3.25 (m, 3H), 2.95 (d, J = 12.8 Hz, 2H), 2.38 (s, 3H), 2.20-2.10 (m, 1H), 1.07 (d, J = 6.9 Hz, 3H). | 544 |
| 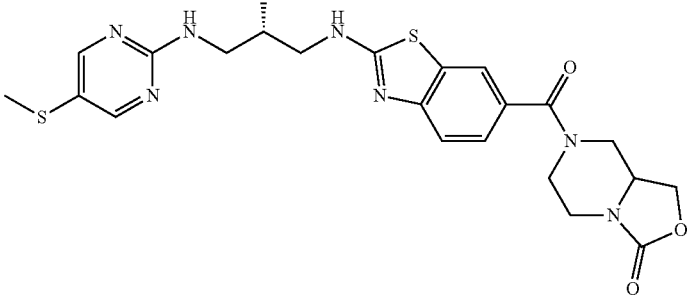 | 44 | ¹H NMR (400 MHz, CDCl₃) δ 8.38 (s, 2H), 7.70 (d, J = 1.5 Hz, 1H), 7.53 (d, J = 8.4 Hz, 1H), 7.33 (dd, J = 1.8, 8.3 Hz, 1H), 6.85-6.85 (m, 1H), 5.71 (dd, J = 6.6, 6.6 Hz, 1H), 4.72-4.12 (m, 3H), 3.98 (d, J = 7.8 Hz, 1H), 3.90-3.81 (m, 2H), 3.63-3.48 (m, 2H), 3.43-3.25 (m, 2H), 3.08-3.06 (m, 2H), 2.89-2.83 (m, 1H), 2.37 (s, 3H), 2.20-2.10 (m, 1H), 1.07 (d, J = 6.9 Hz, 3H). | 514 |
| 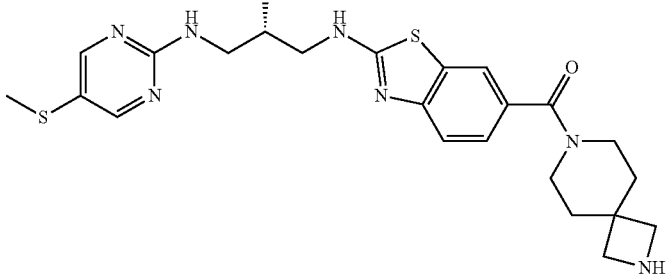 | 45 | ¹H NMR (400 MHz, CDCl₃) δ 8.55-8.54 (m, 1H), 8.37 (s, 2H), 7.64 (s, 1H), 7.50 (d, J = 8.3 Hz. 1H), 6.86-6.86 (m, 1H), 5.80 (dd, J = 6.5, 6.5 Hz, 1H), 3.74 (s, 4H), 3.63-3.46 (m, 6H), 3.42-3.24 (m, 2H), 2.37 (s, 3H), 2.20-2.09 (m, 1H), 1.83-1.86 (m, 4H), 1.06 (J = 6.9 Hz, 3H), NH proton not observed. | 498 |
| 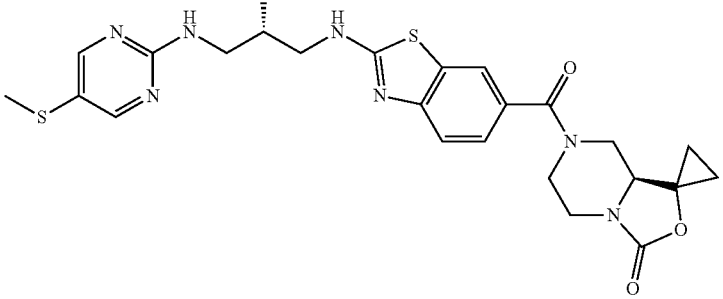 | 46 | ¹H NMR (400 MHz, CDCl₃) δ 8.38 (s, 2H), 7.69 (d, J = 1.5 Hz. 1H), 7.53 (d. J = 8.4 Hz, 1H), 7.32 (dd, J = 1.7, 8.3 Hz, 1H), 6.95 (s, 1H), 5.71 (dd, J = 6.6, 6.6 Hz, 1H), 4.18-4.18 (m, 2H), 3.91 (d, J = 9.7 Hz, 1H), 3.79-3.74 (m, 1H), 3.63-3.48 (m, 2H), 3.43-3.26 (m, 2H), 3.10 (d, J = 8.8 Hz, 2H), 2.91-2.88 (m, 1H), 2.38 (s, 3H), 2.20-2.10 (m, 1H), 1.26-1.12 (m, 2H), 1.07 (d, J = 6.9 Hz, 3H), 0.78-0.75 (m, 2H). | 540 |

TABLE 1-continued

| Structure | Ex. # | 1H NMR | LC-MS (M + H)+ |
|---|---|---|---|
| 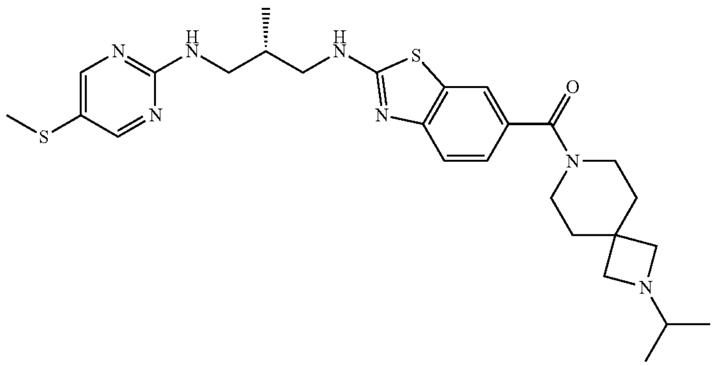 [SMILES: CSc1cnc(NC[C@H](C)CNc2nc3ccc(C(=O)N4CCC5(CC4)CN(C(C)C)C5)cc3s2)nc1] | 47 | ¹H NMR (400 MHz, CDCl₃) δ 8.42 (s, 1H), 8.38 (s, 2H), 7.64 (d, J = 1.4 Hz, 1H), 7.52-7.49 (m, 1H), 7.30 (dd, J = 1.8, 8.3 Hz, 1H), 5.72 (dd, J = 6.7, 6.7 Hz, 1H), 3.63-3.47 (m, 9H), 3.43-3.25 (m, 3H), 2.96-2.89 (m, 1H), 2.37 (s, 3H), 2.20-2.12 (m, 1H), 1.87 (t, J = 6.1 Hz, 4H), 1.20 (d, J = 6.4 Hz, 6H), 1.07 (d, J = 6.9 Hz, 3H). | 540 |
| 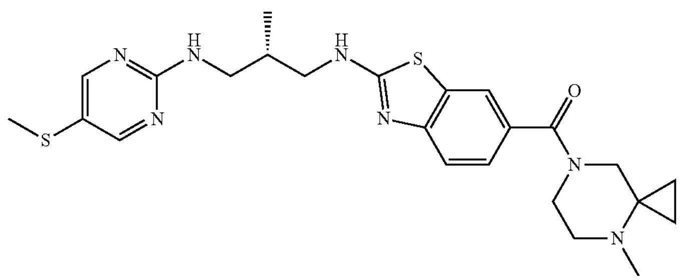 [SMILES: CSc1cnc(NC[C@H](C)CNc2nc3ccc(C(=O)N4CCN(C)C5(CC5)C4)cc3s2)nc1] | 48 | ¹H NMR (400 MHz, CDCl₃) δ 8.38 (s, 2H), 7.67 (s, 1H), 7.51 (d, J = 8.3 Hz, 1H), 7.31 (d, J = 8.0 Hz, 1H), 6.75-6.68 (m, 1H), 5.75 (dd, J = 6.7, 6.7 Hz, 1H), 3.63-3.46 (m, 4H), 3.42-3.26 (m, 2H), 2.92-2.91 (m, 2H), 2.39 (d, J = 18.2 Hz, 6H), 2.20-2.09 (m, 1H), 1.70 (s, 4H), 1.06 (d, J = 6.9 Hz, 3H), 0.69 (s, 2H). | 498 |
| 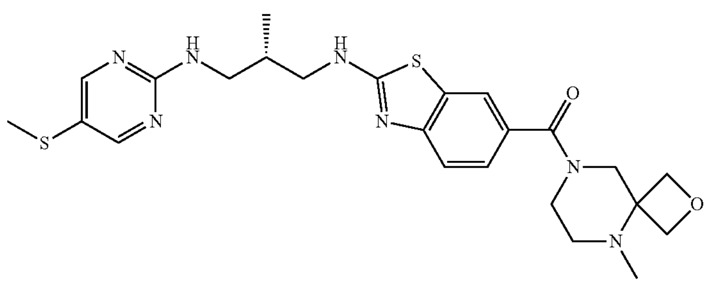 [SMILES: CSc1cnc(NC[C@H](C)CNc2nc3ccc(C(=O)N4CCN(C)C5(COC5)C4)cc3s2)nc1] | 49 | ¹H NMR (400 MHz, CDCl₃) δ 8.37 (s, 2H), 7.68 (d, J =1.4 Hz, 1H), 7.52 (d, J = 8.3 Hz, 1H), 7.33 (dd, J = 1.5, 8.3 Hz, 1H), 5.86 (dd, J = 6.6, 6.6 Hz, 1H), 4.78 (d, J = 6.8 Hz, 2H), 4.25 (s, 2H), 3.89-3.84 (m, 2H), 3.70-3.26 (m, 6H), 2.58 (s, 3H), 2.51 (dd, J = 4.7, 4.7 Hz, 2H), 2.37 (s, 3H), 2.20-2.11 (m, 1H), 1.07 (d, J = 6.9 Hz, 3H), NH proton not observed. | 514 |
| 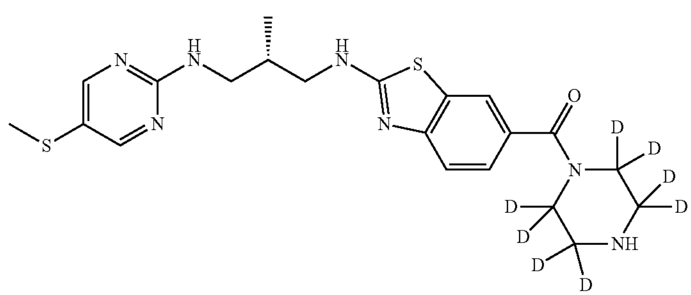 [SMILES: [2H]C1([2H])NC([2H])([2H])C([2H])([2H])N(C(=O)c2ccc3nc(NC[C@@H](C)CNc4ncc(SC)cn4)sc3c2)C1([2H])[2H]] | 50 | ¹H NMR (400 MHz, CDCl₃) δ 8.38 (s, 2H), 7.68 (d, J = 1.4 Hz, 1H), 7.53-7.50 (m, 1H). 7.33 (td, J = 1.4, 8.5 Hz, 1H), 6.68 (s, 1H), 5.69 (t, J = 6.6 Hz, 1H), 3.62-3.47 (m, 2H), 3.42-3.26 (m, 2H), 2.37 (s, 3H), 2.20-2.08 (m, 1H), 1.06 (d, J = 6.9 Hz, 3H), NH not observed. | 466 |

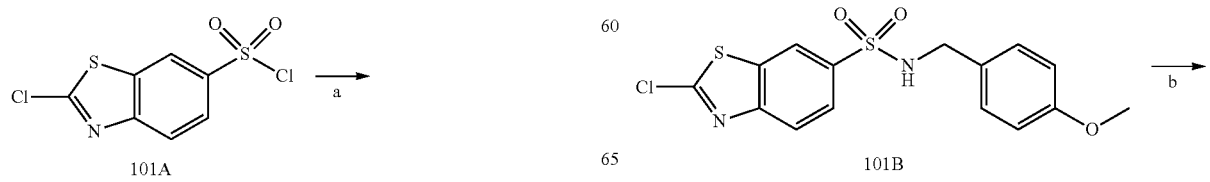

Scheme 2

57
-continued

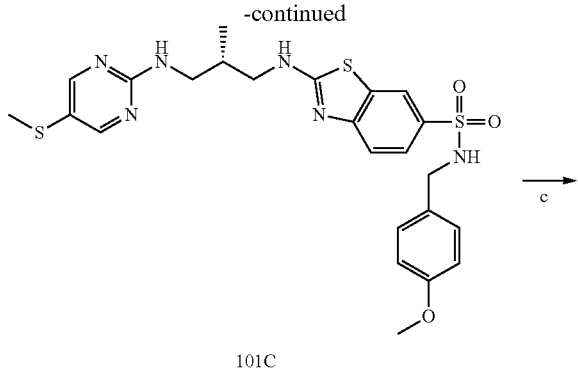

101C

87 a) (4-Methoxyphenyl)methanamine, Et₃N, THF, b) Et₃N, DMF, 100E, c) TFA, DCM

58

General Method 6

2-Chloro-N-(4-methoxybenzyl)benzo[d]thiazole-6-sulfonamide (101B)

(4-Methoxyphenyl)methanamine (134 mg, 0.97 mmol, 1.05 eq) was added dropwise to an ice cooled solution of 2-chlorobenzothiazole-6-sulfonyl chloride (101A) (250 mg, 0.932 mmol, 1.0 eq), triethylamine (0.39 mL, 2.79 mmol, 3.0 eq) in tetrahydrofuran (10 mL), and the mixture stirred at 0° C. for 1 hour. The reaction mixture was concentrated under reduced pressure to give a solid which was washed with ice cold water (10 mL), ice cold tetrahydrofuran (10 mL) and then dried under vacuum to give the desired 2-chloro-N-(4-methoxybenzyl)benzo[d]thiazole-6-sulfonamide as a white solid (101B). Yield: 295 mg (85%). ¹H NMR (400 MHz, DMSO) δ 8.56 (d, J=1.6 Hz, 1H), 8.24 (s, 1H), 8.11 (d, J=8.7 Hz, 1H), 7.90 (dd, J=1.9, 8.7 Hz, 1H), 7.10 (d, J=8.8 Hz, 2H), 6.76 (d, J=8.8 Hz, 2H), 3.98 (s, 2H), 3.67 (s, 3H); MS (ESI+) m/z 369 (M+H)⁺.

The intermediates in Table 2 were synthesized using conditions analogous to those described for intermediate 101B:

TABLE 2

| Structure | Compound No. | ¹H NMR | LC-MS (H + M)⁺ |
|---|---|---|---|
| | Intermediate | ¹H NMR (400 MHz, CDCl₃) δ 8.33 (1H, d, J = 1.6 Hz), 8.12 (1H, d, J = 8.5 Hz), 7.95 (1H, dd, J = 1.8, 8.6 Hz), 4.55 (1H, d, J = 3.9 Hz), 4.08 (2H, dd, J = 6.5, 9.3 Hz), 3.64 (2H, dd, J = 5.3, 9.2 Hz), 2.13-2.13 (1H, m). | 305 |
| | Intermediate | Not acquired | 263 |
| | Intermediate | Not acquired | 418 |

TABLE 2-continued

| Structure | Compound No. | ¹H NMR | LC-MS (H + M)⁺ |
|---|---|---|---|
| [2-chloro-benzo[d]thiazole-6-sulfonyl glycine ethyl ester structure] | Intermediate | ¹H NMR (400 MHz, CDCl₃) δ 8.36 (d, J = 1.8 Hz, 1H), 8.07 (d, J = 8.7 Hz, 1H), 7.96 (dd, J = 1.8, 8.6 Hz, 1H), 5.13 (dd, J = 5.3, 5.3 Hz, 1H), 4.07 (q, J = 7.2 Hz 2H), 3.82 (d, J = 5.5 Hz, 2H), 1.17 (dd, J = 7.2, 7.2 Hz, 3H). | 335 |
| [2-chloro-benzo[d]thiazole-6-sulfonamide ethanolamine structure] | Intermediate | ¹H NMR (400 MHz, CDCl₃) δ 8.38 (d, J = 1.8 Hz, 1H), 8.07 (d, J = 8.5 Hz, 1H), 7.97 (dd, J = 1.8, 8.6 Hz, 1H), 5.18 (s, 1H), 3.73 (dd, J = 4.3, 4.3 Hz, 2H), 3.15 (dd, J = 5.8, 10.4 Hz, 2H), 2.01-2.01 (m, 1H). | 293 |
| [2-chloro-benzo[d]thiazole-6-sulfonyl-2,6-diazaspiro[3.3]heptane-Boc structure] | Intermediate | Not acquired | 430 |

(S)—N-(4-Methoxybenzyl)-2-((2-methyl-3-((5-(methylthio)pyrimidin-2-yl)amino)propyl) amino) benzo[d]thiazole-6-sulfonamide (101C)

Methodology applied was analogous to that described in General method 3.

Yield: 298 mg, (69%). ¹H NMR (400 MHz, DMSO) δ 8.56 (1H, d, J=1.6 Hz), 8.24 (1H, s), 8.11 (1H, d, J=8.7 Hz), 7.90 (1H, dd, J=1.9, 8.7 Hz), 7.10 (2H, d, J=8.8 Hz), 6.76 (2H, d, J=8.8 Hz), 3.98 (2H, s), 3.67 (3H, s); MS (ESI+) m/z 545 (M+H)⁺.

(S)-2-((2-Methyl-3-((5-(methylthio)pyrimidin-2-yl)amino)propyl)amino)benzo[d]thiazole-6-sulfonamide (Example 87)

Trifluoroacetic acid (5 mL) was added dropwise to an ice cooled solution of N-(4-methoxybenzyl)-2-((2-methyl-3-((5-(methylthio)pyrimidin-2-yl)amino)propyl) amino)benzo[d]thiazole-6-sulfonamide (101C) (250 mg, 0.459 mmol, 1.0 eq) in anhydrous dichloromethane (5 mL). The mixture was stirred on ice for 30 minutes and then allowed to warm to ambient temperature over 18 h. The reaction mixture was diluted with dichloromethane (15 mL) and saturated sodium hydrogen carbonate (15 mL) was added slowly. The organic phase was separated, washed with brine (5 mL), dried over magnesium sulphate and then concentrated to dryness under reduced pressure. The crude residue obtained was purified by flash chromatography (eluting DCM to methanol, 0-10%) give the desired (S)-2-((2-methyl-3-((5-(methylthio)pyrimidin-2-yl)amino)propyl)amino) benzo[d]thiazole-6-sulfonamide (Example 87) as a white solid. Yield: 190 mg (97%). ¹H NMR (400 MHz, DMSO) δ 8.40 (dd, J=5.5, 5.5 Hz, 1H), 8.34 (s, 2H), 8.12 (d, J=1.6 Hz, 1H), 7.66 (dd, J=2.0, 8.4 Hz, 1H), 7.51 (dd, J=6.0, 6.0 Hz, 1H), 7.44 (d, J=8.5 Hz, 1H), 7.21 (s, 2H), 3.49-3.42 (m, 1H), 3.31-3.23 (m, 3H), 2.34 (s, 3H), 2.17-2.07 (m, 1H), 0.96 (d, J=6.8 Hz, 3H); MS (ESI+) m/z 425 (M+H)⁺. Using the procedures described in Scheme 2, following General Method 3, the following examples were prepared:

TABLE 3

| Structure | Ex. # | ¹H NMR | LC-MS (M + H)⁺ |
|---|---|---|---|
| [Structure: 5-(methylthio)pyrimidin-2-yl-NH-CH2-CH(CH3)-CH2-NH-benzothiazol-2-yl-6-SO2-N(azetidine-3-OH)] | 88 | ¹H NMR (400 MHz, CDCl₃) δ 8.38 (s, 2H), 8.05 (d, J = 1.5 Hz, 1H), 7.74 (dd, J = 1.9, 8.5 Hz, 1H), 7.60 (d, J = 8.5 Hz, 1H), 7.16 (s, 1H), 5.70 (dd, J = 6.8, 6.8 Hz, 1H), 4.50-4.45 (m, 1H), 4.05-4.01 (m, 2H), 3.62-3.57 (m, 3H), 3.54 (dd, J = 4.1, 13.6 Hz, 1H), 3.43-3.26 (m, 2H), 2.38 (s, 3H), 2.21-2.05 (m, 1H), 1.08 (d, J = 6.9 Hz, 3H). | 481 |
| [Structure: analogous with SO2-NHMe] | 89 | ¹H NMR (400 MHz, DMSO) δ 8.45 (dd, J = 5.4, 5.4 Hz, 1H), 8.33 (s, 2H), 8.11 (d, J = 1.9 Hz, 1H), 7.60 (dd, J = 1.9, 8.5 Hz, 1H), 7.51 (dd, J = 5.7, 5.7 Hz, 1H), 7.47 (d, J = 8.5 Hz, 1H), 7.26 (q, J = 5.1 Hz, 1H), 3.50-3.42 (m, 1H), 3.31-3.20 (m, 3H), 2.41-2.34 (m, 6H), 2.29-2.07 (m, 1H), 0.96 (d, J = 6.8 Hz, 3H). | 439 |
| [Structure: analogous with SO2-piperazine] | 90 | ¹H NMR (400 MHz, CDCl₃) δ 8.38 (s, 2H), 7.96 (d, J = 1.6 Hz, 1H), 7.64 (dd, J = 1.8, 8.5 Hz, 1H), 7.57 (d, J = 8.5 Hz, 1H), 5.86 (t, J = 13.1 Hz, 1H), 3.64-3.26 (m, 6H), 3.08-2.95 (m, 8H), 2.38 (s, 3H), 2.21-2.11 (m, 1H), 1.08 (d, J = 6.9 Hz, 3H). | 494 |
| [Structure: analogous with SO2-morpholine] | 91 | ¹H NMR (400 MHz, CDCl₃) δ 8.39 (2H, s), 7.97 (1H, d, J = 1.8 Hz), 7.65 (1H, dd, J = 1.8, 8.5 Hz), 7.59 (1H, d, J = 8.5 Hz), 7.11 (1H, s), 5.63 (1H, t, J = 10.5 Hz), 3.77-3.73 (4H, m), 3.65-3.52 (2H, m), 3.43-3.26 (2H, m), 3.04-2.95 (4H, m), 2.38 (3H, s), 2.21-2.10 (1H, m), 1.08 (3H, d, J = 6.9 Hz); | 495 |
| [Structure: analogous with SO2-NH-CH2-CO2Et] | 92 | ¹H NMR (400 MHz, MeOD) δ 8.33 (2H, s), 8.11 (1H, d, J = 1.6 Hz), 7.74 (1H, dd, J = 2.0, 8.5 Hz), 7.52 (1H, d, J = 8.5 Hz), 4.00 (2H, q, J = 7.2 Hz), 3.77 (2H, s), 3.49 (2H, d, J = 6.1 Hz), 3.42-3.40 (2H, m), 2.35 (3H, s), 2.25-2.16 (1H, in), 1.15-1.06 (6H, m); N—CH₃ obscured by MeOH peak | 511 |
| [Structure: analogous with SO2-NH-CH2CH2-OH] | 93 | ¹H NMR (400 MHz, CDCl₃) δ 8.37 (s, 2H), 8.07 (d, J = 1.6 Hz, 1H), 7.74 (dd, J = 1.9, 8.5 Hz, 1H), 7.54 (d, J = 8.5 Hz, 1H), 7.18 (s, 1H), 5.80 (dd, J = 6.5, 6.5 Hz, 1H), 5.02 (dd, J = 6.1, 6.1 Hz, 1H), 3.73-3.70 (m, 2H), 3.64-3.50 (m, 2H), 3.43-3.25 (m, 2H), 3.13 (dd, J = 5.9, 10.4 Hz, 2H), 2.38 (s, 3H), 2.21-2.10 (m, 1H), 1.07 (d, J = 7.0 Hz, 3H). | 469 |

TABLE 3-continued
| Structure | Ex. # | ¹H NMR | LC-MS (M + H)⁺ |
|---|---|---|---|
| 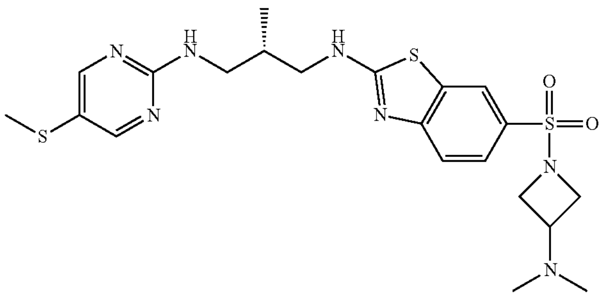 [SMILES: CSc1cnc(NC[C@H](C)CNc2nc3ccc(S(=O)(=O)N4CC(N(C)C)C4)cc3s2)nc1] | 94 | ¹H NMR (400 MHz, CDCl₃) δ 8.39 (2H, s), 8.05 (1H, d, J = 1.6 Hz), 7.74 (1H, dd, J = 1.9, 8.5 Hz), 7.61 (1H, d, J = 8.5 Hz), 5.68 (1H, dd, J = 6.7, 6.7 Hz), 3.81 (2H, dd, J = 7.6, 7.6 Hz), 3.64-3.53 (4H, m), 3.43-3.26 (2H, m), 3.06-2.98 (1H, m), 2.38 (3H, s), 2.21-2.11 (1H, m), 2.02 (6H, s), 1.33-1.24 (1H, m), 1.08 (3H, d, J = 6.9 Hz). | 508 |
| 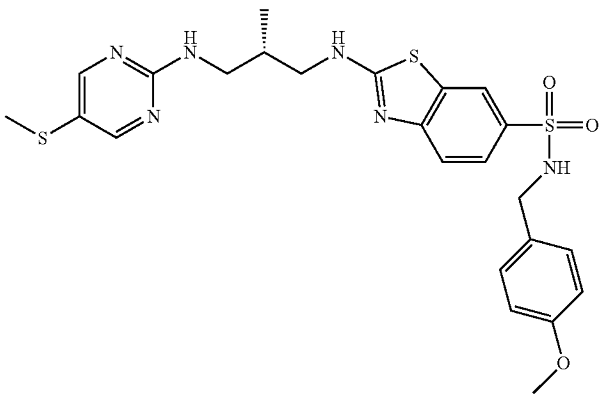 [SMILES: COc1ccc(CNS(=O)(=O)c2ccc3nc(NC[C@@H](C)CNc4ncc(SC)cn4)sc3c2)cc1] | 95 | ¹H NMR (400 MHz, DMSO) δ 8.44 (dd, J = 5.5, 5.5 Hz, 1H), 8.34 (s, 2H), 8.07 (d, J = 1.9 Hz, 1H), 7.88 (dd, J = 6.0, 6.0 Hz, 1H), 7.62 (dd, J = 2.0, 8.5 Hz, 1H), 7.52 (dd, J = 6.0, 6.0 Hz, 1H), 7.43 (d, J = 8.5 Hz, 1H), 7.14 (d, J = 8.8 Hz, 2H), 6.81 (d, J = 8.8 Hz, 2H), 3.89 (d, J = 5.8 Hz, 2H), 3.70 (s, 3H), 3.52-3.42 (m, 1H), 3.32-3.23 (m, 3H), 2.34 (s, 3H), 2.17-2.07 (m, 1H), 0.97 (d, J = 6.7 Hz, 3H). | 545 |
| 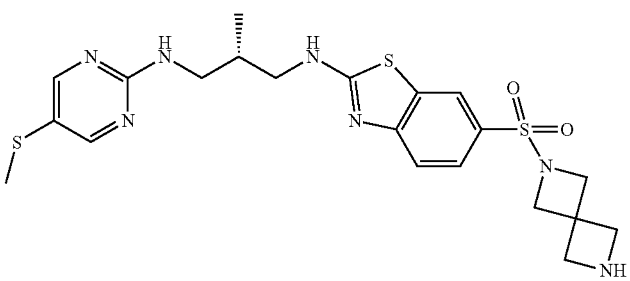 [SMILES: CSc1cnc(NC[C@H](C)CNc2nc3ccc(S(=O)(=O)N4CC5(CNC5)C4)cc3s2)nc1] | 96 | ¹H NMR (400 MHz, DMSO) δ 8.63 (s, 1H), 8.55-8.46 (m, 2H), 8.35 (s, 2H), 8.20 (d, J = 1.9 Hz, 1H), 7.61 (dd, J = 1.9, 8.5 Hz, 1H), 7.52 (d, J = 8.4 Hz, 1H), 3.94-3.85 (m, 9H), 3.38-3.21 (m, 3H), 2.35 (s, 3H), 2.18-2.08 (m, 1H), 0.97 (d, J = 6.8 Hz, 3H). | 505 |
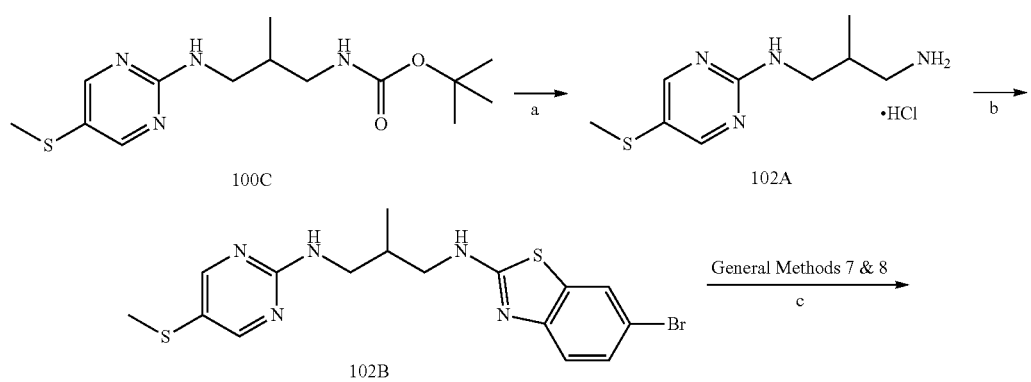
Scheme 3

-continued

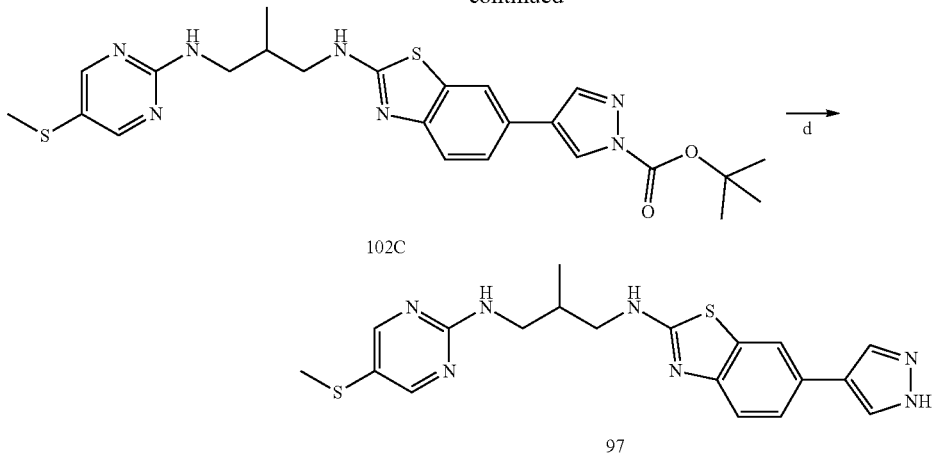

a) 4M HCl in 1,4-dioxane; b) 6-Bromo-2-chlorobenzothiazole, Et₃N, DMF; c) General Method 7, Het-B(OR)₂, Cs₂CO₃, Pd(PPh₃)₄, water, DMF; Or, General Method 8, Het-Sn(nBu)₃ Pd(PPh₃)₄, DMF; d) 4M HCl in 1,4-dioxane.

2-Methyl-$N^1$-(5-(methylthio)pyrimidin-2-yl)propane-1,3-diamine hydrochloride (102A)

Methodology applied was analogous to General Method 2.

A solution of hydrogen chloride (54 mL, 4M in 1,4-dioxane) was added to tert-butyl (2-methyl-3-((5-(methylthio)pyrimidin-2-yl)amino)propyl)carbamate (100C) (4.25 g, 13.60 mmol) and the mixture stirred at room temperature for 1 hour. The solvents were removed under vacuum to afford the desired 2-methyl-$N^1$-(5-(methylthio)pyrimidin-2-yl)propane-1,3-diamine hydrochloride (102A) as a pale yellow semi-solid. The semi-crude sample was taken on into the next reaction without further purification.

$N^1$-(6-Bromobenzo[d]thiazol-2-yl)-2-methyl-$N^3$-(5-(methylthio)pyrimidin-2-yl)propane-1,3-diamine (102B)

Methodology applied was analogous to General Method 3.

6-Bromo-2-chlorobenzothiazole (828 mg, 3.33 mmol, 0.95 eq) was added to a stirred suspension of 2-methyl-$N^1$-(5-(methylthio)pyrimidin-2-yl)propane-1,3-diamine hydrochloride (102A) (1.00 g, 3.51 mmol, 1.0 eq) and cesium carbonate (3.43 g, 10.52 mmol, 3.0 eq) in anhydrous dimethylformamide (25 mL) under nitrogen. The mixture was stirred at room temperature for 72 h and was then concentrated under vacuum to ~3 mL. Water (25 mL) was added and the mixture was extracted with ethyl acetate (3×50 mL). The combined organic phases were washed with water (20 mL) and brine (25 mL) then dried over magnesium sulfate. The solvents were removed under vacuum to give a crude yellow oil which was purified by flash chromatography (eluting isohexane to ethyl acetate, 0-100%) to give the desired $N^1$-(6-bromobenzo[d]thiazol-2-yl)-2-methyl-$N^3$-(5-(methylthio)pyrimidin-2-yl)propane-1,3-diamine (102B) as a sticky yellow solid. Yield: 266 mg (18%). ¹H NMR (400 MHz, CDCl₃) δ 8.37 (s, 2H), 7.66 (d, J=0.6 Hz, 1H), 7.37 (d, J=1.9 Hz, 2H), 6.58 (s, 1H), 5.69 (dd, J=6.3, 6.3 Hz, 1H), 3.67-3.23 (m, 4H), 2.37 (s, 3H), 2.17-2.09 (m, 1H), 1.06 (d, J=6.9 Hz, 3H).

General Method 7 tert-Butyl 4-(2-((2-methyl-3-((5-(methylthio)pyrimidin-2-yl)amino)propyl)amino)benzo[d]thiazol-6-yl)-1H-pyrazole-1-carboxylate (102C)

A solution of $N^1$-(6-bromobenzo[d]thiazol-2-yl)-2-methyl-$N^3$-(5-(methylthio)pyrimidin-2-yl)propane-1,3-diamine (102B) (50 mg, 0.12 mmol, 1.0 eq) was added to a solution of (1-(tert-butoxycarbonyl)-1H-pyrazol-4-yl)boronic acid (27.8 mg, 0.13 mmol, 1.0 eq), cesium carbonate (58 mg, 0.18 mmol, 1.5 eq) and tetrakis(triphenylphosphine) palladium (O) (7 mg, 0.01 mmol, 0.05 eq) in water (0.20 mL) and N,N-dimethylformamide (0.80 mL) under nitrogen. The reaction mixture was heated to 90° C. for 16 h. An additional aliquot of (1-(tert-butoxycarbonyl)-1H-pyrazol-4-yl)boronic acid (27.8 mg, 0.13 mmol, 1.0 eq) and tetrakis (triphenylphosphine) palladium (O) (7 mg, 0.01 mmol, 0.05 eq) was added to the reaction and the mixture was heated to 90° C. under nitrogen for a further 16 h. The solvents were removed under reduced pressure; water (2 mL) was added and the mixture was extracted with ethyl acetate (3×5 mL). The combined organic phases were washed with water (2 mL) and brine (2 mL), dried by passing through a phase separator and then concentrated under vacuum. The crude residue obtained was purified by flash chromatography (eluting isohexane to ethyl acetate, 0-75%) to give the desired tert-butyl 4-(2-((2-methyl-3-((5-(methylthio)pyrimidin-2-yl)amino)propyl)amino)benzo[d]thiazol-6-yl)-1H-pyrazole-1-carboxylate (102C) as an off-white solid. The semi-crude product was taken through to the next reaction without further purification.

$N^1$-(6-(1H-Pyrazol-4-yl)benzo[d]thiazol-2-yl)-2-methyl-$N^3$-(5-(methylthio)pyrimidin-2-yl)propane-1,3-diamine (Example 97)

A solution of hydrogen chloride (2 mL, 4M in 1,4-dioxane) was added to tert-butyl 4-(2-((2-methyl-3-((5-(methylthio)pyrimidin-2-yl)amino)propyl)amino)benzo[d]thiazol-6-yl)-1H-pyrazole-1-carboxylate (102C) (100 mg, 0.12 mmol) and the mixture stirred at room temperature for 1 hour. The solvents were removed under vacuum to afford the desired $N^1$-(6-(1H-pyrazol-4-yl)benzo[d]thiazol-2-yl)-2- methyl-N³-(5-(methylthio)pyrimidin-2-yl)propane-1,3-diamine (Example 97) as an off-white solid.

Using the procedures described in Scheme 3, according to General Method 7, the following examples were prepared:

mL, 0.21 mmol, 1.0 eq) and tetrakis(triphenylphosphine) palladium (O) (23 mg, 0.02 mmol, 0.1 eq) were added to the reaction mixture, heating to 110° C. for 18 h. The reaction was cooled to room temperature, diluted with water (2 mL)

TABLE 4

| Structure | Ex. # | 1H NMR | LC-MS (M + H)⁺ |
|---|---|---|---|
| [structure] | 97 | ¹H NMR (400 MHz, CDCl₃) δ 8.37 (s, 2H), 7.84 (s, 2H), 7.69 (d, J = 1.6 Hz, 1H), 7.53 (d, J = 8.3 Hz, 1H), 7.43 (dd, J = 1.8, 8.4 Hz, 1H), 6.00-5.91 (m, 1H), 3.63-3.26 (m, 4H), 2.36 (s, 3H), 2.21-2.11 (m, 1H), 1.07 (d, J = 6.9 Hz, 3H) NH exchangeable proton not observed. | 412 |
| [structure] | 98 | ¹H NMR (400 MHz, CDCl₃) δ 8.38 (s, 2H), 7.74 (s, 1H), 7.66 (d, J = 1.3 Hz, 1H), 7.58 (s, 1H), 7.52 (d, J = 8.4 Hz, 1H), 7.39 (dd, J = 1.7, 8.3 Hz, 1H), 6.61-6.61 (m, 1H), 5.76 (dd, J = 6.3, 6.3 Hz, 1H), 3.95 (s, 3H), 3.63-3.47 (m, 2H), 3.43-3.26 (m, 2H), 2.36 (s, 3H), 2.19-2.11 (m, 1H), 1.07 (d, J = 6.9 Hz, 3H). | 426 |
| [structure] | 99 | ¹H NMR (400 MHz, CDCl₃) δ 8.39 (s, 2H), 7.59 (d, J = 8.3 Hz, 1H), 7.43 (d, J = 1.6 Hz, 1H), 7.16 (dd, J =1.8, 8.3 Hz, 1H), 6.64-6.64 (m, 1H), 5.74 (dd, J = 6.2, 6.2 Hz, 1H), 3.64-3.49 (m, 2H), 3.43-3.27 (m, 2H), 2.41 (s, 3H), 2.37 (s, 3H), 2.27 (s, 3H), 2.18-2.14 (m, 1H), 1.08 (d, J = 6.8 Hz, 3H). | 441 |
| [structure] | 100 | ¹H NMR (400 MHz, CDCl₃) δ 8.39 (s, 2H), 8.14 (dd, J = 1.8, 5.0 Hz, 1H), 7.79 (d, J = 1.8 Hz, 1H), 7.64-7.57 (m, 2H), 7.47 (dd, J = 1.7, 8.3 Hz, 1H), 6.97 (dd, J = 5.0, 7.3 Hz, 1H), 6.61-6.61 (m, 1H), 5.74 (dd, J = 6.3, 6.3 Hz, 1H), 3.98 (s, 3H), 3.63-3.50 (m, 2H), 3.43-3.27 (m, 2H), 2.37 (s, 3H), 2.20-2.11 (m, 1H), 1.07 (d, J = 6.9 Hz, 3H). | 453 |

General Method 8

2-Methyl-N¹-(5-(methylthio)pyrimidin-2-yl)-N³-(6-(oxazol-2-yl)benzo[d]thiazol-2-yl)propane-1,3-diamine (Example 101)

N'-(6-Bromobenzo[d]thiazol-2-yl)-2-methyl-N³-(5-(methylthio)pyrimidin-2-yl)propane-1,3-diamine (102B) (90 mg, 0.21 mmol, 1.0 eq) was added to a solution of 2-(tri-n-butylstannyl)oxazole (0.044 mL, 0.21 mmol, 1.0 eq) and tetrakis(triphenylphosphine) palladium (O) (23 mg, 0.02 mmol, 0.1 eq) in N,N-dimethylformamide (0.80 mL) under nitrogen. The reaction mixture was heated to 90° C. for 16 h. A further aliquot of 2-(tri-n-butylstannyl)oxazole (0.044 mL, 0.21 mmol, 1.0 eq) and tetrakis(triphenylphosphine) palladium (O) (23 mg, 0.02 mmol, 0.1 eq) were added to the reaction mixture, heating to 110° C. for 18 h. The reaction was cooled to room temperature, diluted with water (2 mL) and extracted with ethyl acetate (3×5 mL). The combined organic phase was washed with water (2 mL) and brine (2 mL), filtered through a celite pad, and dried by passing through a phase separator before concentrating to dryness under vacuum. The crude residue obtained was twice purified by flash chromatography (first eluting isohexane to ethyl acetate, 0-100%, then ethyl acetate to methanol, 0-10%) to give a semi-crude residue which was further purified by reverse phase preparative HPLC to give the desired 2-methyl-N¹-(5-(methylthio)pyrimidin-2-yl)-N³-(6-(oxazol-2-yl)benzo[d]thiazol-2-yl)propane-1,3-diamine (101) as an off-white solid.

Using the procedures described in Scheme 3, according to General Method 8, the following examples were prepared:

TABLE 5

| Structure | Ex. # | 1H NMR | LC-MS (M + H)+ |
|---|---|---|---|
| 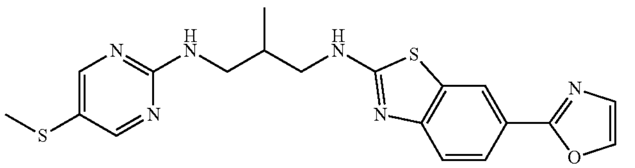 [SMILES: CSc1cnc(NCC(C)CNc2nc3ccc(-c4ncco4)cc3s2)nc1] | 101 | ¹H NMR (400 MHz, CDCl₃) δ 8.39 (s, 2H), 8.26 (d, J = 1.6 Hz, 1H), 7.98 (dd, J = 1.8, 8.5 Hz, 1H), 7.68 (s, 1H), 7.58 (d, J = 8.4 Hz, 1H), 7.21 (s, 1H), 6.75-6.75 (m, 1H), 5.68 (dd, J = 6.3, 6.3 Hz, 1H), 3.65-3.57 (m, 1H), 3.56-3.50 (m, 1H), 3.43-3.28 (m, 2H), 2.37 (s, 3H), 2.17 (s, 1H), 1.07 (d, J = 6.9 Hz, 3H). | 413 |
| 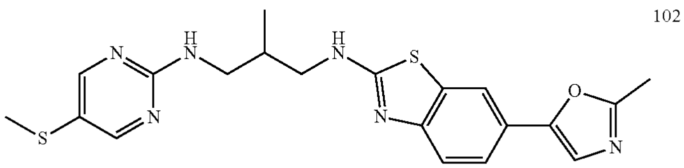 | 102 | ¹H NMR (400 MHz, CDCl₃) δ 8.37 (s, 2H), 7.80 (s, 1H), 7.53 (s, 2H), 7.13 (s, 1H), 6.76 (s, 1H), 5.84 (t, J = 6.9 Hz, 1H), 3.64-3.48 (m, 2H), 3.43-3.25 (m, 2H), 2.52 (s, 3H), 2.36 (s, 3H), 2.19-2.10 (m, 1H), 1.07 (d, J = 6.9 Hz, 3H). | 427 |

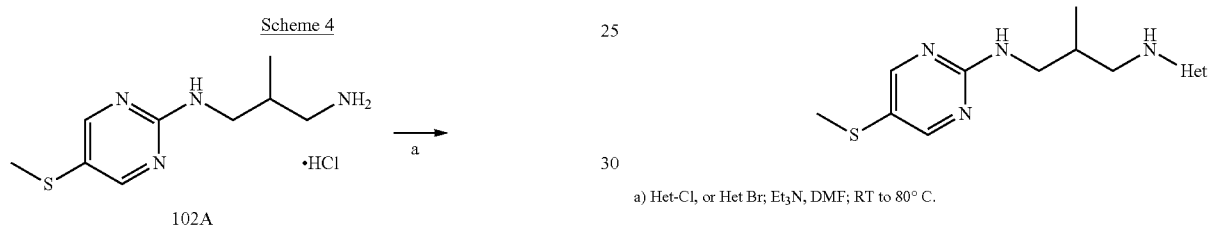

a) Het-Cl, or Het Br; Et₃N, DMF; RT to 80° C.

Using the procedures described in Scheme 4, according to General Method 3, the following examples were prepared:

TABLE 6

| Structure | Ex. # | 1H NMR | LC-MS (M + H)+ |
|---|---|---|---|
| 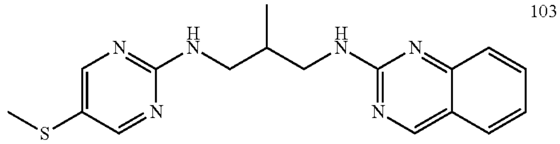 | 103 | ¹H NMR (400 MHz, DMSO) δ 9.10 (s, 1H), 8.34 (s, 2H), 7.79 (d, J = 7.8 Hz, 1H), 7.71-7.66 (m, 1H), 7.59 (s, 1H), 7.46 (d, J = 8.4 Hz, 2H), 7.22 (dd, J = 7.4, 7.4 Hz, 1H), 3.43-3.35 (m, 2H), 3.31-3.25 (m, 2H), 2.34 (s, 3H), 2.12-2.08 (m, 1H), 0.94 (d, J = 6.8 Hz, 3H). | 341 |
| 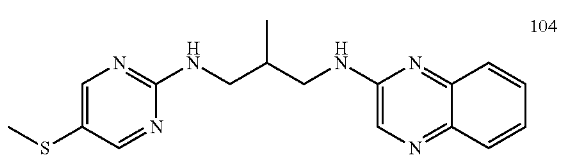 | 104 | ¹H NMR (400 MHz, DMSO) δ 8.33 (s, 3H), 7.75 (d, J = 7.9 Hz, 1H), 7.64 (dd, J = 5.6, 5.6 Hz, 1H), 7.59 (dd, J = 6.1, 6.1 Hz, 1H, 7.53 (d, J = 3.8 Hz, 2H), 7.34-7.28 (m, 1H), 3.45-3.35 (m, 2H), 3.28 (t, J = 6.2 Hz, 2H), 2.34 (s, 3H), 2.16-2.08 (m, 1H), 0.98 (d, J = 6.8 Hz. 3H). | 341 |
| 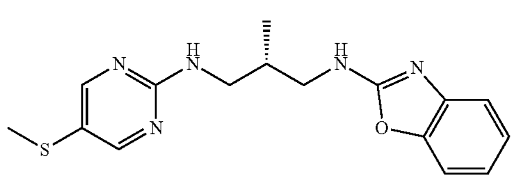 [SMILES: CSc1cnc(NC[C@H](C)CNc2nc3ccccc3o2)nc1] | 105 | ¹H NMR (400 MHz, DMSO) δ 8.32 (s, 2H), 7.92 (dd, J = 5.8, 5.8 Hz, 1H), 7.48 (dd, J = 5.7, 5.7 Hz, 1H), 7.32 (d, J = 7.7 Hz, 1H), 7.22 (d, J = 7.4 Hz, 1H), 7.10 (dd, J = 7.4, 7.4 Hz, 1H), 6.99-6.94 (m, 1H), 3.30-3.16 (m, 4H), 2.34 (s, 3H), 2.13-2.05 (m, 1H), 0.94 (d, J = 6.7 Hz, 3H). | 330 |

TABLE 6-continued

| Structure | Ex. # | $^1$H NMR | LC-MS (M + H)$^+$ |
|---|---|---|---|
| 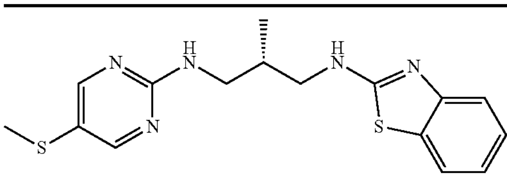 | 106 | $^1$H NMR (400 MHz, DMSO) δ 8.26 (s, 2H), 7.96 (dd, J = 5.6, 5.6 Hz, 1H), 7.57 (d, J = 7.1 Hz, 1H), 7.46 (dd, J = 5.9, 5.9 Hz, 1H), 7.28 (d, J = 7.3 Hz, 1H), 7.16-7.11 (m, 1H), 6.95-6.90 (m, 1H), 3.37-3.30 (m, 1H), 3.23-3.14 (m, 3H), 2.26 (s, 3H), 2.09-1.97 (m, 1H), 0.87 (d, J = 6.8 Hz, 3H). | 346 |
| 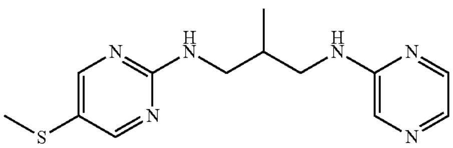 [SMILES: CSc1cnc(NCC(C)CNc2cnccn2)nc1] | 107 | $^1$H NMR (400 MHz, DMSO) δ 8.33 (s, 2H), 7.93 (s, 1H), 7.89 (d, J = 2.6 Hz, 1H), 7.61 (d, J = 2.8 Hz, 1H), 7.44 (dd, J = 5.8, 5.8 Hz, 1H), 7.05 (dd, J = 5.7, 5.7 Hz, 1H), 3.31-3.14 (m, 4H), 2.35 (s, 3H), 2.09-1.99 (m, 1H), 0.92 (d, J = 6.8 Hz, 3H). | 291 |

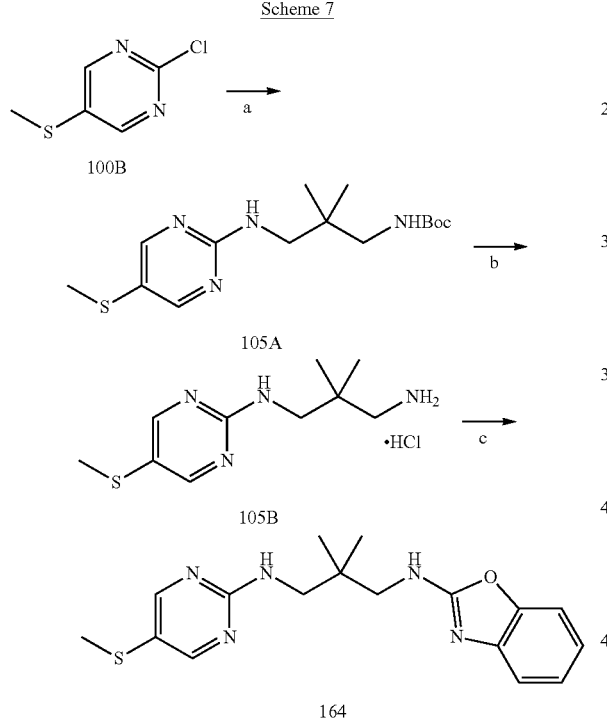

Scheme 7 a) NH$_2$CH$_2$C(CH$_3$)$_2$CH$_2$NHBoc, Cs$_2$CO$_3$, DMF; b) 4M HCl in 1,4-dioxane; c) 2-chlorobenzo[d]oxazole, Cs$_2$CO$_3$, DMF tert-Butyl (2,2-dimethyl-3-((5-(methylthio)pyrimidin-2-yl)amino)propyl)carbamate (105A)

Methodology applied was analogous to those described in General Method 1 except additional heating was required.

tert-Butyl (3-amino-2,2-dimethylpropyl)carbamate (0.13 g, 0.65 mmol, 1.05 eq) was added to a stirred suspension of 2-chloro-5-(methylthio)pyrimidine (100B) (0.10 g, 0.62 mmol, 1.0 eq) and cesium carbonate (0.24 g, 0.75 mmol, 1.2 eq) in anhydrous NN-dimethylformamide (1.5 mL) and the mixture stirred at 80° C. for 4 h. The reaction mixture was concentrated under vacuum, diluted with ethyl acetate (20 mL), washed with water (7.5 mL) and brine (5.0 mL) then dried through a phase separator. The solvents were removed under vacuum to give the desired tert-butyl (2,2-dimethyl-3-((5-(methylthio)pyrimidin-2-yl)amino)propyl)carbamate (105A) as a pale yellow oil. Yield: 0.163 g (81%). $^1$H NMR (400 MHz, DMSO) δ 8.37 (s, 2H), 7.24 (dd, J=6.6, 6.6 Hz, 1H), 6.93 (dd, J=6.3, 6.3 Hz, 1H), 3.20 (d, J=6.8 Hz, 2H), 2.85 (d, J=8.7 Hz, 2H), 2.40 (s, 3H), 1.43 (d, J=3.3 Hz, 9H), 0.83 (s, 6H).

2,2-Dimethyl-N$^1$-(5-(methylthio)pyrimidin-2-yl) propane-1,3-diamine hydrochloride (105B)

Methodology applied was analogous to those described in General Method 2. A solution of hydrogen chloride (5 mL, 4M in 1,4-dioxane) was added to tert-butyl (2,2-dimethyl-3-((5-(methylthio)pyrimidin-2-yl)amino)propyl)carbamate (105A) (0.16 g, 0.50 mmol) and the mixture was stirred at room temperature for 1 hour. The solvents were removed under vacuum to afford the desired 2,2-dimethyl-N$^1$-(5-(methylthio)pyrimidin-2-yl)propane-1,3-diamine hydrochloride (105B) as a pale yellow semi solid. Yield: 0.13 g (100%) HCl salt. $^1$H NMR (400 MHz, DMSO) δ 8.39 (s, 2H), 7.95 (s, 3H), 7.70 (s, 1H), 3.25 (d, J=5.5 Hz, 2H), 2.68-2.61 (m, 2H), 2.38 (s, 3H), 0.96 (s, 6H).

N1-(Benzo[d]oxazol-2-yl)-2,2-dimethyl-N3-(5-(methylthio)pyrimidin-2-yl)propane-1,3-diamine (Example 164)

Methodology applied was analogous to those described in General Method 3 except cesium carbonate was used as a general base.

2-Chlorobenzoxazole (0.06 mL, 0.54 mmol, 0.1 eq) was added to a stirred solution of 2,2-dimethyl-N$^1$-(5-(methylthio)pyrimidin-2-yl)propane-1,3-diamine hydrochloride (105B) (0.13 g, 0.49 mmol, 1.0 eq) and cesium carbonate (0.48 g, 1.48 mmol, 3.0 eq) in anhydrous N,N-dimethylformamide (2.0 mL) under nitrogen. The mixture was stirred at either 80° C. or room temperature for 16 h and was then concentrated under vacuum. Water (2.5 mL) was added and the mixture extracted with ethyl acetate (3×5 mL). The combined organic phases were washed with water (2 mL) and brine (2 mL) then dried through a phase separator. The solvents were removed under vacuum to give a crude yellow oil which was purified by preparative HPLC to give the desired N$^1$-(benzo[d]oxazol-2-yl)-2,2-dimethyl-N$^3$-(5-(methylthio)pyrimidin-2-yl)propane-1,3-diamine (Example 164) as an off-white solid.

Using the procedures described in Scheme 7, according to General Method 3, the following examples were prepared:

TABLE 9

| Structure | Ex. # | ¹H NMR | LC-MS (M + H)⁺ |
|---|---|---|---|
| 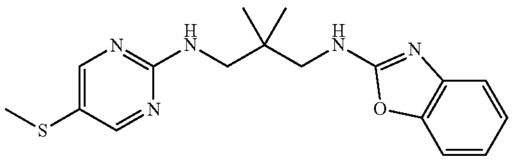 [SMILES: CSc1cnc(NCC(C)(C)CNc2nc3ccccc3o2)nc1] | 164 | ¹H NMR (400 MHz, DMSO) δ 8.33 (s, 2H), 8.21 (s, 1H), 7.53-7.51 (m, 1H), 7.37 (d, J = 7.8 Hz, 1H), 7.24 (d, J = 7.4 Hz, 1H), 7.14 (dd, J = 7.4, 7.4 Hz, 1H), 7.02 (dd, J = 7.3, 7.3 Hz, 1H), 3.30-3.23 (m, 4H), 2.34 (s, 3H), 0.93 (s, 6H). | 344 |
| 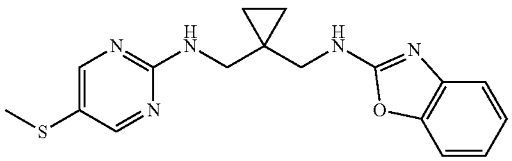 [SMILES: CSc1cnc(NCC2(CNc3nc4ccccc4o3)CC2)nc1] | 165 | ¹H NMR (400 MHz, CDCl₃) δ 8.36 (s, 2H), 7.34 (d, J = 7.5 Hz, 1H), 7.23 (d, J = 7.8 Hz, 1H), 7.15 (dd, J = 7.2, 7.2 Hz, 1H), 7.01 (dd, J = 7.3, 7.3 Hz, 1H), 6.28-6.27 (m, 1H), 5.73 (dd, J = 6.3, 6.3 Hz, 1H), 3.47-3.38 (m, 4H), 2.36 (s, 3H), 0.69-0.65 (m, 2H), 0.58-0.54 (m, 2H). | 342 |
| 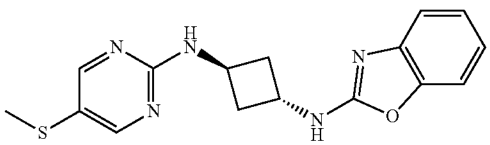 [SMILES: CSc1cnc(N[C@H]2C[C@H](Nc3nc4ccccc4o3)C2)nc1] | 166 | ¹H NMR (400 MHz, DMSO) δ 8.36 (s, 2H), 8.35-8.29 (m, 1H), 7.84 (d, J = 6.7 Hz, 1H), 7.35 (d, J = 7.8 Hz, 1H), 7.25 (d, J = 7.4 Hz, 1H), 7.12 (dd, J = 7.4, 7.4 Hz, 1H), 6.99 (dd, J = 7.3, 7.3 Hz, 1H), 4.47-4.40 (m, 1H), 4.29 (dd, J = 6.5, 12.9 Hz, 1H), 2.38 (d, J = 14.1 Hz, 6H) NH proton not observed. | 328 |
| 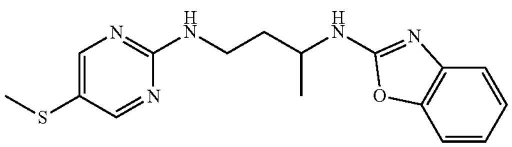 [SMILES: CSc1cnc(NCCC(C)Nc2nc3ccccc3o2)nc1] | 167 | ¹H NMR (400 MHz, DMSO) δ 8.30 (s, 2H), 7.84 (d, J = 8.2 Hz, 1H), 7.41 (dd, J = 5.4. 5.4 Hz, 1H), 7.31 (d, J = 7.7 Hz, 1H), 7.21 (d, J = 7.4 Hz, 1H), 7.10 (dd, J = 7.4, 7.4 Hz, 1H), 6.96 (dd, J = 7.2, 7.2 Hz, 1H), 3.91-3.83 (m, 1H), 3.38-3.34 (m, 2H), 2.32 (s, 3H), 1.85-1.77 (m, 2H), 1.24 (d, J = 6.5 Hz, 3H). | 330 |
| 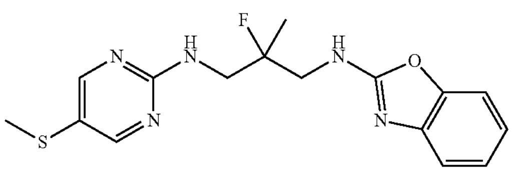 [SMILES: CSc1cnc(NCC(C)(F)CNc2nc3ccccc3o2)nc1] | 168 | ¹H NMR (400 MHz, CDCl₃) δ 8.38 (2H, s), 7.37 (1H, d, J = 7.8 Hz), 7.24 (1H, s), 7.17 (1H, dd, J = 7.6, 7.6 Hz), 7.04 (1H, dd, J = 7.7, 7.7 Hz), 6.23-6.23 (1H, m), 5.95 (1H, dd, J = 6.5, 6.5 Hz), 3.96-3.74 (2H, m), 3.69-3.58 (2H, m), 2.37 (3H, s), 1.47 (3H, d, J = 21.8 Hz); | 348 |
| 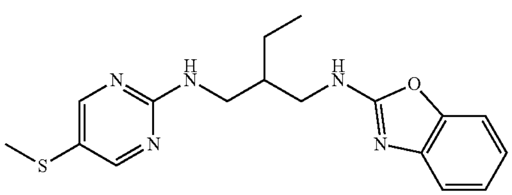 [SMILES: CCC(CNc1ncc(SC)cn1)CNc1nc2ccccc2o1] | 169 | ¹H NMR(400 MHz, DMSO) δ 8.32 (s, 2H), 7.86 (dd, J = 5.3, 5.3 Hz, 1H), 7.44 (dd, J = 6.0, 6.0 Hz, 1H), 7.32 (d, J = 7.5 Hz, 1H), 7.22 (d, J = 7.3 Hz, 1H), 7.10 (dd, J = 7.3, 7.3 Hz, 1H), 6.99-6.94 (m, 1H), 2.34 (s, 3H), 1.94-1.84 (m, 1H), 1.42-1.23 (m, 3H), 0.93 (dd, J = 7.5, 7.5 Hz, 4H), 2H not observed, under water peak. | 344 |
| 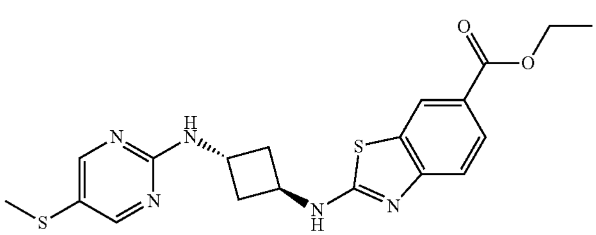 [SMILES: CCOC(=O)c1ccc2nc(N[C@H]3C[C@H](Nc4ncc(SC)cn4)C3)sc2c1] | 170 | ¹H NMR (400 MHz, DMSO) δ 8.86 (d, J = 6.4 Hz, 1H), 8.36 (s, 2H), 8.32 (d, J = 1.8 Hz, 1H), 7.88-7.82 (m, 2H), 7.44 (d, J = 8.4 Hz, 1H), 4.49-4.40 (m, 2H), 4.30 (q, J = 7.1 Hz, 2H), 2.44-2.32 (m, 7H), 1.33 (dd, J = 7.1, 7.1Hz. 3H). | 416 |
| 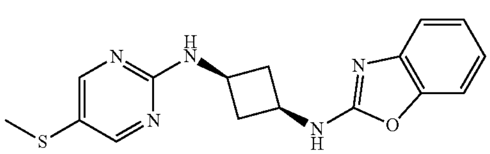 [SMILES: CSc1cnc(N[C@H]2C[C@@H](Nc3nc4ccccc4o3)C2)nc1] | 171 | ¹H NMR (400 MHz, CDCl₃) δ 8.36 (s, 2H), 7.38 (d, J = 7.8 Hz, 1H), 7.25-7.24 (m, 1H), 7.17 (dd, J = 7.5, 7.5 Hz, 1H), 7.04 (dd, J = 7.7, 7.7 Hz, 1H), 5.37 (d, J = 7.0 Hz, 1H), 5.10 (d, J = 7.3 Hz, 1H), 4.26-4.14 (m, 2H), 3.11-3.04 (m, 2H), 2.37 (s, 3H), 2.06-1.98 (m, 2H). | 328 |

TABLE 9-continued

| Structure | Ex. # | ¹H NMR | LC-MS (M + H)⁺ |
|---|---|---|---|
| 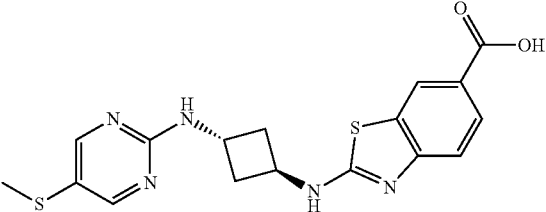 [SMILES: CSc1cnc(N[C@H]2C[C@H](Nc3nc4ccc(C(=O)O)cc4s3)C2)nc1] | 172 | ¹H NMR (400 MHz, DMSO) δ 8.77 (d, J = 5.9 Hz, 1H), 8.36 (s, 2H), 8.27 (d, J = 1.5 Hz, 1H), 7.86 (d, J = 6.7 Hz, 1H), 7.81 (dd, J = 1.8, 8.4 Hz, 1H), 7.40 (d, J = 8.4 Hz, 1H), 4.47-4.38 (m, 2H), 2.47-2.34 (m, 6H). | 388 |
| 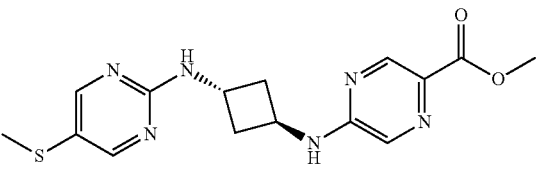 | 173 | ¹H NMR(400 MHz, CDCl₃) δ 8.79 (1H, s), 8.36 (2H, s), 7.89 (1H, s), 5.46 (1H, d, J = 5.9 Hz), 5.38 (1H, d, J = 4.9 Hz), 4.61-4.48 (2H, m), 3.96 (3H, s), 2.49 (3H, dd, J = 6.6, 6.6 Hz), 2.37 (3H, s). | 347 |
| 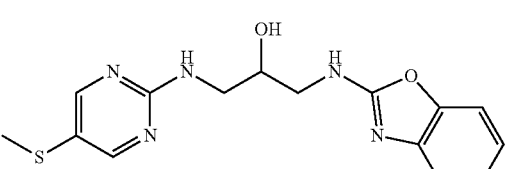 | 174 | ¹H NMR (400 MHz, CDCl₃) δ 8.36 (s, 2H), 7.37 (d, J = 7.7 Hz, 1H), 7.17 (dd, J = 7.4, 7.4 Hz, 1H), 7.07-7.02 (m, 1H), 5.80 (dd, J = 5.7, 5.7 Hz, 1H), 5.63 (s, 1H), 4.82-4.81 (m, 1H), 4.12-4.06 (m, 1H), 3.74-3.49 (m, 4H), 2.38 (s, 3H). | 332 |

Scheme 8

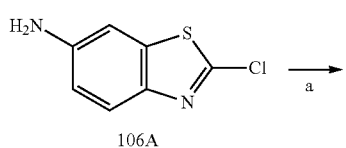

106A

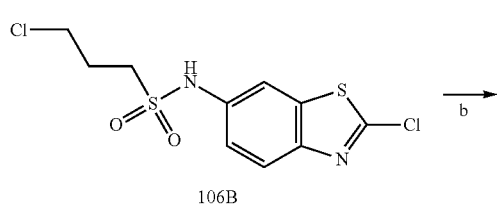

106B

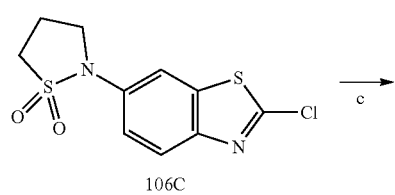

106C

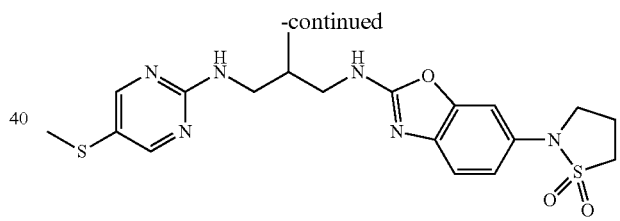

175 a) ClS(O₂)CH₂CH₂CH₂Cl, NaH, DMF b) NaH, DMF c) 102A, Et₃N, Cs₂CO₃

3-Chloro-N-(2-chlorobenzo[d]thiazol-6-yl)propane-1-sulfonamide (106B)

Sodium hydride (60% dispersion in mineral oil) (326 mg, 8.15 mmol, 3.0 eq) was added portion-wise to an ice cooled solution of 2-chlorobenzothiazole-6-amine (500 mg, 2.71 mmol, 1.0 eq) in N,N-dimethylformamide (25 mL) and the mixture stirred for 1 hour under ice cooling. A solution of 3-chloropropane-1-sulfonyl chloride (673 mg, 3.80 mmol, 1.4 eq) in N,N-dimethylformamide (3 mL) was added dropwise and the reaction mixture was then allowed to warm to ambient temperature over 3 h. The reaction mixture was diluted with brine (20 mL) and extracted with ethyl acetate (2×25 mL). The combined organic fractions were combined and concentrated under reduced pressure to give a pale yellow oil that was purified by flash chromatography (eluting iso-hexanes to ethyl acetate, 0-100%) to give the desired product 3-chloro-N-(2-chlorobenzo[d]thiazol-6-yl)propane-1-sulfonamide 106B as an off-white gum.

Yield: 427 mg (48%). ¹H NMR (400 MHz, MeOD) δ 7.87-7.84 (m, 2H), 7.38 (dd, J=2.3, 8.8 Hz, 1H), 3.67 (dd, J=6.3, 6.3 Hz, 2H), 2.27-2.19 (m, 2H). Note CH₂ protons obscured by MeOD.

2-(2-Chlorobenzo[d]thiazol-6-yl)isothiazolidine 1,1-dioxide (106C)

Sodium hydride (60% dispersion in mineral oil) (98 mg, 2.46 mmol, 2.0 eq) was added to an ice cooled solution of 3-chloro-N-(2-chlorobenzo[d]thiazol-6-yl)propane-1-sulfonamide (106B) (400 mg, 1.23 mmol, 1.0 eq) in N,N-dimethylformamide (5 mL). The reaction mixture was stirred for 1 hour under ice cooling and then quenched by the careful addition of a saturated solution of ammonium chloride (20 mL). The resulting mixture was extracted with ethyl acetate (3×20 mL) and the combined organic phases were washed with water (20 mL), brine (20 mL) and then concentrated under vacuum to give a gum. The crude product was purified by flash chromatography (eluting isohexane to ethyl acetate, 0-100%) to give the desired product (106C) as an off-white gum. Yield: 220 mg (62%). ¹H NMR (400 MHz, CDCl₃) δ 7.92 (d, J=8.9 Hz, 1H), 7.72 (d, J=2.1 Hz, 1H), 7.38 (dd, J=2.4, 8.9 Hz, 1H), 3.84 (dd, J=6.5, 6.5 Hz, 2H), 3.43 (dd, J=7.5, 7.5 Hz, 2H), 2.63-2.55 (m, 2H).

2-(2-((2-Methyl-3-((5-(methylthio)pyrimidin-2-yl)amino)propyl)amino)benzo[d]thiazol-6-yl)isothiazolidine 1,1-dioxide (Example 175)

Methodology applied was analogous to those described in General Method 3. Yield: 25 mg (15%). ¹H NMR (400 MHz, DMSO) δ 8.34 (s, 2H), 8.03 (dd, J=5.6, 5.6 Hz, 1H), 7.57 (d, J=2.3 Hz, 1H), 7.51 (dd, J=5.9, 5.9 Hz, 1H), 7.35 (d, J=8.8 Hz, 1H), 7.14 (dd, J=2.4, 8.7 Hz, 1H), 3.72 (dd, J=6.5, 6.5 Hz, 2H), 3.47 (dd, J=7.5, 7.5 Hz, 2H), 3.45-3.38 (m, 1H), 3.30-3.22 (m, 3H), 2.44-2.36 (m, 2H), 2.35 (s, 3H), 2.13-2.06 (m, 1H), 0.95 (d, J=6.8 Hz, 3H); MS (ESI+) m/z 465 (M+H)⁺.

Scheme 9

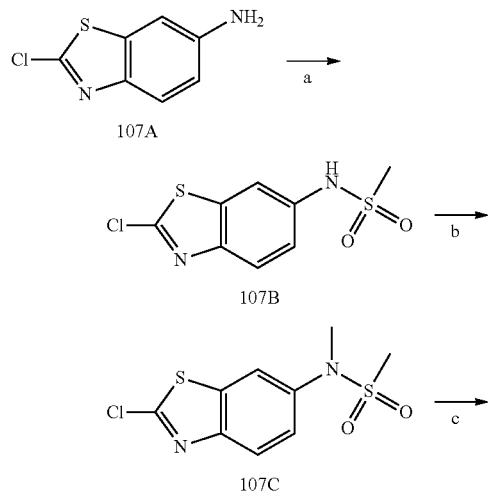

107A
107B
107C

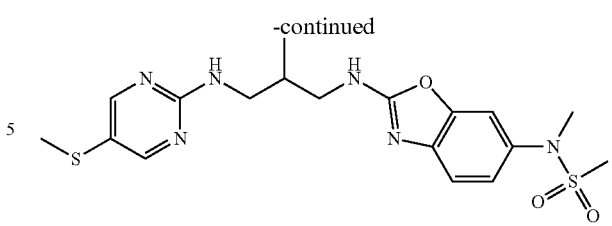

176 a) MeSO₂Cl, pyridine, DCM b) NaH, MeI, THF c) 102A, Et₃N, DMF

N-(2-Chlorobenzo[d]thiazol-6-yl)methanesulfonamide (107B)

Methanesulfonyl chloride (0.055 mL, 0.706 mmol, 1.3 eq) was added dropwise into an ice cooled solution of 2-chlorobenzothiazole-6-amine (100 mg, 0.54 mmol, 1.0 eq) and pyridine (0.066 mL, 0.815 mmol, 1.5 eq) in anhydrous dichloromethane (5 mL). The mixture was stirred at 0° C. for 15 minutes and was then allowed to warm to ambient temperature over 1 hour. The reaction mixture was quenched with water (1 mL). The organic phase was removed and concentrated under reduced pressure to give a pale yellow oil which was purified by flash chromatography (eluting iso-hexanes to ethyl acetate, 0-100%) to give the desired N-(2-chlorobenzo[d]thiazol-6-yl)methanesulfonamide (107B) as a pale yellow gum.

Yield: 135 mg (94.8%)¹H NMR (400 MHz, CDCl₃) δ 7.88 (d, J=8.8 Hz, 1H), 7.79 (d, J=2.1 Hz, 1H), 3.00 (s, 3H). Aromatic H proton obscured by CDCl₃, NH exchangeable proton not observed.

N-(2-Chlorobenzo[d]thiazol-6-yl)-N-methylmethanesulfonamide (107C)

Sodium hydride (60% dispersion in mineral oil) (31 mg, 0.772 mmol, 1.5 eq) was added portion-wise to an ice cooled solution of N-(2-chlorobenzo[d]thiazol-6-yl)methanesulfonamide (107B) (135 mg, 0.515 mmol, 1.0 eq) in anhydrous tetrahydrofuran (2 mL). The mixture was stirred at room temperature for 2 h. Iodomethane (0.048 mL, 0.772 mmol, 1.5 eq) was added and the mixture was stirred at room temperature for a further 2 h. Water (1 mL) was added and the solvents were then removed under high vacuum to give a pale yellow gum that was purified by flash chromatography (eluting iso-hexanes to ethyl acetate, 0-100%) to give the desired N-(2-chlorobenzo[d]thiazol-6-yl)-N-methylmethanesulfonamide (107C) as a pale yellow gum. Yield: 100 mg (70%)¹H NMR (400 MHz, CDCl₃) δ 7.95 (d, J=8.8 Hz, 1H), 7.86 (d, J=2.1 Hz, 1H), 7.48 (dd, J=2.3, 8.8 Hz, 1H), 3.39 (s, 3H), 2.88 (s, 3H).

N-Methyl-N-(2-((2-methyl-3-((5-(methylthio)pyrimidin-2-yl)amino)propyl)amino) benzo[d]thiazol-6-yl)methanesulfonamide (Example 176)

Methodology applied was analogous to those described in General Method 3.

Yield: 89 mg (60%)¹H NMR (400 MHz, CDCl₃) δ 8.38 (s, 2H), 7.62 (d, J=2.0 Hz, 1H), 7.51 (d, J=8.7 Hz, 1H), 7.24 (d, J=3.2 Hz, 1H), 5.74 (dd, J=6.5, 6.5 Hz, 1H), 3.34-3.33 (m, 6H), 2.86 (s, 3H), 2.37 (s, 3H), 2.20-2.10 (m, 1H), 1.06 (d, J=6.9 Hz, 3H). Not all NH exchangeable protons observed; MS (ESI+) m/z 453 (M+H)⁺.

Scheme 10
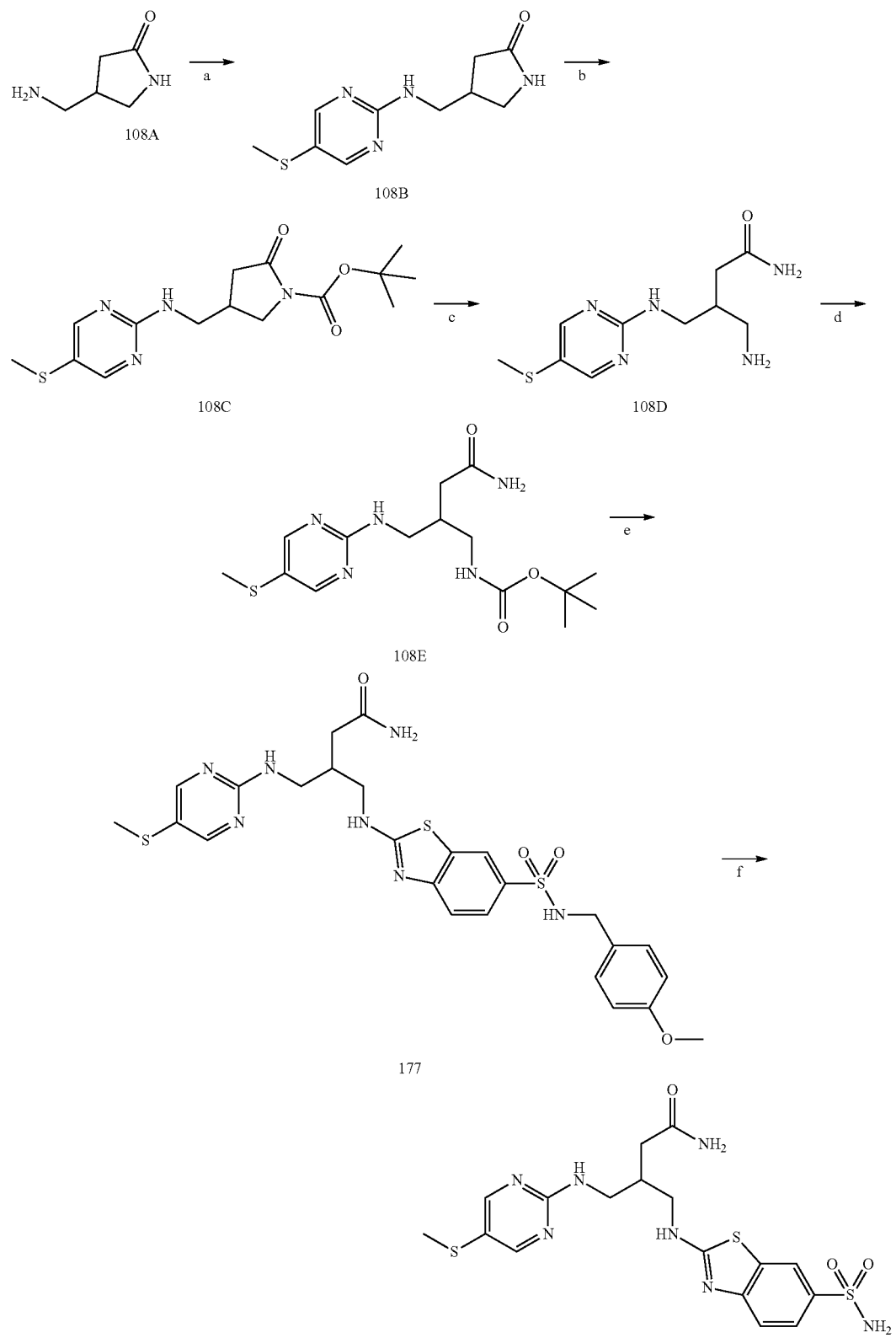
a) 100B, Cs₂CO₃, DMF; b) BOC₂O, Et₃N, DMAP, DCM; c) 1. NH₄OH, 2. HCl; d) 101B, Et₃N, DMF; e) TFA, DCM

4-(((5-(Methylthio)pyrimidin-2-yl)amino)methyl) pyrrolidin-2-one (108B)

Methodology applied was analogous to those described in General Method 1. 5-Aminomethyl-pyrrolidin-2-one (108A) (1.0 g, 8.76 mmol, 1.0 eq) was added to a stirred suspension of 2-chloro-5-(methylthio)pyrimidine (100B) (1.4 g, 8.76 mmol, 1.0 eq) and cesium carbonate (8.56 g, 26.28 mmol, 3.0 eq) in anhydrous dimethylformamide (10 mL). The mixture was heated to 50° C. for 18 h and then concentrated under reduced pressure. The liquor obtained was diluted with ethyl acetate (50 mL), washed with water (10 mL) and brine (10 mL) and then dried through a phase separator. The solvents were removed under reduced pressure to afford a crude residue that was purified by trituration in methanol to give the desired product 4-(((5-(methylthio) pyrimidin-2-yl)amino)methyl)pyrrolidin-2-one (108B) as a yellow solid. The aqueous phase was concentrated under reduced pressure, combined with the filtrate and purified by flash chromatography (eluting dichloromethane to methanol, 0-10%) to give the desired product 4-(((5-(methylthio) pyrimidin-2-yl)amino)methyl)pyrrolidin-2-one (108B) as a yellow solid. Both crops were combined and used in the next step.

Yield: 0.74 g (36%). $^1$H NMR (400 MHz, CDCl$_3$) δ 8.35 (s, 2H), 5.79-5.76 (m, 1H), 5.48 (dd, J=5.5, 5.5 Hz, 1H), 3.57-3.50 (m, 3H), 3.20 (dd, J=5.3, 9.5 Hz, 1H), 2.89-2.84 (m, 1H), 2.53-2.46 (m, 1H), 2.37 (s, 3H), 2.16 (dd, J=6.4, 17.1 Hz, 1H).

tert-Butyl 4-(((5-(methylthio)pyrimidin-2-yl)amino) methyl)-2-oxopyrrolidine-1-carboxylate (108C)

4-Dimethylaminopyridine (5 mg, 0.04 mmol, 0.1 eq) was added to a stirred suspension of 4-(((5-(methylthio)pyrimidin-2-yl)amino)methyl)pyrrolidin-2-one (108B) (100 mg, 0.4 mmol, 1.0 eq), di-tert-butyl dicarbonate (229 mg, 1.0 mmol, 2.5 eq) and triethylamine (0.146 mL, 1.00 mmol, 2.5 eq) in dichloromethane (4.2 mL). The mixture was stirred at room temperature for 72 h and then water (3.0 mL) was added. The mixture was extracted with ethyl acetate (3×5.0 mL) and the combined organic phases were washed with brine (2.5 mL) then dried passing through a phase separator. The solvents were removed under reduced pressure to afford a crude residue which was purified by reverse phase chromatography (eluting 0.1% formic solution to acetonitrile, 5-100%) to give the desired product tert-butyl 4-(((5-(methylthio)pyrimidin-2-yl)amino)methyl)-2-oxopyrrolidine-1-carboxylate (108C).

Yield: 72 mg (53%). $^1$H NMR (400 MHz, DMSO) δ 8.35 (s, 2H), 7.62 (t, J=6.1 Hz, 1H), 3.73 (dd, J=7.8, 10.4 Hz, 1H), 3.50-3.44 (m, 1H), 3.29 (d, J=6.4 Hz, 2H), 2.60-2.55 (m, 2H), 2.36 (s, 3H), 2.28 (dd, J=9.6, 20.9 Hz, 1H), 1.44 (s, 9H).

tert-Butyl (4-amino-2-(((5-(methylthio)pyrimidin-2-yl)amino)methyl)-4-oxobutyl)carbamate (108D)

A solution of ammonium hydroxide (2.2 mL) was added to tert-butyl 4-(((5-(methylthio)pyrimidin-2-yl)amino) methyl)-2-oxopyrrolidine-1-carboxylate (108C) (72 mg, 0.21 mmol) and the mixture was heated at 80° C. for 1.5 h. The mixture was cooled to room temperature then extracted with dichloromethane (3×5 mL). The organic solvents were dried passing through a phase separator then removed under reduced pressure to afford the desired product tert-butyl (4-amino-2-(((5-(methylthio)pyrimidin-2-yl)amino) methyl)-4-oxobutyl)carbamate (108D).

Yield: 61 mg (86%). $^1$H NMR (400 MHz, DMSO) δ 8.33 (s, 2H), 7.32 (s, 1H), 7.25 (dd, J=6.0, 6.0 Hz, 1H), 6.81 (s, 2H), 3.24 (dd, J=6.2, 6.2 Hz, 2H), 2.97 (dd, J=6.0, 6.0 Hz, 2H), 2.36 (s, 3H), 2.18-2.08 (m, 1H), 2.04 (d, J=6.4 Hz, 2H), 1.38 (s, 9H).

4-Amino-3-(((5-(methylthio)pyrimidin-2-yl)amino) methyl)butanamide dihydrochloride salt (108E)

Methodology applied was analogous to those described in General Method 2. A solution of hydrogen chloride (0.7 mL, 4M in 1,4-dioxane) was added to tert-butyl (4-amino-2-(((5-(methylthio)pyrimidin-2-yl)amino)methyl)-4-oxobutyl)carbamate (108D) (61 mg, 0.17 mmol) and the mixture was stirred at room temperature for 2 h. The solvents were removed under reduced pressure to afford the desired product 4-amino-3-(((5-(methylthio)pyrimidin-2-yl)amino) methyl)butanamide dihydrochloride salt (108E) as a pale yellow solid.

Yield: 56 mg (100%) HCl salt.

4-((6-(N-(4-Methoxybenzyl)sulfamoyl)benzo[d] thiazol-2-yl)amino)-3-(((5-(methylthio) pyrimidin-2-yl)amino)methyl)butanamide (177)

Methodology applied was analogous to those described in General Method 3. 2-Chloro-N-(4-methoxybenzyl)benzo[d] thiazole-6-sulfonamide (101B) (70 mg, 0.19 mmol, 1.10 eq) was added to a stirred solution of 4-amino-3-(((5-(methylthio)pyrimidin-2-yl)amino)methyl)butanamide dihydrochloride salt (108E) (56 mg, 0.17 mmol, 1.0 eq) and triethylamine (0.072 mL, 0.51 mmol, 3.0 eq) in anhydrous dimethylformamide (2.0 mL) under nitrogen. The mixture was stirred at room temperature for 72 h and then concentrated under reduced pressure. Water (2.5 mL) was added and the resulting precipitate was collected by filtration, then washed with methanol. The organic filtrate was concentrated under reduced pressure to give a crude residue which was purified by flash chromatography (eluting dichloromethane to methanol, 0-25%) to give the desired product 4-((6-(N-(4-methoxybenzyl)sulfamoyl)benzo[d]thiazol-2-yl)amino)-3-(((5-(methylthio)pyrimidin-2-yl)amino)methyl)butanamide (Example 177) as an off white solid.

Yield: 25 mg (25%). $^1$H NMR (400 MHz, DMSO) δ 8.45 (dd, J=5.6, 5.6 Hz, 1H), 8.33 (s, 2H), 8.08 (d, J=1.8 Hz, 1H), 7.88 (dd, J=6.1, 6.1 Hz, 1H), 7.62 (dd, J=1.9, 8.5 Hz, 1H), 7.49-7.42 (m, 2H), 7.39-7.37 (m, 1H), 7.14 (d, J=8.7 Hz, 2H), 6.87-6.87 (m, 1H), 6.81 (d, J=8.7 Hz, 2H), 3.89 (d, J=6.0 Hz, 2H), 3.70 (s, 3H), 3.48 (d, J=1.1 Hz, 2H), 3.37 (dd, J=6.1, 6.1 Hz, 2H), 2.43-2.37 (m, 1H), 2.34 (s, 3H), 2.22-2.17 (m, 2H).

4-((5-(Methylthio)pyrimidin-2-yl)amino)-3-(((6-sulfamoylbenzo[d]thiazol-2-yl)amino)methyl)butanamide (178)

Trifluoroacetic acid (0.3 mL) was added dropwise to a 0° C. cooled solution of 4-((6-(N-(4-methoxybenzyl)sulfamoyl)benzo[d]thiazol-2-yl)amino)-3-(((5-(methylthio) pyrimidin-2-yl)amino)methyl)butanamide (177) (20 mg, 0.03 mmol, 1.0 eq) in anhydrous dichloromethane (0.3 mL). The mixture was stirred for 30 minutes and then allowed to warm to room temperature over 8 h. A further aliquot of trifluoroacetic acid (1 mL) was added and the mixture was stirred for 16 h. The reaction mixture was concentrated under pressure then carefully made basic with the addition of a saturated aqueous solution of sodium hydrogen carbonate (3 mL). The mixture was extracted with ethyl acetate (3×5 mL). The combined organic phase was washed with brine (3 mL), dried over anhydrous magnesium sulphate and then concentrated under reduced pressure. The crude residue obtained was purified by flash chromatography (eluting dichloromethane to methanol, 0-20%) to give the desired product 4-((5-(methylthio)pyrimidin-2-yl)amino)-3-(((6-sulfamoylbenzo[d]thiazol-2-yl)amino) methyl)butanamide (Example 178) as a white solid.

Yield: 12 mg (75%). $^1$H NMR (400 MHz, DMSO) δ 8.41 (dd, J=5.5, 5.5 Hz, 1H), 8.33 (s, 2H), 8.13 (d, J=1.8 Hz, 1H), 7.67 (dd, J=1.9, 8.5 Hz, 1H), 7.47-7.43 (m, 2H), 7.38 (s, 1H), 7.21 (s, 2H), 6.86 (s, 1H), 3.46-3.46 (m, 2H), 3.36 (dd, J=6.2, 6.2 Hz, 2H), 2.39-2.38 (m, 1H), 2.34 (s, 3H), 2.21-2.17 (m, 2H).

Using the procedures described in Scheme 10, the following example was synthesized:

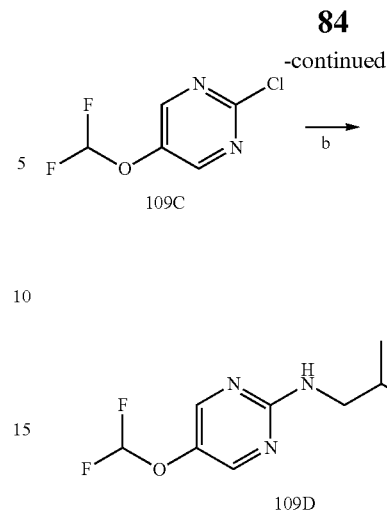

TABLE 10

| Structure | Ex. # | 1H NMR | LC-MS (M + H)+ |
|---|---|---|---|
| 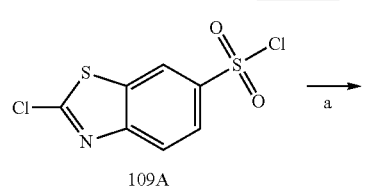 | 179 | $^1$H NMR (400 MHz, DMSO) δ 8.45 (dd, J = 5.4, 5.4 Hz, 1H), 8.33 (s, 2H), 8.08 (d, J = 1.9 Hz, 1H), 7.88 (dd, J = 6.0, 6.0 Hz, 1H), 7.81 (q, J = 4.5 Hz, 1H), 7.62 (dd, J = 1.9, 8.5 Hz, 1H), 7.47-7.41 (m, 2H), 7.14 (d, J = 8.8 Hz, 2H), 6.81 (d, J = 8.8 Hz, 2H), 3.89 (d, J = 4.8 Hz, 2H), 3.70 (s, 3H), 3.52-3.42 (m, 2H), 3.38-3.31 (m, 2H), 2.59 (d, J = 4.5 Hz, 3H), 2.48-2.35 (m, 1H), 2.34 (s, 3H), 2.22-2.17 (m, 2H). | 602 |

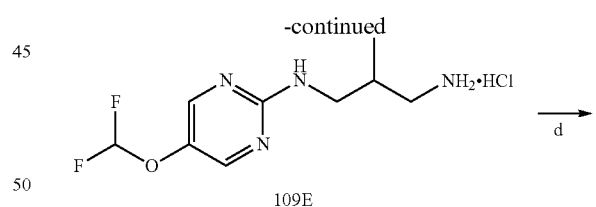

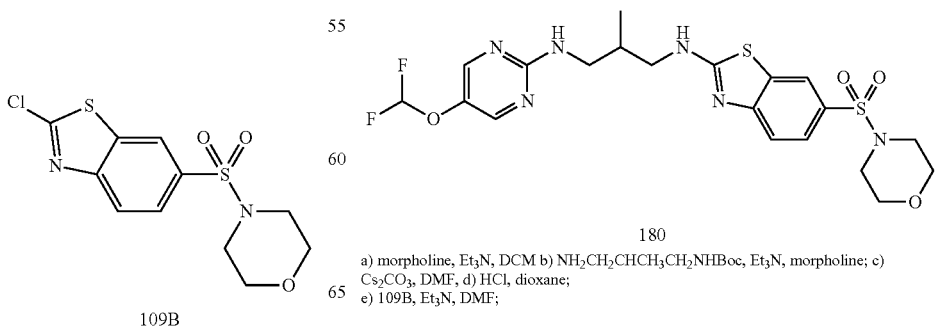

a) morpholine, Et₃N, DCM b) NH₂CH₂CHCH₃CH₂NHBoc, Et₃N, morpholine; c) Cs₂CO₃, DMF, d) HCl, dioxane;
e) 109B, Et₃N, DMF;

4-((2-Chlorobenzo[d]thiazol-6-yl)sulfonyl)morpholine (109B)

Methodology applied was analogous to those described in General Method 6 using dichloromethane as solvent instead of tetrahydrofuran.

Yield: 686 mg. $^1$H NMR (400 MHz, CDCl$_3$) δ 8.25 (d, J=1.8 Hz, 1H), 8.10 (d, J=8.6 Hz, 1H), 7.85 (dd, J=1.3, 8.6 Hz, 1H), 3.75 (dd, J=4.7, 4.7 Hz, 4H), 3.04 (dd, J=4.7, 4.7 Hz, 4H); MS (ESI+) m/z 319 (M+H)+.

tert-Butyl (3-((5-(difluoromethoxy)pyrimidin-2-yl)amino)-2-methylpropyl)carbamate (109D)

Methodology applied was analogous to those described in General Method 1. Yield: 433 mg. $^1$H NMR (400 MHz, CDCl$_3$) δ 8.16-8.15 (m, 2H), 5.05-5.05 (m, 1H), 3.47-3.38 (m, 1H), 3.31-3.17 (m, 2H), 3.04-2.95 (m, 1H), 1.96-1.86 (m, 1H), 1.60-1.58 (m, 1H), 0.96-0.94 (m, 3H); MS (ESI+) m/z 333 (M+H)+.

N1-(5-(Difluoromethoxy)pyrimidin-2-yl)-2-methyl-propane-1,3-diamine hydrochloride (109E)

A solution of hydrogen chloride (2.7 mL, 4M in 1,4-dioxane) was added to tert-butyl (3-((5-(difluoromethoxy)pyrimidin-2-yl)amino)-2-methylpropyl)carbamate (109D) (300 mg, 0.903 mmol) and stirred at room temperature for 15 minutes. The solvents were removed under vacuum to give the crude title compound N1-(5-(difluoromethoxy)pyrimidin-2-yl)-2-methylpropane-1,3-diamine hydrochloride (109E) was taken on to next step without further purification.

Yield: 225 mg (Quant.). MS (ESI+) m/z 233 (M+H)+.

N1-(5-(Difluoromethoxy)pyrimidin-2-yl)-2-methyl-N3-(6-(morpholinosulfonyl) benzo[d]thiazol-2-yl)propane-1,3-diamine (180)

Methodology applied was analogous to those described in General Method 3. Yield: 225 mg. $^1$H NMR (400 MHz, CDCl$_3$) δ 8.21 (s, 2H), 7.97 (d, J=1.5 Hz, 1H), 7.65 (dd, J=1.8, 8.5 Hz, 1H), 7.59 (d, J=8.5 Hz, 1H), 6.91 (s, 1H), 6.43 (t, J=71.6 Hz, 1H), 5.72 (dd, J=6.6, 6.6 Hz, 1H), 3.77-3.73 (m, 4H), 3.62-3.51 (m, 2H), 3.43-3.29 (m, 2H), 3.01 (dd, J=4.6, 4.6 Hz, 4H), 2.21-2.12 (m, 1H), 1.08 (d, J=6.9 Hz, 3H); (ESI+) m/z 515 (M+H)+.

Following the procedures described in Scheme 11, the following examples were synthesized:

TABLE 11

| Structure | Ex. # | $^1$H NMR | LC-MS (M + H)+ |
|---|---|---|---|
| 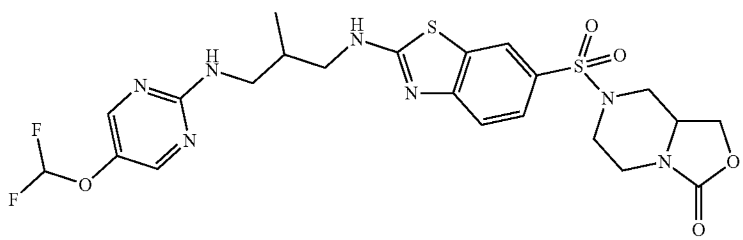 [SMILES: CC(CNc1ncc(OC(F)F)cn1)CNc1nc2ccc(S(=O)(=O)N3CCN4C(=O)OCC4C3)cc2s1] | 181 | $^1$H NMR (400 MHz, CDCl$_3$) δ 8.21 (s, 2H), 7.94 (d, J = 1.5 Hz, 1H), 7.64-7.60 (m, 2H), 6.93 (s, 1H), 6.44 (t, J = 72.8 Hz, 1H), 5.66 (dd, J = 6.1, 6.1 Hz, 1H), 4.44-4.39 (m, 1H), 3.88 (tt, J = 7.5, 7.8 Hz, 3H), 3.80-3.74 (m, 1H), 3.62-3.51 (m, 2H), 3.42-3.17 (m, 3H), 2.37-2.29 (m, 1H), 2.23-2.14 (m, 2H), 1.08 (d, J = 6.9 Hz, 3H). | 570 |
| 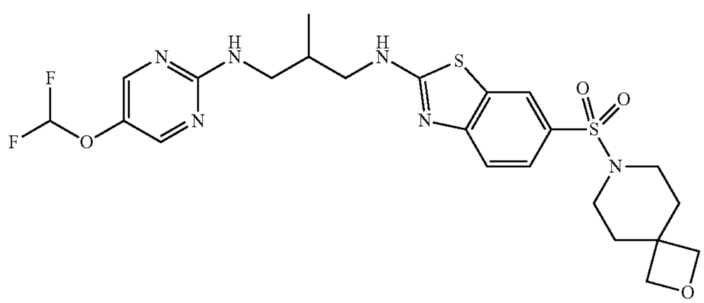 [SMILES: CC(CNc1ncc(OC(F)F)cn1)CNc1nc2ccc(S(=O)(=O)N3CCC4(CC3)COC4)cc2s1] | 182 | $^1$H NMR (400 MHz, CDCl$_3$) δ 8.22 (s, 2H), 7.96-7.95 (m, 1H), 7.65-7.57 (m, 2H), 6.88-6.83 (m, 1H), 5.68-5.62 (m, 1H), 4.31 (s, 4H), 3.62-3.49 (m, 2H), 3.42-3.28 (m, 2H), 2.97-2.92 (m, 4H), 2.19-2.10 (m, 1H), 1.98-1.93 (m, 4H), 1.08 (d, J = 6.9 Hz, 3H). | 555 |
| 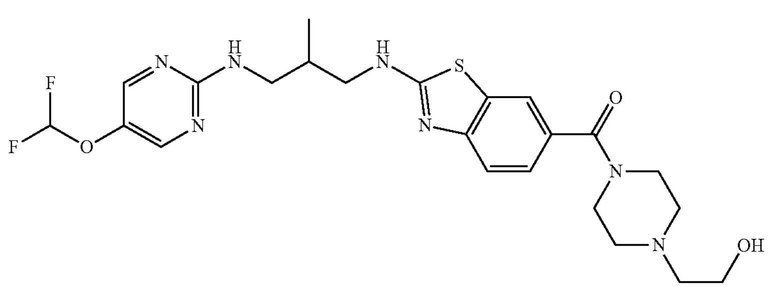 [SMILES: CC(CNc1ncc(OC(F)F)cn1)CNc1nc2ccc(C(=O)N3CCN(CCO)CC3)cc2s1] | 183 | $^1$H NMR (400 MHz, CDCl$_3$) δ 8.21-8.20 (2H, m), 7.68 (1H, d, J = 1.5 Hz), 7.54-7.51 (1H, m), 7.33 (1H, dd, J = 1.5,8.3 Hz), 6.42-6.42 (1H, m), 5.69 (1H, t, J = 6.4 Hz), 3.69-3.48 (6H, m), 3.42-3.28 (2H, m), 2.63-2.56 (6H, m), 2.18-2.09 (1H, m), 1.08-1.05 (3H, m); | 522 |

TABLE 11-continued

| Structure | Ex. # | ¹H NMR | LC-MS (M + H)⁺ |
|---|---|---|---|
| 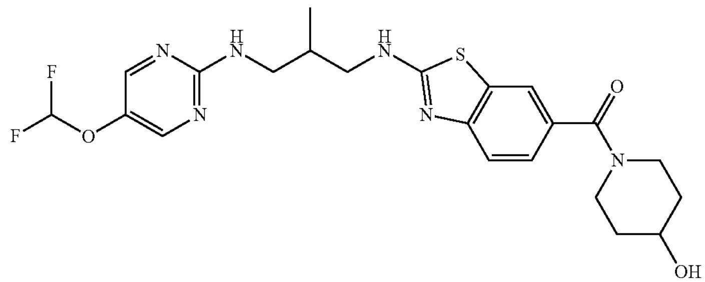 [SMILES: CC(CNc1ncc(OC(F)F)cn1)CNc1nc2ccc(C(=O)N3CCC(O)CC3)cc2s1] | 184 | ¹H NMR (400 MHz, DMSO) δ 8.16-8.15 (m, 3H), 7.65-7.64 (m, 1H), 7.42 (t, J = 5.9 Hz, 1H), 7.29-7.26 (m, 1H), 7.17-7.13 (m, 1H), 4.72-4.65 (m, 1H), 3.71-3.63 (m, 2H), 2.45-2.42 (m, 12H), 2.08-1.98 (m, 1H), 1.67-1.25 (m, 4H), 0.88 (d, J = 6.8 Hz, 3H). | 493 |
| 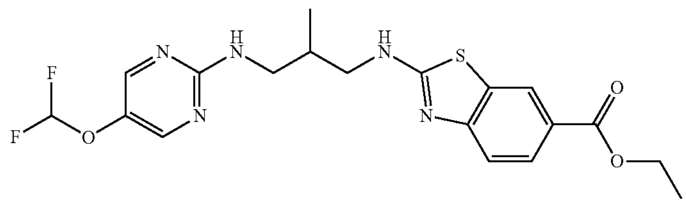 [SMILES: CCOC(=O)c1ccc2nc(NCC(C)CNc3ncc(OC(F)F)cn3)sc2c1] | 185 | ¹H NMR (400 MHz, DMSO) δ 8.44 (t, J = 5.5 Hz, 1H), 8.30-8.23 (m, 3H), 7.82 (dd, J = 1.9, 8.4 Hz, 1H), 7.50 (t, J = 5.9 Hz, 1H), 7.41-7.38 (m, 1H), 4.30 (q, J = 7.1 Hz, 2H), 2.17-2.07 (m, 1H), 1.35-1.30 (m, 3H), 0.98-0.95 (m, 3H). | 438 |
| 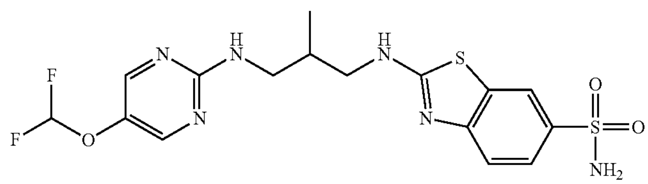 [SMILES: CC(CNc1ncc(OC(F)F)cn1)CNc1nc2ccc(S(N)(=O)=O)cc2s1] | 186 | ¹H NMR (400 MHz, DMSO) δ 8.43-8.39 (m, 1H), 8.25-8.24 (m, 2H), 8.12 (d, J = 1.9 Hz, 1H), 7,66 (dd, J = 1.9, 8.5 Hz, 1H), 7.51-7.43 (m, 2H), 7.21 (d, J = 4.8 Hz, 2H), 2.16-2.07 (m, 1H), 0.98-0.95 (m, 3H). | 445 |

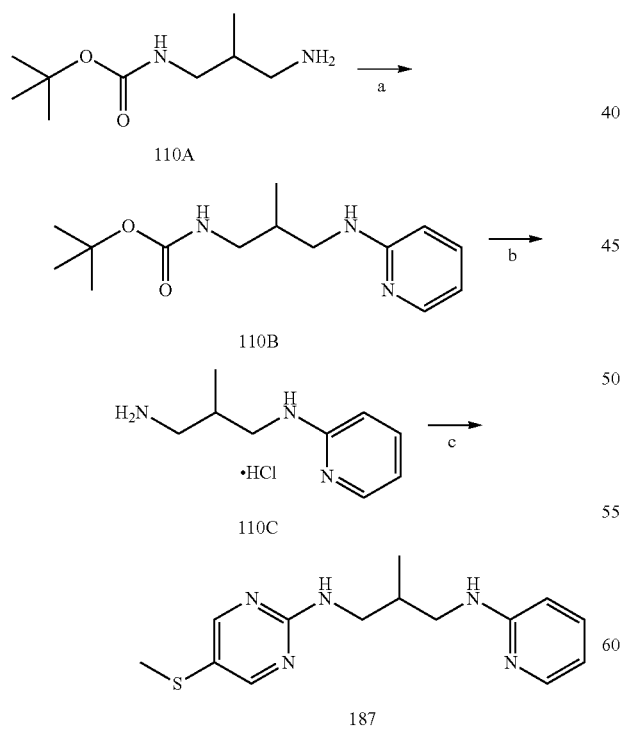

Scheme 12 a) 2-Bromopyridine, NaOtBu, Pd₂(dba)₃, XPhos, 1,4-dioxane; b) 4M HCl in 1,4-dioxane; c) 100B, Cs₂CO₃, DMF tert-Butyl (2-methyl-3-(pyridin-2-ylamino)propyl) carbamate (110B)

A solution of tert-butyl 3-amino-2-methylpropylcarbamate (110A) (150 mg, 0.80 mmol, 1.0 eq) in 1,4-dioxane (2 mL) was added to a solution of 2-bromopyridine (0.076 mL, 0.80 mmol, 1.0 eq), sodium tert-butoxide (383 mg, 3.98 mmol, 5.0 eq), 2-dicyclohexylphosphino-2',4',6'-triisopropylbiphenyl (38 mg, 0.08 mmol, 0.1 eq) and tris(dibenzylideneacetone)dipalladium (O) (73 mg, 0.08 mmol, 0.1 eq) in 1,4-dioxane (10 mL) under nitrogen. The reaction mixture was heated to 70° C. for 72 h. The solvents were removed under reduced pressure and the residue obtained was partitioned between water (2 mL) and ethyl acetate (5 mL). The mixture was filtered through celite and the aqueous phase was then removed and extracted with ethyl acetate (3×5 mL). The combined organic phases were washed with water (2 mL) and brine (2 mL) then dried by passing through a phase separator before concentrating to dryness under vacuum. The crude residue obtained was purified by reverse phase chromatography (eluting 10 mM ammonium bicarbonate aqueous solution to acetonitrile, 5-95%) to give the semi-pure desired tert-butyl (2-methyl-3-(pyridin-2-ylamino)propyl)carbamate (110B) as an off-white solid that was used in the next step without further purification. Yield: 27 mg (12%). MS (ESI+) m/z 266 (M+H)⁺.

2-Methyl-N¹-(pyridin-2-yl)propane-1,3-diamine hydrochloride (110C)

Methodology applied was analogous to those described in General Method 2.

A solution of hydrogen chloride (0.4 mL, 4M in 1,4-dioxane) was added to tert-butyl (2-methyl-3-(pyridin-2- ylamino)propyl)carbamate (108B) (27 mg, 0.10 mmol) and the mixture was stirred at room temperature for 1 hour. The solvents were removed under vacuum to afford the desired product 2-methyl-N1-(pyridin-2-yl)propane-1,3-diamine hydrochloride (110C) as a pale yellow semi-solid. The semi-crude sample was taken on into the next reaction without further purification.

Yield: 25 mg (assumed quant. %).

2-Methyl-$N^1$-(5-(methylthio)pyrimidin-2-yl)-$N^3$-(pyridin-2-yl)propane-1,3-diamine Example 187

Methodology applied was analogous to those described in General Method 3. 2-Chloro-5-methylsulfanyl-pyrimidine (100B) (17 mg, 0.11 mmol, 1.05 eq) was added to a stirred solution of 2-methyl-$N^1$-(pyridin-2-yl)propane-1,3-diamine hydrochloride (110C) (24 mg, 0.10 mmol, 1.0 eq) and cesium carbonate (99 mg, 0.30 mmol, 3.0 eq) in anhydrous N,N-dimethylformamide (0.5 mL) under nitrogen. The mixture was heated to 50° C. for 16 h and was then concentrated under vacuum. Water (2 mL) was added and the mixture was extracted with ethyl acetate (3×5 mL). The combined organic phases were washed with water (2 mL) and brine (2 mL) then dried by passing through a phase separator. The solvents were removed under vacuum to give a crude yellow oil which was purified by reverse phase chromatography (eluting 10 mM ammonium bicarbonate aqueous solution to acetonitrile, 5-95%) to give the desired 2-methyl-$N^1$-(5-(methylthio)pyrimidin-2-yl)-$N^3$-(pyridin-2-yl)propane-1,3-diamine (Example 187) as a sticky yellow solid.

Yield: 1.5 mg (5%). $^1$H NMR (400 MHz, CDCl$_3$) δ 8.35 (s, 2H), 8.10 (dd, J=0.6, 3.6 Hz, 1H), 7.41-7.35 (m, 1H), 6.54 (dd, J=5.3, 6.8 Hz, 1H), 6.38 (d, J=8.4 Hz, 1H), 5.93-5.93 (m, 1H), 4.96-4.96 (m, 1H), 3.53-3.21 (m, 4H), 2.35 (s, 3H), 2.10-2.01 (m, 1H), 1.03 (d, J=6.9 Hz, 3H); MS (ESI+) m/z 290 (M+H)$^+$.

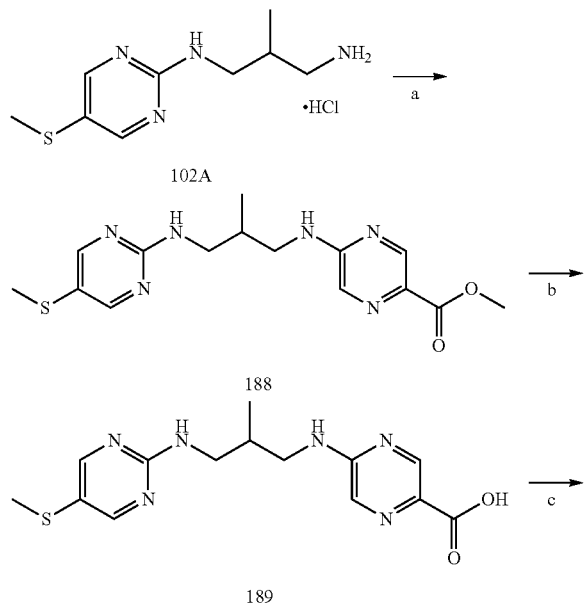

Scheme 13

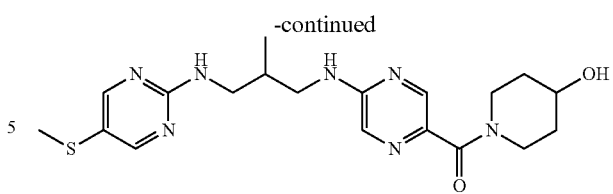

190 a) Methyl 5-bromopyrazine-2-carboxylate, Cs$_2$CO$_3$, DMF; c) LiOH, EtOH, THF; d) piperidin-4-ol, HATU, Et$_3$N, DMF.

Methyl 5-((2-methyl-3-((5-(methylthio)pyrimidin-2-yl)amino)propyl) amino)pyrazine-2-carboxylate (188)

Methodology applied was analogous to those described in General Method 3. Methyl 5-bromopyrazine-2-carboxylate (114 mg, 0.53 mmol, 1.0 eq) was added to a stirred solution of 2-methyl-$N^1$-(5-(methylthio)pyrimidin-2-yl)propane-1,3-diamine hydrochloride (102A) (150 mg, 0.53 mmol, 1.0 eq) and cesium carbonate (514 mg, 1.58 mmol, 3.0 eq) in anhydrous N,N-dimethylformamide (2.0 mL) under nitrogen. The mixture was stirred at room temperature for 16 h and then concentrated under vacuum. Water (2.5 mL) was added and the mixture was extracted with ethyl acetate (3×5 mL). The combined organic phases were washed with water (2 mL) and brine (2.5 mL) then dried passing through a phase separator. The solvents were removed under vacuum to give a brown oil which was purified by flash chromatography (eluting iso-hexanes to ethyl acetate, 0-100%). The semi-crude product obtained was further purified by flash chromatography (eluting dichloromethane to methanol, 0-10%) to give the desired methyl 5-((2-methyl-3-((5-(methylthio)pyrimidin-2-yl)amino)propyl)amino) pyrazine-2-carboxylate (Example 188) as a white solid.

Yield: 60 mg (32%). $^1$H NMR (400 MHz, CDCl$_3$) δ 8.76 (s, 1H), 8.37 (s, 2H), 7.91 (d, J=1.4 Hz, 1H), 6.36-6.36 (m, 1H), 5.56 (dd, J=6.0, 6.0 Hz, 1H), 3.95 (s, 3H), 3.60-3.51 (m, 2H), 3.40-3.26 (m, 2H), 2.38 (s, 3H), 2.10-2.03 (m, 1H), 1.04 (d, J=6.9 Hz, 3H). MS (ESI+) m/z 349 (M+H)$^+$.

5-((2-Methyl-3-((5-(methylthio)pyrimidin-2-yl)amino)propyl)amino)pyrazine-2-carboxylic acid (189)

Methodology applied was analogous to those described in General Method 4. Lithium hydroxide monohydrate (23 mg, 55 mmol, 5.0 eq) was added to a stirred solution of methyl 5-((2-methyl-3-((5-(methylthio)pyrimidin-2-yl)amino)propyl)amino) pyrazine-2-carboxylate (188) (38 mg, 0.11 mmol, 1.0 eq) in ethanol (0.4 mL) and water (0.4 mL). The mixture was stirred at ambient temperature for 72 h and then concentrated under reduced pressure. Water (0.5 mL) was added to the residue and this mixture was acidified to pH ~3 with a solution of aqueous hydrochloric acid (2M). A sticky precipitate was collected under filtration and then extracted with ethyl acetate (3×3 mL), washed with water (1 mL) and then dried by passing through a phase separator. The solvents were removed under vacuum to give the desired 5-((2-methyl-3-((5-(methylthio)pyrimidin-2-yl)amino)propyl)amino)pyrazine-2-carboxylic acid (Example 189) as a pale yellow solid. Yield: 34 mg (94%); $^1$H NMR (400 MHz, DMSO) δ 8.52 (s, 1H), 8.36 (s, 2H), 7.99 (s, 2H), 7.65-7.64

(m, 1H), 3.39-3.20 (m, 4H), 2.36 (s, 3H), 2.12-2.03 (m, 1H), 0.94 (d, J=6.8 Hz, 3H), One NH proton not observed; MS (ESI+) m/z 335 (M+H)⁺.

(4-Hydroxypiperidin-1-yl)(5-((2-methyl-3-((5-(methylthio)pyrimidin-2-yl)amino)propyl) amino) pyrazin-2-yl)methanone (Example 190)

Methodology applied was analogous to those described in General Method 5. 1-[Bis(dimethylamino)methylene]-1H-1,2,3-triazolo[4,5-b]pyridinium 3-oxide hexafluoro phosphate (HATU, 58 mg, 0.15 mmol, 1.5 eq) was added to a solution of 5-((2-methyl-3-((5-(methylthio)pyrimidin-2-yl)amino)propyl)amino)pyrazine-2-carboxylic acid (189) (34 mg, 0.10 mmol, 1.0 eq) and 4-hydroxypiperidine (103 mg, 1.02 mmol, 10 eq) in N,N-dimethylformamide (1 mL) and the reaction mixture was stirred at room temperature for 18 h. The solvents were removed under reduced pressure and the crude residue obtained was purified by reverse phase preparative HPLC to give the desired (4-hydroxypiperidin-1-yl)(5-((2-methyl-3-((5-(methylthio)pyrimidin-2-yl) amino)propyl) amino)pyrazin-2-yl)methanone (Example 190) as an off-white solid.

Yield: 22 mg (53%). ¹H NMR (400 MHz, CDCl₃) δ 8.46 (s, 1H), 8.37 (s, 2H), 7.79 (s, 1H), 5.97-5.97 (m, 1H), 5.71-5.71 (m, 1H), 4.15-4.15 (m, 2H), 4.01-3.94 (m, 1H), 3.58-3.47 (m, 2H), 3.42-3.25 (m, 4H), 2.37 (s, 3H), 2.08 (ddd, J=11.5, 11.5, 5.1 Hz, 1H), 2.00-1.94 (m, 2H), 1.62-1.60 (m, 3H), 1.04 (d, J=6.8 Hz, 3H); MS (ESI+) m/z 418 (M+H)⁺.

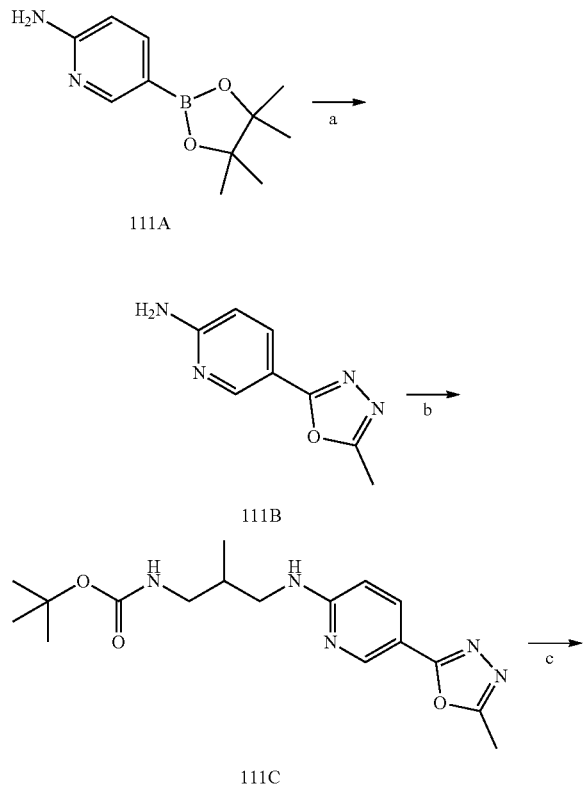

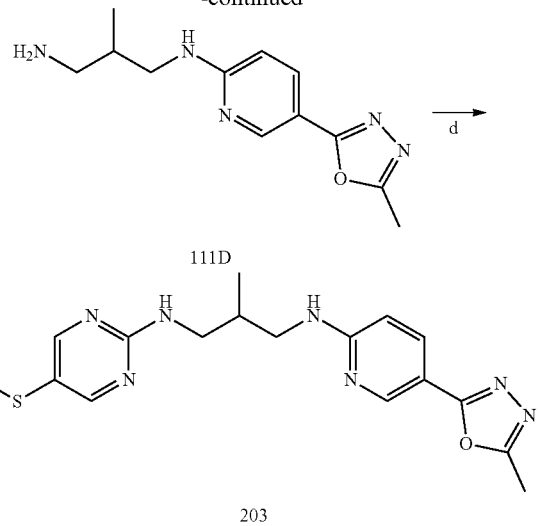

a) Cs₂CO₃, Pd(PPh₃)₄, 2-bromo-5-methyl-1,3,4-oxadiazole, water, 1,4-dioxane; b)tert-Butyl N-(2-methyl-3-oxopropyl)carbamate, acetic acid, mol sieves, Na(CH₃COO)₃BH, DCM; c) 4M HCl in 1,4-dioxane; d) 100B, Cs₂CO₃, DMF.

5-(5-Methyl-1,3,4-oxadiazol-2-yl)pyridin-2-amine (111B)

Methodology applied was analogous to those described in General Method 7. 2-Bromo-5-methyl-1,3,4-oxadiazole (0.58 g, 3.58 mmol, 1.05 eq) was added to a solution of 5-(4,4,5,5-tetramethyl-1,3,2-dioxaborolan-2-yl)pyridin-2-amine (111A) (0.75 g, 3.41 mmol, 1.0 eq), cesium carbonate (3.33 g, 10.22 mmol, 3.0 eq) and tetrakis(triphenylphosphine)palladium (O) (0.39 g, 0.34 mmol, 0.10 eq) in water (5.5 mL) and 1,4-dioxane (22.5 mL) under nitrogen. The reaction mixture was heated to 100° C. for 16 h. The solvents were removed under vacuum, water (20 mL) was added and the mixture extracted with ethyl acetate (6×50 mL). The combined organic phases were washed with water (10 mL) and brine (10 mL), dried by passing through a phase separator and then concentrated under vacuum. The crude residue obtained was purified by reverse phase chromatography (eluting 10 mM ammonium bicarbonate solution to acetonitrile, 5-30%) to give the desired 5-(5-methyl-1,3,4-oxadiazol-2-yl)pyridin-2-amine (111B) as an off-white solid.

Yield: 153 mg (25%). ¹H NMR (400 MHz, DMSO) δ 8.49 (d, J=2.0 Hz, 1H), 7.87 (dd, J=2.4, 8.8 Hz, 1H), 6.75 (s, 2H), 6.57 (d, J=8.8 Hz, 1H), 2.53 (s, 3H).

tert-Butyl (2-methyl-3-((5-(5-methyl-1,3,4-oxadiazol-2-yl)pyridin-2-yl)amino)propyl) carbamate (111C)

tert-Butyl N-(2-methyl-3-oxopropyl)carbamate (111B) (225 mg, 1.21 mmol, 1.2 eq) was added to a solution of 5-(5-methyl-1,3,4-oxadiazol-2-yl)pyridin-2-amine (114B) (153 mg, 1.00 mmol, 1.0 eq), acetic acid (0.230 mL, 4.02 mmol, 4.0 eq) and molecular sieves (type 4 Å, 250 mg) in anhydrous dichloromethane (20 mL). The reaction mixture was stirred at room temperature for 5 minutes and then sodium triacetoxyborohydride (532 mg, 2.51 mmol, 2.5 eq) was added in one portion. The mixture was stirred at room temperature for 40 h. tert-Butyl N-(2-methyl-3-oxopropyl) carbamate (225 mg, 1.21 mmol, 1.2 eq) was added and the reaction mixture stirred at room temperature for a further 72 h. The reaction was quenched by the careful addition of a saturated aqueous solution of sodium hydrogen carbonate (30 mL). The mixture was stirred vigorously for 30 minutes and the dichloromethane layer was then isolated and concentrated under reduced pressure to give a gum. The crude product was purified by flash chromatography (eluting isohexane to ethyl acetate, 0-100%) to give the desired tert-butyl (2-methyl-3-((5-(5-methyl-1,3,4-oxadiazol-2-yl)pyridin-2-yl)amino)propyl) carbamate (111C) as an off-white gum. The crude sample was taken on into the next reaction without further purification.

Yield: 101 mg (29%).

2-Methyl-N$^1$-(5-(5-methyl-1,3,4-oxadiazol-2-yl) pyridin-2-yl)propane-1,3-diamine hydrochloride (111D)

Methodology applied was analogous to those described in General Method 2. A solution of hydrogen chloride (1.2 mL, 4M in 1,4-dioxane) was added to tert-butyl (2-methyl-3-((5-(5-methyl-1,3,4-oxadiazol-2-yl)pyridin-2-yl)amino)propyl) carbamate (110C) (101 mg, 0.29 mmol) and the mixture stirred at room temperature for 1 hour. The solvents were removed under vacuum to afford the desired 2-methyl-N$^1$-(5-(5-methyl-1,3,4-oxadiazol-2-yl)pyridin-2-yl)propane-1,3-diamine hydrochloride (111D) as an off-white solid. The crude sample was taken on into the next reaction without further purification.

Yield: 93 mg (assumed quant. %).

2-Methyl-N$^1$-(5-(5-methyl-1,3,4-oxadiazol-2-yl) pyridin-2-yl)-N$^3$-(5-(methylthio) pyrimidin-2-yl) propane-1,3-diamine (Example 203)

Methodology applied was analogous to those described in General Method 3. 2-Chloro-5-methylsulfanyl-pyrimidine (100B, 51 mg, 0.32 mmol, 1.1 eq) was added to a stirred suspension of 2-methyl-N$^1$-(5-(5-methyl-1,3,4-oxadiazol-2-yl)pyridin-2-yl)propane-1,3-diamine hydrochloride (111D) (93 mg, 0.29 mmol, 1.0 eq) and cesium carbonate (283 mg, 0.87 mmol, 3.0 eq) in anhydrous N,N-dimethylformamide (2.9 mL) under nitrogen. The mixture was stirred at room temperature for 16 h, heated to 40° C. for a further 16 h and then concentrated under vacuum. Water (10 mL) was added and the mixture was extracted with ethyl acetate (3×50 mL). The combined organic phases were washed with water (10 mL) and brine (10 mL) then dried passing through a phase separator. The solvents were removed under vacuum to give a yellow oil which was purified by flash chromatography (eluting isohexane to ethyl acetate, 0-100%) to give a crude residue which was further purified by reverse phase preparative HPLC to give the desired 2-methyl-N$^1$-(5-(5-methyl-1,3,4-oxadiazol-2-yl)pyridin-2-yl)-N$^3$-(5-(methylthio)pyrimidin-2-yl)propane-1,3-diamine (Example 203) as a yellow solid. Yield: 3.5 mg (3%). $^1$H NMR (400 MHz, CDCl$_3$) δ 8.70 (d, J=1.8 Hz, 1H), 8.37 (s, 2H), 8.00 (dd, J=2.3, 8.8 Hz, 1H), 6.47 (d, J=8.1 Hz, 1H), 5.79-5.69 (m, 2H), 3.55-3.25 (m, 4H), 2.59 (s, 3H), 2.37 (s, 3H), 2.12-2.04 (m, 1H), 1.05 (d, J=6.8 Hz, 3H); MS (ESI+) m/z 372 (M+H)$^+$.

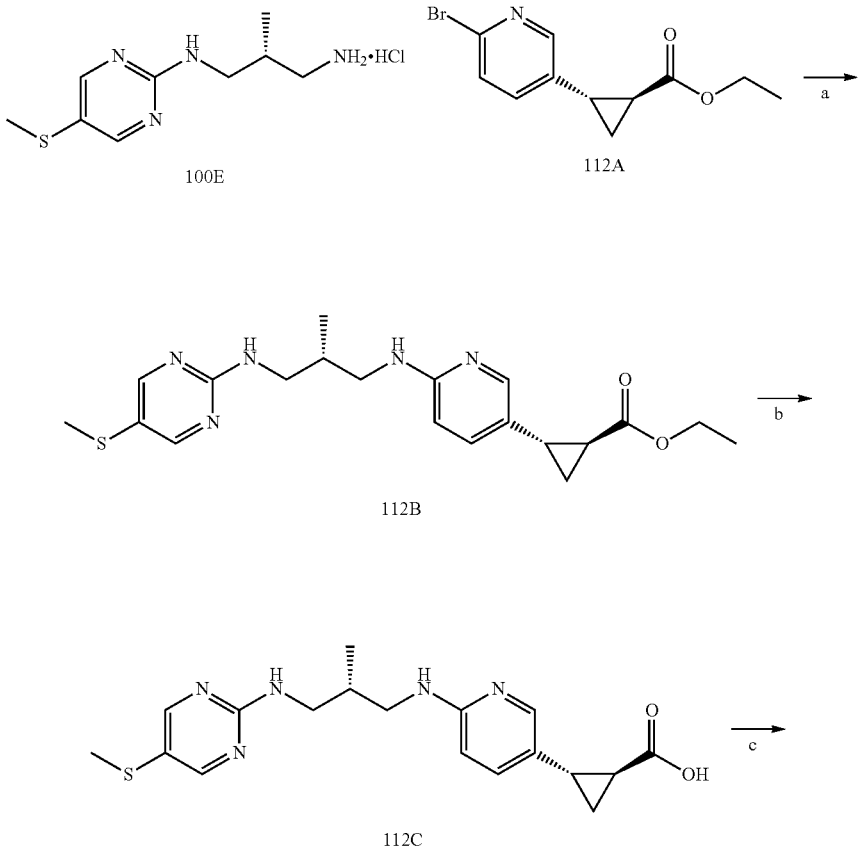

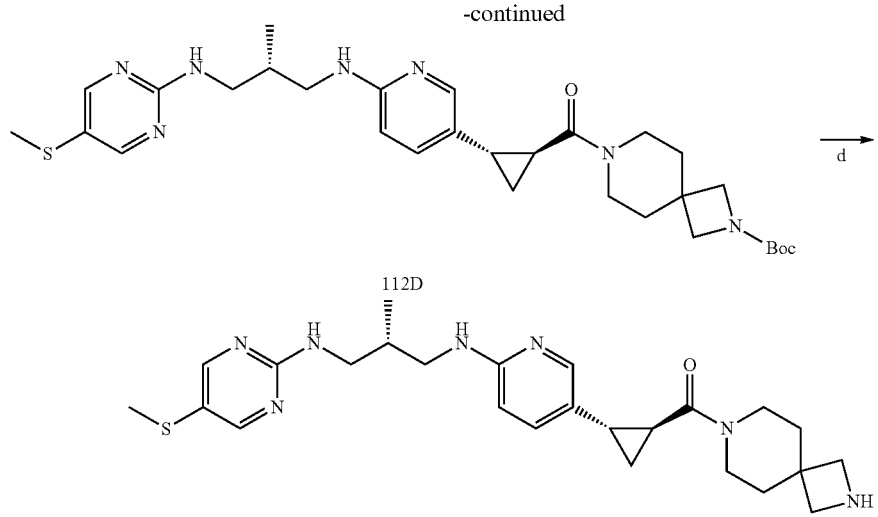

204 a) Cu(I)I, L-Proline, K₃PO₄, DMSO; b) LiOH•H₂O, EtOH, H₂O; c) tert-butyl, 2,7-diazaspiro[3.5]nonane-2-carboxylate, HATU, Et₃N, DMF; d) TFA, DCM

Ethyl 2-(6-(((R)-2-methyl-3-((5-(methylthio)pyrimidin-2-yl)amino)propyl)amino) pyridin-3-yl)cyclopropane-1-carboxylate (112B)

To a reaction tube was added (R)-2-methyl-N'-(5-(methylthio)pyrimidin-2-yl)propane-1,3-diamine hydrochloride (100E) (544 mg, 2.19 mmol), ethyl 2-(6-bromopyridin-3-yl)cyclopropane-1-carboxylate (650 mg, 2.41 mmol), L-Proline (101 mg, 0.875 mmol) potassium phosphate (928 mg, 4.37 mmol) and dimethylsulfoxide (5 mL) and the mixture was sparged with nitrogen for 2 minutes before copper (I) iodide (83 mg, 0.437 mmol) was added. The tube was sealed under nitrogen and heated at 90° C. overnight. The reaction was cooled, diluted with ethyl acetate (20 mL), passed through a celite pad and the filtrate concentrated under vacuum. The resulting residue was diluted with ethyl acetate (30 mL) and water (20 mL) and the aqueous phase was separated and extracted with ethyl acetate (2×30 mL). The combined organics were washed with water (2×40 mL) and then brine (2×50 mL), dried over magnesium sulfate and then concentrated under vacuum to give the crude title compound ethyl 2-(6-(((R)-2-methyl-3-((5-(methylthio)pyrimidin-2-yl)amino)propyl)amino)pyridin-3-yl)cyclopropane-1-carboxylate (112B) as a pale brown oil.

(N.B. Purification via normal phase chromatography could not resolve several close running impurities).

Yield: 284 mg. ¹H NMR (400 MHz, CDCl₃) δ 8.36 (s, 2H), 8.21 (dd, J=2.1, 6.2 Hz, 1H), 7.95 (s, 1H), 7.26-7.19 (m, 1H), 7.12 (d, J=8.1 Hz, 1H), 6.33 (d, J=8.6 Hz, 1H), 4.22-4.15 (m, 2H), 3.53-3.46 (m, 1H), 3.39-3.31 (m, 2H), 3.23-3.17 (m, 1H), 2.49 (ddd, J=11.8, 11.8, 11.8 Hz, 1H), 2.33 (s, 3H), 2.12-2.02 (m, 1H), 1.79-1.74 (m, 1H), 1.55-1.48 (m, 1H), 1.32-1.24 (m, 3H), 1.24-1.17 (m, 1H), 1.02 (d, J=6.8 Hz, 3H); MS (ESI+) m/z 402 (M+H)⁺.

2-(6-(((R)-2-Methyl-3-((5-(methylthio)pyrimidin-2-yl)amino)propyl)amino)pyridin-3-yl)cyclopropane-1-carboxylic acid (112C)

To a solution of ethyl 2-(6-(((R)-2-methyl-3-((5-(methylthio)pyrimidin-2-yl)amino)propyl) amino)pyridin-3-yl)cyclopropane-1-carboxylate (112B, 274 mg, 0.682 mmol) in ethanol (6 mL) and water (4 mL) was added lithium hydroxide monohydrate (143 mg, 3.41 mmol) and the resulting mixture was stirred at room temperature for 1 hour. The mixture was concentrated under vacuum and the residue obtained was diluted with water (8 mL). The solution was adjusted to pH ~2 with a 2M aqueous solution of hydrochloric acid and was then extracted with dichloromethane/methanol (20% methanol in dichloromethane, 2×10 mL). The combined organic layers were passed through a phase separator cartridge and then concentrated under vacuum to give the crude title compound 2-(6-(((R)-2-methyl-3-((5-(methylthio)pyrimidin-2-yl)amino)propyl)amino) pyridin-3-yl)cyclopropane-1-carboxylic acid (112C) as a brown oil which was used directly without further purification.

Yield: 280 mg. MS (ESI+) m/z 374 (M+H)⁺.

tert-Butyl 7-(2-(6-(((R)-2-methyl-3-((5-(methylthio) pyrimidin-2-yl)amino)propyl) amino)pyridin-3-yl) cyclopropane-1-carbonyl)-2,7-diazaspiro[3.5] nonane-2-carboxylate (112D)

tert-Butyl 2,7-diazaspiro[3.5]nonane-2-carboxylate (65 mg, 0.281 mmol) was added to a solution of 2-(6-(((R)-2-methyl-3-((5-(methylthio)pyrimidin-2-yl)amino)propyl) amino) pyridin-3-yl)cyclopropane-1-carboxylic acid (112C, 70 mg, 0.187 mmol), 1-[bis(dimethylamino)methylene]-1H-1,2,3-triazolo[4,5-b]pyridinium 3-oxid hexafluorophosphate (HATU, 86 mg, 0.225 mmol) and triethylamine (0.26 mL, 1.87 mmol) in dimethylformamide (2 mL) and the resulting mixture was stirred at room temperature for 18 h. Once complete the reaction mixture was concentrated under vacuum and the residue obtained was diluted with ethyl acetate (5 mL) and water (3 mL). The aqueous phase was separated and extracted with ethyl acetate (2×5 mL). The combined organics were washed with water (5 mL), brine (2×10 mL), dried over magnesium sulfate and then concentrated under vacuum. The crude residue obtained was purified using column chromatography (eluting 0-10% methanol in dichloromethane) to give the title compound tert-butyl 7-(2-(6-(((R)-2-methyl-3-((5-(methylthio)pyrimidin-2-yl) amino)propyl)amino)pyridin-3-yl)cyclopropane-1-carbonyl)-2,7-diazaspiro[3.5]nonane-2-carboxylate (112D) as an off white solid.

Yield: 69 mg. ¹H NMR (400 MHz, CDCl₃) δ 8.35 (s, 2H), 7.92 (d, J=1.5 Hz, 1H), 7.15 (dd, J=2.1, 8.5 Hz, 1H), 6.34 (d, J=8.6 Hz, 1H), 5.96 (dd, J=6.2, 6.2 Hz, 1H), 5.00 (s, 1H), 3.73-3.63 (m, 5H), 3.49 (s, 4H), 3.38-3.29 (m, 2H), 3.26-3.18 (m, 2H), 2.37-2.30 (m, 4H), 2.10-1.98 (m, 1H), 1.89-1.82 (m, 1H), 1.61-1.53 (m, 2H), 1.44 (s, 9H), 1.29-1.23 (m, 2H), 1.21-1.14 (m, 1H), 1.02 (d, J=6.8 Hz, 3H); MS (ESI+) m/z (M+H)⁺.

(2-(6-(((R)-2-Methyl-3-((5-(methylthio)pyrimidin-2-yl)amino)propyl)amino)pyridin-3-yl)cyclopropyl)(2,7-diazaspiro[3.5]nonan-7-yl)methanone (Example 204)

Trifluoroacetic acid (0.2 mL) was added to a stirred solution of tert-butyl 7-(2-(6-(((R)-2-methyl-3-((5-(methylthio)pyrimidin-2-yl)amino)propyl)amino)pyridin-3-yl)cyclopropane-1-carbonyl)-2,7-diazaspiro[3.5]nonane-2-carboxylate (112D, 69 mg, 0.119 mmol) in dichloromethane (2 mL) and the mixture was stirred at room temperature for 30 minutes. The solvents were removed under vacuum and then azeotroped with dichloromethane (3×5 mL). The crude residue obtained was dissolved in dimethylsulfoxide (1.5 mL) and purified by preparative HPLC. The liquors obtained were dried under vacuum then freeze-dried from an acetonitrile/water mix to afford the title compound (2-(6-(((R)-2-methyl-3-((5-(methylthio)pyrimidin-2-yl)amino)propyl)amino)pyridin-3-yl)cyclopropyl)(2,7-diazaspiro[3.5]nonan-7-yl) methanone (204) as a fluffy white solid.

Yield: 15 mg. ¹H NMR (400 MHz, CDCl₃) δ 8.54 (s, 1H), 8.35 (s, 2H), 7.89-7.86 (m, 1H), 7.16 (dd, J=2.0, 8.6 Hz, 1H), 6.36 (d, J=8.6 Hz, 1H), 5.98 (dd, J=6.9, 6.9 Hz, 1H), 5.49-5.49 (m, 1H), 3.76 (s, 4H), 3.51-3.43 (m, 2H), 3.39-3.30 (m, 3H), 3.22 (dd, J=6.6, 13.4 Hz, 2H), 2.38-2.31 (m, 4H), 2.11-2.01 (m, 1H), 1.89-1.79 (m, 5H), 1.59-1.52 (m, 1H), 1.27-1.14 (m, 1H), 1.03 (d, J=6.8 Hz, 3H); MS (ESI+) m/z 482 (M+H)⁺.

Following the procedures described in Scheme 17, the following examples were synthesized:

TABLE 14

| Structure | Ex. # | ¹H NMR | LC-MS (M + H)⁺ |
|---|---|---|---|
| 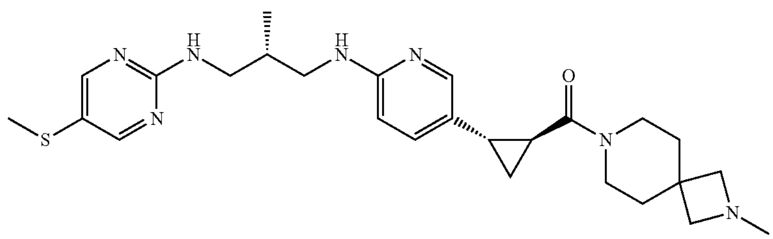 | 205 | ¹H NMR (400 MHz, CDCl₃) δ 8.35 (s, 2H), 7.93 (d, J = 2.0 Hz, 1H), 7.14 (dd, J = 2.3, 8.6 Hz, 1H), 6.33 (d, J = 8.6 Hz, 1H), 5.97-5.90 (m, 1H), 4.90 (dd, J = 6.1, 6.1 Hz, 1H), 3.57-3.11 (m, 10H), 3.06 (d, J = 6.1 Hz, 2H), 2.36 (d, J = 7.1 Hz, 7H), 2.09-1.99 (m, 1H), 1.89-1.82 (m, 2H), 1.82-1.76 (m, 3H), 1.59-1.48 (m, 1H), 1.19-1.12 (m, 1H), 1.02 (d, J = 6.8 Hz, 3H). | 496 |
| 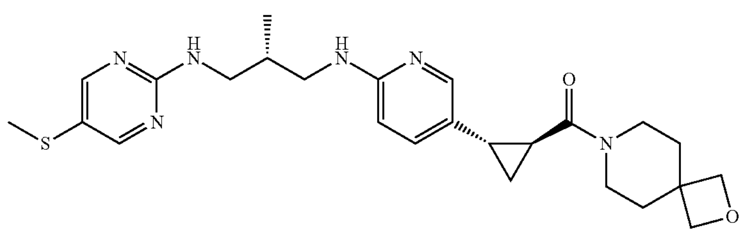 [SMILES: CSc1cnc(NC[C@H](C)CNc2ccc([C@H]3C[C@@H]3C(=O)N3CCC4(CC3)COC4)cn2)nc1] | 206 | ¹H NMR (400 MHz, CDCl₃) δ 8.35 (s, 2H), 7.91 (d, J = 1.8 Hz, 1H), 7.16 (dd, J = 2.3, 8.6 Hz, 1H), 6.35 (d, J = 8.6 Hz, 1H), 5.94-5.91 (m, 1H), 5.14 (s, 1H), 4.46 (d, J = 2.8 Hz, 4H), 3.53-3.44 (m, 6H), 3.39-3.30 (m, 2H), 3.25-3.19 (m, 1H), 2.35 (s, 4H), 2.09-2.01 (m, 1H), 1.90-1.85 (m, 5H), 1.20-1.14 (m, 1H), 1.03 (d, J = 6.8 Hz, 3H). | 483 |
| 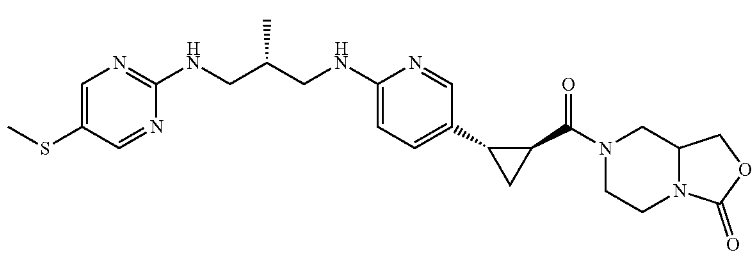 [SMILES: CSc1cnc(NC[C@H](C)CNc2ccc([C@H]3C[C@@H]3C(=O)N3CCN4C(=O)OCC4C3)cn2)nc1] | 207 | ¹H NMR (400 MHz. CDCl₃) δ 8.35 (s, 2H), 7.91 (s, 1H), 7.20 (s, 1H), 6.38 (d, J = 7.3 Hz, 1H), 5.91-5.91 (m, 1H), 5.44-5.18 (m, 1H), 4.72 (dd, J = 20.0, 62.4 Hz, 1H), 4.49-4.43 (m, 1H), 4.13-4.13 (m, 1H), 4.03-3.97 (m, 1H), 3.87-3.87 (m, 2H), 3.53-3.45 (m, 1H), 3.38-3.31 (m, 2H), 3.22 (dd, J = 6.4, 6.4 Hz, 2H), 3.10-3.00 (m, 2H), 2.64 (tt, J = 22.1, 20.6 Hz, 2H), 2.42-2.38 (m, 1H), 2.36 (s, 4H), 2.09-2.01 (m, 1H), 1.87-1.82 (m, 1H), 1.28-1.22 (m, 1H), 1.03 (d, J = 6.8 Hz, 3H). | 498 |

| Structure | Ex. # | ¹H NMR | LC-MS (M + H)⁺ |
|---|---|---|---|
| 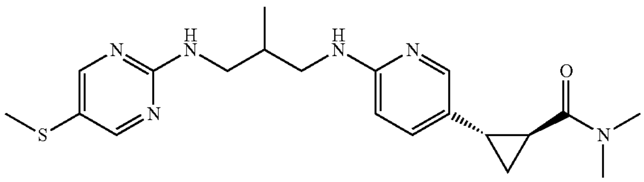 | 208 | ¹H NMR (400 MHz, CDCl₃) δ 8.35 (s, 2H), 7.95 (d, J = 2.4 Hz, 1H), 7.16 (dd, J = 2.4, 8.6 Hz, 1H), 6.33 (d, J = 8.5 Hz, 1H), 5.95-5.92 (m, 1H), 4.88 (dd, J = 6.1, 6.1 Hz, 1H), 3.52-3.17 (m, 4H), 3.14 (s, 3H), 2.99 (s, 3H), 2.36 (s, 4H), 2.06-2.00 (m, 1H), 1.90-1.85(m, 1H), 1.59-1.53 (m, 1H), 1.17 (ddd, J = 4.5, 6.2, 8.3 Hz, 1H), 1.02 (d, J = 6.8 Hz, 3H). | 401 |

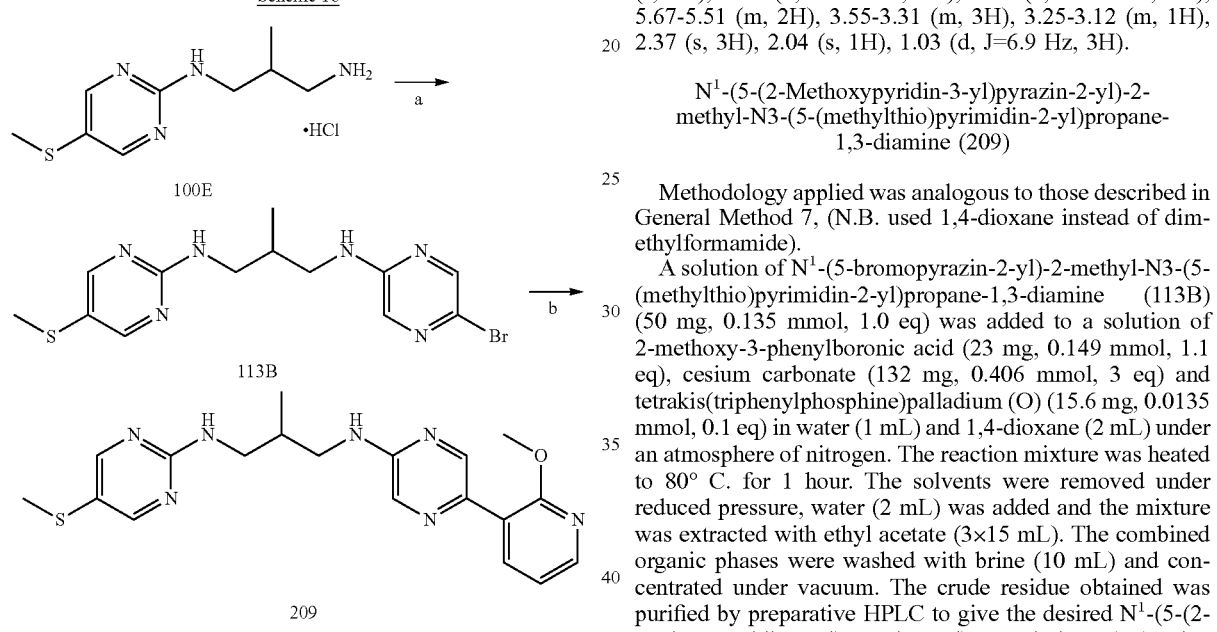

a) 2,5-dibromopyrazine, Cs₂CO₃, DMF, b) (2-methoxypyridin-3-yl)boronic acid, Cs₂CO₃, Pd(PPh₃)₄, dioxane, water N¹-(5-Bromopyrazin-2-yl)-2-methyl-N3-(5-(methylthio)pyrimidin-2-yl)propane-1,3-diamine (113B)

A solution of crude 2-methyl-N-(5-(methylthio)pyrimidin-2-yl)propane-1,3-diamine hydrochloride (100E) (340 mg, 1.60 mmol, 1.0 eq) in dimethylformamide (8 mL) was added to a suspension of 2,5-dibromopyrazine (457 mg, 1.92 mmol, 1.2 eq) and cesium carbonate (1.56 g, 4.80 mmol, 3.0 eq) in dimethylformamide (2 mL). The reaction mixture was heated to 90° C. for 18 h. The solvents were removed under reduced pressure and the residue obtained was partitioned between water (20 mL) and dichloromethane (50 mL). The layers were separated and the aqueous phase was extracted with dichloromethane (3×25 mL). The combined organic phases were washed with brine (25 mL), dried by passing through a phase separator and then concentrated to dryness under vacuum. The crude residue was purified by flash chromatography (eluting with iso-hexanes to ethyl acetate, 0-100%) to give the title compound N¹-(5-bromopyrazin-2-yl)-2-methyl-N³-(5-(methylthio)pyrimidin-2-yl)propane-1,3-diamine (113B) as a pale yellow gum.

Yield: 230 mg (38%). ¹H NMR (400 MHz, CDCl₃) δ 8.36 (s, 2H), 8.06 (d, J=1.3 Hz, 1H), 7.67 (d, J=1.4 Hz, 1H), 5.67-5.51 (m, 2H), 3.55-3.31 (m, 3H), 3.25-3.12 (m, 1H), 2.37 (s, 3H), 2.04 (s, 1H), 1.03 (d, J=6.9 Hz, 3H).

N¹-(5-(2-Methoxypyridin-3-yl)pyrazin-2-yl)-2-methyl-N3-(5-(methylthio)pyrimidin-2-yl)propane-1,3-diamine (209)

Methodology applied was analogous to those described in General Method 7, (N.B. used 1,4-dioxane instead of dimethylformamide).

A solution of N¹-(5-bromopyrazin-2-yl)-2-methyl-N3-(5-(methylthio)pyrimidin-2-yl)propane-1,3-diamine (113B) (50 mg, 0.135 mmol, 1.0 eq) was added to a solution of 2-methoxy-3-phenylboronic acid (23 mg, 0.149 mmol, 1.1 eq), cesium carbonate (132 mg, 0.406 mmol, 3 eq) and tetrakis(triphenylphosphine)palladium (O) (15.6 mg, 0.0135 mmol, 0.1 eq) in water (1 mL) and 1,4-dioxane (2 mL) under an atmosphere of nitrogen. The reaction mixture was heated to 80° C. for 1 hour. The solvents were removed under reduced pressure, water (2 mL) was added and the mixture was extracted with ethyl acetate (3×15 mL). The combined organic phases were washed with brine (10 mL) and concentrated under vacuum. The crude residue obtained was purified by preparative HPLC to give the desired N¹-(5-(2-methoxypyridin-3-yl)pyrazin-2-yl)-2-methyl-N3-(5-(methylthio)pyrimidin-2-yl)propane-1,3-diamine (154) as an off white solid. Yield: 24 mg (44%). ¹H NMR (400 MHz, CDCl₃) δ 8.77 (d, J=1.4 Hz, 1H), 8.37 (s, 2H), 8.18-8.13 (m, 2H), 7.99 (d, J=1.5 Hz, 1H), 7.01 (dd, J=4.9, 7.4 Hz, 1H), 5.69 (dd, J=6.5, 6.5 Hz, 1H), 5.55 (dd, J=6.1, 6.1 Hz, 1H), 4.04 (s, 3H), 3.59-3.48 (m, 2H), 3.42-3.25 (m, 2H), 2.37 (s, 3H), 2.19-2.06 (m, 1H), 1.06 (d, J=6.9 Hz, 3H); MS (ESI+) m/z 398 (M+H)⁺.

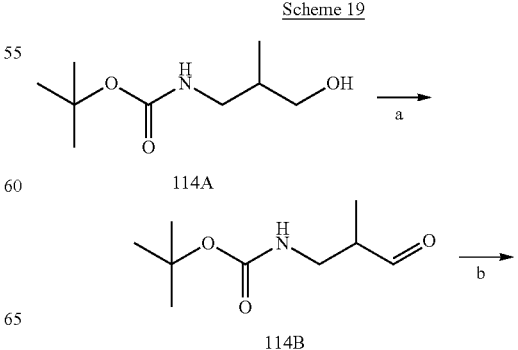

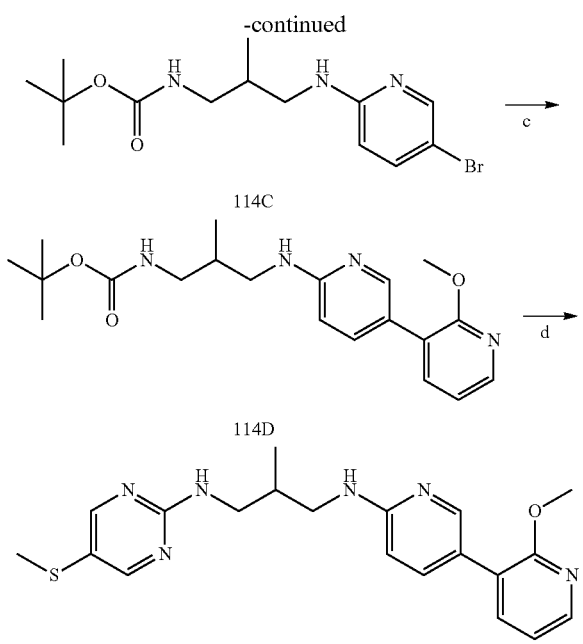

114C

114D

210 a) Dess-Martin periodinane, DCM, b) Na(AcO)$_3$BH, AcOH, mole sieves, 5-bromopyridin-2-amine, c) 2-methoxy-3-(4,4,5,5-tetramethyl-1,3,2-dioxaborolan-2-yl)pyridine, Cs$_2$CO$_3$, Pd(PPh$_3$)$_4$, dioxane, water, d) 4M HCl in dioxane, 2-chloro-5-(methylthio)pyrimidine, Cs$_2$CO$_3$, Et$_3$N, DMF tert-Butyl (2-methyl-3-oxopropyl)carbamate (114B)

Caution—exothermic reaction; Dess-Martin periodinane (2.94 g, 6.94 mmol, 1.3 eq) was added portion-wise over 20 minutes to a solution of tert-butyl (3-hydroxy-2-methylpropyl)carbamate (1.0 g, 5.34 mmol, 1.0 eq) in dichloromethane (50 mL) and the mixture was stirred at room temperature for 2 h. The mixture was diluted with dichloromethane (25 mL) and washed with 1M aqueous sodium dithionite solution (2×10 mL) and saturated aqueous sodium bicarbonate solution (2×10 mL). The organic phase dried passing through a phase separator and then concentrated under vacuum to give crude tert-butyl (2-methyl-3-oxopropyl)carbamate (114B) which was used immediately in the next step without further purification.

tert-Butyl (3-((5-bromopyridin-2-yl)amino)-2-methylpropyl)carbamate (114C)

Methodology applied was analogous to method described in Scheme 13 (for the generation of 109D).
The crude product was purified by flash chromatography (eluting iso-hexanes to ethyl acetate, 0-100%) to give the desired tert-butyl (3-((5-bromopyridin-2-yl)amino)-2-methylpropyl)carbamate (114C) as a pale yellow gum
Yield: 875 mg (47%) (MS (ESI+) m/z 345 (M+H)$^+$.

tert-Butyl(3-((2'-methoxy-[3,3'-bipyridin]-6-yl)amino)-2-methylpropyl)carbamate (114D)

Methodology applied was analogous to those described in General Method 7. Crude tert-butyl(3-((2'-methoxy-[3,3'-bipyridin]-6-yl)amino)-2-methylpropyl)carbamate (114D) was used immediately in the next step without further purification.
Yield: 110 mg, MS (ESI+) m/z 373 (M+H)$^+$.

N1-(2'-Methoxy-[3,3'-bipyridin]-6-yl)-2-methylpropane-1,3-diamine (114E)

Methodology applied was analogous to those described in General Method 2. Crude N$^1$-(2'-methoxy-[3,3'-bipyridin]-6-yl)-2-methylpropane-1,3-diamine (114E) was taken on immediately to the next step without further purification.
Crude yield: 75 mg MS (ESI+) m/z 273 (M+H)$^+$.

N$^1$-(2'-Methoxy-[3,3'-bipyridin]-6-yl)-2-methyl-N3-(5-(methylthio)pyrimidin-2-yl)propane-1,3-diamine (210)

Methodology applied was analogous to those described in General Method 1. The crude residue obtained was purified by preparative HPLC to give the desired product, N$^1$-(2'-methoxy-[3,3'-bipyridin]-6-yl)-2-methyl-N3-(5-(methylthio)pyrimidin-2-yl)propane-1,3-diamine as an off white solid (155)
Yield: 8 mg (7%). $^1$H NMR (400 MHz, CDCl$_3$) δ 8.36 (s, 2H), 8.30 (d, J=2.1 Hz, 1H), 8.11 (dd, J=1.9, 5.0 Hz, 1H), 7.67 (dd, J=2.4, 8.7 Hz, 1H), 7.57 (dd, J=1.9, 7.3 Hz, 1H), 6.95 (dd, J=5.0, 7.3 Hz, 1H), 6.45 (d, J=8.4 Hz, 1H), 5.90 (dd, J=6.3, 6.3 Hz, 1H), 5.11 (dd, J=6.0, 6.0 Hz, 1H), 3.97 (s, 3H), 3.56-3.23 (m, 4H), 2.36 (s, 3H), 2.13-2.04 (m, 1H), 1.05 (d, J=6.9 Hz, 3H); MS (ESI+) m/z 397 (M+H)$^+$.

Scheme 20

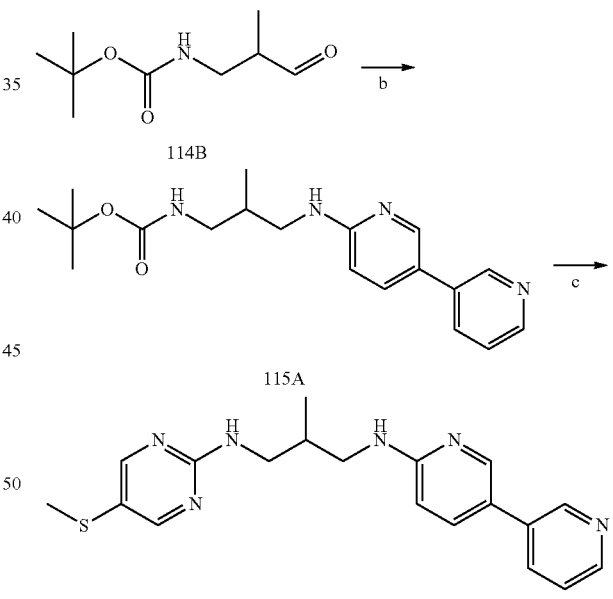

114B

115A

211 a) Dess-Martin periodinane, DCM, b) Na(AcO)$_3$BH, AcOH, mole sieves, [3,3'-bipyridin]-6-amine, c) 4M HCl dioxane, 2-chloro-5-(methylthio)pyrimidine, Cs$_2$CO$_3$, Et3N, DMF tert-Butyl (3-([3,3'-bipyridin]-6-ylamino)-2-methylpropyl)carbamate (115A)

Methodology applied was analogous to scheme 19 (example 115B) to generate the aldehyde (114B), and then using methodology analogous to general method 7. The crude N¹—([3,3'-bipyridin]-6-yl)-2-methylpropane-1,3-diamine (115A) was immediately taken on the next step.

Yield: 253 mg (63%) $^1$H NMR (400 MHz, DMSO) δ 8.82 (d, J=1.8 Hz, 1H), 8.48 (dd, J=1.6, 4.8 Hz, 1H), 8.36 (d, J=2.1 Hz, 1H), 8.00-7.96 (m, 1H), 7.76 (dd, J=2.6, 8.7 Hz, 1H), 7.44-7.40 (m, 1H), 6.90-6.76 (m, 2H), 6.62-6.59 (m, 1H), 4.10 (q, J=5.3 Hz, 1H), 3.19-3.18 (m, 4H), 3.03-2.94 (m, 1H), 2.88-2.80 (m, 1H), 1.93-1.82 (m, 1H), 1.40-1.38 (m, 9H).

N¹—([3,3'-bipyridin]-6-yl)-2-methyl-N³-(5-(methylthio)pyrimidin-2-yl)propane-1,3-diamine (211)

Methodology applied was analogous to method described in Scheme 13 (for the generation of 109D).

The crude residue obtained was purified by reverse phase chromatography (eluting 10 mM ammonium bicarbonate aqueous solution to acetonitrile, 5-95%) to give the desired product, N¹—([3,3'-bipyridin]-6-yl)-2-methyl-N³-(5-(methylthio)pyrimidin-2-yl)propane-1,3-diamine (211) as an off white solid.

Yield: 32 mg (14%). $^1$H NMR (400 MHz, CDCl₃) δ 8.77 (1H, d, J=2.1 Hz), 8.53 (1H, dd, J=1.6, 4.8 Hz), 8.37-8.35 (3H, m), 7.81-7.77 (1H, m), 7.63 (1H, dd, J=2.5, 8.7 Hz), 7.33 (1H, dd, J=4.6, 7.8 Hz), 6.50 (1H, d, J=8.7 Hz), 5.93 (1H, dd, J=6.1, 6.1 Hz), 5.25 (1H, dd, J=6.1, 6.1 Hz), 3.56-3.25 (4H, m), 2.36 (3H, s), 2.18-2.00 (1H, m), 1.06 (3H, d, J=6.9 Hz); MS (ESI+) m/z 367 (M+H)⁺.

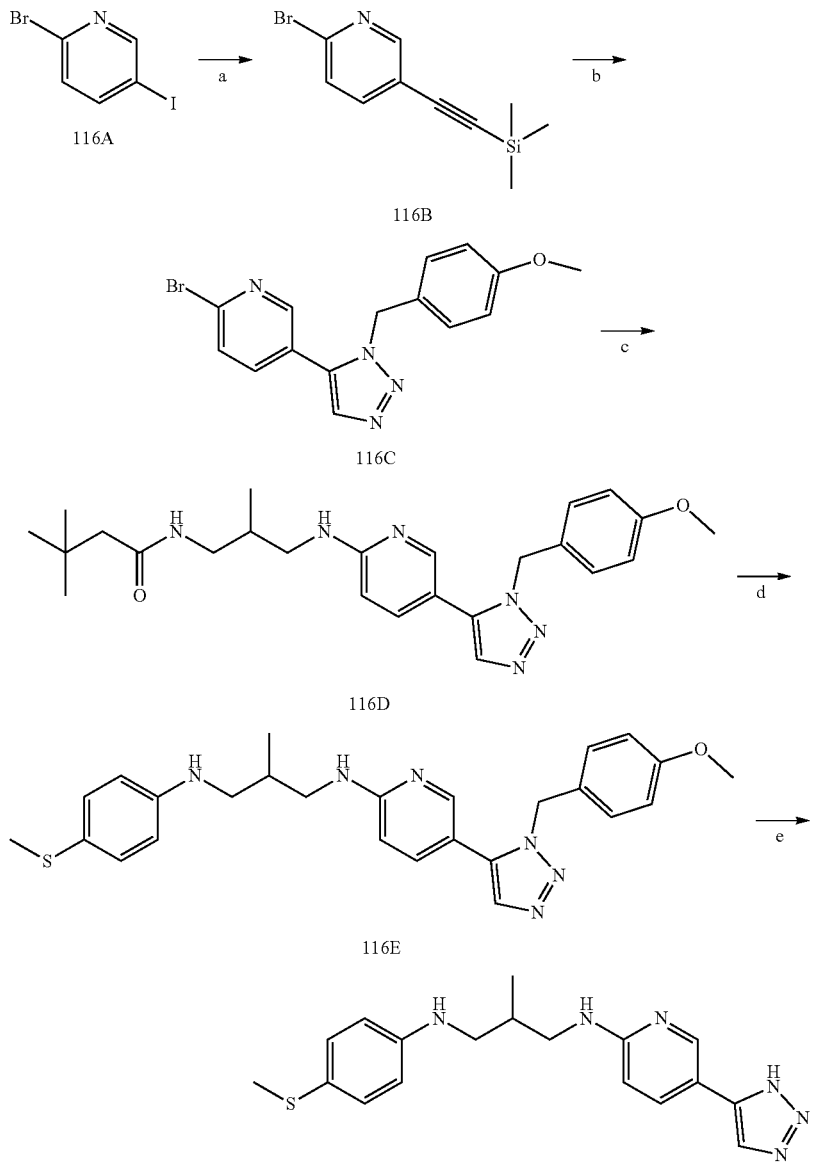

Scheme 21 a) Trimethylsilyacetylene, TEA, Pd(PPh)₃Cl₂, CuI, b) 1-(azidomethyl)-4-methoxybenzene, EtOH, TBAF
c) tert-butyl(3-amino-2-methylpropyl)carbamate, K₃PO₄, L-proline, CuI, DMSO
d) 4M HCl in dioxane, 2-chloro-5-(methylthio)pyrimidine, Cs₂CO₃, DMF, e) TFA, DCM

2-Bromo-5-((trimethylsilyl)ethynyl)pyridine (116B)

Triethylamine (49 mL, 352.25 mmol, 25 eq) was added to 2-bromo-5-iodopyridine (4.0 g, 14.09 mmol, 1.0 eq) followed by ethynyltrimethylsilane (2.9 mL, 21.13 mmol, 1.5 eq), copper (I) iodide (270 mg, 1.41 mmol, 0.1 eq), bis(triphenylphosphine)palladium (II) dichloride (99 mg, 0.14 mmol, 0.01 eq) and the mixture was stirred at room temperature for 17 h. The mixture was concentrated under vacuum to give a crude gum which was purified by flash chromatography (eluting with iso-hexane to ethyl acetate, 0-40%) to give the intermediate 2-bromo-5-((trimethylsilyl)ethynyl)pyridine (116B) as a white solid.

Yield: 2.5 g (69%). MS (ESI+) m/z 254/256 (M+H)$^+$.

2-Bromo-5-(1-(4-methoxybenzyl)-1H-1,2,3-triazol-5-yl)pyridine (116C)

To a solution of 2-bromo-5-((trimethylsilyl)ethynyl)pyridine (116B) (250 mg, 0.983 mmol, 1.0 eq) in ethanol (20 mL) was added 1-(azidomethyl)-4-methoxybenzene (177 mg, 1.08 mmol, 1.1 eq) and the mixture was stirred at room temperature for 1 hour. A solution of 1M tetrabutylammonium fluoride in tetrahydrofuran (0.54 mL, 1.08 mmol, 1.1 eq) was added and the mixture was stirred at room temperature for 18 h. The reaction mixture was concentrated under vacuum and then purified by flash chromatography (eluting with iso-hexane to ethyl acetate, 0-100%) to give 2-bromo-5-(1-(4-methoxybenzyl)-1H-1,2,3-triazol-5-yl)pyridine (116C) as an off white solid. Yield: 0.21 g (61%). MS (ESI+) m/z 347 (M+H)$^+$.

tert-Butyl (3-((5-(1-(4-methoxybenzyl)-1H-1,2,3-triazol-5-yl)pyridin-2-yl)amino)-2-methylpropyl)carbamate (116D)

To a de-gassed solution of 2-bromo-5-(1-(4-methoxybenzyl)-1H-1,2,3-triazol-5-yl)pyridine (116C) (135 mg, 0.391, 1.0 eq) in dimethyl sulfoxide (5 mL) was added tert-butyl (3-amino-2-methylpropyl)carbamate (96 mg, 0.508 mmol, 1.3 eq), L-proline (18 mg, 0.156 mmol, 0.4 eq), potassium phosphate (1.6.5 mg, 0.078 mmol, 0.2 eq) and copper (I) iodide (15 mg, 0.782 mmol, 0.2 eq). The mixture was stirred at 90° C. for 28 h, diluted with water (20 mL) and extracted with dichloromethane (3×20 mL). The organic phases were combined and concentrated under vacuum and the crude residue was purified by flash chromatography (eluting with iso-hexane to ethyl acetate, 0-100%) to give 2-bromo-5-(1-(4-methoxybenzyl)-1H-1,2,3-triazol-5-yl)pyridine (116D) as a pale brown solid.

Yield: 0.080 g (45%). MS (ESI+) m/z 453 (M+H)$^+$.

tert-Butyl (3-((5-(1-(4-methoxybenzyl)-1H-1,2,3-triazol-5-yl)pyridin-2-yl)amino)-2-methylpropyl)carbamate (116E)

Methodology applied was analogous to those described in General Method 2.

Yield: 25 mg (29%). $^1$H NMR (400 MHz, CDCl$_3$) δ 8.42 (d, J=2.0 Hz, 1H), 8.35 (s, 2H), 7.90 (dd, J=2.4, 8.7 Hz, 1H), 7.52 (s, 1H), 6.94-6.90 (m, 2H), 6.44 (d, J=9.0 Hz, 1H), 5.94 (dd, J=6.1, 6.1 Hz, 1H), 5.49 (s, 2H), 5.09 (dd, J=6.3, 6.3 Hz, 1H), 3.81 (s, 4H), 3.53-3.22 (m, 4H), 2.35 (s, 3H), 2.10-2.01 (m, 1H), 1.03 (d, J=6.9 Hz, 3H), (NH not observed).

N$^1$-(5-(1H-1,2,3-Triazol-5-yl)pyridin-2-yl)-2-methyl-N3-(4-(methylthio)phenyl)propane-1,3-diamine (212)

Methodology applied was analogous to those described in General Method 3.

Yield: 18 mg (96%). $^1$H NMR (400 MHz, CDCl$_3$) δ 8.53 (d, J=2.1 Hz, 1H), 8.38 (s, 2H), 7.84 (s, 1H), 7.82 (dd, J=2.3, 8.7 Hz, 1H), 6.45 (d, J=8.4 Hz, 1H), 6.17 (dd, J=6.3, 6.3 Hz, 1H), 5.31 (dd, J=6.0, 6.0 Hz, 1H), 3.57-3.26 (m, 4H), 2.36 (s, 3H), 2.19-2.06 (m, 1H), 1.06 (d, J=6.8 Hz, 3H), (NH not observed); MS (ESI+) m/z 457 (M+H)$^+$.

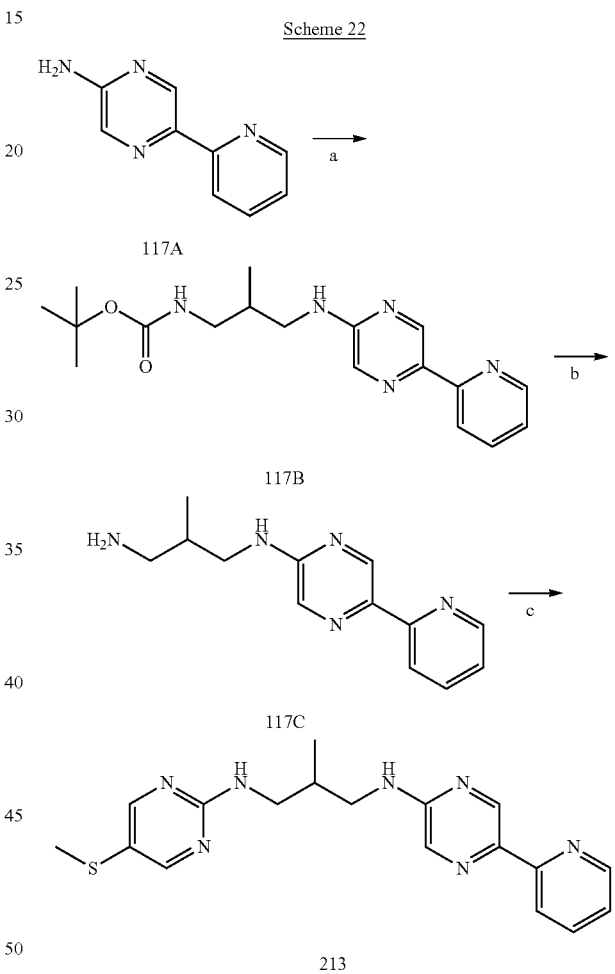

Scheme 22 a) 102b, acetic acid, mol sieves, Na(CH$_3$COO)$_3$BH, DCM; b) 4M HCl in 1,4-dioxane; c) 100B, Cs$_2$CO$_3$, DMF.

tert-Butyl (2-methyl-3-((5-(pyridin-2-yl)pyrazin-2-yl)amino)propyl)carbamate (117B)

To a solution of 5-(pyridin-2-yl)pyrazin-2-amine (200 mg, 1.16 mmol, 1.0 eq) in dichloromethane (10 mL) was added tert-butyl (2-methyl-3-oxopropyl)carbamate (117B) (221 mg, 1.17 mmol, 1.0 eq), 3 Å molecular sieves (750 mg), acetic acid (0.266 mL, 4.65 mmol) and sodium triacetoxyborohydride (616 mg, 2.9 mmol) and the mixture was stirred at room temperature for 18 h. The reaction mixture was diluted with dichloromethane (25 mL) and filtered. The organic phase was washed with water (25 mL) and brine (25 mL) then passed through a phase separator cartridge. The solvents were removed under vacuum to afford crude tert-butyl (2-methyl-3-((5-(pyridin-2-yl)pyrazin-2-yl)amino)propyl)carbamate (117B) which was used in the next step without further purification.

Yield: 310 mg (78%).

2-Methyl-N¹-(5-(pyridin-2-yl)pyrazin-2-yl)propane-1,3-diamine (117C)

Methodology applied was analogous to those described in General Method 2. Yield: 200 mg (100%).

2-Methyl-N¹-(5-(methylthio)pyrimidin-2-yl)-N3-(5-(pyridin-2-yl)pyrazin-2-yl)propane-1,3-diamine (213)

Methodology applied was analogous to those described in General Method 1.

Yield: 20 mg (10%). $^1$H NMR (400 MHz, CDCl$_3$) δ 9.04 (d, J=1.4 Hz, 1H), 8.62-8.61 (m, 1H), 8.37 (s, 2H), 8.10 (d, J=8.0 Hz, 1H), 7.94 (d, J=1.4 Hz, 1H), 7.77-7.72 (m, 1H), 7.20 (dd, J=4.8, 6.5 Hz, 1H), 5.75-5.63 (m, 2H), 3.58-3.50 (m, 2H), 3.42-3.28 (m, 2H), 2.37 (s, 3H), 2.19-2.06 (m, 1H), 1.06 (d, J=6.9 Hz, 3H); MS (ESI+) m/z 368 (M+H)$^+$.

Following the procedures described in Scheme 22, the following examples were synthesized:

TABLE 15

| Structure | Ex. # | 1H NMR | LC-MS (M + H)⁺ |
|---|---|---|---|
| 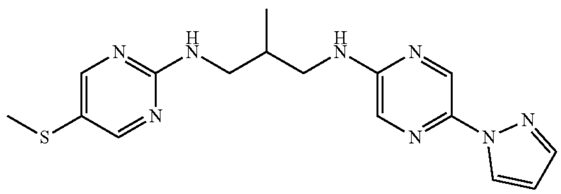 [SMILES: CSc1cnc(NCC(C)CNc2cnc(-n3cccn3)cn2)nc1] | 214 | $^1$H NMR (400 MHz, CDCl$_3$) δ 8.70 (d, J = 1.4 Hz, 1H), 8.37 (s, 2H), 8.27 (d, J = 2.3 Hz, 1H), 7.69 (dd, J = 1.4, 7.0 Hz, 2H), 6.45-6.43 (m, 1H), 5.65 (dd, J = 6.3, 6.3 Hz, 1H), 5.53 (dd, J = 6.1, 6.1 Hz, 1H), 3.57-3.24 (m, 4H), 2.36 (s, 3H), 2.14-2.04 (m, 1H), 1.06 (d, J = 6.9 Hz, 3H). | 357 |
| 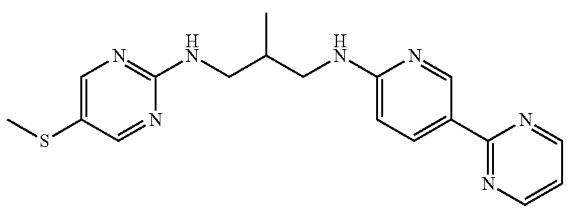 [SMILES: CSc1cnc(NCC(C)CNc2ccc(-c3ncccn3)cn2)nc1] | 215 | $^1$H NMR (400 MHz, CDCl$_3$) δ 9.20 (d, J = 2.0 Hz, 1H), 8.71 (d, J = 4.9 Hz, 2H), 8.40 (dd, J = 2.3, 8.8 Hz, 1H), 8.37 (s, 2H), 7.08 (dd, J = 4.8, 4.8 Hz, 1H), 6.47 (d, J = 8.5 Hz, 1H), 5.88 (dd, J = 6.0, 6.0 Hz, 1H), 5.43 (dd, J = 6.1, 6.1 Hz, 1H), 3.56-3.27 (m, 4H), 2.36 (s, 3H), 2.14-2.00 (m, 1H), 1.06 (d, J = 6.9 Hz, 3H). | 368 |
| 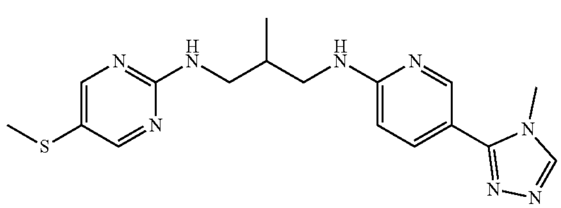 [SMILES: CSc1cnc(NCC(C)CNc2ccc(-c3nncn3C)cn2)nc1] | 216 | $^1$H NMR (400 MHz, CDCl$_3$) δ 8.38-8.36 (m, 3H), 8.16 (s, 1H), 7.78 (dd, J = 2.4, 8.7 Hz, 1H), 6.51 (d, J = 8.4 Hz, 1H), 5.83-5.78 (m, 1H), 5.57 (dd, J = 5.8, 5.8 Hz, 1H), 3.76 (s, 3H), 3.57-3.24 (m, 4H), 2.36 (s, 3H), 2.14-1.99 (m, 1H). | 371 |
| 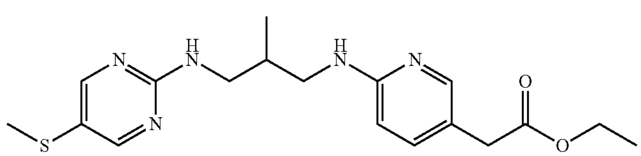 [SMILES: CCOC(=O)Cc1ccc(NCC(C)CNc2ncc(SC)cn2)nc1] | 217 | $^1$H NMR (400 MHz, CDCl$_3$) δ 8.35 (s, 2H), 7.99 (d, J = 2.1 Hz, 1H), 7.36 (dd, J = 2.4, 8.5 Hz, 1H), 6.37 (d, J = 8.5 Hz, 1H), 5.94 (dd, J = 6.0, 6.0 Hz, 1H), 4.96 (dd, J = 5.8, 5.8 Hz, 1H), 4.14 (q, J = 7.2 Hz, 2H), 3.52-3.45 (m, 3H), 3.42-3.31 (m, 2H), 3.26-3.20 (m, 1H), 2.35 (s, 3H), 2.09-2.00 (m, 1H), 1.25 (dd, J = 7.2, 7.2 Hz, 3H), 1.03 (d, J = 6.9 Hz, 3H). | 376 |

Scheme 23

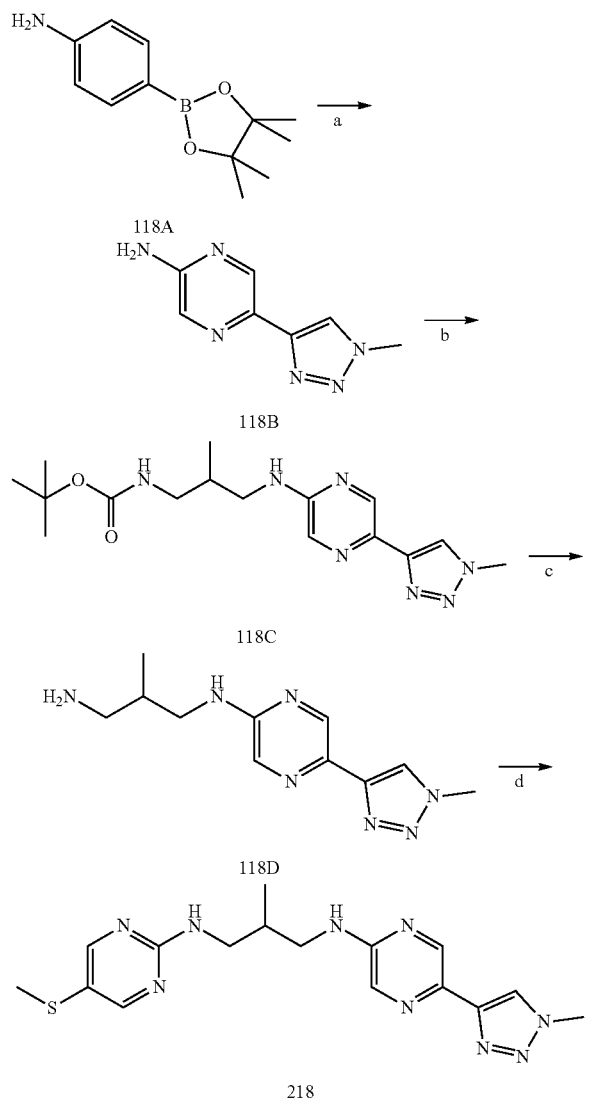

a) 4-bromo-1-methyl-1H-1,2,3-triazole, Cs₂CO₃, Pd(PPh₃)₄, dioxane/water: b) acetic acid, mol sieves, Na(CH₃COO)₃BH, DCM;
c) 4M HCl in dioxane; d) 100B, Cs₂CO₃, DMF

5-(1-Methyl-1H-1,2,3-triazol-4-yl)pyrazin-2-amine (118B)

Methodology applied was analogous to those described in General Method 7, (N.B. used 1,4-dioxane/water used as solvent instead of dimethylformamide) Yield: 158 mg (73%) m/z 176 (M+H)$^+$.

tert-Butyl (2-methyl-3-((5-(1-methyl-1H-1,2,3-triazol-4-yl)pyrazin-2-yl)amino) propyl)carbamate (118C)

Methodology applied was analogous to the method described in Scheme 13 (for the generation of 109D).
Crude tert-butyl (2-methyl-3-(5-(1-methyl-1H-1,2,3-triazol-4-yl)pyrazin-2-yl)amino) propyl)carbamate (118C) was taken on immediately to the next step.
Yield: 101 mg (34%) MS (ESI+) m/z 347 (M+H)$^+$.

2-Methyl-M-(5-(1-methyl-1H-1,2,3-triazol-4-yl)pyrazin-2-yl)propane-1,3-diamine (118D)

Methodology applied was analogous to those described in General Method 2.
Crude 2-methyl-N$^1$-(5-(1-methyl-1H-1,2,3-triazol-4-yl)pyrazin-2-yl)propane-1,3-diamine (106D) was taken on immediately to the next step.
Yield: 71 mg (assumed) MS (ESI+) m/z 367 (M+H)$^+$.

2-Methyl-N1-(5-(1-methyl-1H-1,2,3-triazol-4-yl)pyrazin-2-yl)-N3-(5-(methylthio)pyrimidin-2-yl) propane-1,3-diamine (218)

Methodology applied was analogous to those described in General Method 1.
Yield: 25 mg (23%). $^1$H NMR (400 MHz, CDCl₃) δ 8.35 (s, 3H), 8.30 (s, 1H), 8.05 (dd, J=2.3, 8.9 Hz, 1H), 7.67 (s, 1H), 6.56 (d, J=9.2 Hz, 1H), 6.11-6.06 (m, 1H), 4.14 (s, 3H), 2.63 (s, 4H), 2.35 (s, 3H), 2.19-2.10 (m, 1H), 1.07 (d, J=6.8 Hz, 3H); MS (ESI+) m/z 371 (M+H)$^+$.

Scheme 24

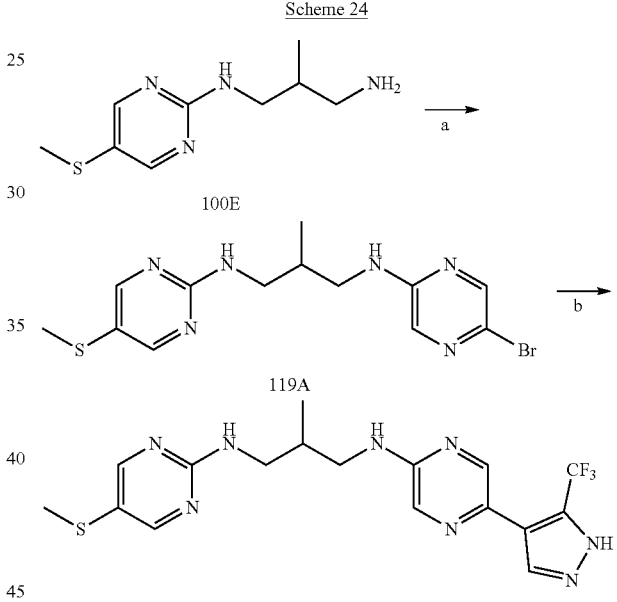

a) 2,5-dibromopyrazine, Et₃N, DMF; b) 2-(4,4,5,5-tetramethyl-1,3,2-dioxaborolan-2-yl)pyrazine, Cs₂CO₃, Pd(PPh₃)₄, 1,4-dioxane, water

N$^1$-(5-Bromopyrazin-2-yl)-2-methyl-N$^3$-(5-(methylthio)pyrimidin-2-yl)propane-1,3-diamine (119a)

Methodology applied was analogous to those described in General Method 3.
Yield: 230 mg (38%). $^1$H NMR (400 MHz, CDCl₃) δ 8.36 (s, 2H), 8.06 (d, J=1.3 Hz, 1H), 7.67 (d, J=1.4 Hz, 1H), 5.67-5.51 (m, 2H), 5.30 (s, 2H), 3.55-3.31 (m, 3H), 3.25-3.12 (m, 1H), 2.37 (s, 3H), 2.04 (s, 1H), 1.03 (d, J=6.9 Hz, 3H).

2-Methyl-N$^1$-(5-(methylthio)pyrimidin-2-yl)-N$^3$-(5-(5-(trifluoromethyl)-1H-pyrazol-4-yl)pyrazin-2-yl) propane-1,3-diamine (219)

Methodology applied was analogous to those described in General Method 7, (N.B. used 1,4-dioxane/water and no additional aliquots of reagents were added) Yield: 18 mg (31%). ¹H NMR (400 MHz, DMSO) δ 13.70 (s, 1H), 8.35-8.34 (m, 2H), 8.26 (d, J=1.0 Hz, 1H), 8.13-8.12 (m, 1H), 8.00 (d, J=1.5 Hz, 1H), 7.55-7.44 (m, 1H), 7.23-7.18 (m, 1H), 3.35-3.18 (m, 4H), 2.35 (s, 3H), 2.11-2.02 (m, 1H), 0.95 (d, J=6.8 Hz, 3H); MS (ESI+) m/z 426 (M+H)⁺.

DMSO) δ 7.34 (s, 2H), 7.27 (d, J=7.6 Hz, 1H), 6.79 (d, J=1.8 Hz, 1H), 5.29 (d, J=7.6 Hz, 1H), 5.08 (d, J=1.5 Hz, 1H), 2.44-2.37 (m, 4H), 1.36 (s, 3H), 1.20-1.11 (m, 1H), (2×NH not observed); MS (ESI+) m/z 330 (M+H)⁺.

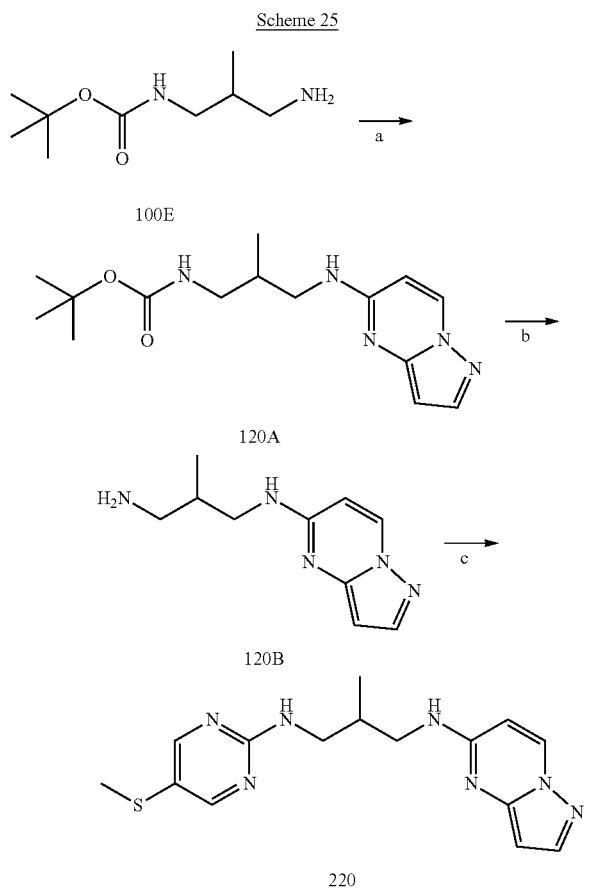

Scheme 25 a) 5-chloropyrazolo[1,5-c]pyrimidine, microwave 140° C., 30 min; b) 4M HCl in 1,4-dioxane; c) 100B, Cs₂CO₃, DMF

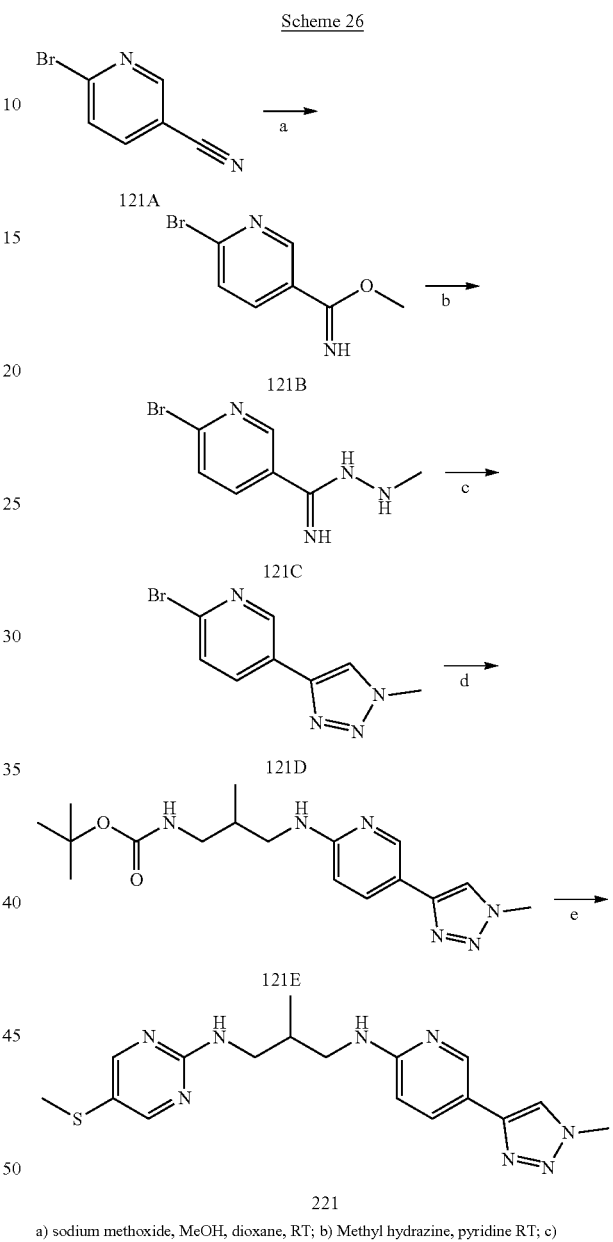

Scheme 26 a) sodium methoxide, MeOH, dioxane, RT; b) Methyl hydrazine, pyridine RT; c) Formic acid, reflux; d) tert-butyl (3-amino-2-methylpropyl) carbamate, Pd(PPh₃)₄, Cs₂CO₃, dioxane, water 80° C. overnight; e) i) 4M HCl in dioxane, ii) Cs₂CO₃, TEA, DMF, 50° C.

tert-Butyl (2-methyl-3-(pyrazolo[1,5-a]pyrimidin-5-ylamino)propyl)carbamate (120A)

A microwave vial containing 5-chloropyrazolo[1,5-c]pyrimidine (500 mg, 3.26 mmol, 1 eq) and tert-butyl (3-amino-2-methylpropyl)carbamate (100E) (6.13 g, 32.56 mmol, 10 eq) was heated to 140° C. for 30 minutes under microwave irradiation. The crude reaction mixture was purified by flash chromatography (eluting with iso-hexane to ethyl acetate, 0-100%) to give tert-butyl (2-methyl-3-(pyrazolo[1,5-c]pyrimidin-5-ylamino)propyl)carbamate (120A)
Yield: 700 mg (70%). MS (ESI+) m/z 306 (M+H)⁺.

2-Methyl-N¹-(pyrazolo[1,5-a]pyrimidin-5-yl)propane-1,3-diamine (120B)

Methodology applied was analogous to those described in General Method 2. MS (ESI+) m/z 229 (M+H)⁺.

tert-Butyl (2-methyl-3-(pyrazolo[1,5-a]pyrimidin-5-ylamino)propyl)carbamate (220)

Methodology applied was analogous to those described in General Method 3. Yield: 20 mg (14%). ¹H NMR (400 MHz, Methyl 6-bromonicotinimidate (121B)

Sodium methoxide (0.71 g, 13.22 mmol, 1.1 eq) was added to an ice cooled solution of 6-bromonicotinonitrile (121A) (2.2 g, 12.02 mmol, 1.0 eq) in dioxane/water (20 mL/20 mL). The mixture was stirred under ice cooling for 30 minutes and then allowed to warm to room temperature. After 1 hour the mixture was diluted with ethyl acetate (200 mL) and water (200 mL). The organic phase was separated and the aqueous phase was further extracted with ethyl acetate (50 mL). The organics were combined and the solvents were removed under vacuum to afford crude methyl 6-bromonicotinimidate (121B) which was used in the next step without further purification.

Yield: 2.5 g (96%).

6-Bromo-N'-methylnicotinimidohydrazide (121C)

Methyl hydrazine (0.73 mL, 13.96 mmol, 1.2 eq) was added to a solution of 6-bromonicotinimidate (121B) (2.5 g, 11.63 mmol, 1.0 eq) and the mixture was stirred at room temperature for 1 hour. The solvents were removed under vacuum to afford crude 6-bromo-N-methylnicotinimidohydrazide (121C) which was used in the next step without further purification.

Yield: 2 g (75%).

2-Bromo-5-(1-methyl-1H-1,2,4-triazol-3-yl)pyridine (121D)

Formic acid (10 mL, 265 mmol, 30.4 eq) was added to 6-bromo-N-methylnicotinimidohydrazide (121C) (2.0 g, 8.73 mmol, 1.0 eq) and the mixture was heated to reflux for 1 hour. The reaction mixture was diluted with water (100 mL) and then extracted with ethyl acetate (3×50 mL). The combined organic phases were washed with a saturated aqueous solution of sodium hydrogen carbonate (50 mL), dried over sodium sulphate and filtered. The solvents were removed under vacuum to afford crude a brown residue which was purified by flash chromatography (eluting with 0-10% methanol in dichloromethane/dichloromethane to give 2-bromo-5-(1-methyl-1H-1,2,4-triazol-3-yl) pyridine (121D) as an off white solid.

Yield: 500 mg (23%). MS (ESI+) m/z 240 (M+H)$^+$.

tert-Butyl (2-methyl-3-((5-(1-methyl-1H-1,2,4-triazol-3-yl)pyridin-2-yl)amino) propyl)carbamate (121E)

Methodology applied was analogous to those described in General Method 7, (N.B. used 1,4-dioxane/water and no additional aliquots of reagents were added).

Yield: 125 mg

2-Methyl-N$^1$-(5-(1-methyl-1H-1,2,4-triazol-3-yl) pyridin-2-yl)-N$^3$-(5-(methylthio)pyrimidin-2-yl)propane-1,3-diamine (221)

Methodology applied was analogous to those described in General Method 2 for the deprotection and then General Method 1.

Yield: 25 mg (18%). $^1$H NMR (400 MHz, DMSO) δ 8.42 (d, J=2.0 Hz, 1H), 8.34 (s, 2H), 8.04 (s, 1H), 7.76 (dd, J=2.4, 8.8 Hz, 1H), 7.48 (dd, J=6.0, 6.0 Hz, 1H), 6.82 (dd, J=5.8, 5.8 Hz, 1H), 6.57 (d, J=8.4 Hz, 1H), 4.16 (s, 3H), 3.32-3.17 (m, 4H), 2.35 (s, 3H), 2.09-1.99 (m, 1H), 0.93 (d, J=6.7 Hz, 3H); MS (ESI+) m/z 371 (M+H)$^+$.

Scheme 27

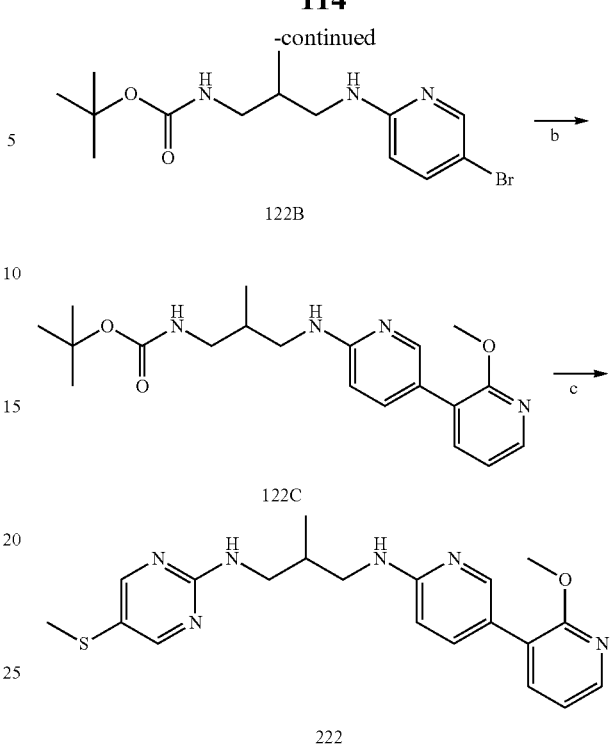

a) tert-butyl N-(2-methyl-3-oxopropyl)carbamate, acetic acid, mol sieves, Na(CH$_3$COO)$_3$BH, DCM; b) (2-methoxypyridin-3-yl)boronic acid, Pd(PPh$_3$)$_4$, Cs$_2$CO$_3$, dioxane, water 80° C. overnight; c) i) 4M HCl in dioxane, ii) Cs$_2$CO$_3$, TEA, DMF 50° C. overnight.

tert-Butyl (3-((5-bromopyridin-2-yl)amino)-2-methylpropyl)carbamate (122B)

tert-Butyl N-(2-methyl-3-oxopropyl)carbamate (100E) (1.0 g, 5.34 mmol, 1.0 eq) was added to a solution of 5-bromopyridin-2-amine (122A) (920 mg, 5.34 mmol, 1.0 eq), acetic acid (1.2 mL, 21.36 mmol, 4.0 eq) and molecular sieves (type 4 Å, 1.0 g) in anhydrous dichloromethane (50 mL). The reaction mixture was stirred at room temperature for 5 minutes and then sodium triacetoxyborohydride (2.83 g, 13.35 mmol, 2.5 eq) was added in one portion. The mixture was stirred at room temperature for 5 h. The reaction was quenched by the careful addition of a saturated aqueous solution of sodium hydrogen carbonate (30 mL). The mixture was stirred vigorously for 30 minutes and the dichloromethane layer was then separated and washed with an aqueous solution of sodium thiosulphate (1M, 15 mL). The organic phase was isolated and concentrated under reduced pressure to give semi-crude tert-butyl (3-((5-bromopyridin-2-yl)amino)-2-methylpropyl)carbamate (122B) as a pale brown gum which was used in the next reaction without further purification.

Yield: 875 mg (47%).

tert-Butyl (3-((2'-methoxy-[3,3'-bipyridin]-6-yl) amino)-2-methylpropyl)carbamate (122C)

Methodology applied was analogous to those described in General Method 7.

Yield: 138 mg.

$N^1$-(2'-Methoxy-[3,3'-bipyridin]-6-yl)-2-methyl-$N^3$-(5-(methylthio)pyrimidin-2-yl)propane-1,3-diamine (222)

Methodology applied was analogous to those described for General Method 2 for the deprotection and then General Method 1.

Yield: 57 mg. $^1$H NMR (400 MHz, CDCl$_3$) δ 8.36 (s, 2H), 8.23 (d, J=2.0 Hz, 1H), 7.68 (dd, J=2.3, 8.7 Hz, 1H), 7.32-7.27 (m, 2H), 7.03-6.95 (m, 2H), 6.48 (d, J=8.7 Hz, 1H), 5.94-5.90 (m, 2H), 3.82 (s, 3H), 3.56-3.47 (m, 1H), 3.44-3.35 (m, 2H), 3.28 (dd, J=6.6, 13.4 Hz, 1H), 2.35 (s, 3H), 2.18-2.07 (m, 1H), 1.06 (d, J=6.9 Hz, 3H); MS (ESI+) m/z 396 (M+H)$^+$.

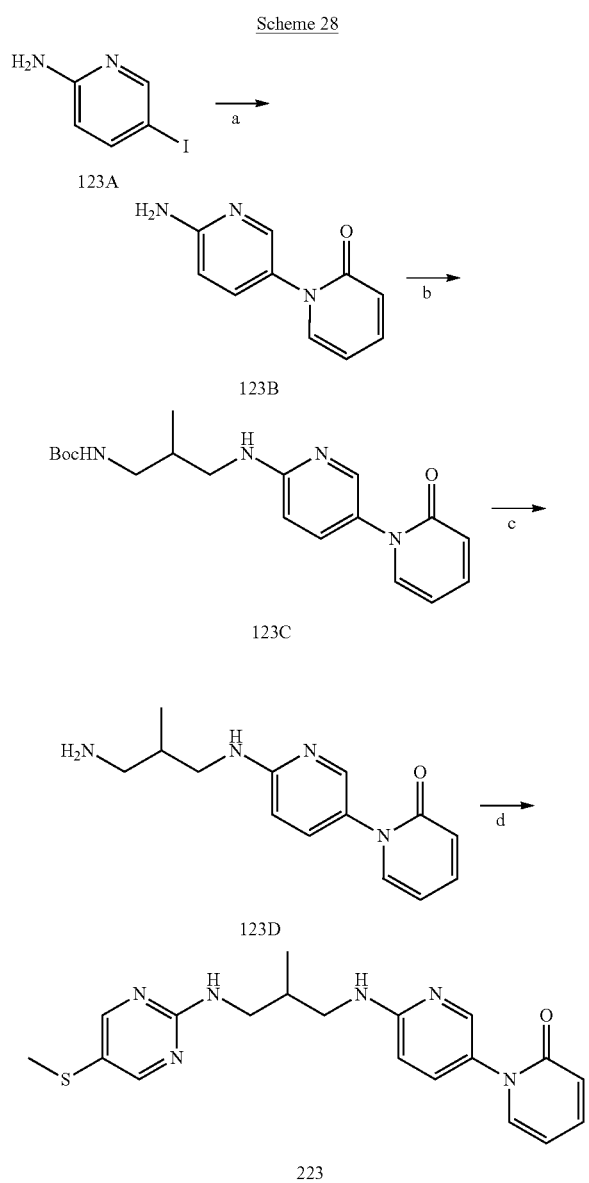

Scheme 28 a) 2-Hydroxypyridine, CuI, 8-Quinolol, K$_2$CO$_3$, DMSO, 130° C.; b) tert-butyl (2-methyl-3-oxopropyl)carbamate, 4A molecular sieves, NaBH(OAc)$_3$, AcOH, DCM, RT; c) 4M HCl in 1,4-dioxane, H$_2$O, RT; d) 2-chloro-5-(methylthio)pyrimidine, Et$_3$N, Cs$_2$CO$_3$, DMF, RT

6'-Chloro-2H-[1,3'-bipyridin]-2-one (123B)

2-Amino-5-iodopyridine (123A) (1.12 g, 5.00 mmol, 1.0 eq) was combined with 2-hydroxypyridine (582 mg, 6.00 mmol, 1.2 eq), potassium carbonate (760 mg, 5.50 mmol, 1.1 eq), copper (I) iodide (143 mg, 0.75 mmol, 0.15 eq) and 8-hydroxyquinoline (110 mg, 0.75 mmol, 0.15 eq) in anhydrous dimethylsulfonamide (5 mL). The mixture was degassed under a stream of nitrogen and then heated at 130° C. for 21 h. The reaction mixture was allowed to cool to room temperature then poured into a mixture of 10% aqueous ammonium hydroxide solution (100 mL) and ethyl acetate (50 mL). Activated charcoal (1 g) was added and the mixture was filtered through a pad of celite, washing with ethyl acetate (2×50 mL). The layers were separated and the aqueous phase was extracted with ethyl acetate (2×50 mL). The combined organic extracts were washed with saturated brine (50 mL), dried over anhydrous magnesium sulfate, filtered and then concentrated under reduced pressure. The crude pale yellow solid was purified by flash chromatography (eluting dichloromethane to methanol, 0-10%) to give the desired product 6'-chloro-2H-[1,3'-bipyridin]-2-one as an off white solid (123B).

Yield: 245 mg, (26%). $^1$H NMR (400 MHz, DMSO) δ 7.88 (1H, d, J=2.5 Hz), 7.60 (1H, ddd, J=0.7, 2.1, 6.8 Hz), 7.49 (1H, ddd, J=2.2, 6.7, 9.1 Hz), 7.41 (1H, dd, J=2.7, 8.7 Hz), 6.52 (1H, dd, J=0.4, 8.8 Hz), 6.45 (1H, ddd, J=0.7, 1.3, 9.2 Hz), 6.28 (1H, ddd, J=6.7, 6.7, 1.3 Hz), 6.23 (2H, s); MS (ESI+) m/z 188 (M+H)$^+$.

tert-Butyl (2-methyl-3-((2-oxo-2H-[1,3'-bipyridin]-6'-yl)amino)propyl)carbamate (123C)

Methodology applied was analogous to those described in Scheme 19.

6'-Chloro-2H-[1,3'-bipyridin]-2-one (123B) was used in excess (245 mg, 1.31 mmol, 1.1 eq). 4 Å Molecular sieves were used in the reaction. The crude product was purified by flash chromatography (eluting dichloromethane to methanol, 0-7%) to give the desired product tert-butyl (2-methyl-3-((2-oxo-2H-[1,3'-bipyridin]-6'-yl)amino) propyl)carbamate (123C) as a pale brown solid.

Yield: 249 mg, (58%). MS (ESI+) m/z 359 (M+H)$^+$.

6'-((2-Methyl-3-((5-(methylthio)pyrimidin-2-yl)amino)propyl)amino)-2H-[1,3'-bipyridin]-2-one (223)

Methodology applied was analogous to those described in General Method 2 using a (4:1) ratio of 4M HCl in 1,4-dioxane-water, followed by General Method 3 using cesium carbonate (3.0 eq) in combination with triethylamine (2.0 eq).

Yield: 152 mg (57% over 2 steps).

$^1$H NMR (400 MHz, DMSO) δ 8.35 (2H, s), 7.91 (1H, d, J=2.6 Hz), 7.61 (1H, ddd, J=0.6, 2.1, 6.8 Hz), 7.52-7.45 (2H, m), 7.40 (1H, dd, J=2.7, 8.9 Hz), 6.90 (1H, dd, J=5.8, 5.8 Hz), 6.57 (1H, dd, J=0.5, 8.9 Hz), 6.45 (1H, ddd, J=0.7, 1.2, 9.2 Hz), 6.28 (1H, ddd, J=6.7, 6.7, 1.4 Hz), 3.33-3.14 (4H, m), 2.35 (3H, s), 2.10-2.00 (1H, m), 0.94 (3H, d, J=6.8 Hz); MS (ESI+) m/z 383 (M+H)$^+$.

Using the procedures described in Scheme 28, the following examples were synthesized:

TABLE 16

| Structure | Ex. # | ¹H NMR | LC-MS (M + H)⁺ |
| --- | --- | --- | --- |
| 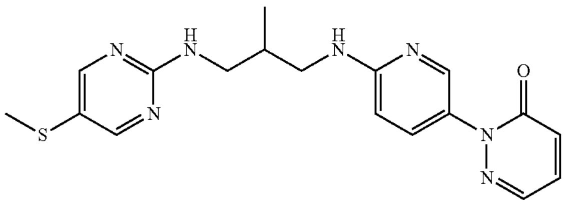 [SMILES: CSc1cnc(NCC(C)CNc2ccc(-n3ncccc3=O)cn2)nc1] | 224 | ¹H NMR (400 MHz, DMSO) δ 8.34 (2H, s), 8.18 (0.5H, s), 8.10 (1H, dd, J = 0.4, 2.6 Hz), 8.03 (1H, dd, J = 1.6, 3.9 Hz), 7.52 (1H, dd, J = 2.7, 9.0 Hz), 7.50-7.45 (2H, m), 7.04 (1H, dd, J = 1.6, 9.4 Hz), 6.91 (1H, dd, J = 5.8, 5.8 Hz), 6.57 (1H, dd, J = 0.5, 9.0 Hz), 3.35-3.15 (4H, m), 2.35 (3H, s), 2.10-2.00 (1H, m), 0.94 (3H, d, J = 6.8 Hz). Partial formate salt. | 384 |
| 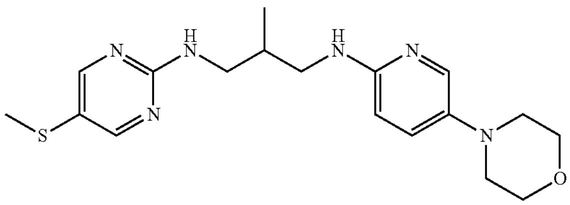 [SMILES: CSc1cnc(NCC(C)CNc2ccc(N3CCOCC3)cn2)nc1] | 225 | ¹H NMR (400 MHz, DMSO) δ 8.34 (2H, s), 8.16 (1H, s), 7.64 (1H, d, J = 2.8 Hz), 7.47 (1H, dd, J = 6.0, 6.0 Hz), 7.19 (1H, dd, J = 2.9, 9.0 Hz), 6.46 (1H, d, J = 8.9 Hz), 6.11 (1H, dd, J = 5.1, 5.1 Hz), 3.75-3.68 (4H, m), 3.30-3.05 (4H, m), 2.94-2.87 (4H, m), 2.35 (3H, s), 2.05-1.92 (1H, m), 0.91 (3H, d, J = 6.8 Hz). Formate salt. | 375 |
| 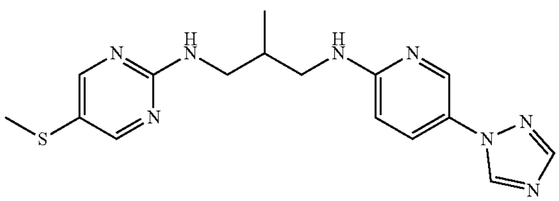 [SMILES: CSc1cnc(NCC(C)CNc2ccc(-n3cncn3)cn2)nc1] | 226 | ¹H NMR (400 MHz, CDCl₃) δ 8.40-8.31 (4H, m), 8.09 (1H, s), 7.65 (1H, dd, J = 2.5, 8.8 Hz), 6.49 (1H, d, J = 8.8 Hz), 5.77 (1H, dd, J = 6.2, 6.2 Hz), 5.44 (1H, dd, J = 5.7, 5.7 Hz), 3.57-3.23 (4H, m), 2.36 (3H, s), 2.13-2.02 (1H, m), 1.05 (3H, d, J = 6.8 Hz). | 357 |
| 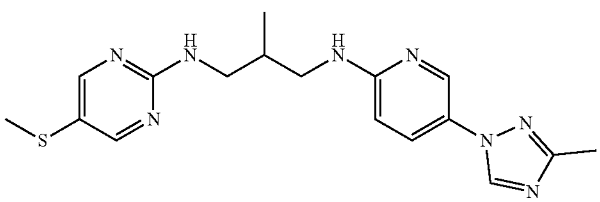 | 227 | ¹H NMR(400 MHz, DMSO) δ 9.04 (1H, s), 8.41-8.33 (3H, m), 8.10 (1H, dd, J = 2.0, 9.3 Hz), 7.59 (4H, br s), 7.03 (1H, d, J = 9.3 Hz), 3.44-3.23 (4H, m), 2.41 (3H, s), 2.39 (3H, s), 2.20-2.09 (1H, m), 1.01 (3H, d, J = 6.6 Hz), Bis(trifluoroacetate) salt. | 371 |
| 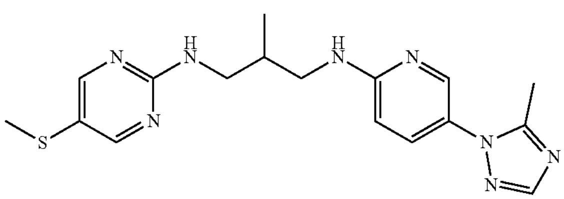 [SMILES: CSc1cnc(NCC(C)CNc2ccc(-n3ncnc3C)cn2)nc1] | 228 | ¹H NMR (400 MHz, DMSO) δ 8.39 (2H, s), 8.23 (1H, d, J = 2.3 Hz), 8.10 (1H, s), 7.78 (1H, dd, J = 2.0, 9.1 Hz), 7.57 (1H, br s), 6.91 (1H, d, J = 9.1 Hz), 5.11 (3H, br s), 3.43-3.24 (4H, m), 2.46 (3H, s), 2.40 (3H, s), 2.19-2.09 (1H, m), 1.01 (3H, d, J = 6.8 Hz), Bis(trifluoroacetate) salt. | 371 |
| 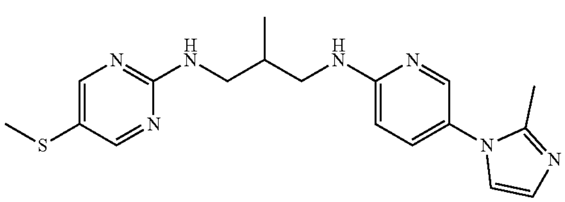 [SMILES: CSc1cnc(NCC(C)CNc2ccc(-n3ccnc3C)cn2)nc1] | 229 | ¹H NMR (400 MHz, DMSO) δ 8.34 (2H, s), 8.16 (1H, s), 7.98 (1H, d, J = 2.4 Hz), 7.47 (1H, dd, J = 6.0, 6.0 Hz), 7.43 (1H, dd, J = 2.7, 8.9 Hz), 7.16 (1H, d, J = 1.4 Hz), 6.92 (1H, dd, J = 5.8, 5.8 Hz), 6.87 (1H, d, J = 1.1 Hz), 6.60 (1H, dd, J = 0.6, 8.9 Hz), 3.35-3.26 (3H, m), 3.26-3.14 (2H, m), 2.35 (2H, s), 2.21 (3H, s), 2.10-2.00 (1H, m), 0.94 (3H, d, J = 6.8 Hz). Formate salt. | 370 |

TABLE 16-continued

| Structure | Ex. # | ¹H NMR | LC-MS (M + H)⁺ |
|---|---|---|---|
| 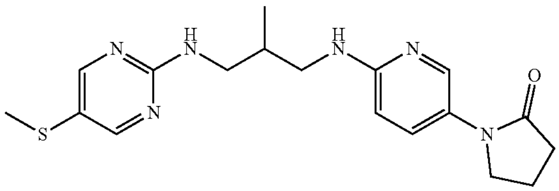 [SMILES: CSc1cnc(NCC(C)CNc2ccc(N3CCCC3=O)cn2)nc1] | 230 | ¹H NMR (400 MHz, CDCl₃) δ 8.35 (2H, s), 8.05 (1H, d, J = 2.4 Hz), 7.92 (1H, dd, J = 2.8, 9.0 Hz), 6.43 (1H, dd, J = 0.5, 9.1 Hz), 5.96 (1H, dd, J = 5.8, 5.8 Hz), 3.80 (2H, ddt, J = 3.5, 3.5, 3.5 Hz), 3.53-3.44 (1H, m), 3.39-3.30 (2H, m), 3.22 (1H, dd, J = 6.8, 13.6 Hz), 2.63-2.53 (3H, m), 2.36 (3H, s), 2.22-2.01 (3H, m), 1.03 (3H, d, J = 6.9 Hz). | 373 |
| 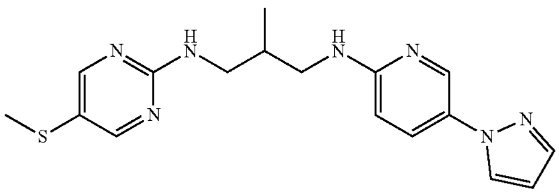 [SMILES: CSc1cnc(NCC(C)CNc2ccc(-n3cccn3)cn2)nc1] | 231 | ¹H NMR (400 MHz, CDCl₃) δ 8.39-8.34 (3H, m), 7.77-7.74 (1H, m), 7.73 (1H, d, J = 2.7 Hz), 7.70 (1H, d, J = 1.5 Hz), 6.47 (1H, dd, J = 0.5, 9.0 Hz), 6.44 (1H, dd, J = 2.1, 2.1 Hz), 5.84 (1H, dd, J = 6.1, 6.1 Hz), 5.19 (1H, dd, J = 6.1, 6.1 Hz), 3.56-3.33 (3H, m), 3.31-3.23 (1H, m), 2.36 (3H, s), 2.12-2.03 (1H, m), 1.05 (3H, d, J = 6.9 Hz). | 356 |
| 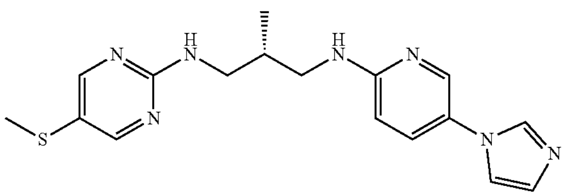 [SMILES: CSc1cnc(NC[C@H](C)CNc2ccc(-n3ccnc3)cn2)nc1] | 232 | ¹H NMR (400 MHz, CDCl₃) δ 8.37 (2H, s), 8.16 (1H, d, J = 2.5 Hz), 7.87-7.76 (1H, m), 7.41 (1H, dd, J = 2.6, 8.9 Hz), 7.22-7.11 (1H, m), 6.48 (1H, d, J = 8.8 Hz), 5.81 (1H, br s), 5.52 (1H, br s), 3.57-3.48 (1H, m), 3.47-3.34 (2H, m), 3.27 (1H, dd, J = 7.2, 13.7 Hz), 2.36 (3H, s), 2.15-2.04 (2H, m), 1.06 (3H, d, J = 6.9 Hz). | 356 |

Scheme 29

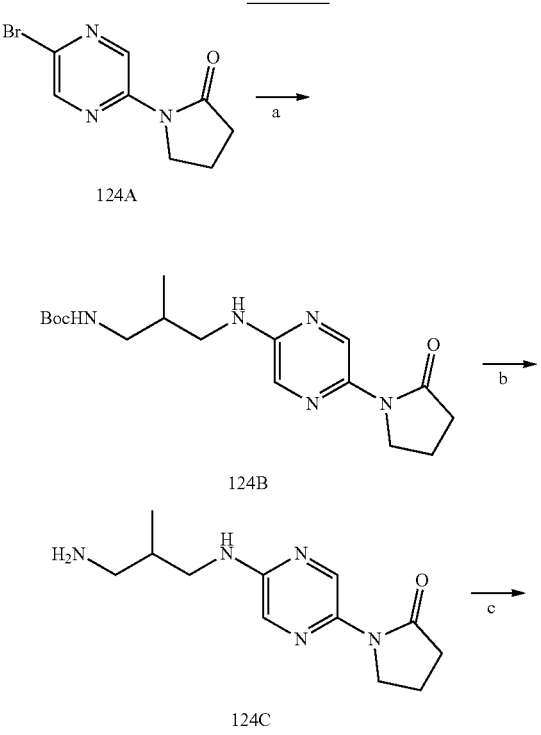

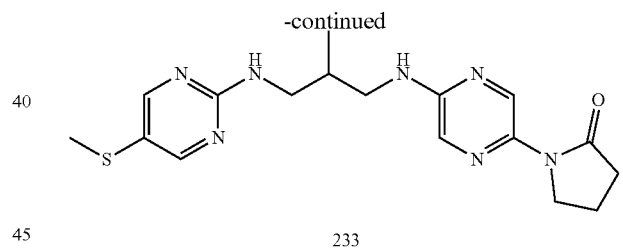

233 a) tert-Butyl N-(3-amino-2-methylpropyl)carbamate, CuI, L-Proline, K₂PO₄, DMSO, 90° C.; b) 4M HCl in 1,4-dioxane, H₂O, RT; c) 2-chloro-5-(methylthio)pyrimidine, Et₃N, Cs₂CO₃, DMF, RT tert-Butyl (2-methyl-3-((5-(2-oxopyrrolidin-1-yl)pyrazin-2-yl)amino)propyl) carbamate (124B)

A solution of tert-butyl N-(3-amino-2-methylpropyl)carbamate (100E) (436 mg, 2.20 mmol, 1.1 eq) in anhydrous dimethylsulfonamide (10 mL) was added to 2-bromo-5-(pyrrolidinon-1-yl)pyrazine (124A) (510 mg, 2.00 mmol, 1.0 eq), potassium phosphate tribasic (866 mg, 4.00 mmol, 2 eq), L-proline (94 mg, 0.80 mmol, 0.4 eq) and copper (I) iodide (76 mg, 0.40 mmol, 0.2 eq). The mixture was degassed and kept under a stream of nitrogen, then heated at 90° C. with stirring for 20 h. The reaction mixture was allowed to cool to room temperature then poured into a mixture of water (50 mL) and ethyl acetate (50 mL). The layers were separated and the aqueous phase was extracted with ethyl acetate (2×50 mL). The combined organic extracts were washed with saturated brine (50 mL), dried over anhydrous magnesium sulfate, filtered and then concentrated under reduced pressure. The crude product was purified by flash chromatography (eluting dichloromethane to methanol, 0-6%) to give the desired product tert-butyl (2-methyl-3-((5-(2-oxopyrrolidin-1-yl)pyrazin-2-yl)amino) propyl)carbamate (124B) as a yellow solid. Yield: 375 mg, (54%). MS (ESI+) m/z 350 (M+H)+.

1-(5-((2-Methyl-3-((5-(methylthio)pyrimidin-2-yl) amino)propyl)amino)pyrazin-2-yl)pyrrolidin-2-one (233)

Methodology applied was analogous to those described in General Method 2 using a [4:1] ratio of 4M HCl in 1,4-dioxane-water, followed by General Method 3. Yield: 71 mg (18% over 2 steps).
$^1$H NMR (400 MHz, CDCl$_3$) δ 9.02 (1H, d, J=1.5 Hz), 8.35 (2H, s), 7.64 (1H, d, J=1.5 Hz), 5.63 (1H, dd, J=6.2, 6.2 Hz), 5.24 (1H, dd, J=5.7, 5.7 Hz), 3.97 (2H, t, J=7.1 Hz), 3.55-3.46 (1H, m), 3.45-3.32 (2H, m), 3.28-3.19 (1H, m), 2.62 (2H, t, J=8.1 Hz), 2.36 (3H, s), 2.20-2.02 (3H, m), 1.03 (3H, d, J=6.8 Hz); MS (ESI+) m/z 374 (M+H)+.

Scheme 30

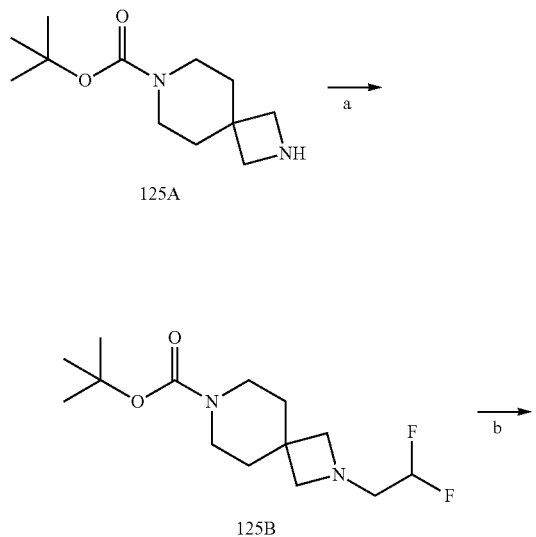

a) RX, K$_2$CO$_3$, DMF, b) TFA, DCM

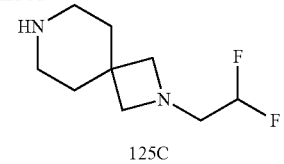

tert-Butyl 2-(2,2-difluoroethyl)-2,7-diazaspiro[3.5] nonane-7-carboxylate (125B)

1,1-Difluoro-2-iodo-ethane (128 mg, 0.67 mmol, 1.2 eq) was added to a suspension of tert-butyl 2,7-diazaspiro[3.5] nonane-7-carboxylate (125A) (126 mg, 0.56 mmol, 1.0 eq), potassium carbonate (231 mg, 1.67 mmol, 3.0 eq) in dimethylformamide (1.0 mL) and the mixture was stirred at 60° C. for 2 h. The reaction mixture was cooled to room temperature, diluted with water and extracted with ethyl acetate. The organic phase was washed with brine, dried by passing through a phase separator and then concentrated under reduced pressure to afford the desired tert-butyl 2-(2, 2-difluoroethyl)-2,7-diazaspiro[3.5]nonane-7-carboxylate (125B) as a pale yellow oil.
Yield: 73 mg (45%). $^1$H NMR (400 MHz, CDCl$_3$) δ 5.87-5.57 (m, 1H), 3.41-3.30 (m, 4H), 3.14 (s, 4H), 2.89-2.77 (m, 2H), 1.76-1.67 (m, 4H), 1.46 (s, 9H).

2-(2,2-Difluoroethyl)-2,7-diazaspiro[3.5]nonane (125C)

Trifluoroacetic acid (1.3 mL) was added dropwise to a solution of tert-butyl difluoroethyl)-2,7-diazaspiro[3.5] nonane-7-carboxylate (125B) (73 mg, 0.25 mmol, 1.0 eq) in dichloromethane (1.3 mL). The mixture was stirred for 30 minutes and then concentrated to dryness under reduced pressure to afford the desired product 2-(2,2-difluoroethyl)-2,7-diazaspiro[3.5]nonane (125C) as a pale yellow oil which was used in the next reaction without further purification.
The intermediates in Table 17 were synthesized using conditions analogous to those described for intermediate 125C:

TABLE 17

| Structure | Compound No. | $^1$H NMR | LC-MS (M + H)+ |
|---|---|---|---|
| | Intermediate | $^1$H NMR (400 MHz, CDCl$_3$) δ 4.67-4.24 (m, 4H), 3.74 (s, 2H), 3.35-3.08 (m, 6H), 1.76-1.66 (m, 4H), NH not observed. | N/A |
| | Intermediate | $^1$H NMR (400 MHz, CDCl$_3$) δ 5.87-5.57 (m, 1H), 3.41-3.30 (m, 4H), 3.14 (s, 4H), 2.89-2.77 (m, 2H), 1.76-1.67(m, 4H), 1.46 (s, 9H). | N/A |

Scheme 31

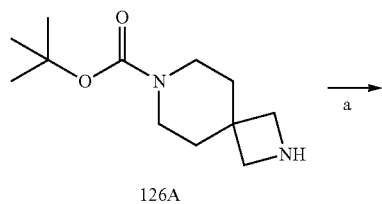

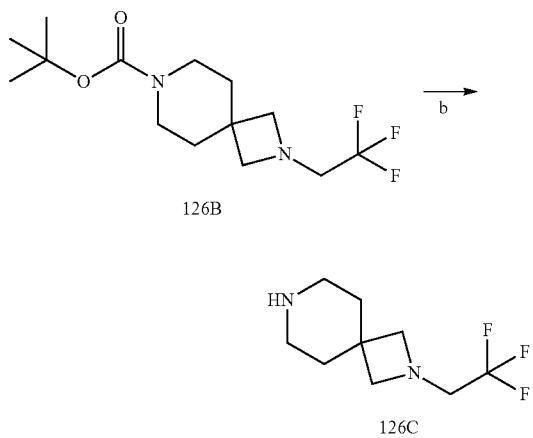

a) ROSO$_2$CF$_3$, Cs$_2$CO$_3$, MeCN, b) TFA, DCM tert-Butyl 2-(2,2,2-trifluoroethyl)-2,7-diazaspiro[3.5]nonane-7-carboxylate (126B)

2,2,2-Trifluoroethyl trifluoromethanesulfonate (153 mL, 1.06 mmol, 1.2 eq) was added to a suspension of tert-butyl 2,7-diazaspiro[3.5]nonane-7-carboxylate (126A) (200 mg, 0.88 mmol, 1.0 eq), cesium carbonate (862 mg, 2.65 mmol, 3.0 eq) in acetonitrile (2.0 mL) and the mixture was stirred at 80° C. for 16 h. The reaction mixture was cooled to room temperature, diluted with water and extracted with ethyl acetate. The combined organic phase was washed with brine, dried passing though a phase separator and then concentrated under reduced pressure to afford tert-butyl 2-(2,2,2-trifluoroethyl)-2,7-diazaspiro[3.5]nonane-7-carboxylate (126B) as a sticky white solid. The sample was used in the next step without further purification.

Yield: 341 mg (Quant.). $^1$H NMR (400 MHz, CDCl$_3$) δ 3.38-3.30 (m, 4H), 3.19 (s, 4H), 3.01 (q, J=9.4 Hz, 2H), 1.73-1.69 (m, 4H), 1.45 (s, 9H).

2-(2,2,2-Trifluoroethyl)-2,7-diazaspiro[3.5]nonane (126C)

Trifluoroacetic acid (1.3 mL) was added dropwise to a solution of tert-butyl 2-(2,2,2-trifluoroethyl)-2,7-diazaspiro[3.5]nonane-7-carboxylate (126B) (110 mg, 0.357 mmol, 1.0 eq) in dichloromethane (1.0 mL). The mixture was stirred for 30 minutes and then concentrated to dryness under reduced pressure to afford 2-(2,2,2-trifluoroethyl)-2,7-diazaspiro[3.5]nonane (126C) as a pale brown oil, which was used directly in the next step without further purification, assumed 100% yield.

Scheme 32

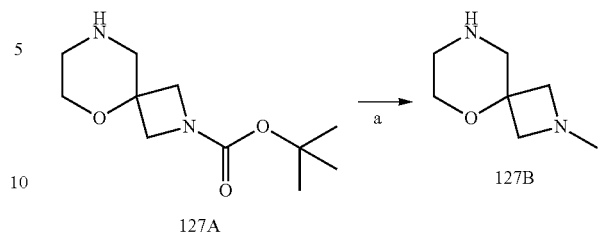

a) LiAlH$_4$, THF

2-Methyl-5-oxa-2,8-diazaspiro[3.5]nonane (127B)

Lithium aluminium hydride (1M solution in tetrahydrofuran, 1.97 mL, 1.97 mmol, 3.0 eq) was added dropwise under nitrogen to a 0° C. cooled solution of tert-butyl 5-oxa-2,8-diazaspiro[3.5]nonane-2-carboxylate (127A) (150 mg, 0.657 mmol, 1.0 eq) in tetrahydrofuran (4.0 mL). The reaction was stirred at 0° C. for 5 minutes, the cooling bath was removed and the reaction was then heated to 70° C. for 16 h (effervescence was observed at 0° C. and 35° C.). The reaction mixture was cooled to 0° C. and quenched by the slow addition of water (0.075 mL), aqueous sodium hydroxide solution (15%, 0.075 mL) and then water (0.22 mL). The cooling bath was removed and the reaction mixture was stirred for 15 minutes, magnesium sulfate was added and stirred for a further 40 minutes. The mixture was dried passing through a phase separator, washed with tetrahydrofuran and diethyl ether and then concentrated to dryness under reduced pressure to afford 2-methyl-5-oxa-2,8-diazaspiro[3.5]nonane (127B) as a pale brown oil. The sample was taken on into the next reaction without further purification.

Yield: assumed 100%. $^1$H NMR (400 MHz, CDCl$_3$) δ 3.63-3.56 (m, 2H), 3.47-3.43 (m, 2H), 3.00 (s, 2H), 2.94-2.86 (m, 2H), 2.83-2.79 (m, 2H), 2.40 (s, 3H), NH not observed.

The intermediate in Table 18 were synthesized using conditions analogous to those described for intermediate 127B:

TABLE 18

| Structure | Compound No. | $^1$H NMR | LC-MS (M + H)$^+$ |
|---|---|---|---|
| 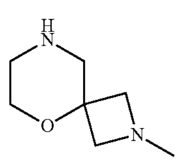 | Intermediate | $^1$H NMR (400 MHz, CDCl$_3$) δ 3.63-3.56 (m, 2H), 3.47-3.43 (m, 2H), 3.00 (s, 2H), 2.94-2.86 (m, 2H), 2.83-2.79 (m, 2H), 2.40 (s, 3H), NH not observed. | — |

Scheme 33

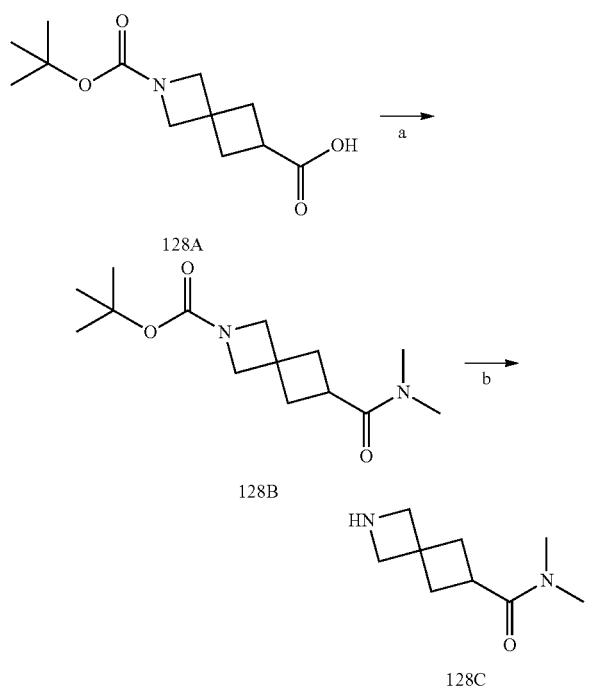

a) HATU, Et₃N, Me₂NH, DMF  b) TFA, DCM tert-Butyl 6-(dimethylcarbamoyl)-2-azaspiro[3.3]heptane-2-carboxylate (128B)

Method used was analogous to those described in General Method 5 using 2-(tert-butoxycarbonyl)-2-azaspiro[3.3]heptane-6-carboxylic acid to afford the desired product tert-butyl 6-(dimethylcarbamoyl)-2-azaspiro[3.3]heptane-2-carboxylate (128B). Yield: 111 mg (Quant.). $^1$H NMR (400 MHz, DMSO) δ 3.87 (s, 2H), 3.70 (s, 2H), 3.23-3.14 (m, 1H), 2.86 (s, 3H), 2.79 (s, 3H), 2.32-2.24 (m, 4H), 1.37-1.36 (m, 9H).

N,N-Dimethyl-2-azaspiro[3.3]heptane-6-carboxamide (128C)

Trifluoroacetic acid (2.1 mL) was added dropwise to a solution of tert-butyl 6-(dimethylcarbamoyl)-2-azaspiro[3.3]heptane-2-carboxylate (128B) (110 mg, 0.357 mmol, 1.0 eq) in dichloromethane (2.1 mL). The mixture was stirred for 30 minutes and then concentrated to dryness under reduced pressure to afford the desired product N,N-dimethyl-2-azaspiro[3.3]heptane-6-carboxamide (128C) as a pale brown oil. The sample was taken on into the next reaction without further purification, assumed 100% yield.

Scheme 34

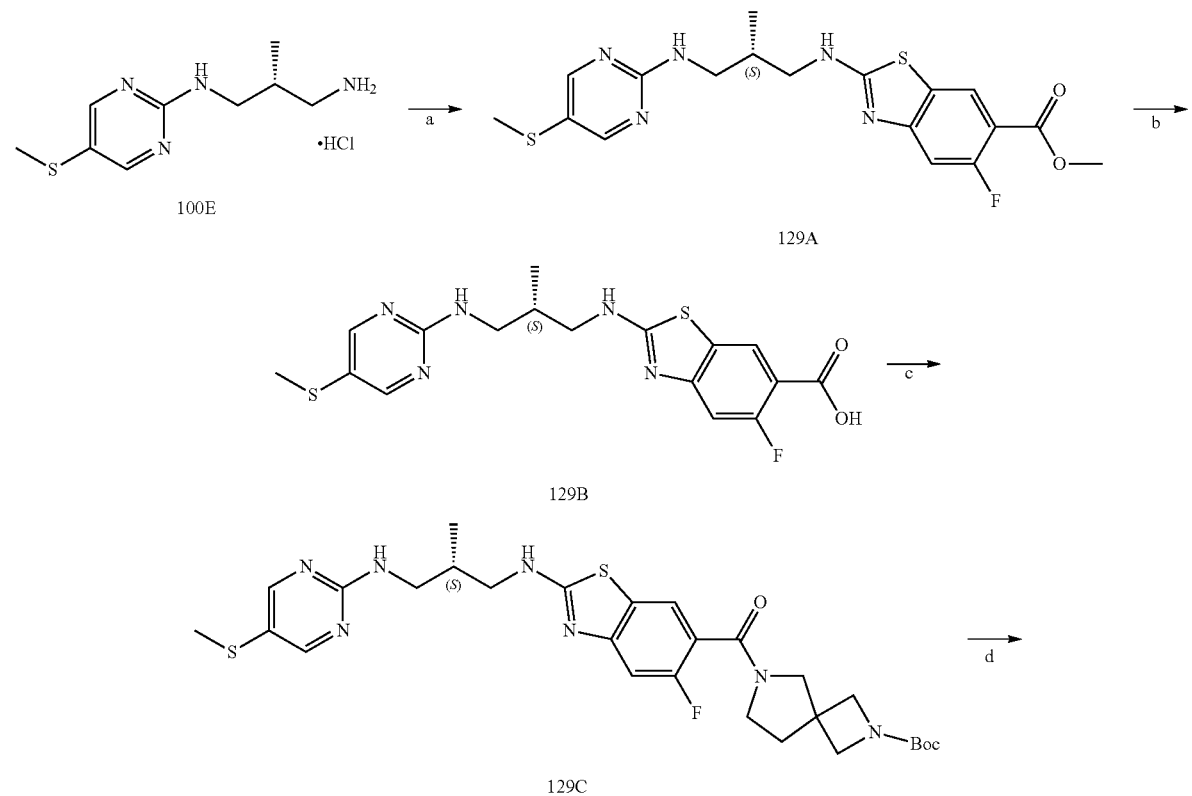

-continued

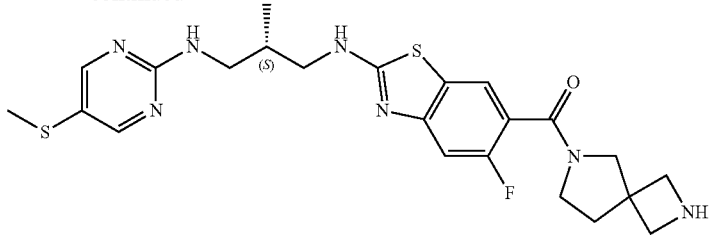

240 a) methyl 2-chloro-5-fluorobenzo[d]thiazole-6-carboxylate, Et₃N, DMF; b) LiOH, MeOH, THF, H₂O; c) Amine, HATU, Et₃N, DMF; d) TFA, DCM

Methyl (S)-5-fluoro-2-((2-methyl-3-((5-(methylthio) pyrimidin-2-yl)amino)propyl)amino) benzo[d]thiazole-6-carboxylate (129A)

Methodology applied was analogous to those described in General Method 3. Yield: 134 mg (20%). $^1$H NMR (400 MHz, CDCl$_3$) δ 8.38 (s, 2H), 8.13 (d, J=6.9 Hz, 1H), 7.21 (d, J=12.2 Hz, 1H), 7.12 (s, 1H), 5.62 (t, J=6.7 Hz, 1H), 3.93 (s, 3H), 3.64-3.46 (m, 2H), 3.42-3.22 (m, 2H), 2.38-2.38 (m, 3H), 2.18-2.09 (m, 1H), 1.07 (d, J=6.9 Hz, 3H); MS (ESI+) m/z 422 (M+H)$^+$.

(S)-5-Fluoro-2-((2-methyl-3-((5-(methylthio)pyrimidin-2-yl)amino)propyl)amino) benzo[d]thiazole-6-carboxylic acid (129B)

Methodology applied was analogous to those described in General Method 4.

Yield: 98 mg (quant.). $^1$H NMR (400 MHz, DMSO) δ 12.82 (s, 1H), 8.57-8.54 (m, 1H), 8.33-8.32 (m, 2H), 8.18 (d, J=7.4 Hz, 1H), 7.50 (t, J=6.1 Hz, 1H), 7.16 (d, J=12.5 Hz, 1H), 2.34 (s, 3H), 2.16-2.06 (m, 1H), 0.97-0.94 (m, 3H). NH exchangeable protons not observed; MS (ESI+) m/z 408 (M+H)$^+$.

tert-Butyl (S)-6-(5-fluoro-2-(((2-methyl-3-((5-(methylthio)pyrimidin-2-yl)amino)propyl)amino)benzo[d]thiazole-6-carbonyl)-2,6-diazaspiro[3.4]octane-2-carboxylate (129C)

Methodology applied was analogous to those described in General Method 5.

Yield: 20 mg (54%). $^1$H NMR (400 MHz, CDCl$_3$) δ 8.27 (d, J=1.8 Hz, 1H), 8.14 (s, 1H), 7.99 (dd, J=1.7, 8.5 Hz, 1H), 7.51 (d, J=8.5 Hz, 1H), 7.00-6.97 (m, 1H), 5.47 (dd, J=6.7, 6.7 Hz, 1H), 4.37 (q, J=7.2 Hz, 2H), 3.63-3.49 (m, 2H), 3.40-3.23 (m, 2H), 2.47 (s, 3H), 2.17-2.09 (m, 1H), 1.40 (dd, J=7.2, 7.2 Hz, 3H), 1.06 (d, J=6.9 Hz, 3H); MS (ESI+) m/z 489 (M+H)$^+$.

(S)-(5-Fluoro-2-((2-methyl-3-((5-(methylthio)pyrimidin-2-yl)amino)propyl)amino)benzo[d]thiazol-6-yl)(2,6-diazaspiro[3.4]octan-6-yl)methanone formate salt (Example 240)

Trifluoroacetic acid (1 mL) was added dropwise to a 0° C. cooled solution of tert-butyl (S)-6-(5-fluoro-2-((2-methyl-3-((5-(methylthio)pyrimidin-2-yl)amino)propyl)amino) benzo [d] thiazole-6-carbonyl)-2,6-diazaspiro[3.4]octane-2-carboxylate (149) (17 mg, 0.0166 mmol, 1.0 eq) in anhydrous dichloromethane (1 mL). The mixture was stirred for 30 minutes and then concentrated under reduced pressure. The crude residue obtained was purified preparative HPLC (formic additive) to give the desired product (S)-(5-fluoro-2-((2-methyl-3-((5-(methylthio)pyrimidin-2-yl)amino)propyl) amino)benzo[d]thiazol-6-yl)(2,6-diazaspiro[3.4]octan-6-yl) methanone formate salt (Example 189) as an off white solid.

Yield: 9 mg (100%). $^1$H NMR (400 MHz, CDCl$_3$) δ 8.38-8.36 (m, 3H), 7.60-7.52 (m, 1H), 5.84-5.72 (m, 1H), 3.98 (d, J=9.0 Hz, 1H), 3.84-3.57 (m, 6H), 3.50-3.24 (m, 4H), 2.86 (s, 12H), 2.38-2.37 (m, 3H), 2.29-2.13 (m, 3H), 1.09-1.04 (m, 3H). NH exchangeable protons not observed; MS (ESI+) m/z 502 (M+H)$^+$.

Using the procedures described in Scheme 34, the following examples were prepared:

TABLE 19

| Structure | Ex. # | 1H NMR | LC-MS (M + H)$^+$ |
|---|---|---|---|
| 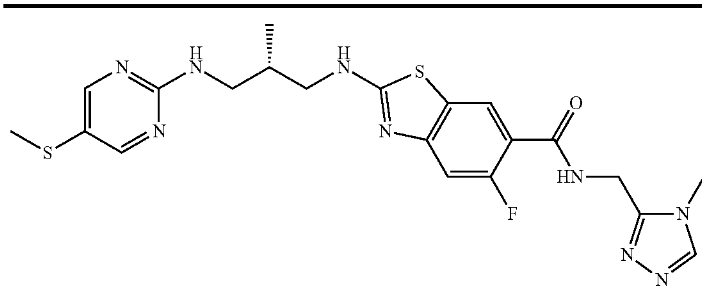 | 241 | $^1$H NMR (400 MHz, CDCl$_3$) δ 8.38-8.37 (m, 2H), 8.24 (d, J = 7.4 Hz, 1H), 8.10 (s, 1H), 7.52-7.44 (m, 1H), 5.72-5.69 (m, 1H), 4.91-4.87 (m, 2H), 3.80-3.78 (m, 3H), 3.64-3.56 (m, 1H), 3.54-3.48 (m, 1H), 3.42-3.24 (m, 2H), 2.38 (s, 3H), 2.20-2.10 (m, 1H), 1.09-1.05 (m, 3H). | 502 |

TABLE 19-continued

| Structure | Ex. # | 1H NMR | LC-MS (M + H)+ |
|---|---|---|---|
| 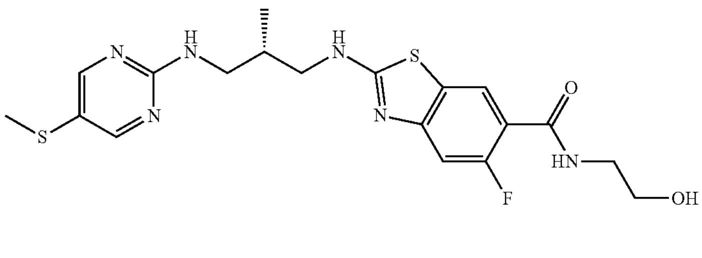 [SMILES: CSc1cnc(NC[C@H](C)CNc2nc3cc(F)c(C(=O)NCCO)cc3s2)nc1] | 242 | 1H NMR (400 MHz, CDCl3) δ 8.37 (s, 2H), 8.28-8.26 (m, 1H), 5.71 (t, J = 6.5 Hz, 1H), 3.86 (t, J = 5.0 Hz, 2H), 3.70-3.57 (m, 3H), 3.53-3.48 (m, 1H), 3.41-3.22 (m, 2H), 2.78 (s, 1H), 2.38 (s, 3H), 2.20-2.11 (m, 1H), 1.08-1.06 (m, 3H). | 451 |
| 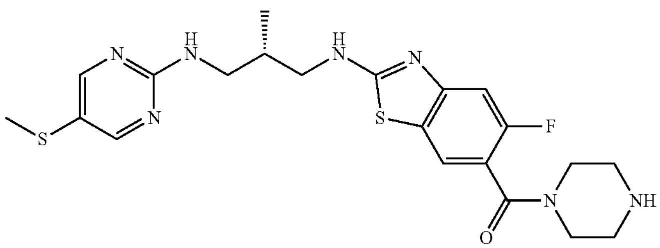 [SMILES: CSc1cnc(NC[C@H](C)CNc2nc3cc(F)c(C(=O)N4CCNCC4)cc3s2)nc1] | 243 | 1H NMR (400 MHz, CDCl3) δ 8.38 (s, 2H), 7.56 (d, J = 6.3 Hz, 1H), 6.85 (t, J = 6.0 Hz, 1H), 5.63 (t, J = 6.7 Hz, 1H), 3.78 (s, 2H), 3.63-3.45 (m, 2H), 3.42-3.22 (m, 4H), 2.95-2.80 (m, 4H), 2.38 (s, 3H), 2.20-2.08 (m, 1H), 1.06 (d, J = 6.9 Hz, 3H). | 478 |

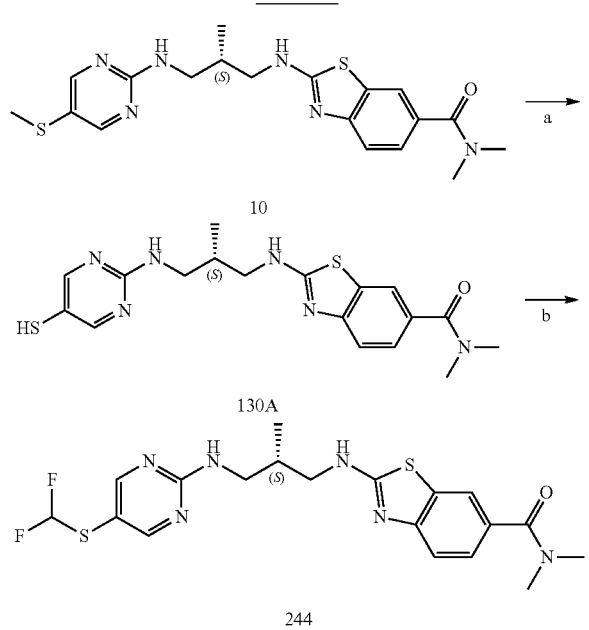

Scheme 35 a) NaSMe, NMP, 160° C., 1 Hr; b) Bromodifluoromethyldiethylphosphonate, KOH, NMP, water

2-((3-((5-Mercaptopyrimidin-2-yl)amino)-2-methylpropyl)amino)-N,N-dimethylbenzo[d]thiazole-6-carboxamide (130A)

N,N-dimethyl-2-((2-methyl-3-((5-(methylthio)pyrimidin-2-yl)amino)propyl)amino) benzo[d]thiazole-6-carboxamide (Compound 10, 75 mg, 0.18 mmol), sodium methanethiolate (126 mg, 1.80 mmol, 10.0 eq and N-methylpyrolidine (1.5 mL) were added to a microwave vessel under nitrogen, sealed and then heated to 160° C. for 1 hour. LCMS analysis indicated complete conversion to the desired thiol 2-((3-((5-((difluoromethyl)thio)pyrimidin-2-yl)amino)-2-methylpropyl) amino)-N,N-dimethyl benzo[d]thiazole-6-carboxamide (130A), which was used directly in the next step without purification.

2-((3-((5-((Difluoromethyl)thio)pyrimidin-2-yl)amino)-2-methylpropyl)amino)-N,N-dimethylbenzo[d]thiazole-6-carboxamide (244)

Potassium hydroxide (201 mg, 3.58 mmol, 20.0 eq) and water (0.5 mL) were added to the crude thiol solution of 2-((3-((5-((difluoromethyl)thio)pyrimidin-2-yl)amino)-2-methylpropyl)amino)-N,N-dimethylbenzo[d]thiazole-6-carboxamide in N-methyl pyrolidine (1.5 mL) and the mixture was cooled to −70° C., freezing to a solid. Bromodifluoromethyldiethylphosphonate (40 uL, 0.215 mmol, 1.2 eq) was added in one portion and the reaction was allowed to warm to ambient temperature over 1 hour then re-cooled to −70° C. A further aliquot of bromodifluoromethyldiethylphosphonate (40 uL, 0.215 mmol, 1.2 eq) was added, and the mixture was allowed to warm to ambient temperature over 1 hour. Water (10 mL) was added and the mixture was extracted with ethyl acetate (3×20 mL). The combined organic phases were washed with water (20 mL) and brine (25 mL) then dried over magnesium sulfate. The solvents were removed under vacuum to give a crude brown oil which was purified by flash chromatography (eluting dichloromethane to methanol, 0-10%) and then by preparative HPLC to give the desired 2-((3-((5-((difluoromethyl)thio)pyrimidin-2-yl)amino)-2-methylpropyl)amino)-N,N-dimethylbenzo[d]thiazole-6-carboxamide (244) as an off white solid.

Yield: 15 mg (19%). 1H NMR (400 MHz, CDCl3) δ 8.42-8.39 (m, 2H), 7.69 (d, J=1.4 Hz, 1H), 7.55-7.52 (m, 1H), 7.36 (dd, J=1.8, 8.3 Hz, 1H), 6.33 (s, 1H), 6.15 (t, J=6.7 Hz, 1H), 3.65-3.51 (m, 2H), 3.43-3.29 (m, 2H), 3.08 (s, 6H), 2.20-2.10 (m, 1H), 1.09-1.06 (m, 3H); MS (ESI+) m/z 453 (M+H)+.

Following methodology described in Scheme 35, the following examples were prepared:

TABLE 20

| Structure | Ex. # | 1H NMR | LC-MS (M + H)+ |
|---|---|---|---|
| 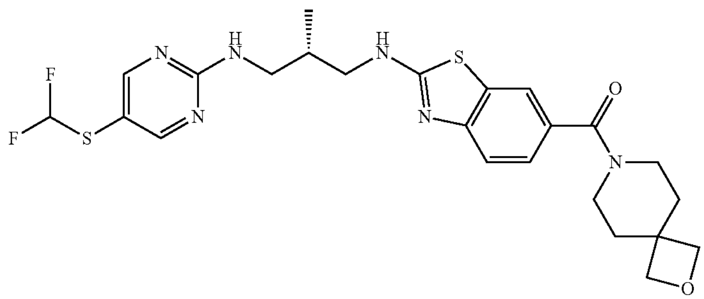 [SMILES: C[C@@H](CNc1ncc(SC(F)F)cn1)CNc1nc2ccc(C(=O)N3CCC4(CC3)COC4)cc2s1] | 245 | ¹H NMR (400 MHz, CDCl₃) δ 8.43 (s, 2H), 7.65 (d, J = 1.4 Hz, 1H), 7.53 (d, J = 7.9 Hz, 1H), 7.31 (dd, J = 1.8, 8.3 Hz, 1H), 6.68 (t, J = 56.8 Hz, 1H), 6.38 (s, 1H), 6.16 (dd, J = 6.5, 6.5 Hz, 1H), 4.48 (s, 4H), 3.64-3.53 (m, 6H), 3.44-3.31 (m, 2H), 2.20-2.12 (m, 1H), 1.91 (s, 4H), 1.07 (d, J = 6.9 Hz, 3H). | 535 |
| 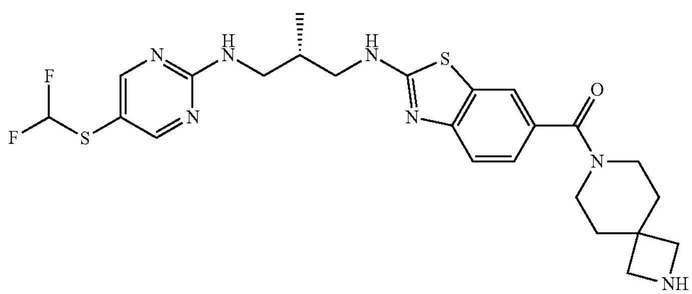 [SMILES: C[C@@H](CNc1ncc(SC(F)F)cn1)CNc1nc2ccc(C(=O)N3CCC4(CC3)CNC4)cc2s1] | 246 | ¹H NMR (400 MHz, CDCl₃) δ 8.42-8.38 (m, 2H), 7.66-7.65 (m, 1H), 7.54-7.52 (m, 1H), 7.33-7.30 (m, 1H), 6.32 (s, 1H), 6.14 (t, J = 6.6 Hz, 1H), 3.64-3.52 (m, 6H), 3.46-3.32 (m, 6H), 2.20-2.12 (m, 1H), 1.83-1.82 (m, 4H), 1.09-1.06 (m, 3H). | 534 |
| 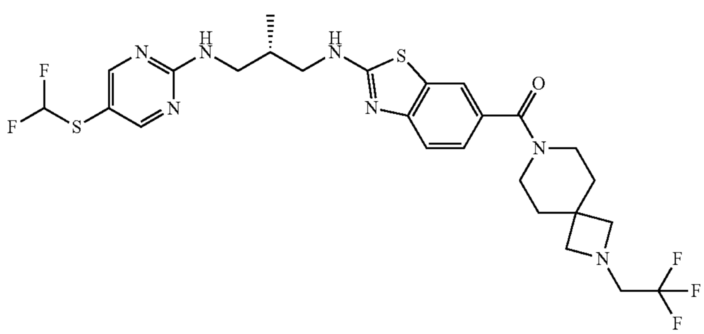 [SMILES: C[C@@H](CNc1ncc(SC(F)F)cn1)CNc1nc2ccc(C(=O)N3CCC4(CC3)CN(CC(F)(F)F)C4)cc2s1] | 247 | ¹H NMR (400 MHz, CDCl₃) δ 8.44-8.39 (m, 2H), 7.66 (d, J = 1.3 Hz, 1H), 7.54-7.51 (m, 1H), 6.12 (t, J = 6.5 Hz, 1H), 3.64-3.51 (m, 6H), 3.44-3.30 (m, 3H), 3.25-3.23 (m, 4H), 3.02 (q, J = 9.4 Hz, 2H), 2.20-2.10 (m, 1H), 1.80-1.77 (m, 4H), 1.07 (d, J = 6.9 Hz, 3H). | 616 |
| 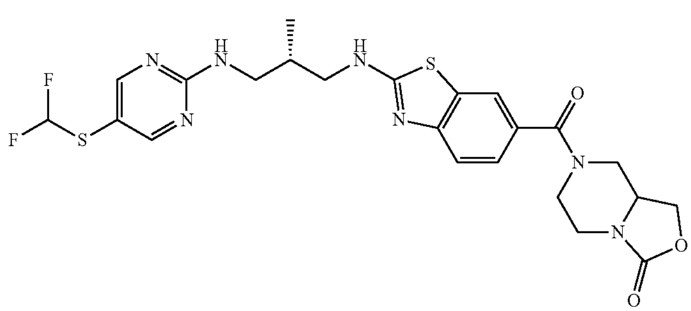 [SMILES: C[C@@H](CNc1ncc(SC(F)F)cn1)CNc1nc2ccc(C(=O)N3CCN4C(=O)OCC4C3)cc2s1] | 248 | ¹H NMR (400 MHz, CDCl₃) δ 8.44-8.38 (m, 4H), 7.70 (d, J = 1.5 Hz, 2H), 7.57-7.54 (m, 2H), 7.36-7.32 (m, 2H), 6.69 (s, 1H), 6.54 (s, 1H), 6.09 (t, J = 6.6 Hz, 2H), 4.45 (t, J = 8.4 Hz, 3H), 4.00-3.82 (m, 6H), 3.65-3.52 (m, 4H), 3.45-3.30 (m, 4H), 3.07 (s, 6H), 2.89-2.83 (m, 2H), 2.62 (s, 1H), 2.20-2.12 (m, 2H), 1.08 (d, J = 6.9 Hz, 6H). | 550 |

TABLE 20-continued
| Structure | Ex. # | 1H NMR | LC-MS (M + H)+ |
|---|---|---|---|
| 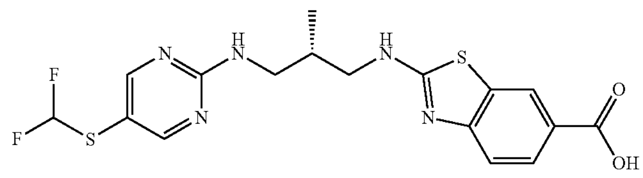 [SMILES: C[C@@H](CNc1ncc(SC(F)F)cn1)CNc1nc2ccc(C(=O)O)cc2s1] | 249 | ¹H NMR (400 MHz, DMSO) δ 8.41-8.35 (m, 3H), 8.25 (d, J = 1.5 Hz, 1H), 7.97-7.92 (m, 1H), 7.81 (dd, J = 1.8, 8.4 Hz, 1H), 7.44-7.35 (m, 1H), 3.51-3.42 (m, 2H), 2.17-2.09 (m, 1H), 0.99-0.96 (m, 3H). | 426 |
Scheme 36
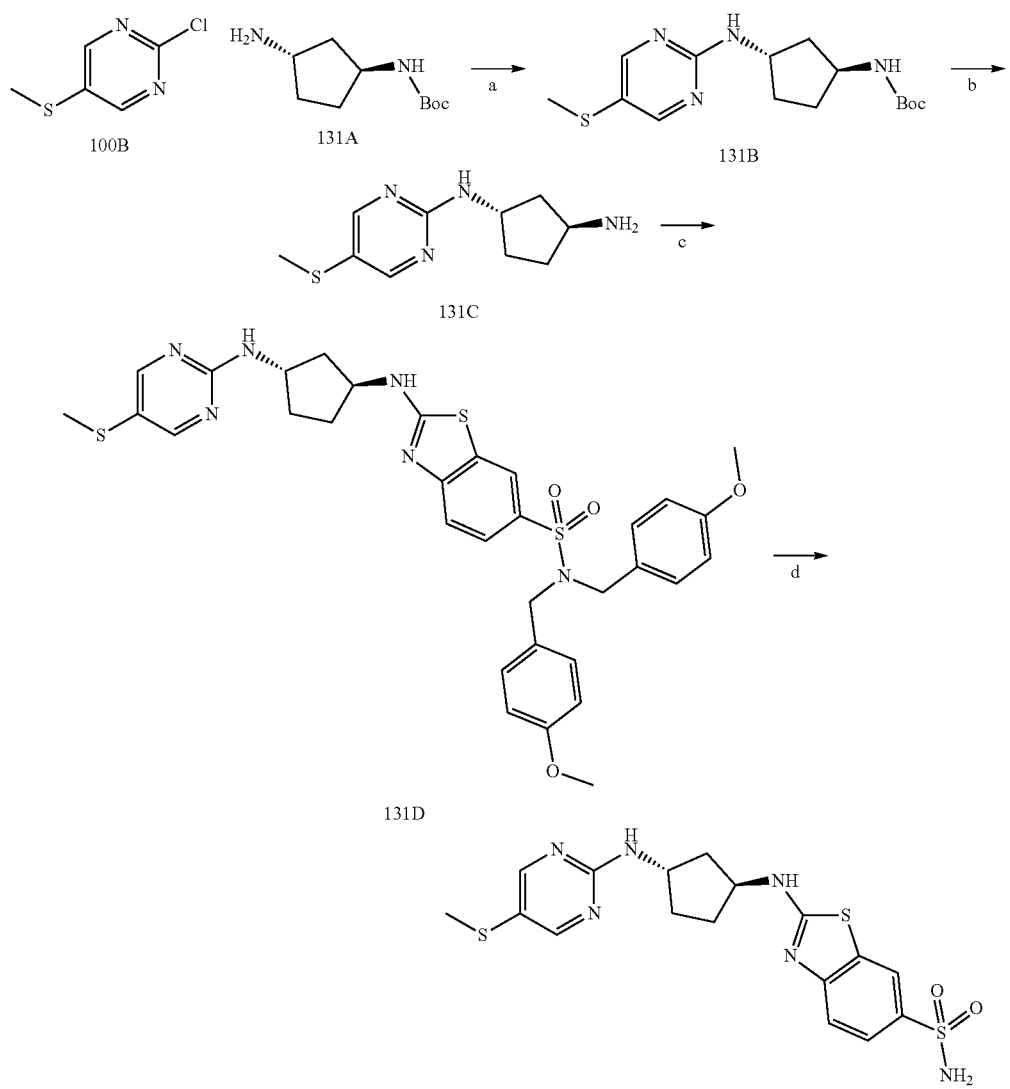
a) Cs₂CO₃, DMF; b) 4M HCl in 1,4-dioxane; c) 2-chlorobenzothiazole, Et₃N, DMF; d) TFA, DCM rac-tert-Butyl ((1R,3R)-3-((5-(methylthio)pyrimidin-2-yl)amino)cyclopentyl)carbamate (131B)

Methodology applied was analogous to those described in General Method 1. Yield: 220 mg (44%). ¹H NMR (400 MHz, CDCl₃) δ 6 8.35-8.34 (m, 4H), 5.35 (s, 1H), 5.18-5.15 (m, 1H), 4.84-4.82 (m, 1H), 4.56-4.53 (m, 1H), 4.36 (dd, J=6.9, 13.8 Hz, 1H), 4.26-4.18 (m, 1H), 4.02-3.94 (m, 2H), 2.55-2.47 (m, 1H), 2.36 (d, J=1.0 Hz, 6H), 2.30-2.16 (m, 2H), 2.10-1.89 (m, 4H), 1.46-1.43 (m, 24H); MS (ESI+) m/z 325 (M+H)⁺.

rac-(1R,3R)—N₁-(5-(Methylthio)pyrimidin-2-yl)cyclopentane-1,3-diamine hydrochloride (131C)

Methodology applied was analogous to those described in General Method 2.
Yield: 250 mg (quant. %). MS (ESI+) m/z 225 (M+H)⁺.
Used in next step without further purification.

rac-N,N-Bis(4-methoxybenzyl)-2-(((trans)-3-((5-(methylthio)pyrimidin-2-yl)amino)cyclopentyl)amino)benzo[d]thiazole-6-sulfonamide (131D)

Methodology applied was analogous to those described in General Method 3. Yield: 52 mg (23%). ¹H NMR (400 MHz, CDCl₃) δ 8.36 (s, 2H), 8.00 (d, J=1.6 Hz, 1H), 7.74 (dd, J=1.9, 8.5 Hz, 1H), 7.58-7.55 (m, 1H), 7.01-6.96 (m, 4H), 6.76-6.73 (m, 4H), 5.59-5.54 (m, 1H), 5.22 (d, J=6.9 Hz, 1H), 4.50-4.44 (m, 1H), 4.35-4.30 (m, 1H), 4.25 (s, 4H), 3.77-3.76 (m, 6H), 2.37-2.37 (m, 6H), 2.23-2.07 (m, 2H); MS (ESI+) m/z 677 (M+H)⁺.

rac-2-(((trans)-3-((5-(Methylthio)pyrimidin-2-yl)amino)cyclopentyl)amino)benzo[d]thiazole-6-sulfonamide (250)

Trifluoroacetic acid (1 mL) was added dropwise to an ice cooled solution of rac-N,N-bis(4-methoxybenzyl)-2-(((trans)-3-((5-(methylthio)pyrimidin-2-yl)amino)cyclopentyl) amino)benzo[d]thiazole-6-sulfonamide (131D) (45 mg, 66.48 mmol, 1.0 eq) in anhydrous dichloromethane (1 mL). The mixture was allowed to warm to ambient temperature over 18 h and was then concentrated to dryness under reduced pressure. The crude residue obtained was purified by preparative HPLC and the clean fractions obtained were freeze dried to give the desired 2-(((trans)-3-((5-(methylthio)pyrimidin-2-yl)amino)cyclopentyl)amino) benzo[d]thiazole-6-sulfonamide (Example 250) as a white powder.
Yield: 23 mg (79%). ¹H NMR (CDCl₃) δ 8.36 (s, 2H), 8.17 (d, J=1.8 Hz, 1H), 7.84 (dd, J=2.0, 8.5 Hz, 1H), 7.59-7.52 (m, 1H), 5.34 (d, J=6.5 Hz, 1H), 4.79 (s, 2H), 4.50-4.43 (m, 1H), 4.34-4.27 (m, 1H), 2.37-2.37 (m, 6H), 2.22-2.07 (m, 2H); MS (ESI+) m/z 437 (M+H)⁺.

Scheme 41

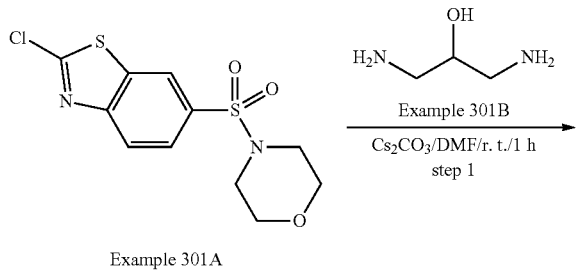

Example 301A

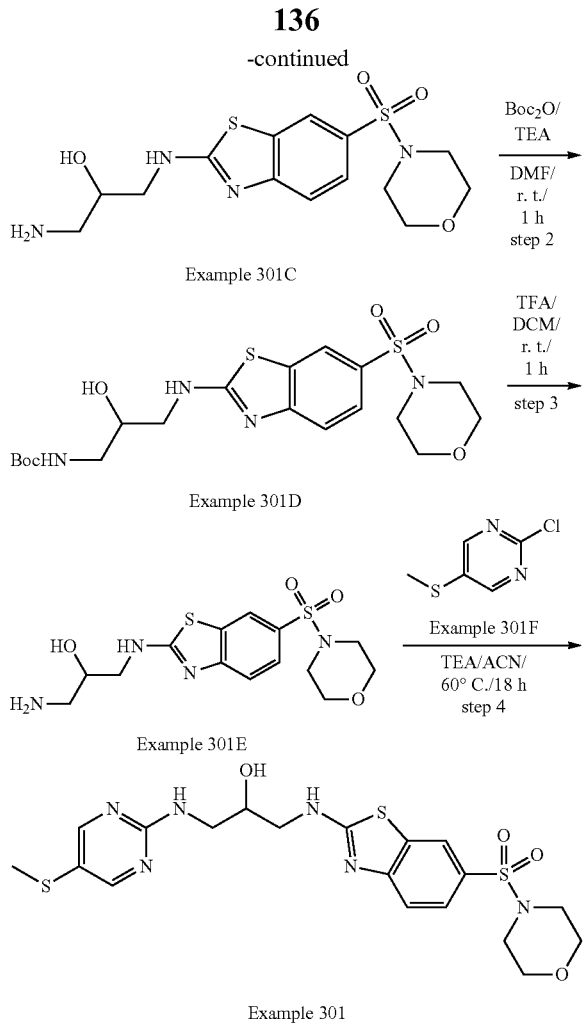

Step 1: Example 301C

To a solution of Example 301A (1 g, 3.14 mmol) in DMF (30 mL) was added Cs₂CO₃ (2.05 g, 6.28 mmol) and Example 301B (5.6 g, 62.8 mmol). The mixture was heated to 25° C. for 1 h. TLC detected the starting material was consumed. The reaction was filtered and the filtrate (crude Example 301C) was used to next step without any purification.

Step 2: Example 301D

A solution of Example 301C was treated with Boc₂O (1.03 g, 4.72 mmol) and stirred at r.t for 2 h. Water (100 mL) was added, then extracted with EA (50 mL×2), washed with water and brine, dried over Na₂SO₄, filtered, and the filtrate was concentrated under reduced pressure, then purified by silica gel chromatography (eluted with petroleum ether/EtOAc=1/5-1/1) to give the desired product (Example 301D, 1.2 g, yield 81%) as a yellow solid. LCMS [M+H]⁺=573

Step 3: Example 301E

To a solution of Example 301D (1.2 g, 2.54 mmol) in DCM (3 mL) was added TFA (1 mL) at r.t. After addition, the reaction mixture was stirred at r.t. for 1 h. TLC detected the starting material was consumed, the mixture was concentrated to give the desired product (Example 301E 945 mg, yield: 100%) as a yellow oil, which used to next step without further purification.

Step 4: Example 301

To a solution of Example 301E (945 mg, 2.54 mmol) in ACN (10 mL) was added TEA (514 mg, 5.08 mmol) and Example 301F (408 mg, 2.54 mmol) at r.t. then to 70° C. for 18 h. TLC detected the starting material was consumed. The reaction was concentrated and purified by silica gel chromatography (eluted with petroleum ether/EtOAc=3/1~5/3) to give the desired product Example 301 (780 mg, yield: 61%) as a white solid. LCMS [M+H]$^+$=497. $^1$H NMR (400 MHz, DMSO-d$_6$) δ 8.78 (s, 1H), 8.34 (s, 2H), 8.12 (d, J=1.6 Hz, 1H), 7.54 (dd, J=8.5, 1.8 Hz, 1H), 7.48 (d, J=8.5 Hz, 1H), 3.94-3.86 (m, 1H), 3.59 (dd, J=16.6, 11.9 Hz, 6H), 3.39 (dd, J=19.4, 5.9 Hz, 4H), 2.85-2.81 (m, 4H), 2.33 (s, 3H).

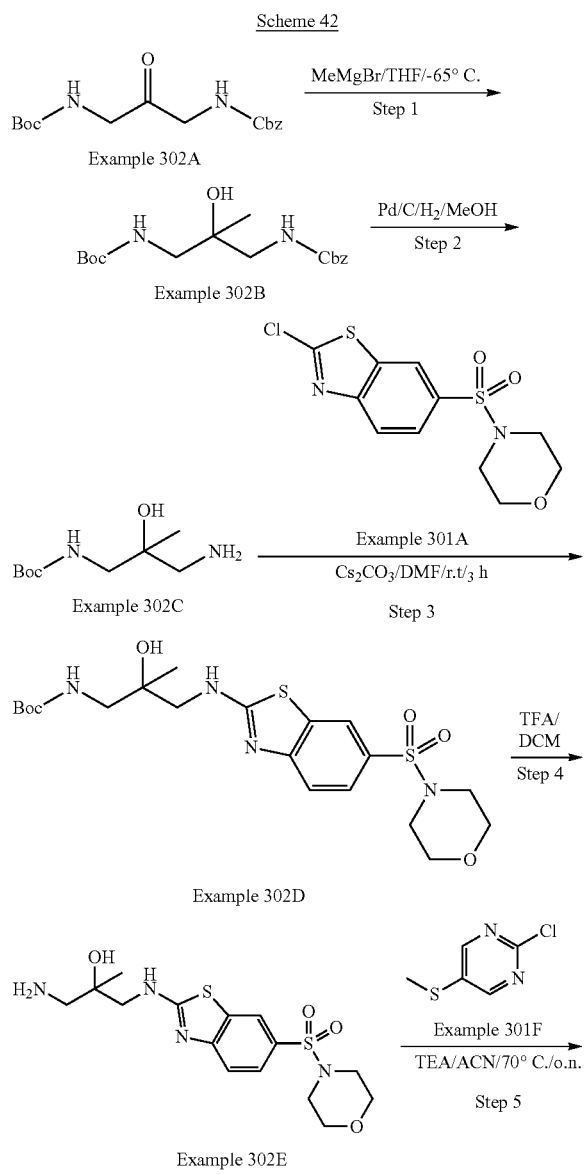

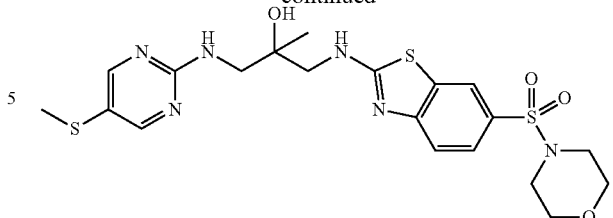

Example 302

Step 1: Example 302B

A solution of Example 302A (6.77 g, 21 mmol) in THF (200 mL) under N$_2$ atmosphere was cooled to −65° C. MeMgBr (21 mL, 63.1 mmol, 3M in THF) was added dropwise, then stirred at −65° C. for 0.5 h. The reaction was warmed to r.t. for 2 h, quenched by addition of water (200 mL). After extraction with EtOAc (200 mL×2), the combined organic layer was dried over anhydrous magnesium sulfate and concentrated under reduced pressure. The residue was purified by silica gel chromatography (eluted with petroleum ether/EtOAc=3/1) to give the desired product Example 302B (4 g, yield 56%) as a yellow oil. LCMS [M+H]$^+$=339

Step 2: Example 302C

To a solution of Example 302B (4 g, 0.012 mmol) in MeOH (40 mL) a suspension of Pd/C (400 mg) catalyst was introduced into the reactor. The vessel was purged with nitrogen and then with hydrogen, and the reaction mixture was stirred at r.t. for 18 h. TLC and LCMS detected the starting material was consumed. Example 302C (4 g, yield: 100%) was obtained by filtration and concentrated and used in the next step without any purification. LCMS [M+H]$^+$=205

Step 3: Example 302D

To a solution of Example 301A (154 mg, 0.48 mmol) in DMF (30 mL) was added Cs$_2$CO$_3$ (313 mg, 0.96 mmol) and Example 302C (982 mg, 4.8 mmol), the mixture was heated to 25° C. for 2 h. TLC detected the starting material was consumed. The reaction was filtered and the filtrate was concentrated under reduced pressure and purified by silica gel chromatography (eluted with petroleum ether/EtOAc=1/11/4) to give the desired product Example 302D (500 mg, yield: 100%) as a white solid. LCMS [M+H]$^+$=487

Step 4: Example 302E

To a solution of Example 302D (486 mg, 2 mmol) in DCM (2 mL) was added TFA (1 mL) at r.t. After addition, the reaction mixture was stirred at r.t. for 1 h. TLC detected the starting material was consumed, the mixture was concentrated to give the desired product Example 302E (532 mg, yield: 100%) as a yellow oil which used to next step without further purification.

Step 5: Example 302

Example 302E (193 mg, 0.5 mmol), TEA (101 mg, 1 mmol) and Example 301F (81 mg, 0.5 mmol) were dissolved in ACN (5 mL), the mixture was heated to 60° C. for 18 h. LCMS detected TM was formed. Purified by Pre-HPLC to give the desired product Example 302 (15 mg, yield: 6%) as a white solid. LCMS [M+H]$^+$=511

$^1$H NMR (400 MHz, CDCl$_3$) δ 8.41 (s, 2H), 7.98 (s, 1H), 7.65 (s, 2H), 6.10 (s, 1H), 3.77-3.72 (m, 4H), 3.67-3.52 (m, 4H), 3.04-2.98 (m, 4H), 2.38 (s, 3H), 1.33 (s, 3H).

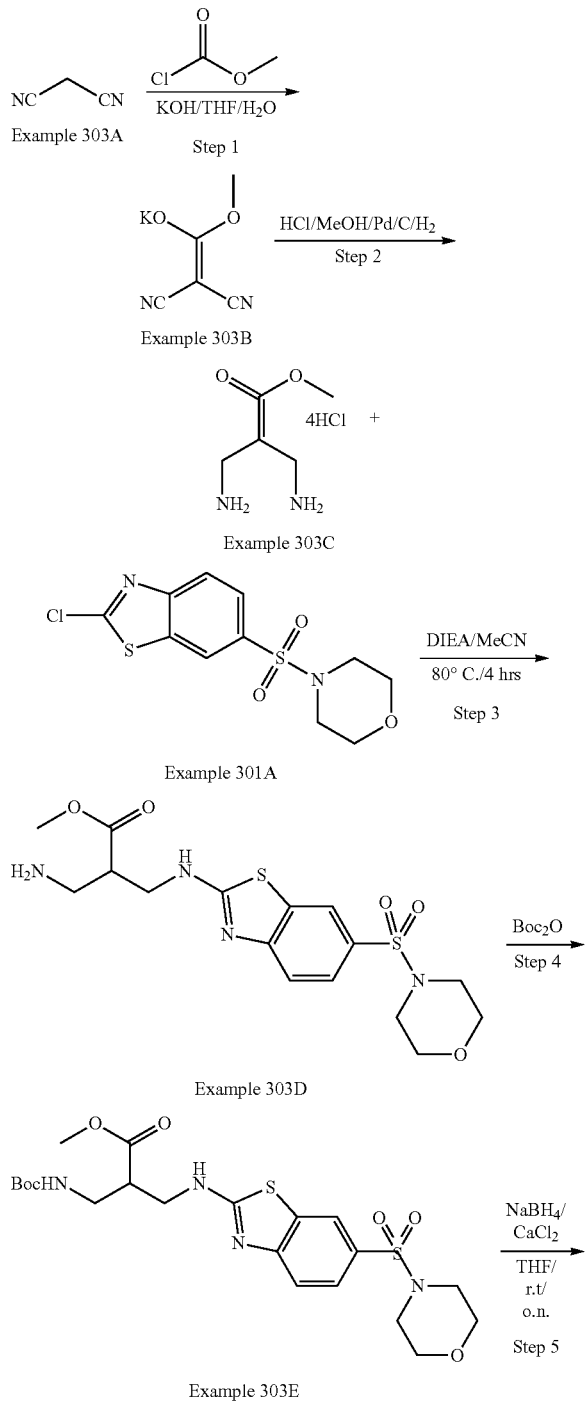

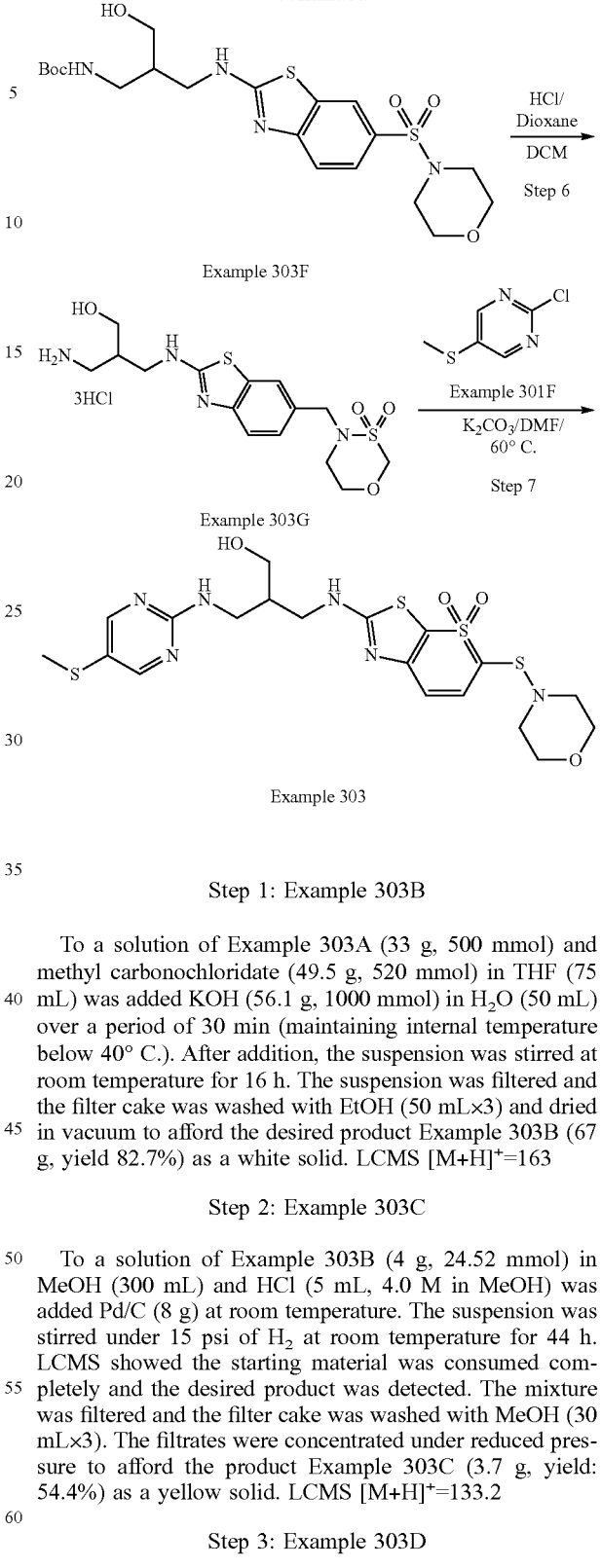

Step 1: Example 303B

To a solution of Example 303A (33 g, 500 mmol) and methyl carbonochloridate (49.5 g, 520 mmol) in THF (75 mL) was added KOH (56.1 g, 1000 mmol) in H$_2$O (50 mL) over a period of 30 min (maintaining internal temperature below 40° C.). After addition, the suspension was stirred at room temperature for 16 h. The suspension was filtered and the filter cake was washed with EtOH (50 mL×3) and dried in vacuum to afford the desired product Example 303B (67 g, yield 82.7%) as a white solid. LCMS [M+H]$^+$=163

Step 2: Example 303C

To a solution of Example 303B (4 g, 24.52 mmol) in MeOH (300 mL) and HCl (5 mL, 4.0 M in MeOH) was added Pd/C (8 g) at room temperature. The suspension was stirred under 15 psi of H$_2$ at room temperature for 44 h. LCMS showed the starting material was consumed completely and the desired product was detected. The mixture was filtered and the filter cake was washed with MeOH (30 mL×3). The filtrates were concentrated under reduced pressure to afford the product Example 303C (3.7 g, yield: 54.4%) as a yellow solid. LCMS [M+H]$^+$=133.2

Step 3: Example 303D

A solution of Example 303C (2.18 g, 7.84 mmol), Example 301A (0.5 g, 1.57 mmol) and DIEA (13.35 g, 103.5 mmol) in MeCN (100 mL) was heated to 80° C. and stirred for 4 h. LCMS showed the starting material was consumed completely and the desired product was detected. The reaction mixture Example 303D was used for the next step without further purification. LCMS [M+H]$^+$=415.5

Step 4: Example 303E

Boc$_2$O (5 g, 22.9 mmol) was added to a solution of Example 303D at room temperature and stirred for 1 h. LCMS showed the starting material was consumed. The reaction was diluted with DCM (200 mL) and washed with water (150 mL×2), brine (200 mL×3), dried over Na$_2$SO$_4$, filtered and concentrated under reduced pressure, which was purified by silica gel chromatography (eluted with petroleum ether/EtOAc=2/1~1/9) to afford the product Example 303E (680 mg, yield: 76.7% over two steps) as a white solid. LCMS [M+H]$^+$=515.5

Step 5: Example 303F

To a solution of Example 303E (840 mg, 1.63 mmol) in THF (20 mL) was added CaCl$_2$ (363 mg, 3.27 mmol) and NaBH$_4$ (124 mg, 3.27 mmol) at room temperature and the reaction was stirred for 16 h. The reaction was poured into sat. aq. NH$_4$Cl (100 mL) and diluted with EtOAc (30 mL) and separated. The aqueous layer was extracted with EtOAc (30 mL×2) and the combined organic layers were concentrated and purified by silica gel chromatography (eluted with petroleum ether/EtOAc=3/1~1/9) to afford the product Example 303F (383 mg, yield: 48.3%) as a white solid. LCMS [M+H]$^+$=487.6

Step 6: Example 303G

To a solution of Example 303F (553 mg, 1.14 mmol) dissolved in DCM (10 mL) was added HCl/Dioxane (4.0 M, 10 mL) at room temperature and the reaction was stirred for 0.5 h. TLC showed the starting material was consumed. The reaction mixture was concentrated under reduced pressure to afford the product Example 303G (563 mg, yield: 100%) as a white solid. LCMS [M+H]$^+$=387.5

Step 7: Example 303

To a solution of Example 303G (563 mg, 1.14 mmol) and K$_2$CO$_3$ (940 mg, 6.82 mmol) in DMF (10 mL) was added Example 301A (183 mg, 1.14 mmol) at room temperature. The reaction was then heated to 60° C. and stirred for 16 h. TLC showed the starting material was consumed. The mixture was cooled to room temperature and diluted with EtOAc (30 mL) and washed with water (20 mL). The aqueous layer was extracted with EtOAc (20 mL×4) and the combined organic layers were washed with brine (20 mL×2), dried over Na$_2$SO$_4$, filtered and concentrated. The residue was purified by silica gel chromatography (eluted with petroleum ether/EtOAc=3/1~1/9) to afford the crude product, which was purified by prep-HPLC to afford the product Example 303 (75.2 mg, yield: 12.93%), as a light yellow solid. LCMS [M+H]$^+$=511

$^1$H NMR (400 MHz, CDCl$_3$) δ 8.37 (s, 2H), 7.96 (s, 1H), 7.66-7.58 (m, 2H), 6.82 (s, 1H), 5.87 (s, 1H), 3.83-3.73 (m, 5H), 3.59-3.44 (m, 5H), 3.01 (s, 4H), 2.38 (s, 3H), 2.14-2.08 (m, 1H).

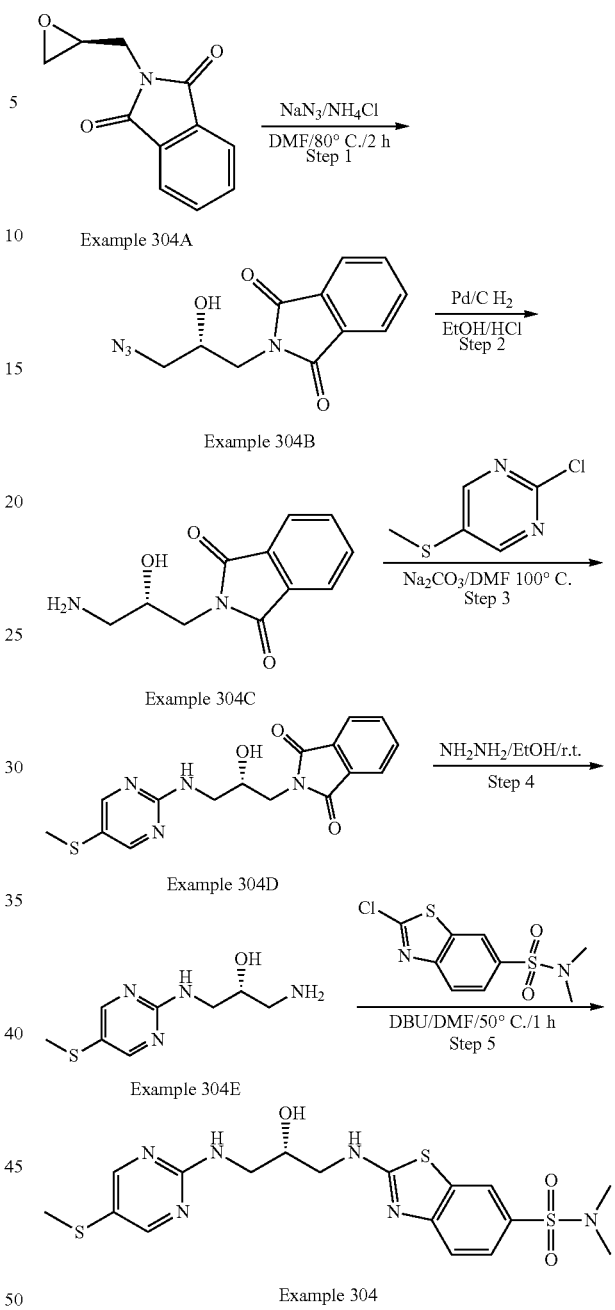

Step 1: Example 304B

Example 304A (23.6 g, 0.12 mol), NaN$_3$ (15.1 g, 0.23 mol) and NH$_4$Cl (7.5 g, 0.14 mol) were suspended in DMF (250 mL), and the resulting mixture was heated to 80° C. for 1 h. After TLC detected the reaction was complete, EtOAc (1 L) was added, and the organic extract was washed with water (200 mL×5), dried over anhydrous magnesium sulfate and concentrated under reduced pressure. The residue was purified by silica gel chromatography (eluted with petroleum ether/EtOAc=5/1) to give the desired product Example 304B (29 g, yield 100%) as a white solid. LCMS [M+H]$^+$=247

Step 2: Example 304C

To a solution of Example 304B (29 g, 0.12 mol) in EtOH (400 mL) was added HCl (22 mL) and Pd/C (1 g), and the heterogeneous mixture was stirred at r.t. for 18 h under Hz. TLC detected the starting material was mostly consumed. The mixture was filtered and the filtrate was concentrated to give the desired product Example 304C (21 g, yield: 100%) as a white solid. LCMS [M+H]$^+$=221

Step 3: Example 304D

To a solution of Example 304C (6.6 g, 3 mol) in DMF (50 mL) was added 2-chloro-5-(methylthio)pyrimidine (2.4 g, 15 mmol) and TEA (7.6 g, 75 mmol). The resulting mixture was stirred at 100° C. for 1 h. TLC detected the starting material was consumed. The reaction mixture was concentrated and purified by silica gel chromatography (eluted with petroleum ether/EtOAc=1/1~1/4) to give the desired product Example 304D (450 mg, yield: 8%) as a white solid. LCMS [M+H]$^+$=345

Step 4: Example 304E

To a solution of Example 304D (450 mg, 1.3 mmol) in EtOH (5 mL) was added hydrazine hydrate (131 mg, 2.6 mmol) at r.t. TLC after 3 h detected the starting material was consumed, at which point the reaction was concentrated and purified by silica gel chromatography (eluted with DCM/MeOH=10/1) to give the desired product Example 304E (120 mg, yield: 43%) as a white solid.

Step 5: Example 304

To solution of Example 304E (43 mg, 0.20 mmol) and 2-chloro-N,N-dimethylbenzo[d]thiazole-6-sulfonamide (37 mg, 0.13 mmol) in DMF (1 mL) was added DBU (40 mg, 0.26 mmol). The resulting mixture was stirred at 50° C. for 1 h. TLC detected the starting material was consumed, and the reaction mixture was concentrated and purified by Pre-TLC to give the desired product Example 304 (30 mg, yield: 51%) as a white solid. LCMS [M+H]$^+$=454.9. $^1$H NMR (400 MHz, CDCl$_3$) δ 8.35 (s, 2H), 7.99 (d, J=1.5 Hz, 1H), 7.67 (dd, J=8.5, 1.7 Hz, 1H), 7.59 (d, J=8.5 Hz, 1H), 5.97 (s, 1H), 4.11 (dd, J=9.3, 4.8 Hz, 1H), 3.74 (dd, J=13.7, 4.3 Hz, 1H), 3.66 (s, 1H), 3.58 (dd, J=13.6, 6.3 Hz, 2H), 2.70 (s, 6H), 2.37 (s, 3H).

Scheme 45

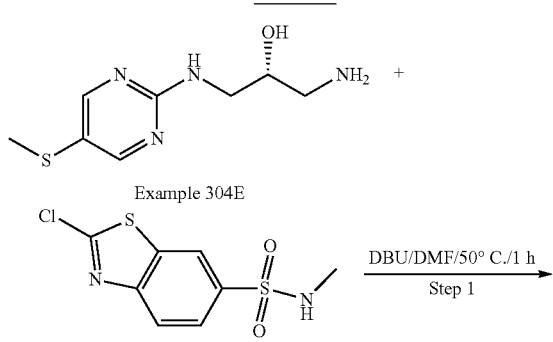

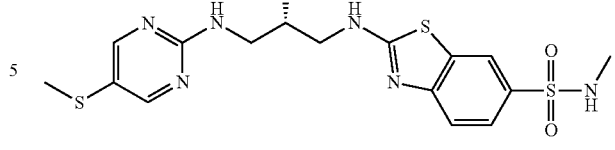

Example 305

Step 1: Example 305

To solution of Example 304E (30 mg, 0.14 mmol) and 2-chloro-N-methylbenzo[d]thiazole-6-sulfonamide (24.5 mg, 0.09 mmol) in DMF (2 mL) was added DBU (47 mg, 0.18 mmol). After addition, the mixture was stirred at 50° C. for 1 h. LCMS determined that starting material was consumed. The mixture was cooled to room temperature, diluted with EtOAc (5 mL) and washed with brine (5 mL). The organic layer was concentrated and purified by Pre-TLC to give the desired product Example 305 (23.8 mg, yield: 60%) as a white solid. LCMS [M+H]$^+$=440.9 $^1$H NMR (400 MHz, MeOD-d$_4$) δ 8.35 (s, 2H), 8.07 (s, 1H), 7.69 (dd, J=8.0, 1H), 7.50 (d, J=8.0 Hz, 1H), 4.06 (m, 0.46H), 3.57 (m, 4H), 2.51 (s, 3H), 2.32 (s, 3H).

Scheme 46

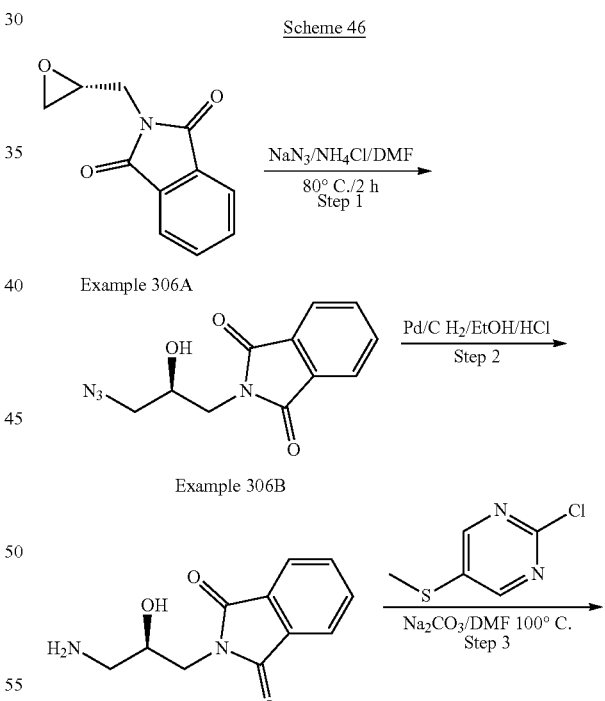

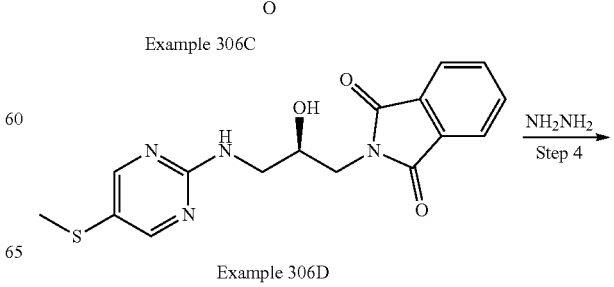

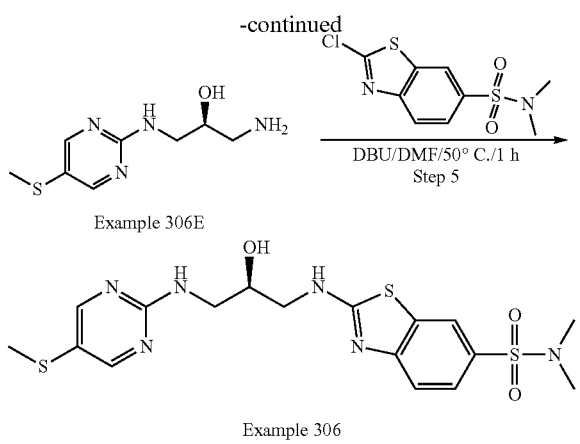

Example 306 (30 mg, yield: 50%) was prepared in analogous fashion as a white solid starting from Example 306A: LCMS [M+H]$^+$=454.9. $^1$H NMR (400 MHz, CDCl$_3$) δ 8.35 (s, 2H), 7.98 (d, J=1.5 Hz, 1H), 7.66 (dd, J=8.5, 1.7 Hz, 1H), 7.58 (d, J=8.5 Hz, 1H), 6.04 (t, J=5.6 Hz, 1H), 4.11 (dd, J=9.3, 5.1 Hz, 1H), 3.74-3.64 (m, 2H), 3.61-3.54 (m, 2H), 2.70 (s, 6H), 2.36 (s, 3H).

Step 1: Example 307A

To a solution of Example 306E (100 mg, 0.47 mmol) in DMF (0.5 mL) was added DBU (89 mg, 0.58 mmol) and methyl 2-chlorobenzo[d]thiazole-6-carboxylate (89 mg, 0.39 mmol). The mixture was heated to 50° C. for 1 h. After TLC determined the starting material was consumed, the mixture was concentrated and purified by silica gel chromatography (eluted with petroleum ether/EtOAc=1/1~1/4) to give the desired product Example 307A (50 mg, yield: 26%) as a white solid. LCMS [M+H]$^+$=406

Step 2: Example 307B

To a solution of Example 307A (50 mg, 0.12 mmol) in THF (1 mL) was added LiOH (0.4 mL, 1M in water) and the resulting mixture was stirred at r.t. for 18 h. After TLC determined the starting material was consumed, the mixture was concentrated and purified by silica gel chromatography (eluted with DCM/MeOH=10/1) to give the desired product Example 307B (5 mg, yield: 11%) as a white solid. LCMS [M+H]$^+$=392

Step 3: Example 307

A solution of Example 307B (10 mg, 0.025 mmol) was charged with dimethylamine hydrochloride (2.5 mg, 0.031

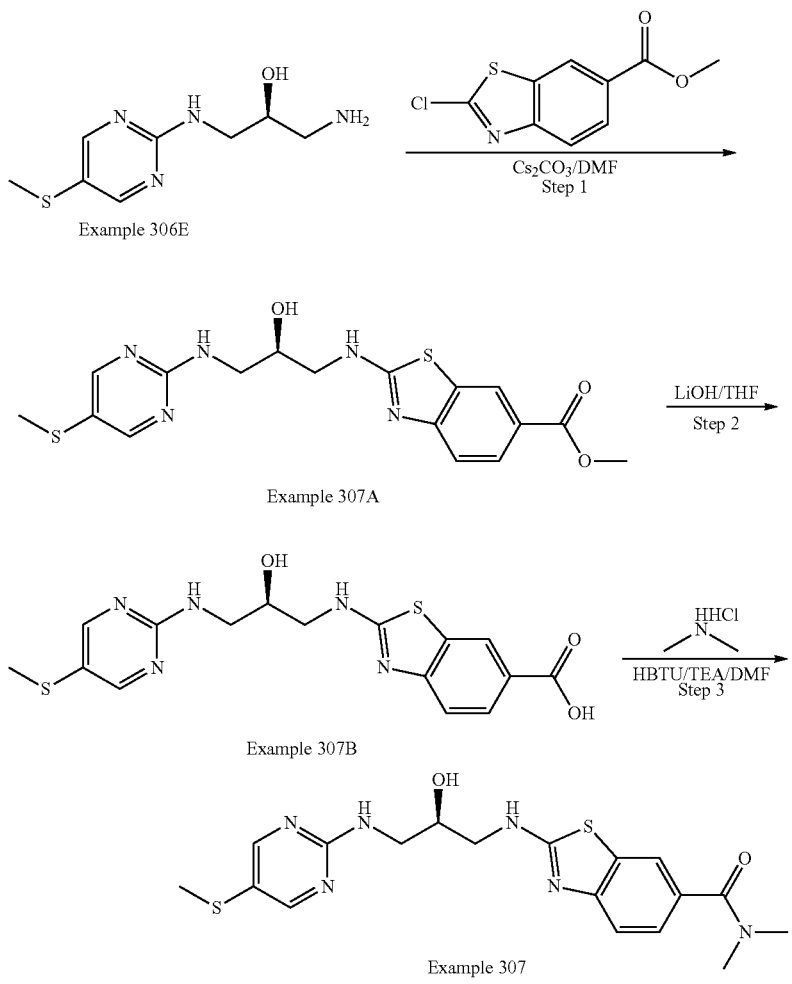

Scheme 47 mmol), TEA (8 mg, 0.075 mmol) and HBTU (14 mg, 0.038 mmol). The resulting mixture was stirred at r.t. for 1 h. After TLC detected the starting material was consumed, the mixture was concentrated and purified by Pre-TLC (eluted with EtOAc) to give the desired product Example 307 (2 mg, yield: 19%) as a white solid. LCMS [M+H]$^+$=419. $^1$H NMR (400 MHz, CDCl$_3$) δ 8.36 (s, 2H), 7.67 (s, 1H), 7.53 (d, J=8.2 Hz, 1H), 7.35 (dd, J=8.3, 1.5 Hz, 1H), 5.91 (s, 1H), 4.14-4.00 (m, 1H), 3.72-3.64 (m, 2H), 3.53 (dd, J=13.8, 6.3 Hz, 2H), 3.07 (s, 6H), 2.37 (s, 3H).
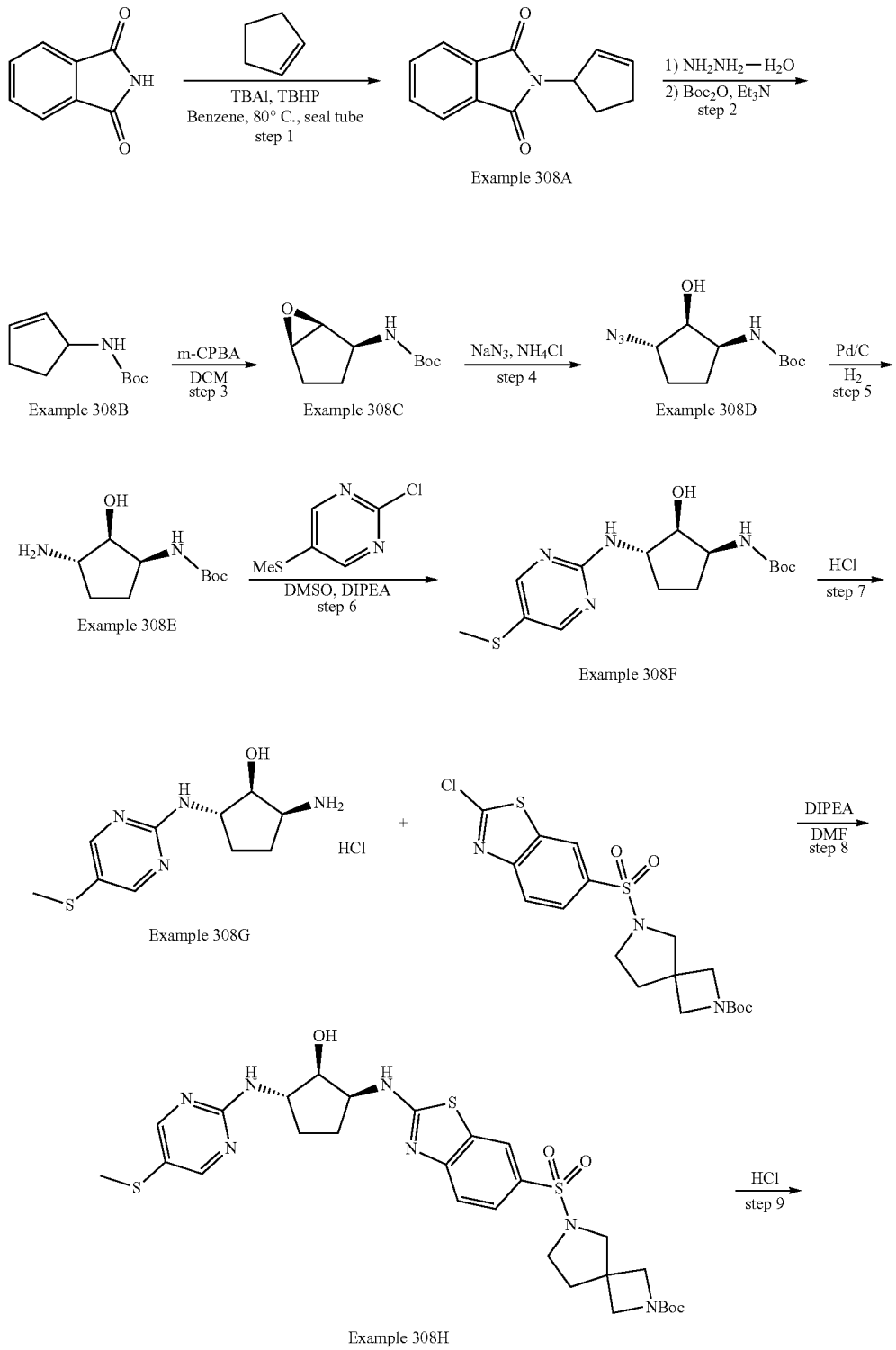
Scheme 48

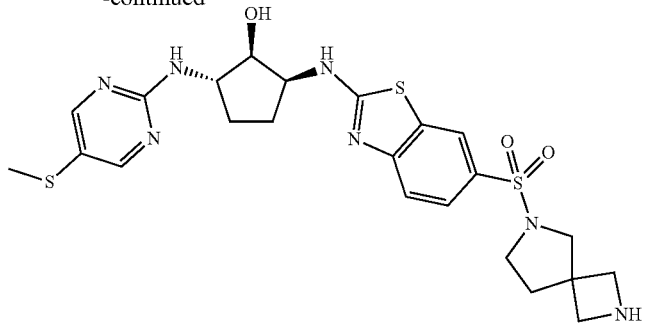

Example 308

Step 2: Example 308A

A Schlenk tube equipped with magnetic stir bar was charged with TBAI (5 g, 13.6 mmol), cyclopentene (9.25 g, 136 mmol), and O-Phthalimide (10 g, 68 mmol) in 250 mL of benzene. A solution of 65% TBHP (18.8 g, 136 mmol) was added before the vial was sealed and the reaction mixture was stirred at 80° C. for 12 h. After cooling to room temperature, the reaction mixture was diluted in ethyl acetate and washed with brine. The aqueous phase was extracted with ethyl acetate. The combined organic layers were concentrated under reduced pressure. The residue was purified by silica gel column chromatography (eluting with PE/ethyl acetate=5/1) to afford the desired compound Example 308A (6.5 g) as a white solid. LCMS [M+H]$^+$=214.
$^1$H NMR (400 MHz, CDCl$_3$) δ 2.08-2.17 (m, 1H), 2.32-2.47 (m, 1H), 2.41-2.53 (m, 1H), 2.80-2.88 (m, 1H), 5.33-5.46 (m, 1H), 5.61-5.70 (m, 1H), 6.07-6.16 (m, 1H), 7.67-7.75 (m, 2H), 7.80-7.87 (m, 2H).

Step 2: Example 308B

To a solution of Example 308A (5 g, 23.5 mmol) in THF (25 mL) was added 50% hydrazine hydrate in H$_2$O (3.52 g, 35.2 mmol). The mixture was stirred at 70° C. for 2 h. The mixture was then filtered and concentrated under reduced pressure. Di-tert-butyl dicarbonate (10.2 g, 47 mmol) was added and the mixture was stirred at room temperature overnight. The reaction mixture was concentrated under reduced pressure, and the residue was purified by silica gel column chromatography (eluting with PE/ethyl acetate=5/1) to afford the desired compound Example 308B (550 mg) as a white solid. LCMS [M+H]$^+$=184.

Step 3: Example 308C

To a solution of Example 308B (700 mg, 3.825 mmol) in DCM (5 mL) was added m-CPBA (790 mg, 4.59 mmol) portion-wise at 0° C. Following addition, the mixture was stirred at room temperature overnight. The resulting mixture was cooled to 0° C. and the m-chlorobenzoic acid filtered off and washed with additional cold DCM. The combined filtrate and wash were stirred with 20% NaHSO$_3$ for 30 min. The DCM layers were separated and extracted with 3 N NaOH (3×30 mL), saturated NaCl (30 mL), and then dried over Na$_2$SO$_4$. Evaporation left a white solid, which was purified by silica gel column chromatography (eluting with PE/ethyl acetate=5/1) to afford the desired compound Example 308C (455 mg) as a white solid. LCMS [M+H]$^+$=144. $^1$H NMR (400 MHz, CDCl$_3$) δ 1.07-1.17 (m, 1H), 1.48 (s, 9H), 1.66-1.76 (m, 1H), 1.89-1.96 (m, 1H), 2.05-2.16 (m, 1H), 3.41-3.50 (m, 1H), 3.53 (br s, 1H), 4.07-4.26 (m, 1H), 4.63-4.77 (m, 1H).

Step 4: Example 308D

A mixture of Example 308C (445 mg, 2.28 mmol), NaN$_3$ (297 mg, 4.57 mmol), NH$_4$Cl (61 mg, 1.14 mmol), 2-methoxyethanol (5 mL) and H$_2$O (1 mL) was stirred in a bath maintained at 80° C. for 16 hr. The resulting solution was evaporated to dryness, and the residue was dissolved in H$_2$O (5 mL). This solution was saturated with NaCl and then extracted with DCM (4×5 mL). The DCM solution was evaporated, the residue was purified by silica gel column chromatography (eluting with MeOH/DCM=3%-5%) to afford the desired compound Example 308D (420 mg) as a colorless oil. LCMS [M+H]$^+$=188.

Step 5: Example 308E

A suspension of Example 308D (420 mg, 1.74 mmol), Pd/C (cat.) in EtOH (5 mL) was stirred at r.t. for 16 h under H$_2$ atmosphere. The mixture was filtered and concentrated in vacuo. The residue was dried and used directly in the next step without further purification Example 308E (320 mg). LCMS [M+H]$^+$=217.

Step 6: Example 308F

A mixture of Example 308E (150 mg, 0.694 mmol), 2-chloro-5-(methylthio)pyrimidine (111 mg, 0.694 mmol), DIPEA (180 mg, 1.4 mmol) in DMSO (5 mL) was stirred at 130° C. for 3 hr. The resulting solution was cooled to room temperature, poured into water, and extracted with EtOAc (3×10 mL). The combined organic layers were concentrated under reduced pressure. The residue was purified by silica gel column chromatography (eluting with PE/EA=2/1) to afford the desired compound Example 308F (100 mg) as a colorless oil. LCMS [M+H]$^+$=341.
$^1$H NMR (400 MHz, CDCl$_3$) δ 1.45 (s, 9H), 1.75-1.85 (m, 1H), 2.13-2.21 (m, 1H), 2.23-2.30 (m, 1H), 2.38 (s, 3H), 3.83-4.05 (m, 3H), 5.33 (br s, 1H), 5.57 (br s, 1H), 8.35 (s, 2H).

Step 7: Example 308G

To a solution of Example 308F (100 mg, 0.294 mmol) in DCM (3 mL) was added 4 M HCl in dioxane (3 mL). The mixture was stirred at room temperature for 2 h. The mixture was concentrated under reduced pressure, dried and used directly in the next step without further purification Example 308G (70.6 mg). LCMS [M+H]⁺=241.

Step 8: Example 308H

A mixture of Example 308G (70.6 mg, 0.256 mmol), tert-butyl 6-((2-chlorobenzo[d]thiazol-6-yl)sulfonyl)-2,6-diazaspiro[3.4]octane-2-carboxylate (130 mg, 0.294 mmol), DIPEA (99 mg, 0.768 mmol) in DMF (4 mL) was stirred at 40° C. for 2 days. The resulting solution was cooled to room temperature, poured into water, and extracted with EtOAc (3×10 mL). The combined organic layers were concentrated under reduced pressure. The residue was purified by silica gel column chromatography (eluting with MeOH/DCM=5%) to afford the desired compound Example 308I1 (70 mg) as a white solid. LCMS [M+H]⁺=648.

Step 9: Example 308

To a solution of Example 308H (70 mg, 0.108 mmol) in DCM (3 mL) was added 4 M HCl in dioxane (3 mL). The mixture was stirred at room temperature for 2 h. The reaction mixture was concentrated and purified by prep-HPLC to afford the title compound Example 308 (20 mg) as a white solid. LCMS [M+H]⁺=548.

¹H NMR (400 MHz, DMSO-d₆) δ 1.47-1.56 (m, 1H), 1.63-1.73 (m, 1H), 1.97 (t, J=6.98 Hz, 2H), 2.06-2.23 (m, 2H), 2.31-2.41 (m, 3H), 3.19 (t, J=6.98 Hz, 2H), 3.35 (s, 2H), 3.68 (t, J=6.04 Hz, 4H), 3.95-4.02 (m, 1H), 4.15 (br. s., 1H), 4.38 (br. s., 1H), 7.48 (d, J=8.33 Hz, 1H), 7.59 (dd, J=8.33, 1.88 Hz, 2H), 8.16 (d, J=1.88 Hz, 1H), 8.37 (s, 2H), 8.49 (d, J=7.79 Hz, 2H), 8.66 (br. s., 1H).

Scheme 49

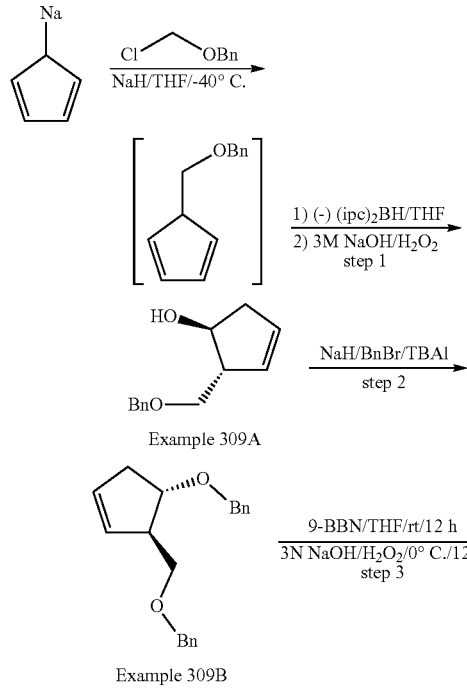

Example 309A

Example 309B

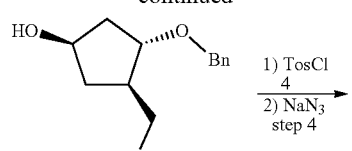

Example 309C

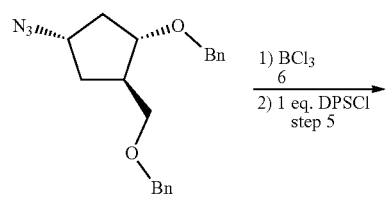

Example 309D

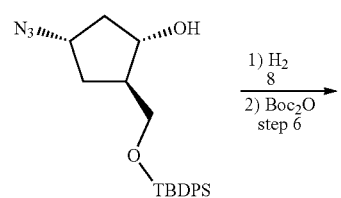

Example 309E

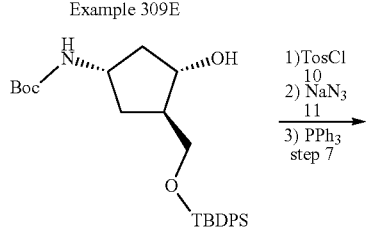

Example 309F

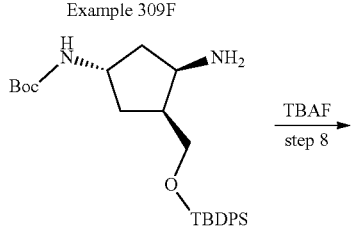

Example 309G

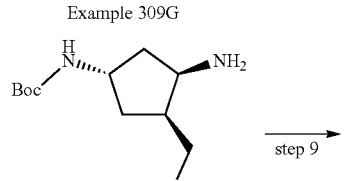

Example 309H

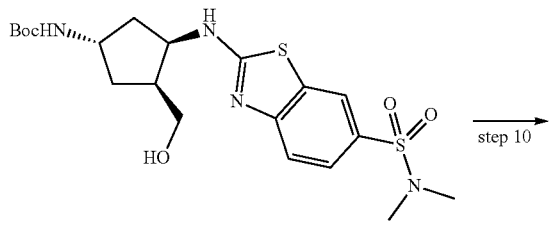

Example 309I

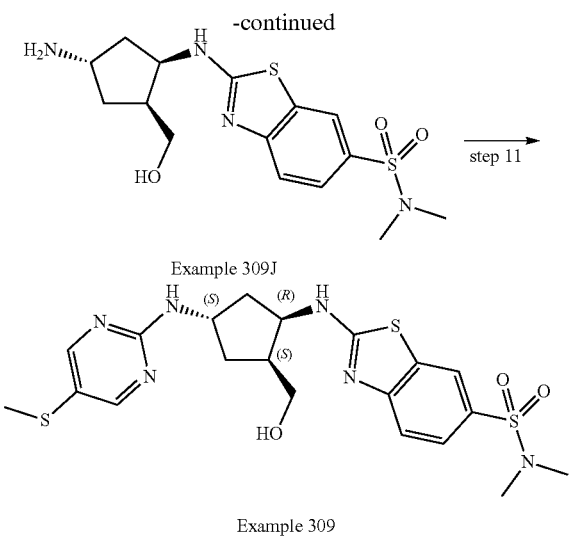

Example 309

Step 1: Example 309A

Sodium cyclopentadienylide (2 M solution in THF, 50 mL, 100 mmol, 1 equiv) was added dropwise to a solution of benzylchloromethyl ether (90%, 23 g, 130 mmol, 1.3 equiv) in DMF (200 mL) at −40° C. After 20 min of vigorous stirring at −40° C., the reaction mixture was poured into a 2:1 mixture of pentane/ice-cold water (900 mL). After shaking and allowing the phases to separate, the organic layer was washed twice with 150 mL of cold water and dried over $Na_2SO_4$ with stirring, maintaining the temperature below 0° C. to avoid isomerization of the double bonds. After removal of the drying agent by filtration, the pentane was removed in vacuo at 0° C. to afford (benzyloxymethyl)cyclopent-2,4-ene 1 as a pale orange oil. The resulting crude material was kept at 0° C. under argon and diluted with THF (160 mL), cooled to −78° C., and added dropwise via a cannula to a suspension of (−)-Ipc2BH (1 M solution in THF, 100 mL, 100 mmol, 1 equiv) in THF (400 mL) at −78° C. The mixture was allowed to warm slowly to −10° C. and stirred for 3 days at that temperature. The reaction was then quenched by addition of MeOH (40 mL), followed by a 3 M aqueous solution of NaOH (40 mL) and 30% $H_2O_2$ (40 mL). After 24 h of vigorous stirring at room temperature, the THF was removed under reduced pressure and the remaining aqueous suspension was partitioned between EtOAc (400 mL) and brine (200 mL). After extraction, the organic layer was dried over $Na_2SO_4$ and concentrated in vacuo. The crude orange oil was purified by column chromatography (eluent: 9:1-8:2 heptane:EtOAc) to give Example 309A (4.8 g, 23.53 mmol, 23%) as a pale yellow oil. Rf=0.29 (eluent: 7:3 heptane:EtOAc); 1H NMR (400 MHz, CDCl$_3$) δ 2.23-2.32 (m, 1H), 2.35 (s, 1H), 2.63-2.73 (m, 1H), 2.81-2.88 (m, 1H), 3.28 (t, J=8.9 Hz, 1H), 3.53 (dd, J=5.4, 9.1 Hz, 1H), 4.29 (td, J=4.1, 7.0 Hz, 1H), 4.52 (s, 2H), 5.53-5.58 (m, 1H), 5.70-5.74 (m, 1H), 7.24-7.37 (m, 5H).

Step 2: Example 309B

To a solution of Example 309A (4.8 g, 23.53 mmol, 1 equiv) in anhydrous THF (100 mL) was added NaH (50% in mineral oil, 1.13 g, 28.2 mmol, 1.2 equiv) at 0° C. and the mixture was stirred for 20 min at temperature. Benzyl bromide (BnBr, 3.6 mL, 30.5 mmol, 1.3 equiv) and tetra-butylammonium iodide (TBAI, 100 mg, 0.3 mmol, 0.01 equiv) were then added at 0° C. and the reaction mixture was stirred at room temperature. After 15 h, crushed ice was added carefully and the mixture was stirred for 30 min. After extraction with EtOAc (150 mL), the organic layer was washed with $H_2O$ (150 mL), brine (150 mL), dried over $Na_2SO_4$ and concentrated in vacuo. Purification by column chromatography (eluent: 98:2-95:5 heptane:EtOAc) gave Example 309B (6.3 g, 21.4 mmol, 80%) as a colorless syrup. Rf=0.41 (eluent: 9:1 heptane:EtOAc). LCMS [M+H]$^+$=295.1H NMR (500 MHz, CDCl$_3$) δ 2.42 (d, J=17.4 Hz, 1H), 2.65-2.70 (m, 1H), 3.07 (brs, 1H), 3.33 and 3.44 (ABX, JAB=9.2 Hz, JAX=5.7 Hz, JBX=7.3 Hz, 2H), 4.08 (ddd, J=3.0, 3.3, 7.0 Hz, 1H), 4.51 (d, J=3.4 Hz, 2H), 4.54 (s, 2H), 5.64-5.66 (m, 1H), 5.74-5.75 (m, 1H), 7.22-7.34 (m, 10H).

Step 3: Example 309C

A 0.5 M solution of 9-BBN in THF (88 mL, 44 mmol) was added dropwise to a solution of Example 309B (6.50 g, 22.0 mmol) in anhydrous THF (10 mL) at 0° C. under nitrogen. The reaction was slowly warmed to r.t. overnight. The reaction was cooled to 0° C. and treated sequentially with EtOH (7 mL), 3 N NaOH solution (20 mL), and $H_2O_2$ (33%, 20 mL). The resulting mixture was stirred at r.t. overnight. The resulting residue was filtered and washed with EtOAc (200 mL). To this suspension, water was added (150 mL) and after separation of the phases, the aqueous layer was extracted with EtOAc (3×50 mL). The combined organic layers were dried ($Na_2SO_4$) and concentrated to dryness. The crude product was purified on silica gel (eluent: 1:1 heptane:EtOAc) gave Example 309C (6.0 g, 19.3 mmol, 87%) as a yellow oil. LCMS [M+H]$^+$=313. 1H NMR (400 MHz, CDCl$_3$) δ 7.35-7.25 (m, 10H, CH-arom.), 4.52 (s, 2H, CH2-benzyl), 4.49 (d, 1H, J=11.8 Hz, CHH-benzyl), 4.44 (d, 1H, J=11.8 Hz, CHH-benzyl), 4.33-4.28 (m, 1H, H-1), 4.07 (ddd, 1H, J=6.6 Hz, 6.6 Hz, 4.1 Hz, H-3), 3.53 (dd, 1H, J=9.0 Hz, 4.2 Hz, OCHH), 3.49 (d, 1H, J=9.0 Hz, 4.3 Hz, OCHH), 2.35-2.25 (m, 2H, H-4, H-5a), 2.05 (dddd, 1H, J=13.5 Hz, 6.7 Hz, 3.5 Hz, 1.7 Hz, H-2a), 1.89-1.82 (m, 1H, H-2b), 1.52-1.46 (m, 1H, H-5b).

Step 4: Example 309D

Compound Example 309C (6.0 g, 19.3 mmol) was dissolved in dry pyridine (30 mL) and cooled to 0° C. TosCl (5.5 g, 28.9 mmol) was added in portions over a period of 30 min. After the addition, the reaction was stirred at room temperature for 18 h. The suspension was diluted with ethyl acetate (300 mL) and $H_2O$ (200 mL). The organic phase was separated, washed with sat. NH$_4$C$_1$ solution (3×200 mL), brine (100 mL) and dried over MgSO4. The solvent was evaporated and the residue was purified by flash chromatography silica gel (hexane/ethyl acetate 5:1) to give (1R, 3S,4R)-3-(benzyloxy)-4-((benzyloxy)methyl)cyclopentyl 4-methylbenzenesulfonate (1.4 g, 3.0 mmol, 15%) as a colourless oil. Rf=0.26 (20% ethyl acetate in hexane). LCMS [M+H]$^+$=467. 1H NMR (400 MHz, CDCl$_3$) δ7.79 (m, 2H), 7.38-7.27 (m, 12H), 5.05-4.99 (m, 1H), 4.50 (s, 2H), 4.45 (s, 2H), 3.96-3.92 (m, 1H), 3.48-3.40 (td, 2H, J=6.3 Hz), 2.45 (s, 3H), 2.33-2.20 (m, 2H), 2.14-2.01 (m, 2H), 1.69-1.62 (m, 1H).

Compound (1R,3S,4R)-3-(benzyloxy)-4-((benzyloxy) methyl)cyclopentyl 4-methylbenzenesulfonate (1.4 g, 3.0 mmol) was dissolved in dry DMF (20 mL) and NaN$_3$ (2.1 g, 15.4 mmol) was added. The mixture was stirred at 60° C. for 14 h. After the addition of ethyl acetate (300 mL), the organic layer was washed with sat. NaHCO₃ solution (2×100 mL) and brine (100 mL) and dried over MgSO₄. The solvent was removed under reduced pressure. The residue was purified by flash chromatography silica gel (hexane/ethyl acetate 10:1) to give Example 309D (1.0 g, 2.95 mmol, 95%) as a colourless oil. Rf=0.54 (20% ethyl acetate in hexane). LCMS [M+H]⁺=338. ¹H NMR (400 MHz, CDCl₃) δ 7.39-7.25 (m, 10H), 4.52 (dd, J=26.0, 18.6 Hz, 2H), 4.49 (s, 2H), 3.97-3.89 (m, 1H), 3.86 (td, J=7.0, 5.1 Hz, 1H), 3.44 (d, J=5.5 Hz, 2H), 2.54-2.43 (m, 1H), 2.24 (td, J=13.8, 6.8 Hz, 1H), 1.99 (dddd, J=13.4, 8.7, 4.7, 1.3 Hz, 1H), 1.84 (dddd, J=28.2, 20.8, 9.5, 4.2 Hz, 2H).

Step 5: Example 309E

Compound Example 309D (1.0 g, 2.95 mmol) was dissolved in dry CH₂Cl₂ (20 mL) and cooled to −78° C. A solution of 1M BCl₃ (40 mL) in CH₂Cl₂ was added by means of a dropping funnel over a period of 45 min and the mixture was stirred at −78° C. for 3 h, then warmed up to room temperature. The reaction was quenched with dry MeOH (20 mL) at −78° C. and was allowed to warm up to room temperature overnight. The solvents were evaporated and the residue was purified on silica gel (hexane/ethyl acetate 1:1) to give (1S,2R,4S)-4-azido-2-(hydroxymethyl)cyclopentanol (420 mg, 2.67 mmol, 90%) obtained as a yellow oil. LCMS [M+H]⁺=158. ¹H NMR (400 MHz, CDCl₃) δ 4.07 (dd, J=13.3, 6.0 Hz, 1H), 4.02-3.95 (m, 1H), 3.79 (ddd, J=10.4, 5.2, 3.0 Hz, 1H), 3.56 (dd, J=10.4, 8.0 Hz, 1H), 2.36-2.20 (m, 4H), 1.99-1.92 (m, 1H), 1.77 (dddd, J=14.0, 6.0, 4.5, 1.6 Hz, 1H), 1.58 (dddd, J=13.9, 9.8, 6.8 Hz, 1H).

Compound (1S,2R,4S)-4-azido-2-(hydroxymethyl)cyclopentanol (0.42 g, 2.67 mmol) was dissolved in dry DMF (10 mL), and imidazole (198 mg, 2.94 mmol) was added at room temperature. After the portion-wise addition of TBDPSCl (808 mg, 2.94 mmol) at 0° C., the mixture was stirred at room temperature for 16 h. The reaction was diluted with CH₂Cl₂ (200 mL), washed once with sat. NH₄Cl (70 mL) and with brine (50 mL) and dried over MgSO₄. The solvent was removed in vacuo and the crude product was purified by silica gel (hexane/ethyl acetate 10:1) to give Example 309E (630 mg, 1.6 mmol, 60%) obtained as a yellow oil. LCMS [M+H]⁺=360. ¹H NMR (400 MHz, CDCl₃) δ 7.69-7.66 (m, 4H), 7.49-7.40 (m, 6H), 4.15 (dd, J=7.0, 7.0 Hz, 1H), 4.02-3.99 (m, 1H), 3.81 (dd, J=4.8, 4.8 Hz, 1H), 3.59 (dd, J=7.2, 7.2 Hz, 1H), 2.35-2.28 (m, 2H), 1.91-1.88 (m, 1H), 1.83-1.78 (m, 1H), 1.70-1.62 (m, 1H), 1.08 (s, 9H).

Step 6: Example 309F

10% Pd/C (63 mg) was added to a suspension of compound Example 309E (630 g, 1.6 mmol) in dry EtOH (100 mL). The reaction was evacuated twice to exchange the inert gas atmosphere, and then connected to two balloons that were filled with H₂. The suspension was vigorously stirred at room temperature for 15 h. The palladium catalyst was removed by using a PTFE-Filter (Whatman Puradisc) and the solvent was removed under reduced pressure. The amine (588 g, 100%) was obtained as a colorless liquid, and was used without further purification. LCMS [M+H]⁺=370.

To a solution of amine (588 mg, 1.6 mmol) in DCM (50 mL) at 0° C. was added Boc₂O (700 mg, 3.2 mmol) in DCM (10 mL) and stirred at 0° C., then stirred at RT for 2 h. The reaction mixture was concentrated and the crude product was purified by silica gel (hexane/ethyl acetate 5:1) to give Example 309F (650 mg, 1.38 mmol, 87%) obtained as a colourless oil. LCMS [M+H]⁺=470. ¹H NMR (400 MHz, CDCl₃) δ 7.68-7.65 (m, 4H), 7.48-7.40 (m, 6H), 4.97 (br s, 1H), 4.20 (m, 1H), 4.02 (br s, 1H), 3.74 (dd, J=4.2, 4.2 Hz, 1H), 3.51 (dd, J=8.4, 8.4 Hz, 1H), 2.29-2.22 (m, 2H), 1.78-1.57 (m, 3H), 1.45 (s, 9H), 1.07 (s, 9H).

Step 7: Example 309G

Compound Example 309F (630 mg, 1.34 mmol), DIEA (300 mg, 2.28 mmol) and DMAP (278 mg, 2.28 mmol) in DCM (50 mL) was added TosCl (384 mg, 2.0 mmol) at 0° C. The mixture was stirred at RT for 14 h and then concentrated to dryness. The crude product was purified by silica gel (hexane/ethyl acetate 10:1) to give (1S,2R,4S)-4-((tert-butoxycarbonyl)amino)-2-(((tert-butyldiphenylsilyl)oxy)methyl)cyclopentyl 4-methylbenzenesulfonate (590 mg, 0.94 mmol, 70%) obtained as a colourless oil. LCMS [M+H]⁺=625.

(1S,2R,4S)-4-((tert-butoxycarbonyl)amino)-2-(((tert-butyldiphenylsilyl)oxy)methyl) cyclopentyl 4-methylbenzenesulfonate (590 g, 0.94 mmol) was dissolved in dry DMF (10 mL) and NaN₃ (92 mg, 1.4 mmol) was added. The mixture was stirred at 60° C. for 14 h. After the addition of ethyl acetate (100 mL), the organic layer was washed with sat. NaHCO₃ solution (2×50 mL) and brine (50 mL) and dried over MgSO₄. The solvent was removed under reduced pressure. The residue was purified by flash chromatography silica gel (hexane/ethyl acetate 5:1) to give tert-butyl ((1S, 3R,4S)-3-azido-4-(((tert-butyldiphenylsilyl)oxy)methyl)cyclopentyl)carbamate (460 mg, 0.93 mmol, 99%) as a colourless oil. Rf=0.54 (20% ethyl acetate in hexane). LCMS [M+H]⁺=496. ¹H NMR (400 MHz, CDCl₃) δ 7.72-7.67 (m, 4H), 7.46-7.40 (m, 6H), 4.45 (br s, 1H), 4.20 (m, 1H), 4.08 (br s, 1H), 3.79-3.72 (m, 1H), 3.68-3.62 (m, 1H), 2.41-2.35 (m, 2H), 1.80-1.47 (m, 5H), 1.46 (s, 9H), 1.08 (s, 9H).

10% Pd/C (46 mg) was added to a suspension of tert-butyl ((1S,3R,4S)-3-azido-4-(((tert-butyldiphenylsilyl)oxy)methyl)cyclopentyl)carbamate (460 g, 0.93 mmol) in dry EtOH (50 mL). The reaction was evacuated twice to exchange the inert gas atmosphere, and then connected to two balloons that were filled with Hz. The suspension was vigorously stirred at room temperature for 15 h. The palladium catalyst was removed by using a PTFE-Filter (Whatman Puradisc) and the solvent was removed under reduced pressure. The amine Example 309G (460 mg, 0.93 mmol, quant.) was obtained as a colourless liquid, and was used without further purification. LCMS [M+H]⁺=470

Step 8: Example 309H

To a solution of compound Example 309G (70 mg, 0.17 mmol) in THF (5 mL) was added 1M TBAF (1.7 mL, 0.17 mmol) at 0° C. under N2, then stirred at RT for 2 h. The reaction mixture was concentrated to give crude product 13, the crude product was next step. LCMS [M+H]⁺=231.

Step 9: Example 309I

A mixture of compound Example 309I1 (crude, 0.17 mmol), 2-chloro-N,N-dimethylbenzo[d]thiazole-6-sulfonamide (46 mg, 0.17 mmol) and DIEA (65 mg, 0.51 mmol) in DMSO was stirred at 60° C. for overnight. The mixture was purified by Prep-HPLC to give compound Example 309I (38 mg, 47%) as white solid. LCMS [M+H]⁺=472.

Step 10: Example 309J

A solution of 4M HCl/dioxane (5 L) was added to compound Example 309I (38 mg, 0.08 mmol) in DCM (1 mL) and the mixture was stirred at RT for 1 h. The mixture was concentrated to give compound Example 309J (30 mg, 100%) as white solid. LCMS [M+H]⁺=372.

Step 16: Example 309

A mixture of compound Example 309J (30 mg, 0.08 mmol), 2-chloro-5-(methylthio)pyrimidine (15 mg, 0.09 mmol) and DIEA (34 mg, 0.25 mmol) in DMSO (2.5 mL) was stirred at 120° C. for 4 h. The mixture was purified by Prep-HPLC to give compound Example 309 (5 mg, 12%) as white solid. LCMS [M+H]⁺=496.

$^1$H NMR (400 MHz, CD3OD) δ 8.36 (s, 2H), 8.09 (d, J=1.6 Hz, 1H), 7.68 (dd, J=2.0, 1.6 Hz, 1H), 7.56 (d, J=8.4 Hz, 1H), 4.62 (br s, 5H), 4.54 (br m, 1H), 3.63-3.58 (m, 2H), 2.70 (s, 3H), 2.69-2.65 (m, 1H), 2.37 (s, 3H), 2.36-2.28 (m, 1H), 2.16-2.10 (m, 1H), 2.05-1.99 (m, 1H), 1.86-1.82 (m, 1H).

Scheme 50

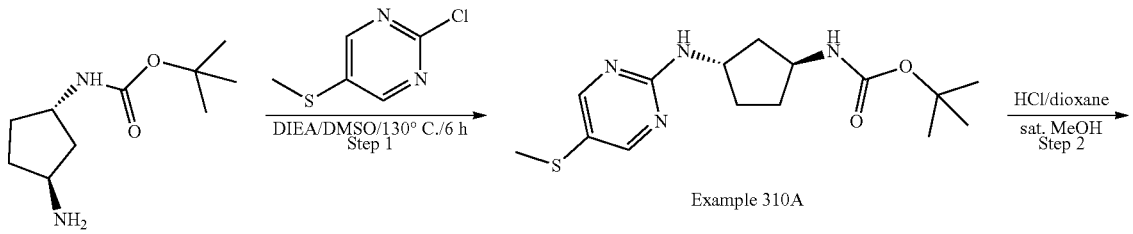

Example 310A

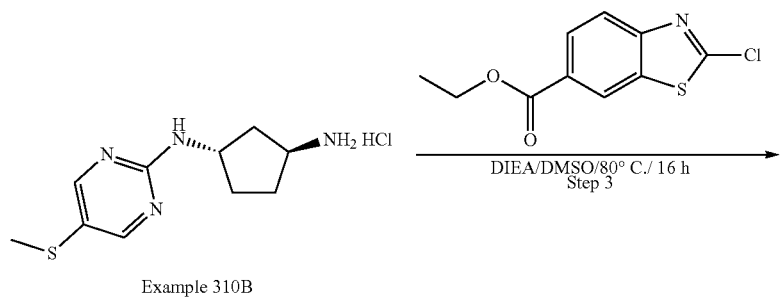

Example 310B

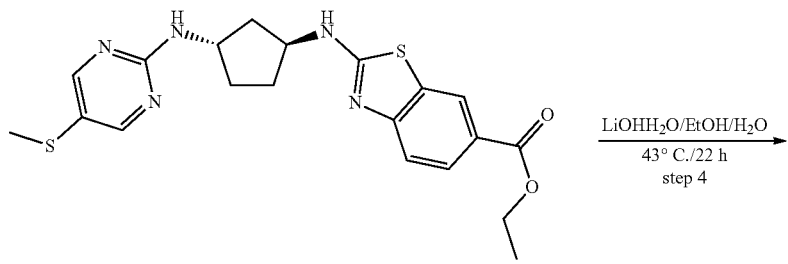

Example 310C

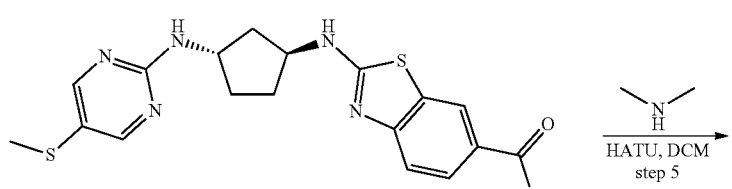

Example 310D

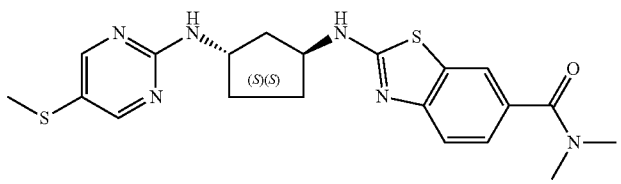

Example 310

Step 1: Example 310A

To a mixture of tert-butyl ((1S,3S)-3-aminocyclopentyl) carbamate (1.5 g, 7.5 mmol), 2-chloro-5-(methylthio)pyrimidine (1.3 g, 8.3 mmol) in dimethyl sulfoxide (28 mL) was added N,N-Diisopropylethylamine (3.7 mL, 22.5 mmol) at room temperature. The resulting mixture was stirred at 130° C. for 6.5 h under $N_2$ atmosphere. To the mixture was then added water (90 mL) and ethyl acetate (160 mL). The combined organic layers were washed with brine (100 mL), dried over anhydrous sodium sulfate, filtered and evaporated. The residue was purified by silica gel column chromatography (PE:EA=20:1~PE:EA=6:1) to give Example 310A (1.8 g, yield 76%) as a yellow oil. LCMS [M+H]$^+$=325.

Step 2: Example 310B

To a mixture of Example 310A (1.8 g, 5.7 mmol) in methanol (2 mL) was added HCl/dioxane (8.0 mL, 4 mol/L) at room temperature. The resulting mixture was stirred at room temperature for 2.5 h under $N_2$ atmosphere. The mixture was then evaporated to give Example 310B (1.5 g, yield 100%) as a brown solid. LCMS [M+H]$^+$=225.

Step 3: Example 310C

To a mixture of Example 310B (1.5 g, 5.7 mmol), ethyl 2-chlorobenzo[d]thiazole-6-carboxylate (1.4 g, 5.7 mmol) in DMSO (28 mL) was added DIEA (2.9 mL, 17.3 mmol) at room temperature. The resulting mixture was stirred at 80° C. for 18 h under N2 atmosphere. To the mixture was then added water (80 mL) and ethyl acetate (150 mL). The combined organic layers were washed with brine (90 mL), dried over anhydrous sodium sulfate, filtered and evaporated. The residue was purified by silica gel column chromatography (PE:EA=30:1~5:1) to give Example 310C (1.9 g, yield 77%) as a yellow solid. LCMS [M+H]$^+$=430.

Step 4: Example 310D

To a mixture of Example 310C (1.9 g, 4.4 mmol) in ethanol (20 mL) and water (10 mL) was added lithium hydroxide monohydrate (372 mg, 8.9 mmol) at room temperature. The resulting mixture was stirred at room temperature for 18 h under nitrogen atmosphere. The mixture was then concentrated. To the residue was added water (60 mL) and HCl (3 mol/L) until pH=5. The precipitate was filtered and the filter cake was dried to give Example 310D (1.5 g, yield 84%) as a brown solid. LCMS [M+H]$^+$=402.
$^1$H NMR (400 MHz, DMSO-d$_6$) δ 8.49-8.47 (d, J 6.8 Hz, 1H), 8.34 (s, 2H), 8.26-8.25 (d, J 1.6 Hz, 1H), 7.81-7.79 (m, 1H), 7.55-7.53 (d, J 7.2 Hz, 1H), 7.40-7.38 (d, J 8.4 Hz, 1H), 4.39-4.33 (m, 2H), 2.35 (s, 3H), 2.21-2.19 (m, 2H), 2.12-2.10 (m, 2H), 1.98-1.94 (t, J 13.6 Hz, 1H).

Step E: Example 310

A mixture of Example 310D (30 mg, 0.075 mmol), dimethylamine (6.75 mg, 0.15 mmol), HATU (28.5 mg, 0.075 mmol) in DCM was stirred at room temperature for 2 h. The resulting solution was concentrated under reduced pressure. The residue was purified by Prep-HPLC to afford the title compound Example 310 (20 mg) as a yellow solid. LCMS [M+H]$^+$=429. $^1$H NMR (600 MHz, DMSO-d$_6$) δ 1.54-1.64 (m, 2H), 1.98 (t, J=6.75 Hz, 2H), 2.09-2.16 (m, 1H), 2.18-2.27 (m, 1H), 2.36 (s, 3H), 2.97 (s, 6H), 4.35 (br s, 2H), 7.30 (dd, J=8.35, 1.49 Hz, 1H), 7.40 (d, J=8.24 Hz, 1H), 7.57 (br s, 1H), 7.74-7.81 (m, 1H), 8.35 (s, 2H), 8.58 (br s, 1H).

Using the above procedures, the following examples were synthesized:

TABLE 31

| Structure | Ex. # | $^1$H NMR | LC-MS (M + H)$^+$ |
|---|---|---|---|
| 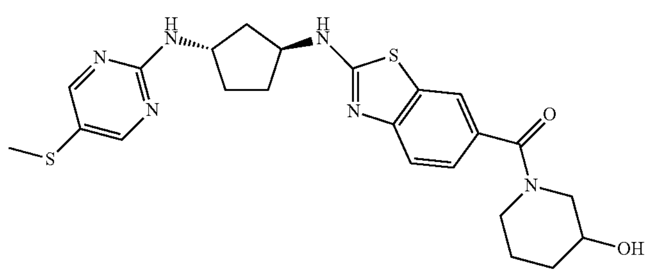 [SMILES: CSc1cnc(N[C@H]2CC[C@H](Nc3nc4ccc(C(=O)N5CCCC(O)C5)cc4s3)C2)nc1] | 311 | $^1$H NMR (400 MHz, DMSO-d$_6$) δ 8.34 (s, 2H), 8.29 (d, J = 6.7 Hz, 1H), 7.72 (d, J = 1.3 Hz, 1H), 7.53 (d, J = 7.3 Hz, 1H), 7.37 (d, J = 8.3 Hz, 1H), 7.23 (d, J = 8.3 Hz, 1H), 4.96-4.79 (m, 1H), 4.34 (td, J = 6.9, 13.7 Hz, 2H), 3.53-3.44 (m, 2H), 3.14-3.03 (m, 2H), 2.97-2.84 (m, 1H), 2.34 (s, 3H), 2.24-2.05 (m, 2H), 1.95 (t, J = 6.7 Hz, 2H), 1.89-1.80 (m, 1H), 1.75-1.62 (m, 1H), 1.61-1.50 (m, 2H), 1.45-1.32 (m, 2H). | 485 |

TABLE 31-continued

| Structure | Ex. # | ¹H NMR | LC-MS (M + H)⁺ |
|---|---|---|---|
| 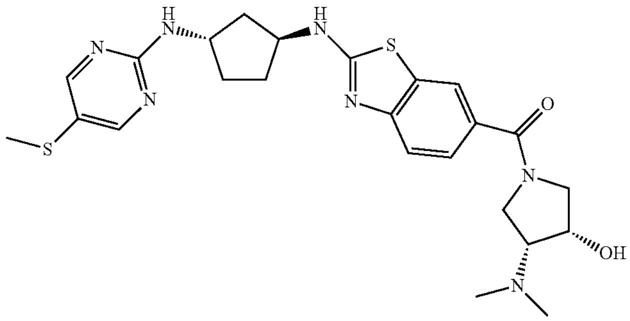 [SMILES: CSc1cnc(N[C@H]2CC[C@H](Nc3nc4ccc(C(=O)N5C[C@@H](N(C)C)[C@@H](O)C5)cc4s3)C2)nc1] | 312 | ¹H NMR (400 MHz, DMSO-d₆) δ 8.34 (s, 2H), 8.32 (d, J = 7.3 Hz, 1H), 7.87 (s, 1H), 7.53 (d, J = 7.3 Hz, 1H), 7.42-7.34 (m, 2H), 4.48-4.39 (m, 1H), 4.35 (td, J = 6.5, 13.5 Hz, 2H), 4.20-4.05 (m, 1H), 3.79-3.34 (m, 4H), 2.34 (s, 3H), 2.24-2.17 (m, 4H), 2.15-2.06 (m, 4H), 1.95 (t, J = 6.7 Hz, 2H), 1.61-1.52 (m, 2H). | 514 |
| 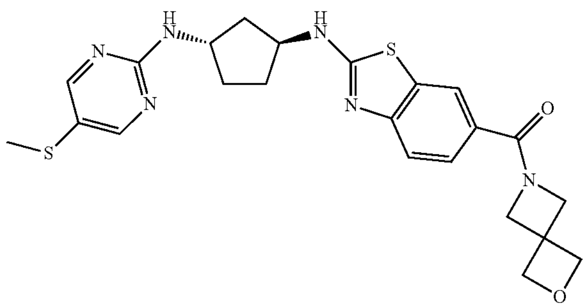 [SMILES: CSc1cnc(N[C@H]2CC[C@H](Nc3nc4ccc(C(=O)N5CC6(COC6)C5)cc4s3)C2)nc1] | 313 | ¹H NMR (400 MHz, DMSO-d₆) δ 8.39 (d, J = 6.7 Hz, 1H), 8.34 (s, 2H), 7.97 (d, J = 1.6 Hz, 1H), 7.53 (d, J = 7.3 Hz, 1H), 7.48 (dd, J = 1.7, 8.5 Hz, 1H), 7.37 (d, J = 8.3 Hz, 1H), 4.68 (s, 4H), 4.51 (br s, 2H), 4.34 (td, J = 6.9, 13.7 Hz, 2H), 4.19 (br s, 2H), 2.34 (s, 3H), 2.24-2.05 (m, 2H), 1.95 (t, J = 6.6 Hz, 2H), 1.62-1.51 (m, 2H). | 483 |
| 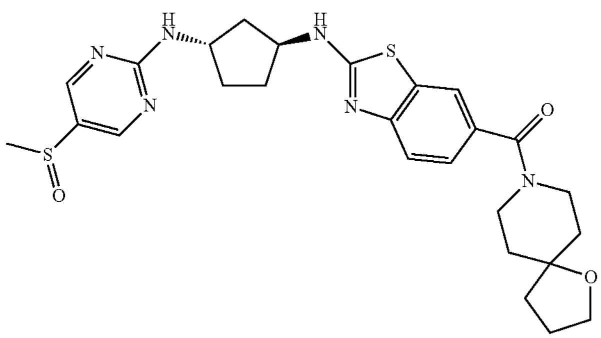 [SMILES: CS(=O)c1cnc(N[C@H]2CC[C@H](Nc3nc4ccc(C(=O)N5CCC6(CCCO6)CC5)cc4s3)C2)nc1] | 314 | ¹H NMR (400 MHz, DMSO-d₆) δ 8.58 (s, 2H), 8.31 (d, J = 6.7 Hz, 1H), 8.05 (d, J = 7.3 Hz, 1H), 7.74 (d, J = 1.6 Hz, 1H), 7.37 (d, J = 8.1 Hz, 1H), 7.24 (dd, J = 1.7, 8.2 Hz, 1H), 4.49-4.30 (m, 2H), 3.74 (t, J = 6.6 Hz, 2H), 3.40-3.29 (m, 4H), 2.83 (s, 3H), 2.25-2.08 (m, 2H), 1.98 (t, J = 6.7 Hz, 2H), 1.87 (quin, J = 7.1 Hz, 2H), 1.69 (t, J = 7.4 Hz, 2H), 1.64-1.49 (m, 6H). | 541 |
| 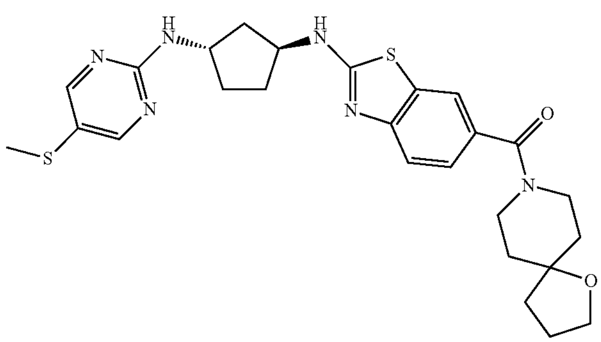 [SMILES: CSc1cnc(N[C@H]2CC[C@H](Nc3nc4ccc(C(=O)N5CCC6(CCCO6)CC5)cc4s3)C2)nc1] | 315 | ¹H NMR (400 MHz, DMSO-d₆) δ 8.34 (s, 2H), 8.29 (d, J = 7.0 Hz, 1H), 7.73 (d, J = 1.6 Hz, 1H), 7.53 (d, J = 7.3 Hz, 1H), 7.37 (d, J = 8.3 Hz, 1H), 7.23 (dd, J = 1.7, 8.2 Hz, 1H), 4.38-4.29 (m, 2H), 3.73 (t, J = 6.7 Hz, 2H), 3.40-3.26 (m, 4H), 2.34 (s, 3H), 2.24-2.05 (m, 2H), 1.95 (t, J = 6.9 Hz, 2H), 1.87 (quin, J = 7.1 Hz, 2H), 1.68 (t, J = 7.4 Hz, 2H), 1.62-1.47 (m, 6H). | 525 |

TABLE 31-continued

| Structure | Ex. # | ¹H NMR | LC-MS (M + H)⁺ |
|---|---|---|---|
| 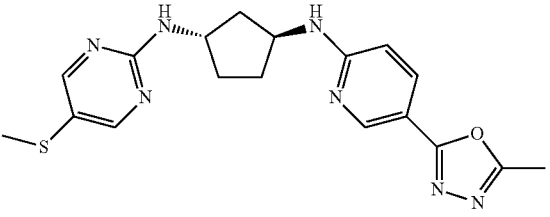 | 316 | ¹H NMR (400 MHz, DMSO-d₆) δ 8.53 (d, J = 2.1 Hz, 1H), 8.33 (s, 2H), 7.84 (dd, J = 2.4, 8.9 Hz, 1H), 7.51 (d, J = 7.3 Hz, 1H), 7.42 (d, J = 7.0 Hz, 1H), 6.59 (d, J = 8.9 Hz, 1H), 4.42-4.28 (m, 2H), 2.52 (s, 3H), 2.34 (s, 3H), 2.19-2.06 (m, 2H), 1.97-1.81 (m, 2H), 1.58-1.44 (m, 2H). | 384 |
| 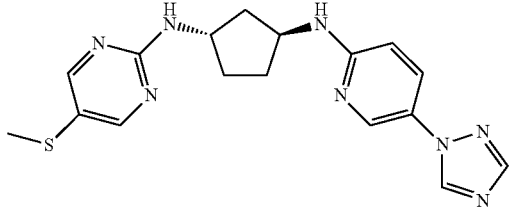 [SMILES: CSc1cnc(N[C@H]2CC[C@H](Nc3ccc(-n4cncn4)cn3)C2)nc1] | 317 | ¹H NMR (400 MHz, DMSO-d₆) δ 9.34 (s, 1H), 8.33 (s, 2H), 8.26 (s, 1H), 8.08 (d, J = 5.6 Hz, 1H), 7.49 (d, J = 7.3 Hz, 1H), 6.99 (dd, J = 1.7, 5.5 Hz, 2H), 6.90 (d, J = 1.6 Hz, 1H), 4.39-4.27 (m, 2H), 2.34 (s, 3H), 2.18-2.06 (m, 2H), 1.95-1.81 (m, 2H), 1.57-1.44 (m, 2H). | 369 |
| 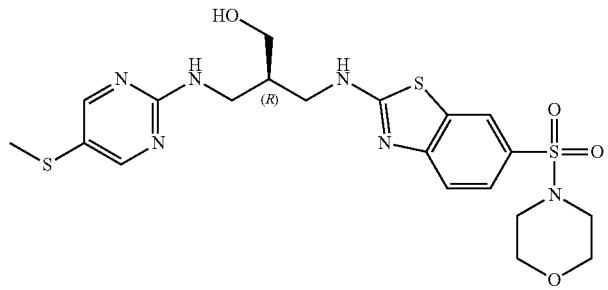 | 318 | ¹H NMR (400 MHz, CDCl3) δ 8.38 (s, 2H), 7.97 (d, J = 1.6 Hz, 1H), 7.70-7.59 (m, 2H), 6.95 (br s, 1H), 6.00 (br s, 1H), 3.84 (dd, J = 4.7, 13.8 Hz, 1H), 3.78-3.71 (m, 4H), 3.66-3.50 (m, 5H), 3.07-2.95 (m, 4H), 2.39 (s, 3H), 2.17-2.08 (m, 1H). | 511 |
| 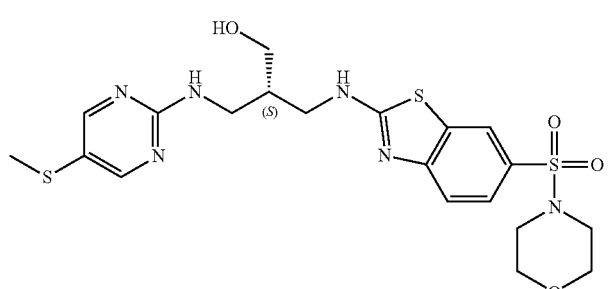 | 319 | ¹H NMR (400 MHz, CDCl3) δ 8.38 (s, 2H), 7.97 (d, J = 1.6 Hz, 1H), 7.70-7.59 (m, 2H), 6.95 (br s, 1H), 6.00 (br s, 1H), 3.84 (dd, J = 4.7, 13.8 Hz, 1H), 3.78-3.71 (m, 4H), 3.66-3.50 (m, 5H), 3.07-2.95 (m, 4H), 2.39 (s, 3H), 2.17-2.08 (m, 1H). | 511 |
| 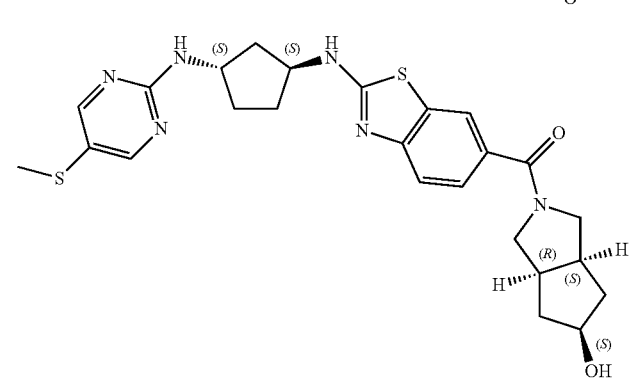 | 320 | ¹H NMR (400 MHz, DMSO-d₆) δ 8.34 (s, 2H), 8.30 (d, J = 6.9 Hz, 1H), 7.82 (s, 1H), 7.53 (d, J = 7.3 Hz, 1H), 7.38-7.31 (m, 2H), 4.65 (br s, 1H), 4.35 (td, J = 6.8, 13.7 Hz, 2H), 4.06 (quin, J = 6.3 Hz, 1H), 3.68-3.58 (m, 2H), 3.57-3.38 (m, 2H), 2.59-2.52 (m, 2H), 2.34 (s, 3H), 2.24-2.05 (m, 2H), 2.03-1.89 (m, 4H), 1.63-1.50 (m, 2H), 1.36-1.25 (m, | 525 |

TABLE 31-continued

| Structure | Ex. # | ¹H NMR | LC-MS (M + H)⁺ |
|---|---|---|---|
| | | 2H). | |
| 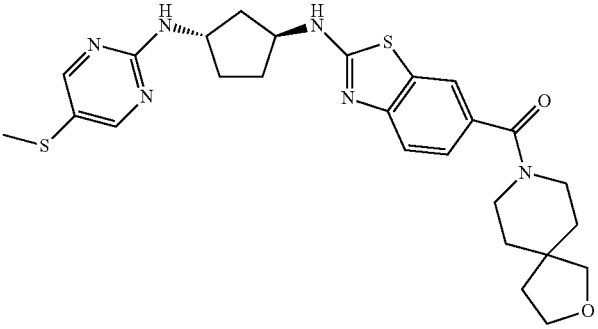 [SMILES: CSc1cnc(N[C@H]2CC[C@H](Nc3nc4ccc(C(=O)N5CCC6(CCOC6)CC5)cc4s3)C2)nc1] | 321 | ¹H NMR (400 MHz, DMSO-d₆) δ 8.34 (s, 2H), 8.29 (d, J = 6.7 Hz, 1H), 7.73 (s, 1H), 7.53 (d, J = 7.4 Hz, 1H), 7.37 (d, J = 8.2 Hz, 1H), 7.23 (d, J = 8.2 Hz, 1H), 4.40-4.27 (m, 2H), 3.74 (t, J = 7.2 Hz, 2H), 3.63-3.37 (m, 4H), 3.47 (s, 2H), 2.34 (s, 3H), 2.24-2.04 (m, 2H), 1.95 (t, J = 6.6 Hz, 2H), 1.74 (t, J = 7.1 Hz, 2H), 1.62-1.43 (m, 6H). | 487 |
| 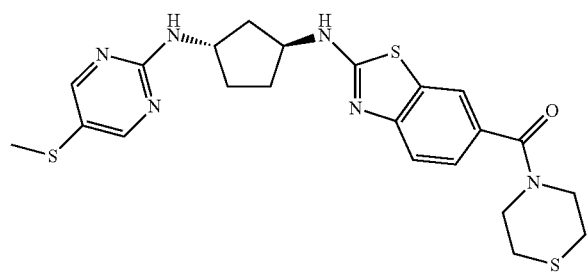 [SMILES: CSc1cnc(N[C@H]2CC[C@H](Nc3nc4ccc(C(=O)N5CCSCC5)cc4s3)C2)nc1] | 322 | ¹H NMR (400 MHz, DMSO-d₆) δ 8.34 (s, 2H), 8.31 (d, J = 6.9 Hz, 1H), 7.75 (s, 1H), 7.53 (d, J = 7.3 Hz, 1H), 7.38 (d, J = 8.2 Hz, 1H), 7.24 (d, J = 8.1 Hz, 1H), 4.34 (td, J = 6.9, 13.7 Hz, 2H), 3.72 (br. s., 4H), 2.63 (br. s., 4H), 2.34 (s, 3H), 2.24-2.05 (m, 2H), 1.95 (t, J = 6.6 Hz, 2H), 1.62-1.49 (m, 2H). | 519 |
| 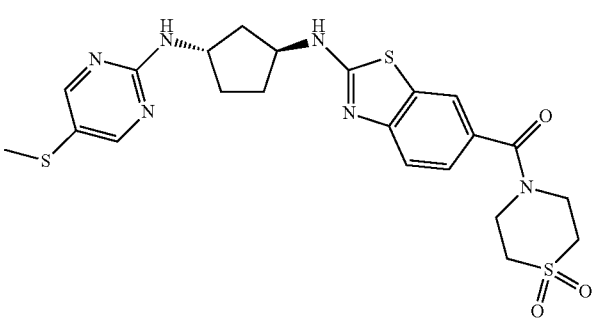 [SMILES: CSc1cnc(N[C@H]2CC[C@H](Nc3nc4ccc(C(=O)N5CCS(=O)(=O)CC5)cc4s3)C2)nc1] | 323 | ¹H NMR (400 MHz, DMSO-d₆) δ 8.35 (d, J = 6.7 Hz, 1H), 8.34 (s, 2H), 7.84 (s, 1H), 7.53 (d, J = 7.4 Hz, 1H), 7.43-7.32 (m, 2H), 4.39-4.30 (m, 2H), 3.88 (br s, 4H), 3.24 (br s, 4H), 2.34 (s, 3H), 2.25-2.05 (m, 2H), 1.95 (t, J = 6.6 Hz, 2H), 1.63-1.48 (m, 2H). | 511 |
| 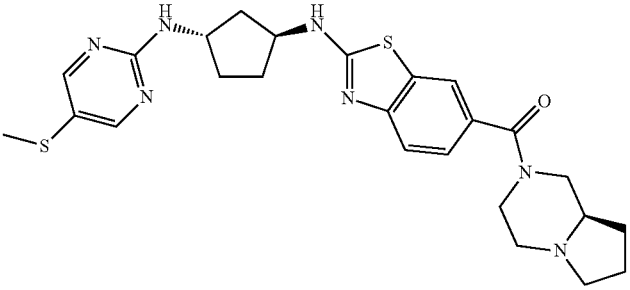 [SMILES: CSc1cnc(N[C@H]2CC[C@H](Nc3nc4ccc(C(=O)N5CCN6CCC[C@@H]6C5)cc4s3)C2)nc1] | 324 | ¹H NMR (400 MHz, DMSO-d₆) δ 8.34 (s, 2H), 8.30 (d, J = 6.7 Hz, 1H), 7.74 (d, J = 1.6 Hz, 1H), 7.53 (d, J = 7.3 Hz, 1H), 7.38 (d, J = 8.1 Hz, 1H), 7.23 (dd, J = 1.6, 8.3 Hz, 1H), 4.59-4.18 (m, 2H), 4.34 (td, J = 6.9, 13.7 Hz, 2H), 3.92-3.48 (m, 2H), 3.11-2.86 (m, 4H), 2.34 (s, 3H), 2.24-2.00 (m, 4H), 1.95 (t, J = 6.7 Hz, 2H), 1.89-1.80 (m, 1H), 1.76-1.50 (m, 4H). | 510 |

TABLE 31-continued

| Structure | Ex. # | ¹H NMR | LC-MS (M + H)⁺ |
|---|---|---|---|
| 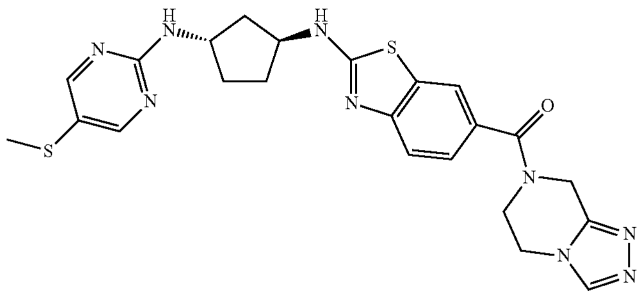 [SMILES: CSc1cnc(N[C@H]2CC[C@H](Nc3nc4ccc(C(=O)N5CCn6cnnc6C5)cc4s3)C2)nc1] | 325 | ¹H NMR (400 MHz, DMSO-d₆) δ 8.52 (s, 1H), 8.37 (d, J = 7.0 Hz, 1H), 8.34 (s, 2H), 7.87 (d, J = 1.3 Hz, 1H), 7.54 (d, J = 7.3 Hz, 1H), 7.42 (d, J = 8.3 Hz, 1H), 7.36 (dd, J = 1.7, 8.2 Hz, 1H), 4.87 (s, 2H), 4.41-4.30 (m, 2H), 4.15 (t, J = 5.4 Hz, 2H), 3.89 (br s, 2H), 2.34 (s, 3H), 2.25-2.06 (m, 2H), 1.96 (t, J = 6.7 Hz, 2H), 1.63-1.50 (m, 2H). | 508 |
| 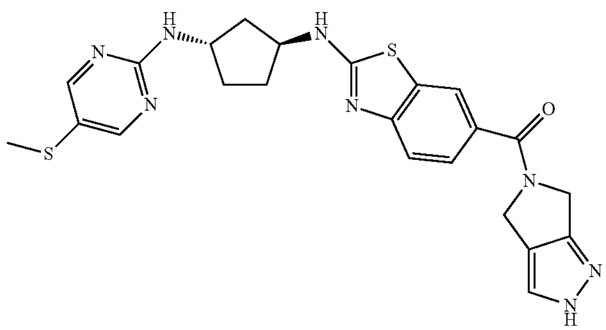 [SMILES: CSc1cnc(N[C@H]2CC[C@H](Nc3nc4ccc(C(=O)N5Cc6c[nH]nc6C5)cc4s3)C2)nc1] | 326 | ¹H NMR (400 MHz, DMSO-d₆) δ 12.71 (br s, 1H), 8.38-8.30 (m, 3H), 7.97 (d, J = 5.1 Hz, 1H), 7.60-7.44 (m, 3H), 7.42-7.37 (m, 1H), 4.61 (br s, 2H), 4.57 (br s, 2H), 4.40-4.31 (m, 2H), 2.35 (s, 3H), 2.25-2.06 (m, 2H), 1.96 (t, J = 6.7 Hz, 2 H), 1.63-1.51 (m, 2H). | 493 |
| 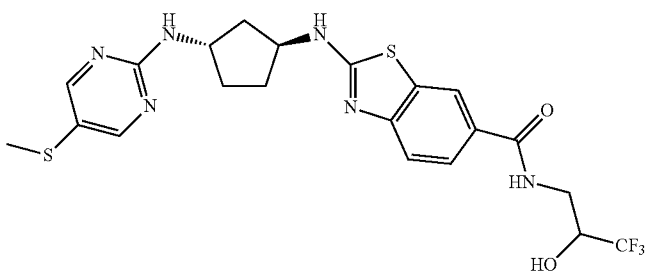 [SMILES: CSc1cnc(N[C@H]2CC[C@H](Nc3nc4ccc(C(=O)NCC(O)C(F)(F)F)cc4s3)C2)nc1] | 327 | ¹H NMR (400 MHz, DMSO-d₆) δ 8.57 (t, J = 5.6 Hz, 1H), 8.41 (d, J = 7.0 Hz, 1H), 8.34 (s, 2H), 8.18 (d, J = 1.6 Hz, 1H), 7.75 (dd, J = 1.7, 8.5 Hz, 1H), 7.54 (d, J = 7.3 Hz, 1H), 7.40 (d, J = 8.3 Hz, 1H), 6.48 (d, J = 6.4 Hz, 1H), 4.40-4.30 (m, 2H), 4.24-4.12 (m, 1H), 3.61 (td, J = 5.0, 13.3 Hz, 1H), 3.29-3.24 (m, 1H), 2.34 (s, 3H), 2.24-2.06 (m, 2H), 1.95 (t, J = 6.7 Hz, 2H), 1.63-1.51 (m, 2H). | 513 |
| 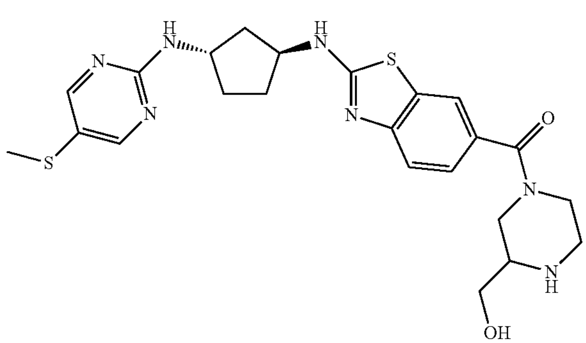 [SMILES: CSc1cnc(N[C@H]2CC[C@H](Nc3nc4ccc(C(=O)N5CCNC(CO)C5)cc4s3)C2)nc1] | 328 | ¹H NMR (400 MHz, DMSO-d₆) δ 8.34 (s, 2H), 8.30 (d, J = 7.0 Hz, 1H), 7.74-7.70 (m, 1H), 7.54 (d, J = 7.3 Hz, 1H), 7.37 (d, J = 8.3 Hz, 1H), 7.22 (dd, J = 1.6, 8.3 Hz, 1H), 4.63 (br s, 1H), 4.40-4.29 (m, 2H), 3.82-3.56 (m, 1H), 3.41-3.12 (m, 4H), 2.86 (br s, 2H), 2.63-2.53 (m, 2H), 2.34 (s, 3H), 2.24-2.04 (m, 2H), 1.95 (t, J = 6.6 Hz, 2H), 1.62-1.49 (m, 2H). | 500 |

TABLE 31-continued

| Structure | Ex. # | ¹H NMR | LC-MS (M + H)⁺ |
|---|---|---|---|
| 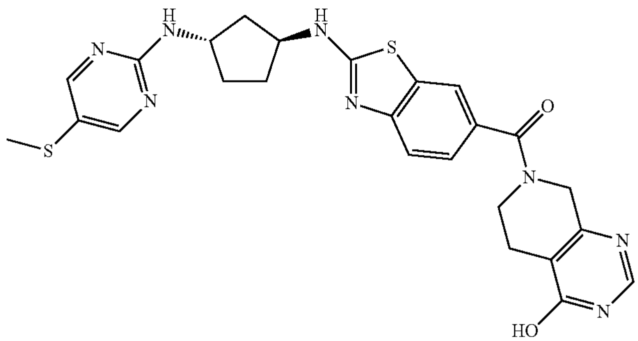 [SMILES: CSc1cnc(N[C@H]2CC[C@H](Nc3nc4ccc(C(=O)N5CCc6c(O)ncnc6C5)cc4s3)C2)nc1] | 329 | ¹H NMR (400 MHz, DMSO-d₆) δ 12.45 (br s, 1H), 8.34 (s, 2H), 8.34 (d, J = 7.0 Hz, 1H), 8.06 (br s, 1H), 7.82 (d, J = 1.5 Hz, 1H), 7.54 (d, J = 7.4 Hz, 1H), 7.40 (d, J = 8.2 Hz, 1H), 7.31 (dd, J = 1.7, 8.3 Hz, 1H), 4.43 (br s, 2H), 4.39-4.31 (m, 2H), 3.65 (br s, 2H), 3.30 (br s, 2H), 2.34 (s, 3H), 2.25-2.06 (m, 2H), 1.96 (t, J = 6.7 Hz, 2H), 1.63-1.50 (m, 2H). | 535 |
| 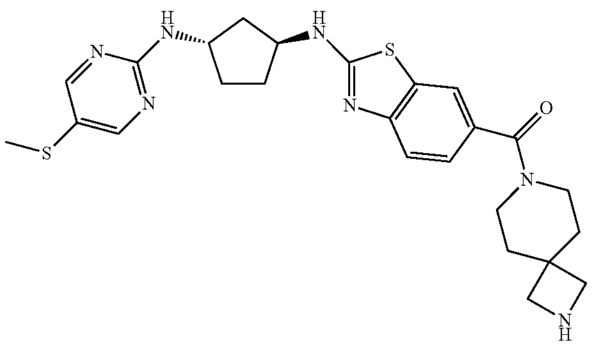 [SMILES: CSc1cnc(N[C@H]2CC[C@H](Nc3nc4ccc(C(=O)N5CCC6(CC5)CNC6)cc4s3)C2)nc1] | 330 | ¹H NMR (400 MHz, DMSO-d₆) δ 8.34 (s, 2H), 8.30 (d, J = 6.7 Hz, 1H), 7.71 (d, J = 1.6 Hz, 1H), 7.54 (d, J = 7.3 Hz, 1H), 7.37 (d, J = 8.3 Hz, 1H), 7.21 (dd, J = 1.7, 8.2 Hz, 1H), 4.34 (td, J = 6.8, 13.8 Hz, 2H), 3.37 (br s, 4H), 3.23 (br s, 4H), 2.34 (s, 3H), 2.23-2.05 (m, 2H), 1.95 (t, J = 6.7 Hz, 2H), 1.68 (br s, 4H), 1.60-1.50 (m, 2H). | 510 |
| 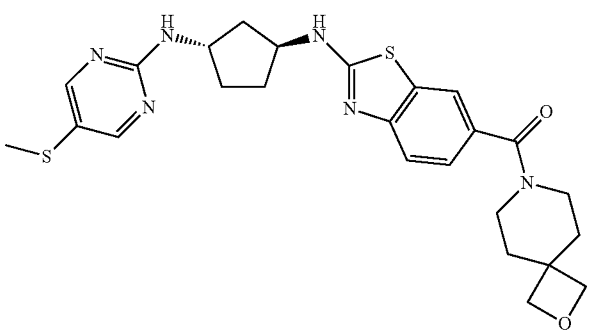 [SMILES: CSc1cnc(N[C@H]2CC[C@H](Nc3nc4ccc(C(=O)N5CCC6(CC5)COC6)cc4s3)C2)nc1] | 331 | ¹H NMR (400 MHz, DMSO-d₆) δ 8.35 (s, 2H), 8.31 (d, J = 6.8 Hz, 1H), 7.72 (d, J = 1.6 Hz, 1H), 7.54 (d, J = 7.2 Hz, 1H), 7.38 (d, J = 8.0 Hz, 1H), 7.22 (dd, J = 8.0, 1.6 Hz, 1H), 4.34 (s, 6H), 3.40 (br s, 4H), 2.35 (s, 3H), 2.24-2.08 (m, 2H), 1.96 (t, J = 6.8 Hz, 2H), 1.80 (br s, 4H), 1.60-1.54 (m, 2H). | 511 |
| 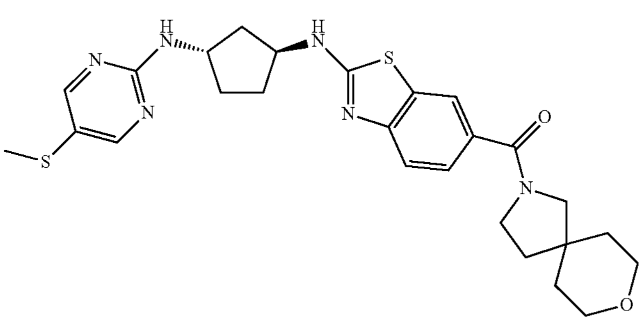 [SMILES: CSc1cnc(N[C@H]2CC[C@H](Nc3nc4ccc(C(=O)N5CCC6(CCOCC6)C5)cc4s3)C2)nc1] | 332 | ¹H NMR (400 MHz, DMSO-d₆) δ 8.35 (s, 2H), 8.32 (d, J = 6.8 Hz, 1H), 7.89 (d, J = 14.8 Hz, 1H), 7.54 (d, J = 7.2 Hz, 1H), 7.38 (s, 2H), 4.41-4.32 (m, 2H), 3.66-3.49 (m, 5H), 3.48-3.35 (m, 3H), 2.35 (s, 3H), 2.24-2.08 (m, 2H), 1.96 (t, J = 6.8 Hz, 2H), 1.80 (d, J = 25.2 Hz, 2H), 1.62-1.52 (m, 4H), 1.43 (br s, 2H). | 515 |

TABLE 31-continued

| Structure | Ex. # | ¹H NMR | LC-MS (M + H)⁺ |
|---|---|---|---|
| 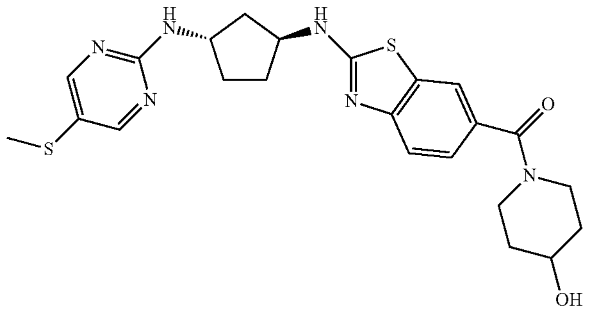 [SMILES: CSc1cnc(N[C@H]2CC[C@H](Nc3nc4ccc(C(=O)N5CCC(O)CC5)cc4s3)C2)nc1] | 333 | ¹H NMR (400 MHz, DMSO-d₆) δ 8.35 (s, 2H), 8.30 (d, J = 6.8 Hz, 1H), 7.73 (d, J = 1.6 Hz, 1H), 7.54 (d, J = 7.2 Hz, 1H), 7.38 (d, J = 8.4 Hz, 1H), 7.23 (dd, J = 8.4, 1.6 Hz, 1H), 4.78 (d, J = 3.2 Hz, 1H), 4.40-4.32 (m, 2H), 3.73 (d, J = 3.2 Hz, 2H), 3.21-3.14 (m, 3H), 2.35 (s, 3H), 2.24-2.07 (m, 2H), 1.96 (t, J = 6.8 Hz, 2H), 1.73 (br s, 2H), 1.60-1.54 (m, 2H), 1.35 (d, J = 8.4 Hz, 2H). | 485 |
| 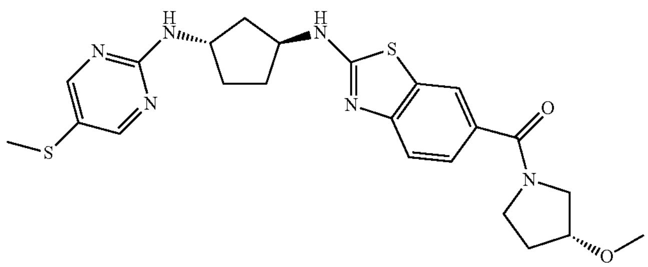 | 334 | ¹H NMR (400 MHz, DMSO-d₆) δ 8.35 (s, 2H), 8.33 (d, J = 6.8 Hz, 1H), 7.89 (br s, 1H), 7.54 (d, J = 7.2 Hz, 1H), 7.41-7.36 (m, 2H), 4.39-4.32 (m, 2H), 3.97 (d, J = 30 Hz, 1H), 3.68-3.42 (m, 3H), 3.27 (s, 2H), 3.16 (s, 2H), 2.35 (s, 3H), 2.24-2.08 (m, 2H), 1.96 (t, J = 6.8 Hz, 4H), 1.62-1.52 (m, 2H). | 485 |
| 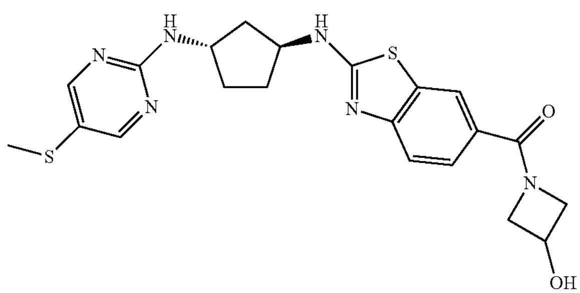 [SMILES: CSc1cnc(N[C@H]2CC[C@H](Nc3nc4ccc(C(=O)N5CC(O)C5)cc4s3)C2)nc1] | 335 | ¹H NMR (400 MHz, DMSO-d₆) δ 8.38 (d, J = 6.8 Hz, 1H), 8.35 (s, 2H), 7.98 (d, J = .6 Hz, 1H), 7.54-7.48 (m, 2H), 7.37 (d, J = 8.4 Hz, 1H), 5.72 (br s, 1H), 4.49 (br s, 2H), 4.39-4.34 (m, 2H), 4.28-4.19 (m, 1H), 4.06-4.01 (m, 1H), 3.84-3.74 (m, 1H), 2.35 (s, 3H), 2.25-2.07 (m, 2H), 1.96 (t, J = 6.8 Hz, 2H), 1.60-1.52 (m, 2H). | 457 |
| 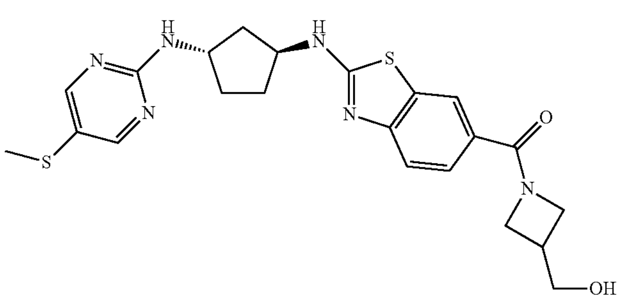 [SMILES: CSc1cnc(N[C@H]2CC[C@H](Nc3nc4ccc(C(=O)N5CC(CO)C5)cc4s3)C2)nc1] | 336 | ¹H NMR (400 MHz, DMSO-d₆) δ 8.38 (d, J = 7.2 Hz, 1H), 8.35 (s, 2H), 7.98 (d, J = 1.6 Hz, 1H), 7.55-7.48 (m, 2H), 7.37 (d, J = 8.4 Hz, 1H), 4.80 (t, J = 6.8 Hz, 1H), 4.38-4.30 (m, 3H), 4.03 (d, J = 6.4 Hz, 2H), 3.78-3.73 (m, 1H), 3.54 (t, J = 5.6 Hz, 2H), 2.35 (s, 3H), 2.24-2.07 (m, 2H), 2.03-1.94 (m, 3H), 1.58-1.53 (m, 2H). | 471 |

TABLE 31-continued

| Structure | Ex. # | ¹H NMR | LC-MS (M + H)⁺ |
|---|---|---|---|
| 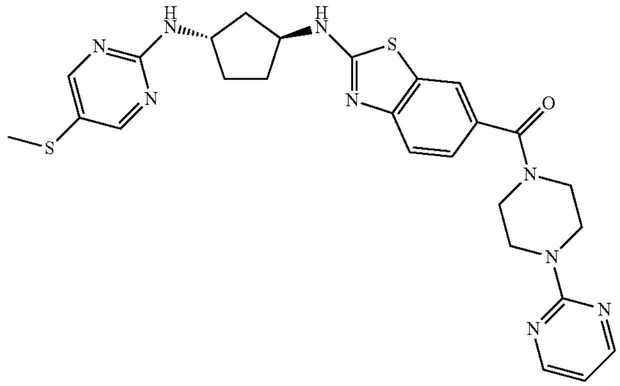 [SMILES: CSc1cnc(N[C@H]2CC[C@H](Nc3nc4ccc(C(=O)N5CCN(c6ncccn6)CC5)cc4s3)C2)nc1] | 337 | ¹H NMR (400 MHz, DMSO-d₆) δ 8.38 (d, J = 8.4 Hz, 2H), 8.34 (s, 2H), 8.32 (s, 1H), 7.80 (s, 1H), 7.53 (d, J = 7.2 Hz, 1H), 7.40 (d, J = 8.0 Hz, 1H), 7.31 (d, J = 8.4 Hz, 1H), 6.66 (t, J = 4.8 Hz, 1H), 4.36 (q, J = 13.2, 6.4 Hz, 2H), 3.79 (s, 4H), 3.58 (br s, 4H), 2.35 (s, 3H), 2.24-2.07 (m, 2H), 1.96 (t, J = 6.8 Hz, 2H), 1.58-1.53 (m, 2H). | 548 |
| 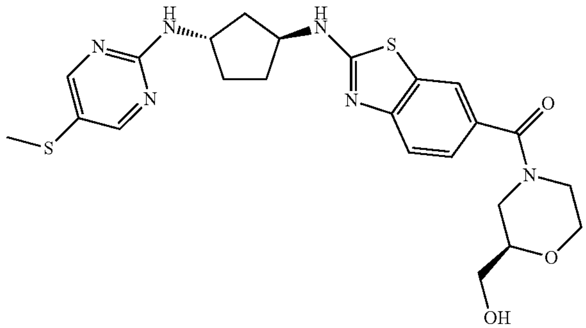 [SMILES: CSc1cnc(N[C@H]2CC[C@H](Nc3nc4ccc(C(=O)N5CCO[C@@H](CO)C5)cc4s3)C2)nc1] | 338 | ¹H NMR (400 MHz, DMSO-d₆) δ 8.34 (s, 2H), 8.32 (d, J = 6.8 Hz, 1H), 7.76 (s, 1H), 7.53 (d, J = 7.2 Hz, 1H), 7.38 (d, J = 7.2 Hz, 1H), 7.26 (d, J = 8.4 Hz, 1H), 4.76 (br s, 1H), 4.35 (q, J = 13.6, 7.2 Hz, 2H), 3.84-3.82 (m, 1H), 3.49-3.33 (m, 4H), 3.29-2.58 (m, 4H), 2.35 (s, 3H), 2.23-2.07 (m, 2H), 1.96 (t, J = 6.8 Hz, 2H), 1.61-1.53 (m, 2H). | 501 |
| 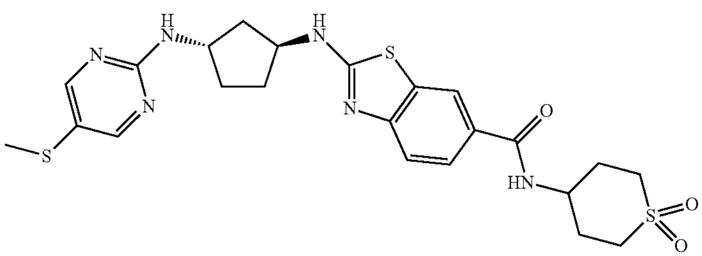 [SMILES: CSc1cnc(N[C@H]2CC[C@H](Nc3nc4ccc(C(=O)NC5CCS(=O)(=O)CC5)cc4s3)C2)nc1] | 339 | ¹H NMR (400 MHz, DMSO-d₆) δ 8.41 (d, J = 6.8 Hz, 1H), 8.35 (s, 2H), 8.29 (d, J = 7.6 Hz, 1H), 8.18 (d, J = 2.0 Hz, 1H), 7.75 (dd, J = 8.4, 2.0 Hz, 1H), 7.55 (d, J = 7.2 Hz, 1H), 7.39 (d, J = 8.4 Hz, 1H), 4.36 (q, J = 13.6, 6.8 Hz, 2H), 4.21-4.17 (m, 1H), 3.30-3.24 (m, 2H), 3.14 (d, J = 12.8 Hz, 2H), 2.35 (s, 3H), 2.23-2.06 (m, 6H), 1.96 (t, J = 6.8 Hz, 2H), 1.60-1.54 (m, 2H). | 533 |
| 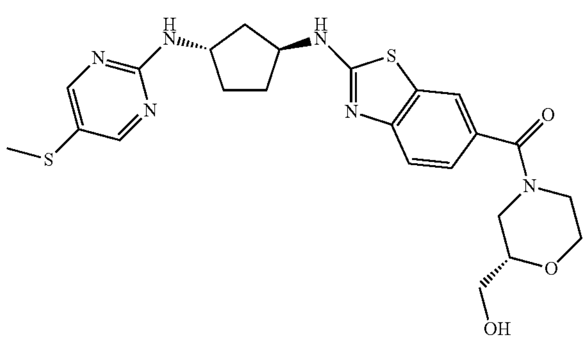 [SMILES: CSc1cnc(N[C@H]2CC[C@H](Nc3nc4ccc(C(=O)N5CCO[C@H](CO)C5)cc4s3)C2)nc1] | 340 | ¹H NMR (400 MHz, DMSO-d₆) δ 8.23 (s, 2H), 7.62 (s, 1H), 7.37 (d, J = 8.4 Hz, 1H), 7.25 (d, J = 8.4 Hz, 1H), 4.35-4.27 (m, 2H), 4.03-3.82 (m, 1H), 3.55-3.37 (m, 4H), 2.25 (s, 3H), 2.23-2.07 (m, 2H), 1.98 (t, J = 7.2 Hz, 2H), 1.63-1.51 (m, 2H), 1.25-1.12 (m, 4H). | 501 |

TABLE 31-continued

| Structure | Ex. # | ¹H NMR | LC-MS (M + H)⁺ |
|---|---|---|---|
| 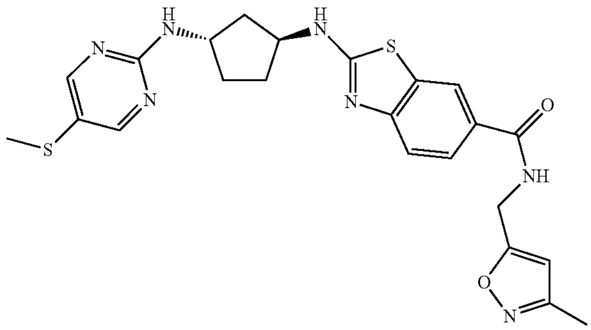 | 341 | ¹H NMR (400 MHz, DMSO-d₆) δ 9.00 (t, J = 5.6 Hz, 1H), 8.42 (d, J = 6.8 Hz, 1H), 8.34 (s, 2H), 8.19 (s, 1H), 7.76 (d, J = 8.8 Hz, 1H), 7.54 (d, J = 7.2 Hz, 1H), 7.40 (d, J = 8.4 Hz, 1H), 6.20 (s, 1H), 4.53 (d, J = 5.6 Hz, 2H), 4.36 (t, J = 6.4 Hz, 2H), 2.34 (s, 3H), 2.23-2.06 (m, 2H), 2.19 (s, 3H), 1.95 (t, J = 6.8 Hz, 2H), 1.57-1.53 (m, 2H). | 496 |
| 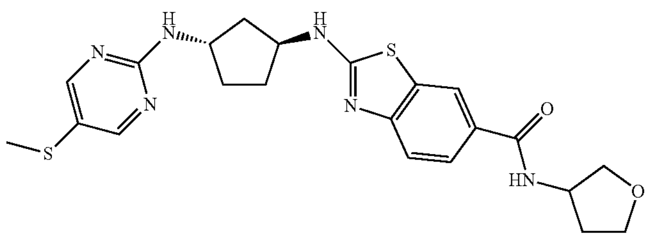 [SMILES: CSc1cnc(N[C@H]2CC[C@H](Nc3nc4ccc(C(=O)NC5CCOC5)cc4s3)C2)nc1] | 342 | ¹H NMR (400 MHz, DMSO-d₆) δ 8.39-8.71 (m, 1H), 8.34 (s, 2H), 8.18 (s, 1H), 7.75 (d, J = 8.4 Hz, 1H), 7.54 (d, J = 7.2 Hz, 1H), 7.43-7.37 (m, 2H), 4.45-4.33 (m, 3H), 3.87-3.82 (m, 2H), 3.71 (q, J = 14.0, 8.0 Hz, 1H), 3.57 (q, J = 8.8, 4.0 Hz, 1H), 2.34 (s, 3H), 2.22-2.07 (m, 3H), 2.01-1.89 (m, 3H), 1.59-1.53 (m, 2H). | 471 |
| 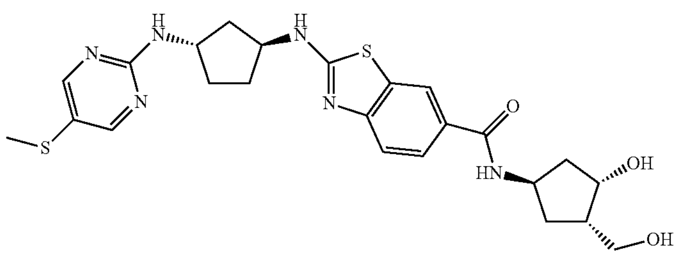 [SMILES: CSc1cnc(N[C@H]2CC[C@H](Nc3nc4ccc(C(=O)N[C@@H]5C[C@@H](CO)[C@@H](O)C5)cc4s3)C2)nc1] | 343 | ¹H NMR (400 MHz, DMSO-d₆) δ 8.36 (d, J = 7.2 Hz, 1H), 8.34 (s, 2H), 8.20-8.14 (m, 2H), 7.72 (d, J = 8.4 Hz, 1H), 7.54 (d, J = 7.2 Hz, 1H), 7.37 (d, J = 8.0 Hz, 1H), 4.49-4.45 (m, 1H), 4.38-4.31 (m, 3H), 4.25 (t, J = 5.2 Hz, 1H), 4.18 (d, J = 4.4 Hz, 1H), 3.58-3.53 (m, 1H), 3.39-3.35 (m, 1H), 2.34 (s, 3H), 2.22-2.07 (m, 3H), 1.95 (d, J = 6.8 Hz, 3H), 1.79-1.70 (m, 2H), 1.61-1.55 (m, 3H). | 515 |
| 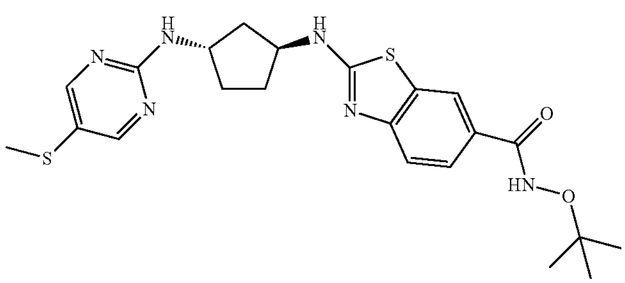 [SMILES: CSc1cnc(N[C@H]2CC[C@H](Nc3nc4ccc(C(=O)NOC(C)(C)C)cc4s3)C2)nc1] | 344 | ¹H NMR (400 MHz, DMSO-d₆) δ 10.81 (s, 1H), 8.41 (d, J = 7.2 Hz, 1H), 8.35 (s, 2H), 8.09 (d, J = 1.6 Hz, 1H), 7.65 (dd, J = 8.0, 1.6 Hz, 1H), 7.55 (d, J = 7.6 Hz, 1H), 7.40 (d, J = 8.8 Hz, 1H), 4.40-4.33 (m, 2H), 2.35 (s, 3H), 2.24-2.06 (m, 2H), 1.96 (d, J = 6.8 Hz, 2H), 1.76-1.52 (m, 2H), 1.24 (s, 9H). | 473 |

TABLE 31-continued

| Structure | Ex. # | ¹H NMR | LC-MS (M + H)⁺ |
|---|---|---|---|
| 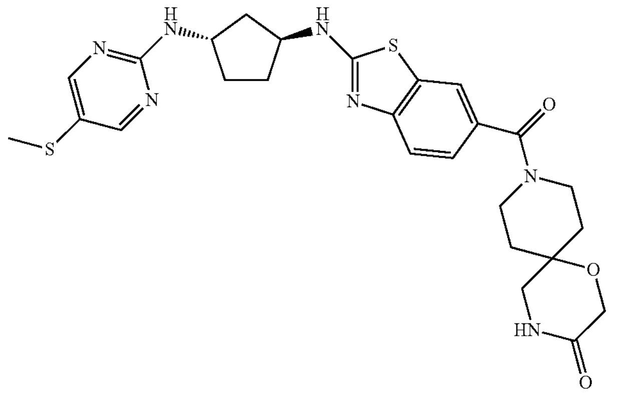 [SMILES: CSc1cnc(N[C@H]2CC[C@H](Nc3nc4ccc(C(=O)N5CCC6(CC5)CNC(=O)CO6)cc4s3)C2)nc1] | 345 | ¹H NMR (400 MHz, DMSO-d₆) δ 8.35 (s, 2H), 8.31 (d, J = 6.8 Hz, 1H), 7.99 (s, 1H), 7.75 (d, J = 1.6 Hz, 1H), 7.55 (d, J = 7.2 Hz, 1H), 7.38 (d, J = 8.0 Hz, 1H), 7.26 (dd, J = 8.4, 1.6 Hz, 1H), 4.38-4.32 (m, 2H), 4.01 (s, 1H), 3.31 (s, 2H), 3.13 (d, J = 2.4 Hz, 1H), 2.68 (t, J = 2.0 Hz, 1H), 2.68-2.51 (m, 3H), 2.35 (s, 3H), 2.23-2.06 (m, 2H), 1.96 (d, J = 6.8 Hz, 2H), 1.85-1.78 (m, 2H), 1.63-1.54 (m, 4H). | 554 |
| 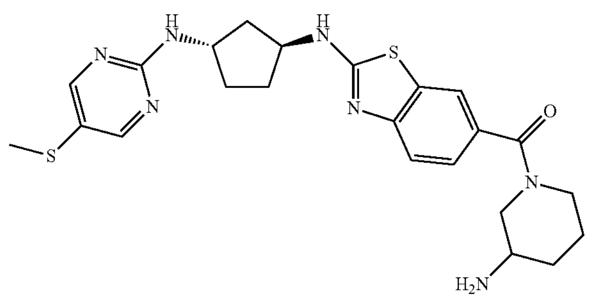 [SMILES: CSc1cnc(N[C@H]2CC[C@H](Nc3nc4ccc(C(=O)N5CCCC(N)C5)cc4s3)C2)nc1] | 346 | ¹H NMR (400 MHz, DMSO-d₆) δ 8.35 (s, 2H), 8.30 (d, J = 6.4 Hz, 1H), 7.72 (d, J = 1.6 Hz, 1H), 7.55 (d, J = 7.2 Hz, 1H), 7.37 (d, J = 8.0 Hz, 1H), 7.23 (dd, J = 8.0, 1.6 Hz, 1H), 4.38-4.32 (m, 2H), 2.89-2.56 (m, 4H), 2.49-2.44 (m, 2H), 2.35 (s, 3H), 2.34-2.32 (m, 1H), 2.23-2.06 (m, 4H), 1.96 (d, J = 6.8 Hz, 2H), 1.86-1.78 (m, 2H), 1.62-1.53 (m, 2H). | 484 |
| 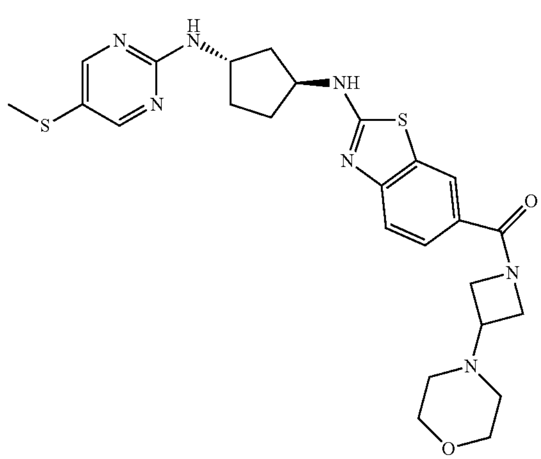 [SMILES: CSc1cnc(N[C@H]2CC[C@H](Nc3nc4ccc(C(=O)N5CC(N6CCOCC6)C5)cc4s3)C2)nc1] | 347 | ¹H NMR (400 MHz, DMSO-d₆) δ 8.36 (s, 2H), 7.96 (d, J = 2.0 Hz, 1H), 7.60 (dd, J = 8.4, 1.6 Hz, 1H). 7.47 (d, J = 8.4 Hz, 1H), 4.46-4.42 (m, 3H), 4.30-4.22 (m, 3H), 4.07-4.04 (m, 1H), 3.74 (t, J = 8.8 Hz, 4H), 3.32-3.26 (m, 1H), 2.45 (s, 3H), 2.37 (s, 3H), 2.36-2.25 (m, 2H), 2.12-2.09 (m, 2H), 1.74-1.71 (m, 2H). | 526 |

TABLE 31-continued

| Structure | Ex. # | ¹H NMR | LC-MS (M + H)⁺ |
|---|---|---|---|
| 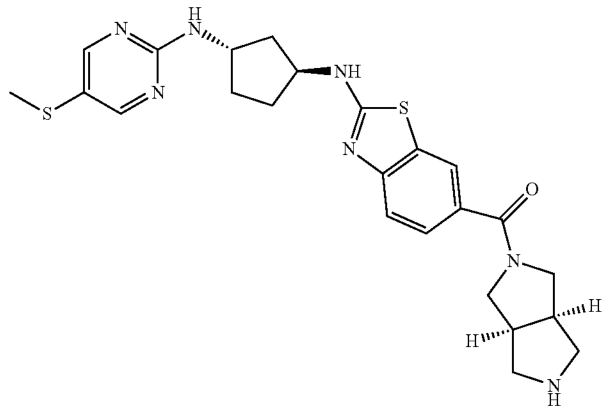 [SMILES: CSc1cnc(N[C@H]2CC[C@H](Nc3nc4ccc(C(=O)N5C[C@H]6CNC[C@H]6C5)cc4s3)C2)nc1] | 348 | ¹H NMR (400 MHz, DMSO-d₆) δ 8.44 (s, 2H), 7.96 (d, J = 2.0 Hz, 1H), 7.60 (dd, J = 8.4, 1.6 Hz, 1H). 7.54 (d, J = 8.4 Hz, 1H), 4.46-4.42 (m, 3H), 4.30-4.22 (m, 3H), 4.07-4.04 (m, 1H), 3.64 (t, J = 8.4 Hz, 4H), 3.25 (s, 3H), 2.40 (s, 3H), 2.37 (m, 1H), 2.35-2.27 (m, 2H), 2.25-2.22 (m, 2H), 1.87-1.73 (m, 2H). | 496 |
| 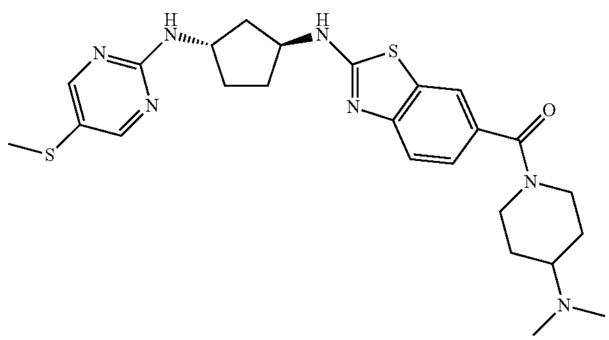 | 349 | ¹H NMR (400 MHz, DMSO-d₆) δ 8.38-8.25 (m, 3H), 7.75 (d, J = 1.34 Hz, 1H), 7.53 (d, J = 7.25 Hz, 1H), 7.38 (d, J = 8.19 Hz, 1H), 7.25 (dd, J = 8.19, 1.48 Hz, 1H), 4.35 (dt, J = 13.57, 6.65 Hz, 2H), 2.92 (d, J = 15.58 Hz, 3H), 2.43 (br s, 5H), 2.35 (s, 3H), 2.24-2.15 (m, 1H), 2.15-2.05 (m, 1H), 1.96 (t, J = 6.72 Hz, 2H), 1.87 (br s, 2H), 1.62-1.40 (m, 4H). | 512 |
| 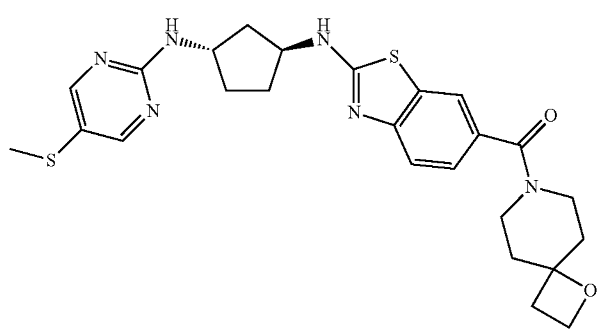 [SMILES: CSc1cnc(N[C@H]2CC[C@H](Nc3nc4ccc(C(=O)N5CCC6(CCO6)CC5)cc4s3)C2)nc1] | 350 | ¹H NMR (400 MHz, DMSO-d₆) δ 8.45-8.18 (m, 3H), 7.75 (d, J = 1.61 Hz, 1H), 7.54 (d, J = 7.25 Hz, 1H), 7.38 (d, J = 8.33 Hz, 1H), 7.24 (dd, J = 8.19, 1.75 Hz, 1H), 4.48-4.30 (m, 4H), 4.35 (dt, J = 13.57, 6.65 Hz, 2H), 2.92 (d, J = 15.58 Hz, 3H), 2.43 (br s, 5H), 2.42-2.29 (m, 5H), 2.24-2.15 (m, 1H), 2.15-2.05 (m, 1H), 2.02-1.96 (m, 3H), 1.80 (br s, 4H), 1.61-1.40 (m, 2H). | 511 |

TABLE 31-continued

| Structure | Ex. # | ¹H NMR | LC-MS (M + H)⁺ |
|---|---|---|---|
| 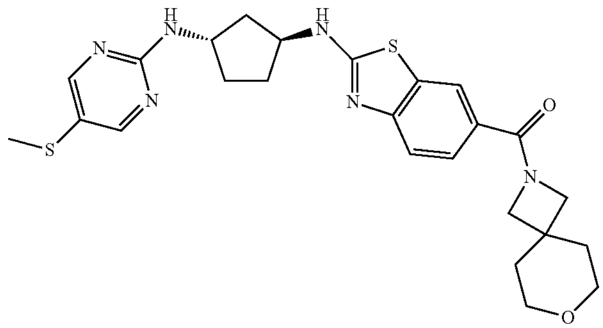 [SMILES: CSc1cnc(N[C@H]2CC[C@H](Nc3nc4ccc(C(=O)N5CC6(CCOCC6)C5)cc4s3)C2)nc1] | 351 | ¹H NMR (400 MHz, DMSO-d₆) δ 8.45-8.26 (m, 3H), 8.02 (d, J = 1.61 Hz, 1H), 7.60-7.48 (m, 2H), 7.38 (d, J = 8.33 Hz, 1H), 4.42-4.30 (m, 2H), 4.11 (br s, 2H), 3.78 (br s, 2H), 3.52 (d, J = 16.39 Hz, 4H), 2.36 (s, 3H), 2.20 (d, J = 5.10 Hz, 1H), 2.12 (d, J = 6.98 Hz, 1H), 1.96 (t, J = 6.72 Hz, 2H), 1.71 (t, J = 5.10 Hz, 4H), 1.62-1.52 (m, 2H). | 511 |
| 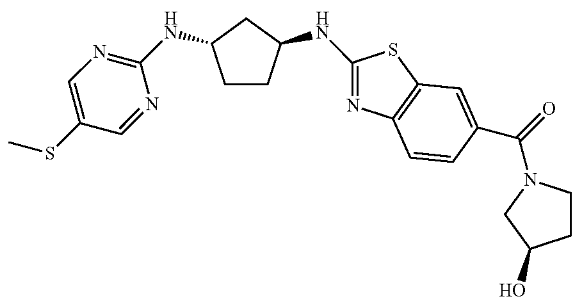 [SMILES: CSc1cnc(N[C@H]2CC[C@H](Nc3nc4ccc(C(=O)N5CC[C@@H](O)C5)cc4s3)C2)nc1] | 352 | ¹H NMR (400 MHz, DMSO-d₆) δ 8.45-8.22 (m, 3 H), 7.87 (br s, 1H), 7.53 (d, J = 7.25 Hz, 1H), 7.43-7.32 (m, 2H), 4.91 (br s, 1H), 4.46-4.27 (m, 2H), 4.23 (br s, 1H), 3.68-3.14 (m, 3H), 3.33-3.24 (m, 1H), 2.35 (s, 3H), 2.05-2.24 (m, 2H), 1.96 (t, J = 6.72 Hz, 3H), 1.79 (br s, 1H), 1.62-1.47 (m, 2H). | 471 |
| 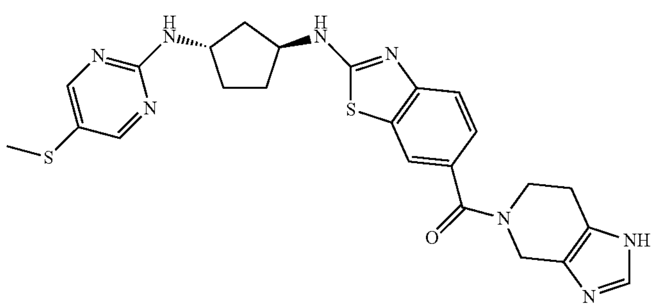 [SMILES: CSc1cnc(N[C@H]2CC[C@H](Nc3nc4ccc(C(=O)N5CCc6[nH]cnc6C5)cc4s3)C2)nc1] | 353 | ¹H NMR (400 MHz, DMSO-d₆) δ 11.91 (br s, 1H), 8.41-8.26 (m, 3H), 7.81 (s, 1H), 7.55 (d, J = 7.25 Hz, 1H), 7.50 (br s, 1H), 7.41 (d, J = 8.33 Hz, 1H), 7.34-7.26 (m, 1H), 4.52 (d, J = 40 Hz, 2H), 4.41-4.29 (m, 2H), 3.70 (br s, 2H), 2.70 (br s, 2H), 2.62 (br s, 1H), 2.36 (s, 3H), 2.26-2.16 (m, 1H), 2.15-2.07 (m, 1H), 1.97 (t, J = 6.72 Hz, 2H), 1.64-1.51 (m, 2H). | 507 |
| 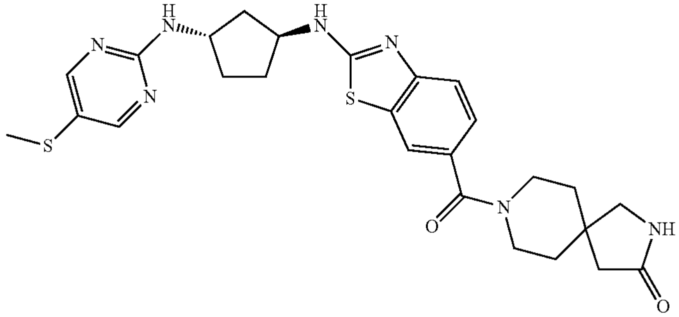 [SMILES: CSc1cnc(N[C@H]2CC[C@H](Nc3nc4ccc(C(=O)N5CCC6(CC5)CNC(=O)C6)cc4s3)C2)nc1] | 354 | ¹H NMR (400 MHz, DMSO-d6) δ 8.38-8.25 (m, 3H), 7.75 (d, J = 1.34 Hz, 1H), 7.53 (d, J = 7.25 Hz, 1H), 7.38 (d, J = 8.19 Hz, 1H), 7.25 (dd, J = 8.19, 1.48 Hz, 1H), 4.35 (dt, J = 13.57, 6.65 Hz, 2H), 2.92 (d, J = 15.58 Hz, 3H), 2.43 (br s, 5H), 2.35 (s, 3H), 2.15-2.24 (m, 1H), 2.05-2.15 (m, 1H), 1.96 (t, J = 6.72 Hz, 2H), 1.87 (br s, 2H), 1.40-1.62 (m, 4H). | 538 |

TABLE 31-continued

| Structure | Ex. # | ¹H NMR | LC-MS (M + H)⁺ |
|---|---|---|---|
| 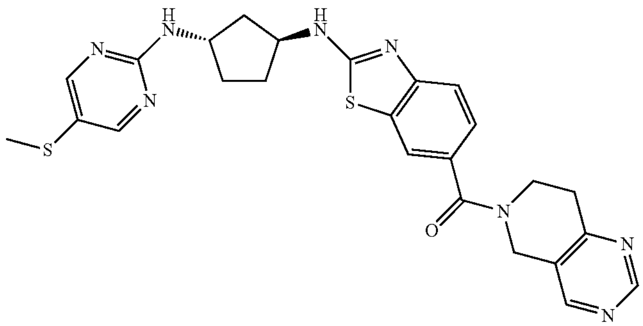 [SMILES: CSc1cnc(N[C@H]2CC[C@H](Nc3nc4ccc(C(=O)N5CCc6ncncc6C5)cc4s3)C2)nc1] | 355 | ¹H NMR (400 MHz, DMSO-d₆) δ 8.97 (s, 1H), 8.65 (br s, 1H), 8.47-8.47 (m, 1H), 7.86 (d, J = 1.34 Hz, 1H), 7.55 (d, J = 7.25 Hz, 1H), 7.42 (d, J = 8.06 Hz, 1H), 7.38-7.32 (m, 1H), 4.78 (s, 2H), 4.41-4.30 (m, 2H), 3.82 (br s, 2H), 3.04-2.93 (m, 2H), 2.36 (s, 3H), 2.26-2.16 (m, 1H), 2.15-2.07 (m, 1H), 1.97 (t, J = 6.72 Hz, 2H), 1.64-1.51 (m, 2H). | 519 |
| 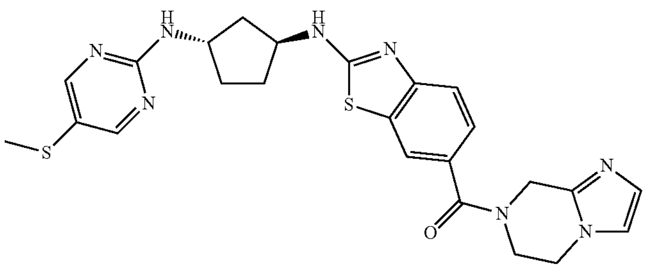 [SMILES: CSc1cnc(N[C@H]2CC[C@H](Nc3nc4ccc(C(=O)N5CCn6ccnc6C5)cc4s3)C2)nc1] | 356 | ¹H NMR (400 MHz, DMSO-d₆) δ 8.42-8.31 (m, 3H), 7.87 (d, J = 1.34 Hz, 1H), 7.55 (d, J = 7.52 Hz, 1H), 7.43 (d, J = 8.33 Hz, 1H), 7.36 (dd, J = 8.33, 1.88 Hz, 1H), 7.14 (s, 1H), 6.90 (s, 1H), 4.73 (s, 2H), 4.43-4.29 (m, 2H), 4.12-4.03 (m, 2H), 3.92 (br s, 2H), 2.36 (s, 3H), 2.26-2.16 (m, 1H), 2.15-2.07 (m, 1H), 1.97 (t, J = 6.72 Hz, 2H), 1.64-1.48 (m, 2H). | 507 |
| 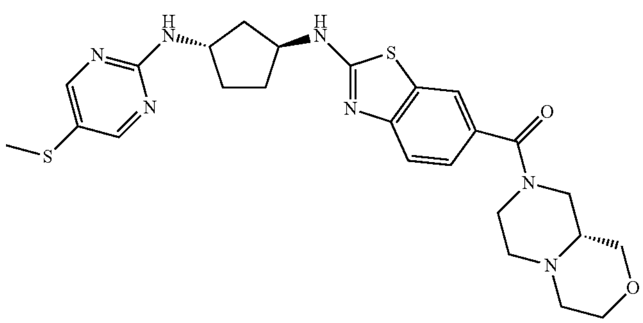 [SMILES: CSc1cnc(N[C@H]2CC[C@H](Nc3nc4ccc(C(=O)N5CCN6CCOC[C@H]6C5)cc4s3)C2)nc1] | 357 | ¹H NMR (400 MHz, CDCl3) δ 8.38 (s, 2H), 7.69-7.74 (m, 1H), 7.53 (d, J = 8.33 Hz, 1H), 7.35 (dd, J = 1.61, 8.33 Hz, 1H), 5.35 (d, J = 6.72 Hz, 1H), 4.42-4.53 (m, 1H), 4.32 (t, J = 6.18 Hz, 1H), 3.88 (d, J = 11.28 Hz, 1H), 3.74 (t, J = 10.61 Hz, 2H), 3.28 (br. s, 2H), 2.73 (d, J = 11.55 Hz, 3H), 2.32-2.49 (m, 8H), 2.07-2.22 (m, 3H), 1.59-1.72 (m, 3H). | 526 |
| 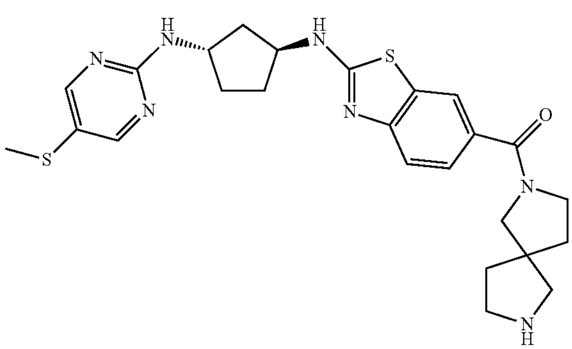 [SMILES: CSc1cnc(N[C@H]2CC[C@H](Nc3nc4ccc(C(=O)N5CCC6(CCNC6)C5)cc4s3)C2)nc1] | 358 | ¹H NMR (400 MHz, DMSO-d₆) δ 8.85 (br s, 1H), 8.42 (br s, 1H), 8.35 (s, 2H), 7.91 (d, J = 16.39 Hz, 1H), 7.55 (d, J = 6.18 Hz, 1H), 7.35-7.47 (m, 2H), 4.34 (d, J = 6.45 Hz, 2H), 3.38-3.55 (m, 4H), 3.31 (br s, 1H), 3.24 (br s, 1H), 3.17 (br s, 1H), 3.08 (br s, 1H), 2.35 (s, 3H), 2.06-2.25 (m, 2H), | 510 |

TABLE 31-continued
| Structure | Ex. # | ¹H NMR | LC-MS (M + H)⁺ |
|---|---|---|---|
| | | 1.96 (t, J = 6.45 Hz, 5H), 1.86 (br s, 1H), 1.50-1.63 (m, 2H). | |
| 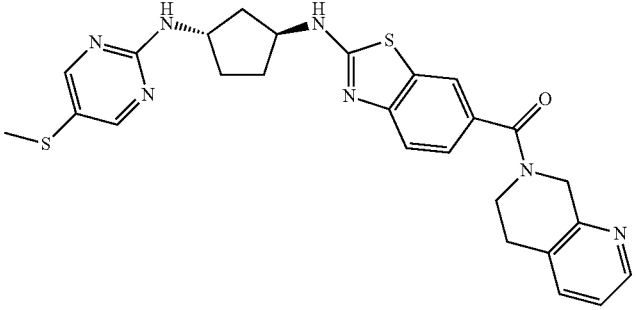 [SMILES: CSc1cnc(N[C@H]2CC[C@H](Nc3nc4ccc(C(=O)N5CCc6cccnc6C5)cc4s3)C2)nc1] | 359 | ¹H NMR (CDCl₃, 400 MHz) δ 8.49 (d, J = 4.03 Hz, 1H), 8.38 (s, 2H), 7.79 (d, J = 1.61 Hz, 1H), 7.59 (d, J = 8.33 Hz, 1H), 7.43-7.47 (m, 1H), 7.29 (s, 2H), 5.35 (d, J = 6.72 Hz, 1H), 4.87 (br s, 2H), 4.49 (d, J = 6.98 Hz, 1H), 4.32 (s, 1H), 3.94 (br s, 2H), 3.17 (t, J = 5.78 Hz, 2H), 2.37-2.47 (m, 5H), 2.18-2.26 (m, 2H), 1.67 (s, 1H). | 518 |
| 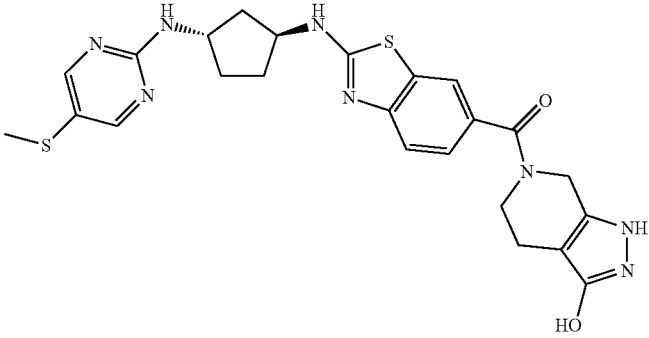 [SMILES: CSc1cnc(N[C@H]2CC[C@H](Nc3nc4ccc(C(=O)N5CCc6c(O)n[nH]c6C5)cc4s3)C2)nc1] | 360 | ¹H NMR (400 MHz, DMSO-d₆) δ 8.31-8.38 (m, 3H), 7.80 (d, J = 1.53 Hz, 1H), 7.54 (d, J = 7.32 Hz, 1H), 7.40 (d, J = 8.24 Hz, 1H), 7.29 (dd, J = 1.53, 8.24 Hz, 1H), 4.52 (br s, 2H), 4.30-4.42 (m, 2H), 2.41 (t, J = 5.49 Hz, 2H), 2.35 (s, 3H), 2.20 (d, J = 7.32 Hz, 1H), 2.11 (d, J = 7.02 Hz, 1H), 1.96 (t, J = 6.71 Hz, 2H), 1.57 (dd, J = 3.97, 7.02 Hz, 2H). | 523 |
| 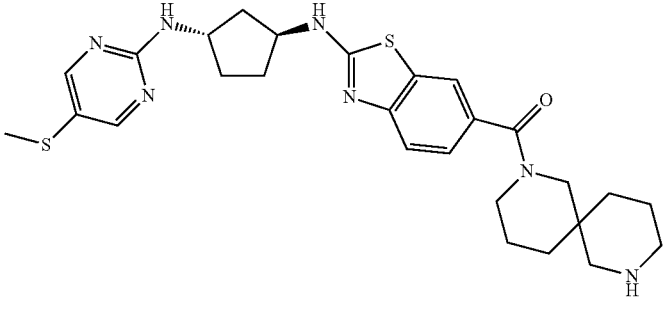 [SMILES: CSc1cnc(N[C@H]2CC[C@H](Nc3nc4ccc(C(=O)N5CCCC6(CCCNC6)C5)cc4s3)C2)nc1] | 361 | ¹H NMR (400 MHz, DMSO-d₆) δ 8.80 (br s, 1H), 8.54 (br s, 1H), 8.36 (s, 2H), 7.81 (br s, 1H), 7.62 (br s, 1H), 7.46 (d, J = 8.19 Hz, 1H), 7.31 (d, J = 7.66 Hz, 1H), 4.37 (d, J = 6.72 Hz, 2H), 3.69 (dd, J = 4.84, 13.03 Hz, 2H), 3.27 (br s, 2H), 2.92 (br s, 4H), 2.31-2.40 (m, 3H), 2.08-2.28 (m, 2H), 1.98-2.02 (m, 2H), 1.50-1.69 (m, 8H) | 510 |

TABLE 31-continued

| Structure | Ex. # | ¹H NMR | LC-MS (M + H)⁺ |
|---|---|---|---|
| 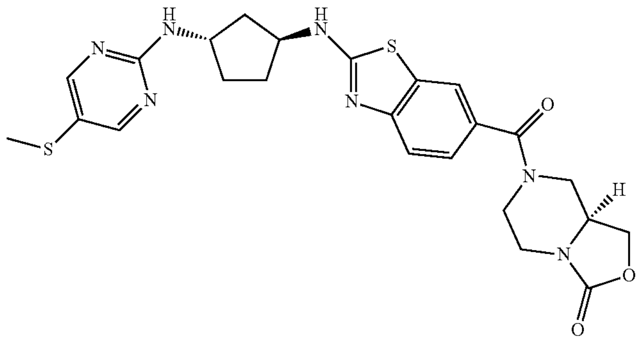 [SMILES: CSc1cnc(N[C@H]2CC[C@H](Nc3nc4ccc(C(=O)N5CCN6C(=O)OC[C@@H]6C5)cc4s3)C2)nc1] | 362 | ¹H NMR (400 MHz, CDCl3) δ 8.36 (s, 2H), 7.72 (s, 1H), 7.53 (d, J = 8.33 Hz, 1H), 7.34 (d, J = 8.19 Hz, 1H), 5.73 (br. s., 1H), 5.31 (d, J = 6.85 Hz, 1H), 4.40-4.50 (m, 2H), 4.24-4.33 (m, 1H), 3.98 (br s, 1H), 3.85 (d, J = 9.67 Hz, 2H), 2.99-3.15 (m, 2H), 2.86 (br s, 1H), 2.26-2.51 (m, 5H), 2.04-2.21 (m, 2H), 1.53-1.63 (m, 2H). | 526 |
| 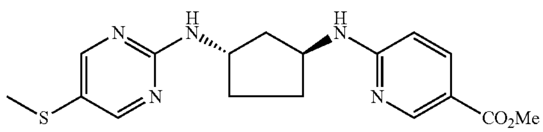 [SMILES: COC(=O)c1ccc(N[C@H]2CC[C@H](Nc3ncc(SC)cn3)C2)nc1] | 363 | ¹H NMR (400 MHz, DMSO-d₆) δ 8.50 (d, J = 1.88 Hz, 1H), 8.36 (s, 2 H), 8.22 (br s, 1H), 7.94 (d, J = 8.06 Hz, 1H), 7.56 (br s, 1H), 6.71 (d, J = 9.13 Hz, 1H), 4.35 (br s, 2H), 3.80 (s, 3 H) 2.36 (s, 3H), 2.24-2.04 (m, 2H), 1.02-1.86 (m, 2H), 1.66-1.45 (m, 2H). | 360 |
| 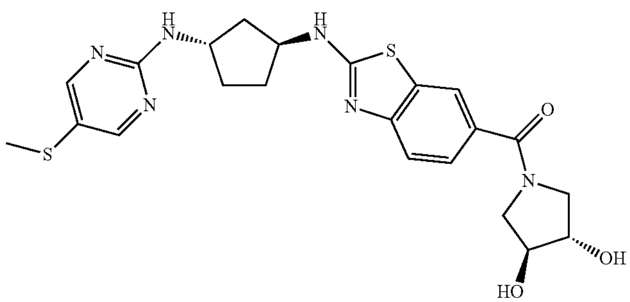 [SMILES: CSc1cnc(N[C@H]2CC[C@H](Nc3nc4ccc(C(=O)N5C[C@H](O)[C@@H](O)C5)cc4s3)C2)nc1] | 364 | ¹H NMR (DMSO-d₆, 400 MHz) δ 8.35 (s, 2H), 8.33 (d, J = 7.2 Hz, 1H), 7.89 (s, 1H), 7.55 (d, J = 7.2 Hz, 1H), 7.37 (d, J = 1.2 Hz, 2H), 5.19 (br m, 1H), 5.08 (br m, 1H), 4.39-4.33 (m, 2H), 3.97 (br m, 1H), 3.90 (br m, 1H), 3.78-3.76 (m, 1H), 3.70-3.65 (br m, 1H), 3.30-3.23 (m, 2H), 2.35 (s, 3H), 2.22-2.06 (m, 2H), 1.96 (t, J = 6.8 Hz, 2H), 1.61-1.54 (m, 2H). | 487 |
| 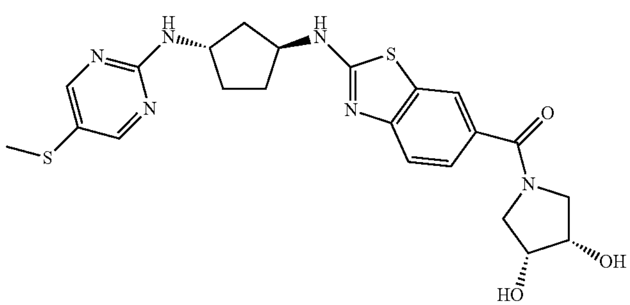 [SMILES: CSc1cnc(N[C@H]2CC[C@H](Nc3nc4ccc(C(=O)N5C[C@@H](O)[C@@H](O)C5)cc4s3)C2)nc1] | 365 | ¹H NMR (DMSO-d₆, 400 MHz) δ 8.35 (s, 2H), 8.33 (d, J = 7.2 Hz, 1H), 7.89 (s, 1H), 7.55 (d, J = 7.2 Hz, 1H), 7.37 (d, J = 1.2 Hz, 2H), 4.94 (br m, 2H), 4.39-4.33 (m, 2H), 4.09 (br m, 1H), 3.99 (br m, 1H), 3.60-3.56 (m, 2H), 2.35 (s, 3H), 2.22-2.06 (m, 2H), 1.96 (t, J = 6.8 Hz, 2H), 1.61-1.54 (m, 2H). | 487 |

TABLE 31-continued

| Structure | Ex. # | ¹H NMR | LC-MS (M + H)⁺ |
|---|---|---|---|
| 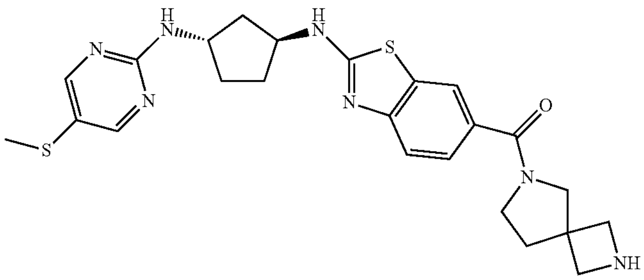 [SMILES: CSc1cnc(N[C@H]2CC[C@H](Nc3nc4ccc(C(=O)N5CCC6(CNC6)C5)cc4s3)C2)nc1] | 366 | ¹H NMR (400 MHz, DMSO-d₆ + D₂O) δ 8.35 (s, 2H), 7.91 (s, 1H), 7.44 (s, 2H), 4.40-4.33 (m, 2H), 4.5-4.02 (m, 2H), 3.90-3.85 (m, 3H), 3.74-3.72 (m, 2H), 3.52 (t, J = 6.8 Hz, 2H), 2.35 (s, 3H), 2.22-2.06 (m, 2H), 1.96 (t, J = 6.8 Hz, 2H), 1.61-1.54 (m, 2H). | 496 |
| 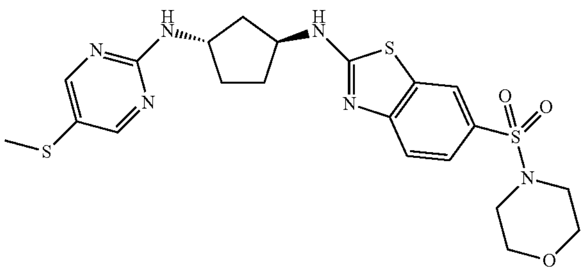 [SMILES: CSc1cnc(N[C@H]2CC[C@H](Nc3nc4ccc(S(=O)(=O)N5CCOCC5)cc4s3)C2)nc1] | 367 | ¹H NMR (DMSO-d₆, 400 MHz) δ 8.65 (d, J = 6.4 Hz, 2H), 8.35 (s, 2H), 8.13 (s, 1H), 7.7.56-7.53 (m, 3H), 4.40-4.33 (m, 2H), 3.63 (t, J = 4.4 Hz, 4H), 2.84 (t, J = 4.4 Hz, 4H), 2.35 (s, 3H), 2.22-2.06 (m, 2H), 1.96 (t, J = 6.8 Hz, 2H), 1.61-1.54 (m, 2H). | 507 |
| 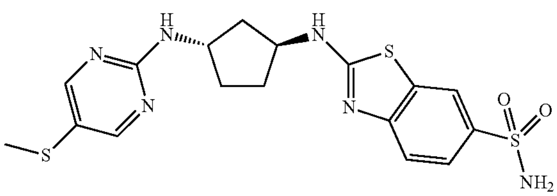 [SMILES: CSc1cnc(N[C@H]2CC[C@H](Nc3nc4ccc(S(N)(=O)=O)cc4s3)C2)nc1] | 368 | ¹H NMR (DMSO-d₆, 400 MHz) δ 8.52 (d, J = 7.2 Hz, 1H), 8.35 (s, 2H), 8.13 (d, J = 1.6 Hz, 1H), 7.66 (dd, J = 2.0, 2.0 Hz, 1H), 7.56 (d, J = 7.2 Hz, 1H), 7.47 (d, J = 8.8 Hz, 1H), 7.22 (br s, 2H), 4.40-4.33 (m, 2H), 2.35 (s, 3H), 2.22-2.06 (m, 2H), 1.96 (t, J = 6.8 Hz, 2H), 1.61-1.54 (m, 2H). | 437 |
| 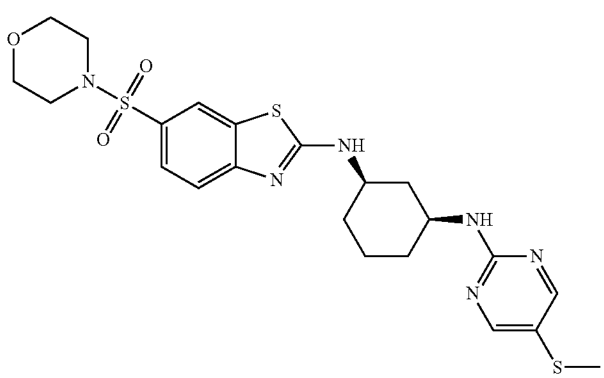 [SMILES: CSc1cnc(N[C@H]2CCC[C@@H](Nc3nc4ccc(S(=O)(=O)N5CCOCC5)cc4s3)C2)nc1] | 369 | ¹H NMR (400 MHz, DMSO-d₆) δ 8.63 (d, J = 7.32 Hz, 1H), 8.33 (s, 2H), 8.11 (s, 1H), 7.58-7.49 (m, 2H), 7.44 (d, J = 7.93 Hz, 1H), 4.29 (br s, 1H), 4.19-4.09 (m, 1H), 3.69-3.54 (m, 4H), 2.83 (br s, 4H), 2.34 (s, 3H), 1.90 (br s, 1H), 1.81 (d, J = 8.24 Hz, 2H), 1.67 (br s, 4H), 1.36 (br s, 1H), 1.23 (s, 1H). | 521 |

TABLE 31-continued

| Structure | Ex. # | ¹H NMR | LC-MS (M + H)⁺ |
|---|---|---|---|
| 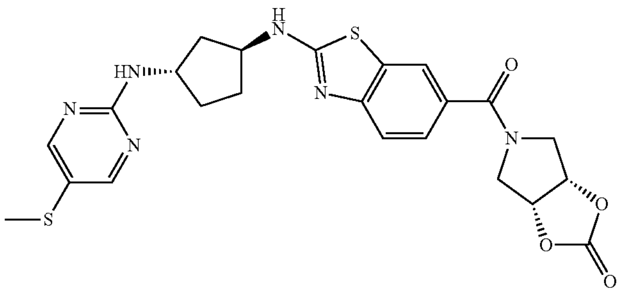 [SMILES: CSc1cnc(N[C@H]2CC[C@H](Nc3nc4ccc(C(=O)N5C[C@@H]6OC(=O)O[C@@H]6C5)cc4s3)C2)nc1] | 370 | ¹H NMR (400 MHz, CD₃OD) δ 8.54 (s, 2H), 8.01 (s, 1H), 7.69-7.62 (m, 2H), 5.52 (s, 2H), 4.64-4.59 (m, 2H), 3.88-3.84 (m, 2H), 2.57-2.44 (m, 5H), 2.31-2.24 (m, 2H), 1.92-1.83 (m, 2H), 1.56-1.49 (m, 4H). | 513 |

Scheme 51

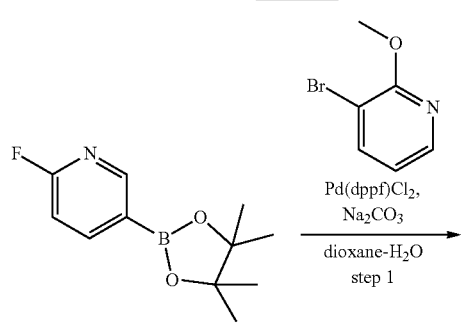

Step 1: Example 371A

The mixture of 2-fluoro-5-(4,4,5,5-tetramethyl-1,3,2-dioxaborolan-2-yl)pyridine (1.0 g, 4.5 mmol), 3-bromo-2-methoxypyridine (930 mg, 4.9 mmol), Pd(dppf)Cl₂ (320 mg, 0.45 mmol) and Na₂CO₃ (950 mg, 9.0 mmol) in dioxane: H₂O=4:1 (50 mL) was stirred at 110° C. under N₂ atmosphere overnight. The mixture was cooled to room temperature and water (50 mL) was added. The mixture was extracted with EtOAc (20 mL×3), and the combined organic layers were washed with brine (50 mL), dried over Na₂SO₄, filtered, concentrated; the residue was purified by chromatography on silica gel eluting with petroleum ether: EtOAc=5:1 to afford Example 371A (660 mg, 72%) as a white solid.

Step 2: Example 371

The mixture of (1S, 3S)-N1-(5-(methylthio)pyrimidin-2-yl)cyclopentane-1,3-diamine hydrochloride (100 mg, 0.38 mmol), Example 371A (86 mg, 0.42 mmol) and Cs₂CO₃ (376 mg, 1.15 mmol) in DMSO (5 mL) was stirred at 130° C. for 2 days. The mixture was cooled to room temperature and water (10 mL) was added. The mixture was extracted with EtOAc (10 mL×5), the combined organic layers were washed with brine (20 mL), dried over Na₂SO₄, filtered, concentrated. The residue was purified by prep-HPLC to afford Example 371 (10 mg, 6.4%). LCMS [M+H]⁺=409.

¹H NMR (400 MHz, CD₃OD) δ 8.41 (s, 2H), 8.20-8.17 (m, 2H), 8.09 (s, 1H), 7.82 (d, J=7.2 Hz, 1H), 7.13-7.07 (m, 2H), 4.51-4.49 (m, 1H), 4.29-4.27 (m, 1H), 3.99 (s, 1H), 2.41-2.33 (m, 2H), 2.38 (s, 3H), 2.19-2.15 (m, 2H), 1.78-1.75 (m, 1H).

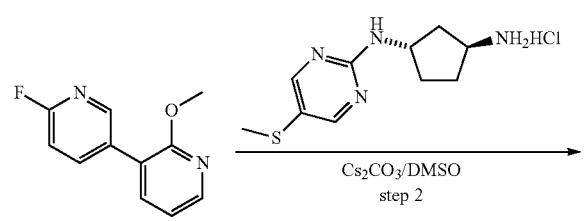

Example 371A

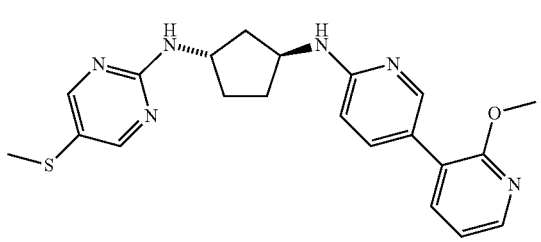

Example 371

Scheme 52

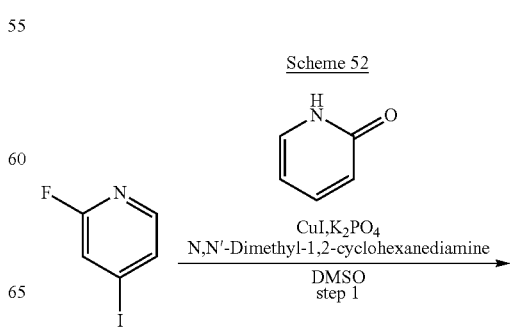

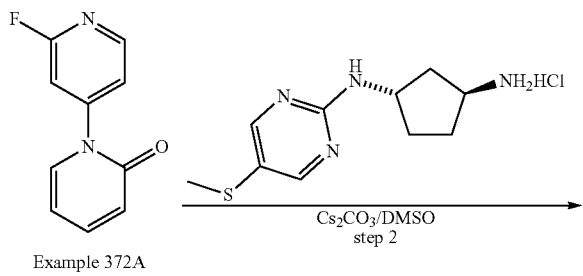

Example 372A

Cs₂CO₃/DMSO
step 2

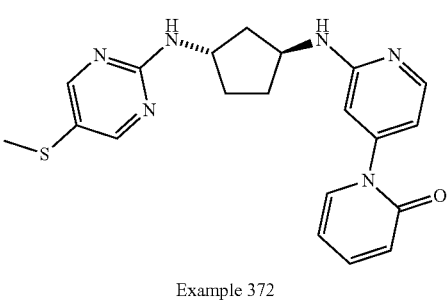

Example 372

Step 1: Example 372A

The mixture of 2-fluoro-4-iodopyridine (200 mg, 0.9 mmol), pyridin-2(1H)-one (102 mg, 1.1 mmol), CuI (17 mg, 0.09 mmol), N,N'-Dimethyl-1,2-cyclohexanediamine (19 mg, 0.17 mmol) and $K_3PO_4$ (381 mg, 1.8 mmol) in DMSO (5 mL) was stirred at 100° C. under $N_2$ atmosphere for 3 h. The mixture was cooled and water (20 mL) was added. The mixture was extracted with EtOAc (20 mL×3), and the combined organic layers were washed with brine (50 mL), dried over $Na_2SO_4$, filtered, concentrated gave crude product, which was purified by chromatography on silica gel eluting with petroleum ether:EtOAc=5:1-1:1 to afford Example 372A (97 mg, 57%) as an off-white solid.

Step 2: Example 372

The mixture of Example 372A (50 mg, 0.19 mmol), (1S,3S)-N1-(5-(methylthio) pyrimidin-2-yl) cyclopentane-1,3-diamine hydrochloride (40 mg, 0.21 mmol) and $Cs_2CO_3$ (185 mg, 0.57 mmol) in DMSO (3 mL) was stirred at 130° C. for 2 days. The mixture was cooled and water (10 mL) was added. The mixture was extracted with EtOAc (10 mL×5), the combined organic layers were washed with brine (20 mL), dried over $Na_2SO_4$, filtered, concentrated. The residue was purified by prep-HPLC to afford Example 372 (10 mg, 13%). LCMS $[M+H]^+$=395. $^1$H NMR (400 MHz, $CD_3OD$) δ 8.39 (s, 2H), 7.99 (d, J=7.2 Hz, 1H), 7.70-7.64 (m, 2H), 7.20 (s, 1H), 7.05-7.03 (m, 1H), 7.67 (d, J=9.2 Hz, 1H), 6.58-6.54 (m, 1H), 4.51-4.47 (m, 1H), 4.29-4.27 (m, 1H), 2.42-2.33 (m, 2H), 2.38 (s, 3H), 2.20-2.14 (m, 2H), 1.78-1.74 (m, 1H).

Using the above procedures, the following example was synthesized:

| Structure | Ex. # | $^1$H NMR | LC-MS $(M + H)^+$ |
|---|---|---|---|
| 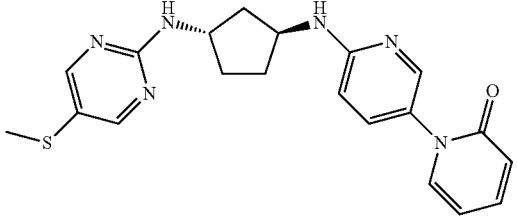 [SMILES: CSc1cnc(N[C@H]2CC[C@H](Nc3ccc(-n4ccccc4=O)cn3)C2)nc1] | 373 | $^1$H NMR ($CD_3OD$, 400 MHz) δ 8.42 (s, 2H), 8.11-8.10 (d, J = 2.0 Hz, 1H), 7.99-7.96 (dd, J = 2.0 Hz, J = 2.4 Hz 1H), 7.97-7.96 (d, J = 2.4 Hz, 1H), 7.69-7.64 (m, 2H), 7.16-7.13 (d, J = 9.2 Hz, 1H), 6.68-6.66 (d, J = 9.2 Hz, 1H), 6.55-6.51 (m, 1H), 4.52-4.49 (t, J = 6.8 Hz 1H), 4.31-4.28 (m, 1H), 2.43-2.33 (m, 2H), 2.33 (s, 3H), 2.21-2.15 (m, 2H), 1.82-1.74 (m, 2H). | 395 |
| 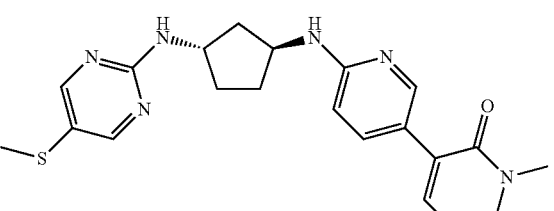 | 375 | $^1$H NMR ($CD_3OD$, 400 MHz) δ 8.49 (d, J = 1.8 Hz, 1H), 8.36 (s, 2H), 8.23 (dd, J = 9.5, 2.1Hz, 1H), 7.83 (dd, J = 7.2, 1.9 Hz, 1H), 7.73 (d, J = 1.9 Hz, 1H), 7.09 (d, J = 9.5 Hz, 1H), 6.49 (t, J = 6.9 Hz, 1H), 4.51-4.39 (m, 1H), 4.24 (t, J = 5.2 Hz, 1H), 3.64 (s, 3H), 2.46-2.25 (m, 5H), 2.21-2.03 (m, 2H), 1.80-1.65 (m, 2H). | 409 |

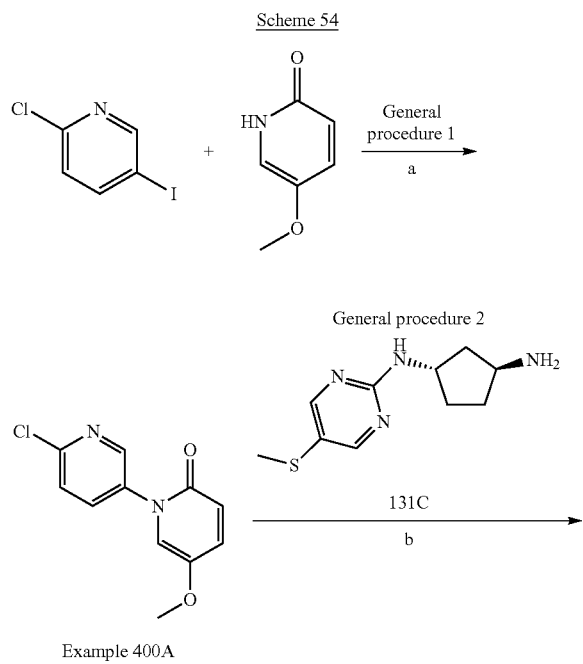

Scheme 54

Example 400A

Example 400 a) CuI, K₃PO₄, N,N'-Dimethyl-1,2-cyclohexanediamine DMSO 120° C.;
b) tBuXphos Pd G₃, tBuOK, dioxane 110° C.

General Method 1

6'-chloro-5-methoxy-2H[1,3'-bipyridin]-2-one (Example 400A)

A mixture of compound 2-chloro-5-iodopyridine (191 mg, 0.8 mmol, 1.0 eq), 5-methoxypyridin-2(1H)-one (100 mg, 0.8 mmol, 1.0 eq), CuI (15 mg, 0.08 mmol, 0.1 eq), N,N'-Dimethyl-1, 2-cyclohexanediamine (23 mg, 0.16 mmol, 0.2 eq) and K₃PO₄ (339 mg, 1.6 mmol, 0.2 eq) in DMSO (5 mL) was stirred at 120° C. under N₂ atmosphere overnight. The mixture was cooled to room temperature and water (20 mL) was added. The mixture was extracted with EtOAc (20 mL×2), The combined organic layers were washed with brine (30 mL), dried over Na₂SO₄, filtered, concentrated and purified by chromatography on silica gel eluting with PE:EA=1:1 to afford 400A (60 mg, 0.23 mmol, 32%) as an off-white solid.

General Procedure 2

5-methoxy-6'-(((1S,3S)-3-((5-(methylthio) pyrimidin-2-yl) amino) cyclopentyl) amino)-2H-[1,3'-bipyridin]-2-one (Example 400)

The mixture of 400A (53 mg, 0.22 mmol, 1.0 eq), 131C (50 mg, 0.22 mmol. 1.0 eq), tBuXphos Pd G3 (18 mg, 0.022 mmol, 0.1 eq) and tBuOK (49 mg, 0.44 mmol, 0.2 eq) in dioxane (5 mL) was stirred at 110° C. under N₂ atmosphere overnight. The mixture was cooled to room temperature and filtered. The filtrate was concentrated and purified by Prep-TLC and then Prep-HPLC to afford compound 400 (50 mg, 53%, TFA salt) as an off-white solid. LCMS [M+H]⁺=425.

¹H NMR (400 MHz, CD₃OD) δ 8.36 (s, 2H), 8.09 (s, 1H), 7.95 (d, J=9.6 Hz, 1H), 7.50 (d, J=9.6 Hz, 1H), 7.23 (s, 1H), 7.10 (d, J=9.6 Hz, 1H), 6.61 (d, J=9.6 Hz, 1H), 4.48-4.46 (m, 1H), 4.25-4.23 (m, 1H), 3.73 (s, 3H), 2.40-2.35 (m, 5H), 2.16-2.13 (m, 2H), 1.76-1.74 (m, 2H).

Using the above procedures, the following example was synthesized:

| Structure | Ex. # | ¹H NMR | LC-MS (M + H)⁺ |
|---|---|---|---|
| 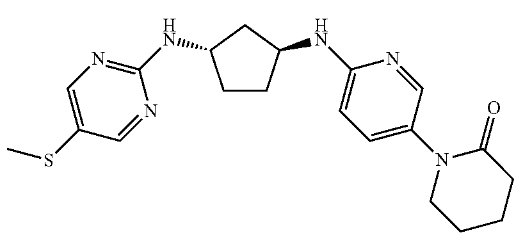 [SMILES: CSc1cnc(N[C@H]2CC[C@H](Nc3ccc(N4CCCCC4=O)cn3)C2)nc1] | 401 | 1H NMR (400 MHz, CD₃OD) δ: 8.35 (s, 2H), 7.88-7.85 (m, 2H), 7.06-7.04 (m, 1H) 4.47-4.43 (t, J = 14 Hz, 1H), 4.23-4.19 (m, 1H), 3.67-3.64 (t, J = 11.2 Hz, 2H), 2.53-2.50 (t, J = 12.4 Hz, 2H), 2.40-2.2.28 (m, 5H), 2.14-2.09 (m, 2H), 2.00-1.93 (m, 4H), 1.75-1.69 (m, 2H). | 399.4 |

Scheme 55

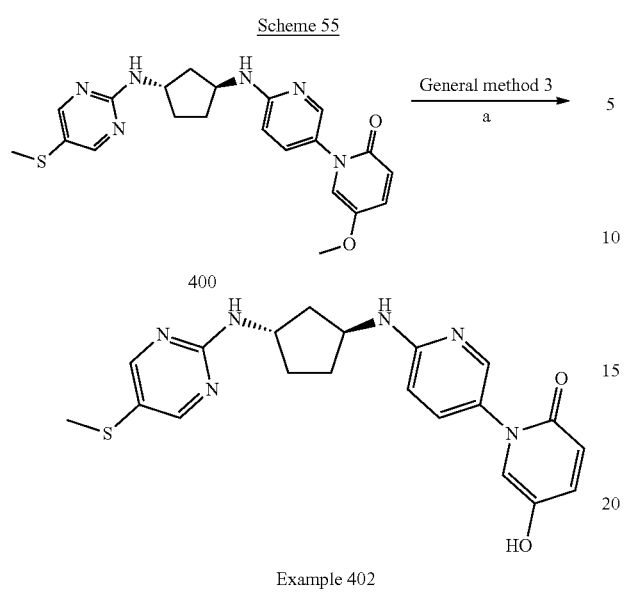

a) BBr₃, DCM

5-hydroxy-6'-(((1S,3S)-3-((5-(methylthio) pyrimidin-2-yl) amino) cyclopentyl) amino)-2H-[1,3'-bipyridin]-2-one (Example 402)

To a solution of 400 (50 mg, 0.12 mmol, 1.0 eq) in DCM (10 mL) was added BBr₃ (1 mL) at 0° C. The mixture was stirred at rt overnight, quenched with MeOH and then concentrated. The residue was purified by Prep-TLC and then Prep-HPLC to afford compound Example 402 (50 mg, 53%, TFA salt) as an off-white solid: ¹H NMR (400 MHz, CD₃OD) δ 8.37 (s, 2H), 8.06 (s, 1H), 7.94 (d, J=9.6 Hz, 1H), 7.45 (d, J=9.6 Hz, 1H), 7.12-7.09 (m, 2H), 6.58 (d, J=9.6 Hz, 1H), 4.49-4.46 (m, 1H), 4.31-4.28 (m, 1H), 2.42-2.30 (m, 5H), 2.17-2.13 (m, 2H), 1.79-1.73 (m, 2H). [M+H]⁺=411.

Scheme 56

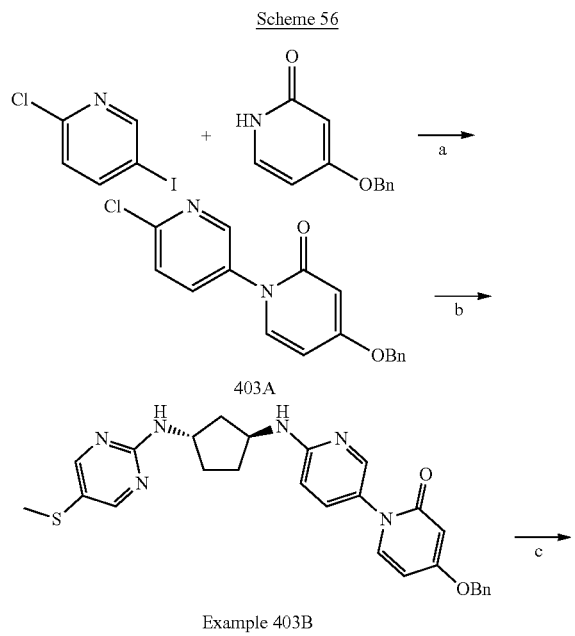

a) General procedure 1; b) General procedure 2; c) General procedure 3.

4-hydroxy-5'-(((1S,3S)-3-((5-(methylthio) pyrimidin-2-yl) amino) cyclopentyl) amino)-2H-[1,2'-bipyridin]-2-one (Example 403)

Methods analogous to those described in General Method 1, General Method 2 and General Method 3 from starting material 4-(benzyloxy) pyridin-2(1H)-one afforded the title compound: ¹H NMR (400 MHz, CD₃OD) δ 8.32 (s, 2H), 7.89 (d, J=2.2 Hz, 1H), 7.45 (d, J=7.5 Hz, 2H), 7.39 (dd, J=9.0, 2.7 Hz, 1H), 6.60 (d, J=8.6 Hz, 1H), 6.13 (dd, J=7.5, 2.6 Hz, 1H), 5.88 (d, J=8.6, 2.5 Hz, 1H), 4.48-4.25 (m, 2H), 2.35 (s, 3H), 2.32-2.19 (m, 2H), 2.06-1.92 (m, 2H), 1.70-1.52 (m, 2H). [M+H]⁺=411.49.

Scheme 57 a) Pd(dppf)Cl₂, Na₂CO₃, dioxane/H₂O, 105° C.

General Procedure 4

6'-chloro-4-methoxy-3,3'-bipyridine (404)

A mixture of (6-chloropyridin-3-yl) boronic acid (1.0 g, 6.4 mmol, 1 eq), 3-bromo-4-methoxypyridine (1.2 g, 6.4 mmol, 1 eq), Pd(dppf)Cl₂ (468 mg, 0.64 mmol, 0.1 eq) and Na₂CO₃ (1.3 g, 12.8 mmol, 2 eq) in dioxane (8 mL) and water (2 mL) was stirred at 105° C. under N₂ atmosphere overnight. The mixture was cooled down to room temperature and quenched with water (10 mL). The mixture was extracted with EtOAc (20 mL×3). The combined organic layers were washed with brine (50 mL), dried over Na₂SO₄, filtered, concentrated. The residue was purified by chromatography on silica gel eluting with petroleum ether:EtOAc=5:1 to afford compound 404 (200 mg, 14%) as a brown solid.

Using the above procedures, the following examples were synthesized:

| Structure | Ex. # |
|---|---|
| (6-fluoropyridin-3-yl)-1-methylpyridin-2(1H)-one structure | 405 |
| 2-chloro-5-(5-fluoro-2-methoxyphenyl)pyridine structure | 406 |
| 2-chloro-5-(2-methoxyphenyl)pyridine structure | 407 |

Scheme 58

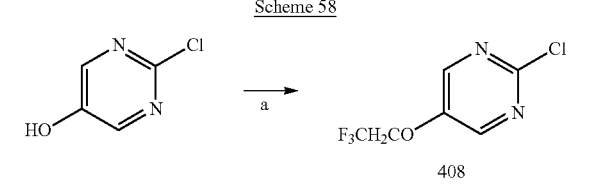

a) 2,2,2-trifluoroethyl trifluoromethanesulfonate, Cs₂CO₃, DMF, rt

2-chloro-5-(2, 2, 2-trifluoroethoxy) pyrimidine (408)

To a solution of 2-chloropyrimidin-5-ol (0.5 g, 3.8 mmol, 1.0 eq) and CS₂CO₃ (1.49 g, 4.6 mmol, 1.2 eq) in DMF (20 mL) was added 2, 2, 2-trifluoroethyl trifluoromethane-sulfonate (0.97 g, 4.2 mmol, 1.1 eq). The resulting suspension was stirred at room temperature for 16 h and then partitioned between EtOAc (30 mL) and water (80 mL). The separated aqueous layer was extracted with EtOAc (20 mL×3. The combined organic layers were washed with brine (20 mL), dried over Na₂SO₄, filtered and concentrated to afford to afford 408 (0.74 g), which was used to next step directly. LCMS [M+H]⁺=213.

Scheme 59

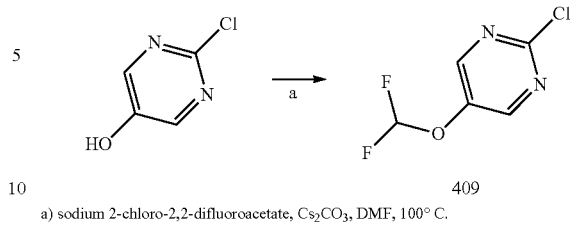

a) sodium 2-chloro-2,2-difluoroacetate, Cs₂CO₃, DMF, 100° C.

2-chloro-5-(difluoromethoxy) pyrimidine (409)

A solution of 2-chloropyrimidin-5-ol (101.6 g, 0.76 mol, 1.0 eq) in DMF (2000 mL) was charged with Cs₂CO₃ (300 g, 0.92 mol, 1.2 eq) and then stirred at room temperature for 1.5 h. Sodium 2-chloro-2,2-difluoroacetate (340 g, 2.3 mol, 3.0 eq) was added, and the reaction mixture was stirred at 100° C. for 3.5 h. The reaction mixture was poured in water (5 L) and extracted with EA (3×1 L). The combined organic phases were dried over anhydrous Na₂SO₄ and concentrated. The residue was purified by flash chromatograph on silica gel (PE:EA=10:1) to afford 409 (70 g).

Scheme 60

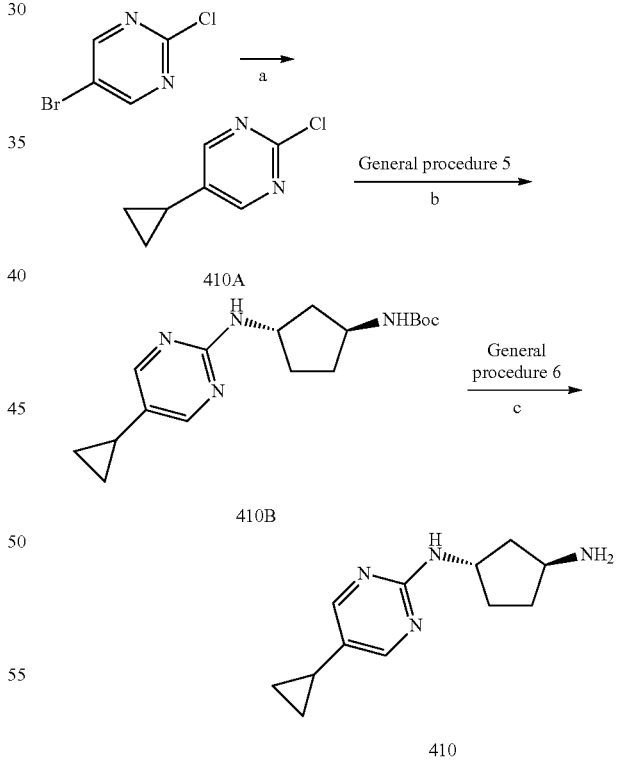

a) cyclopropylboronic acid, Cs₂CO₃, Pd(dppf)Cl₂, dioxane, 110° C.; b) tert-butyl ((1S,3S)-3-aminocyclopentyl)carbamate, DIPEA, DMSO, 110° C.; c) HCl in dioxane, MeOH

2-chloro-5-cyclopropylpyrimidine (410A)

To the solution of 5-bromo-2-chloropyrimidine (100 g, 518 mmol, 1.0 eq), cyclopropylboronic acid (53 g, 616 mmol, 1.2 eq) and Pd(dppf)Cl$_2$ (10 g, 13.7 mmol, 0.03 eq) in dioxane (1.5 L) was added Cs$_2$CO$_3$ (250 g, 769 mmol, 1.5 eq) and stirred at 110° C. for 12 h under N$_2$. The reaction mixture was cooled to room temperature and filtered. The filtrate was concentrated under reduced pressure and the residue was purified by silica gel column chromatography (elute with hexane:ethyl acetate=15:1) to afford 410A (55 g) as a yellow solid. LCMS [M+H]=155.

General Procedure 5

Tert-butyl ((1S, 3S)-3-((5-cyclopropylpyrimidin-2-yl) amino) cyclopentyl) carbamate (410B)

A mixture of 410A (40 g, 260 mmol, 1 eq) tert-butyl ((1S,3S)-3-aminocyclopentyl) carbamate (55 g, 275 mmol, 1.05 eq) and DIPEA (105 g, 814 mmol, 3.13 eq) in DMSO (400 mL) was stirred at 110° C. for 12 h under N$_2$. The mixture was then cooled down to room temperature and diluted with water (1000 mL). The resulting mixture was extracted with EtOAc (100 mL×3), and the combined organic layers were washed with brine, dried over Na$_2$SO$_4$, filtered and concentrated. The residue was purified by chromatography on silica gel (eluting with hexane:ethyl acetate=5:1 to 4:1) to afford compound 410B (55 g) as a pale solid. LCMS [M+H]$^+$=319.

General Procedure 6

(1S, 3S)—N(5-cyclopropylpyrimidin-2-yl) cyclopentane-1, 3-diamine (410C)

To a solution of 410B (44 g, 13.8 mmol, 1.0 eq) in MeOH (250 mL) was added HCl (4M in dioxane, 250 mL) dropwise and resulting solution was stirred at room temperature for 2.5 h. After the reaction was completed, the mixture was concentrated to dryness under vacuum. The residue was re-dissolved in MeOH (500 mL) and ion exchange resin (Ambersep® 900 OH$^-$ form) was added to adjust the pH to about 8. The mixture was filtered off and the filtrate was concentrated to afford 410C (44.5) as yellow oil. LCMS [M+H]$^+$=219.

Using the above procedures, the following examples were synthesized:

| Structure | Ex. # |
|---|---|
| 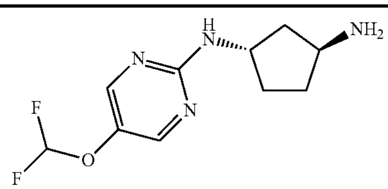 | 411 |
| 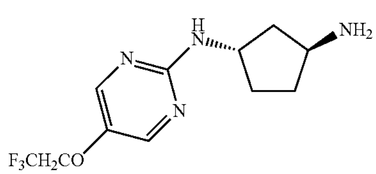 | 412 |
| 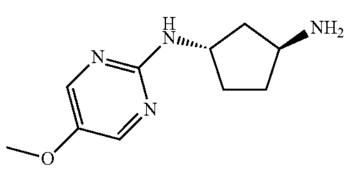 | 413 |
|  | 414 |
|  | 415 |
|  | 415A |

Scheme 61

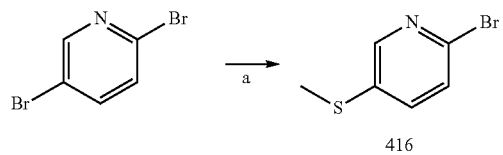

a) 1,2-dimethyldisulfane, n-BuLi, THF, -78° C.

2-bromo-5-(methylthio) pyridine (416)

A solution of 2,5-dibromopyridine (1 g, 4.22 mmol, 1 eq) in THF (20 mL) was cooled to -78° C. under N$_2$. Then, n-BuLi (2.5 M, 1.77 mL, 4.43 mmol, 1.05 eq) was added dropwise at -78° C. The reaction mixture was stirred for 20 minutes, followed by the slow addition of 1,2-dimethyldisulfane (0.411 mL, 4.64 mmol, 1.1 eq). The reaction mixture was stirred for another 1 hour before quenched by saturated NH$_4$Cl. The reaction mixture was extracted with EA (100 mL) and water (100 mL), and then washed with brine. The organic phase was dried over anhydrous Na$_2$SO$_4$. The mixture was filtered and concentrated under reduced pressure. The crude residue was purified by flash chromatography on silica gel (PE:EA=10:1) to give 416 (86.8 mg): ESI [M+H]$^+$=204.1 $^1$H NMR (400 MHz, CDCl$_3$) δ 8.25 (t, J=6.2 Hz, 1H), 7.41 (ddd, J=8.9, 8.3, 1.6 Hz, 2H), 2.58-2.40 (m, 3H).

Scheme 62

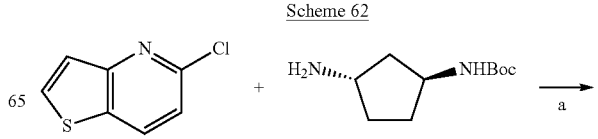

-continued

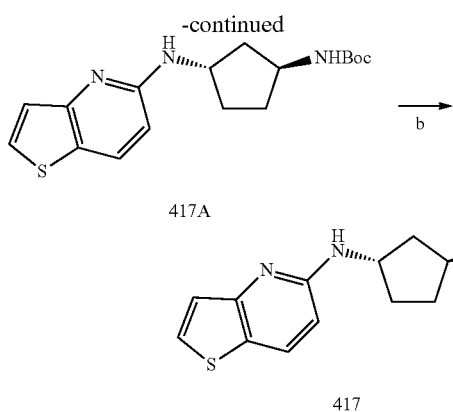

417A

417 a) General procedure 2; b) General procedure 6

(1S,3S)-N1-(thieno[3,2-b]pyridin-5-yl) cyclopentane-1,3-diamine (417)

Methods analogous to those described in General Method 2 and General Method 6 from starting material 5-chlorothieno[3,2-b]pyridine allowed the synthesis of the title compound.
sing the above procedures, the following example was synthesized:

| Structure | Ex. # | $^1$H NMR | LC-MS $(M + H)^+$ |
|---|---|---|---|
| (structure) | 418 | | 224.3 | mmol, 1.2 eq), Cu (OAc)$_2$ (7.9 g, 43.71 mmol, 2.8 eq), pyridine (2.5 mL, 31.22 mmol, 2.0 eq) and 4 Å molecular sieves (8 g) in DCM (60 mL) was stirred at room temperature for 48 h. The mixture was filtered through celite, and the filtrate was concentrated and purified by flash column (petroleum ether:EtOAc: 1:1) to obtain Example 419 as a yellow solid (170 mg, 5.3% yield).

$^1$H NMR (400 MHz, CDCl$_3$) δ 8.43 (d, J=2.6 Hz, 1H), 8.15 (s, 1H), 7.97 (d, J=6.8 Hz, 1H), 7.80 (dd, J=8.4, 2.8 Hz, 1H), 7.53 (d, J=8.5 Hz, 1H), 6.59 (dd, J=6.8, 0.8 Hz, 1H); MS (ESI+) m/z 208.0 (M+H)$^+$

Using the procedures described in Scheme 63, the following examples were prepared:

| Structure | Ex. # |
|---|---|
| (structure) | 420 |
| (structure) | 421 |
| (structure) | 422 |

Scheme 63

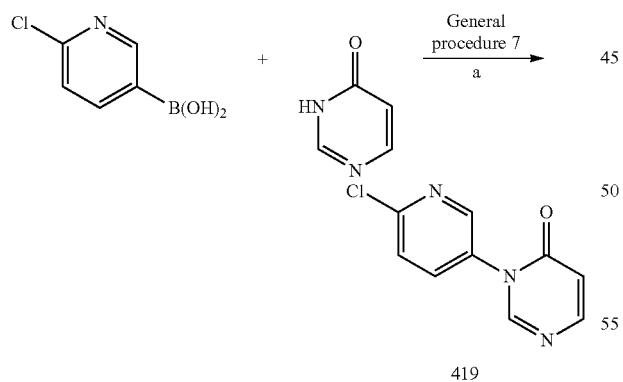

a) Cu(OAc)$_2$, pyridine, 4Å MS, DCM, rt

General Procedure 7

3-(6-chloropyridin-3-yl) pyrimidin-4(3H)-one (419)

A solution of pyrimidin-4(3H)-one (1.5 g, 15.61 mmol, 1.0 eq), (6-chloropyridin-3-yl) boronic acid (2.9 g, 18.73

Scheme 64

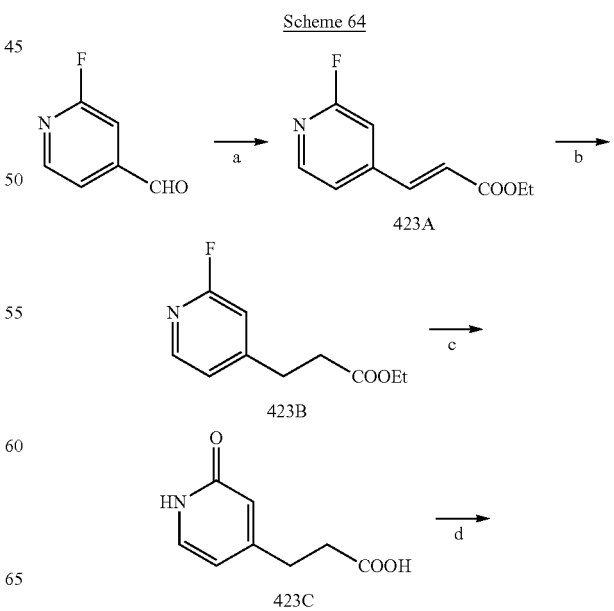

-continued

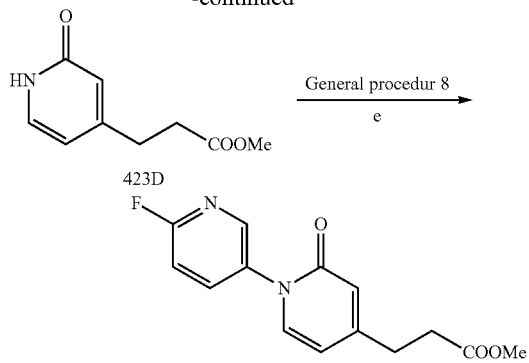

Example 423
a) Ethyl 2-(ethoxy(propoxy)phosphoryl)acetate, NaH, THF, 0° C.-rt; b) H₂, 10% Pd/C, EtOH; c) HCl, 100° C.;
d) MeOH, H₂SO₄, reflux;
e) 2-fluoro-5-iodopyridine, CuI, N, N'-Dimethyl-1,2-cyclohexanediamine, K₂CO₃, dioxane, 110° C.

Ethyl (E)-3-(2-fluoropyridin-4-yl) acrylate (423A)

To a suspension of 60% NaH (1.54 g, 38.4 mmol, 1.2 eq) in THF (15 mL) was added dropwise a solution of ethyl 2-(ethoxy(propoxy)phosphoryl) acetate (8.6 g, 38.4 mmol, 1.2 eq) in THF at 0° C. under $N_2$ atmosphere. The mixture was stirred at 0° C. for 25 min followed by addition of a solution of 2-fluoroisonicotinaldehyde (4.0 g, 32.0 mmol, 1.0 eq) in DMF (15 mL). The resulting mixture was stirred at room temperature for 16 h, and then quenched by sat. aq. $NH_4Cl$ at 0° C. The aqueous phase was extracted with ethyl acetate. The combined organic layers were washed with brine, dried over $Na_2SO_4$ and concentrated under vacuum. The residue was purified by column chromatography (PE to PE:EA=1:15) to give 423A (3.0 g, 50% yield) as a white solid. LCMS: m/z 196 [M+H],⁺, rt 2.890 min. ¹H-NMR (400 MHz, CDCl₃) δ 8.26 (d, J=5.2 Hz, 1H), 7.59 (d, J=16.1 Hz, 1H), 7.29-7.26 (m, 1H), 7.00 (d, J=1.7 Hz, 1H), 6.60 (d, J=16.0 Hz, 1H), 4.30 (q, J=7.1 Hz, 2H), 1.35 (t, J=7.1 Hz, 3H).

Ethyl 3-(2-fluoropyridin-4-yl) propanoate (423B)

To a solution of 423A (3.0 g, 20.5 mmol) in EtOH (20 mL) was added 10% Pd/C (400 mg). The reaction system was purged with $H_2$ and the mixture was stirred under $H_2$ atmosphere overnight. Pd/C was filtered off and the filtrate was concentrated under vacuum to give 423B (2.3 g, yield 76.7%), which was used directly:LCMS: m/z 198.1 [M+H]⁺, rt 2.801 min. ¹H-NMR (400 MHz, CDCl₃) δ 8.12 (d, J=5.5 Hz, 1H), 7.04 (d, J=4.8 Hz, 1H), 6.78 (d, J=4.0 Hz, 1H), 4.13 (p, J=6.8 Hz, 2H), 3.03-2.97 (m, 2H), 2.66 (t, J=7.6 Hz, 2H), 1.24 (t, J=6.7 Hz, 3H).

3-(2-oxo-1,2-dihydropyridin-4-yl) propanoic acid (423C)

To a 100 mL flask with 423B (1.53 g, 7.77 mmol) was added concentrated HCl (5 mL). The mixture was heated to 100° C. for 16 h. The mixture was then cooled to room temperature and 2 mL of water was added. Solid NaHCO₃ was added portion-wise to adjust pH to 6. The mixture was extracted with 30% i-PrOH in CHCl₃, the combined organic layers were dried over Na₂SO₄ and concentrated. The residue was purified by column chromatography (MeOH/DCM) to give 423C (1.6 g, yield 91%), which was used to next step directly. LCMS: m/z 167.8 [M+H]⁺; ¹H NMR (400 MHz, CDCl₃) δ 8.14 (d, J=5.1 Hz, 1H), 7.05 (dt, J=5.3, 1.7 Hz, 1H), 6.82-6.76 (m, 1H), 3.01 (t, J=7.5 Hz, 2H), 2.73 (t, J=7.5 Hz, 2H).

Methyl 3-(2-oxo-1,2-dihydropyridin-4-yl) propanoate (423D)

To a 100 mL flask with a solution of crude 423C (1.6 g) in MeOH (28 mL) was added 98% H₂SO₄ (0.15 mL). The reaction was heated to 90° C. for 16 h and then cooled to room temperature. Sat. aq. NaCl was added to above mixture, which was extracted with 30% i-PrOH in CHCl₃. The combined organic layers were dried over Na₂SO₄ and concentrated. The residue was purified by column chromatography (MeOH:DCM=1:15) to give product 423D (702 mg, yield 55%). LCMS: m/z 182.1 [M+H]

General Procedure 8

Methyl 3-(6'-fluoro-2-oxo-2H-[1,3'-bipyridin]-4-yl) propanoate (423)

To a sealed tube was added 423D (100.0 mg, 0.55 mmol, 1.0 eq), 2-fluoro-5-iodopyridine (147 mg, 0.66 mmol, 1.2 eq), CuI (21.0 mg, 0.10 mmol, 0.2 eq), N, N'-Dimethyl-1,2-cyclohexanediamine (15.5 mg, 0.10 mmol, 0.2 eq), and K₂CO₃ (151.0 mg, 1.10 mmol, 2.0 eq). Dioxane (3 mL) was added and the resulting mixture was purged with N₂ and stirred at 110° C. for 16 h. The mixture was then diluted with dichloromethane and filtered. The filtrate was washed with water and separated. Aqueous phase was extracted with dichloromethane three times. The combined organic layers were dried over Na₂SO₄, concentrated and purified by silica gel chromatography to give 423 (42 mg, yield 27.6%). LCMS: m/z 278.08 [M+H]

Scheme 65

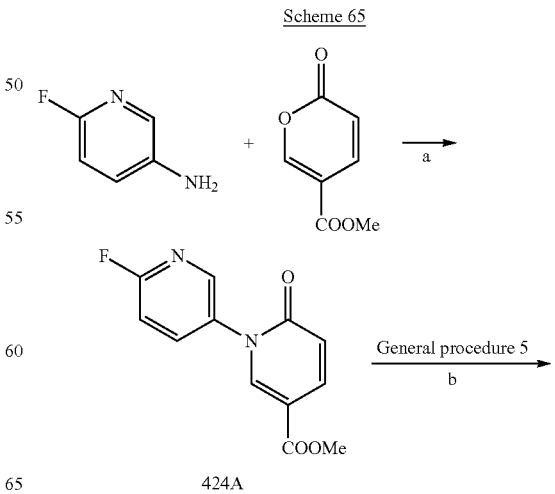

424A

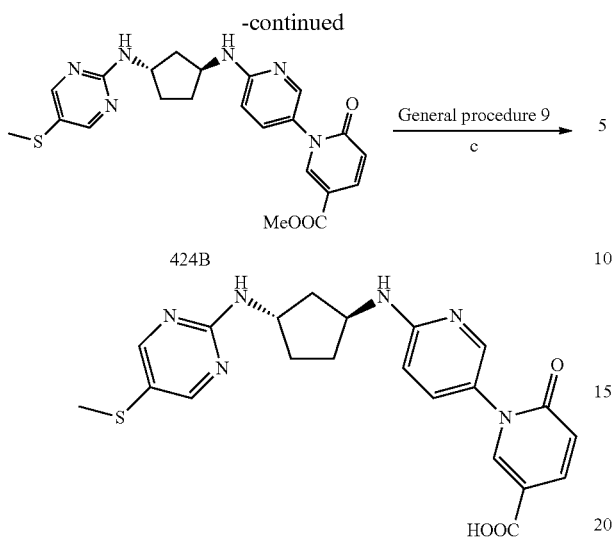

424B

Example 424
a) EtOH, reflux; b)131C, General procedure 5; c) NaOH, MeOH/H$_2$O, 50° C.

Methyl 6'-fluoro-2-oxo-2H-[1,3'-bipyridine]-5-carboxylate (424A)

A mixture of 6-fluoropyridin-3-amine (1.1 g, 10 mmol, 1.0 eq) and methyl 2-oxo-2H-pyran-5-carboxylate (1.5 g, 10 mmol, 1.0 eq) in EtOH (10 mL) was stirred at reflux overnight, and then cooled down to room temperature. The resulting precipitate was collected by filteration and purified by chromatography on silica gel eluting with petroleum ether:EtOAc=2:1 to afford compound 424A (440 mg, 18%) as an off-white solid.

Methyl 6'-(((1S,3S)-3-((5-(methylthio) pyrimidin-2-yl) amino) cyclopentyl) amino)-2-oxo-2H-[1,3'-bipyridine]-5-carboxylate (424B)

Methods analogous to those described above from starting material 131C and 424A afforded 424B.

General Procedure 9

6'-(((1S, 3S)-3-((5-(methylthio) pyrimidin-2-yl) amino) cyclopentyl) amino)-2-oxo-2H-[1, 3'-bipyridine]-5-carboxylic acid (Example 424)

To a solution of compound 424B (100 mg, 0.22 mmol, 1.0 eq) in MeOH:H$_2$O=5:1 (10 mL) was added NaOH (35 mg, 0.88 mmol, 4.0 eq). The mixture was stirred at 50° C. for 3 h and then acidified to pH=5-6 after cooling down to room temperature. The resulting mixture was concentrated and re-dissolved in THF (50 mL). The solid was filtered off and the filtrate was concentrated and triturated with EA:MeOH=5:1 to afford Example 424 (90 mg, 93%) as a light yellow solid: $^1$H NMR (400 MHz, DMSO-d$_6$) δ: 8.35 (s, 2H), 8.25 s, 1H), 8.10 1H), 7.87 (d, J=9.2 Hz, 1H), 7.56 (s, 1H), 6.87 (s, 1H), 6.51 (d, J=9.2 Hz, 1H), 4.36-4.33 (m, 2H), 2.35 (s, 3H), 2.22-2.10 (m, 2H), 2.01-1.93 (m, 2H), 1.57-1.55 (m, 2H).

Using the above procedures, the following examples were synthesized:

| Structure | Ex. # | $^1$H NMR | LC-MS (M + H)$^+$ |
|---|---|---|---|
| 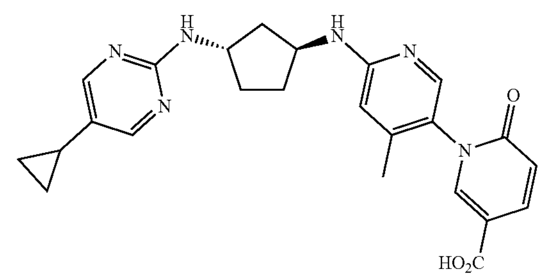 [SMILES: Cc1cc(N[C@H]2CC[C@H](Nc3ncc(C4CC4)cn3)C2)ncc1-n1cc(C(=O)O)ccc1=O] | 425 | $^1$H NMR (400 MHz, CD$_3$OD) δ 8.35 (d, J = 2.3 Hz, 1H), 8.31 (s, 2H), 8.11 (dd, J = 9.6, 2.5 Hz, 1H), 8.06 (s, 1H), 7.00 (s, 1H), 6.67 (d, J = 9.6 Hz, 1H), 4.58-4.51 (m, 1H), 4.33-4.27 (m, 1H), 2.50-2.28 (m, 2H), 2.24-2.10 (m, 5H), 1.93-1.82 (m, 1H), 1.82-1.73 (m, 2H), 1.06-0.96 (m, 2H), 0.78-0.65 (m, 2H). | 447.5 |
| 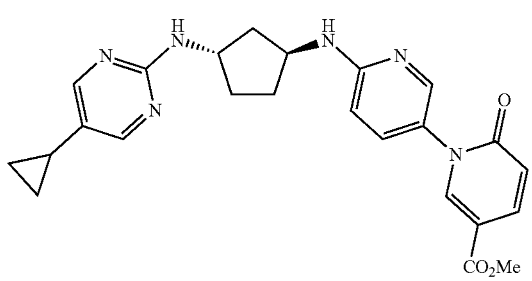 [SMILES: COC(=O)c1ccc(=O)n(-c2ccc(N[C@H]3CC[C@H](Nc4ncc(C5CC5)cn4)C3)nc2)c1] | 426 | 1H NMR (400 MHz, CD$_3$OD) δ 8.40 (d, J = 1.6 Hz, 1H), 8.25 (d, J = 21.6 Hz, 2H), 8.11 (s, 1H), 8.06-8.03 (m, 1H), 7.87 (t, J = 9.2 Hz, 1H), 7.03 (d, J = 9.2 Hz, 1H), 6.63 (d, J = 9.6 Hz, 1H), 4.50 (d, J = 6.0 Hz, 1H), 4.31 (d, J = 4.8 Hz, 1H), 3.86 (s, 3H), 2.40-2.32 (m, 2H), 2.18 (t, J = 12.8 Hz, 2H), 1.86-1.75 (m, 3H), 0.99-0.97 (m, 2H), 0.69 (d, J = 4.8 Hz, 2H). | |

-continued
| Structure | Ex. # | ¹H NMR | LC-MS (M + H)⁺ |
|---|---|---|---|
| 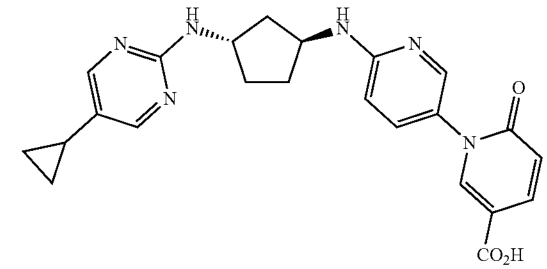 [SMILES: O=C(O)c1ccc(=O)n(-c2ccc(N[C@H]3CC[C@H](Nc4ncc(C5CC5)cn4)C3)nc2)c1] | 427 | 1H NMR (400 MHz, CD₃OD) δ 8.37-8.36 (d, J = 2.4 Hz, 1H), 8.19 (s, 2H), 8.10-8.06 (m, 2H), 8.04-8.03 (d, J = 2.4 Hz, 1H), 7.85-7.83 (d, J = 8.0 Hz, 1H), 7.00-6.97 (d, J = 9.6 Hz, 1H), 6.64-6.62 (d, J = 9.6 Hz, 1H), 4.46-4.42 (t, J = 13.6 Hz, 1H), 4.31-4.29 (t, J = 11.2 Hz, 1H), 2.39-2.31 (m, 2H), 2.15-2.11 (t, J = 16.4 Hz, 1H), 1.83-1.72 (m, 3H), 0.98-0.94 (m, 2H), 0.68-0.64 (m, 2H). | 433.4 |
| 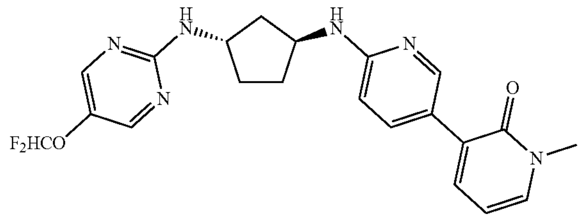 [SMILES: Cn1cccc(-c2ccc(N[C@H]3CC[C@H](Nc4ncc(OC(F)F)cn4)C3)nc2)c1=O] | 428 | 1H NMR (400 MHz, CD₃OD) δ: 8.49-8.48 (d, J = 2.0 Hz, 1H), 8.24-8.19 (m, 3H), 7.83-7.81 (m, 1H), 7.74-7.72 (m, 1H), 7.09-7.07 (d, J = 9.2 Hz, 1H), 6.88-6.47 (m, 2H), 4.47-4.40 (m, 1H), 4.27-4.21 (m, 1H), 3.66-3.64 (d, J = 9.6 Hz 3H), 2.44-2.26 (m, 2H), 2.19-2.07 (m, 2H), 1.77-1.65 (m, 2H). | 429 |
| 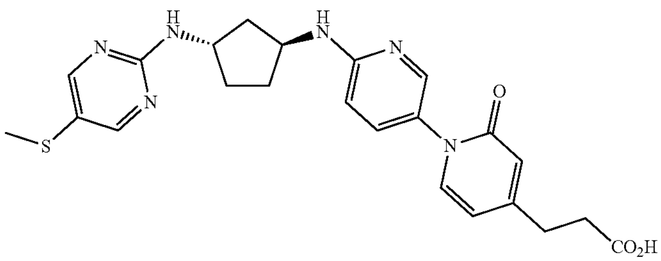 [SMILES: CSc1cnc(N[C@H]2CC[C@H](Nc3ccc(-n4ccc(CCC(=O)O)cc4=O)cn3)C2)nc1] | 429 | ¹H-NMR (400 MHz, CDCl₃) δ 10.40 (s, 1H), 10.14 (s, 1H), 7.92 (s, 2H), 7.36 (d, J = 9.5 Hz, 1H), 7.21 (d, J = 7.3 Hz, 1H), 6.57 (s, 1H), 6.28 (d, J = 6.9 Hz, 1H), 4.62 (s, 1H), 4.31 (s, 1H), 2.87 (q, J = 7.1 Hz, 3H), 2.72 (d, J = 7.5 Hz, 3H), 2.44 (s, 3H), 2.43-2.25 (m, 3H), 2.08 (dt, J = 14.2, 7.7 Hz, 1H), 1.97-1.71 (m, 2H). | 467 |
| 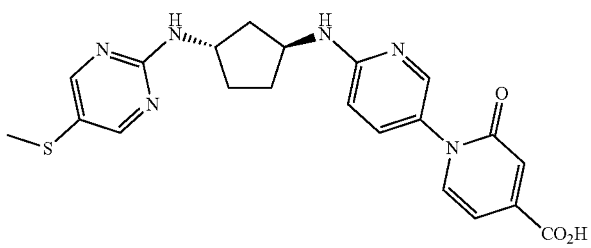 [SMILES: CSc1cnc(N[C@H]2CC[C@H](Nc3ccc(-n4ccc(C(=O)O)cc4=O)cn3)C2)nc1] | 430 | ¹H NMR (400 MHz, CD₃OD): δ 8.378 (s, 2H), 8.12 (s, 1H), 7.93 (s, 1H), 7.73-7.72 (d, J = 7.2 Hz, 1H), 7.21 (s, 1H), 7.10-7.08 (d, J = 9.6 Hz, 1H), 6.92-6.90 (m, 1H), 4.48 (s, 1H), 4.29 (s, 1H), 2.38-2.33 (m, 5H), 2.16-2.14 (d, J = 7.2 Hz, 2H), 1.76-1.75 (d, J = 3.6 Hz, 2H). | 439 |
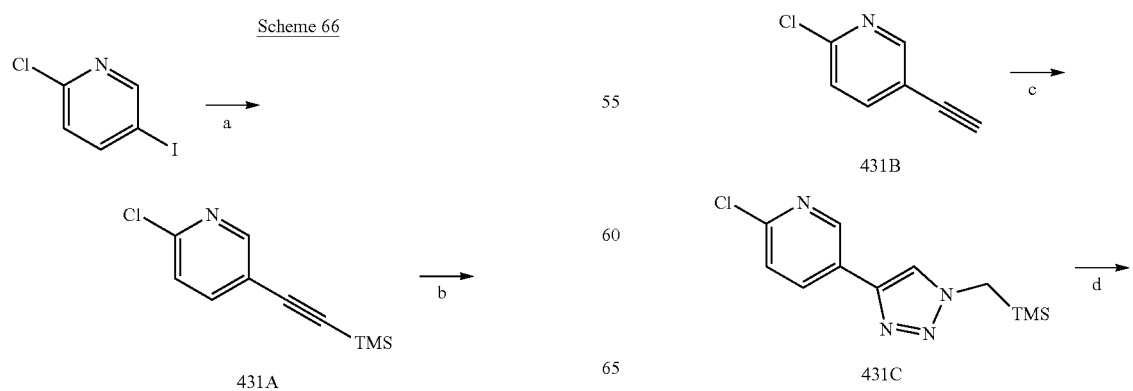
Scheme 66

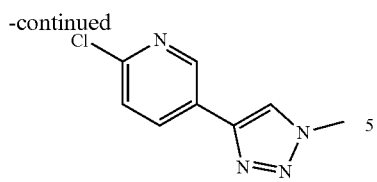

Example 431
a) Ethynyltrimethylsilane, CuI, Pd(PPh₃)Cl₂, Et₃N, 120° C.; b) K₂CO₃, MeOH, rt; c) (azidomethyl)trimethylsilane, CuI, Et₃N, THF, rt; d) TBAF, THF, rt;

2-chloro-5-((trimethylsilyl)ethynyl) pyridine (431A)

To a degassed solution of 2-chloro-5-iodopyridine (5 g, 20.88 mmol, 1.0 eq) in triethylamine (35 mL) were added ethynyltrimethylsilane (3.2 mL, 22.97 mmol, 1.1 eq), CuI (397.7 mg, 2.09 mmol, 0.1 eq) and Pd(PPh₃)₂Cl₂ (1.5 g, 2.09 mmol, 0.1 eq). The reaction mixture was stirred at room temperature for 16 h under Nitrogen. Water (150 mL) was added and the system was extracted with Et₂O (100 mL×2). The combined organic layers were dried over Na₂SO₄, filtered and then concentrated under reduced pressure. The resulting crude 431A (6.2 g, black solid) was used for the next step without further purification. MS (ESI+) m/z 209.9 (M+H)+

2-chloro-5-ethynylpyridine (431B)

A solution of 431A (crude, 20.88 mmol, 1.0 eq) and K₂CO₃ (2.9 g, 20.88 mmol, 1.0 eq) in methanol (50 mL) was stirred at room temperature for 2 h. Following solvent removal under reduced pressure, DCM was added (150 mL) and the mixture was filtered. The filtration was concentrated and purify by flash column (petroleum ether:EtOAc=10:1) to afford compound 432B as a yellow solid (1.0 g, 34.8% yield in two steps). MS (ESI+) m/z 138.1 (M+H)⁺; ¹H NMR (400 MHz, DMSO-d₆) δ: 8.55 (d, J=2.1 Hz, 1H), 7.98 (dd, J=8.4, 2.4 Hz, 1H), 7.57 (d, J=8.3 Hz, 1H), 4.56 (s, 1H).

2-chloro-5-(1-((trimethylsilyl)methyl)-1H-1,2,3-triazol-4-yl) pyridine (431C)

A solution of 431B (345 mg, 2.54 mmol, 1.0 eq), (azidomethyl)trimethylsilane (327 mg, 2.54 mmol, 1.0 eq), CuI (48 mg, 0.25 mmol, 0.1 eq), NEt₃ (513 mg, 5.08 mmol, 2.0 eq) in THF (10 mL) was stirred at room temperature for 16 h. The reaction mixture was then concentrated to afford 431C (673 mg) which was used without further purification.

2-chloro-5-(1-methyl-1H-1,2,3-triazol-4-yl) pyridine (431)

To a solution of 431C in THF (10 mL) was added TBAF (0.80 g, 3.0 mmol, 1.2 eq) and the resulting solution was stirred at room temperature for 2 h. The reaction mixture was concentrated under reduced pressure and crude product was purified by column chromatography on silica gel (PE:EA=1:1) to afford 431 (150 mg).

Scheme 67

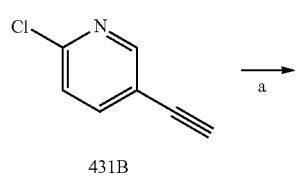

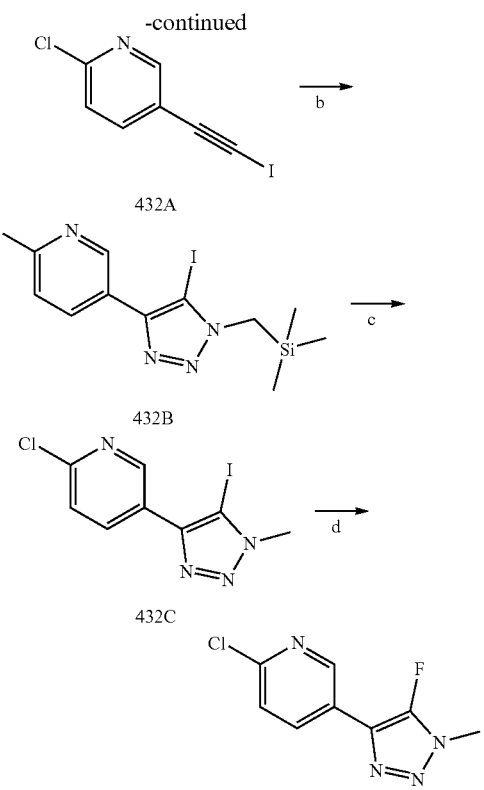

a) LDA, I₂, THF, -78° C.; b) (azidomethyl)trimethylsilane, Et₃N, CuI, THF, rt; c)TBAF, THF/H₂O, rt d) KF, CH₃CN/H₂O, MW. 160° C.

2-chloro-5-(iodoethynyl) pyridine (432A)

LDA (4.4 mL, 8.73 mmol, 1.2 eq) was added dropwise to a solution of 431B (1.0 g, 7.27 mmol, 1.0 eq) in THF (15 mL) at -78° C. under nitrogen. The mixture was stirred at -78° C. for 0.5 hour, then a solution of iodine (2.0 g, 8.00 mmol, 1.1 eq) in THF (10 mL) was added dropwise. The resulting solution was slowly warmed to room temperature and stirred for another 5 h, and then quenched by addition of sat. ammonium chloride solution (25 mL). The organic layer was separated and the aqueous layer extracted with EtOAc (50 mL). The combined organic layers were washed with Na₂S₂O₃ (25 mL×2) and brine (30 mL), dried over Na₂SO₄ and concentrated under reduced pressure. The resulting residue was purified by flash column (petroleum ether:EtOAc: 20:1) to afford 432A as yellow solid (1.56 g, 82.1% yield). MS (ESI+) m/z 263.9 (M+H)⁺; ¹H NMR (400 MHz, DMSO-d₆) δ: 8.51 (d, J=2.0 Hz, 1H), 7.94 (dd, J=8.3, 2.4 Hz, 1H), 7.55 (d, J=8.3 Hz, 1H).

2-chloro-5-(5-iodo-1-((trimethylsilyl)methyl)-1H-1,2,3-triazol-4-yl) pyridine (432B)

CuI (108.4 mg, 5.69 mmol, 1.0 eq) and Et₃N (1.6 mL, 11.39 mmol, 2.0 eq) were stirred in THF (60 mL) at room temperature under nitrogen for 1 hour. A solution of 432A (1.5 g, 5.69 mmol, 1.0 eq) and (azidomethyl)trimethylsilane (735.8 mg, 5.69 mmol, 1.0 eq) in THF (20 mL) was added in a single portion to above catalyst solution. Then, the mixture was stirred at room temperature for 16 h. The reaction was quenched by addition of 10% ammonium chloride solution (15 mL) and concentrated. The residue was washed with water (30 mL) and EtOAc (8 mL) to afford 432B as yellow solid (1.6 g, 72.7% yield), which was used to next step directly. $^1$H NMR (400 MHz, DMSO-d$_6$) δ 8.74 (d, J=2.3 Hz, 1H), 8.14 (dd, J=8.3, 2.5 Hz, 1H), 7.51 (d, J=8.4 Hz, 1H), 3.80 (s, 2H), 0.00 (s, 9H). MS (ESI+) m/z 393.0 (M+H)$^+$ 2-chloro-5-(5-iodo-1-methyl-1H-1,2,3-triazol-4-yl)pyridine (432C)

To a solution of 432B (1.6 g, 4.07 mmol, 1.0 eq) in THF (70 mL) was added water (0.15 mL, 8.15 mmol, 2.0 eq), followed by addition of TBAF (4.9 mL, 4.89 mmol, 1.2 eq) dropwise at 0° C. The resulting reaction mixture was stirred at 0° C. for 15 min and poured into water (100 mL), which ws extracted with DCM (300 mL). The separated organic layer was washed with brine (80 mL), dried over Na$_2$SO$_4$ and concentrated. The residue was purified by flashed column (petroleum ether:EtOAc:DCM: 2:1:1) to obtain 432B as yellow solid (810 mg, 62.3% yield). MS (ESI+) m/z 320.9 (M+H)$^+$; $^1$H NMR (400 MHz, DMSO-d$_6$) δ: 8.91 (d, J=2.1 Hz, 1H), 8.32 (dd, J=8.4, 2.5 Hz, 1H), 7.70 (d, J=8.4 Hz, 1H), 4.13 (s, 3H).

2-chloro-5-(5-fluoro-1-methyl-1H-1,2,3-triazol-4-yl)pyridine (432)

A suspension of 406B (800 mg, 2.50 mmol, 1.0 eq) and KF (1.5 g, 25.00 mmol, 10.0 eq) in acetonitrile/water (14 mL, 1:1) was reacted in microwave reactor at 160° C. for 20 min. After evaporation under reduced pressure, the residue was dissolved with DCM (300 mL) and filtered. The filtrate was concentrated and purified by flash column (petroleum ether:EtOAc:DCM: 2:1:1) to afford Example 432 as yellow solid (220 mg, 41.4% yield). MS (ESI+) m/z 213.0 (M+H)$^+$; $^1$H NMR (400 MHz, DMSO-d$_6$) δ 8.77 (d, J=2.4 Hz, 1H), 8.17 (dd, J=8.3, 2.4 Hz, 1H), 7.67 (d, J=8.3 Hz, 1H), 4.01 (s, 3H).

4-nitrophenyl (6-bromopyridin-3-yl) carbamate (433A)

To a solution of 6-bromopyridin-3-amine (600 mg, 3.47 mmol, 1.0 eq) in acetonitrile (20 mL) was added 4-nitrophenyl carbonochloridate (768.9 mg, 3.81 mmol, in 4 mL acetonitrile, 1.1 eq) dropwise, and the system temperature was maintained below 40° C. After the addition, the mixture was continued to stir at room temperature for 30 min and a yellow precipitate was observed. The precipitate was filtered and washed with acetonitrile (2 mL) to afford 433A as a yellow solid (1.1 g, ~50% purity), which was used in the next step without further purification.

General Procedure 10

3-(6-bromopyridin-3-yl)-1-methylimidazolidine-2,4-dione (Example 433)

A solution of methyl 2-(methylamino) acetate hydrochloride (454.1 mg, 3.25 mmol, 1.0 eq) and DIPEA (1.7 mL, 9.76 mmol, 3.0 eq) in acetonitrile (15 mL) was stirred at room temperature for 15 min. 433A (1.1 g, 3.25 mmol, 1.0 eq) was added, and the resulting system was continued to stir at room temperature for 10 min. The mixture was concentrated and the residue was purified by flash column (petroleum ether:EtOAc: 1:1) to afford compound Example 433 as a yellow oil (510 mg, 54.6% yield by two steps). MS (ESI+) m/z 270.1 (M+H)$^+$; $^1$H NMR (400 MHz, DMSO-d$_6$) δ 8.48-8.52 (m, 1H), 7.82-7.89 (m, 2H), 4.19 (s, 2H), 3.00 (s, 3H).

Scheme 68

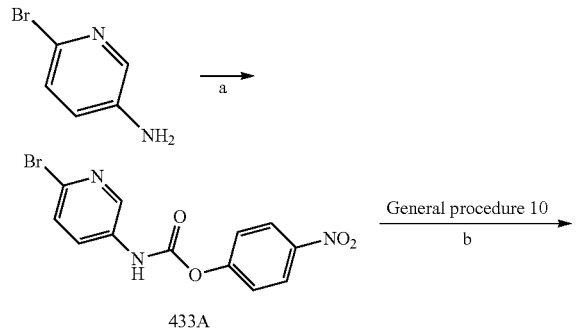

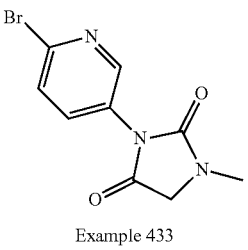

Example 433 a) 4-nitrophenyl carbonochloridate, CH$_3$CN; b) methyl 2-(methylamino)acetate hydrochloride, DIPEA, CH$_3$CN Scheme 69

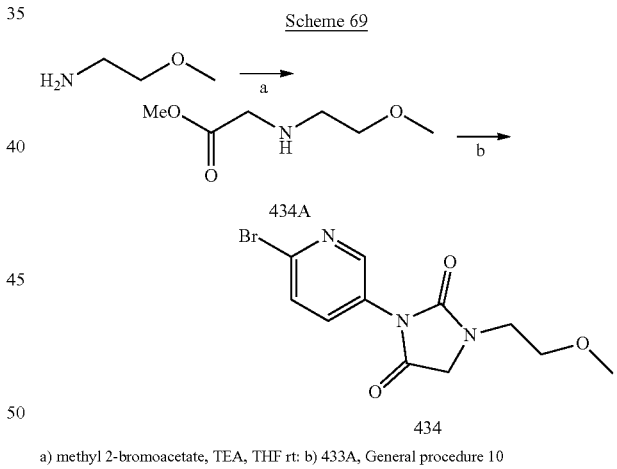

a) methyl 2-bromoacetate, TEA, THF rt: b) 433A, General procedure 10

Methyl (2-methoxyethyl) glycinate (434A)

To a solution of 2-methoxyethan-1-amine (2.9 mL, 33.36 mmol, 1.0 eq) in THF (40 mL) was added dropwise Et$_3$N (9.3 mL, 66.90 mmol, 2.0 eq), followed by the addition of methyl 2-bromoacetate (2.8 mL, 29.58 mmol, 0.9 eq). The reaction mixture was stirred at room temperature for 19 h. The reaction mixture was diluted with EA then washed with water and brine. The organic phase was dried over Na$_2$SO$_4$, filtered and concentrated under reduced pressure. The crude residue was purified by flash chromatography on silica gel (DCM:MeOH=20:1) to afford 434A (830 mg) as a colorless liquid. ¹H NMR (400 MHz, DMSO-d₆) δ 3.62 (s, 3H), 3.38-3.34 (m, 4H), 3.23 (s, 3H), 2.65 (t, J=5.6 Hz, 2H).

3-(6-bromopyridin-3-yl)-1-(2-methoxyethyl) imidazolidine-2, 4-dione (Example 434)

Methods analogous to those described above from starting material 434A and 433A afforded Example 434 as a yellow solid: ¹H NMR (400 MHz, CDCl₃) δ 8.59 (d, J=2.6 Hz, 1H), 7.74 (dd, J=8.5, 2.7 Hz, 1H), 7.58 (d, J=8.5 Hz, 1H), 4.22 (s, 2H), 3.70-3.64 (m, 2H), 3.64-3.60 (m, 2H), 3.39 (s, 3H). ESI (M+H)=314.3.

Scheme 70

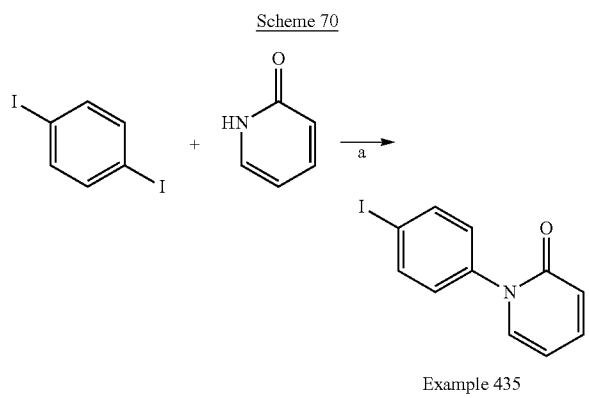

a) CuI K₂CO₃ DMSO 130° C.

1-(4-iodophenyl) pyridin-2(1H)-one (435)

A solution of 1,4-diiodobenzene (1.0 g, 3.0 mmol, 1.0 eq), pyridin-2(1H)-one (288 mg, 3 mmol, 1.0 eq), CuI (58 mg, 0.3 mmol, 0.1 eq) and K₂CO₃ (828 mg, 6 mmol, 2.0 eq) in DMSO (10 mL) was stirred at 130° C. under N₂ for 2 h. The reaction mixture was cooled down to room temperature and diluted with ethyl acetate (30 mL). The organic mixture was washed with water and brine in turn, dried over Na₂SO₄, filtered and concentrated under reduced pressure. The crude residue was purified by flash chromatography on silica gel (PE:EA=10:1 to EA) to afford 200 mg of Example 435 as a white solid. ESI (M+H)⁺=298.09

Scheme 71

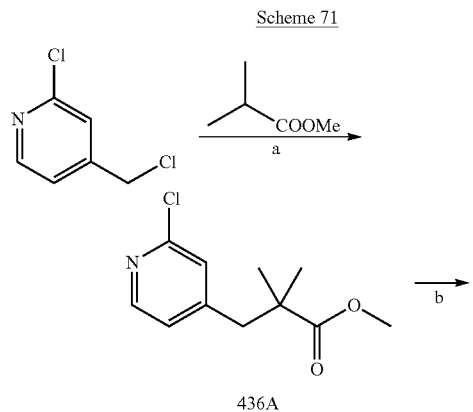

-continued

General procedure 8

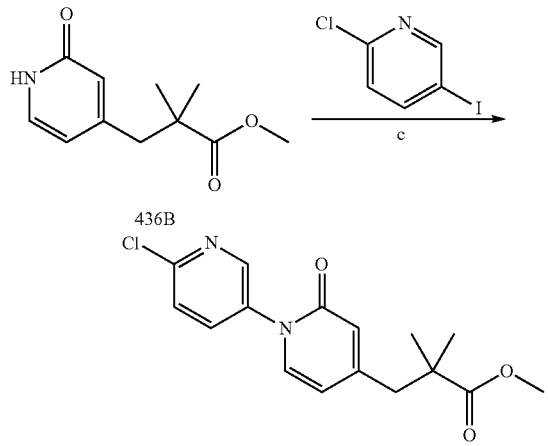

a) LDA, THF, -78° C.; b)CH₃COONa acetic acid MW 160° C.;
c) N₁,N₂-dimethylcyclohexane-1,2-diamine K₂CO₃ CuI dioxane 110° C.;

Methyl 3-(2-chloropyridin-4-yl)-2,2-dimethylpropanoate (436A)

A solution of methyl isobutyrate (3.3 g, 32.0 mmol, 2.08 eq) in THF (25 mL) was added dropwise to a solution of LDA (17 mL, 34.0 mmol, 2.2 eq) in THF (50 mL) at -78° C. under N₂ atmosphere over 15 min. The resulting mixture was stirred at -78° C. for 45 minutes, and then treated with a solution of 2-chloro-4-(chloromethyl) pyridine (2.5 g, 15.4 mmol, 1.0 eq) in THF (6 mL) over 5 minutes. The cooling bath was removed, and the reaction mixture was stirred for 18 h at rt. 1.0 N aq. hydrochloric acid was added dropwise to above solution (50 mL) to quench the reaction. The organic phase was separated, the aqueous phase was extracted with ethyl acetate. The combined organic layers were washed with water, dried over sodium sulfate, and concentrated under vacuum. The crude product was purified by column chromatograph to provide compound 436A (3.2 g) as a yellow oil: LCMS: m/z 228.0. ¹H NMR (400 MHz, CDCl₃) δ 8.33-8.21 (m, 1H), 7.16-7.07 (m, 1H), 6.98 (dd, J=5.1, 1.5 Hz, 1H), 3.68 (s, 3H), 2.84 (s, 2H), 1.21 (s, 6H).

Methyl 2,2-dimethyl-3-(2-oxo-1,2-dihydropyridin-4-yl) propanoate (436B)

A solution of 436A (1.2 g, 5.3 mmol, 1.0 eq) sodium acetate (868 mg, 10.6 mmol, 2.0 eq) in acetic acid (5.3 mL) was heated in a microwave reactor at 160° C. for 1 h. The mixture was concentrated under vacuum and the residue was poured into water. The aqueous phase was extracted twice with 15% isopropanol in DCM. The combined organic layers were washed with sat. aq. NaHCO₃ and dried over Na₂SO₄, and concentrated under vacuum. The crude residue was purified by flash chromatography on silica gel (DCM:MeOH=20:1) to afford 436B (330 mg) as a white solid: ESI [M+H]⁺=210.24.

General Procedure 11

Methyl 3-(6'-chloro-2-oxo-2H-[1,3'-bipyridin]-4-yl)-2,2-dimethylpropanoate (436C)

A suspension of 436B (330 mg, 1.58 mmol, 1.0 eq), 2-chloro-5-iodopyridine (567 mg, 2.37 mmol, 1.5 eq), N₁, $N_2$-dimethylcyclohexane-1,2-diamine (44.8 mg, 0.316 mmol, 0.2 eq), CuI (60 mg, 0.316 mmol, 0.2 eq) and $K_3CO_3$ (436 mg, 3.16 mmol, 2.0 eq) in dioxane (8 mL) was stirred at 110° C. for overnight under $N_2$. The reaction mixture was cooled to room temperature and concentrated under reduced pressure. The crude residue was purified by flash chromatography on silica gel (PE:EtOAc=3:1 to PE:EtOAc=1:1) to afford 436C (350 mg) as a yellow oil: ESI $[M+H]^+$=321.77.

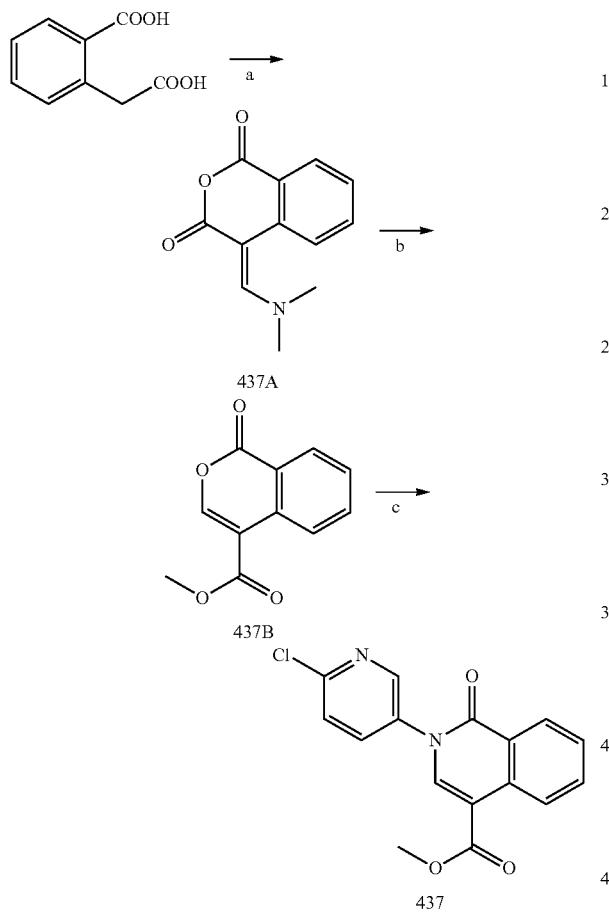

a) POCl3, DMF, 0° C.; b) HCl, MeOH, rf; c) 6-chloropyridin-3-amine, HOAc, 120° C.

(E)-4-((dimethylamino) methylene) isochromane-1,3-Dione (437A)

Phosphoryl chloride (10 mL, 107 mmol, 2.1 eq) was added, with stirring, to a solution of 2-(carboxymethyl) benzoic acid (10 g, 50 mmol, 1.0 eq) in DMF (100 mL) at 0° C. The resulting mixture was stirred for a further 1 h, and then poured into ice water. The precipitate formed was collected by filtration and washed with water to give the 437A as a yellow solid (10 g).

Methyl 1-oxo-1H-isochromene-4-carboxylate (437B)

Dry hydrogen chloride gas was passed through a stirring solution of 437A (6.2 g, 0.03 mmol, 1.0 eq) in methanol (180 mL) at room temperature for 2 h. The solution was heated under reflux for 2 h and then concentrated under reduced pressure. The residue was diluted with water and then extracted with DCM (20 mL×3). The combined organic layers were washed with brine (20 mL), dried over $Na_2SO_4$, filtered and concentrated. The crude residue was purified by column chromatography on silica gel (PE:EA=3:1) to afford 437B (1.9 g).

Methyl 2-(6-chloropyridin-3-yl)-1-oxo-1,2-dihydroisoquinoline-4-carboxylate (Example 437)

A solution of 437B (0.83 g, 0.41 mmol, 1.0 eq) and 6-chloropyridin-3-amine (0.53 g, 0.41 mmol, 1.0 eq) in AcOH (15 mL) was heated to 120° C. and stirred for 2 h. The system was cooled down to room temperature and concentrated under reduced pressure. The crude residue was purified by column chromatography on solica gel (PE:EA=10:1) to afford Example 437 (400 mg).

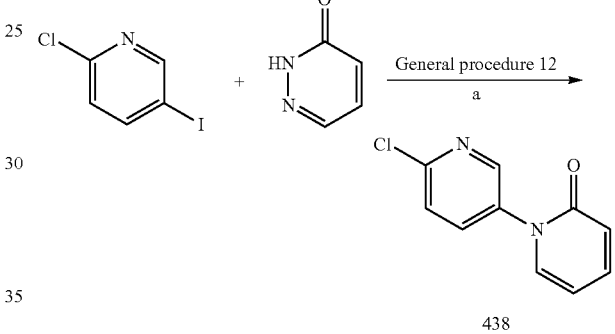

a) CuI, $K_2CO_3$, $N_1,N_2$-dimethylcyclohexane-1,2-diamine, DMSO, 120° C.

General Procedure 12

2-(6-chloropyridin-3-yl) pyridazin-3(2H)-one (438)

A mixture of 2-chloro-5-iodopyridine (5.95 g, 25 mmol, 1.0 eq), pyridazin-3(2H)-one (2.52 g, 26.3 mmol, 1.05 eq), CuI (475 mg, 2.5 mmol, 0.1 eq), trans-N,N'-Dimethyl-1,2-cyclohexanediamine (534 mg, 3.76 mmol, 0.15 eq) and $K_2CO_3$ (6.9 g, 50 mmol, 2.0 eq) in DMSO (25 mL) was stirred at 120° C. under $N_2$ atmosphere overnight. The mixture was cooled down to room temperature and filtered. The filtrate was diluted with water and then extracted with EA (200 mL×2). The combined organic layers were washed with brine, dried over $Na_2SO_4$, filtered, concentrated. The resulting residue was purified by chromatography on silica gel eluting with PE:EA=5:1-1:1 to afford 438 (3.6 g, 69%) as a white solid.

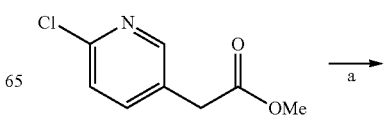

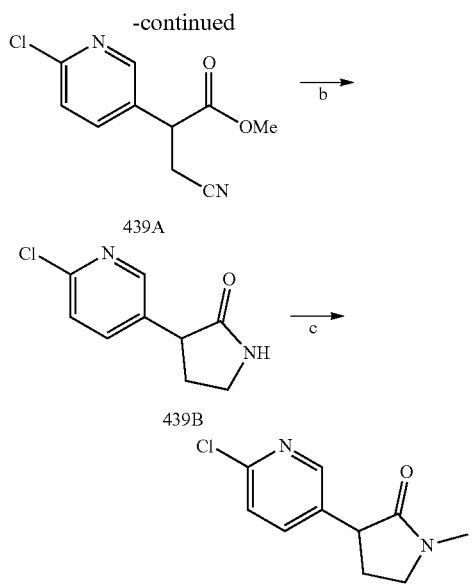

Example 439
a) LiHMDS, BrCH₂CN, -78° C.; b)NaBH₄, CoCl₂, THF/H₂O, 0° C.-rt; c) NaH, MeI, THF, 0° C.-rt

Methyl 2-(6-chloropyridin-3-yl)-3-cyanopropanoate (439A)

To a cold (−78° C.) solution of methyl 2-(6-chloropyridin-3-yl) acetate (3.0 g, 16.2 mmol, 1.0 eq) in THF (30 mL) was added dropwise LiHMDS (24.24 mL, 24.24 mmol, 1.5 eq). The reaction mixture was stirred at −78° C. for 2 h. 2-bromoacetonitrile (1.7 mL, 24.24 mmol, 1.5 eq) was added dropwise at −78° C. The reaction mixture was stirred at at −78° C. for another 2 h before it was quenched by water. The reaction mixture was extracted with EA three times. The combined organic phases were washed with brine, dried over Na₂SO₄, filtered and concentrated under reduced pressure. The crude residue was purified by flash chromatography on silica gel (PE:EA=2:1) to afford 439A (1.46 g) as a yellow oil. ESI (M+H)=225.3

3-(6-chloropyridin-3-yl) pyrrolidin-2-one (439B)

To a cold (0 □) solution of 439A (700 mg, 3.1 mmol, 1.0 eq) and CoCl₂ (370 mg, 1.56 mmol, 0.5 eq) in THF/water (6 mL/3 mL) was added NaBH₄ (590 mg, 15.6 mmol, 5.0 eq) under N₂ at 0 □. The reaction mixture was stirred for 2 h while the temperature was allowed to warm up to room temperature. The reaction was then quenched with saturated NH₄Cl and filtered through celite. The filtrate was extracted with DCM three times. The combined organic layers were washed with brine, dried over Na₂SO₄, filtered and concentrated under reduced pressure. The crude residue was purified by flash chromatography on silica gel (PE:EA=1:1) to afford 439B (360 mg) as a white solid: $^1$H NMR (400 MHz, CDCl₃) δ 8.32 (d, J=2.5 Hz, 1H), 7.64 (dd, J=8.3, 2.5 Hz, 1H), 7.33 (d, J=8.3 Hz, 1H), 3.65 (t, J=9.4 Hz, 1H), 3.54-3.50 (m, 2H), 2.66 (ddd, J=13.5, 9.4, 4.9 Hz, 1H), 2.32-2.15 (m, 1H). ESI (M+H)⁺=197.2.

3-(6-chloropyridin-3-yl)-1-methylpyrrolidin-2-one (Example 439)

To a cold (0 □) solution of 439B (210 mg, 1.1 mmol, 1.0 eq) in THF (10 mL) was added 60% NaH (64 mg, 1.6 mmol, 1.5 eq). The reaction mixture was stirred at 0 □ for 15 minutes before the addition of iodomethane (0.053 mL, 0.8 mmol, 0.8 eq) in THF (0.5 mL) dropwise. The resulting solution was continued to stir for another 2 h at 0° C. and quenched with saturated NH₄Cl. The system was partitioned and separated, and the aqueous phase was then extracted with EA three times. The combined organic phases were dried over Na₂SO₄, filtered and concentrated under reduced pressure. The crude residue was purified by flash chromatography on silica gel (PE:EA=1:4) to afford Example 439 (80 mg) as a brown oil. ESI (M+H)=211.2

Using the above procedures, the following examples were synthesized:

| Structure | Ex. # | $^1$H NMR | LC-MS (M + H)⁺ |
|---|---|---|---|
| 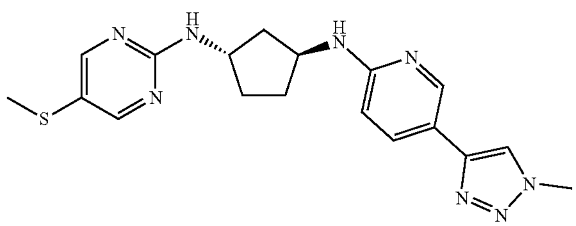 | 440 | $^1$H NMR (400 MHz, CD₃OD) δ: 8.37 (s, 1H), 8.33 (s, 2H), 8.13 (s, 1H), 7.81 (d, J = 7.2 Hz, 1H), 6.60 (d, J = 7.2 Hz, 1H), 4.40-4.32 (m, 2H), 4.13 (s, 3H), 2.28-2.24 (m, 2H), 2.35 (s, 3H), 2.28-2.24 (m, 2H), 2.03-1.97 (m, 2H), 1.63-1.60 (m, 2H). | 383 |
| 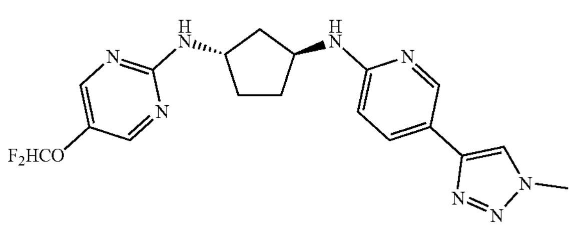 [SMILES: Cn1cc(-c2ccc(N[C@H]3CC[C@H](Nc4ncc(OC(F)F)cn4)C3)nc2)nn1] | 441 | $^1$H NMR (400 MHz, CD₃OD) δ 8.37 (d, J = 2 Hz, 1H), 8.16 (s, 2H), 8.13 (s, 1H) 7.82 (dd, J = 9.2 Hz, 2.4 Hz, 1H), 6.69 (t, J = 73.6 Hz, 1H), 6.60 (d, J = 8.4 Hz, 1H), 4.39-4.31 (m, 2H), 4.15 (s, 3H), 2.29-2.22 (m, 2H), 2.04-1.96 (m, 2H), 1.63-1.58 (m, 2H). | 403.1 |

-continued

| Structure | Ex. # | ¹H NMR | LC-MS (M + H)⁺ |
|---|---|---|---|
| 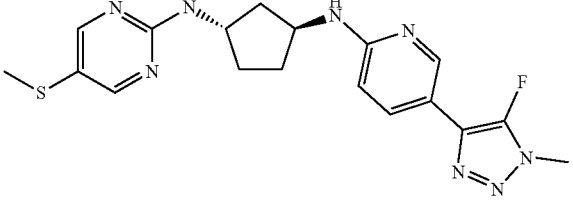 | 442 | ¹H NMR (400 MHz, CD₃OD) δ: 8.37 (s, 2H), 8.25 (dd, J = 9.4, 2.0 Hz, 1H), 8.13 (d, J = 1.6 Hz, 1H), 7.18 (d, J = 9.4 Hz, 1H), 4.44-4.51 (m, 1H), 4.19-4.32 (m, 1H), 4.03 (d, J = 1.1 Hz, 3H), 2.25-2.47 (m, 5H), 2.10-2.22 (m, 2H), 1.68-1.83 (m, 2H) | 401 |
| 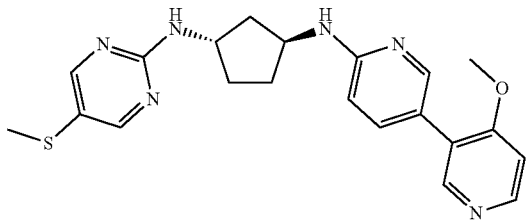 [SMILES: COc1ccncc1-c1ccc(N[C@H]2CC[C@H](Nc3ncc(SC)cn3)C2)nc1] | 443 | ¹H NMR (400 MHz, CD₃OD) δ: 8.36-8.28 (m, 4H), 8.08 (s, 1H), 7.61 (d, J = 8.8 Hz, 1H), 7.13 (d, J = 5.6 Hz, 1H), 6.59 (d, J = 8.8 Hz, 1H), 4.42-4.30 (m, 2H), 3.93 (s, 3H), 2.35 (s, 3H), 2.29-2.25 (m, 2H), 2.04-1.98 (m, 2H), 1.63-1.60 (m, 2H). | 409 |
| 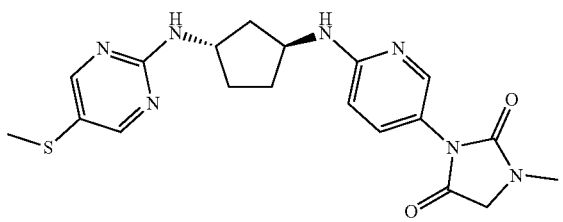 | 444 | ¹H NMR (METHANOL-d₄) δ: 8.32 (s, 2H), 7.91 (d, J = 2.3 Hz, 1H), 7.36 (dd, J = 8.9, 2.4 Hz, 1H), 6.57 (d, J = 9.0 Hz, 1H), 4.37-4.45 (m, 1H), 4.23-4.35 (m, 1H), 4.08 (s, 2H), 3.02 (s, 3H), 2.34 (s, 3H), 2.20-2.31 (m, 2H), 1.93-2.07 (m, 2H), 1.52-1.67 (m, 2H) | 414 |
| 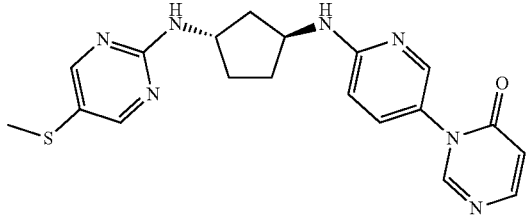 [SMILES: CSc1cnc(N[C@H]2CC[C@H](Nc3ccc(-n4cnccc4=O)cn3)C2)nc1] | 445 | ¹H NMR (400 MHz, CD₃OD): δ 8.33-8.47 (m, 3H), 8.15 (d, J = 2.3 Hz, 1H), 8.03 (d, J = 6.8 Hz, 1H), 7.93 (dd, J = 9.6, 2.4 Hz, 1H), 7.09 (d, J = 9.6 Hz, 1H), 6.59 (dd, J = 6.8, 0.8 Hz, 1H), 4.39-4.51 (m, 1H), 4.22-4.33 (m, 1H), 2.27-2.47 (m, 5H), 2.06-2.22 (m, 2H), 1.68-1.85 (m, 2H) | 396 |
| 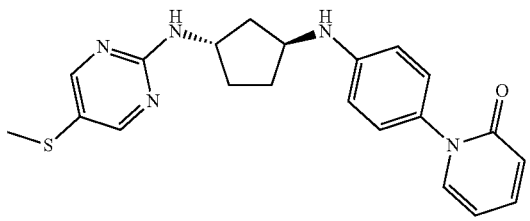 [SMILES: CSc1cnc(N[C@H]2CC[C@H](Nc3ccc(-n4ccccc4=O)cc3)C2)nc1] | 446 | ¹H NMR (400 MHz, CD₃OD) δ 8.32 (s, 2H), 7.64-7.47 (m, 2H), 7.15-7.03 (m, 2H), 6.75-6.68 (m, 2H), 6.60 (d, J = 8.9 Hz, 1H), 6.44 (t, J = 6.7, 1.3 Hz, 1H), 4.41 (m, 2H), 3.99 (m, 2H), 2.35 (s, 3H), 2.30-2.17 (m, 2H), 2.03-1.93 (m, 2H), 1.69-1.50 (m, 2H). | 394.5 |
| 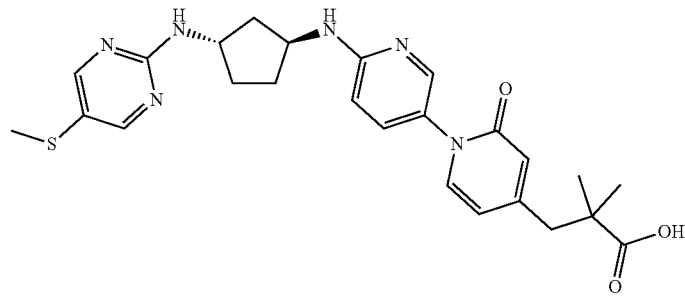 [SMILES: CSc1cnc(N[C@H]2CC[C@H](Nc3ccc(-n4ccc(CC(C)(C)C(=O)O)cc4=O)cn3)C2)nc1] | 447 | ¹H NMR (400 MHz, CD₃OD) δ 8.23 (s, 2H), 7.83 (d, J = 2.4 Hz, 1H), 7.41-7.29 (m, 2H), 6.82 (s, 1H), 6.51 (d, J = 8.9 Hz, 1H), 6.35 (s, 1H), 6.26 (dd, J = 7.0, 1.8 Hz, 1H), 4.33-4.18 (m, 2H), 2.70 (s, 2H), 2.25 (s, 3H), 2.21-2.10 (m, 2H), 1.96-1.80 (m, 2H), 1.56-1.41 (m, 2H), 1.30 (s, 6H). | 495 |

-continued

| Structure | Ex. # | ¹H NMR | LC-MS (M + H)⁺ |
|---|---|---|---|
| 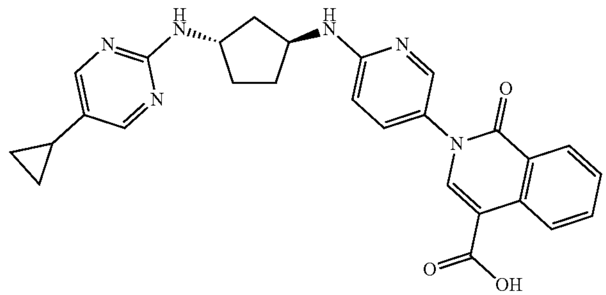 [SMILES: O=C(O)c1cn(-c2ccc(N[C@H]3CC[C@H](Nc4ncc(C5CC5)cn4)C3)nc2)c(=O)c2ccccc12] | 448 | 1H NMR (400 MHz, DMSO-d₆) δ: 12.87 (s, 1H), 8.87-8.85 (d, J = 8.4 Hz, 1H), 8.31-8.29 (m, 1H), 8.15 (s, 1H), 8.07 (s, 2H), 8.06 (d, J = 5.6 Hz, 1H), 7.87-7.83 (m, 1H), 7.63-7.59 (m, 1H), 7.52-7.50 (m, 1H), 7.02-6.97 (m, 2H), 6.58-6.55 (d, J = 8.8 Hz, 1H), 4.35-4.30 (m, 2H), 2.18-2.07 (m, 2H), 1.93-1.66 (m, 2H), 1.75-1.69 (m, 1H), 1.55-1.47 (m, 2H), 0.86-0.81 (m, 2H), 0.62-0.58 (m, 2H). | 483.3 |
| 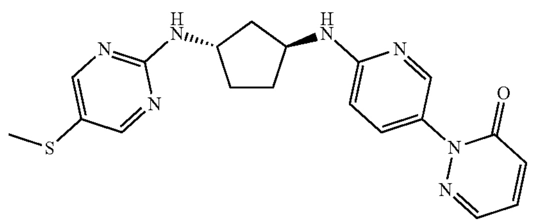 | 449 | ¹H NMR (400 MHz, CD₃OD) δ 8.42-8.31 (m, 3H), 8.21 (dd, J = 9.7, 2.4 Hz, 1H), 8.07 (dd, J = 3.9, 1.6 Hz, 1H), 7.49 (dd, J = 9.5, 3.9 Hz, 1H), 7.16-7.05 (m, 1H), 4.47 (p, J = 6.8 Hz, 1H), 4.31-4.18 (m, 1H), 2.50-2.24 (m, 2H), 2.22-2.04 (m, 1H), 1.86-1.64 (m, 1H). | 395.5 |
| 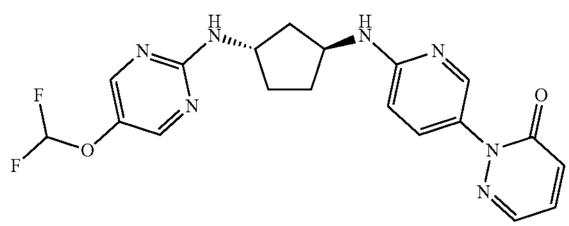 [SMILES: O=c1cccnn1-c1ccc(N[C@H]2CC[C@H](Nc3ncc(OC(F)F)cn3)C2)nc1] | 450 | 1H NMR (400 MHz, CD₃OD) δ 8.16-8.14 (t, J = 7.6 Hz, 3H), 8.03-8.01 (m, 1H), 7.62-7.59 (m, 1H), 7.47-7.44 (m, 1H), 7.07-7.04 (m, 1H), 6.87-6.50 (m, 2H), 4.40-4.32 (m, 2H), 2.28-2.24 (m, 2H), 2.03-2.00 (m, 2H), 1.62-1.57 (m, 2H). | 416.5 |
| 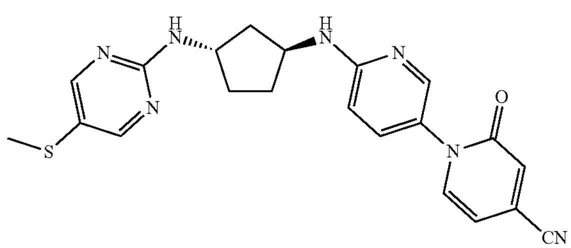 [SMILES: CSc1cnc(N[C@H]2CC[C@H](Nc3ccc(-n4ccc(C#N)cc4=O)cn3)C2)nc1] | 451 | ¹H NMR (400 MHz, CD₃OD) δ 8.32 (s, 2H), 7.96 (d, J = 2.8 Hz, 1H), 7.76 (d, J = 7.2 Hz, 1H), 7.45 (dd, J = 2.8, 9.2 Hz, 1H), 7.01 (d, J = 1.2 Hz, 1H), 6.60 (d, J = 9.2 Hz, 1H), 6.57 (dd, J = 2.0, 7.2 Hz, 1H), 4.41-4.34 (m, 2H), 2.41 (s, 3H), 2.34-2.23 (m, 2H), 2.02-1.97 (m, 2H), 1.62-1.59 (m, 2H). | |
| 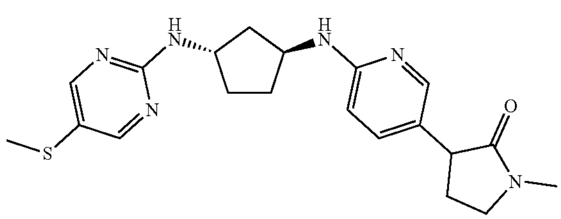 | 452 | ¹H NMR (400 MHz, CD₃OD) δ 8.39 (s, 2H), 7.82 (dd, J = 9.4, 2.1 Hz, 1H), 7.75 (d, J = 2.0 Hz, 1H), 7.06 (d, J = 9.3 Hz, 1H), 4.47 (p, J = 7.0 Hz, 1H), 4.27-4.14 (m, 1H), 3.75 (t, J = 9.6 Hz, 1H), 3.57-3.44 (m, 2H), 2.93 (d, J = 10.0 Hz, 3H), 2.60-2.47 (m, 1H), 2.45-2.25 (m, 5H), 2.18-2.02 (m, 3H), 1.80-1.65 (m, 2H). | 399.3 |
| 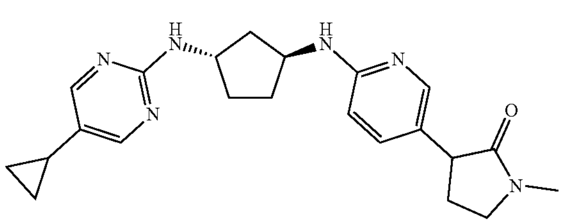 [SMILES: CN1CCC(c2ccc(N[C@H]3CC[C@H](Nc4ncc(C5CC5)cn4)C3)nc2)C1=O] | 453 | ¹H NMR (400 MHz, MeOD) δ 8.06 (s, 2H), 7.80 (d, J = 2.3 Hz, 1H), 7.31 (dd, J = 8.7, 2.4 Hz, 1H), 6.55 (d, J = 8.7 Hz, 1H), 4.40-4.30 (m, 1H), 4.29-4.19 (m, 1H), 3.58 (t, J = 9.2 Hz, 1H), 3.53-3.45 (m, 2H), 2.9 (s, 3H), 2.54-2.43 (m, 1H), 2.30-2.16 (m, 2H), 2.09-1.99 (m, 1H), 1.99-1.89 (m, 2H), 1.79-1.70 (m, 1H), 1.63-1.50 (m, 2H), 0.95-0.84 (m, 2H), 0.65-0.55 (m, 2H). | |

-continued

| Structure | Ex. # | ¹H NMR | LC-MS (M + H)⁺ |
|---|---|---|---|
| 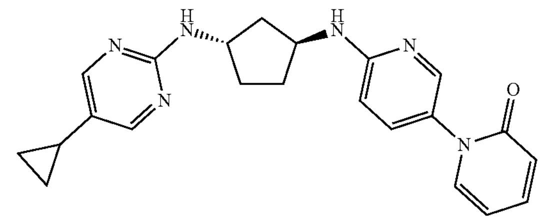 [SMILES: O=c1ccccn1-c1ccc(N[C@H]2CC[C@H](Nc3ncc(C4CC4)cn3)C2)nc1] | 454 | ¹H NMR (400 MHz, CD₃OD) δ: 8.07 (s, 2H), 7.93 (s, 1H), 7.59-7.56 (m, 2H), 7.45-7.42 (m, 1H), 6.62-6.59 (m, 2H), 6.46-6.45 (m, 1H), 4.28-4.25 (m, 2H), 2.15-2.10 (m, 2H), 2.00-1.97 (m, 2H), 1.80-1.75 (m, 1H), 1.60-1.50 (m, 2H), 0.92-0.89 (m, 2H), 0.61-0.59 (m, 2H). | 389.2 |
| 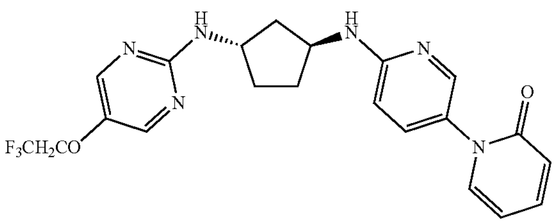 | 455 | ¹H NMR (400 MHz, CD₃OD) δ: 8.14 (s, 2H), 7.93 (t, J = 2.8 Hz, 1H), 7.62-7.56 (m, 2H), 7.44 (dd, J = 8.8 HZ, 2.4 Hz, 1H), 6.61 (d, J = 8.8 Hz, 2H), 6.46 (dt, J = 1.6 Hz, 6.8 Hz 1H), 4.531 (q, J = 8.8 Hz, 2H), 4.36-4.31 (m, 2H), 2.27-2.23 (m, 2H), 2.01-1.97 (m, 2H), 1.62-1.56 (m, 2H). | 447.1 |
| 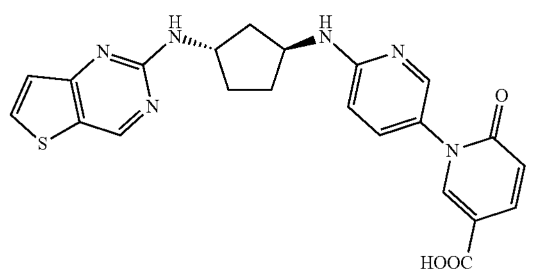 [SMILES: O=C(O)c1ccc(=O)n(-c2ccc(N[C@H]3CC[C@H](Nc4ncc5sccc5n4)C3)nc2)c1] | 456 | 1H NMR (400 MHz, CD₃OD) δ 8.84 (s, 1H), 8.25 (d, J = 0.8 Hz, 1H), 8.09-7.98 (m, 3H), 7.47 (dd, J = 8.4 Hz, 2.8 Hz, 1H), 7.19-7.17 (m, 1H), 6.63 (d, J = 9.2 Hz, 1H), 6.59 (d, J = 9.6 Hz, 1H), 4.51-4.48 (m, 1H), 4.39-4.366 (m, 1H), 2.34-2.27 (m, 2H), 2.08-2.04 (m, 2H), 1.69-1.61 (m, 2H). | 449.4 |
| 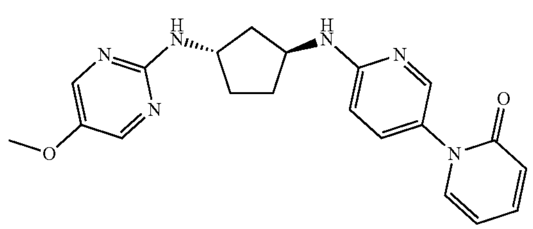 [SMILES: COc1cnc(N[C@H]2CC[C@H](Nc3ccc(-n4ccccc4=O)cn3)C2)nc1] | 457 | ¹H NMR (400 MHz, CD₃OD) δ 8.24 (s, 2H), 8.09 (d, J = 2.2 Hz, 1H), 7.96 (dd, J = 9.6, 2.4 Hz, 1H), 7.70-7.59 (m, 2H), 7.14 (d, J = 9.6 Hz, 1H), 6.65 (dd, J = 10.0, 1.2 Hz, 1H), 6.51 (td, J = 6.8, 1.2 Hz, 1H), 4.47 (m, 1H), 4.37-4.26 (m, 1H), 3.85 (s, 3H), 2.39 (m, 1H), 2.26-2.13 (m, 2H), 1.88-1.71 (m, 2H). | 379.4 |
| 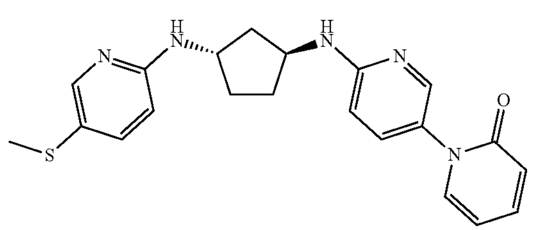 [SMILES: CSc1ccc(N[C@H]2CC[C@H](Nc3ccc(-n4ccccc4=O)cn3)C2)nc1] | 458 | ¹H NMR (400 MHz, MeOD) δ 7.97 (d, J = 2.2 Hz, 1H), 7.94 (d, J = 2.5 Hz, 1H), 7.64-7.56 (m, 2H), 7.50 (dd, J = 8.8, 2.4 Hz, 1H), 7.44 (dd, J = 9.0, 2.7 Hz, 1H), 6.64-6.58 (m, 2H), 6.47 (ddd, J = 11.0, 8.0, 5.0 Hz, 2H), 4.30 (dp, J = 25.7, 6.4 Hz, 2H), 2.32 (d, J = 15.9 Hz, 3H), 2.29-2.18 (m, 2H), 1.99 (q, J = 6.9 Hz, 2H), 1.66-1.51 (m, 2H) | 394.4 |
| 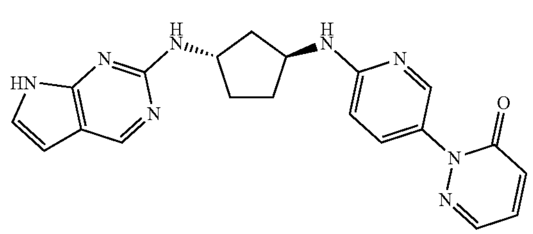 [SMILES: O=c1cccnn1-c1ccc(N[C@H]2CC[C@H](Nc3ncc4cc[nH]c4n3)C2)nc1] | 458A | ¹H NMR (400 MHz, CD₃OD) δ 8.36 (s, 1H), 8.05 (s, 1H), 7.92 (s, 1H), 7.50 (d, J = 8.8 Hz, 1H), 7.35 (d, J = 9.2 Hz, 1H), 6.96 (d, J = 9.2 Hz, 1H), 6.90 (s, 1H), 6.50 (d, J = 8.8 Hz, 1H), 6.25 (s, 1H), 4.30-4.28 (m, 1H), 4.26-4.25 (m, 1H), 2.21-2.18 (m, 2H), 1.97-1.93 (m, 2H), 1.54-1.52 (m, 2H). | 389 |

| Structure | Ex. # | ¹H NMR | LC-MS (M + H)⁺ |
|---|---|---|---|
| 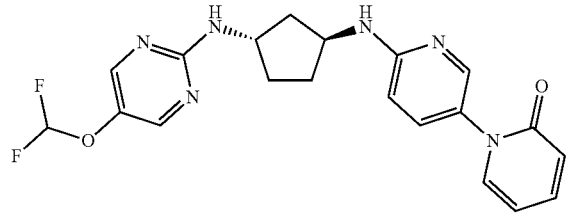 | 458B | ¹H NMR (400 MHz, CD₃OD) δ 8.15 (d, J = 9.1 Hz, 2H), 7.94 (d, J = 2.3 Hz, 1H), 7.66-7.53 (m, 2H), 7.44 (dd, J = 9.0, 2.7 Hz, 1H), 6.69 (t, J = 73.6 Hz, 1H), 6.55 (d, J = 9.2 Hz, 2H), 6.48-6.44 (m, 2H), 4.45-4.28 (m, 2H), 2.33-2.16 (m, 2H), 2.11-1.91 (m, 2H), 1.70-1.51 (m, 2H). | 415.2 |

Scheme 75

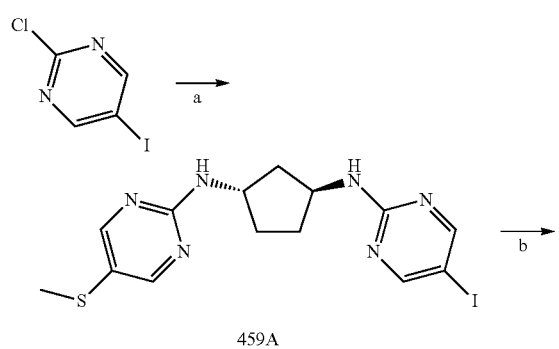

459A a) 131C, General procedure 5; b) pyridin-2(1H)-one, General procedure 1.

1-(2-(((1S,3S)-3-((5-(methylthio) pyrimidin-2-yl) amino) cyclopentyl) amino) pyrimidin-5-yl) pyridin-2(1H)-one (Example 459)

Methods analogous to those described in General Method 5 and General Method 1 from starting material 2-chloro-5-iodopyrimidine afforded the title compound: ¹H NMR (400 MHz, CD₃OD) δ 8.41-8.40 (d, J=2.4 Hz, 2H), 8.34 (s, 2H), 7.63-7.59 (m, 2H), 6.63-6.61 (d, J=8.8 Hz, 1H), 6.49-6.46 (m, 1H), 4.49-4.41 (m, 2H), 2.40-2.39 (d, J=1.2 Hz, 3H), 2.31-2.25 (m, 2H), 2.08-2.05 (t, J=13.6 Hz, 2H), 1.69-1.64 (m, 2H).

Using the above procedures, the following example was synthesized:

| Structure | Ex. # | ¹H NMR | LC-MS (M + H)⁺ |
|---|---|---|---|
| 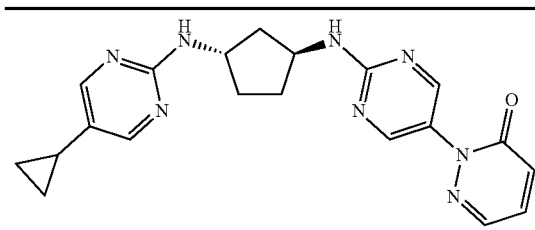 | 460 | ¹H NMR (400 MHz, CD₃OD) δ 8.51 (s, 2H), 8.07 (s, 2H), 8.04 (dd, J = 3.9, 1.5 Hz, 1H), 7.47 (dd, J = 9.5, 3.9 Hz, 1H), 7.07 (dd, J = 9.5, 1.5 Hz, 1H), 4.51-4.43 (m, 1H), 4.42-4.34 (m, 1H), 2.26 (td, J = 10.3, 4.6 Hz, 2H), 2.01 (dt, J = 11.3, 5.5 Hz, 2H), 1.75 (td, J = 8.6, 4.5 Hz, 1H), 1.68-1.54 (m, 2H), 0.94-0.85 (m, 2H), 0.66-0.55 (m, 2H). | 391.3 |

-continued

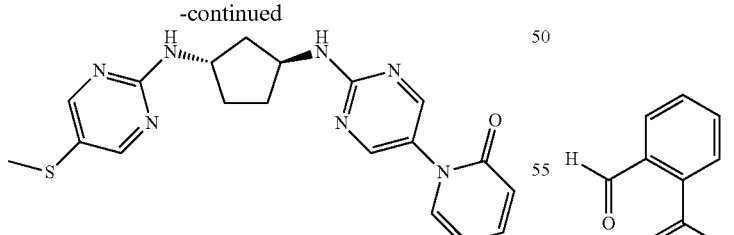

Example 459

Scheme 76

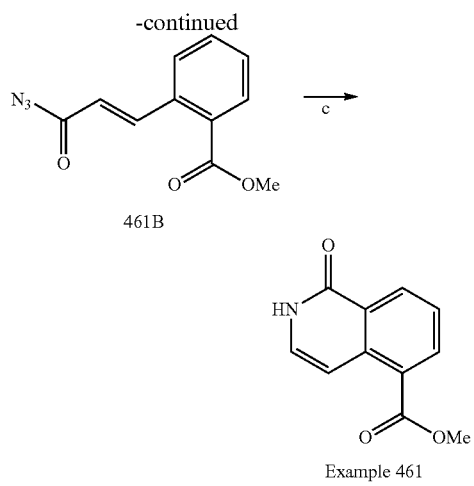

461B

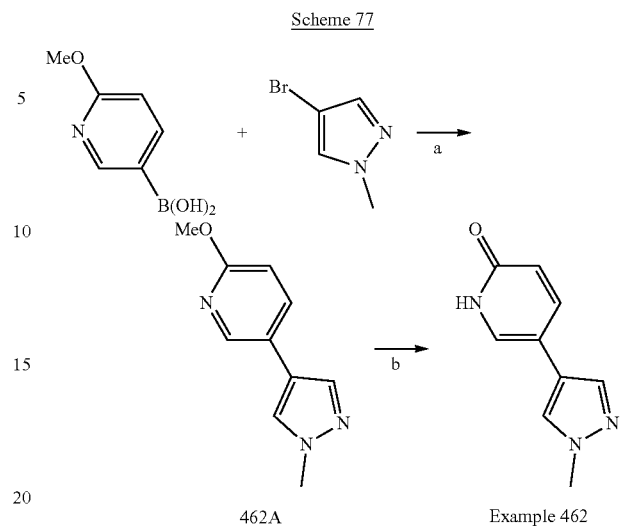

Scheme 77

462A  Example 462 a) Pd(dppf)Cl₂, Cs₂CO₃, dioxane/H₂O, 110° C.; b)HBr, EtOH, 80° C.

Example 461 a) malonic acid, morpholine, pyridine, 100° C.; b) DPPA, Et3N, toluene, rt; c)diphenylmethane, 80-240° C.

(E)-3-(2-(methoxycarbonyl) phenyl) acrylic acid (461A)

A mixture of methyl 2-formylbenzoate (2.5 g, 15.23 mmol, 1.0 eq), malonic acid (1.8 g, 17.67 mmol, and 1.16 eq), morpholine (0.15 mL) and pyridine (4 mL) was stirred at 100° C. for 4 h. After cooling to room temperature, the resulting solution was poured into a mixture of crushed ice (50 g) and 35% aq. HCl (25 mL). The precipitate was filtered, washed with water (25 mL×2). Then, the white solid was recrystallized from methanol to afford 461A (2.0 g, 63.7% yield): $^1$H NMR (400 MHz, CDCl$_3$) δ 8.58 (d, J=15.9 Hz, 1H), 7.99 (dd, J=7.8, 1.1 Hz, 1H), 7.61-7.68 (m, 1H), 7.53-7.60 (m, 1H), 7.41-7.51 (m, 1H), 6.33 (d, J=15.9 Hz, 1H), 3.95 (s, 3H).

(E)-Methyl 2-(3-azido-3-oxoprop-1-en-1-yl) benzoate (461B)

To a solution of 461A (1.2 g, 5.82 mmol, 1.0 eq) and Et$_3$N (1.6 mL 11.64 mmol, 2.0 eq) in toluene (15 mL) was added DPPA (1.2 mL, 5.53 mmol, 0.95 eq) dropwise. The mixture was continued to stir at room temperature for 16 h. The solution was concentrated and purified by flash column (petroleum ether:EtOAc=10:1) to afford 461B as white solid (1.0 g, 74.6% yield): $^1$H NMR (400 MHz, CDCl$_3$) δ 8.56 (d, J=15.8 Hz, 1H), 8.00 (dd, J=7.8, 0.9 Hz, 1H), 7.53-7.67 (m, 2H), 7.42-7.53 (m, 1H), 6.31 (d, J=15.8 Hz, 1H), 3.95 (s, 3H).

Methyl 1-oxo-1,2-dihydroisoquinoline-5-carboxylate (461)

A solution of 461B (500 mg, 2.16 mmol, 1.0 eq) in diphenylmethane (3 mL) was stirred at 80° C. for 1 hour under nitrogen. Then, the mixture was continued to stir at 240° C. for 3 h. After cooling to room temperature, the mixture was purified by flash column (petroleum ether: EtOAc: 2:1) to afford crude product and further purified by Prep-HPLC to afford Example 461 as a white solid (30 mg, 6.8% yield): MS (ESI+) m/z 204.0 (M+H)$^+$; $^1$H NMR (400 MHz, DMSO-d$_6$) δ 11.51 (br. s., 1H), 8.46 (d, J=7.9 Hz, 1H), 8.27 (d, J=6.9 Hz, 1H), 7.57 (t, J=7.8 Hz, 1H), 7.24-7.46 (m, 2H), 3.90 (s, 3H).

2-methoxy-5-(1-methyl-1H-pyrazol-4-yl) pyridine (462A)

A suspension of (6-methoxypyridin-3-yl) boronic acid (820 mg, 5.4 mmol, 1.0 eq), 4-bromo-1-methyl-1H-pyrazole (1.04 g, 6.4 mmol, 1.2 eq), Pd(dppf)Cl$_2$ (392.3 mg, 0.54 mmol, 0.1 eq) and Cs$_2$CO$_3$ (3.5 g, 10.8 mmol, 2.0 eq) in dioxane/water (40 mL/10 mL) was stirred at 110° C. under N$_2$ for 16 h. The reaction mixture was partitioned between ethyl acetate and water. The organic phase was separated and washed with brine, dried over Na$_2$SO$_4$, filtered and concentrated under reduced pressure. The crude residue was purified by flash chromatography on silica gel (DCM:MeOH=20:1) to afford 462A (662.4 mg) as a yellow solid: ESI (M+H)+=190.1.

5-(1-methyl-1H-pyrazol-4-yl) pyridin-2(1H)-one (Example 462)

To a solution of 462A (200 mg, 1.1 mmol) in EtOH (0.5 mL) was added HBr solution (40% in H$_2$O, 2.5 mL). The reaction mixture was stirred at 80□ for 20 h. The reaction mixture was cooled to room temperature and basified by adding aqueous NH$_3$ dropwise. The solvent was evaporated under reduced pressure and the crude residue was purified by flash chromatography (DCM:MeOH:NH$_4$OH)=10:1:0.1) to afford Example 462 (120 mg) as a grey solid. $^1$H NMR (400 MHz, CD$_3$OD) δ 7.94 (dd, J=9.4, 2.6 Hz, 1H), 7.77 (d, J=2.3 Hz, 1H), 7.65 (s, 1H), 7.38 (d, J=1.1 Hz, 1H), 6.57 (dd, J=21.7, 9.3 Hz, 1H), 3.76 (s, 3H). ESI (M+H)$^+$=176.1.

Scheme 78.

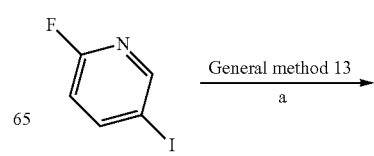

General method 13
a

-continued

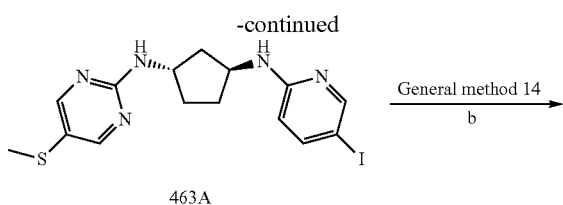

463A

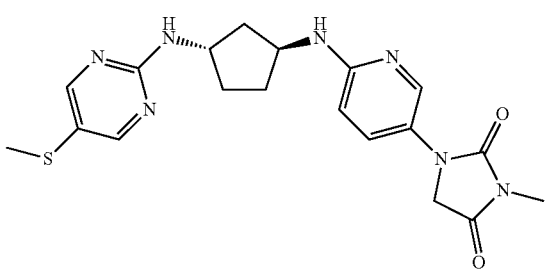

Example 463 a) 131C, K₂CO₃, DMSO, 140° C.; b) 3-methylimidazolidine-2,4-dione, CuI, N₁,N₂-dimethylcycloheane-1,2-diamine, K₃PO₄, i-PrOH, MW. 110° C.

General Method 13

(1S, 3S)—N(5-iodopyridin-2-yl)-N³-(5-(methylthio) pyrimidin-2-yl) cyclopentane-1, 3-diamine (463A)

A suspension of 131C (150 mg, 0.669 mmol, 1.0 eq), 2-fluoro-5-iodopyridine (178.9 mg, 0.802 mmol, 1.2 eq) and K₂CO₃ (277.2 mg, 2.006 mmol, 3.0 eq) in DMSO (5 mL) was stirred at 140° C. under N₂ for 16.5 h. The reaction mixture was cooled down to room temperature and filtered. The filtrate was diluted with ethyl acetate and washed with water and brine, dried over Na₂SO₄, filtered and concentrated under reduced vacuum. The crude residue was purified by flash chromatography on silica gel (PE:EA=1:1) to give 463A (125.5 mg). ESI (M+H)=428.1.

General Method 14

3-Methyl-1-(6-(((1S, 3S)-3-((5-(methylthio) pyrimidin-2-yl) amino) cyclopentyl) amino) pyridin-3-yl) imidazolidine-2, 4-dione (463)

A suspension of 463A (65.5 mg, 0.153 mmol, 1.0 eq), 3-methylimidazolidine-2, 4-dione (35.0 mg, 0.307 mmol, 2.0 eq), N₁, N₂-dimethylcyclohexane-1, 2-diamine (10.9 mg, 0.077 mmol, 0.5 eq), CuI (14.6 mg, 0.077 mmol, 0.5 eq) and K₃PO₄ (97.6 mg, 0.460 mmol, 3.0 eq) in i-PrOH (3 mL) was purged with N₂. The reaction mixture was stirred at 110° C. under microwave irradiation for 4 h. The reaction mixture was concentrated under reduced pressure. The crude residue was purified by flash chromatography on silica gel (DCM:MeOH=20:1) to give Example 463 (20 mg) as a white powder: ¹H NMR (400 MHz, TFA-d₄) δ 8.8 (brs, 2H), 8.40 (d, J=2.4 Hz, 1H), 8.25 (dd, J=9.8, 2.3 Hz, 1H), 7.23 (d, J=9.8 Hz, 1H), 4.83-4.78 (m, 1H), 4.68 (s, 2H), 4.56-4.39 (m, 1H), 3.28 (s, 3H), 2.62-2.49 (m, 2H), 2.54 (s, 3H), 2.45-2.30 (m, 2H), 1.96-1.88 (m, 2H). ESI (M+H)=414.3.

Using the above procedures, the following examples were synthesized:

| Structure | Ex. # | ¹H NMR | LC-MS (M + H)⁺ |
|---|---|---|---|
| 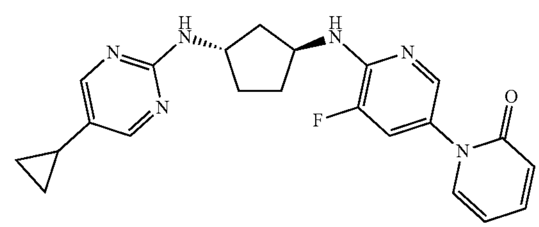 [SMILES: O=c1ccccn1-c1cnc(N[C@H]2CC[C@H](Nc3ncc(C4CC4)cn3)C2)c(F)c1] | 464 | ¹H NMR (400 MHz, CD₃OD) δ 8.31 (s, 2H), 7.85 (d, J = 2.1 Hz, 1H), 7.67-7.53 (m, 2H), 7.44 (dd, J = 11.4, 2.2 Hz, 1H), 6.62 (d, J = 8.9 Hz, 1H), 6.47 (td, J = 6.8, 1.3 Hz, 1H), 4.58 (p, J = 6.8 Hz, 1H), 4.43 (dd, J = 13.0, 6.7 Hz, 1H), 2.43-2.25 (m, 2H), 2.15-2.04 (m, 2H), 1.94-1.81 (m, 1H), 1.78-1.58 (m, 2H), 1.07-0.97 (m, 2H), 0.78-0.67 (m, 2H). | 407.5 |
| 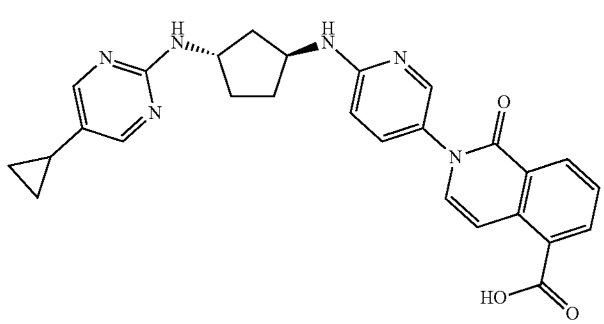 [SMILES: O=C(O)c1cccc2c(=O)n(-c3ccc(N[C@H]4CC[C@H](Nc5ncc(C6CC6)cn5)C4)nc3)ccc12] | 465 | ¹H NMR (400 MHz, DMSO-d₆) δ: 13.34 (br. s., 1H), 8.49 (d, J = 7.4 Hz, 1H), 8.33 (dd, J = 7.6, 1.3 Hz, 1H), 7.99-8.11 (m, 3H), 7.46-7.70 (m, 4H), 7.08 (d, J = 6.1 Hz, 1H), 6.66 (d, J = 8.9 Hz, 1H), 4.25-4.48 (m, 2H), 2.06-2.25 (m, 2H), 1.84-2.02 (m, 2H), 1.65-1.78 (m, 1H), 1.42-1.60 (m, 2H), 0.78-0.92 (m, 2H), 0.54-0.68 (m, 2H) | 483.3 |

| Structure | Ex. # | ¹H NMR | LC-MS (M + H)⁺ |
|---|---|---|---|
| 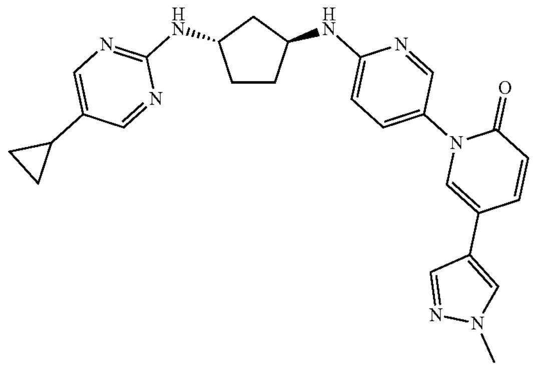 [SMILES: Cn1cc(-c2ccc(=O)n(-c3ccc(N[C@H]4CC[C@H](Nc5ncc(C6CC6)cn5)C4)nc3)c2)cn1] | 466 | ¹H NMR (400 MHz, CD₃OD) δ 8.30 (s, 2H), 8.14 (d, J = 2.2 Hz, 1H), 7.96 (dd, J = 9.5, 2.4 Hz, 1H), 7.89 (dd, J = 8.7, 2.1 Hz, 3H), 7.75 (d, J = 0.5 Hz, 1H), 7.10 (d, J = 9.5 Hz, 1H), 6.70 (dd, J = 8.4, 1.9 Hz, 1H), 4.59-4.48 (m, 1H), 4.38-4.26 (m, 1H), 3.91 (s, 3H), 2.49-2.28 (m, 2H), 2.21 (dt, J = 13.2, 6.7 Hz, 2H), 1.86 (tt, J = 7.9, 4.9 Hz, 1H), 1.82-1.68 (m, 2H), 1.06-0.97 (m, 2H), 0.76-0.62 (m, 2H). | 469.3 |

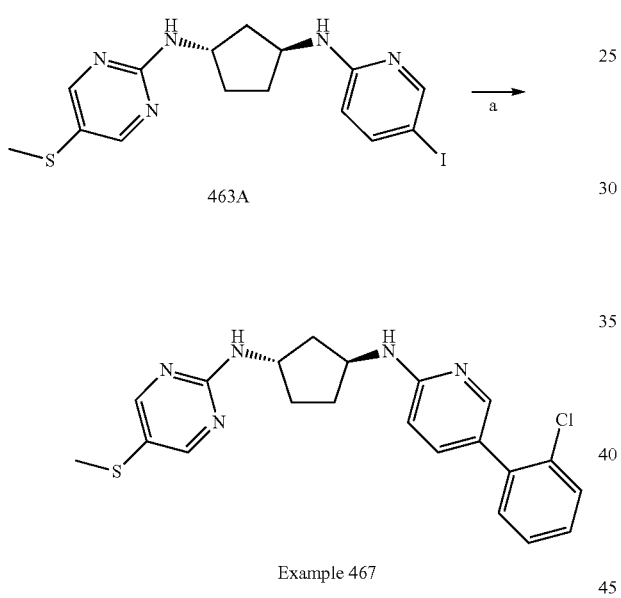

Scheme 79

Example 467 a) (2-chlorophenyl)boronic acid, General procedure 4

(1S, 3S)—N¹-(5-(2-chlorophenyl) pyridin-2-yl)-N³-(5-(methylthio) pyrimidin-2-yl) cyclopentane-1, 3-diamine (Example 467)

Methods analogous to those described in General Method 4 from starting material 463A and (2-chlorophenyl) boronic acid afforded the title compound: ¹H NMR (400 MHz, CDCl₃) δ 10.20 (s, 1H), 8.53 (brs, 1H), 8.45 (s, 2H), 7.95 (dd, J=9.2, 1.4 Hz, 1H), 7.83 (s, 1H), 7.56-7.47 (m, 1H), 7.36 (dd, J=5.9, 3.4 Hz, 2H), 7.25-7.27 (m, 1H), 7.13 (d, J=9.3 Hz, 1H), 4.59 (brs, 1H), 4.24 (brs, 1H), 2.52-2.29 (m, 5H), 2.20 (ddt, J=20.7, 13.8, 7.0 Hz, 2H), 1.99-1.86 (m, 1H), 1.74 (dt, J=13.0, 6.6 Hz, 1H). ESI (M+H)=412.3.

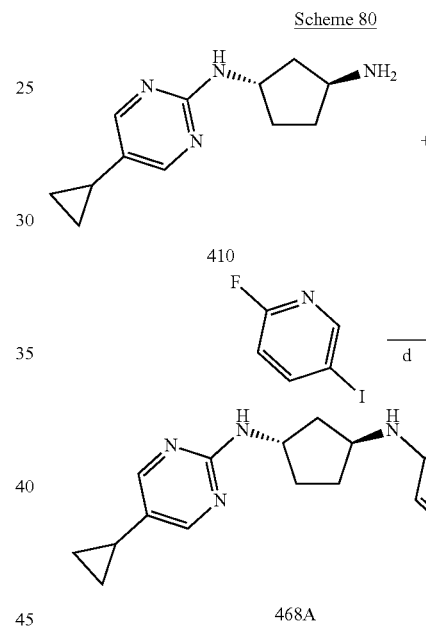

Scheme 80

Example 468 d) General method 6;
e) pyridazine-3(2H)-one, CuI, (1S,2S)-N¹,N²-dimethylcyclohexane-1,2-diamine, K₂CO₃, DMSO, 135° C.

(1S, 3S)—N¹-(5-cyclopropylpyrimidin-2-yl)-N³-(5-iodopyridin-2-yl) cyclopentane-1, 3-diamine (468A)

Methods analogous to those described above from starting material 425C (44.5 g, 208.7 mmol, 1.0 eq) afforded 425D (24.7 g) as a pale solid. LCMS [M+H]⁺=422.

2-(6-(((1S, 3S)-3-((5-cyclopropylpyrimidin-2-yl)amino) cyclopentyl) amino) pyridin-3-yl) pyridazin-3(2H)-one (Example 468)

To a solution of 468A (18.7 g, 44.4 mmol, 1.0 eq), pyridazin-3(2H)-one (8.53 g, 88.8 mmol, 2.0 eq), (1S, 2S)—N$^1$,N$^2$-dimethylcyclohexane-1,2-diamine (1.26 g, 8.88 mmol, 0.2 eq) and CuI (0.85 g, 4.44 mmol, 0.1 eq) in DMSO (150 mL) was added K$_2$CO$_3$ (18.5 g, 133.2 mmol, 3.0 eq) and the resulting system was stirred at 135° C. for 12 h under N$_2$. The reaction mixture was cooled to room temperature and poured into water (1 L) and extracted with ethyl acetate (150 mL×3). The combined organic layers were washed with brine and dried over anhydrous Na$_2$SO$_4$. The ethyl acetate phase was filtered and concentrated under reduced pressure. The residue was purified by silica gel column chromatography (elute with DCM:MeOH=100:1 to 50:1) to afford Example 468 (25.3 g) as a light yellow solid: $^1$H NMR (400 MHz, CD$_3$OD) δ 8.15 (d, J 2.5 Hz, 1H), 8.07 (s, 2H), 8.02 (dd, J=3.9, 1.6 Hz, 2H), 7.60 (dd, J=9.0, 2.6 Hz, 1H), 7.46 (dd, J=9.4, 3.9 Hz, 1H), 7.06 (dd, J=9.5, 1.6 Hz, 1H), 6.59 (d, J=9.0 Hz, 1H), 4.42-4.27 (m, 2H), 2.34-2.18 (m, 2H), 1.99 (t, J=6.8 Hz, 2H), 1.81-1.70 (m, 1H), 1.65-1.53 (m, 2H), 0.95-0.85 (m, 2H), 0.66-0.54 (m, 2H). LCMS [M+H]$^+$=390.

Using the above procedures, the following examples were synthesized:

| Structure | Ex. # | $^1$H NMR | LC-MS (M + H)$^+$ |
|---|---|---|---|
| 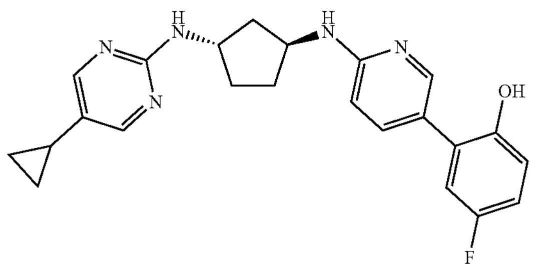 [SMILES: Oc1ccc(F)cc1-c1ccc(N[C@H]2CC[C@H](Nc3ncc(C4CC4)cn3)C2)nc1] | 469 | $^1$H NMR (400 MHz, CD$_3$OD) δ 8.17 (d, J = 1.8 Hz, 1H), 8.07 (s, 2H), 7.70 (dd, J = 8.8, 2.4 Hz, 1H), 7.04-6.93 (m, 1H), 6.83 (dd, J = 7.0, 2.8 Hz, 2H), 6.59 (d, J = 8.9 Hz, 1H), 4.42-4.24 (m, 2H), 2.37-2.15 (m, 3H), 2.10-1.91 (m, 3H), 1.75 (ddd, J = 13.5, 8.4, 5.1 Hz, 1H), 1.60 (dd, J = 12.7, 8.8 Hz, 2H), 0.96-0.85 (m, 2H), 0.60 (dt, J = 6.2, 4.7 Hz, 2H). | 406.3 |
| 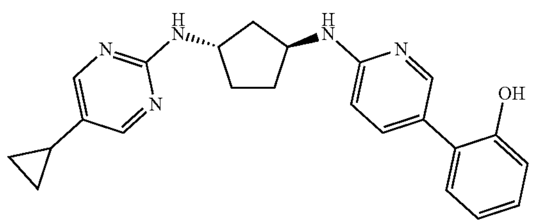 [SMILES: Oc1ccccc1-c1ccc(N[C@H]2CC[C@H](Nc3ncc(C4CC4)cn3)C2)nc1] | 470 | $^1$H NMR (400 MHz, CDCl$_3$) δ 8.16 (s, 1H), 8.09 (s, 2H), 7.76 (d, J = 8.5 Hz, 1H), 7.23-7.13 (m, 2H), 7.01 (d, J = 8.1 Hz, 1H), 6.95 (t, J = 7.3 Hz, 1H), 6.60 (d, J = 8.5 Hz, 1H), 5.14 (s, 1H), 4.43 (d, J = 5.3 Hz, 1H), 4.17 (s, 1H), 2.36-2.26 (m, 2H), 2.14-1.95 (m, 3H), 1.75-1.64 (m, 2H), 1.58 (s, 1H), 0.90 (d, J = 7.6 Hz, 2H), 0.58 (d, J = 5.0 Hz, 2H). | 388.3 |
| 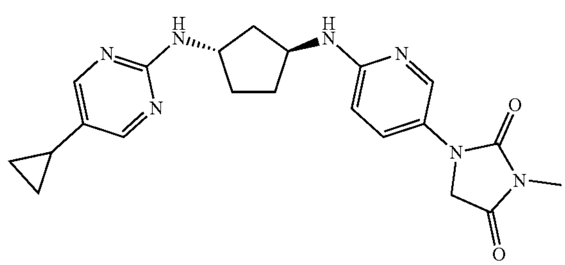 [SMILES: CN1C(=O)CN(c2ccc(N[C@H]3CC[C@H](Nc4ncc(C5CC5)cn4)C3)nc2)C1=O] | 471 | $^1$H NMR (400 MHz, CDCl$_3$) δ 8.09 (s, 2H), 8.05 (s, 1H), 7.87 (d, J = 8.8 Hz, 1H), 6.52 (d, J = 9.0 Hz, 1H), 5.49 (s, 1H), 5.35 (s, 1H), 4.50-4.35 (m, 1H), 4.25 (s, 2H), 4.21 (s, 1H), 3.11 (s, 3H), 2.32 (dd, J = 10.2, 5.3 Hz, 2H), 1.72 (td, J = 8.5, 4.3 Hz, 1H), 1.67-1.53 (m, 2H), 0.92 (dd, J = 13.2, 6.0 Hz, 2H), 0.59 (q, J = 5.0 Hz, 2H). | 408.4 |
| 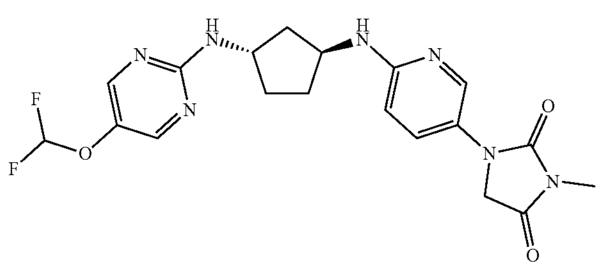 [SMILES: CN1C(=O)CN(c2ccc(N[C@H]3CC[C@H](Nc4ncc(OC(F)F)cn4)C3)nc2)C1=O] | 472 | $^1$H NMR (400 MHz, TFA-d) δ 8.47 (t, J = 103.6 Hz, 4H), 7.24 (s, 1H), 6.61 (t, J = 70.1 Hz, 1H), 4.84 (s, 1H), 4.68 (s, 2H), 4.44 (s, 1H), 3.28 (s, 3H), 2.57 (s, 2H), 2.39 (d, J = 18.4 Hz, 2H), 1.93 (s, 2H). | 434.3 |

-continued

| Structure | Ex. # | ¹H NMR | LC-MS (M + H)⁺ |
|---|---|---|---|
| 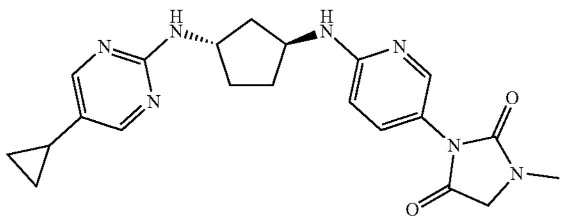 [SMILES: CN1CC(=O)N(c2ccc(N[C@H]3CC[C@H](Nc4ncc(C5CC5)cn4)C3)nc2)C1=O] | 473 | ¹H NMR (400 MHz, CD3OD) δ 8.07 (s, 2H), 7.91 (d, J = 2.1 Hz, 1H), 7.36 (dd, J = 9.0, 2.6 Hz, 1H), 6.58 (d, J = 9.0 Hz, 1H), 4.42-4.25 (m, 2H), 4.08 (s, 2H), 3.02 (s, 3H), 2.30-2.16 (m, 2H), 2.03-1.93 (m, 2H), 1.75 (ddd, J = 17.0, 8.5, 5.2 Hz, 1H), 1.63-1.52 (m, 2H), 0.90 (ddd, J = 12.8, 7.4, 4.1 Hz, 2H), 0.65-0.58 (m, 2H). | 408.4 |
| 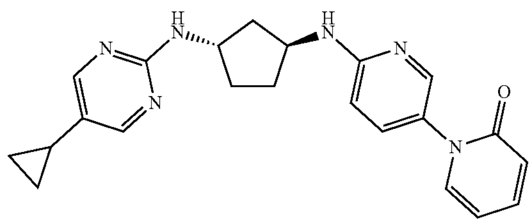 [SMILES: O=c1ccccn1-c1ccc(N[C@H]2CC[C@H](Nc3ncc(C4CC4)cn3)C2)nc1] | 474 | ¹H NMR (400 MHz, CD₃OD) δ 7.93 (s, 2H), 7.93 (d, J = 0.4 Hz, 1H), 7.62-7.56 (m, 2H), 7.45-7.42 (m, 1H), 6.62-6.59 (m, 2H), 6.47-6.43 (m, 1H), 4.38-4.31 (m, 2H), 2.27-2.23 (m, 2H), 2.00-1.97 (t, J = 13.6 Hz, 2H), 1.77-1.73 (m, 1H), 1.62-1.56 (m, 2H), 0.93-0.89 (m, 2H) 0.68-0.64 (m, 2H). | 389 |
| 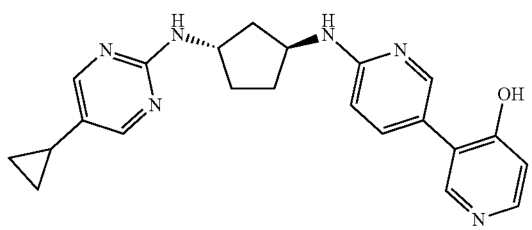 [SMILES: Oc1ccncc1-c1ccc(N[C@H]2CC[C@H](Nc3ncc(C4CC4)cn3)C2)nc1] | 475 | ¹H NMR (400 MHz, CD₃OD) δ 8.39-8.39 (d, J = 1.6 Hz, 1H), 8.15-8.12 (m, 4H), 7.84-7.82 (m, 1H), 7.09-7.06 (d, J = 9.2 Hz, 1H), 6.61-6.59 (d, J = 7.2 Hz, 1H), 4.47-4.40 (m, 1H), 4.27-4.21 (m, 1H), 2.43-2.26 (m, 2H), 2.18-2.03 (m, 2H), 2.43-2.26 (m, 2H), 2.18-2.03 (m, 2H), 1.81-1.66 (m, 3H), 0.95-0.89 (m, 2H), 0.64-0.60 (m, 2H). | 391 |
| 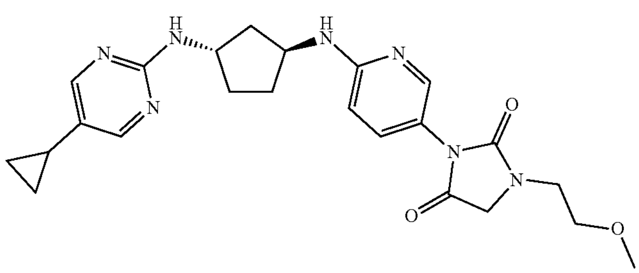 [SMILES: COCCN1CC(=O)N(c2ccc(N[C@H]3CC[C@H](Nc4ncc(C5CC5)cn4)C3)nc2)C1=O] | 476 | ¹H NMR (400 MHz, CD₃OD) δ 8.26 (s, 2H), 8.03 (d, J = 2.0 Hz, 1H), 7.98 (dd, J = 9.6, 2.4 Hz, 1H), 7.09 (d, J = 9.6 Hz, 1H), 4.50 (p, J = 6.8 Hz, 1H), 4.27 (dd, J = 12.4, 6.2 Hz, 1H), 4.20 (s, 2H), 3.69-3.58 (m, 4H), 3.38 (s, 3H), 2.50-2.24 (m, 2H), 2.24-2.08 (m, 2H), 1.84 (tt, J = 8.5, 5.2 Hz, 1H), 1.81-1.70 (m, 2H), 1.05-0.93 (m, 2H), 0.77-0.60 (m, 2H). | 452.5 |
| 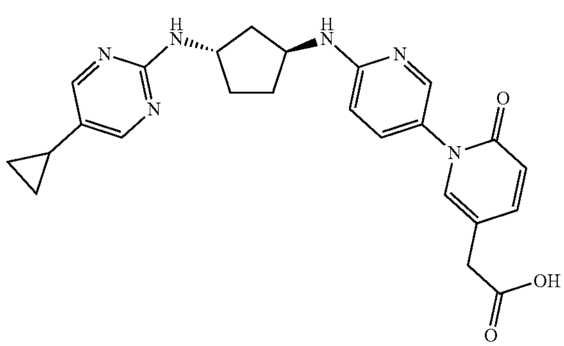 [SMILES: O=C(O)Cc1ccc(=O)n(-c2ccc(N[C@H]3CC[C@H](Nc4ncc(C5CC5)cn4)C3)nc2)c1] | 477 | 1H NMR (400 MHz, CD₃OD) δ: 8.15 (s, 2H), 8.08-8.01 (m, 1H), 7.79-7.77 (d, J = 9.6 Hz, 1H), 7.62-7.54 (m, 1H), 7.54-7.53 (d, J = 2 Hz, 1H), 6.96-6.93 (d, J = 9.2 Hz, 1H), 6.63-6.60 (t, J = 9.2 Hz, 1H), 4.46-4.39 (m, 1H), 4.32-4.27 (m, 1H), 3.49-3.47 (m, 2H), 2.40-2.26 (m, 2H), 2.12-2.00 (m, 2H), 1.83-1.76 (m, 1H), 1.74-1.65 (m, 2H), 0.97-0.88 (m, 2H), 0.66-0.61 (m, 2H). | 447.4 |

Scheme 74

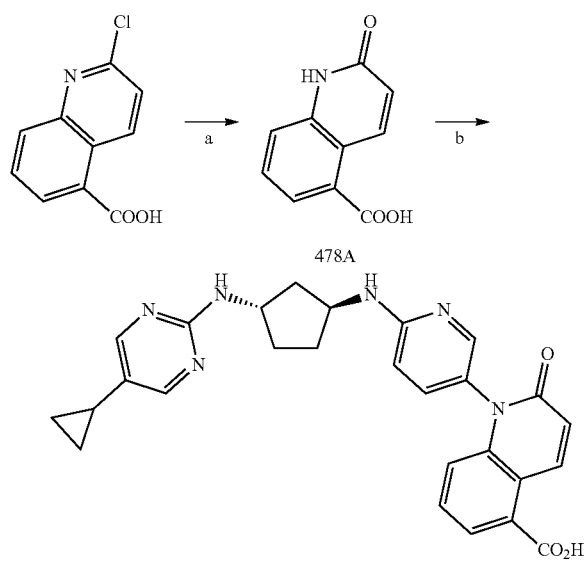

Example 478
a) AcOH, H₂O, 130° C.; b) CuI, K₂CO₃, quinolin-8-ol, DMSO, 120° C., MW.

2-oxo-1,2-dihydroquinoline-5-carboxylic acid (478A)

A suspension of 2-chloroquinoline-5-carboxylic acid (300 mg, 1.45 mmol, 1.0 eq) in AcOH (5 mL) and H₂O (2 mL) was stirred at 130° C. overnight. The reaction was cooled to 0° C. and stirred for 0.5 h. The precipitate was collected by filtration, and the solid was dried in vacuum to give 478A (250 mg).

1-(6-(((1S, 3S)-3-((5-cyclopropylpyrimidin-2-yl) amino) cyclopentyl) amino) pyridin-3-yl)-2-oxo-1, 2-dihydroquinoline-5-carboxylic acid (Example 478)

A suspension of 478A (18 mg, 0.1 mmol, 1.0 eq), (1S, 3S)-N1-(5-cyclopropylpyrimidin-2-yl)-N3-(5-iodopyridin-2-yl) cyclopentane-1,3-diamine (40 mg, 0.1 mmol, 1.0 eq), quinolin-8-ol (3 mg, 0.02 mmol, 0.2 eq), CuI (4 mg, 0.02 mmol, 0.2 eq), K₂CO₃ (20 mg, 0.15 mmol, 1.5 eq), in DMSO (3 mL) was purged with Na. The reaction mixture was then stirred at 120° C. under microwave irradiation for 2 h. The reaction mixture was filtered and the filtrate was partitioned between ethyl acetate (5 mL) and water (10 mL). After separation, the aqueous phase was concentrated under reduced pressure. The crude residue was purified by Prep-HPLC to give Example 478 (4.7 mg): ¹H NMR (400 MHz, CD₃OD) δ 9.11 (d, J=10.1 Hz, 1H), 8.25 (s, 2H), 8.05 (s, 1H), 7.95 (d, J=7.5 Hz, 1H), 7.79 (d, J=9.4 Hz, 1H), 7.67-7.50 (m, 1H), 7.27-7.15 (m, 2H), 6.84 (d, J=10.1 Hz, 1H), 4.58-4.45 (m, 1H), 4.38-4.28 (m, 1H), 2.53-2.28 (m, 2H), 2.27-2.06 (m, 2H), 1.91-1.68 (m, 3H), 1.03-0.92 (m, 2H), 0.73-0.63 (d, J=4.5 Hz, 2H). ESI (M+H)⁺=483.

Using the above procedures, the following examples were synthesized:

| Structure | Ex. # | ¹H NMR | LC-MS (M + H)⁺ |
|---|---|---|---|
| 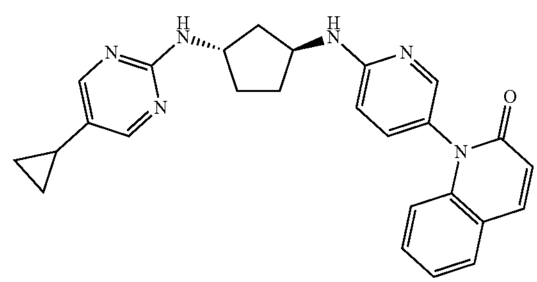 [SMILES: O=c1ccc2ccccc2n1-c1ccc(N[C@H]2CC[C@H](Nc3ncc(C4CC4)cn3)C2)nc1] | 479 | ¹H NMR (400 MHz, MeOD) δ 8.22 (s, 2H), 8.11-8.01 (m, 2H), 7.83-7.73 (m, 2H), 7.53 (t, J = 7.9 Hz, 1H), 7.34 (t, J = 7.4 Hz, 1H), 7.18 (d, J = 9.4 Hz, 1H), 7.00 (d, J = 8.5 Hz, 1H), 6.75 (d, J = 9.6 Hz, 1H), 4.56-4.44 (m, 1H), 4.38-4.28 (m, 1H), 2.51-2.29 (m, 2H), 2.28-2.12 (m, 2H), 1.90-1.68 (m, 3H), 1.03-0.91 (m, 1H), 0.76-0.60 (m, 1H) | 439 |
| 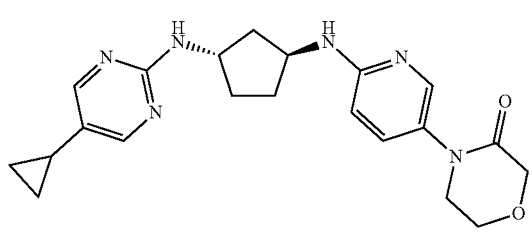 [SMILES: O=C1COCCN1c1ccc(N[C@H]2CC[C@H](Nc3ncc(C4CC4)cn3)C2)nc1] | 480 | ¹H NMR (400 MHz, CD₃OD) δ 8.07 (s, 2H), 7.91 (d, J = 2.3 Hz, 1H), 7.38 (dd, J = 9.0, 2.6 Hz, 1H), 6.56 (d, J = 8.9 Hz, 1H), 4.40-4.30 (m, 1H), 4.31-4.22 (m, 3H), 4.04-3.97 (m, 2H), 3.73-3.64 (m, 2H), 2.31-2.15 (m, 2H), 1.99-1.91 (m, 2H), 1.80-1.70 (m, 1H), 1.64-1.50 (m, 2H), 0.94-0.86 (m, 2H), 0.63-0.56 (m, 2H). | 395 |

Scheme 75

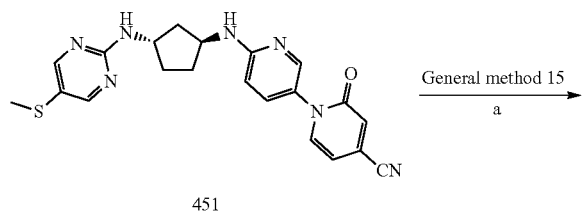

a) NaN₃, NH₄Cl, DMF, 100° C.

General Method 15

6'-(((1S,3S)-3-((5-(methylthio) pyrimidin-2-yl) amino) cyclopentyl) amino)-4-(2H-tetrazol-5-yl)- 2H-[1, 3'-bipyridin]-2-one (Example 481)

A mixture of 451 (35 mg, 0.083 mmol, 1.0 eq), NH₄Cl (44 mg, 0.83 mmol, 10.0 eq) and NaN₃ (54 mg, 0.83 mmol, 10.0 eq) in DMF (2 mL) was stirred at 100° C. for 5 h. The mixture was cooled down to room temperature and filtered. The filtrate was purified by Prep-HPLC to give Example 481 (13 mg, 33.7%) as a yellow solid. ¹H NMR (400 MHz, CD₃OD) δ ppm: 8.37 (s, 2H), 8.15 (d, J=2.0 Hz, 1H), 7.98 (dd, J=2.1 Hz, 9.6 Hz, 1H), 7.83 (dd, J=0.4 Hz, 7.2 Hz, 1H), 7.34 (d, J=1.2 Hz, 1H), 7.10-7.15 (m, 2H), 4.46-4.50 (m, 1H), 4.27-4.31 (m, 1H), 2.43-2.43 (m, 5H), 2.11-2.18 (m, 2H), 1.71-1.80 (m, 2H). LCMS [M+H]⁺=463.4.

Using the above procedures, the following examples were synthesized:

| Structure | Ex. # | ¹H NMR | LC-MS (M + H)⁺ |
|---|---|---|---|
| 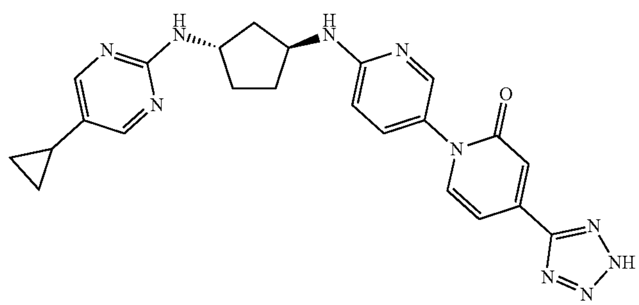 [SMILES: O=c1cc(-c2nn[nH]n2)ccn1-c1ccc(N[C@H]2CC[C@H](Nc3ncc(C4CC4)cn3)C2)nc1] | 482 | ¹H NMR (400 MHz, CD₃OD) δ ppm 8.28 (s, 2H), 8.14 (d, J = 2.4 Hz, 1H), 7.94 (d, J = 9.6 Hz, 1H), 7.82 (d, J = 6.4 Hz, 1H), 7.33 (d, J = 1.2 Hz, 1H), 7.14 (dd, J = 2.0, 7.2 Hz, 1H), 7.07 (d, J = 9.2 Hz, 1H), 4.52-4.51 (m, 1H), 4.34-4.31 (m, 1H), 2.43-2.30 (m, 2H), 2.19-2.14 (m, 2H), 1.78-1.72 (m, , 3H) 0.99-0.97 (m, 2H), 0.72-0.689 (m, 2H). | 457.5 |
| 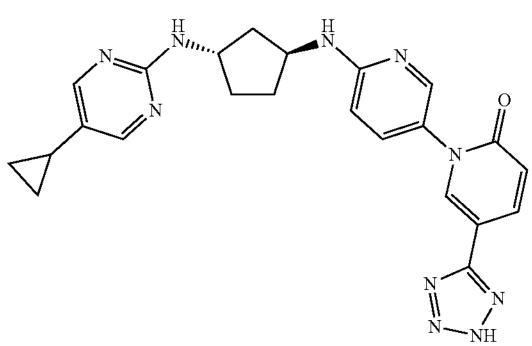 [SMILES: O=c1ccc(-c2nn[nH]n2)cn1-c1ccc(N[C@H]2CC[C@H](Nc3ncc(C4CC4)cn3)C2)nc1] | 483 | ¹H NMR (400 MHz, CD₃OD) δ 8.42 (d, J = 2.8 Hz, 1H), 8.23 (s, 2H), 8.17-8.14 (m, 2H), 7.92-7.89 (m, 1H), 7.02 (dd, J = 2.8, 8.8 Hz, 1H), 6.80 (dd, J = 0.8, 9.6 Hz, 1H), 4.50-4.47 (m, 1H), 4.34-4.31 (m, 1H), 2.43-2.30 (m, 2H), 2.17-2.14 (m, 2H), 1.85-1.70 (m, 3H), 1.01-0.96 (m, 2H), 0.71-0.67 (m, 2H). | 457.4 |

Scheme 76

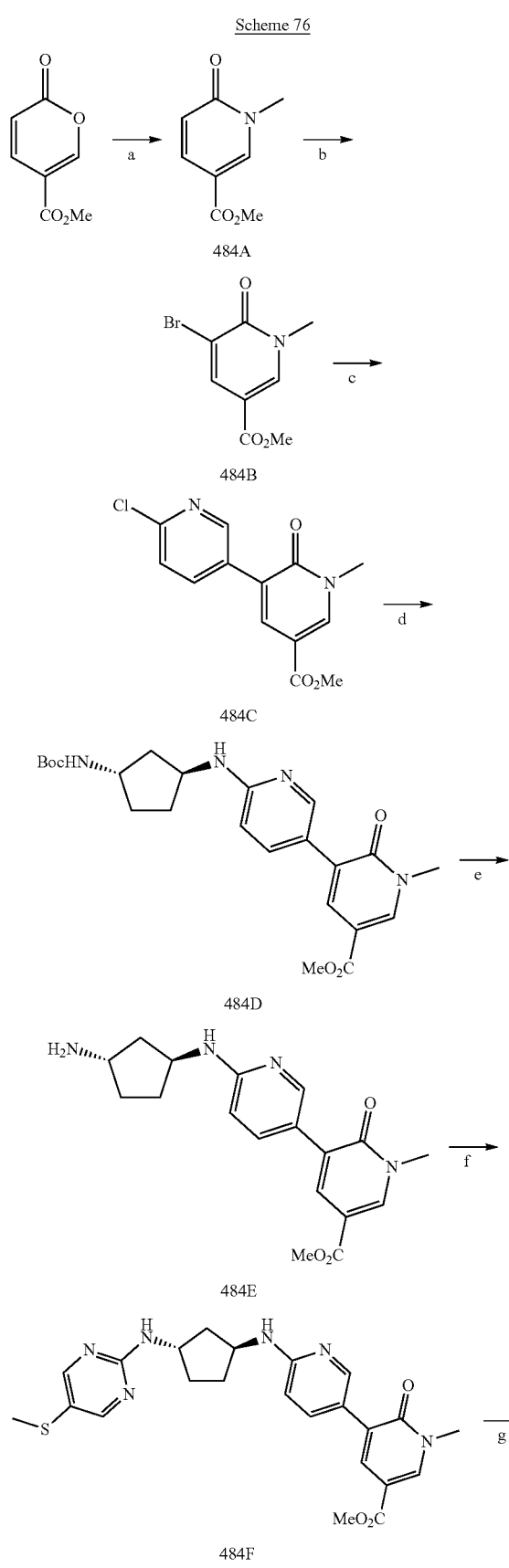

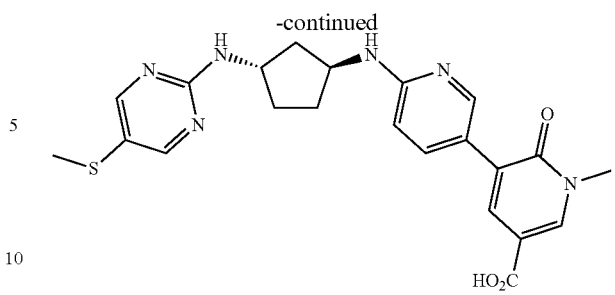

Example 484 a) MeNH$_2$, EtOH, 60° C.; b) NBS, HOAc, 80° C.; c) (6-chloropyridin-3-yl)boronic acid, General procedure 4; d) tert-butyl ((1S,3S)-3-aminocyclopentyl)carbamate, General procedure 2; e) TFA, DCM; f) 2-chloro-5-(methylthio)pyrimidine, General procedure 6: g) General procedure 7.

Methyl 1-methyl-6-oxo-1, 6-dihydropyridine-3-carboxylate (484A)

A solution of methyl 2-oxo-2H-pyran-5-carboxylate (3 g, 19.465 mmol, 1.0 eq) and methylamine (33% in EtOH, 1.904 g, 20.439 mmol, 1.05 eq) in EtOH (10 mL) was stirred at 60° C. for 18 h in sealed tube. The reaction mixture was cooled down to room temperature and concentrated under reduced pressure. The crude residue was purified by flash chromatography on silica gel (PE:EA=1:2) to afford 484A (393.6 mg) as a yellow solid. ESI (M+H)$^+$=168.1

Methyl 5-bromo-1-methyl-6-oxo-1, 6-dihydropyridine-3-carboxylate (484B)

A solution of 484A (393.6 mg, 2.355 mmol, 1 eq) and NBS (628.6 mg, 3.532 mmol, 1.5 eq) in AcOH (16 mL) was stirred at 80□ for 2 h. The reaction mixture was cooled down to room temperature and concentrated under reduce pressure. The crude residue was purified by flash chromatography on silica gel (PE:EA=1:1) to afford 484B (377.3 mg) as a white solid: $^1$H NMR (400 MHz, CDCl$_3$) δ 8.26 (d, J=2.3 Hz, 1H), 8.18 (d, J=2.3 Hz, 1H), 3.90 (s, 3H), 3.68 (s, 3H). ESI (M+H)=246.0.

Methyl 6'-chloro-1-methyl-2-oxo-1, 2-dihydro-[3, 3'-bipyridine]-5-carboxylate (484C)

Methods analogous to those described above from starting material 484B and (6-chloropyridin-3-yl) boronic acid afforded 484C: $^1$H NMR (400 MHz, CDCl$_3$) δ 8.68 (d, J=2.2 Hz, 1H), 8.27 (d, J=2.3 Hz, 1H), 8.21-8.13 (m, 1H), 8.08 (d, J=2.4 Hz, 1H), 7.39 (t, J=11.7 Hz, 1H), 3.91 (s, 3H), 3.69 (s, 3H). ESI (M+H)=279.2

Methyl 6'-(((1S, 3S)-3-((tert-butoxycarbonyl) amino) cyclopentyl) amino)-1-methyl-2-oxo-1, 2-dihydro-[3, 3'-bipyridine]-5-carboxylate (484D)

Methods analogous to those described above from starting material 484C and tert-butyl ((1S,3S)-3-aminocyclopentyl) carbamate afforded 484D: ESI (M+H)=443.3

Methyl 6'-(((1S, 3S)-3-aminocyclopentyl) amino)-1-methyl-2-oxo-1, 2-dihydro-[3, bipyridine]-5-carboxylate (484E)

To a solution of 484D (35 mg) in DCM (1 mL) was added dropwise TFA (1 mL). The reaction mixture was stirred at room temperature for 30 minutes and then concentrated under reduced pressure. The residue was dissolved in MeOH, followed by the addition of ion-exchange resins (Ambersep® 900 OH⁻ form) to adjust the pH level to 8. The mixture was filtered and the filtrate was concentrated under reduced pressure to give 484E (27 mg) 8 as yellow oil.

Methyl 1-methyl-6'-((((1S, 3S)-3-((5-(methylthio) pyrimidin-2-yl) amino) cyclopentyl) amino)-2-oxo-1, 2-dihydro-[3, 3'-bipyridine]-5-carboxylate (484F)

Methods analogous to those described above from starting material 484E and 2-chloro-5-(methylthio) pyrimidine afforded 484F: ESI (M+H)=467.2.

1-methyl-6'-(((1S, 3S)-3-((5-(methylthio) pyrimidin-2-yl) amino) cyclopentyl) amino)-2-oxo-1, 2-dihydro-[3,3'-bipyridine]-5-carboxylic acid (Example 484)

Methods analogous to those described above from starting material 484F afforded Example 484: ¹H NMR (400 MHz, CD₃OD) δ 8.51 (dd, J=14.0, 2.1 Hz, 2H), 8.35 (s, 2H), 8.25 (dd, J=10.7, 2.2 Hz, 2H), 7.10 (d, J=9.5 Hz, 1H), 4.51-4.41 (m, 1H), 4.31-4.20 (m, 1H), 3.69 (s, 3H), 2.49-2.39 (m, 1H), 2.35 (d, J=7.6 Hz, 3H), 2.33-2.27 (m, 1H), 2.22-2.07 (m, 2H), 1.84-1.65 (m, 2H). ESI (M+H)=453.3.

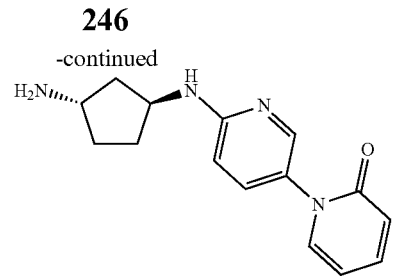

485 a) General proceudre 2; b) General procedure 6

6'-(((1S,3S)-3-aminocyclopentyl) amino)-2H-[1,3'-bipyridin]-2-one (485)

Methods analogous to those described in General Method 2 and General procedure 6 from starting material 6'-chloro-2H-[1,3'-bipyridin]-2-one afforded 485: m/z 271.0 [M+H]⁺.

Using the above procedures, the following example was synthesized:

| Structure | Ex. # | ¹H NMR | LC-MS (M + H)⁺ |
|---|---|---|---|
| 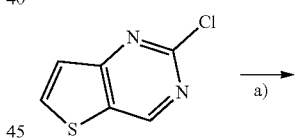 | 486 | | 271.1 |

Scheme 77

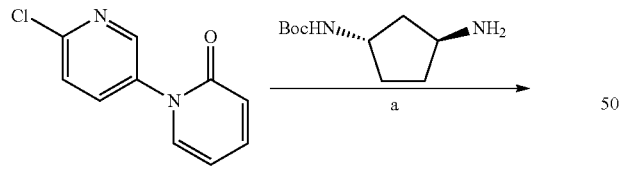

485A

Scheme 78

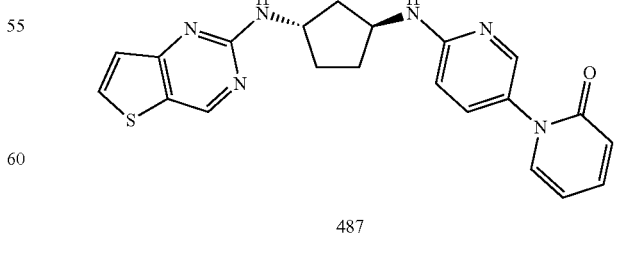

487 a) DIPEA, DMA, 150° C.

6'-(((1S, 3S)-3-(thieno [3, 2-d]pyrimidin-2-ylamino) cyclopentyl) amino)-2H-[1, 3'-bipyridin]-2-one (487)

A solution of 485 (150 mg, 0.405 mmol, 1.0 eq,), DIPEA (260 mg, 2.0 mmol, 5.0 eq) and 2-chlorothieno[3,2-d]pyrimidine (69 mg, 0.405 mmol, 1.0 eq) in DMA (2 mL) was stirred at 150° C. for 30 min. The resulting mixture was diluted with ethyl acetate (10 mL), washed with water (2×10 mL), and the aqueous phase was extracted with ethyl acetate (4×20 mL). The combined organic layers were concentrated under vacuum and purified with Prep-HPLC to give 487 (12 mg) as white solid: LCMS m/z 405 [M+H]t $^1$H NMR (400 MHz, CDCl$_3$) δ 10.73 (brs, 1H), 10.21 (brs, 1H), 9.03 (brs, 1H), 8.19 (d, J=5.3 Hz, 1H), 7.92 (dd, J 9.4, 2.3 Hz, 1H), 7.83 (d, J 2.3 Hz, 1H), 7.54-7.43 (m, 2H), 7.41 (d, J 5.5 Hz, 1H), 7.26-7.21 (m, 1H), 6.69 (dd, J 9.3, 1.2 Hz, 1H), 6.38-6.29 (m, 1H), 4.81-4.59 (m, 1H), 4.53-4.25 (m, 1H), 2.52-2.31 (m, 3H), 2.08 (dt, J 14.3, 7.8 Hz, 1H), 1.98-1.77 (m, 2H).

Using the above procedures, the following example was synthesized:

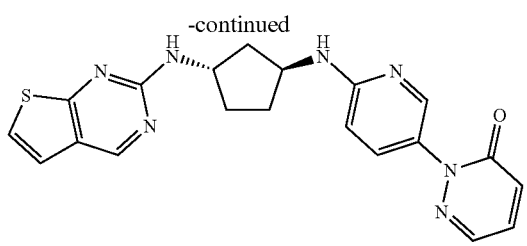

a) 486 DIPEA, DMSO 100° C.

2-(6-(((1S, 3S)-3-(thieno [2, 3-d]pyrimidin-2-ylamino) cyclopentyl) amino) pyridin-3-yl) pyridazin-3(2H)-one (489)

A solution of 486 (50 mg, 0.18 mmol), 5-chlorothiazolo[4,5-d]pyrimidine (30.5 mg, 0.18 mmol,), DIPEA (70 mg, 0.54 mmol,) in DMSO (5 mL) was stirred at 100° C. under N2 for overnight. The reaction mixture was extracted with

| Structure | Ex. # | $^1$H NMR | LC-MS (M + H)$^+$ |
|---|---|---|---|
| 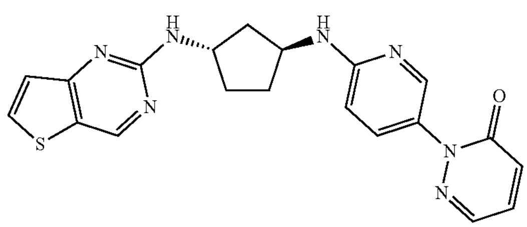 [SMILES: O=c1cccnn1-c1ccc(N[C@H]2CC[C@H](Nc3ncc4sccc4n3)C2)nc1] | 488 | $^1$H NMR (400 MHz, CD$_3$OD) δ 8.83 (s, 1H), 8.16 (dd, J = 2.7, 0.7 Hz, 1H), 8.05 (dd, J = 5.3, 1.4 Hz, 1H), 8.01 (dt, J = 3.0, 1.5 Hz, 1H), 7.61 (dd, J = 9.0, 2.7 Hz, 1H), 7.45 (ddd, J = 9.5, 4.2, 1.5 Hz, 1H), 7.18 (d, J = 5.4 Hz, 1H), 7.05 (dd, J = 9.4, 1.6 Hz, 1H), 6.60 (d, J = 9.1 Hz, 1H), 5.49 (s, 1H), 4.49 (p, J = 6.2 Hz, 1H), 4.36 (p, J = 6.3 Hz, 1H), 2.40-2.22 (m, 2H), 2.12-1.98 (m, 2H), 1.63 (ddt, J = 15.5, 9.8, 5.0 Hz, 2H). | 406.1 |

Scheme 79

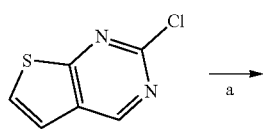

EA and water. The organic phase was washed with brine, dried over Na$_2$SO$_4$, filtered and concentrated under reduced pressure. The crude residue was purified by prep-TLC and prep-HPLC to afford 2.6 mg of 489 (2.3 mg): ESI (M+H)$^+$=406.48; $^1$H NMR (400 MHz, CD$_3$OD) δ 8.76 (s, 1H), 8.39 (d, J=2.2 Hz, 1H), 8.22 (d, J=9.7 Hz, 1H), 8.10 (d, J=3.8, 1.6 Hz, 1H), 7.52 (dd, J=9.5, 3.9 Hz, 1H), 7.22 (d, J=6.0 Hz, 2H), 7.16-7.06 (m, 2H), 4.67-4.48 (m, 1H), 4.36-4.23 (m, 1H), 2.52-2.31 (m, 2H), 2.30-2.12 (m, 2H), 1.86-1.69 (m, 2H).

Using the above procedures, the following examples were synthesized:

| Structure | Ex. # | ¹H NMR | LC-MS (M + H)⁺ |
|---|---|---|---|
| (structure) | 490 | ¹H NMR (400 MHz, CD₃OD) δ 8.80 (m, 1H), 8.38 (s, 1H), 8.18 (m., 1H), 8.09 (dd, J = 3.9, 1.6 Hz, 1H), 7.52 (dd, J = 9.5, 3.9 Hz, 1H), 7.17-7.05 (m, 2H), 7.00 (m, 1H), 4.58 (m, 1H), 4.32 (m, 1H), 2.69 (s, 3H), 2.52-2.30 (m, 2H), 2.21 (m 2H), 1.80 (m, 2H). | 420.5 |
| (structure) | 491 | ¹H NMR (400 MHz, CD₃OD) δ 8.49 (s, 2H), 7.95-7.74 (m, 1H), 7.63-7.57 (m, 2H), 7.44 (dd, J = 2.4, 8.8 Hz, 1H), 6.60-6.63 (m, 2H), 6.44-6.48 (m, 1H), 4.52-4.48 (m, 1H), 4.37-4.34 (m, 1H), 2.31-2.24 (m, 2H), 2.07-2.00 (m, 2H), 1.66-1.61 (m, 2H). | 417.3 |
| (structure) | 492 | ¹H NMR (400 MHz, CD₃OD) δ 8.57 (s, 1H), 8.50 (s, 1H), 7.94 (dd, J = 0.4, 2.8 Hz, 1H), 7.63-7.57 (m, 2H), 7.46-7.43 (m, 1H), 6.62-6.60 (m, 2H), 6.48-6.44 (m, 1H), 4.52-4.50 (m, 1H), 4.36-4.34 (m, 1H), 2.28-2.25 (m, 2H), 2.05-1.77 (m, 2H), 1.62-1.66 (m, 2H). | 374.2 |
| (structure) | 493 | ¹H NMR (400 MHz, CD₃OD) δ 8.22 (s, 2H), 7.93 (dd, J = 0.4, 2.8 Hz, 1H), 7.63-7.57 (m, 2H), 7.44 (dd, J = 2.8, 9.2 Hz, 1H), 6.63-6.60 (m, 2H), 6.48-6.44 (m, 1H), 4.39-4.32 (m, 2H), 2.28-2.23 (m, 2H), 2.02-1.97 (m, 2H), 1.64-1.58 (m, 2H). | 383.3 |

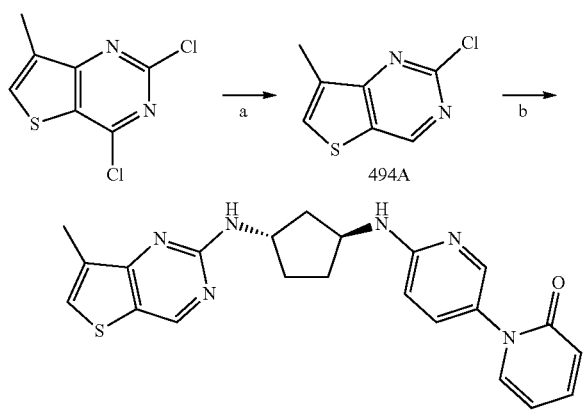

Scheme 80 a) H₂, Pd(OH)₂, NaOAc, EA/iPrOH, rt; b) K₂CO₃, DMSO 140° C.

2-chloro-7-methylthieno [3, 2-d]pyrimidine (494A)

A suspension of 2,4-dichloro-7-methylthieno[3,2-d]pyrimidine (500 mg, 2.3 mmol, 1 eq), Pd(OH)₂ (20% on carbon, 200 mg, 0.14 mmol, 0.55 eq) and NaOAc (400 mg, 4.8 mmol, 2.0 eq) in EA (8 mL) and i-PrOH (1 mL) was stirred in a Parr apparatus under H₂ atmosphere (50 psi) for 18 h at room temperature. The reaction mixture was filtered on celite and the filtrate was concentrated under reduced pressure. The crude residue was purified by flash chromatography on silica gel (PE:EA=4:1) to give 494A (320 mg) as a white powder. ESI (M+H)⁺=185.0; ¹H NMR (400 MHz, CDCl₃) δ 9.09 (s, 1H), 7.73 (q, J=1.1 Hz, 1H), 2.51 (d, J=1.2 Hz, 3H).

6'-(((1S, 3S)-3-((7-methylthieno [3, 2-d]pyrimidin-2-yl) amino) cyclopentyl) amino)-2H-[1, 3'-bipyridin]-2-one (494)

A suspension of 494A (28.45 mg, 0.1541 mmol, 1.0 eq), 485 (50 mg, 0.185 mmol, 1.2 eq) and K₂CO₃ (63.9 mg, 0.462 mmol, 3.0 eq) in DMSO (5 mL) was stirred at 140° C. for 16 h under N₂. The reaction mixture was extracted with DCM and water. The organic phase was washed with brine, dried over Na₂SO₄, filtered and concentrated under reduced pressure. The crude residue was purified by flash chromatography on silica gel (DCM:MeOH=20:1) to give 494 (10.4 mg) as a white powder. ¹H NMR (400 MHz, DMSO-d₆) δ 7.92 (d, J=2.6 Hz, 1H), 7.60 (dd, J=6.8, 1.8 Hz, 1H), 7.47 (ddd, J=9.0, 6.6, 2.1 Hz, 1H), 7.39 (dd, J=8.9, 2.7 Hz, 1H), 7.21 (d, J=7.2 Hz, 1H), 6.92 (d, J=7.0 Hz, 1H), 6.53 (d, J=9.1 Hz, 1H), 6.44 (d, J=8.9 Hz, 1H), 6.27 (td, J=6.7, 1.3 Hz, 1H), 4.52-4.39 (m, 1H), 4.38-4.26 (m, 1H), 2.27 (d, J=0.9 Hz, 3H), 2.16 (dd, J=9.8, 5.4 Hz, 2H), 2.03-1.86 (m, 3H), 1.63-1.47 (m, 1H). ESI (M+H)⁺=419.3

Using the above procedures, the following example was synthesized:

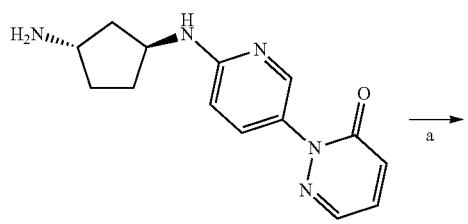

486

| Structure | Ex. # | ¹H NMR | LC-MS (M + H)⁺ |
|---|---|---|---|
| 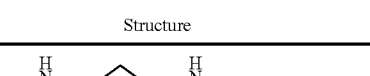 | 495 | ¹H NMR (400 MHz, CDCl₃) δ 10.53 (s, 1H), 10.27 (s, 1H), 8.56 (brs, 2H) 7.91 (d, J = 9.3 Hz, 1H), 7.83 (s, 1H), 7.49-7.37 (m, 2H), 7.24 (d, J = 5.8 Hz, 1H), 6.67 (d, J = 9.3 Hz, 1H), 6.32 (t, J = 6.6 Hz, 1H), 4.60 (s, 1H), 4.42-4.25 (m, 1H), 2.48-2.28 (m, 3H), 2.25 (s, 3H), 2.11-1.99 (m, 1H), 1.98-1.84 (m, 1H), 1.79 (ddd, J = 12.5, 11.1, 7.0 Hz, 1H). | 363.4 |

Scheme 81

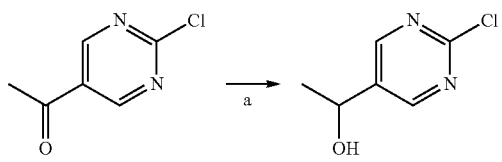

a) NaBH₄, MeOH, 0° C.

1-(2-chloropyrimidin-5-yl) ethan-1-ol (496)

To the solution of 1-(2-chloropyrimidin-5-yl) ethan-1-one (500 mg, 3.2 mmol, 1.0 eq) in MeOH (15 mL) was added NaBH₄ (240 mg, 6.4 mmol, 2.0 eq) at 0° C. After stirring at room temperature for 2 h, water (5 mL) was added to above mixture to quench the reaction. The resulting mixture was concentrated under reduced pressure, and the crude residue was purified by silica gel column chromatography (hexane: ethyl acetate=5:1 to ethyl acetate) to give 496 as a pale solid (100 mg). ESI [M+H]⁺=159.1.

Scheme 82

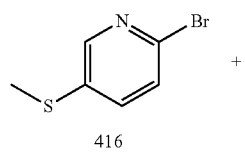

+

-continued

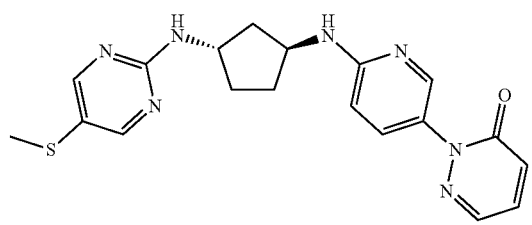

497 a) General procedure 2

2-(6-(((1S,3S)-3-((5-(methylthio) pyridin-2-yl) amino) cyclopentyl) amino) pyridin-3-yl) pyridazin-3(2H)-one (497)

Methods analogous to those described in General Method 2 from starting material 416 and 486 afforded 497: ¹H NMR (400 MHz, CD₃OD) δ 8.28 (d, J=2.3 Hz, 1H), 8.04 (dd, J=9.6, 2.3 Hz, 1H), 7.97 (dd, J=3.8, 1.5 Hz, 1H), 7.82 (dd, J=9.4, 2.2 Hz, 1H), 7.63 (d, J=2.0 Hz, 1H), 7.40 (dd, J=9.5, 3.9 Hz, 1H), 7.00 (ddd, J=9.6, 6.5, 5.0 Hz, 3H), 4.37-4.20 (m, 2H), 2.39 (s, 3H), 2.37-2.29 (m, 2H), 2.17 (t, J=6.4 Hz, 2H), 1.80-1.67 (m, 2H). ESI (M+H)⁺=395.3

Using the above procedures, the following example was synthesized:

| Structure | Ex. # | ¹H NMR | LC-MS (M + H)⁺ |
|---|---|---|---|
| 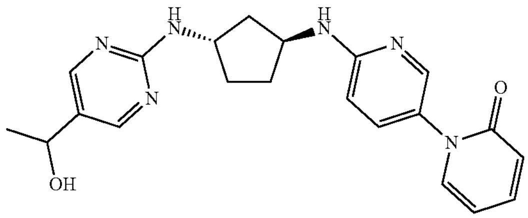 [SMILES: CC(O)c1cnc(N[C@H]2CC[C@H](Nc3ccc(-n4ccccc4=O)cn3)C2)nc1] | 498 | ¹H NMR (400 MHz, CD$_3$OD) δ 8.27 (s, 2H), 7.59 (t, J = 8.3 Hz, 1H), 7.64-7.53 (m, 2H), 7.44 (m, 1H), 6.61 (d, J = 9 Hz, 2H), 6.64 (m, 1H), 4.72 (q, J = 6.5 Hz, 1H), 4.37 (m, 2H), 2.25 (m, 2H), 1.99 (m, 2H), 1.60 (m, 2H), 1.43 (d, J = 10 Hz, 3H). | 393.2 |

Scheme 83

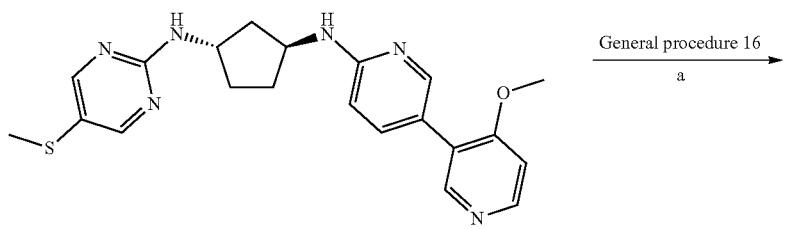

402

General procedure 16
a

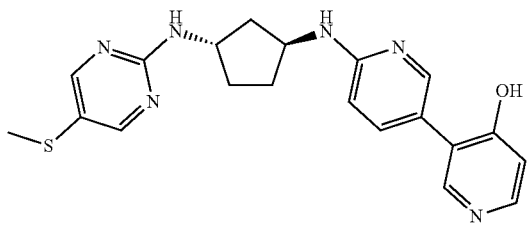

Example 499 a) LiCl, pTsOH, NMP, 180° C.

General Procedure 16

6'-(((1S, 3S)-3-((5-(methylthio) pyrimidin-2-yl) amino) cyclopentyl) amino)-[3, bipyridin]-4-ol (Example 499)

To a solution of compound 402 (40 mg, 0.1 mmol, 1 eq) in NMP (3 mL) was added LiCl (42 mg, 1 mmol, 10 eq) and p-Toluenesulfonic acid (172 mg, 1 mmol, 10 eq). The mixture was stirred at 180° C. for 4 h and cooled down to room temperature. The mixture was diluted with water (10 mL) and then basified with sat. NaHCO$_3$ to pH=10. The resulting mixture was extracted with ethyl acetate (10 mL×6), the combined organic layers were washed with brine (20 mL), dried over Na$_2$SO$_4$, filtered and concentrated. The resulting residue was purified by Prep-HPLC to afford Example 499 (10 mg, 26%) as a yellow solid: LCMS [M+H]⁺=395; ¹H NMR (400 MHz, CD$_3$OD) δ: 8.33 (s, 2H), 8.18 (s, 1H), 7.88 (s, 1H), 7.77-7.72 (m, 1H), 6.63 (d, J=9.2 Hz, 1H), 6.52 (d, J=9.2 Hz, 1H), 4.45-4.35 (m, 2H), 2.35 (s, 3H), 2.30-2.24 (m, 2H), 2.04-1.98 (m, 2H), 1.63-1.60 (m, 2H).

Using the above procedures, the following example was synthesized:

| Structure | Ex. # | ¹H NMR | LC-MS (M + H)⁺ |
|---|---|---|---|
| (structure shown) | 499A | ¹H NMR (400 MHz, CD₃OD) δ 7.94 (d, J = 2.3 Hz, 1H), 7.67-7.53 (m, 2H), 7.43 (dd, J = 9.0, 2.7 Hz, 1H), 6.65-6.55 (m, 2H), 6.46 (td, J = 6.8, 1.3 Hz, 1H), 4.40-4.25 (m, 2H), 2.31-2.19 (m, 2H), 1.98 (t, J = 6.7 Hz, 2H), 1.68-1.49 (m, 3H), 0.84-0.73 (m, 2H), 0.49 (s, 2H). | 405 |

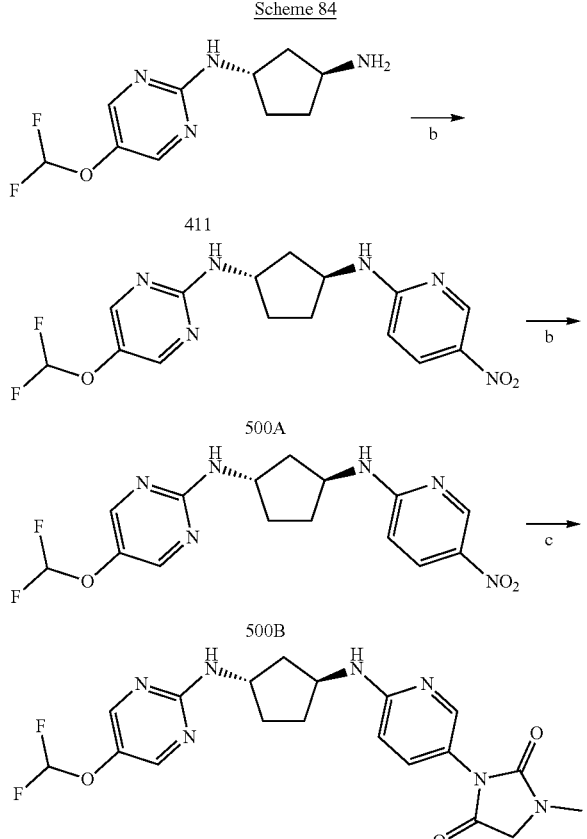

Scheme 84

Example 500 a) 2-chloro-5-nitropyridine, K₂CO₃, DMF, 80° C.; b) H₂, 10% Pd/C, rt;
c) 1)4-nitrophenyl carbonochloridate, DIPEA, CH₃CN; 2) methylglycinate hydrochloride, DIPEA, rt.

(1S, 3S)—N(5-(difluoromethoxy) pyrimidin-2-yl)-N3-(5-nitropyridin-2-yl) cyclopentane-1,3-diamine (500A)

A suspension of 411 (43 g, 176 mmol, 1.0 eq), 2-chloro-5-nitropyridine (27.9 g, 176 mmol, 1.0 eq) and K₂CO₃ (48.6 g, 382 mmol, 2.0 eq) in DMSO (500 mL) was stirred at 80° C. for 16 h. The reaction mixture was cooled down to room temperature and filtered. The filtrate was partitioned between EA (400 mL) and water (400 mL); and the aqueous phase was extracted with EA (300 mL). The combined organic phases were washed with brine (400 mL) and then concentrated under reduced pressure. The crude residue was purified by column chromatography on silica gel (PE:EA=3:1) to give 500A (52 g).

N²-(((1S, 3S)-3-((5-(difluoromethoxy) pyrimidin-2-yl) amino) cyclopentyl) pyridine-2,5-diamine (500B)

To a solution of 500A (45 g, 123 mmol, 1.0 eq) in MeOH (450 mL) was added 10% Pd/C (4.5 g). Then the reaction mixture was degassed with H₂ three times and stirred under H₂ at room temperature for 8 h. The reaction mixture was filtered thropough celit. The filtrate was concentrated to remove solvent, and the residue was purified by column chromatography on silica gel (EA:MeOH=30:1) to give 500B (31 g)

3-(6-(((1S,3S)-3-((5-(difluoromethoxy) pyrimidin-2-yl) amino) cyclopentyl) amino) pyridin-3-yl)-1-methylimidazolidine-2,4-dione (Example 500)

A solution of 500B (27.2 g, 81 mmol, 1.0 eq) and 4-nitrophenyl carbonochloridate (16.3 g, 81 mmol, 1.0 eq) in acetonitrile (280 mL) was stirred at room temperature for 1 hr. Methyl methylglycinate hydrochloride (11.8 g, 84 mmol, 1.1 eq) and DIPEA (31.3 g, 24.2 mmol, 3.0 eq) was added into the reaction and stirred for further 16 h. The reaction mixture was concentrated to remove most solvent, and the residue was partionated between DCM (70 mL) and water (70 mL). The organic phase was separated and concentrated. The resulting residue was purified by column chromatography on silica gel (DCM:MeOH=40:1) to give crude product as slurry. The compound was further purified by trituration in PE/EA (4:1, 40 mL) and de-colored with activated carbon in MeOH to give Example 500 (25 g): ¹H NMR (400 MHz, CD₃OD) δ 8.16 (s, 2H), 7.91 (d, J=2.1 Hz, 1H), 7.36 (dd, J=9.0, 2.6 Hz, 1H), 6.93-6.43 (m, 2H), 4.47-4.25 (m, 2H), 4.08 (s, 2H), 3.02 (s, 3H), 2.35-2.19 (m, 2H), 2.12-1.87 (m, 2H), 1.69-1.46 (m, 2H).

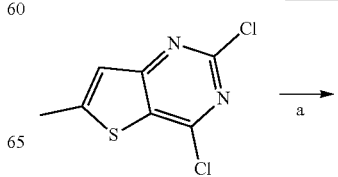

Scheme 85

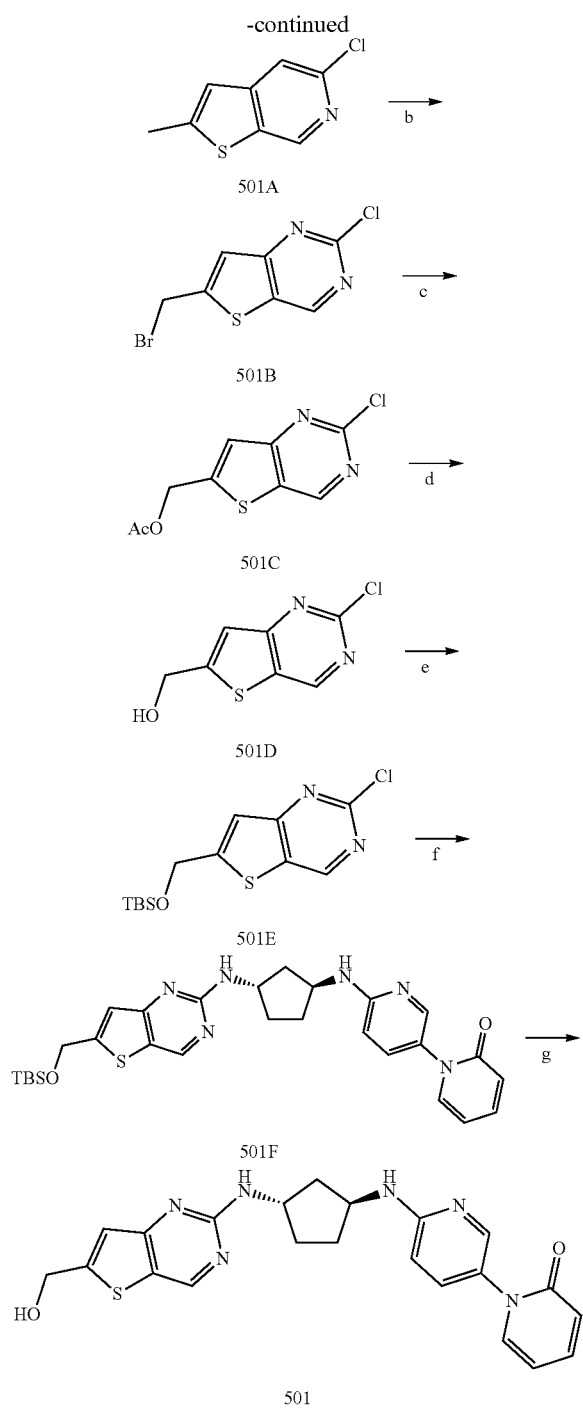

a) Zn, AcOH, MeOH, b) NBS, AIBN, CCl₄, c) AcOCs, DMF, d) K₂CO₃, DMF, e) TBSCl, Et₃N, DMF f) 485, General procedure 5; g) TBAF 2-chloro-6-methylthieno [3, 2-d]pyrimidine (501A)

A solution of 2,4-dichloro-6-methylthieno[3,2-d]pyrimidine (1.5 g, 6.85 mmol, 1.0 eq), zinc (1.8 g, 27.39 mmol, 4.0 eq) and acetic acid (2.4 mL, 41.08 mmol, 6.0 eq) in methanol (30 mL) was stirred at 70° C. for 16 h. After cooling to room temperature, the mixture was filtered, and the filter cake was washed with methanol (30 mL×2). The filtrate was concentrated and purified by flash column (petroleum ether:E-tOAc=4:1) to obtain 501A (620 mg, 47.6% yield) as a white solid. MS (ESI+) m/z 185.0 (M+H)⁺6-(bromomethyl)-2-chlorothieno[3,2-d]pyrimidine (501B) A solution of 501A (600 mg, 3.25 mmol, 1.0 eq), N-Bromosuccinimide (694.0 mg, 3.90 mmol, 1.2 eq) and AIBN (26.7 mg, 0.16 mmol, 0.05 eq) in carbon tetrachloride (20 mL) was refluxed in a sealed tube for 16 h. After cooling to room temperature, the mixture was concentrated and purified by flash column (petroleum ether:EtOAc: 4:1) to obtain 501B (614 mg, 71.2% yield) as a yellow solid. MS (ESI+) m/z 262.9 (M+H)⁺

(2-chlorothieno [3,2-d]pyrimidin-6-yl)methyl acetate (501C)

A solution of 510B (600 mg, 2.3 mmol, 1.0 eq) and cesium acetate (2.2 g, 11.4 mmol, 5.0 eq) in DMF (15 mL) was stirred at room temperature for 30 min. The mixture was diluted with EtOAc (100 mL), washed with water (80 mL) and brine (60 mL), dried over Na₂SO₄. After the filtration, the filtrate was concentrated and purified by flash column (petroleum ether:EtOAc: 4:1) to obtain 501C (373 mg, 67.5% yield) as a white solid. MS (ESI+) m/z 243.0 (M+H)⁺; ¹H NMR (400 MHz, CDCl₃) δ 9.07 (s, 1H), 7.39-7.52 (m, 1H), 5.43 (d, J=0.9 Hz, 2H), 2.17 (s, 3H).

(2-chlorothieno [3, 2-d]pyrimidin-6-yl) methanol (501D)

A solution of 501C (160 mg, 0.66 mmol, 1.0 eq) and potassium carbonate (136.7 mg, 0.99 mmol, 1.5 eq) in methanol (15 mL) was stirred at room temperature for 1 h. Then, the mixture was concentrated and purified by flash column (petroleum ether:EtOAc: 1:1) to obtain 501D (100 mg, 75.8% yield) as white solid: MS (ESI+) m/z 201.0 (M+H)⁺

6-(((tert-butyldimethylsilyl)oxy)methyl)-2-chlorothieno[3,2-d]pyrimidine (501E)

A solution of 501D (100 mg, 0.50 mmol, 1.0 eq) in DMF (5 mL) was cooled to 0° C. TBSCl (97.6 mg, 0.65 mmol, 1.3 eq) was added followed by triethylamine (0.14 mL, 1.00 mmol, 2.0 eq). The mixture was stirred at room temperature for 16 h. The mixture was diluted with ethyl acetate (60 mL), washed with water (60 mL) and brine (30 mL), dried over Na₂SO₄. The filtrate was concentrated and purified by flash column (petroleum ether:EtOAc: 4:1) to obtain 501D (126 mg, 80.5% yield) as white solid: MS (ESI+) m/z 315.2 (M+H)⁺

6'-(((1 S,3S)-3-((6-(((tert-butyldimethylsilyl)oxy) methyl)thieno [3,2-d]pyrimidin-2-yl)amino)cyclopentyl)amino)-2H-[1,3'-bipyridin]-2-one (501F)

Methods analogous to those described in General Method 5 from starting material 501E and 485 afforded 501F.

6'-(((1S, 3S)-3-((6-(hydroxymethyl) thieno[3,2-d] pyrimidin-2-yl)amino)cyclopentyl)amino)-2H-[1,3'-bipyridin]-2-one (501)

TBAF (3 mL) was added to the solution of 501F (crude, 0.16 mmol, 1.0 eq) in DMSO (10 mL) and stirred for 30 min. Then, the mixture was diluted with water (50 mL) and extracted with EtOAc (50 mL×2), dried over Na₂SO₄. The filtrate was concentrated and purified by flash column on silica gel (DCM:MeOH: 15:1) to afford crude compound, which was further purified by Prep-HPLC to obtain pure 501 (2.3 mg, 3.3% yield by two steps) as white solid: MS (ESI+) m/z 435.1 (M+H)+

¹H NMR (400 MHz, CD₃OD) δ 8.84 (s, 1H), 7.98 (d, J=2.0 Hz, 1H), 7.82 (dd, J=9.6, 2.4 Hz, 1H), 7.47-7.61 (m, 2H), 7.06 (d, J=0.8 Hz, 1H), 6.99 (d, J=9.5 Hz, 1H), 6.55 (dt, J=9.1, 1.0 Hz, 1H), 6.41 (td, J=6.8, 1.3 Hz, 1H), 4.83 (d, J=1.1 Hz, 2H), 4.50 (t, J=6.8 Hz, 1H), 4.17-4.28 (m, 1H), 2.22-2.39 (m, 2H), 2.07-2.17 (m, 2H), 1.63-1.77 (m, 2H).

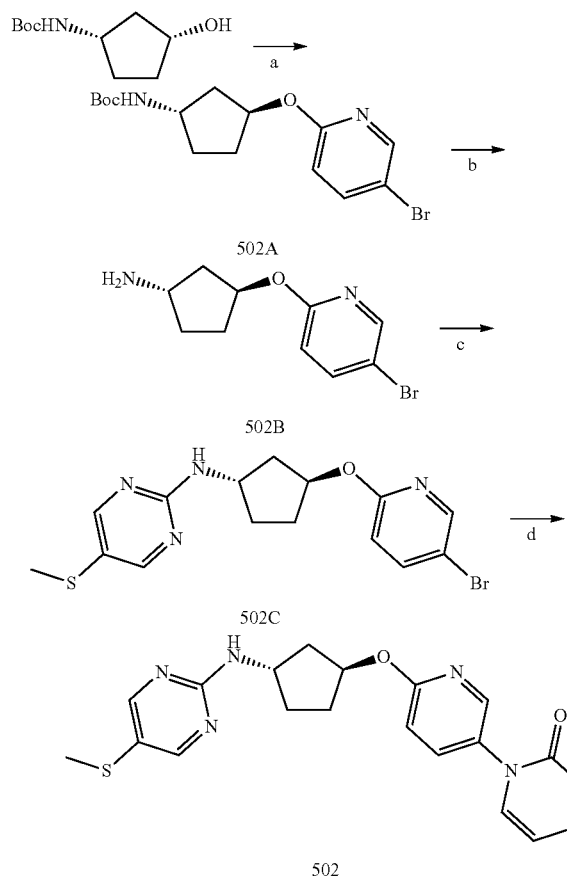

502 a) 5-bromopyridin-2-ol, PPh₃, DEAD, THF, 0° C.; b) General procedure 6 3) General procedure 5;
d) pyridin-2(1H)-one. General procedure 14.

Tert-butyl ((1S, 3S)-3((5-bromopyridin-2-yl) oxy) cyclopentyl) carbamate (502A)

To a cold (0 □) solution of tert-butyl ((1S, 3R)-3-hydroxycyclopentyl) carbamate (865 mg, 4.3 mmol, 1.5 eq) and 5-bromopyridin-2-ol (500 mg, 2.9 mmol, 1.0 eq) in THF (20 mL) was added PPh₃ (1.884 g, 7.2 mmol, 2.5 eq), followed by addition of DEAD (1.04 mL, 7.2 mmol, 2.5 eq) dropwise under N₂. The reaction mixture was stirred at 0□ for 1.5 h. The reaction mixture was then partitioned between EA and water. The separated organic phase was washed with brine and dried over Na₂SO₄, filtered and concentrated under reduced pressure. The crude residue was purified by flash chromatography on silica gel (PE:EA=5:1) to afford 502A (1.02 g) as a white solid: ESI (M+H)⁺=357.2. ¹H NMR (400 MHz, CDCl₃) δ 8.15 (d, J=2.4 Hz, 1H), 7.60 (ddd, J=13.9, 7.8, 6.1 Hz, 1H), 6.58 (d, J=8.8 Hz, 1H), 4.50 (s, 1H), 4.20 (s, 1H), 2.20 (tt, J=12.3, 6.3 Hz, 3H), 1.87-1.72 (m, 2H), 1.58 (d, J=13.9 Hz, 1H), 1.44 (s, 9H).

(1S, 3S)-3-((5-bromopyridin-2-yl) oxy) cyclopentan-1-amine (502B)

Methods analogous to those described in General Method 6 from starting material 502A afforded 502B as yellow oil.

N-((1S, 3S)-3-((5-bromopyridin-2-yl) oxy) cyclopentyl)-5-(methylthio)pyrimidin-2-amine (502C)

Methods analogous to those described in General Method 5 from starting material 502B and 2-chloro-5-(methylthio) pyrimidine afforded 502C a yellow solid: ESI (M+H)⁺=381.1

6'-(((1S, 3S)-3-((5-(methylthio) pyrimidin-2-yl) amino) cyclopentyl) oxy)-2H-[1, 3'-bipyridin]-2-one (502)

Methods analogous to those described in General Method 14 from starting material 502 and pyridin-2(1H)-one afforded 502 a white solid: ESI (M+H)⁺=396.3. ¹H NMR (400 MHz, CD₃OD) δ 8.40 (s, 2H), 8.21-8.14 (m, 1H), 7.74 (dd, J=8.8, 2.8 Hz, 1H), 7.66-7.57 (m, 2H), 6.90 (dd, J=8.8, 0.5 Hz, 1H), 6.63 (dt, J=8.9, 1.1 Hz, 1H), 6.49 (td, J 6.8, 1.3 Hz, 1H), 5.61-5.53 (m, 1H), 4.51 (p, J=7.1 Hz, 1H), 2.39 (s, 3H), 2.37-2.26 (m, 3H), 2.08-1.99 (m, 1H), 1.91 (tdd, J=10.0, 7.7, 2.7 Hz, 1H), 1.74-1.60 (m, 1H).

Scheme 87

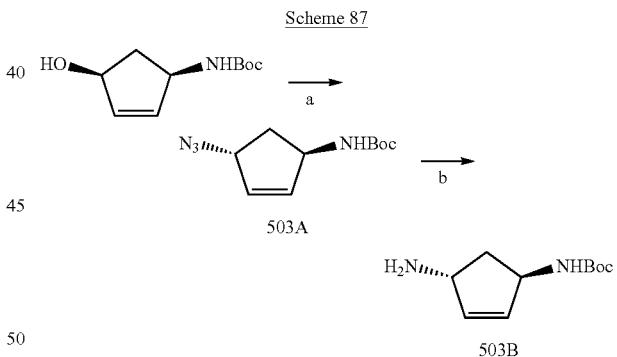

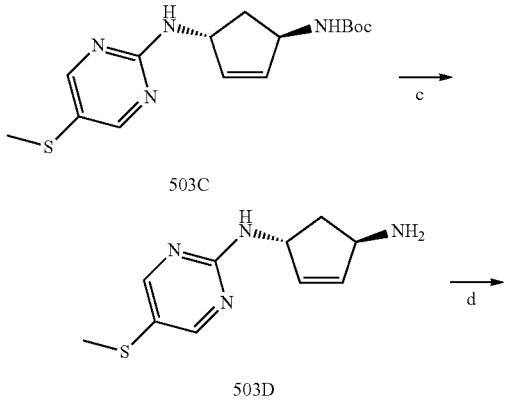

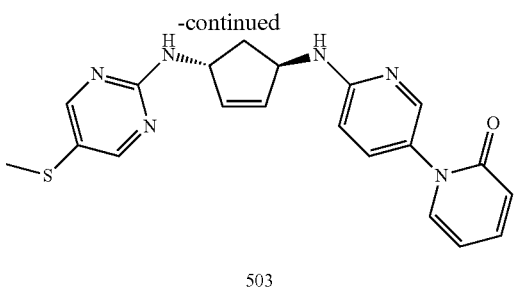

503 a) DPPA, DBU, rt; b) PPh₃, H₂O, THF, 50° C.; c) General procedure 5; d) General procedure 6; e) General procedure 2.

tert-butyl ((1R,4R)-4-azidocyclopent-2-en-1-yl)carbamate (503A)

To a solution of tert-butyl ((1R,4S)-4-hydroxycyclopent-2-en-1-yl)carbamate (200 mg, 1.0 mmol, 1.0 eq) in THF (10 mL) was added DPPA (414 mg, 1.5 mmol, 1.5 eq) and DBU (230 mg, 1.5 mmol, 1.5 eq) at room temperature and then stirred for 2 days. Water (10 mL) was added to above solution, which was then extracted with EtOAc (10 mL×3). The combined organic layers were washed with brine (30 mL), dried over Na₂SO₄, filtered, concentrated and purified by chromatography on silica gel eluting with PE:EA=5:1 to afford 503A (200 mg, 89%) as a white solid.

Tert-butyl ((1R, 4R)-4-aminocyclopent-2-en-1-yl) carbamate (503B)

To a solution of 503A (200 mg, 0.9 mmol, 1.0 eq) in THF:H₂O=4:1 (10 mL) was added PPh₃ (234 mg, 0.9 mmol, 1.0 eq) at room temperature under N₂ atmosphere. The mixture was then stirred at 50° C. overnight and then cooled down to room temperature. The filtrate was concentrated and purified by chromatography on silica gel eluting with DCM:MeOH=20:1-3:1 to afford 503B (100 mg, 57%) as a semi solid.

tert-butyl ((1R,4R)-4-((5-(methylthio)pyrimidin-2-yl)amino)cyclopent-2-en-1-yl)carbamate (503C)

Methods analogous to those described in General Method 5 from starting material 503B and 2-chloro-5-(methylthio)pyrimidine afforded 503C as a brown solid.

(1R, 3R)-N1-(5-(methylthio) pyrimidin-2-yl) cyclopent-4-ene-1,3-diamine (503D)

Methods analogous to those described in General Method 6 from starting material 503C afforded 503D as brown oil, which was used in the next step directly.

6'-(((1R, 4R)-4-((5-(methylthio) pyrimidin-2-yl) amino) cyclopent-2-en-1-yl) amino)-2H-[1,3'-bipyridin]-2-one (503)

Methods analogous to those described in General Method 2 from starting material 503D afforded 503 as a off-white solid: LCMS [M+H]⁺=393; ¹H NMR (400 MHz, CD₃OD) δ 8.34 (s, 2H), 7.96 (s, 1H), 7.65-7.55 (m, 2H), 7.48-7.45 (m, 1H), 6.63-6.60 (m, 2H), 6.50-6.46 (m, 1H), 6.02-6.00 (m, 2H), 5.20-5.15 (m, 2H), 2.35 (s, 3H), 2.20-2.16 (m, 2H).

Scheme 88

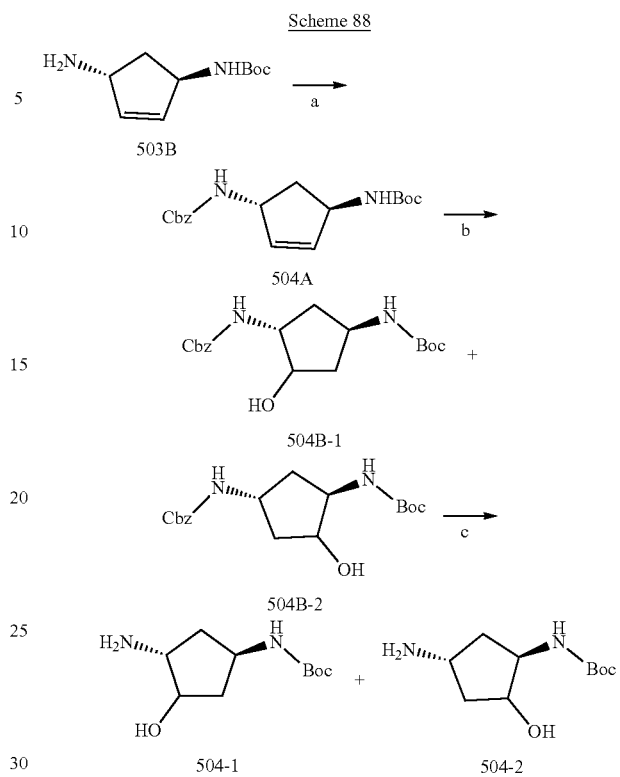

a) CBz—Cl, Na₂CO₃, THF, H₂O; b) BH₃·THF, H₂O₂, NaOH; c) Pd(OH)₂/C, MeOH.

Benzyl tert-butyl ((1R, 3R)-cyclopent-4-ene-1,3-diyl)dicarbamate (504A)

To a solution of 503B (0.5 g, 2.5 mmol, 1.0 eq) in THF (10 mL) and H₂O (2 mL) was added Na₂CO₃ (0.65 g, 5.8 mmol, 2.5 eq) and Cbz-Cl (510 mg, 3.0 mmol, 1.2 eq). The resulting solution was stirred at room temperature for 2.5 h. The reaction mixture was poured into water (50 mL) and extracted with ethyl acetate (25 mL×3). The combined organic layers were washed with brine and dried over anhydrous Na₂SO₄. The filtrate was concentrated under reduced pressure. The crude residue was purified by silica gel column chromatography (hexane:ethyl acetate=5:1) to give 504A (566 mg) as a pale solid. ESI [M+H]⁺=333.

Benzyl tert-butyl ((1R,3R)-4-hydroxycyclopentane-1,3-diyl)dicarbamate (504B-1) & benzyl tert-butyl ((1R,3R)-4-hydroxycyclopentane-1,3-diyl)dicarbamate (504B-2)

To a solution of 504A (524 mg, 1.7 mmol, 1 eq) in THF (10 mL) was added BH3.THF (1N, 7.8 mL, 7.8 mmol, 4.5 eq) at 0° C. The resulting solution was stirred at room temperature for 6 h. H₂O (7.5 mL) and NaOH (3M, 12 mL) was added, followed by H₂O₂ (30%, 20 mL). The mixture was stirred at room temperature for another 10 min before addition of EtOH (7.5 mL). The resulting mixture was stirred at room temperature for 20 h. After pouring into water (20 mL), the mixture was extracted with ethyl acetate (15 mL×6). The combined organic layers were washed with brine and dried over anhydrous Na₂SO₄. The organic phase was filtered off and concentrated under reduced pressure. The crude residue was purified by silica gel chromatography (hexane:ethyl acetate=10:1 to 1:2) to afford the title compounds (566 mg in total) as a pale solid: ESI [M+H]⁺=351.

tert-butyl ((1R,3R)-3-amino-4-hydroxycyclopentyl)carbamate (504-1) & tert-butyl ((1R,4R)-4-amino-2-hydroxycyclopentyl)carbamate (504-2)

360 mg of starting material (1.1 mmol, 1 eq) in MeOH (25 mL) was stirred with Pd(OH)₂ (100 mg) under H₂ at room temperature for 19 hr. The catalyst was removed by filtration and the filtrate was concentrated to afford the title compound as a pale solid. Yield: 200 mg. ESI [M+H]⁺=217.

Using the procedures described above, the following examples were synthesized:

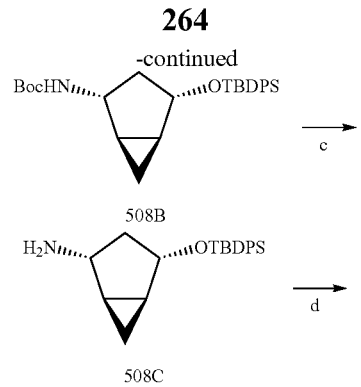

| Structure | Ex. # | ¹H NMR | LC-MS (M + H)⁺ |
|---|---|---|---|
| 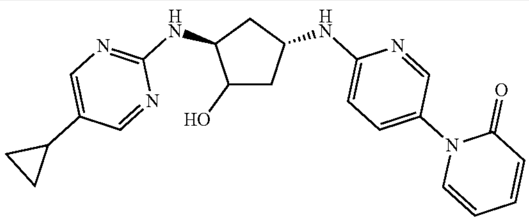 [SMILES: O=c1ccccn1-c1ccc(N[C@@H]2CC(O)[C@@H](Nc3ncc(C4CC4)cn3)C2)nc1] | 505 | ¹H NMR (400 MHz, CD₃OD) δ 8.10 (s, 2H), 7.94 (s, 1H), 7.67-7.54 (m, 2H), 7.45 (dd, J = 9.0, 2.6 Hz, 1H), 6.62 (dd, J = 9.0, 3.0 Hz, 2H), 6.46 (t, J = 6.7 Hz, 1H), 4.40-4.28 (m, 1H), 4.10 (m, 2H), 2.65-2.47 (m, 1H), 2.23-2.11 (m, 1H), 2.06 (m, 1H), 1.76 (m, 1H), 1.63 (m, 1H), 0.98-0.78 (m, 2H), 0.66-0.51 (m, 2H). | 405.2 |
| 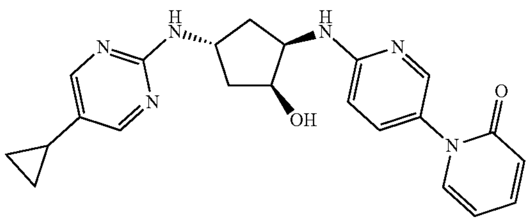 [SMILES: O=c1ccccn1-c1ccc(N[C@@H]2C[C@@H](Nc3ncc(C4CC4)cn3)C[C@@H]2O)nc1] | 506 | ¹H NMR (400 MHz, MeOD) δ 8.13-8.04 (s, 2H), 7.96 (s, 1H), 7.65-7.53 (m, 2H), 7.53-7.38 (m, 1H), 6.74-6.56 (m, 2H), 6.46 (m, 1H), 4.39 (m, 1H), 4.16-3.96 (m, 2H), 2.51 (m, 1H), 2.19 (m, 1H), 2.04 (m, 1H), 1.76 (m, 1H), 1.71-1.58 (m, 1H), 0.97-0.84 (m, 2H), 0.67-0.54 (m, 2H). | 405.2 |
| 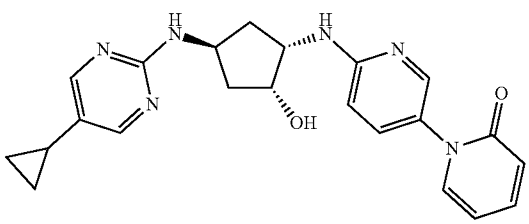 [SMILES: O=c1ccccn1-c1ccc(N[C@H]2C[C@H](Nc3ncc(C4CC4)cn3)C[C@H]2O)nc1] | 507 | ¹H NMR (400 MHz, MeOD) δ 8.10-8.04 (s, 2H), 7.95 (s, 1H), 7.59 (m, 2H), 7.50-7.41 (m, 1H), 6.79-6.56 (m, 2H), 6.46 (m, 1H), 4.55-4.44 (m, 1H), 4.41-4.27 (m, 2H), 2.27 (m, 1H), 2.22-2.09 (m, 1H), 2.06-1.93 (m, 1H), 1.93-1.80 (m, 1H), 1.81-1.66 (m, 1H), 0.97-0.80 (m, 2H), 0.68-0.49 (m, 2H). | 405.2 |

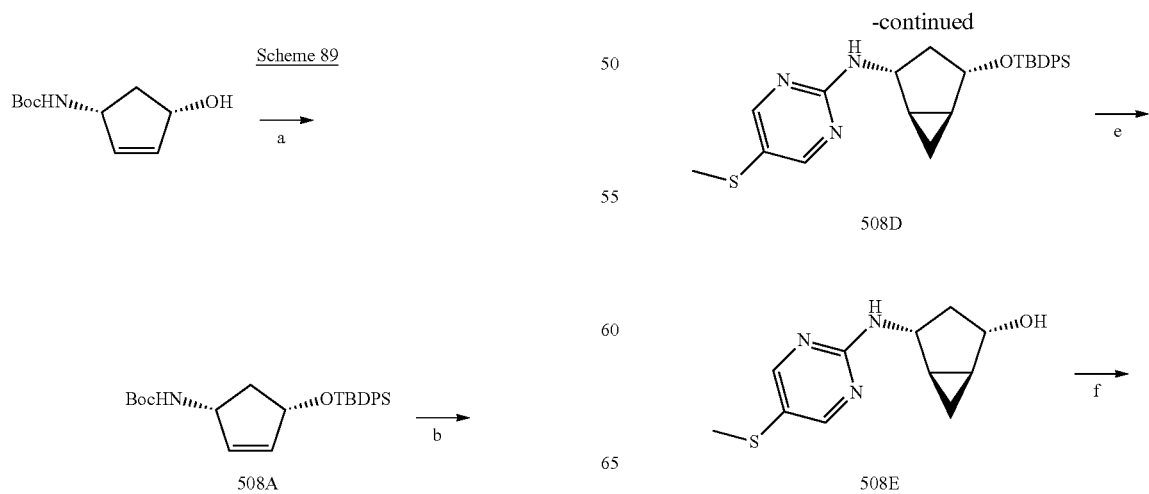

Scheme 89

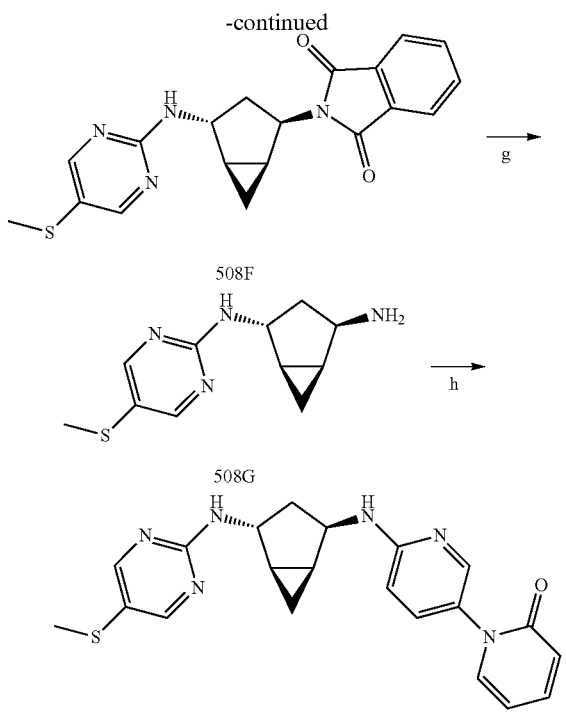

508 a) TBDPSCl, imidazole, DMF, rt; b) Et$_2$N, CH$_2$I$_2$, DCM, -15-0° C.; c) TFA, DCM, rt; d) General procedure 5; e) pyridine HF, THF, rt; f) isoindoline-1,3-dione, PPh$_3$, DEAD, THF, rt; g) hydrazine hydrate, EtOH, rt; h) General procedure 2.

tert-butyl ((1R,4S)-4-((tert-butyldiphenylsilyl)oxy)cyclopent-2-en-1-yl)carbamate (508A)

To a cold (0 □) solution of tert-butyl ((1R, 4S)-4-hydroxycyclopent-2-en-1-yl) carbamate (500 mg, 2.5 mmol, 1.0 eq) and imidazole (342 mg, 5.0 mmol, 2.0 eq) in DMF (10 mL) was added dropwise TBDPSCl (0.85 mL, 3 mmol, 1.3 eq). The reaction mixture was then stirred for 16 h while the temperature was allowed to rise to room temperature. The reaction mixture was partitioned between EA and water. The separated organic layer was washed with brine, dried over Na$_2$SO$_4$, filtered and concentrated under reduced pressure. The crude residue was purified by reverse-phase flash chromatography (CH$_3$CN:H$_2$O=40%-90%) to afford 508A (869.2 mg) as a clear oil: $^1$H NMR (400 MHz, DMSO-d$_6$) δ 7.65 (dd, J=6.8, 1.0 Hz, 4H), 7.53-7.41 (m, 6H), 7.10 (d, J=7.8 Hz, 1H), 4.67 (t, J 6.7 Hz, 1H), 4.25 (dd, J=14.6, 7.2 Hz, 1H), 3.20 (d, J=4.0 Hz, 1H), 2.53 (dt, J=3.6, 1.8 Hz, 1H), 2.52-2.43 (m, 1H), 1.60-1.49 (m, 1H), 1.39 (s, 9H), 1.03 (s, 9H).

tert-butyl ((1R,2R,4S,5S)-4-((tert-butyldiphenylsilyl)oxy)bicyclo[3.1.0]hexan-2-yl)carbamate (508B)

To a cold (-15 □) solution of Et$_2$Zn (4.6 mL, 4.6 mmol, 3.0 eq) in dry DCM (5 mL) was added dropwise diiodomethane (0.74 mL, 9.2 mmol, 6 eq) in DCM (4 mL). The reaction mixture was stirred at -15 □ for 10 minutes until a white precipitate formed. Then 508A (670 mg, 1.5 mmol, 1.0 eq) in DCM (5 mL) was added dropwise to the reaction mixture. The stirring was continued for 22 h while the temperature was allowed to warm to room temperature gradually. The reaction was quenched by addition of saturated NH$_4$Cl, and then it was partitioned between DCM and water. The separated organic phase was washed with brine, dried over Na$_2$SO$_4$, filtered and concentrated under reduced pressure. The crude residue was purified by flash chromatography on silica gel (PE:EA=10:1) to afford 508B (280 mg) as a colorless oil. $^1$H NMR (400 MHz, CDCl$_3$) δ 7.75-7.59 (m, 4H), 7.47-7.30 (m, 6H), 4.66-4.50 (m, 1H), 4.39 (td, J=8.0, 4.8 Hz, 1H), 4.01 (s, 1H), 2.17-2.07 (m, 1H), 1.44 (d, J=7.8 Hz, 9H), 1.34-1.24 (m, 2H), 1.05 (d, J=5.7 Hz, 9H), 0.83 (dt, J=9.0, 2.9 Hz, 1H), 0.46-0.33 (m, 1H).

(1R, 2R, 4S, 5S)-4-((tert-butyldiphenylsilyl) oxy) bicyclo [3.1.0]hexan-2-amine (508C)

To a solution of 508B (230 mg) in DCM (3 mL) was added TFA (5 mL). The reaction mixture was stirred at room temperature for 1 h and then concentrated under reduced pressure. The residue was redissolved in MeOH and the pH level was increased to 8 by adding ion-exchange resins. The filtrate was concentrated under reduced pressure to afford 508C (189.2 mg) as a yellow oil.

N-((1R,2R,4S,5S)-4-((tert-butyldiphenylsilyl)oxy)bicyclo[3.1.0]hexan-2-yl)-5-(methylthio)pyrimidin-2-amine (508D)

Methods analogous to those described in General Method 5 from starting material 504C and 2-chloro-5-(methylthio) pyrimidine afforded 504D as a brown oil.

(1S,2S,4R,5R)-4-((5-(methylthio) pyrimidin-2-yl) amino)bicyclo[3.1.0]hexan-2-ol (508E)

To a solution of 508D (50 mg) in THF (2 mL) was added dropwise pyridine HF (0.5 mL). The reaction mixture was stirred for 4 h at room temperature and then partitioned between EA and water. The separated organic phase was washed with brine. The organic phase was dried over Na$_2$SO$_4$, filtered and concentrated under reduced pressure. The crude residue was purified by flash chromatography on silica gel (DCM:MeOH=10:1) to afford 508E (54.4 mg) as a light yellow oil. ESI (M+H)+=238.3

2-((1S,2R,4R,5R)-4-((5-(methylthio)pyrimidin-2-yl)amino)bicyclo[3.1.0]hexan-2-yl)isoindoline-1,3-dione (508F)

To a solution of 508E (50 mg, 0.2 mmol, 1.0 eq), isoindoline-1,3-dione (37 mg, 0.25 mmol, 1.2 eq) and PPh$_3$ (600 mg, 2.3 mmol, 10.0 eq) in THF (10 mL) was added dropwise DEAD (398 mg, 2.3 mmol, 10.0 eq) at 0□ under N$_2$. The reaction mixture was stirred for 2 h while the temperature was allowed to rise to room temperature gradually. The reaction mixture was concentrated under reduced pressure. The crude residue was purified by flash chromatography on silica gel (PE:EA=1:1) twice to afford 508F (214 mg, contaminated with impurities) as a yellow oil. ESI (M+H)+=367.4

(1R,2R,4R,5S)-N2-(5-(methylthio)pyrimidin-2-yl) bicyclo[3.1.0]hexane-2,4-diamine (508G)

A solution of 508F (214 mg, 0.584 mmol) and hydrazine hydrate (0.2 mL) in EtOH (5 mL) was stirred at 60 □ under N$_2$ for 2 h. The reaction mixture was concentrated under reduced pressure and purified by flash chromatography on silica gel (DCM:MeOH=20:1) to afford 508G (30 mg) as a yellow oil: ESI (M+H)+=237.4

6'-((((1S,2R,4R,5R)-4-((5-(methylthio)pyrimidin-2-yl)amino)bicyclo[3.1.0]hexan-2-yl)amino)-2H-[1,3'-bipyridin]-2-one (508)

Methods analogous to those described in General Method 2 from starting material 508G afforded 508 as a yellow solid: ESI (M+H)+=407.4. $^1$H NMR (400 MHz, CD$_3$OD) δ 8.35 (s, 2H), 8.07 (d, J=2.2 Hz, 1H), 7.93 (dd, J=9.6, 2.4 Hz, 1H), 7.72-7.57 (m, 2H), 7.12 (d, J=9.5 Hz, 1H), 6.65 (d, J=9.0 Hz, 1H), 6.51 (td, J=6.8, 1.2 Hz, 1H), 4.23 (d, J=5.9 Hz, 1H), 2.36 (s, 3H), 2.22-2.10 (m, 1H), 1.93 (dt, J=9.7, 4.3 Hz, 1H), 1.61 (dt, J=9.9, 6.4 Hz, 2H), 0.76 (dt, J=7.8, 3.9 Hz, 1H), 0.69 (dd, J=14.0, 7.9 Hz, 1H).

C. Biological Assays

Human recombinant PCSK9 was expressed as follows:

```
Protein sequence:
                                        (SEQ ID NO: 7)
QEDEDGDYEELVLALRSEEDGLAEAPEHGTTATFHRCAKDPWRLPGTYVV

VLKEETHLSQSERTARRLQAQAARRGYLTKILHVFHGLLPGFLVKMSGDL

LELALKLPHVDYIEEDSSVFAQSIPWNLERITPPRYRADEYQPPDGGSLV

EVYLLDTSIQSDHREIEGRVMVTDFENVPEEDGTRFHRQASKCDSHGTHL

AGVVSGRDAGVAKGASMRSLRVLNCQGKGTVSGTLIGLEFIRKSQLVQPV

GPLVVLLPLAGGYSRVLNAACQRLARAGVVLVTAAGNFRDDACLYSPASA

PEVITVGATNAQDQPVTLGTLGTNFGRCVDLFAPGEDIIGASSDCSTCFV

SQSGTSQAAAHVAGIAAMMLSAEPELTLAELRQRLIHFSAKDVINEAWFP

EDQRVLTPNLVAALPPSTHGAGWQLFCRTVWSAHSGPTRMATAVARCAPD

EELLSCSSFSRSGKRRGERMEAQGGKLVCRAHNAFGGEGVYAIARCCLLP

QANCSVHTAPPAEASMGTRVHCHQQGHVLTGCSSHWEVEDLGTHKPPVLR

PRGQPNQCVGHREASIHASCCHAPGLECKVKEHGIPAPQEQVTVACEEGW

TLTGCSALPGTSHVLGAYAVDNTCVVRSRDVSTTGSTSEGAVTAVAICCR

SRHLAQASQELQSGSGGLNDIFEAQKIEWHENLYFQGHHHHHH
```

The following assay method was used to identify and evaluate compounds of Formula (I) that are effective in inhibiting PCSK9 function.

Example: PCSK9 SPR Assay

Surface plasmon resonance data was collected on a Biacore™ T200 or 3000 system (GE Healthcare) at 25° C. Streptavidin was immobilized on a CM5 (GE Healthcare) or CMD500d sensor chip (XanTec Bioanalytics) using standard amine-coupling chemistry at 25° C. with HBS-N (10 mM HEPES, 0.15 M NaCl, pH 7.4) as the running buffer. Briefly, the carboxymethyl dextran surface was activated with a 12 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μL/min. For capture of streptavidin, protein was diluted to 0.2 mg/mL in 10 mM sodium acetate (pH 4.5) and captured by injecting 100 μL onto the activated chip surface. Residual activated groups were blocked with a 7 min injection of 1 M ethanolamine (pH 8.5). Avi-tagged PCSK9 protein was captured on the streptavidin surface by injection of 150 μL of protein diluted to 16 pg/mL in FIBS-N, 0.05% tween-20, 0.1 mM CaCl$_2$). Typical surface densities obtained were 8000-10000 RU. SPR binding data were obtained using an appropriate dilution series of each compound at a flow rate of 30 μL/min, with a capture time of 100 s and dissociation times of 300 s. Running buffer for compound binding studies was FIBS-N, 0.05% tween-20, 0.1 mM CaCl$_2$, 4% DMSO. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using a simple 1:1 binding model to determine $k_a$, $k_d$ and $K_D$ values.

The ability of compounds Formula (I) or pharmaceutically acceptable salts thereof to bind and inhibit PCSK9 was established with the representative compounds of Formula (I) listed in the table below:

| PCSK9 Affinity (nM) | Category |
|---|---|
| $K_D$ = 2,000-20,000 nM | + |
| $K_D$ = 200-2,000 nM | ++ |
| $K_D$ < 200 nM | +++ |

| Example # | $K_D$ |
|---|---|
| 1 | +++ |
| 2 | ++ |
| 3 | ++ |
| 4 | +++ |
| 5 | +++ |
| 6 | ++ |
| 7 | +++ |
| 8 | ++ |
| 9 | ++ |
| 10 | +++ |
| 11 | +++ |
| 12 | +++ |
| 13 | +++ |
| 14 | ++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | ++ |
| 26 | +++ |
| 27 | +++ |
| 28 | +++ |
| 29 | ++ |
| 30 | ++ |
| 31 | +++ |
| 32 | +++ |
| 33 | +++ |
| 34 | +++ |
| 35 | +++ |
| 36 | +++ |
| 37 | ++ |
| 38 | +++ |
| 39 | +++ |
| 40 | +++ |
| 41 | +++ |
| 42 | ++ |
| 43 | +++ |
| 44 | +++ |
| 45 | +++ |
| 46 | +++ |
| 47 | +++ |

| Example # | $K_D$ |
|---|---|
| 48 | +++ |
| 49 | +++ |
| 50 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | ++ |
| 98 | ++ |
| 99 | ++ |
| 100 | ++ |
| 102 | ++ |
| 103 | + |
| 104 | + |
| 105 | +++ |
| 106 | ++ |
| 107 | ++ |
| 164 | + |
| 165 | ++ |
| 166 | ++ |
| 167 | + |
| 168 | ++ |
| 169 | + |
| 170 | ++ |
| 171 | + |
| 172 | + |
| 173 | + |
| 174 | + |
| 175 | +++ |
| 176 | +++ |
| 177 | + |
| 178 | + |
| 179 | + |
| 180 | +++ |
| 181 | +++ |
| 182 | +++ |
| 183 | +++ |
| 184 | +++ |
| 185 | ++ |
| 186 | ++ |
| 187 | ++ |
| 188 | +++ |
| 189 | ++ |
| 190 | + |
| 203 | +++ |
| 204 | ++ |
| 205 | ++ |
| 206 | +++ |
| 207 | +++ |
| 208 | ++ |
| 209 | ++ |
| 210 | ++ |
| 211 | ++ |
| 212 | +++ |
| 213 | + |
| 214 | + |
| 215 | ++ |
| 216 | ++ |
| 217 | +++ |
| 218 | + |
| 219 | ++ |
| 220 | + |
| 221 | ++ |
| 222 | ++ |
| 223 | +++ |
| 224 | +++ |
| 225 | ++ |
| 226 | ++ |
| 227 | ++ |
| 228 | ++ |
| 229 | ++ |

| Example # | $K_D$ |
|---|---|
| 230 | +++ |
| 231 | ++ |
| 232 | ++ |
| 233 | ++ |
| 240 | +++ |
| 241 | +++ |
| 242 | ++ |
| 243 | +++ |
| 244 | ++ |
| 245 | +++ |
| 246 | +++ |
| 247 | +++ |
| 248 | +++ |
| 249 | ++ |
| 250 | +++ |
| 301 | ++ |
| 302 | +++ |
| 303 | + |
| 304 | ++ |
| 305 | ++ |
| 306 | ++ |
| 307 | ++ |
| 308 | ++ |
| 309 | ++ |
| 310 | +++ |
| 311 | +++ |
| 312 | +++ |
| 313 | +++ |
| 314 | +++ |
| 315 | +++ |
| 316 | ++ |
| 317 | ++ |
| 318 | +++ |
| 319 | + |
| 320 | +++ |
| 321 | +++ |
| 322 | +++ |
| 323 | +++ |
| 324 | +++ |
| 325 | +++ |
| 326 | +++ |
| 327 | +++ |
| 328 | +++ |
| 329 | +++ |
| 330 | +++ |
| 331 | +++ |
| 332 | +++ |
| 333 | +++ |
| 334 | +++ |
| 335 | +++ |
| 336 | +++ |
| 337 | +++ |
| 338 | +++ |
| 339 | +++ |
| 340 | +++ |
| 341 | +++ |
| 342 | +++ |
| 343 | +++ |
| 344 | ++ |
| 345 | +++ |
| 346 | +++ |
| 347 | +++ |
| 348 | +++ |
| 349 | +++ |
| 350 | +++ |
| 351 | +++ |
| 352 | +++ |
| 353 | +++ |
| 354 | +++ |
| 355 | +++ |
| 356 | +++ |
| 357 | +++ |
| 358 | +++ |
| 359 | +++ |
| 360 | +++ |
| 361 | +++ |
| 362 | +++ |

| Example # | K$_D$ |
|---|---|
| 363 | +++ |
| 364 | +++ |
| 365 | +++ |
| 366 | +++ |
| 367 | +++ |
| 368 | +++ |
| 369 | + |
| 370 | +++ |
| 371 | +++ |
| 372 | + |
| 373 | +++ |
| 375 | +++ |
| 400 | +++ |
| 401 | +++ |
| 402 | +++ |
| 403 | +++ |
| 424 | +++ |
| 425 | +++ |
| 426 | +++ |
| 427 | +++ |
| 428 | +++ |
| 429 | +++ |
| 430 | +++ |
| 440 | +++ |
| 441 | +++ |
| 442 | +++ |
| 443 | +++ |
| 444 | +++ |
| 445 | +++ |
| 446 | +++ |
| 447 | +++ |
| 448 | +++ |
| 449 | +++ |
| 450 | +++ |
| 451 | +++ |
| 452 | +++ |
| 453 | +++ |
| 454 | +++ |
| 455 | +++ |
| 456 | +++ |
| 457 | +++ |
| 458 | +++ |
| 458A | +++ |
| 458B | +++ |
| 459 | +++ |
| 460 | +++ |
| 463 | +++ |
| 464 | +++ |
| 465 | +++ |
| 466 | +++ |
| 467 | +++ |
| 468 | +++ |
| 469 | +++ |
| 470 | +++ |
| 471 | +++ |
| 472 | +++ |
| 473 | +++ |
| 474 | +++ |
| 475 | +++ |
| 476 | +++ |
| 477 | +++ |
| 478 | +++ |
| 479 | +++ |
| 480 | +++ |
| 481 | +++ |
| 482 | +++ |
| 483 | +++ |
| 484 | +++ |
| 487 | +++ |
| 488 | +++ |
| 489 | +++ |
| 490 | +++ |
| 491 | +++ |
| 492 | +++ |
| 493 | +++ |
| 494 | +++ |
| 495 | +++ |
| 497 | +++ |
| 498 | +++ |
| 499 | +++ |
| 499A | +++ |
| 500 | +++ |
| 501 | +++ |
| 502 | +++ |
| 503 | +++ |
| 505 | +++ |
| 506 | +++ |
| 507 | +++ |
| 508 | +++ |

Example: In vitro cellular assay to measure the effects of compounds on secreted PCSK9 levels, cellular LDLR levels and cell viability Compound screening was performed in 96 well tissue culture plates with 25,000 HepG2 cells plated in 200 μl of assay media (DMEM—Gibco 31966-021 with 10% lipoprotein depleted FBS-Sigma S5394). Cell plates were incubated overnight (20-24 hrs) and then assay media was removed, cells washed with 200 μl DMEM, and 200 μl compound or vehicle (0.3% DMSO) in assay media was added to each well. After 48 hours incubation with compound the following analyses were performed.

For measurement of secreted PCSK9 levels a 100 μl samples of the cell culture assay media were collected and stored at −80° C. prior to analysis using a PCSK9 (human) AlphaLISA Detection Kit (Perkin Elmer AL270F). Samples (5 μl) of cell culture assay media were transferred to 384 well white optiPlate (Perkin Elmer-6007290). Also included were 5μl samples of assay media alone to determine assay background and assay media samples spiked with a known concentration of recombinant human PCSK9 (standard curve). To each 5 μl sample 20 μl of a solution of AlphaLISA AntiPCSK9 acceptor beads (final concentration 10 μg/ml) and Biotinylated Antibody Anti-PCSK9 (final concentration 1 nM) diluted in AlphaLISA immunoassay buffer (all provided in the AlphaLISA Detection Kit) were added and plates incubated a room temperature 1 hour. Following incubation 25 μl of a solution of streptavidin donor beads (final concentration 40 μg/ml) diluted in AlphaLISA immunoassay buffer was added to each sample and samples incubated for a further 1 hour at room temperature protected from light. In the presence of the PCSK9 (analyte), the donor and acceptor beads come into close proximity. The light emission at 615 nm is then measured on an Enspire Alpha plate reader following excitation. The percentage inhibition was calculated using the following formula after the concentration of PCSK9 was determined using the standard curve values: (1−(test well value−mean background value)/(mean vehicle value−mean background value))*100

The cell viability analysis was performed on the same cell plates as the PCSK9 analysis, after the sample of cell media had been collected. The assay is based on the reduction of MTS tetrazolium compound by viable cells to generate a coloured formazan product that is soluble in cell culture media. To each cell well, containing 100 μl of remaining culture media, 20 μl MTS reagent (Promega G543) was added. Also included were wells containing 100 μl assay media plus MTS reagent without cells to determine the background measurements. Plates were incubated at 37° C. for 1 hour and the optical density (OD) measured at a wavelength of 490 nm. OD values were converted to % change in viability values using the following formula: −(1−(test well value−mean background value)/(mean vehicle value−mean background value))*100

Cellular LDLR levels were determined using Human LDL R Immunoassay (R&D systems DLDLR0) and all reagents provided in the immunoassay unless stated. HepG2 cells were treated as described above and following the 48 hours compound incubation, media was removed, cells washed with phosphate buffered saline solution and cells lysed in 50 μL of lysis buffer (25 mM Tris-HCl pH 7.4, 150 mM NaCl, 1 mM EDTA, 1% NP-40 and 5% glycerol) with protease inhibitors (Halt inhibitor cocktail—Pierce 78430). Lysates were cleared by centrifugation and samples stored at −80° C. prior analysis in the immunoassay. In addition to the samples a standard curve of a known concentration of recombinant LDLR diluted in calibrator diluent was included and no LDLR to determine assay background. Samples (30 μl) were incubated in microplate well strips (pre-coated with capture antibody) with 50 μl assay diluent for 2 hours at room temperature. Then the microplate well strips were washed four times with wash buffer and 200 μl of Human LDLR conjugate added. After a further 2 hour incubation at room temperature plates were washed as before and 200 μl of substrate solution added. After 20 minutes 50 μl of stop solution was applied and the optical density of each well measured at 450 nm and wavelength correction of 540 nm applied. The percentage increase was calculated using the following formula after the concentration of LDLR was determined using the standard curve values: (test well value−mean background value)/(mean vehicle value−mean background value)*100

As a positive control, an inhibitor of PCSK9 translation, R-4-(3H-[1,2,3]triazolo[4,5-b]pyridin-3-yl)-N-(3-chloropyridin-2-yl)-N-(piperidin-3-yl)benzamide (SI-1), was synthesized according to WO 2014170786.

Using the assays above, the ability of compounds Formula (I) or pharmaceutically acceptable salts thereof to inhibit PCSK9 function was established with the representative compounds of Formula (I) listed in the table below:

| Example # | Inhibitor Concentration (μM) | Inhibition of PCSK9 Secretion (%) | Increase in LDLR (%) | Change in Cell Viability (%) |
|---|---|---|---|---|
| 10 | 75 | 56 | 32 | 1 |
| 17 | 75 | 40 | 58 | −6 |
| 88 | 75 | 61 | 90 | −9 |
| 89 | 75 | 57 | 136 | −14 |
| 91 | 75 | 52 | 76 | −2 |
| 128 | 75 | 48 | 125 | 12 |
| 159 | 75 | 49 | 116 | 11 |
| 175 | 75 | 72 | 109 | −8 |
| SI-1 | 18.8 | 95 | 47 | 7 |

D. Pharmacophore Characterization

PCSK9(31-692)-AVI-TEV-His6 was expressed using HEK293 cells and purified from the growth medium by nickel-affinity chromatography followed by size exclusion chromatography. Pure protein was concentrated to ~8 mg/mL, mixed with inhibitor compound to a final concentration of 1 mM and incubated at 4° C. for four hours.

Co-crystals were grown by the hanging drop method of vapour diffusion in 24-well format. Crystals were cryo-cooled for synchrotron data collection at ESRF beamline ID30A-1 on a Pilatus3 2M detector or DLS beamline i04 on a Pilatus 6M-F detector.

Crystallographic Parameters

The following crystallographic parameters are given for compounds 5, 87, 105 and 188.

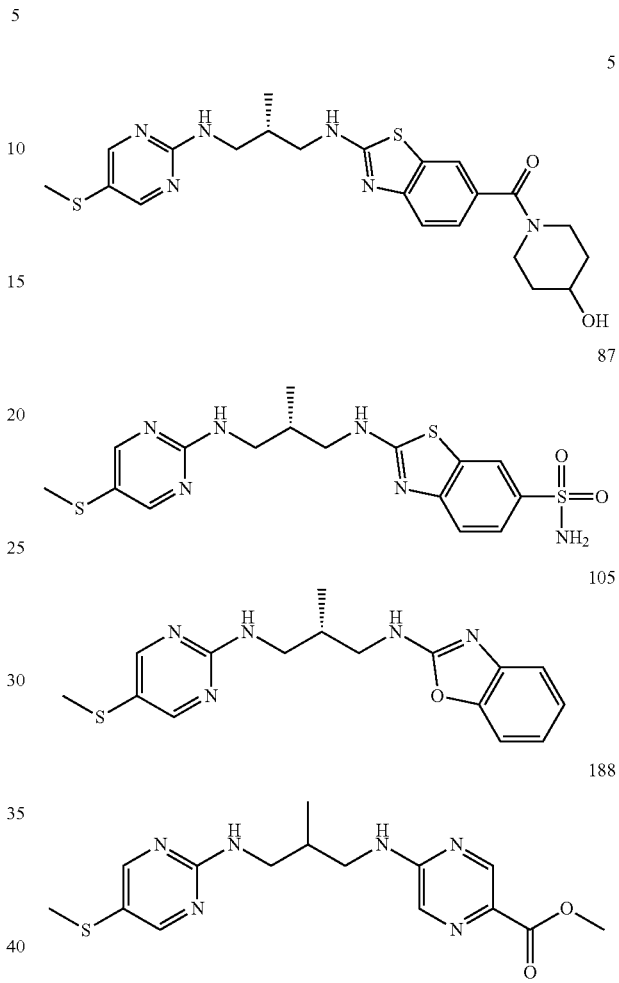

| Example # | 5 | 87 | 105 | 188 |
|---|---|---|---|---|
| Wavelength (Å) | | | | |
| Resolution range (Å) | 58.01-2.48 (2.58-2.48) | 74.17-2.44 (2.48-2.44) | 89.37-2.95 (3.05-2.95) | 74.65-2.44 (2.48-2.44) |
| Space group | P 21 21 21 | P 21 21 21 | P 21 21 21 | P 21 21 21 |
| Unit cell | 63.04 | 62.99 | 119.39 | 63.07 |
| | 70.80 | 70.64 | 132.60 | 70.71 |
| | 148.23 | 148.34 | 134.77 | 149.30 |
| Total reflections | 158294 | 160732 | 284167 | 163750 |
| Unique reflections | 24142 | 25385 | 45785 | 25629 |
| Multiplicity | 6.6 (6.6) | 6.3 (5.9) | 6.2 (6.3) | 6.4 (5.9) |
| Completeness (%) | 99.1 (92.6) | 100.0 (96.7) | 100.0 (100.0) | 100.0 (100.0) |
| Mean I/sigma(I) | 9.2 (1.7) | 5.8 (1.1) | 7.3 (1.6) | 4.8 (1.3) |
| Wilson B-factor | 88.5 | 34.335 | 48.1 | |
| R-merge | 0.164 (1.119) | 0.200 (1.429) | 0.110 (0.743) | 0.286 (1.264) |
| R-meas | 0.193 (1.317) | 0.218 (1.581) | 0.133 (0.890) | 0.311 (1.388) |
| CC1/2 | 0.993 (0.609) | 0.991 (0.618) | 0.994 (0.828) | 0.980 (0.539) |

| Example # | 5 | 87 | 105 | 188 |
|---|---|---|---|---|
| CC* | | | | |
| R-work | 0.2070 | 0.2333 | 0.2135 | 0.2419 |
| R-free | 0.2555 | 0.2951 | 0.2530 | 0.2990 |
| Number of non-hydrogen atoms | 4352 | 4499 | | 4478 |
| macromolecules | 4258 | 4357 | 8635 | 4345 |
| ligands | 32 | 27 | 46 | 24 |
| water | 56 | 109 | 0 | 103 |
| Protein residues | 574 | 580 | | 580 |
| RMS(bonds) | 0.008 | 0.008 | 0.008 | 0.010 |
| RMS(angles) | 1.358 | 1.359 | 1.368 | 1.365 |
| Ramachandran favored (%) | 95.00 | 96.45 | 93.30 | 95.41 |
| Ramachandran outliers (%) | 0.36 | 0.35 | 1.12 | 0.71 |
| Average B-factor | | | | |
| macromolecules | 40.54 | 42.65 | 68.38 | 31.06 |
| ligands | 45.17 | 39.89 | 92.21 | 26.97 |
| solvent | 36.14 | 39.77 | — | 23.91 |

Sequence Listing of Exemplary PCSK9 Isoforms (Uniprot ID provided)

Q8NBP7#VAR_017197
SEQID NO: 1
MGTVSSRRSWWPLPLLLLLLLLLGPAGARAQEDEDGDYEELVLALLSEED
GLAEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMML
SAEPELTLAELRQRLIHFSAKDVINEAWFPEDQRVLTPNLVAALPPSTHG
AGWQLFCRTVWSAHSGPTRMATAVARCAPDEELLScSSFSRSGKRRGERM
EAQGGKLVCRAHNAFGGEGVYAIARCCLLPQANCSVHTAPPAEASMGTRV
HCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAV
DNTCVVRSRDVSTTGSTSEGAVTAVAICCRSRHLAQASQELQ

Q8NBP7#VAR_017198
SEQID NO: 2
MGTVSSRRSWWPLPLLLLLLLLLGPAGARAQEDEDGDYEELVLALRSEED
GLVEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMML
SAEPELTLAELRQRLIHFSAKDVINEAWFPEDQRVLTPNLVAALPPSTHG
AGWQLFCRTVWSAHSGPTRMATAVARCAPDEELLScSSFSRSGKRRGERM
EAQGGKLVCRAHNAFGGEGVYAIARCCLLPQANCSVHTAPPAEASMGTRV
HCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAV
DNTCVVRSRDVSTTGSTSEGAVTAVAICCRSRHLAQASQELQ

Q8NBP7#VAR_021337
SEQID NO: 3
MGTVSSRRSWWPLPLLLLLLLLLGPAGARAQEDEDGDYEELVLALRSEED
GLAEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMML
SAEPELTLAELRQRLIHFSAKDVISEAWFPEDQRVLTPNLVAALPPSTHG
AGWQLFCRTVWSAHSGPTRMATAVARCAPDEELLScSSFSRSGKRRGERM
EAQGGKLVCRAHNAFGGEGVYAIARCCLLPQANCSVHTAPPAEASMGTRV
HCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAV
DNTCVVRSRDVSTTGSTSEGAVTAVAICCRSRHLAQASQELQ

Q8NBP7#VAR_021338
SEQID NO: 4
MGTVSSRRSWWPLPLLLLLLLLLGPAGARAQEDEDGDYEELVLALRSEED
GLAEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL
RVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMML
SAEPELTLAELRQRLIHFSAKDVINEAWFPEDQRVLTPNLVATLPPSTHG
AGWQLFCRTVWSAHSGPTRMATAVARCAPDEELLScSSFSRSGKRRGERM
EAQGGKLVCRAHNAFGGEGVYAIARCCLLPQANCSVHTAPPAEASMGTRV
HCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAV
DNTCVVRSRDVSTTGSTSEGAVTAVAICCRSRHLAQASQELQ

Q8NBP7#VAR_021339
SEQID NO: 5
MGTVSSRRSWWPLPLLLLLLLLLGPAGARAQEDEDGDYEELVLALRSEED
GLAEAPEHGTTATFHRCAKDPWRLPGTYVVVLKEETHLSQSERTARRLQA
QAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRV
MVTDFENVPEEDGTRFHRQASKCDSHGTHLAGVVSGRDAGVAKGASMRSL

-continued

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAIARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQ

Q8NBP7#VAR_017201

SEQID NO: 6

MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEEAVTAVAICCRSRHLAQASQELQ

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of inhibiting PCSK9, comprising contacting PCSK9 with an inhibitor of PCSK9 that binds to a binding pocket defined by amino acid residues Val589 and Ser636 of human PCSK9, wherein the inhibitor of PCSK9 binds to the binding pocket with an affinity ($K_D$) of less than 20,000 nM.

2. The method of claim 1, wherein the inhibitor is an allosteric inhibitor.

3. The method of claim 1, wherein the method comprises contacting the surface of a cell that secretes PCSK9 with the inhibitor.

4. The method of claim 1, wherein the method comprises contacting intracellular PCSK9 with the inhibitor.

5. The method of claim 1, wherein the method comprises contacting PCSK9 that is circulating in plasma with the inhibitor.

6. The method of claim 1, wherein the inhibitor comprises an H-bond acceptor/donor group having two H-bond acceptor moieties and one H-bond donor moiety disposed to donate an H-bond to and accept an H-bond from the backbone amide functionality of residue Val589, and accept an H-bond from the hydroxymethyl sidechain of Ser636 of human PCSK9.

7. The method of claim 1, wherein the inhibitor comprises an H-bond acceptor/donor group having two H-bond donor moieties and one H-bond acceptor moiety disposed to donate an H-bond to and accept an H-bond from the backbone amide functionality of residue Val589, and donate an H-bond to the hydroxymethyl sidechain of Ser636 of human PCSK9.

8. The method of claim 1, wherein the inhibitor comprises a pyrimidinyl ring and the two H-bond acceptor moieties are the two nitrogen atoms present on the pyrimidinyl ring.

9. The method of claim 8, wherein the inhibitor comprises a 2-NH-pyrimidinyl moiety and the one H-bond donor moiety is the amino hydrogen atom.

10. The method of claim 1, wherein the inhibitor further comprises one or more of:
    a) an H-bond acceptor moiety disposed to bind with amino acid residues Ser642, His643 or Val 644,
    b) an H-bond donor moiety disposed to bind with amino acid residue Ala637 or Thr641, and
    c) a cation-pi stacking interaction moiety disposed to bind with amino acid residue Arg495 or His591,
    wherein the H-bond acceptor/donor group is bound to amino acid residues Val589 and Ser636 of human PCSK9.

11. The method of claim 1, wherein the inhibitor further comprises an H-bond acceptor moiety disposed to bind with amino acid residue Glu612.

12. The method of claim 1, wherein the inhibitor interacts with at least one residue in the M2 C-terminal domain and at least one residue in the M3 C-terminal domain.

13. The method of claim 1, wherein the inhibitor further interacts with at least one residue in the M1 C-terminal domain.

14. The method of claim 1, wherein the inhibitor interacts with at least one residue in the M1 C-terminal domain and at least one residue in the M3 C-terminal domain.

15. The method of claim 1, wherein the inhibitor interacts with at least one residue in the M1 C-terminal domain and at least one residue in the M2 C-terminal domain.

16. The method of claim 1, wherein the inhibitor interacts with a pocket in PCSK9 between amino acid residues 558-590 in the M2 C-terminal domain and amino acids residues 631-650 in the M3 C-terminal domain.

17. The method of claim 1, wherein the inhibitor interacts with at least one residue in beta strand 3 and beta strand 5 of the M2 C-terminal domain and beta strand 3 and beta strand 4 of the M3 C-terminal domain.

18. The method of claim 17, wherein the inhibitor interacts with a pocket in PCSK9 created between amino acid residues 558-566 in beta strand 3 of the M2 C-terminal domain and amino acids residues 587-590 in beta strand 5 of the M2 C-terminal domain.

19. The method of claim 18, wherein the inhibitor interacts with a pocket in PCSK9 created between amino acid residues 631-637 in beta strand 3 of the M3 C-terminal domain and amino acids residues 644-650 in beta strand 4 of the M3 C-terminal domain.

20. The method of claim 1, wherein the inhibitor is a compound of formula (I):

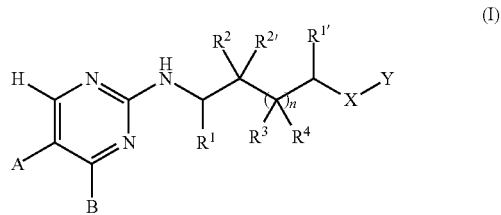

wherein:
A is selected from H, halo, hydroxy, alkyl, thioalkyl, alkenyl, alkoxy, acyloxy, cyano, cycloalkyl, —C(O)OR$^6$, and —C(O)NR$^6$R$^7$;
B is selected from H, alkyl, and halo, or
A and B are taken together with the carbon atoms to which they are attached to form a 5- or 6-membered heteroaryl;
X is NR$^5$ or O;
R$^1$ and R$^{1'}$ are each independently selected from H and alkyl; or
    if n is 0, R$^1$ and R$^{1'}$, together with the atoms to which they are attached, form a 4-8 membered cycloalkyl or cycloalkenyl ring;
R$^2$ is selected from H, halo, alkyl, alkoxy, amidoalkyl, aminoalkyl, hydroxyalkyl, alkylamino, cyano, and hydroxy; or R¹ and R², together with the atoms to which they are attached, form a 3-8 membered cycloalkyl or heterocyclyl ring; or R¹' and R², together with the atoms to which they are attached, form a 3-8 membered cycloalkyl or heterocyclyl ring;

R²' is selected from H, halo, alkyl, alkoxy, amidoalkyl, aminoalkyl, and cyano, or R² and R²', taken together with the carbon atom to which they are attached, form a 3- to 8-membered cycloalkyl or heterocyclyl ring;

each R³ and R⁴ is independently H or alkyl; or

R² and R³, together with the atoms to which they are attached, form a 3-8 membered cycloalkyl or heterocyclyl ring; and R⁵ is H or alkyl; or R¹ and R⁵, together with the atoms to which they are attached, form a 6-8 membered cycloalkyl or heterocyclyl ring; or R² and R⁵, together with the atoms to which they are attached, form a 5-8 membered cycloalkyl or heterocyclyl ring;

each R⁶ and R⁷ is independently H or alkyl;

Y is selected from aryl, heteroaryl and heterocyclyl; and n is 0 or 1.

21. The method of claim 10, wherein the inhibitor has one H-bond acceptor moiety disposed to bind with amino acid residue Ser642, one H-bond acceptor moiety disposed to bind with amino acid residue Val644, and one H-bond donor moiety disposed to bind with amino acid residue Ala637.

22. The method of claim 21, wherein the inhibitor is

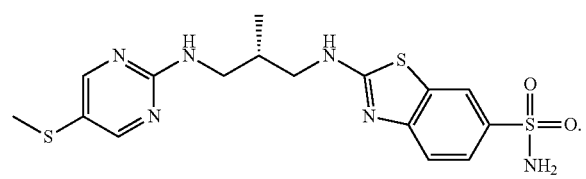 [SMILES: CSc1cnc(NC[C@H](C)CNc2nc3ccc(S(N)(=O)=O)cc3s2)nc1]

23. The method of claim 10, wherein the inhibitor has one H-bond donor moiety disposed to bind with amino acid residue Ala637, and one cation-pi stacking interaction moiety disposed to bind with amino acid Arg495.

24. The method of claim 23, wherein the compound is

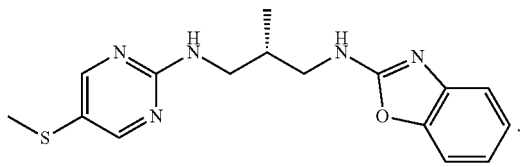 [SMILES: CSc1cnc(NC[C@H](C)CNc2nc3ccccc3o2)nc1]

25. The method of claim 10, wherein the inhibitor has one H-bond donor moiety disposed to bind with amino acid residue Ala637, one H-bond donor moiety disposed to bind with amino acid residue Thr641, one H-bond acceptor moiety disposed to bind with amino acid residue His643, one cation-pi stacking interaction moiety disposed to bind with amino acid residue Arg495, and cation-pi stacking interaction moiety disposed to bind with amino acid residue His591.

26. The method of claim 25, wherein the compound is

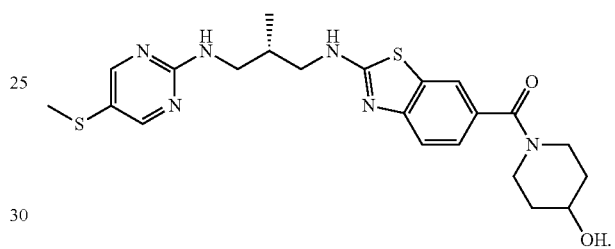

27. The method of claim 10, wherein the inhibitor has one H-bond donor moiety disposed to bind with amino acid residue Ala637, one H-bond acceptor moiety disposed to bind with amino acid residue Val644, and one cation-pi stacking interaction moiety disposed to bind with amino acid 591.

28. The method of claim 27, wherein the compound is

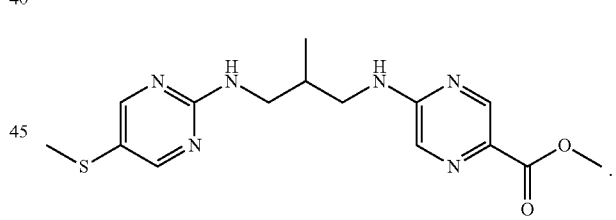

* * * * *

SEQUENCE LISTING

<160> NUMBER OF SEQ ID NOS: 7

<210> SEQ ID NO 1
<211> LENGTH: 692
<212> TYPE: PRT
<213> ORGANISM: Homo sapiens

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Leu Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160
```

```
Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
        180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575
```

```
Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 2
<211> LENGTH: 692
<212> TYPE: PRT
<213> ORGANISM: Homo sapiens

<400> SEQUENCE: 2

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Val Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240
```

```
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
Leu Ala Gly Gly Tyr Ser Arg Val Leu Asn Ala Ala Cys Gln Arg Leu
    290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
    530                 535                 540
Ser Met Gly Thr Arg Val His Cys His Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
```

```
Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 3
<211> LENGTH: 692
<212> TYPE: PRT
<213> ORGANISM: Homo sapiens

<400> SEQUENCE: 3

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65              70                  75                  80

Val Leu Lys Glu Glu Thr His Leu Ser Gln Ser Glu Arg Thr Ala Arg
            85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335
```

```
Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Ser Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690
```

<210> SEQ ID NO 4
<211> LENGTH: 692
<212> TYPE: PRT
<213> ORGANISM: Homo sapiens

<400> SEQUENCE: 4

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
                35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400
```

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Thr Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 5
<211> LENGTH: 692
<212> TYPE: PRT
<213> ORGANISM: Homo sapiens

<400> SEQUENCE: 5

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

```
His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
            130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Ile Ala Arg Cys Ala Pro Asp
465                 470                 475                 480
```

-continued

```
Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 6
<211> LENGTH: 692
<212> TYPE: PRT
<213> ORGANISM: Homo sapiens

<400> SEQUENCE: 6

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160
```

```
Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575
```

```
Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
        690

<210> SEQ ID NO 7
<211> LENGTH: 693
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65              70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240
```

```
Ile Arg Lys Ser Gln Leu Val Gln Pro Val Gly Pro Leu Val Val Leu
            245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
            290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
            325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
            370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
            405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
            435                 440                 445

Pro Asp Glu Glu Leu Leu Ser Cys Ser Ser Phe Ser Arg Ser Gly Lys
            450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
            485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
            530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
            565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
            645                 650                 655
```

```
Ala Ser Gln Glu Leu Gln Ser Gly Ser Gly Gly Leu Asn Asp Ile Phe
            660                 665                 670

Glu Ala Gln Lys Ile Glu Trp His Glu Asn Leu Tyr Phe Gln Gly His
        675                 680                 685

His His His His His
    690
```